US011541130B2

(12) United States Patent
Debs et al.

(10) Patent No.: US 11,541,130 B2
(45) Date of Patent: *Jan. 3, 2023

(54) SYSTEMS AND METHODS FOR NUCLEIC ACID EXPRESSION IN VIVO

(71) Applicant: DNARx, San Francisco, CA (US)

(72) Inventors: Robert James Debs, San Francisco, CA (US); Timothy D. Heath, Madison, WI (US); Chakkrapong Handumrongkul, Richmond, VA (US)

(73) Assignee: DNARx

( * ) Notice: Subject to any disclaimer, the term of this patent is extended or adjusted under 35 U.S.C. 154(b) by 1076 days.

This patent is subject to a terminal disclaimer.

(21) Appl. No.: 15/934,587

(22) Filed: Mar. 23, 2018

(65) Prior Publication Data

US 2018/0280539 A1 Oct. 4, 2018

Related U.S. Application Data

(60) Provisional application No. 62/475,477, filed on Mar. 23, 2017.

(51) Int. Cl.

| | |
|---|---|
| ***A61K 48/00*** | (2006.01) |
| ***C12N 15/88*** | (2006.01) |
| ***C12N 15/85*** | (2006.01) |
| ***A61K 31/7105*** | (2006.01) |
| ***A61K 39/395*** | (2006.01) |
| ***A61K 9/127*** | (2006.01) |
| ***C12N 15/10*** | (2006.01) |
| ***C07K 16/10*** | (2006.01) |
| ***C07K 16/40*** | (2006.01) |
| ***A61K 9/00*** | (2006.01) |
| ***C12N 15/87*** | (2006.01) |
| ***A61K 39/00*** | (2006.01) |

(52) U.S. Cl.

CPC .......... *A61K 48/005* (2013.01); *A61K 9/0019* (2013.01); *A61K 9/127* (2013.01); *A61K 9/1272* (2013.01); *A61K 31/7105* (2013.01); *A61K 39/39558* (2013.01); *C07K 16/1018* (2013.01); *C07K 16/40* (2013.01); *C12N 15/102* (2013.01); *C12N 15/85* (2013.01); *C12N 15/87* (2013.01); *C12N 15/88* (2013.01); *A61K 2039/505* (2013.01); *A61K 2039/507* (2013.01); *A61K 2039/53* (2013.01); *A61K 2039/55561* (2013.01); *C07K 2317/10* (2013.01); *C07K 2317/76* (2013.01); *C12N 2310/20* (2017.05)

(58) Field of Classification Search

CPC .... A61K 48/005; A61K 9/0019; A61K 9/127; A61K 9/1272; A61K 31/7015; A61K 39/39558; A61K 2039/505; A61K 2039/507; A61K 2039/53; A61K 2039/55561; C07K 16/1018; C07K 16/40; C07K 2317/10; C07K 2317/76; C12N 15/102; C12N 15/85; C12N 15/87; C12N 2310/20

USPC ................. 514/44 R; 424/450, 147.1, 283.1; 435/455, 320.1

See application file for complete search history.

(56) References Cited

U.S. PATENT DOCUMENTS

| | | | | |
|---|---|---|---|---|
| 6,074,667 | A | 6/2000 | Kinnuen et al. | |
| 6,133,026 | A | 10/2000 | Huang et al. | |
| 6,806,084 | B1 | 10/2004 | Debs et al. | |
| 7,244,609 | B2 | 7/2007 | Drocourt et al. | |
| 7,592,010 | B2 | 9/2009 | Rosen et al. | |
| 7,592,440 | B2 | 9/2009 | Freier et al. | |
| 7,919,472 | B2 | 4/2011 | Monia et al. | |
| 8,236,280 | B2 | 8/2012 | Reinke | |
| 9,045,754 | B2 | 6/2015 | Bhanot et al. | |
| 9,132,202 | B2 | 9/2015 | Tabor | |
| 10,086,089 | B2 * | 10/2018 | Debs | C07K 16/00 |
| 10,905,777 | B2 * | 2/2021 | Debs | C07K 16/2887 |
| 2002/0108132 | A1 | 8/2002 | Rapp | |
| 2004/0219677 | A1 | 11/2004 | Drocourt et al. | |
| 2005/0142109 | A1 | 6/2005 | Liu et al. | |
| 2006/0160184 | A1 | 7/2006 | Hoogenboom et al. | |
| 2007/0003521 | A1 | 1/2007 | Yew | |
| 2009/0252713 | A1 | 10/2009 | Soubrier | |
| 2014/0120157 | A1 | 5/2014 | Chang et al. | |
| 2015/0071903 | A1 | 3/2015 | Liu et al. | |

(Continued)

FOREIGN PATENT DOCUMENTS

| | | |
|---|---|---|
| CN | 101812177 | 8/2010 |
| CN | 101970687 | 2/2011 |

(Continued)

OTHER PUBLICATIONS

Tan et al. (2001) Mol. Ther., vol. 3(5), 673-682.*

(Continued)

*Primary Examiner* — Anne Marie S Wehbe
(74) *Attorney, Agent, or Firm* — Jones Day

(57) ABSTRACT

The present invention provides compositions, systems, kits, and methods for expression of one or more biomolecules in a subject, human or non-human mammal, (e.g., at therapeutic levels for the extended periods of time required to produce therapeutic effects). In certain embodiments, compositions, systems, kits, and methods are provided that comprise a first composition comprising polycationic structures (e.g., empty cationic liposomes, cationic micelles, cationic emulsions, or cationic polymers) and a second composition comprising expression vectors (e.g., non-viral expression vectors not associated with liposomes or other carriers) encoding one or more biomolecules of interest.

10 Claims, 110 Drawing Sheets

Specification includes a Sequence Listing.

(56) References Cited

U.S. PATENT DOCUMENTS

| | | | | |
|---|---|---|---|---|
| 2015/0079155 | A1 | 3/2015 | Jensen et al. | |
| 2017/0080108 | A1 | 3/2017 | Debs et al. | |
| 2017/0266282 | A1* | 9/2017 | Weiner | C07K 16/1063 |
| 2018/0280539 | A1 | 10/2018 | Debs et al. | |
| 2019/0046661 | A1 | 2/2019 | Debs et al. | |
| 2019/0083653 | A1 | 3/2019 | Debs et al. | |

FOREIGN PATENT DOCUMENTS

| | | |
|---|---|---|
| CN | 102366411 | 3/2012 |
| EP | 2061514 | 11/2014 |
| JP | 2002-524473 | 8/2002 |
| WO | WO 1998/07408 | 2/1998 |
| WO | WO 1999/065465 | 12/1999 |
| WO | WO 2000/014262 | 3/2000 |
| WO | WO 2001/075092 | 10/2001 |
| WO | WO 2009/061515 | 5/2009 |
| WO | WO 2014/100073 | 6/2014 |
| WO | WO 2016/028682 | 2/2016 |
| WO | WO 2017/049132 | 3/2017 |
| WO | WO 2018/175932 | 9/2018 |
| WO | WO 2022/067091 | 3/2022 |

OTHER PUBLICATIONS

De Wolf et al. (2008) Pharm. Res., vol. 25(7), 1654-1662.*

Lee et al., Dexamethasone-loaded peptide micelles for delivery of the heme oxygenase-1 gene to ischemic brain. Control Release. Feb. 28, 2012;158(1):131-8.

Mishra et al., Dexamethasone-loaded reconstitutable charged polymeric (PLGA)n-b-bPEI micelles for enhanced nuclear delivery of gene therapeutics. Macromol Biosci. Jun. 2014;14(6):831-41.

Extended European Search Report for EP18770192.5, dated Jul. 29, 2020, 11 pages.

Bauer et al., The impact of intragenic CpG content on gene expression. Nucleic Acids Res. Jul. 2010;38(12):3891-908.

Davies et al., The use of CpG-free plasmids to mediate persistent gene expression following repeated aerosol delivery of pDNA/PEI complexes. Biomaterials. Aug. 2012;33(22):5618-27.

Argyros et al., Development of S/MAR minicircles for enhanced and persistent transgene expression in the mouse liver. J Mol Med (Berl). May 2011;89(5):515-29.

Bar et al., Effect of HIV Antibody VRC01 on Viral Rebound after Treatment Interruption. N Engl J Med. Nov. 24, 2016;375(21):2037-2050.

Barrett et al., Regulation of eukaryotic gene expression by the untranslated gene regions and other non-coding elements. Cell Mol Life Sci. Nov. 2012;69(21):3613-34.

Bryan et al., Implications of protein fold switching. Retrieved from www.elsevierblogs.com/currentcommnts/p=962. Feb. 4, 2013, 4 pages.

Caskey et al., Antibody 10-1074 suppresses viremia in HIV-1-infected individuals. Nat Med. Feb. 2017;23(2):185-191.

De Wolf et al., Plasmid CpG depletion improves degree and duration of tumor gene expression after intravenous administration of polyplexes. Pharm Res. Jul. 2008;25(7):1654-62.

Felgner et al., Enhanced gene delivery and mechanism studies with a novel series of cationic lipid formulations. J Biol Chem. Jan. 28, 1994;269(4):2550-61.

Gill et al., Progress and prospects: the design and production of plasmid vectors. Gene Ther. Feb. 2009;16(2):165-71.

Kaur et al., Addressing the challenge: current and future directions in ovarian cancer therapy. Curr Gene Ther. Dec. 2009;9(6):434-58.

Kotterman et al., Engineering adeno-associated viruses for clinical gene therapy. Nat Rev Genet. Jul. 2014;15(7):445-51.

Kroon et al., Liposomal delivery of dexamethasone attenuates prostate cancer bone metastatic tumor growth in vivo. Prostate. Jun. 2015;75(8):815-24.

Lenzi et al., Gene Transfer Research: The Evolution of the Clinical Science. Committee on the Independent Review and Assesment of the Activities of the NIH Recombinant DNA Advisory Committee. NCBI Bookshelf. 2014. 16 pages.

Liu et al., Cationic liposome-mediated intravenous gene delivery. J Biol Chem. Oct. 20, 1995;270(42):24864-70.

Liu et al., Factors influencing the efficiency of cationic liposome-mediated intravenous gene delivery. Nat Biotechnol. Feb. 1997;15(2):167-73.

Maqbool et al., The substrate-binding protein in bacterial ABC transporters: dissecting roles in the evolution of substrate specificity. Biochem Soc Trans. Oct. 2015;43(5):1011-7.

Scheid et al., HIV-1 antibody 3BNC117 suppresses viral rebound in humans during treatment interruption. Nature. Jul. 28, 2016;535(7613):556-60.

Sellins et al., Type I interferons potently suppress gene expression following gene delivery using liposome(−)DNA complexes. Mol Ther. Sep. 2005;12(3):451-9.

Song et al., Free liposomes enhance the transfection activity of DNA/lipid complexes in vivo by intravenous administration. Biochim Biophys Acta. Jun. 24, 1998;1372(1):141-50.

Song et al., Enhanced gene expression in mouse lung by prolonging the retention time of intravenously injected plasmid DNA. Gene Ther. Nov. 1998;5(11):1531-7.

Tan et al., Sequential injection of cationic liposome and plasmid DNA effectively transfects the lung with minimal inflammatory toxicity. Mol Ther. May 2001;3(5 Pt 1):673-82.

Tu et al., Non-replicating Epstein-Barr virus-based plasmids extend gene expression and can improve gene therapy in vivo. J Biol Chem. Sep. 29, 2000;275(39):30408-16.

Zhang et al., Mechanistic studies of sequential injection of cationic liposome and plasmid DNA. Mol Ther. Feb. 2006;13(2):429-37.

International Search Report and Written Opinion for PCT/US2016/052205, dated Dec. 15, 2016, 17 pages.

International Search Report and Written Opinion for PCT/US2018/024096, dated Aug. 8, 2018, 14 pages.

Gao et al., Potentiation of cationic liposome-mediated gene delivery by polycations. Biochemistry. Jan. 23, 1996;35(3):1027-36.

Extended European Search Report for EP16847422.9 dated Apr. 10, 2019, 11 pages.

Kim et al., Combined delivery of dexamethasone and plasmid DNA in an animal model of LPS-induced acute lung injury. J Control Release. Nov. 30, 2011;156(1):60-9.

Przybylsa et al., Partial correction of the alpha-galactosidase A deficiency and reduction of glycolipid storage in Fabry mice using synthetic vectors. J Gene Med. Jan. 2004;6(1):85-92.

Handumrongkul et al., "Distinct sets of cellular genes control the expression of transfected, nuclear-localized genes," *Mol. Ther.*, 5(2):186-194 (2002).

Handumrongkul et al., "Durable multitransgene expression in vivo using systemic, nonviral DNA delivery," *Science Advances*, 5(11):eaax0217 (2019).

Liu et al., "Strain-based genetic differences regulate the efficiency of systemic gene delivery as well as expression," *J. Biol. Chem.*, 277(7):4966-4972 (2002).

* cited by examiner

FIG. 1

CpG free hG-CSF nucleic acid Sequence (SEQ ID NO:1)
Atggctggacctgccacccagagccccatgaagctgatggccctgcagctgctgctgtggcacagtgcactctggacagt
gcaggaagccacccccctgggccctgccagctccctgccccagagcttcctgctcaagtgcttagagcaagtgaggaaga
tccaggggatggggcagctctccaggagaagctgtgtgccacctacaagctgtgccaccctgaggagctggtgctgctg
ggacactctctgggcatcccctgggctcccctgagcagctgccccagccaggccctgcagctggcaggctgcttgagcca
actccatagtggcctttttcctctaccaggggctcctgcaggccctggaagggatctcccctgagttgggtcccaccttgg
acacactgcagctggatgttgctgactttgccaccaccatctggcagcagatggaagaactgggaatggcccctgccctg
cagcccacccagggtgccatgcctgcctttgcctctgctttccagagaagggcaggaggggtcctggttgcctcccatct
gcagagcttcctggaggtgtcctacagagttctaagacaccttgcccagccctga CpG free hG-CSF Protein (SEQ ID NO:2)

MAGPATQSPMKLMALQLLLWHSALWTVQEATPLGPASSLPQSFLLKCLEQVRKIQGDGAALQEKLVSECATYKLCHPEEL
VLLGHSLGIPWAPLSSCPSQALQLAGCLSQLHSGLFLYQGLLQALEGISPELGPTLDTLQLDVADFATTIWQQMEELGMA
PALQPTQGAMPAFASAFQRRAGGVLVASHLQSFLEVSYRVLRHLAQP

FIG. 5

715.1 2a : RINhe-ΔmCMVΔEF1I126-BstEII-GAK-ΔantiCD20-H-F2(RAKR)-P2A-ΔantiCD20-L-BglII-MixpA/BV2
(SEQ ID NO:3)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGGGCTGGTCCCTGATCCTGCTGTT
CCTGGTGGCTGTGGCCACCAGAGTGCTGAGCCAGGTGCAGCTGCAGCAGCCTGGGGCTGAGCTTGTGAAACCTGGGGCCTCTGTGAAGATGAGCTGCAAGGCCTCT
GGCTACACCTTCACCAGCTACAACATGCACTGGGTCAAGCAGACCCCTGGCAGAGGCCTGGAATGGATTGGAGCCATCTACCCTGGCAATGGGGACACCTCCTACAA
CCAGAAGTTCAAGGGCAAGGCCACCCTGACAGCTGACAAGAGCAGCAGCACAGCCTACATGCAGCTGTCCAGCCTGACCTCTGAGGACTCTGCTGTGTACTACTGTG
CCAGGTCCACCTACTATGGGGGAGACTGGTACTTCAATGTGTGGGGAGCTGGCACCACAGTGACAGTGTCTGCTGCCAGCACCAAGGGCCCCTCTGTGTTTCCTCTG
GCCCCCAGCAGCAAGAGCACCTCTGGGGGAACAGCTGCCCTGGGCTGCCTTGTGAAGGACTACTTCCCTGAGCCTGTGACTGTGTCCTGGAACTCTGGGGCCCTGAC
ATCTGGGGTGCACACCTTCCCTGCAGTGCTGCAGTCCAGTGGCCTGTACTCCCTGTCCTCTGTTGTGACAGTGCCCAGCTCCAGCCTGGGCACCCAGACCTACATCTGC
AATGTGAACCACAAGCCCAGCAACACCAAGGTGGACAAGAAGGCTGAGCCCAAGAGCTGTGACAAGACCCACACCTGTCCCCCCTGTCCTGCCCCTGAACTGCTGG
GAGGACCTTCTGTGTTCCTGTTCCCACCCAAGCCCAAGGATACCCTGATGATCAGCAGAACCCCTGAAGTGACCTGTGTGGTGGTGGATGTGTCCCATGAGGACCCA
GAAGTGAAGTTCAATTGGTATGTGGATGGGGTGGAAGTGCACAATGCCAAGACCAAGCCCAGAGAGGAACAGTACAACAGCACCTACAGAGTGGTGTCTGTGCTG
ACTGTGCTGCACCAGGACTGGCTGAATGGCAAAGAGTACAAGTGCAAGGTGTCCAACAAGGCCCTGCCAGCCCCCATTGAGAAAACCATCAGCAAGGCCAAGGGCC
AGCCTAGAGAACCCCAGGTGTACACACTGCCCCCTAGCAGGGATGAGCTGACCAAGAACCAGGTGTCCCTGACATGCCTTGTGAAAGGCTTCTACCCCTCTGACATT
GCTGTGGAATGGGAGAGCAATGGACAGCCTGAGAACAACTACAAGACCACCCCCCCTGTGCTGGACTCTGATGGCTCATTCTTCCTGTACAGCAAGCTGACAGTGGA
CAAGTCCAGATGGCAGCAGGGCAATGTGTTCAGCTGCTCTGTGATGCATGAGGCCCTGCACAACCACTACACCCAGAAAAGCCTGTCCCTGTCCCCTGGCAAG*AGAG*
*CAAAGAGGGGAAGTGGAGCTACTAACTTCAGCCTGCTGAAGCAGGCTGGAGATGTGGAGGAGAACCCTGGACCT*ATGGACTTCCAGGTGCAGATCATCAGCTTTCT
GCTGATCTCTGCCTCTGTGATCATGAGCAGAGGCCAGATTGTGCTGAGCCAGAGCCCTGCCATCCTGTCTGCAAGCCCTGGGGAGAAAGTGACCATGACCTGCAGAG
CCAGCAGCTCTGTGTCCTACATCCACTGGTTCCAGCAGAAGCCTGGCAGCAGCCCCAAGCCTTGGATCTATGCCACCAGCAACCTGGCATCTGGGGTGCCAGTCAGA
TTCTCTGGCTCTGGATCTGGCACCAGCTACAGCCTGACCATCAGCAGAGTGGAAGCTGAGGATGCTGCCACCTACTACTGCCAGCAGTGGACCAGCAATCCCCCCACC
TTTGGAGGGGGCACCAAGCTGGAAATCAAGAGAACAGTGGCTGCCCCCTCTGTGTTCATCTTCCCACCCTCTGATGAGCAGCTGAAGTCTGGAACAGCCTCTGTTGT
GTGCCTGCTGAACAACTTCTACCCCAGAGAAGCCAAGGTGCAGTGGAAGGTGGACAATGCCCTGCAGTCTGGCAACTCCCAGGAATCTGTGACAGAGCAGGACAGC
AAGGACTCCACCTACTCCCTGAGCAGCACCCTGACCCTGAGCAAGGCTGACTATGAGAAGCACAAAGTGTATGCCTGTGAAGTGACCCACCAGGGCCTGTCCAGCCC
TGTGACCAAGAGCTTCAACAGAGGGGAGAGCTGAAGATCTACTTCTGGCTAATAAAAGATCAGAGCTCTAGTGATCTGTGTGTTGGTTTTTTGTGTCTGCATTCTAGC
TCTAGTGATCAGCAGTTCAACCTGTTGATAGTATGTACTAAGCTCTCATGTTTAATGTACTAAGCTCTCATGTTTAATGAACTAAACCCTCATGGCTAATGTACTAAGCT
CTCATGGCTAATGTACTAAGCTCTCATGTTTCATGTACTAAGCTCTCATGTTTGAACAATAAAATTAATATAAATCAGCAACTTAAATAGCCTCTAAGGTTTTAAGTTTT
ATAAGAAAAAAAAGAATATATAAGGCTTTTAAAGGTTTTAAGGTTTCCTAGGTTATCCTCATATGAGCTCTTAGAAAAACTCATCCAGCATCAAATGAAACTGCAATTT
ATTCATATCAGGATTATCAATACCATATTTTTGAAAAAGTCTTTTCTGTAATGAAGGAGAAAACTCACCCAGGCAGTTCCATAGGATGGCAAGATCCTGGTATCTGTCT
GCAATTCCAACTCTTCCAACATCAATACAACCTATTAATTTCCCCTCATCAAAAATAAGGTTATCAAGTGAGAAATCACCATGAGTGACCACTGAATCTGGTGAGAATG
GCAAAAGATTATGCATTTCTTTCCAGACTTGTTCAACAGGCCAGCCATTTCTCTCATCATCAAAATCACTGGCATCAACCAAACCATTATTCATTCTTGATTGGGCCTGA
GCCAGTCTAAATACTCTATCAGAGTTAAAAGGACAATTACAAACAGGAATGGAATGCAATCTTCTCAGGAACACTGCCAGGGCATCAACAATATTTTCACCTGAATCA
GGATATTCTTCCAATACCTGGAATGCTGTTTTCCCTGGGATGGCAGTGGTGAGTAACCATGCATCATCAGGAGTTCTGATAAAATGCTTGATGGTTGGAAGAGGCAT
AAATTCAGTCAGCCAGTTTAGTCTGACCATCTCATCTGTAACATCATTGGCAACAGAACCTTTGCCATGTTTCAGAAACAACTCTGGGGCATCTGGCTTCCCATACAAT
CTATAGATTGTGGCACCTGATTGCCCAACATTATCTCTAGCCCATTTATACCCATATAAATCAGCATCCATGTTGGAATTTAATCTTGGCCTGGAGCAAGAGGTTTCTCT
TTGAATATGGCTCATACATGTGCACCTCCTATAGTGAGTTGTATTATACTATGCAGATATACTATGCCAATGTTTAATTGTCAG

FIG. 6

718.1 : Dual Cassette anti-CD20

DraIIRINhe ΔmCMV-EF1-I126-BstEII-aCD20H-BglII-polyA-ΔhCMV-EF1-I126-BstEII-aCD20L-BglII-polyA BV2
(SEQ ID NO:4)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGCTGGTCCCTGATCCTGCTGTTCCTGGTGGCTGTGGCCACCAGAGTGCTGAGCCAGGTGCAGCTGCAGCAGCCTGGGGCTGAGCTTGTGAAACCTGGGGC
CTCTGTGAAGATGAGCTGCAAGGCCTCTGGCTACACCTTCACCAGCTACAACATGCACTGGGTCAAGCAGACCCCTGGCAGAGGCCTGGAATGGATTGGAGCCATCT
ACCCTGGCAATGGGGACACCTCCTACAACCAGAAGTTCAAGGGCAAGGCCACCCTGACAGCTGACAAGAGCAGCAGCACAGCCTACATGCAGCTGTCCAGCCTGAC
CTCTGAGGACTCTGCTGTGTACTACTGTGCCAGGTCCACCTACTATGGGGGAGACTGGTACTTCAATGTGTGGGGAGCTGGCACCACAGTGACAGTGTCTGCTGCCA
GCACCAAGGGCCCCTCTGTGTTTCCTCTGGCCCCCAGCAGCAAGAGCACCTCTGGGGGAACAGCTGCCCTGGGCTGCCTTGTGAAGGACTACTTCCCTGAGCCTGTG
ACTGTGTCCTGGAACTCTGGGGCCCTGACATCTGGGGTGCACACCTTCCCTGCAGTGCTGCAGTCCAGTGGCCTGTACTCCCTGTCCTCTGTTGTGACAGTGCCCAGC
TCCAGCCTGGGCACCCAGACCTACATCTGCAATGTGAACCACAAGCCCAGCAACACCAAGGTGGACAAGAAGGCTGAGCCCAAGAGCTGTGACAAGACCCACACCT
GTCCCCCCTGTCCTGCCCCTGAACTGCTGGGAGGACCTTCTGTGTTCCTGTTCCCACCCAAGCCCAAGGATACCCTGATGATCAGCAGAACCCCTGAAGTGACCTGTG
TGGTGGTGGATGTGTCCCATGAGGACCCAGAAGTGAAGTTCAATTGGTATGTGGATGGGGTGGAAGTGCACAATGCCAAGACCAAGCCCAGAGAGGAACAGTACA
ACAGCACCTACAGAGTGGTGTCTGTGCTGACTGTGCTGCACCAGGACTGGCTGAATGGCAAAGAGTACAAGTGCAAGGTGTCCAACAAGGCCCTGCCAGCCCCCATT
GAGAAAACCATCAGCAAGGCCAAGGGCCAGCCTAGAGAACCCCAGGTGTACACACTGCCCCCTAGCAGGGATGAGCTGACCAAGAACCAGGTGTCCCTGACATGCC
TTGTGAAAGGCTTCTACCCCTCTGACATTGCTGTGGAATGGGAGAGCAATGGACAGCCTGAGAACAACTACAAGACCACCCCCCCTGTGCTGGACTCTGATGGCTCA
TTCTTCCTGTACAGCAAGCTGACAGTGGACAAGTCCAGATGGCAGCAGGGCAATGTGTTCAGCTGCTCTGTGATGCATGAGGCCCTGCACAACCACTACACCCAGAA
AAGCCTGTCCCTGTCCCCTGGCAAGTGAAGATCTACTTCTGGCTAATAAAAGATCAGAGCTCTAGTGATCTGTGTGTTGGTTTTTTGTGTCTGCATTCTAGCTGTTACA
TAACTTATGGTAAATGGCCTGCCTGGCTGACTGCCCAATGACCCCTGCCCAATGATGTCAATAATGATGTATGTTCCCATGTAATGCCAATAGGGACTTTCCATTGATG
TCAATGGGTGGAGTATTTATGGTAACTGCCCACTTGGCAGTACATCAAGTGTATCATATGCCAAGTATGCCCCCTATTGATGTCAATGATGGTAAATGGCCTGCCTGG
CATTATGCCCAGTACATGACCTTATGGGACTTTCCTACTTGGCAGTACATCTATGTATTAGTCATTGCTATTACCATGGATTAGTGGAGAAGAGCATGCTTGAGGGCTG
AGTGCCCCTCAGTGGGCAGAGAGCACATGGCCCACAGTCCCTGAGAAGTTGGGGGGAGGGGTGGGCAATTGAACTGGTGCCTAGAGAAGGTGGGGCTTGGGTAA
ACTGGGAAAGTGATGTGGTGTACTGGCTCCACCTTTTTCCCCAGGGTGGGGGAGAACCATATATAAGTGCAGTAGTCTCTGTGAACATTCAAGCTTCTGCCTTCTCCC
TCCTGTGAGTTTGGATGCACCTACTAGATATCTTGGTAAGTCACTGACTGTCTATGCCTGGGAAAGGGTGGGCAGGAGGTGGGGCAGTGCAGGAAAAGTGGCACTG
TGAACCCTGCAGCCCTAGACAATTGTACTAACCTTCTTCTCTTTCCTCTCCTGACAGGTTGGTAACCAAGCCACCATGGACTTCCAGGTGCAGATCATCAGCTTTCTGCT
GATCTCTGCCTCTGTGATCATGAGCAGAGGCCAGATTGTGCTGAGCCAGAGCCCTGCCATCCTGTCTGCAAGCCCTGGGGAGAAAGTGACCATGACCTGCAGAGCCA
GCAGCTCTGTGTCCTACATCCACTGGTTCCAGCAGAAGCCTGGCAGCAGCCCCAAGCCTTGGATCTATGCCACCAGCAACCTGGCATCTGGGGTGCCAGTCAGATTCT
CTGGCTCTGGATCTGGCACCAGCTACAGCCTGACCATCAGCAGAGTGGAAGCTGAGGATGCTGCCACCTACTACTGCCAGCAGTGGACCAGCAATCCCCCCACCTTT
GGAGGGGGCACCAAGCTGGAAATCAAGAGAACAGTGGCTGCCCCCTCTGTGTTCATCTTCCCACCCTCTGATGAGCAGCTGAAGTCTGGAACAGCCTCTGTTGTGTG
CCTGCTGAACAACTTCTACCCCAGAGAAGCCAAGGTGCAGTGGAAGGTGGACAATGCCCTGCAGTCTGGCAACTCCCAGGAATCTGTGACAGAGCAGGACAGCAAG
GACTCCACCTACTCCCTGAGCAGCACCCTGACCCTGAGCAAGGCTGACTATGAGAAGCACAAAGTGTATGCCTGTGAAGTGACCCACCAGGGCCTGTCCAGCCCTGT
GACCAAGAGCTTCAACAGAGGGGAGAGCTGAAGATCTACTTCTGGCTAATAAAAGATCAGAGCTCTAGTGATCTGTGTGTTGGTTTTTTGTGTCTGCATTCTAGCTCT
AGTGATCAGCAGTTCAACCTGTTGATAGTATGTACTAAGCTCTCATGTTTAATGTACTAAGCTCTCATGTTTAATGAACTAAACCCTCATGGCTAATGTACTAAGCTCTC
ATGGCTAATGTACTAAGCTCTCATGTTTCATGTACTAAGCTCTCATGTTTGAACAATAAAATTAATATAAATCAGCAACTTAAATAGCCTCTAAGGTTTTAAGTTTTATA
AGAAAAAAAAGAATATATAAGGCTTTTAAAGGTTTTAAGGTTTCCTAGGTTATCCTCATATGAGCTCTTAGAAAAACTCATCCAGCATCAAATGAAACTGCAATTTATT
CATATCAGGATTATCAATACCATATTTTTGAAAAAGTCTTTTCTGTAATGAAGGAGAAAACTCACCCAGGCAGTTCCATAGGATGGCAAGATCCTGGTATCTGTCTGCA
ATTCCAACTCTTCCAACATCAATACAACCTATTAATTTCCCCTCATCAAAAATAAGGTTATCAAGTGAGAAATCACCATGAGTGACCACTGAATCTGGTGAGAATGGCA
AAAGATTATGCATTTCTTTCCAGACTTGTTCAACAGGCCAGCCATTTCTCTCATCATCAAAATCACTGGCATCAACCAAACCATTATTCATTCTTGATTGGGCCTGAGCC
AGTCTAAATACTCTATCAGAGTTAAAAGGACAATTACAAACAGGAATGGAATGCAATCTTCTCAGGAACACTGCCAGGGCATCAACAATATTTTCACCTGAATCAGGA
TATTCTTCCAATACCTGGAATGCTGTTTTCCCTGGGATGGCAGTGGTGAGTAACCATGCATCATCAGGAGTTCTGATAAAATGCTTGATGGTTGGAAGAGGCATAAAT
TCAGTCAGCCAGTTTAGTCTGACCATCTCATCTGTAACATCATTGGCAACAGAACCTTTGCCATGTTTCAGAAACAACTCTGGGGCATCTGGCTTCCCATACAATCTAT
AGATTGTGGCACCTGATTGCCCAACATTATCTCTAGCCCATTTATACCCATATAAATCAGCATCCATGTTGGAATTTAATCTTGGCCTGGAGCAAGAGGTTTCTCTTTGA
ATATGGCTCATACATGTGCACCTCCTATAGTGAGTTGTATTATACTATGCAGATATACTATGCCAATGTTTAATTGTCAG

FIG. 7

902.8 (P2A) : Complete G5: F3P2A (Bicistronic antiCD20)

DraIIRINhe-ΔmCMVΔEF1I126-BstEII- ΔantiCD20-H-F3(RKRR)-P2A-ΔantiCD20-L-BglII-MixpA-BV2

(SEQ ID NO:5)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGGGCTGGTCCCTGATCCTGCTGTT
CCTGGTGGCTGTGGCCACCAGAGTGCTGAGCCAGGTGCAGCTGCAGCAGCCTGGGGCTGAGCTTGTGAAACCTGGGGCCTCTGTGAAGATGAGCTGCAAGGCCTCT
GGCTACACCTTCACCAGCTACAACATGCACTGGGTCAAGCAGACCCCTGGCAGAGGCCTGGAATGGATTGGAGCCATCTACCCTGGCAATGGGGACACCTCCTACAA
CCAGAAGTTCAAGGGCAAGGCCACCCTGACAGCTGACAAGAGCAGCAGCACAGCCTACATGCAGCTGTCCAGCCTGACCTCTGAGGACTCTGCTGTGTACTACTGTG
CCAGGTCCACCTACTATGGGGGAGACTGGTACTTCAATGTGTGGGGAGCTGGCACCACAGTGACAGTGTCTGCTGCCAGCACCAAGGGCCCCTCTGTGTTTCCTCTG
GCCCCCAGCAGCAAGAGCACCTCTGGGGGAACAGCTGCCCTGGGCTGCCTTGTGAAGGACTACTTCCCTGAGCCTGTGACTGTGTCCTGGAACTCTGGGGCCCTGAC
ATCTGGGGTGCACACCTTCCCTGCAGTGCTGCAGTCCAGTGGCCTGTACTCCCTGTCCTCTGTTGTGACAGTGCCCAGCTCCAGCCTGGGCACCCAGACCTACATCTGC
AATGTGAACCACAAGCCCAGCAACACCAAGGTGGACAAGAAGGCTGAGCCCAAGAGCTGTGACAAGACCCACACCTGTCCCCCCTGTCCTGCCCCTGAACTGCTGG
GAGGACCTTCTGTGTTCCTGTTCCCACCCAAGCCCAAGGATACCCTGATGATCAGCAGAACCCCTGAAGTGACCTGTGTGGTGGTGGATGTGTCCCATGAGGACCCA
GAAGTGAAGTTCAATTGGTATGTGGATGGGGTGGAAGTGCACAATGCCAAGACCAAGCCCAGAGAGGAACAGTACAACAGCACCTACAGAGTGGTGTCTGTGCTG
ACTGTGCTGCACCAGGACTGGCTGAATGGCAAAGAGTACAAGTGCAAGGTGTCCAACAAGGCCCTGCCAGCCCCCATTGAGAAAACCATCAGCAAGGCCAAGGGCC
AGCCTAGAGAACCCCAGGTGTACACACTGCCCCCTAGCAGGGATGAGCTGACCAAGAACCAGGTGTCCCTGACATGCCTTGTGAAAGGCTTCTACCCCTCTGACATT
GCTGTGGAATGGGAGAGCAATGGACAGCCTGAGAACAACTACAAGACCACCCCCCCTGTGCTGGACTCTGATGGCTCATTCTTCCTGTACAGCAAGCTGACAGTGGA
CAAGTCCAGATGGCAGCAGGGCAATGTGTTCAGCTGCTCTGTGATGCATGAGGCCCTGCACAACCACTACACCCAGAAAAGCCTGTCCCTGTCCCCTGGCAAG*AGAA*
*AGAGAAGGAGTGGAAGTGGAGCTACTAACTTCAGCCTGCTGAAGCAGGCTGGAGATGTGGAGGAGAACCCTGGACCT*ATGGACTTCCAGGTGCAGATCATCAGCTT
TCTGCTGATCTCTGCCTCTGTGATCATGAGCAGAGGCCAGATTGTGCTGAGCCAGAGCCCTGCCATCCTGTCTGCAAGCCCTGGGGAGAAAGTGACCATGACCTGCA
GAGCCAGCAGCTCTGTGTCCTACATCCACTGGTTCCAGCAGAAGCCTGGCAGCAGCCCCAAGCCTTGGATCTATGCCACCAGCAACCTGGCATCTGGGGTGCCAGTC
AGATTCTCTGGCTCTGGATCTGGCACCAGCTACAGCCTGACCATCAGCAGAGTGGAAGCTGAGGATGCTGCCACCTACTACTGCCAGCAGTGGACCAGCAATCCCCC
CACCTTTGGAGGGGGCACCAAGCTGGAAATCAAGAGAACAGTGGCTGCCCCCTCTGTGTTCATCTTCCCACCCTCTGATGAGCAGCTGAAGTCTGGAACAGCCTCTG
TTGTGTGCCTGCTGAACAACTTCTACCCCAGAGAAGCCAAGGTGCAGTGGAAGGTGGACAATGCCCTGCAGTCTGGCAACTCCCAGGAATCTGTGACAGAGCAGGA
CAGCAAGGACTCCACCTACTCCCTGAGCAGCACCCTGACCCTGAGCAAGGCTGACTATGAGAAGCACAAAGTGTATGCCTGTGAAGTGACCCACCAGGGCCTGTCCA
GCCCTGTGACCAAGAGCTTCAACAGAGGGGAGAGCTGAAGATCTACTTCTGGCTAATAAAAGATCAGAGCTCTAGTGATCTGTGTGTTGGTTTTTTGTGTCTGCATTC
TAGCTCTAGTGATCAGCAGTTCAACCTGTTGATAGTATGTACTAAGCTCTCATGTTTAATGTACTAAGCTCTCATGTTTAATGAACTAAACCCTCATGGCTAATGTACTA
AGCTCTCATGGCTAATGTACTAAGCTCTCATGTTTCATGTACTAAGCTCTCATGTTTGAACAATAAAATTAATATAAATCAGCAACTTAAATAGCCTCTAAGGTTTTAAG
TTTTATAAGAAAAAAAAGAATATATAAGGCTTTTAAAGGTTTTAAGGTTTCCTAGGTTATCCTCATATGAGCTCTTAGAAAAACTCATCCAGCATCAAATGAAACTGCA
ATTTATTCATATCAGGATTATCAATACCATATTTTTGAAAAAGTCTTTTCTGTAATGAAGGAGAAAACTCACCCAGGCAGTTCCATAGGATGGCAAGATCCTGGTATCT
GTCTGCAATTCCAACTCTTCCAACATCAATACAACCTATTAATTTCCCCTCATCAAAAATAAGGTTATCAAGTGAGAAATCACCATGAGTGACCACTGAATCTGGTGAG
AATGGCAAAAGATTATGCATTTCTTTCCAGACTTGTTCAACAGGCCAGCCATTTCTCTCATCATCAAAATCACTGGCATCAACCAAACCATTATTCATTCTTGATTGGGC
CTGAGCCAGTCTAAATACTCTATCAGAGTTAAAAGGACAATTACAAACAGGAATGGAATGCAATCTTCTCAGGAACACTGCCAGGGCATCAACAATATTTTCACCTGA
ATCAGGATATTCTTCCAATACCTGGAATGCTGTTTTCCCTGGGATGGCAGTGGTGAGTAACCATGCATCATCAGGAGTTCTGATAAAATGCTTGATGGTTGGAAGAG
GCATAAATTCAGTCAGCCAGTTTAGTCTGACCATCTCATCTGTAACATCATTGGCAACAGAACCTTTGCCATGTTTCAGAAACAACTCTGGGGCATCTGGCTTCCCATA
CAATCTATAGATTGTGGCACCTGATTGCCCAACATTATCTCTAGCCCATTTATACCCATATAAATCAGCATCCATGTTGGAATTTAATCTTGGCCTGGAGCAAGAGGTT
TCTCTTTGAATATGGCTCATACATGTGCACCTCCTATAGTGAGTTGTATTATACTATGCAGATATACTATGCCAATGTTTAATTGTCAG

FIG. 8

113.2 : SuperEnhancer Dual Cassette anti-CD20 (SEQ ID NO:6)

DraIIRINhe-SuperEnhancer-ΔmCMV-EF1-I126-BstEII-aCD20H-BglII-polyA- SuperEnhancer-ΔhCMV-EF1-I126-BstEII-aCD20L-BglII-polyA BV2

CACTATGTGGACATGAATTCAATTGGCTAGCAAAACAAATGACATCATTCCTGATTATAATAATTTTAATTGTGCTTTACAAGTAGAATTCTACTTGTAAAGAGAGTTT
AATTTGAAAAACAAATTAGTCATTATTAAACATGTTAACAATTGTGTATAAAAATGACATCAGTTTAATGATGACATCATCTCTTGATTATGTTTTACAAGTAGAATTCT
ACTTGTAAAGCTGGTTCAGTTTTGAAAAACAAATGACATCATCTCTTGATTATGTTTTACAAGTAGAATTCTACTTGTAAAAGTGAGTTTAGTTTTAAAAAACAAATGA
CATCATTCAGTTTTGAAAAACAAATGACATCATCTCTTGATTGTGTTTTACAAGTAGAATTCTACTTGTAAAGTGAGTTCAGTTTTGAAAAACAAATGACCCTCTCATA
CAATTGTTGAACAATTTTAATAAATAATCTTTACAAGATTTCTAGCAGGAGTCAATGGGAAAAACCCATTGGAGCCAAGTACACTGACTCAATAGGGACTTTCCATTG
GGTTTTGCCCAGTACATAAGGTCAATAGGGGGTGAGTCAACAGGAAAGTCCCATTGGAGCCAAGTACATTGAGTCAATAGGGACTTTCCAATGGGTTTTGCCCAG
TACATAAGGTCAATGGGAGGTAAGCCAATGGGTTTTTCCCATTACTGACATGTATACTGAGTCATTAGGGACTTTCCAATGGGTTTTGCCCAGTACATAAGGTCAAT
AGGGGTGAATCAACAGGAAAGTCCCATTGGAGCCAAGTACACTGAGTCAATAGGGACTTTCCATTGGGTTTTGCCCAGTACAAAAGGTCAATAGGGGGTGAGTCA
ATGGGTTTTTCCCATTATTGGCACATACATAAGGTCAATAGGGGTGACTAGTGGAGAAGAGCATGCTTGAGGGCTGAGTGCCCCTCAGTGGGCAGAGAGCACATG
GCCCACAGTCCCTGAGAAGTTGGGGGGAGGGGTGGGCAATTGAACTGGTGCCTAGAGAAGGTGGGGCTTGGGTAAACTGGGAAAGTGATGTGGTGTACTGGCT
CCACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCACTGAC
TGTCTATGCCTGGGAAAGGGTGGGCAGGAGATGGGGCAGTGCAGGAAAAGTGGCACTATGAACCCTGCAGCCCTAGACAATTGTACTAACCTTCTTCTCTTTCCT
CTCCTGACAGGTTGGTAACCAAGCCACCATGGGCTGGTCCCTGATCCTGCTGTTCCTGGTGGCTGTGGCCACCAGAGTGCTGAGCCAGGTGCAGCTGCAGCAG
CCTGGGGCTGAGCTTGTGAAACCTGGGGCCTCTGTGAAGATGAGCTGCAAGGCCTCTGGCTACACCTTCACCAGCTACAACATGCACTGGGTCAAGCAGACCCC
TGGCAGAGGCCTGGAATGGATTGGAGCCATCTACCCTGGCAATGGGGACACCTCCTACAACCAGAAGTTCAAGGGCAAGGCCACCCTGACAGCTGACAAGAGCA
GCAGCACAGCCTACATGCAGCTGTCCAGCCTGACCTCTGAGGACTCTGCTGTGTACTACTGTGCCAGGTCCACCTACTATGGGGGAGACTGGTACTTCAATGTGT
GGGGAGCTGGCACCACAGTGACAGTGTCTGCTGCCAGCACCAAGGGCCCCTCTGTGTTTCCTCTGGCCCCCAGCAGCAAGAGCACCTCTGGGGGAACAGCTGC
CCTGGGCTGCCTTGTGAAGGACTACTTCCCTGAGCCTGTGACTGTGTCCTGGAACTCTGGGGCCCTGACATCTGGGGTGCACACCTTCCCTGCAGTGCTGCAGT
CCAGTGGCCTGTACTCCCTGTCCTCTGTTGTGACAGTGCCCAGCTCCAGCCTGGGCACCCAGACCTACATCTGCAATGTGAACCACAAGCCCAGCAACACCAAG
GTGGACAAGAAGGCTGAGCCCAAGAGCTGTGACAAGACCCACACCTGTCCCCCCTGTCCTGCCCCTGAACTGCTGGGAGGACCTTCTGTGTTCCTGTTCCCACC
CAAGCCCAAGGATACCCTGATGATCAGCAGAACCCCTGAAGTGACCTGTGTGGTGGTGGATGTGTCCCATGAGGACCCAGAAGTGAAGTTCAATTGGTATGTGGA
TGGGGTGGAAGTGCACAATGCCAAGACCAAGCCCAGAGAGGAACAGTACAACAGCACCTACAGAGTGGTGTCTGTGCTGACTGTGCTGCACCAGGACTGGCTGA
ATGGCAAAGAGTACAAGTGCAAGGTGTCCAACAAGGCCCTGCCAGCCCCCATTGAGAAAACCATCAGCAAGGCCAAGGGCCAGCCTAGAGAACCCCAGGTGTAC
ACACTGCCCCCTAGCAGGGATGAGCTGACCAAGAACCAGGTGTCCCTGACATGCCTTGTGAAAGGCTTCTACCCCTCTGACATTGCTGTGGAATGGGAGAGCAAT
GGACAGCCTGAGAACAACTACAAGACCACCCCCCCTGTGCTGGACTCTGATGGCTCATTCTTCCTGTACAGCAAGCTGACAGTGGACAAGTCCAGATGGCAGCA
GGGCAATGTGTTCAGCTGCTCTGTGATGCATGAGGCCCTGCACAACCACTACACCCAGAAAAGCCTGTCCCTGTCCCCTGGCAAGTGAAGATCTACTTCTGGCTA
ATAAAAGATCAGAGCTCTAGTGATCTGTGTGTTGGTTTTTTGTGTCTGCATTCTAGCAAAACAAATGACATCATTCCTGATTATAATAATTTTAATTGTGCTTTACAAG
TAGAATTCTACTTGTAAAGAGAGTTTAATTTGAAAAACAAATTAGTCATTATTAAACATGTTAACAATTGTGTATAAAAATGACATCAGTTTAATGATGACATCATCTCT
TGATTATGTTTTACAAGTAGAATTCTACTTGTAAAGCTGGTTCAGTTTTGAAAAACAAATGACATCATCTCTTGATTATGTTTTACAAGTAGAATTCTACTTGTAAAAG
TGAGTTTAGTTTTAAAAAACAAATGACATCATTCAGTTTTGAAAAACAAATGACATCATCTCTTGATTGTGTTTTACAAGTAGAATTCTACTTGTAAAGTGAGTTCAGT
TTTGAAAAACAAATGACCCTCTCATACAATTGTTGAACAATTTTAATAAATAATCTTTACAAGATTTCTAGCTGTTACATAACTTATGGTAAATGGCCTGCCTGGCTGA
CTGCCCAATGACCCCTGCCCAATGATGTCAATAATGATGTATGTTCCCATGTAATGCCAATAGGGACTTTCCATTGATGTCAATGGGTGGAGTATTTATGGTAACTG
CCCACTTGGCAGTACATCAAGTGTATCATATGCCAAGTATGCCCCCTATTGATGTCAATGATGGTAAATGGCCTGCCTGGCATTATGCCCAGTACATGACCTTATG
GGACTTTCCTACTTGGCAGTACATCTATGTATTAGTCATTGCTATTACCATGGATTAGTGGAGAAGAGCATGCTTGAGGGCTGAGTGCCCCTCAGTGGGCAGAGA
GCACATGGCCCACAGTCCCTGAGAAGTTGGGGGGAGGGGTGGGCAATTGAACTGGTGCCTAGAGAAGGTGGGGCTTGGGTAAACTGGGAAAGTGATGTGGTGT
ACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGATGCA
CCTACTAGATATCTTGGTAAGTCACTGACTGTCTATGCCTGGGAAAGGGTGGGCAGGAGGTGGGGCAGTGCAGGAAAAGTGGCACTGTGAACCCTGCAGCCCTA
GACAATTGTACTAACCTTCTTCTCTTTCCTCTCCTGACAGGTTGGTAACCAAGCCACCATGGACTTCCAGGTGCAGATCATCAGCTTTCTGCTGATCTCTGCCTCTG
TGATCATGAGCAGAGGCCAGATTGTGCTGAGCCAGAGCCCTGCCATCCTGTCTGCAAGCCCTGGGGAGAAAGTGACCATGACCTGCAGAGCCAGCAGCTCTGTG
TCCTACATCCACTGGTTCCAGCAGAAGCCTGGCAGCAGCCCCAAGCCTTGGATCTATGCCACCAGCAACCTGGCATCTGGGGTGCCAGTCAGATTCTCTGGCTCT
GGATCTGGCACCAGCTACAGCCTGACCATCAGCAGAGTGGAAGCTGAGGATGCTGCCACCTACTACTGCCAGCAGTGGACCAGCAATCCCCCCACCTTTGGAGG
GGGCACCAAGCTGGAAATCAAGAGAACAGTGGCTGCCCCCTCTGTGTTCATCTTCCCACCCTCTGATGAGCAGCTGAAGTCTGGAACAGCCTCTGTTGTGTGCCT
GCTGAACAACTTCTACCCCAGAGAAGCCAAGGTGCAGTGGAAGGTGGACAATGCCCTGCAGTCTGGCAACTCCCAGGAATCTGTGACAGAGCAGGACAGCAAGG
ACTCCACCTACTCCCTGAGCAGCACCCTGACCCTGAGCAAGGCTGACTATGAGAAGCACAAAGTGTATGCCTGTGAAGTGACCCACCAGGGCCTGTCCAGCCCT
GTGACCAAGAGCTTCAACAGAGGGGAGAGCTGAAGATCTACTTCTGGCTAATAAAAGATCAGAGCTCTAGTGATCTGTGTGTTGGTTTTTTGTGTCTGCATTCTAG
CTCTAGTGATCAGCAGTTCAACCTGTTGATAGTATGTACTAAGCTCTCATGTTTAATGTACTAAGCTCTCATGTTTAATGAACTAAACCCTCATGGCTAATGTACTAA
GCTCTCATGGCTAATGTACTAAGCTCTCATGTTTCATGTACTAAGCTCTCATGTTTGAACAATAAAATTAATATAAATCAGCAACTTAAATAGCCTCTAAGGTTTTAAG
TTTTATAAGAAAAAAAAGAATATATAAGGCTTTTAAAGGTTTTAAGGTTTCCTAGGTTATCCTCATATGAGCTCTTAGAAAAACTCATCCAGCATCAAATGAAACTGCA
ATTTATTCATATCAGGATTATCAATACCATATTTTTGAAAAAGTCTTTTCTGTAATGAAGGAGAAAACTCACCCAGGCAGTTCCATAGGATGGCAAGATCCTGGTATC
TGTCTGCAATTCCAACTCTTCCAACATCAATACAACCTATTAATTTCCCCTCATCAAAAATAAGGTTATCAAGTGAGAAATCACCATGAGTGACCACTGAATCTGGTG
AGAATGGCAAAAGATTATGCATTTCTTTCCAGACTTGTTCAACAGGCCAGCCATTTCTCTCATCATCAAAATCACTGGCATCAACCAAACCATTATTCATTCTTGATT
GGGCCTGAGCCAGTCTAAATACTCTATCAGAGTTAAAAGGACAATTACAAACAGGAATGGAATGCAATCTTCTCAGGAACACTGCCAGGGCATCAACAATATTTTC
ACCTGAATCAGGATATTCTTCCAATACCTGGAATGCTGTTTTCCCTGGGATGGCAGTGGTGAGTAACCATGCATCATCAGGAGTTCTGATAAAATGCTTGATGGTT
GGAAGAGGCATAAATTCAGTCAGCCAGTTTAGTCTGACCATCTCATCTGTAACATCATTGGCAACAGAACCTTTGCCATGTTTCAGAAACAACTCTGGGGCATCTG
GCTTCCCATACAATCTATAGATTGTGGCACCTGATTGCCCAACATTATCTCTAGCCCATTTATACCCATATAAATCAGCATCCATGTTGGAATTTAATCTTGGCCTGG
AGCAAGAGGTTTCTCTTTGAATATGGCTCATACATGTGCACCTCCTATAGTGAGTTGTATTATACTATGCAGATATACTATGCCAATGTTTAATTGTCAG

FIG. 13

Anti-p65 Ribozyme: DraIIIRINhe-ΔmCMVΔEF1I126-BstEII-p65 Ribozyme-1-BglII-MixpA/BV2 (081016 # 2)

(SEQ ID NO:7)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCTT
TCCGTGAAACTGATGAGTCCGTGAGGACGAAACACCTCAGATCTACTTCTGGCTAATAAAAGATCAGAGCTCTAGTGATCTGTGTGTTGGTTTTTTGTGTCTGCATTCT
AGCTCTAGTGATCAGCAGTTCAACCTGTTGATAGTATGTACTAAGCTCTCATGTTTAATGTACTAAGCTCTCATGTTTAATGAACTAAACCCTCATGGCTAATGTACTAA
GCTCTCATGGCTAATGTACTAAGCTCTCATGTTTCATGTACTAAGCTCTCATGTTTGAACAATAAAATTAATATAAATCAGCAACTTAAATAGCCTCTAAGGTTTTAAGT
TTTATAAGAAAAAAAAGAATATATAAGGCTTTTAAAGGTTTTAAGGTTTCCTAGGTTATCCTCATATGAGCTCTTAGAAAAACTCATCCAGCATCAAATGAAACTGCAA
TTTATTCATATCAGGATTATCAATACCATATTTTTGAAAAAGTCTTTTCTGTAATGAAGGAGAAAACTCACCCAGGCAGTTCCATAGGATGGCAAGATCCTGGTATCTG
TCTGCAATTCCAACTCTTCCAACATCAATACAACCTATTAATTTCCCCTCATCAAAAATAAGGTTATCAAGTGAGAAATCACCATGAGTGACCACTGAATCTGGTGAGA
ATGGCAAAAGATTATGCATTTCTTTCCAGACTTGTTCAACAGGCCAGCCATTTCTCTCATCATCAAAATCACTGGCATCAACCAAACCATTATTCATTCTTGATTGGGCC
TGAGCCAGTCTAAATACTCTATCAGAGTTAAAAGGACAATTACAAACAGGAATGGAATGCAATCTTCTCAGGAACACTGCCAGGGCATCAACAATATTTTCACCTGAA
TCAGGATATTCTTCCAATACCTGGAATGCTGTTTTCCCTGGGATGGCAGTGGTGAGTAACCATGCATCATCAGGAGTTCTGATAAAATGCTTGATGGTTGGAAGAGGC
ATAAATTCAGTCAGCCAGTTTAGTCTGACCATCTCATCTGTAACATCATTGGCAACAGAACCTTTGCCATGTTTCAGAAACAACTCTGGGGCATCTGGCTTCCCATACA
ATCTATAGATTGTGGCACCTGATTGCCCAACATTATCTCTAGCCCATTTATACCCATATAAATCAGCATCCATGTTGGAATTTAATCTTGGCCTGGAGCAAGAGGTTTCT
CTTTGAATATGGCTCATACATGTGCACCTCCTATAGTGAGTTGTATTATACTATGCAGATATACTATGCCAATGTTTAATTGTCAG

FIG. 14

Anti-p65 CRISPR1 : Genscript px458-relA1 (SEQ ID NO:8)

GAGGGCCTATTTCCCATGATTCCTTCATATTTGCATATACGATACAAGGCTGTTAGAGAGATAATTGGAATTAATTTGACTGTAAACACAAAGATATTAGTACAAAATACGTGACGTAGAAAG
TAATAATTTCTTGGGTAGTTTGCAGTTTTAAAATTATGTTTTAAAATGGACTATCATATGCTTACCGTAACTTGAAAGTATTTCGATTTCTTGGCTTTATATATCTTGTGGAAAGGACGAAACAC
CGCGATTCCGCTATAAATGCGGTTTTAGAGCTAGAAATAGCAAGTTAAAATAAGGCTAGTCCGTTATCAACTTGAAAAAGTGGCACCGAGTCGGTGCTTTTTTGTTTTAGAGCTAGAAATAG
CAAGTTAAAATAAGGCTAGTCCGTTTTTAGCGCGTGCGCCAATTCTGCAGACAAATGGCTCTAGAGGTACCCGTTACATAACTTACGGTAAATGGCCCGCCTGGCTGACCGCCCAACGAC
CCCCGCCCATTGACGTCAATAGTAACGCCAATAGGGACTTTCCATTGACGTCAATGGGTGGAGTATTTACGGTAAACTGCCCACTTGGCAGTACATCAAGTGTATCATATGCCAAGTACGC
CCCCTATTGACGTCAATGACGGTAAATGGCCCGCCTGGCATTGTGCCCAGTACATGACCTTATGGGACTTTCCTACTTGGCAGTACATCTACGTATTAGTCATCGCTATTACCATGGTCGA
GGTGAGCCCCACGTTCTGCTTCACTCTCCCCATCTCCCCCCCCTCCCCACCCCCAATTTTGTATTTATTTATTTTTTAATTATTTTGTGCAGCGATGGGGGCGGGGGGGGGGGGGGGGCG
CGCGCCAGGCGGGGCGGGGCGGGGCGAGGGGCGGGGCGGGGCGAGGCGGAGAGGTGCGGCGGCAGCCAATCAGAGCGGCGCGCTCCGAAAGTTTCCTTTTATGGCGAGGCGGCG
GCGGCGGCGGCCCTATAAAAAGCGAAGCGCGCGGCGGGCGGGAGTCGCTGCGCGCTGCCTTCGCCCCGTGCCCCGCTCCGCCGCCGCCTCGCGCCGCCCGCCCCGGCTCTGACTGA
CCGCGTTACTCCCACAGGTGAGCGGGCGGGACGGCCCTTCTCCTCCGGGCTGTAATTAGCTGAGCAAGAGGTAAGGGTTTAAGGGATGGTTGGTTGGTGGGGTATTAATGTTTAATTAC
CTGGAGCACCTGCCTGAAATCACTTTTTTTCAGGTTGGACCGGTGCCACCATGGACTATAAGGACCACGACGGAGACTACAAGGATCATGATATTGATTACAAAGACGATGACGATAAGAT
GGCCCCAAAGAAGAAGCGGAAGGTCGGTATCCACGGAGTCCCAGCAGCCGACAAGAAGTACAGCATCGGCCTGGACATCGGCACCAACTCTGTGGGCTGGGCCGTGATCACCGACGA
GTACAAGGTGCCCAGCAAGAAATTCAAGGTGCTGGGCAACACCGACCGGCACAGCATCAAGAAGAACCTGATCGGAGCCCTGCTGTTCGACAGCGGCGAAACAGCCGAGGCCACCCGG
CTGAAGAGAACCGCCAGAAGAAGATACACCAGACGGAAGAACCGGATCTGCTATCTGCAAGAGATCTTCAGCAACGAGATGGCCAAGGTGGACGACAGCTTCTTCCACAGACTGGAAGA
GTCCTTCCTGGTGGAAGAGGATAAGAAGCACGAGCGGCACCCCATCTTCGGCAACATCGTGGACGAGGTGGCCTACCACGAGAAGTACCCCACCATCTACCACCTGAGAAAGAAACTGG
TGGACAGCACCGACAAGGCCGACCTGCGGCTGATCTATCTGGCCCTGGCCCACATGATCAAGTTCCGGGGCCACTTCCTGATCGAGGGCGACCTGAACCCCGACAACAGCGACGTGGA
CAAGCTGTTCATCCAGCTGGTGCAGACCTACAACCAGCTGTTCGAGGAAAACCCCATCAACGCCAGCGGCGTGGACGCCAAGGCCATCCTGTCTGCCAGACTGAGCAAGAGCAGACGG
CTGGAAAATCTGATCGCCCAGCTGCCCGGCGAGAAGAAGAATGGCCTGTTCGGAAACCTGATTGCCCTGAGCCTGGGCCTGACCCCCAACTTCAAGAGCAACTTCGACCTGGCCGAGGA
TGCCAAACTGCAGCTGAGCAAGGACACCTACGACGACGACCTGGACAACCTGCTGGCCCAGATCGGCGACCAGTACGCCGACCTGTTTCTGGCCGCCAAGAACCTGTCCGACGCCATC
CTGCTGAGCGACATCCTGAGAGTGAACACCGAGATCACCAAGGCCCCCCTGAGCGCCTCTATGATCAAGAGATACGACGAGCACCACCAGGACCTGACCCTGCTGAAAGCTCTCGTGCG
GCAGCAGCTGCCTGAGAAGTACAAAGAGATTTTCTTCGACCAGAGCAAGAACGGCTACGCCGGCTACATTGACGGCGGAGCCAGCCAGGAAGAGTTCTACAAGTTCATCAAGCCCATCC
TGGAAAAGATGGACGGCACCGAGGAACTGCTCGTGAAGCTGAACAGAGAGGACCTGCTGCGGAAGCAGCGGACCTTCGACAACGGCAGCATCCCCCACCAGATCCACCTGGGAGAGCT
GCACGCCATTCTGCGGCGGCAGGAAGATTTTTACCCATTCCTGAAGGACAACCGGGAAAAGATCGAGAAGATCCTGACCTTCCGCATCCCCTACTACGTGGGCCCTCTGGCCAGGGGAA
ACAGCAGATTCGCCTGGATGACCAGAAAGAGCGAGGAAACCATCACCCCCTGGAACTTCGAGGAAGTGGTGGACAAGGGCGCTTCCGCCCAGAGCTTCATCGAGCGGATGACCAACTTC
GATAAGAACCTGCCCAACGAGAAGGTGCTGCCCAAGCACAGCCTGCTGTACGAGTACTTCACCGTGTATAACGAGCTGACCAAAGTGAAATACGTGACCGAGGGAATGAGAAAGCCCGC
CTTCCTGAGCGGCGAGCAGAAAAAGGCCATCGTGGACCTGCTGTTCAAGACCAACCGGAAAGTGACCGTGAAGCAGCTGAAAGAGGACTACTTCAAGAAAATCGAGTGCTTCGACTCCG
TGGAAATCTCCGGCGTGGAAGATCGGTTCAACGCCTCCCTGGGCACATACCACGATCTGCTGAAAATTATCAAGGACAAGGACTTCCTGGACAATGAGGAAAACGAGGACATTCTGGAAG
ATATCGTGCTGACCCTGACACTGTTTGAGGACAGAGAGATGATCGAGGAACGGCTGAAAACCTATGCCCACCTGTTCGACGACAAAGTGATGAAGCAGCTGAAGCGGCGGAGATACACC
GGCTGGGGCAGGCTGAGCCGGAAGCTGATCAACGGCATCCGGGACAAGCAGTCCGGCAAGACAATCCTGGATTTCCTGAAGTCCGACGGCTTCGCCAACAGAAACTTCATGCAGCTGA
TCCACGACGACAGCCTGACCTTTAAAGAGGACATCCAGAAAGCCCAGGTGTCCGGCCAGGGCGATAGCCTGCACGAGCACATTGCCAATCTGGCCGGCAGCCCCGCCATTAAGAAGGG
CATCCTGCAGACAGTGAAGGTGGTGGACGAGCTCGTGAAAGTGATGGGCCGGCACAAGCCCGAGAACATCGTGATCGAAATGGCCAGAGAGAACCAGACCACCCAGAAGGGACAGAAG
AACAGCCGCGAGAGAATGAAGCGGATCGAAGAGGGCATCAAAGAGCTGGGCAGCCAGATCCTGAAAGAACACCCCGTGGAAAACACCCAGCTGCAGAACGAGAAGCTGTACCTGTACT
ACCTGCAGAATGGGCGGGATATGTACGTGGACCAGGAACTGGACATCAACCGGCTGTCCGACTACGATGTGGACCATATCGTGCCTCAGAGCTTTCTGAAGGACGACTCCATCGACAAC
AAGGTGCTGACCAGAAGCGACAAGAACCGGGGCAAGAGCGACAACGTGCCCTCCGAAGAGGTCGTGAAGAAGATGAAGAACTACTGGCGGCAGCTGCTGAACGCCAAGCTGATTACCC
AGAGAAAGTTCGACAATCTGACCAAGGCCGAGAGAGGCGGCCTGAGCGAACTGGATAAGGCCGGCTTCATCAAGAGACAGCTGGTGGAAACCCGGCAGATCACAAAGCACGTGGCACA
GATCCTGGACTCCCGGATGAACACTAAGTACGACGAGAATGACAAGCTGATCCGGGAAGTGAAAGTGATCACCCTGAAGTCCAAGCTGGTGTCCGATTTCCGGAAGGATTTCCAGTTTTA
CAAAGTGCGCGAGATCAACAACTACCACCACGCCCACGACGCCTACCTGAACGCCGTCGTGGGAACCGCCCTGATCAAAAAGTACCCTAAGCTGGAAAGCGAGTTCGTGTACGGCGACT
ACAAGGTGTACGACGTGCGGAAGATGATCGCCAAGAGCGAGCAGGAAATCGGCAAGGCTACCGCCAAGTACTTCTTCTACAGCAACATCATGAACTTTTTCAAGACCGAGATTACCCTGG
CCAACGGCGAGATCCGGAAGCGGCCTCTGATCGAGACAAACGGCGAAACCGGGGAGATCGTGTGGGATAAGGGCCGGGATTTTGCCACCGTGCGGAAAGTGCTGAGCATGCCCCAAG
TGAATATCGTGAAAAAGACCGAGGTGCAGACAGGCGGCTTCAGCAAAGAGTCTATCCTGCCCAAGAGGAACAGCGATAAGCTGATCGCCAGAAAGAAGGACTGGGACCCTAAGAAGTAC
GGCGGCTTCGACAGCCCCACCGTGGCCTATTCTGTGCTGGTGGTGGCCAAAGTGGAAAAGGGCAAGTCCAAGAAACTGAAGAGTGTGAAAGAGCTGCTGGGGATCACCATCATGGAAA
GAAGCAGCTTCGAGAAGAATCCCATCGACTTTCTGGAAGCCAAGGGCTACAAAGAAGTGAAAAAGGACCTGATCATCAAGCTGCCTAAGTACTCCCTGTTCGAGCTGGAAAACGGCCGGA
AGAGAATGCTGGCCTCTGCCGGCGAACTGCAGAAGGGAAACGAACTGGCCCTGCCCTCCAAATATGTGAACTTCCTGTACCTGGCCAGCCACTATGAGAAGCTGAAGGGCTCCCCCGAG
GATAATGAGCAGAAACAGCTGTTTGTGGAACAGCACAAGCACTACCTGGACGAGATCATCGAGCAGATCAGCGAGTTCTCCAAGAGAGTGATCCTGGCCGACGCTAATCTGGACAAAGTG
CTGTCCGCCTACAACAAGCACCGGGATAAGCCCATCAGAGAGCAGGCCGAGAATATCATCCACCTGTTTACCCTGACCAATCTGGGAGCCCCTGCCGCCTTCAAGTACTTTGACACCACC
ATCGACCGGAAGAGGTACACCAGCACCAAAGAGGTGCTGGACGCCACCCTGATCCACCAGAGCATCACCGGCCTGTACGAGACACGGATCGACCTGTCTCAGCTGGGAGGCGACAAAA
GGCCGGCGGCCACGAAAAAGGCCGGCCAGGCAAAAAAGAAAAAGGAATTCGGCAGTGGAGAGGGCAGAGGAAGTCTGCTAACATGCGGTGACGTCGAGGAGAATCCTGGCCCAGTGA
GCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATGCCACCTACGGC
AAGCTGACCCTGAAGTTCATCTGCACCACCGGCAAGCTGCCCGTGCCCTGGCCCACCCTCGTGACCACCCTGACCTACGGCGTGCAGTGCTTCAGCCGCTACCCCGACCACATGAAGCA
GCACGACTTCTTCAAGTCCGCCATGCCCGAAGGCTACGTCCAGGAGCGCACCATCTTCTTCAAGGACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTGGGGCACAAGCTGGAGTACAACTACAACAGCCACAACGTCTATATCATGGCCGACAAGCAGAAGAA
CGGCATCAAGGTGAACTTCAAGATCCGCCACAACATCGAGGACGGCAGCGTGCAGCTCGCCGACCACTACCAGCAGAACACCCCCATCGGCGACGGCCCCGTGCTGCTGCCCGACAAC
CACTACCTGAGCACCCAGTCCGCCCTGAGCAAAGACCCCAACGAGAAGCGCGATCACATGGTCCTGCTGGAGTTCGTGACCGCCGCCGGGATCACTCTCGGCATGGACGAGCTGTACA
AGGAATTCTAACTAGAGCTCGCTGATCAGCCTCGACTGTGCCTTCTAGTTGCCAGCCATCTGTTGTTTGCCCCTCCCCCGTGCCTTCCTTGACCCTGGAAGGTGCCACTCCCACTGTCCTT
TCCTAATAAAATGAGGAAATTGCATCGCATTGTCTGAGTAGGTGTCATTCTATTCTGGGGGGTGGGGTGGGGCAGGACAGCAAGGGGGAGGATTGGGAAGACAATAGCAGGCATGCTGG
GGAGCGGCCGCAGGAACCCCTAGTGATGGAGTTGGCCACTCCCTCTCTGCGCGCTCGCTCGCTCACTGAGGCCGGGCGACCAAAGGTCGCCCGACGCCCGGGCTTTGCCCGGGCGG
CCTCAGTGAGCGAGCGAGCGCGCAGCTGCCTGCAGGGGCGCCTGATGCGGTATTTTCTCCTTACGCATCTGTGCGGTATTTCACACCGCATACGTCAAAGCAACCATAGTACGCGCCCT
GTAGCGGCGCATTAAGCGCGGCGGGTGTGGTGGTTACGCGCAGCGTGACCGCTACACTTGCCAGCGCCTTAGCGCCCGCTCCTTTCGCTTTCTTCCCTTCCTTTCTCGCCACGTTCGCC
GGCTTTCCCCGTCAAGCTCTAAATCGGGGGCTCCCTTTAGGGTTCCGATTTAGTGCTTTACGGCACCTCGACCCCAAAAAACTTGATTTGGGTGATGGTTCACGTAGTGGGCCATCGCCC
TGATAGACGGTTTTTCGCCCTTTGACGTTGGAGTCCACGTTCTTTAATAGTGGACTCTTGTTCCAAACTGGAACAACACTCAACTCTATCTCGGGCTATTCTTTTGATTTATAAGGGATTTTG
CCGATTTCGGTCTATTGGTTAAAAAATGAGCTGATTTAACAAAAATTTAACGCGAATTTTAACAAAATATTAACGTTTACAATTTTATGGTGCACTCTCAGTACAATCTGCTCTGATGCCGCAT
AGTTAAGCCAGCCCCGACACCCGCCAACACCCGCTGACGCGCCCTGACGGGCTTGTCTGCTCCCGGCATCCGCTTACAGACAAGCTGTGACCGTCTCcgggagctgcatgtgtcagaggttttcaccgtc
atcaccgaaacgcgcgagACGAAAGGGCCTCGTGATACGCCTATTTTTATAGGTTAATGTCATGATAATAATGGTTTCTTAGACGTCAGGTGGCACTTTTCGGGGAAATGTGCGCGGAACCCCTAT
TTGTTTATTTTTCTAAATACATTCAAATATGTATCCGCTCATGAGACAATAACCCTGATAAATGCTTCAATAATATTGAAAAAGGAAGAGTATGAGTATTCAACATTTCCGTGTCGCCCTTATTC
CCTTTTTTGCGGCATTTTGCCTTCCTGTTTTTGCTCACCCAGAAACGCTGGTGAAAGTAAAAGATGCTGAAGATCAGTTGGGTGCACGAGTGGGTTACATCGAACTGGATCTCAACAGCGG
TAAGATCCTTGAGAGTTTTCGCCCCGAAGAACGTTTTCCAATGATGAGCACTTTTAAAGTTCTGCTATGTGGCGCGGTATTATCCCGTATTGACGCCGGGCAAGAGCAACTCGGTCGCCGC
ATACACTATTCTCAGAATGACTTGGTTGAGTACTCACCAGTCACAGAAAAGCATCTTACGGATGGCATGACAGTAAGAGAATTATGCAGTGCTGCCATAACCATGAGTGATAACACTGCGG
CCAACTTACTTCTGACAACGATCGGAGGACCGAAGGAGCTAACCGCTTTTTTGCACAACATGGGGGATCATGTAACTCGCCTTGATCGTTGGGAACCGGAGCTGAATGAAGCCATACCAA
ACGACGAGCGTGACACCACGATGCCTGTAGCAATGGCAACAACGTTGCGCAAACTATTAACTGGCGAACTACTTACTCTAGCTTCCCGGCAACAATTAATAGACTGGATGGAGGCGGATA
AAGTTGCAGGACCACTTCTGCGCTCGGCCCTTCCGGCTGGCTGGTTTATTGCTGATAAATCTGGAGCCGGTGAGCGTGGAAGCCGCGGTATCATTGCAGCACTGGGGCCAGATGGTAAG
CCCTCCCGTATCGTAGTTATCTACACGACGGGGAGTCAGGCAACTATGGATGAACGAAATAGACAGATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAGGTGAAGATCCTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGTGTAGCCGTAGTTAGGCCACCACTTCAAGAACTCTGTAGCACCGCCTACATACCTCGC
TCTGCTAATCCTGTTACCAGTGGCTGCTGCCAGTGGCGATAAGTCGTGTCTTACCGGGTTGGACTCAAGACGATAGTTACCGGATAAGGCGCAGCGGTCGGGCTGAACGGGGGGTTCGT
GCACACAGCCCAGCTTGGAGCGAACGACCTACACCGAACTGAGATACCTACAGCGTGAGCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTATAGTCCTGTCGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTCCTGGCCTTTTGCTGGCCTTTTGCTCACATGT

FIG. 15

Anti-p65 CRISPR2 : Genscript px458-relA4 (SEQ ID NO:9)

GAGGGCCTATTTCCCATGATTCCTTCATATTTGCATATACGATACAAGGCTGTTAGAGAGATAATTGGAATTAATTTGACTGTAAACACAAAGATATTAGTACAAAATACGTGACGTAGAAAG
TAATAATTTCTTGGGTAGTTTGCAGTTTTAAAATTATGTTTTAAAATGGACTATCATATGCTTACCGTAACTTGAAAGTATTTCGATTTCTTGGCTTTATATATCTTGTGGAAAGGACGAAACAC
CCTGCCGGGATGGCTACTATGGTTTTAGAGCTAGAAATAGCAAGTTAAAATAAGGCTAGTCCGTTATCAACTTGAAAAAGTGGCACCGAGTCGGTGCTTTTTTGTTTTAGAGCTAGAAATAG
CAAGTTAAAATAAGGCTAGTCCGTTTTTAGCGCGTGCGCCAATTCTGCAGACAAATGGCTCTAGAGGTACCCGTTACATAACTTACGGTAAATGGCCCGCCTGGCTGACCGCCCAACGAC
CCCCGCCCATTGACGTCAATAGTAACGCCAATAGGGACTTTCCATTGACGTCAATGGGTGGAGTATTTACGGTAAACTGCCCACTTGGCAGTACATCAAGTGTATCATATGCCAAGTACGC
CCCCTATTGACGTCAATGACGGTAAATGGCCCGCCTGGCATTGTGCCCAGTACATGACCTTATGGGACTTTCCTACTTGGCAGTACATCTACGTATTAGTCATCGCTATTACCATGGTCGA
GGTGAGCCCCACGTTCTGCTTCACTCTCCCCATCTCCCCCCCCTCCCCACCCCCAATTTTGTATTTATTTATTTTTTAATTATTTTGTGCAGCGATGGGGGCGGGGGGGGGGGGGGGGCG
CGCGCCAGGCGGGGCGGGGCGGGGCGAGGGGCGGGGCGGGGCGAGGCGGAGAGGTGCGGCGGCAGCCAATCAGAGCGGCGCGCTCCGAAAGTTTCCTTTTATGGCGAGGCGGCG
GCGGCGGCGGCCCTATAAAAAGCGAAGCGCGCGGCGGGCGGGAGTCGCTGCGCGCTGCCTTCGCCCCGTGCCCCGCTCCGCCGCCGCCTCGCGCCGCCCGCCCCGGCTCTGACTGA
CCGCGTTACTCCCACAGGTGAGCGGGCGGGACGGCCCTTCTCCTCCGGGCTGTAATTAGCTGAGCAAGAGGTAAGGGTTTAAGGGATGGTTGGTTGGTGGGGTATTAATGTTTAATTAC
CTGGAGCACCTGCCTGAAATCACTTTTTTTCAGGTTGGACCGGTGCCACCATGGACTATAAGGACCACGACGGAGACTACAAGGATCATGATATTGATTACAAAGACGATGACGATAAGAT
GGCCCCAAAGAAGAAGCGGAAGGTCGGTATCCACGGAGTCCCAGCAGCCGACAAGAAGTACAGCATCGGCCTGGACATCGGCACCAACTCTGTGGGCTGGGCCGTGATCACCGACGA
GTACAAGGTGCCCAGCAAGAAATTCAAGGTGCTGGGCAACACCGACCGGCACAGCATCAAGAAGAACCTGATCGGAGCCCTGCTGTTCGACAGCGGCGAAACAGCCGAGGCCACCCGG
CTGAAGAGAACCGCCAGAAGAAGATACACCAGACGGAAGAACCGGATCTGCTATCTGCAAGAGATCTTCAGCAACGAGATGGCCAAGGTGGACGACAGCTTCTTCCACAGACTGGAAGA
GTCCTTCCTGGTGGAAGAGGATAAGAAGCACGAGCGGCACCCCATCTTCGGCAACATCGTGGACGAGGTGGCCTACCACGAGAAGTACCCCACCATCTACCACCTGAGAAAGAAACTGG
TGGACAGCACCGACAAGGCCGACCTGCGGCTGATCTATCTGGCCCTGGCCCACATGATCAAGTTCCGGGGCCACTTCCTGATCGAGGGCGACCTGAACCCCGACAACAGCGACGTGGA
CAAGCTGTTCATCCAGCTGGTGCAGACCTACAACCAGCTGTTCGAGGAAAACCCCATCAACGCCAGCGGCGTGGACGCCAAGGCCATCCTGTCTGCCAGACTGAGCAAGAGCAGACGG
CTGGAAAATCTGATCGCCCAGCTGCCCGGCGAGAAGAAGAATGGCCTGTTCGGAAACCTGATTGCCCTGAGCCTGGGCCTGACCCCCAACTTCAAGAGCAACTTCGACCTGGCCGAGGA
TGCCAAACTGCAGCTGAGCAAGGACACCTACGACGACGACCTGGACAACCTGCTGGCCCAGATCGGCGACCAGTACGCCGACCTGTTTCTGGCCGCCAAGAACCTGTCCGACGCCATC
CTGCTGAGCGACATCCTGAGAGTGAACACCGAGATCACCAAGGCCCCCCTGAGCGCCTCTATGATCAAGAGATACGACGAGCACCACCAGGACCTGACCCTGCTGAAAGCTCTCGTGCG
GCAGCAGCTGCCTGAGAAGTACAAAGAGATTTTCTTCGACCAGAGCAAGAACGGCTACGCCGGCTACATTGACGGCGGAGCCAGCCAGGAAGAGTTCTACAAGTTCATCAAGCCCATCC
TGGAAAAGATGGACGGCACCGAGGAACTGCTCGTGAAGCTGAACAGAGAGGACCTGCTGCGGAAGCAGCGGACCTTCGACAACGGCAGCATCCCCCACCAGATCCACCTGGGAGAGCT
GCACGCCATTCTGCGGCGGCAGGAAGATTTTTACCCATTCCTGAAGGACAACCGGGAAAAGATCGAGAAGATCCTGACCTTCCGCATCCCCTACTACGTGGGCCCTCTGGCCAGGGGAA
ACAGCAGATTCGCCTGGATGACCAGAAAGAGCGAGGAAACCATCACCCCCTGGAACTTCGAGGAAGTGGTGGACAAGGGCGCTTCCGCCCAGAGCTTCATCGAGCGGATGACCAACTTC
GATAAGAACCTGCCCAACGAGAAGGTGCTGCCCAAGCACAGCCTGCTGTACGAGTACTTCACCGTGTATAACGAGCTGACCAAAGTGAAATACGTGACCGAGGGAATGAGAAAGCCCGC
CTTCCTGAGCGGCGAGCAGAAAAAGGCCATCGTGGACCTGCTGTTCAAGACCAACCGGAAAGTGACCGTGAAGCAGCTGAAAGAGGACTACTTCAAGAAAATCGAGTGCTTCGACTCCG
TGGAAATCTCCGGCGTGGAAGATCGGTTCAACGCCTCCCTGGGCACATACCACGATCTGCTGAAAATTATCAAGGACAAGGACTTCCTGGACAATGAGGAAAACGAGGACATTCTGGAAG
ATATCGTGCTGACCCTGACACTGTTTGAGGACAGAGAGATGATCGAGGAACGGCTGAAAACCTATGCCCACCTGTTCGACGACAAAGTGATGAAGCAGCTGAAGCGGCGGAGATACACC
GGCTGGGGCAGGCTGAGCCGGAAGCTGATCAACGGCATCCGGGACAAGCAGTCCGGCAAGACAATCCTGGATTTCCTGAAGTCCGACGGCTTCGCCAACAGAAACTTCATGCAGCTGA
TCCACGACGACAGCCTGACCTTTAAAGAGGACATCCAGAAAGCCCAGGTGTCCGGCCAGGGCGATAGCCTGCACGAGCACATTGCCAATCTGGCCGGCAGCCCCGCCATTAAGAAGGG
CATCCTGCAGACAGTGAAGGTGGTGGACGAGCTCGTGAAAGTGATGGGCCGGCACAAGCCCGAGAACATCGTGATCGAAATGGCCAGAGAGAACCAGACCACCCAGAAGGGACAGAAG
AACAGCCGCGAGAGAATGAAGCGGATCGAAGAGGGCATCAAAGAGCTGGGCAGCCAGATCCTGAAAGAACACCCCGTGGAAAACACCCAGCTGCAGAACGAGAAGCTGTACCTGTACT
ACCTGCAGAATGGGCGGGATATGTACGTGGACCAGGAACTGGACATCAACCGGCTGTCCGACTACGATGTGGACCATATCGTGCCTCAGAGCTTTCTGAAGGACGACTCCATCGACAAC
AAGGTGCTGACCAGAAGCGACAAGAACCGGGGCAAGAGCGACAACGTGCCCTCCGAAGAGGTCGTGAAGAAGATGAAGAACTACTGGCGGCAGCTGCTGAACGCCAAGCTGATTACCC
AGAGAAAGTTCGACAATCTGACCAAGGCCGAGAGAGGCGGCCTGAGCGAACTGGATAAGGCCGGCTTCATCAAGAGACAGCTGGTGGAAACCCGGCAGATCACAAAGCACGTGGCACA
GATCCTGGACTCCCGGATGAACACTAAGTACGACGAGAATGACAAGCTGATCCGGGAAGTGAAAGTGATCACCCTGAAGTCCAAGCTGGTGTCCGATTTCCGGAAGGATTTCCAGTTTTA
CAAAGTGCGCGAGATCAACAACTACCACCACGCCCACGACGCCTACCTGAACGCCGTCGTGGGAACCGCCCTGATCAAAAAGTACCCTAAGCTGGAAAGCGAGTTCGTGTACGGCGACT
ACAAGGTGTACGACGTGCGGAAGATGATCGCCAAGAGCGAGCAGGAAATCGGCAAGGCTACCGCCAAGTACTTCTTCTACAGCAACATCATGAACTTTTTCAAGACCGAGATTACCCTGG
CCAACGGCGAGATCCGGAAGCGGCCTCTGATCGAGACAAACGGCGAAACCGGGGAGATCGTGTGGGATAAGGGCCGGGATTTTGCCACCGTGCGGAAAGTGCTGAGCATGCCCCAAG
TGAATATCGTGAAAAAGACCGAGGTGCAGACAGGCGGCTTCAGCAAAGAGTCTATCCTGCCCAAGAGGAACAGCGATAAGCTGATCGCCAGAAAGAAGGACTGGGACCCTAAGAAGTAC
GGCGGCTTCGACAGCCCCACCGTGGCCTATTCTGTGCTGGTGGTGGCCAAAGTGGAAAAGGGCAAGTCCAAGAAACTGAAGAGTGTGAAAGAGCTGCTGGGGATCACCATCATGGAAA
GAAGCAGCTTCGAGAAGAATCCCATCGACTTTCTGGAAGCCAAGGGCTACAAAGAAGTGAAAAAGGACCTGATCATCAAGCTGCCTAAGTACTCCCTGTTCGAGCTGGAAAACGGCCGGA
AGAGAATGCTGGCCTCTGCCGGCGAACTGCAGAAGGGAAACGAACTGGCCCTGCCCTCCAAATATGTGAACTTCCTGTACCTGGCCAGCCACTATGAGAAGCTGAAGGGCTCCCCCGAG
GATAATGAGCAGAAACAGCTGTTTGTGGAACAGCACAAGCACTACCTGGACGAGATCATCGAGCAGATCAGCGAGTTCTCCAAGAGAGTGATCCTGGCCGACGCTAATCTGGACAAAGTG
CTGTCCGCCTACAACAAGCACCGGGATAAGCCCATCAGAGAGCAGGCCGAGAATATCATCCACCTGTTTACCCTGACCAATCTGGGAGCCCCTGCCGCCTTCAAGTACTTTGACACCACC
ATCGACCGGAAGAGGTACACCAGCACCAAAGAGGTGCTGGACGCCACCCTGATCCACCAGAGCATCACCGGCCTGTACGAGACACGGATCGACCTGTCTCAGCTGGGAGGCGACAAAA
GGCCGGCGGCCACGAAAAAGGCCGGCCAGGCAAAAAAGAAAAAGGAATTCGGCAGTGGAGAGGGCAGAGGAAGTCTGCTAACATGCGGTGACGTCGAGGAGAATCCTGGCCCAGTGA
GCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATGCCACCTACGGC
AAGCTGACCCTGAAGTTCATCTGCACCACCGGCAAGCTGCCCGTGCCCTGGCCCACCCTCGTGACCACCCTGACCTACGGCGTGCAGTGCTTCAGCCGCTACCCCGACCACATGAAGCA
GCACGACTTCTTCAAGTCCGCCATGCCCGAAGGCTACGTCCAGGAGCGCACCATCTTCTTCAAGGACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTGGGGCACAAGCTGGAGTACAACTACAACAGCCACAACGTCTATATCATGGCCGACAAGCAGAAGAA
CGGCATCAAGGTGAACTTCAAGATCCGCCACAACATCGAGGACGGCAGCGTGCAGCTCGCCGACCACTACCAGCAGAACACCCCCATCGGCGACGGCCCCGTGCTGCTGCCCGACAAC
CACTACCTGAGCACCCAGTCCGCCCTGAGCAAAGACCCCAACGAGAAGCGCGATCACATGGTCCTGCTGGAGTTCGTGACCGCCGCCGGGATCACTCTCGGCATGGACGAGCTGTACA
AGGAATTCTAACTAGAGCTCGCTGATCAGCCTCGACTGTGCCTTCTAGTTGCCAGCCATCTGTTGTTTGCCCCTCCCCCGTGCCTTCCTTGACCCTGGAAGGTGCCACTCCCACTGTCCTT
TCCTAATAAAATGAGGAAATTGCATCGCATTGTCTGAGTAGGTGTCATTCTATTCTGGGGGGTGGGGTGGGGCAGGACAGCAAGGGGGAGGATTGGGAAGAGAATAGCAGGCATGCTGG
GGAGCGGCCGCAGGAACCCCTAGTGATGGAGTTGGCCACTCCCTCTCTGCGCGCTCGCTCGCTCACTGAGGCCGGGCGACCAAAGGTCGCCCGACGCCCGGGCTTTGCCCGGGCGG
CCTCAGTGAGCGAGCGAGCGCGCAGCTGCCTGCAGGGGCGCCTGATGCGGTATTTTCTCCTTACGCATCTGTGCGGTATTTCACACCGCATACGTCAAAGCAACCATAGTACGCGCCCT
GTAGCGGCGCATTAAGCGCGGCGGGTGTGGTGGTTACGCGCAGCGTGACCGCTACACTTGCCAGCGCCTTAGCGCCCGCTCCTTTCGCTTTCTTCCCTTCCTTTCTCGCCACGTTCGCC
GGCTTTCCCCGTCAAGCTCTAAATCGGGGGCTCCCTTTAGGGTTCCGATTTAGTGCTTTACGGCACCTCGACCCCAAAAAACTTGATTTGGGTGATGGTTCACGTAGTGGGCCATCGCCC
TGATAGACGGTTTTTCGCCCTTTGACGTTGGAGTCCACGTTCTTTAATAGTGGACTCTTGTTCCAAACTGGAACAACACTCAACTCTATCTCGGGCTATTCTTTTGATTTATAAGGGATTTTG
CCGATTTCGGTCTATTGGTTAAAAAATGAGCTGATTTAACAAAAATTTAACGCGAATTTTAACAAAATATTAACGTTTACAATTTTATGGTGCACTCTCAGTACAATCTGCTCTGATGCCGCAT
AGTTAAGCCAGCCCCGACACCCGCCAACACCCGCTGACGCGCCCTGACGGGCTTGTCTGCTCCCGGCATCCGCTTACAGACAAGCTGTGACCGTCTccgggagctgcatgtgtcagaggttttcaccgtc
atcaccgaaacgcgcgagACGAAAGGGCCTCGTGATACGCCTATTTTTATAGGTTAATGTCATGATAATAATGGTTTCTTAGACGTCAGGTGGCACTTTTCGGGGAAATGTGCGCGGAACCCCTAT
TTGTTTATTTTTCTAAATACATTCAAATATGTATCCGCTCATGAGACAATAACCCTGATAAATGCTTCAATAATATTGAAAAAGGAAGAGTATGAGTATTCAACATTTCCGTGTCGCCCTTATTC
CCTTTTTTGCGGCATTTTGCCTTCCTGTTTTTGCTCACCCAGAAACGCTGGTGAAAGTAAAAGATGCTGAAGATCAGTTGGGTGCACGAGTGGGTTACATCGAACTGGATCTCAACAGCGG
TAAGATCCTTGAGAGTTTTCGCCCCGAAGAACGTTTTCCAATGATGAGCACTTTTAAAGTTCTGCTATGTGGCGCGGTATTATCCCGTATTGACGCCGGGCAAGAGCAACTCGGTCGCCGC
ATACACTATTCTCAGAATGACTTGGTTGAGTACTCACCAGTCACAGAAAAGCATCTTACGGATGGCATGACAGTAAGAGAATTATGCAGTGCTGCCATAACCATGAGTGATAACACTGCGG
CCAACTTACTTCTGACAACGATCGGAGGACCGAAGGAGCTAACCGCTTTTTTGCACAACATGGGGGATCATGTAACTCGCCTTGATCGTTGGGAACCGGAGCTGAATGAAGCCATACCAA
ACGACGAGCGTGACACCACGATGCCTGTAGCAATGGCAACAACGTTGCGCAAACTATTAACTGGCGAACTACTTACTCTAGCTTCCCGGCAACAATTAATAGACTGGATGGAGGCGGATA
AAGTTGCAGGACCACTTCTGCGCTCGGCCCTTCCGGCTGGCTGGTTTATTGCTGATAAATCTGGAGCCGGTGAGCGTGGAAGCCGCGGTATCATTGCAGCACTGGGGCCAGATGGTAAG
CCCTCCCGTATCGTAGTTATCTACACGACGGGGAGTCAGGCAACTATGGATGAACGAAATAGACAGATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAGGTGAAGATCCTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGTGTAGCCGTAGTTAGGCCACCACTTCAAGAACTCTGTAGCACCGCCTACATACCTCGC
TCTGCTAATCCTGTTACCAGTGGCTGCTGCCAGTGGCGATAAGTCGTGTCTTACCGGGTTGGACTCAAGACGATAGTTACCGGATAAGGCGCAGCGGTCGGGCTGAACGGGGGGTTCGT
GCACACAGCCCAGCTTGGAGCGAACGACCTACACCGAACTGAGATACCTACAGCGTGAGCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTATAGTCCTGTCGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTCCTGGCCTTTTGCTGGCCTTTTGCTCACATGT

FIG. 16

Anti-PECAM CRISPR : Genscript px458-PECAM1-4 (SEQ ID NO:10)

GAGGGCCTATTTCCCATGATTCCTTCATATTTGCATATACGATACAAGGCTGTTAGAGAGATAATTGGAATTAATTTGACTGTAAACACAAAGATATTAGTACAAAATACGTGACGTAGAAAG
TAATAATTTCTTGGGTAGTTTGCAGTTTTAAAATTATGTTTTAAAATGGACTATCATATGCTTACCGTAACTTGAAAGTATTTCGATTTCTTGGCTTTATATATCTTGTGGAAAGGACGAAACAC
CCCTGTCCGGATTCAAATTGCGTTTTAGAGCTAGAAATAGCAAGTTAAAATAAGGCTAGTCCGTTATCAACTTGAAAAAGTGGCACCGAGTCGGTGCTTTTTTGTTTTAGAGCTAGAAATAG
CAAGTTAAAATAAGGCTAGTCCGTTTTTAGCGCGTGCGCCAATTCTGCAGACAAATGGCTCTAGAGGTACCCGTTACATAACTTACGGTAAATGGCCCGCCTGGCTGACCGCCCAACGAC
CCCCGCCCATTGACGTCAATAGTAACGCCAATAGGGACTTTCCATTGACGTCAATGGGTGGAGTATTTACGGTAAACTGCCCACTTGGCAGTACATCAAGTGTATCATATGCCAAGTACGC
CCCCTATTGACGTCAATGACGGTAAATGGCCCGCCTGGCATTGTGCCCAGTACATGACCTTATGGGACTTTCCTACTTGGCAGTACATCTACGTATTAGTCATCGCTATTACCATGGTCGA
GGTGAGCCCCACGTTCTGCTTCACTCTCCCCATCTCCCCCCCCTCCCCACCCCCAATTTTGTATTTATTTATTTTTTAATTATTTTGTGCAGCGATGGGGGCGGGGGGGGGGGGGGGGCG
CGCGCCAGGCGGGGCGGGGCGGGGCGAGGGGCGGGGCGGGGCGAGGCGGAGAGGTGCGGCGGCAGCCAATCAGAGCGGCGCGCTCCGAAAGTTTCCTTTTATGGCGAGGCGGCG
GCGGCGGCGGCCCTATAAAAAGCGAAGCGCGCGGCGGGCGGGAGTCGCTGCGCGCTGCCTTCGCCCCGTGCCCCGCTCCGCCGCCGCCTCGCGCCGCCCGCCCCGGCTCTGACTGA
CCGCGTTACTCCCACAGGTGAGCGGGCGGGACGGCCCTTCTCCTCCGGGCTGTAATTAGCTGAGCAAGAGGTAAGGGTTTAAGGGATGGTTGGTTGGTGGGGTATTAATGTTTAATTAC
CTGGAGCACCTGCCTGAAATCACTTTTTTTCAGGTTGGACCGGTGCCACCATGGACTATAAGGACCACGACGGAGACTACAAGGATCATGATATTGATTACAAAGACGATGACGATAAGAT
GGCCCCAAAGAAGAAGCGGAAGGTCGGTATCCACGGAGTCCCAGCAGCCGACAAGAAGTACAGCATCGGCCTGGACATCGGCACCAACTCTGTGGGCTGGGCCGTGATCACCGACGA
GTACAAGGTGCCCAGCAAGAAATTCAAGGTGCTGGGCAACACCGACCGGCACAGCATCAAGAAGAACCTGATCGGAGCCCTGCTGTTCGACAGCGGCGAAACAGCCGAGGCCACCCGG
CTGAAGAGAACCGCCAGAAGAAGATACACCAGACGGAAGAACCGGATCTGCTATCTGCAAGAGATCTTCAGCAACGAGATGGCCAAGGTGGACGACAGCTTCTTCCACAGACTGGAAGA
GTCCTTCCTGGTGGAAGAGGATAAGAAGCACGAGCGGCACCCCATCTTCGGCAACATCGTGGACGAGGTGGCCTACCACGAGAAGTACCCCACCATCTACCACCTGAGAAAGAAACTGG
TGGACAGCACCGACAAGGCCGACCTGCGGCTGATCTATCTGGCCCTGGCCCACATGATCAAGTTCCGGGGCCACTTCCTGATCGAGGGCGACCTGAACCCCGACAACAGCGACGTGGA
CAAGCTGTTCATCCAGCTGGTGCAGACCTACAACCAGCTGTTCGAGGAAAACCCCATCAACGCCAGCGGCGTGGACGCCAAGGCCATCCTGTCTGCCAGACTGAGCAAGAGCAGACGG
CTGGAAAATCTGATCGCCCAGCTGCCCGGCGAGAAGAAGAATGGCCTGTTCGGAAACCTGATTGCCCTGAGCCTGGGCCTGACCCCCAACTTCAAGAGCAACTTCGACCTGGCCGAGGA
TGCCAAACTGCAGCTGAGCAAGGACACCTACGACGACGACCTGGACAACCTGCTGGCCCAGATCGGCGACCAGTACGCCGACCTGTTTCTGGCCGCCAAGAACCTGTCCGACGCCATC
CTGCTGAGCGACATCCTGAGAGTGAACACCGAGATCACCAAGGCCCCCCTGAGCGCCTCTATGATCAAGAGATACGACGAGCACCACCAGGACCTGACCCTGCTGAAAGCTCTCGTGCG
GCAGCAGCTGCCTGAGAAGTACAAAGAGATTTTCTTCGACCAGAGCAAGAACGGCTACGCCGGCTACATTGACGGCGGAGCCAGCCAGGAAGAGTTCTACAAGTTCATCAAGCCCATCC
TGGAAAAGATGGACGGCACCGAGGAACTGCTCGTGAAGCTGAACAGAGAGGACCTGCTGCGGAAGCAGCGGACCTTCGACAACGGCAGCATCCCCCACCAGATCCACCTGGGAGAGCT
GCACGCCATTCTGCGGCGGCAGGAAGATTTTTACCCATTCCTGAAGGACAACCGGGAAAAGATCGAGAAGATCCTGACCTTCCGCATCCCCTACTACGTGGGCCCTCTGGCCAGGGGAA
ACAGCAGATTCGCCTGGATGACCAGAAAGAGCGAGGAAACCATCACCCCCTGGAACTTCGAGGAAGTGGTGGACAAGGGCGCTTCCGCCCAGAGCTTCATCGAGCGGATGACCAACTTC
GATAAGAACCTGCCCAACGAGAAGGTGCTGCCCAAGCACAGCCTGCTGTACGAGTACTTCACCGTGTATAACGAGCTGACCAAAGTGAAATACGTGACCGAGGGAATGAGAAAGCCCGC
CTTCCTGAGCGGCGAGCAGAAAAAGGCCATCGTGGACCTGCTGTTCAAGACCAACCGGAAAGTGACCGTGAAGCAGCTGAAAGAGGACTACTTCAAGAAAATCGAGTGCTTCGACTCCG
TGGAAATCTCCGGCGTGGAAGATCGGTTCAACGCCTCCCTGGGCACATACCACGATCTGCTGAAAATTATCAAGGACAAGGACTTCCTGGACAATGAGGAAAACGAGGACATTCTGGAAG
ATATCGTGCTGACCCTGACACTGTTTGAGGACAGAGAGATGATCGAGGAACGGCTGAAAACCTATGCCCACCTGTTCGACGACAAAGTGATGAAGCAGCTGAAGCGGCGGAGATACACC
GGCTGGGGCAGGCTGAGCCGGAAGCTGATCAACGGCATCCGGGACAAGCAGTCCGGCAAGACAATCCTGGATTTCCTGAAGTCCGACGGCTTCGCCAACAGAAACTTCATGCAGCTGA
TCCACGACGACAGCCTGACCTTTAAAGAGGACATCCAGAAAGCCCAGGTGTCCGGCCAGGGCGATAGCCTGCACGAGCACATTGCCAATCTGGCCGGCAGCCCCGCCATTAAGAAGGG
CATCCTGCAGACAGTGAAGGTGGTGGACGAGCTCGTGAAAGTGATGGGCCGGCACAAGCCCGAGAACATCGTGATCGAAATGGCCAGAGAGAACCAGACCACCCAGAAGGGACAGAAG
AACAGCCGCGAGAGAATGAAGCGGATCGAAGAGGGCATCAAAGAGCTGGGCAGCCAGATCCTGAAAGAACACCCCGTGGAAAACACCCAGCTGCAGAACGAGAAGCTGTACCTGTACT
ACCTGCAGAATGGGCGGGATATGTACGTGGACCAGGAACTGGACATCAACCGGCTGTCCGACTACGATGTGGACCATATCGTGCCTCAGAGCTTTCTGAAGGACGACTCCATCGACAAC
AAGGTGCTGACCAGAAGCGACAAGAACCGGGGCAAGAGCGACAACGTGCCCTCCGAAGAGGTCGTGAAGAAGATGAAGAACTACTGGCGGCAGCTGCTGAACGCCAAGCTGATTACCC
AGAGAAAGTTCGACAATCTGACCAAGGCCGAGAGAGGCGGCCTGAGCGAACTGGATAAGGCCGGCTTCATCAAGAGACAGCTGGTGGAAACCCGGCAGATCACAAAGCACGTGGCACA
GATCCTGGACTCCCGGATGAACACTAAGTACGACGAGAATGACAAGCTGATCCGGGAAGTGAAAGTGATCACCCTGAAGTCCAAGCTGGTGTCCGATTTCCGGAAGGATTTCCAGTTTTA
CAAAGTGCGCGAGATCAACAACTACCACCACGCCCACGACGCCTACCTGAACGCCGTCGTGGGAACCGCCCTGATCAAAAAGTACCCTAAGCTGGAAAGCGAGTTCGTGTACGGCGACT
ACAAGGTGTACGACGTGCGGAAGATGATCGCCAAGAGCGAGCAGGAAATCGGCAAGGCTACCGCCAAGTACTTCTTCTACAGCAACATCATGAACTTTTTCAAGACCGAGATTACCCTGG
CCAACGGCGAGATCCGGAAGCGGCCTCTGATCGAGACAAACGGCGAAACCGGGGAGATCGTGTGGGATAAGGGCCGGGATTTTGCCACCGTGCGGAAAGTGCTGAGCATGCCCCAAG
TGAATATCGTGAAAAAGACCGAGGTGCAGACAGGCGGCTTCAGCAAAGAGTCTATCCTGCCCAAGAGGAACAGCGATAAGCTGATCGCCAGAAAGAAGGACTGGGACCCTAAGAAGTAC
GGCGGCTTCGACAGCCCCACCGTGGCCTATTCTGTGCTGGTGGTGGCCAAAGTGGAAAAGGGCAAGTCCAAGAAACTGAAGAGTGTGAAAGAGCTGCTGGGGATCACCATCATGGAAA
GAAGCAGCTTCGAGAAGAATCCCATCGACTTTCTGGAAGCCAAGGGCTACAAAGAAGTGAAAAAGGACCTGATCATCAAGCTGCCTAAGTACTCCCTGTTCGAGCTGGAAAACGGCCGGA
AGAGAATGCTGGCCTCTGCCGGCGAACTGCAGAAGGGAAACGAACTGGCCCTGCCCTCCAAATATGTGAACTTCCTGTACCTGGCCAGCCACTATGAGAAGCTGAAGGGCTCCCCCGAG
GATAATGAGCAGAAACAGCTGTTTGTGGAACAGCACAAGCACTACCTGGACGAGATCATCGAGCAGATCAGCGAGTTCTCCAAGAGAGTGATCCTGGCCGACGCTAATCTGGACAAAGTG
CTGTCCGCCTACAACAAGCACCGGGATAAGCCCATCAGAGAGCAGGCCGAGAATATCATCCACCTGTTTACCCTGACCAATCTGGGAGCCCCTGCCGCCTTCAAGTACTTTGACACCACC
ATCGACCGGAAGAGGTACACCAGCACCAAAGAGGTGCTGGACGCCACCCTGATCCACCAGAGCATCACCGGCCTGTACGAGACACGGATCGACCTGTCTCAGCTGGGAGGCGACAAAA
GGCCGGCGGCCACGAAAAAGGCCGGCCAGGCAAAAAAGAAAAAGGAATTCGGCAGTGGAGAGGGCAGAGGAAGTCTGCTAACATGCGGTGACGTCGAGGAGAATCCTGGCCCAGTGA
GCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATGCCACCTACGGC
AAGCTGACCCTGAAGTTCATCTGCACCACCGGCAAGCTGCCCGTGCCCTGGCCCACCCTCGTGACCACCCTGACCTACGGCGTGCAGTGCTTCAGCCGCTACCCCGACCACATGAAGCA
GCACGACTTCTTCAAGTCCGCCATGCCCGAAGGCTACGTCCAGGAGCGCACCATCTTCTTCAAGGACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTGGGGCACAAGCTGGAGTACAACTACAACAGCCACAACGTCTATATCATGGCCGACAAGCAGAAGAA
CGGCATCAAGGTGAACTTCAAGATCCGCCACAACATCGAGGACGGCAGCGTGCAGCTCGCCGACCACTACCAGCAGAACACCCCCATCGGCGACGGCCCCGTGCTGCTGCCCGACAAC
CACTACCTGAGCACCCAGTCCGCCCTGAGCAAAGACCCCAACGAGAAGCGCGATCACATGGTCCTGCTGGAGTTCGTGACCGCCGCCGGGATCACTCTCGGCATGGACGAGCTGTACA
AGGAATTCTAACTAGAGCTCGCTGATCAGCCTCGACTGTGCCTTCTAGTTGCCAGCCATCTGTTGTTTGCCCCTCCCCCGTGCCTTCCTTGACCCTGGAAGGTGCCACTCCCACTGTCCTT
TCCTAATAAAATGAGGAAATTGCATCGCATTGTCTGAGTAGGTGTCATTCTATTCTGGGGGGTGGGGTGGGGCAGGACAGCAAGGGGGAGGATTGGGAAGAGAATAGCAGGCATGCTGG
GGAGCGGCCGCAGGAACCCCTAGTGATGGAGTTGGCCACTCCCTCTCTGCGCGCTCGCTCGCTCACTGAGGCCGGGCGACCAAAGGTCGCCCGACGCCCGGGCTTTGCCCGGGCGG
CCTCAGTGAGCGAGCGAGCGCGCAGCTGCCTGCAGGGGCGCCTGATGCGGTATTTTCTCCTTACGCATCTGTGCGGTATTTCACACCGCATACGTCAAAGCAACCATAGTACGCGCCCT
GTAGCGGCGCATTAAGCGCGGCGGGTGTGGTGGTTACGCGCAGCGTGACCGCTACACTTGCCAGCGCCTTAGCGCCCGCTCCTTTCGCTTTCTTCCCTTCCTTTCTCGCCACGTTCGCC
GGCTTTCCCCGTCAAGCTCTAAATCGGGGGCTCCCTTTAGGGTTCCGATTTAGTGCTTTACGGCACCTCGACCCCAAAAAACTTGATTTGGGTGATGGTTCACGTAGTGGGCCATCGCCC
TGATAGACGGTTTTTCGCCCTTTGACGTTGGAGTCCACGTTCTTTAATAGTGGACTCTTGTTCCAAACTGGAACAACACTCAACTCTATCTCGGGCTATTCTTTTGATTTATAAGGGATTTTG
CCGATTTCGGTCTATTGGTTAAAAAATGAGCTGATTTAACAAAAATTTAACGCGAATTTTAACAAAATATTAACGTTTACAATTTTATGGTGCACTCTCAGTACAATCTGCTCTGATGCCGCAT
AGTTAAGCCAGCCCCGACACCCGCCAACACCCGCTGACGCGCCCTGACGGGCTTGTCTGCTCCCGGCATCCGCTTACAGACAAGCTGTGACCGTCTccgggagctgcatgtgtcagaggttttcaccgtc
atcaccgaaacgcgcgagACGAAAGGGCCTCGTGATACGCCTATTTTTATAGGTTAATGTCATGATAATAATGGTTTCTTAGACGTCAGGTGGCACTTTTCGGGGAAATGTGCGCGGAACCCCTAT
TTGTTTATTTTTCTAAATACATTCAAATATGTATCCGCTCATGAGACAATAACCCTGATAAATGCTTCAATAATATTGAAAAAGGAAGAGTATGAGTATTCAACATTTCCGTGTCGCCCTTATTC
CCTTTTTTGCGGCATTTTGCCTTCCTGTTTTTGCTCACCCAGAAACGCTGGTGAAAGTAAAAGATGCTGAAGATCAGTTGGGTGCACGAGTGGGTTACATCGAACTGGATCTCAACAGCGG
TAAGATCCTTGAGAGTTTTCGCCCCGAAGAACGTTTTCCAATGATGAGCACTTTTAAAGTTCTGCTATGTGGCGCGGTATTATCCCGTATTGACGCCGGGCAAGAGCAACTCGGTCGCCGC
ATACACTATTCTCAGAATGACTTGGTTGAGTACTCACCAGTCACAGAAAAGCATCTTACGGATGGCATGACAGTAAGAGAATTATGCAGTGCTGCCATAACCATGAGTGATAACACTGCGG
CCAACTTACTTCTGACAACGATCGGAGGACCGAAGGAGCTAACCGCTTTTTTGCACAACATGGGGGATCATGTAACTCGCCTTGATCGTTGGGAACCGGAGCTGAATGAAGCCATACCAA
ACGACGAGCGTGACACCACGATGCCTGTAGCAATGGCAACAACGTTGCGCAAACTATTAACTGGCGAACTACTTACTCTAGCTTCCCGGCAACAATTAATAGACTGGATGGAGGCGGATA
AAGTTGCAGGACCACTTCTGCGCTCGGCCCTTCCGGCTGGCTGGTTTATTGCTGATAAATCTGGAGCCGGTGAGCGTGGAAGCCGCGGTATCATTGCAGCACTGGGGCCAGATGGTAAG
CCCTCCCGTATCGTAGTTATCTACACGACGGGGAGTCAGGCAACTATGGATGAACGAAATAGACAGATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAGGTGAAGATCCTTTTTGATAATCTCATGACCAAAATCCCTTAACGTGAGTTTTCGTTCCACTGAGCGTCA
GACCCCGTAGAAAAGATCAAAGGATCTTCTTGAGATCCTTTTTTTCTGCGCGTAATCTGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGTGTAGCCGTAGTTAGGCCACCACTTCAAGAACTCTGTAGCACCGCCTACATACCTCGC
TCTGCTAATCCTGTTACCAGTGGCTGCTGCCAGTGGCGATAAGTCGTGTCTTACCGGGTTGGACTCAAGACGATAGTTACCGGATAAGGCGCAGCGGTCGGGCTGAACGGGGGGTTCGT
GCACACAGCCCAGCTTGGAGCGAACGACCTACACCGAACTGAGATACCTACAGCGTGAGCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGGTATCTTTATAGTCCTGTCGGGTTTCGCCACCTCTGACTTGAGCGTCGATTTTTGTGATGCTCGTCAG
GGGGGCGGAGCCTATGGAAAAACGCCAGCAACGCGGCCTTTTTACGGTTCCTGGCCTTTTGCTGGCCTTTTGCTCACATGT

FIG. 19

Anti-p65 Antisense: DraIIRINhe ΔmCMV-7SK-AS-p65-Ch-ΔmCMV EF1-I126-tdTomato/BV2 (092416 # 4)

(SEQ ID NO:11)

CAGCACTATGTGGACATGAATTCAATTGGCTAGCAGGAGTCAATGGGAAAAACCCATTGGAGCCAAGTACACTGACTCAATAGGGACTTTCCATTGGGTTTTGCCCA
GTACATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAA
TGGGAGGTAAGCCAATGGGTTTTTCCCATTACTGACATGTATACTGAGTCATTAGGGACTTTCCAATGGGTTTTGCCCAGTACATAAGGTCAATAGGGGTGAATCAAC
AGGAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATT
ATTGGCACATACATAAGGTCAATAGGGGTGACTAGTGCTGCAGTATTTAGCATGCCCCACCCATCTGCAAGGCATTCTGGATAGTGTCAAAACAGCTGGAAATCAAG
TCTGTTTATCTCAAACTTTAGCATTTTGGGAATAAATGATATTTGCTATGCTGGTTAAATTAGATTTTAGTTAAATTTCCTGCTGAAGCTCTAGTATGATAAGTAACTTG
ACCTAAGTGTAAAGTTGAGATTTCCTTCAGGTTTATATAGTCCCTATCAGTGATAGAGACCTCAGATATCGTGAAATACACCTCTCTAGCAGGAGTCAATGGGAAAAA
CCCATTGGAGCCAAGTACACTGACTCAATAGGGACTTTCCATTGGGTTTTGCCCAGTACATAAGGTCAATAGGGGGTGAGTCAACAGGAAAGTCCCATTGGAGCCAA
GTACATTGAGTCAATAGGGACTTTCCAATGGGTTTTGCCCAGTACATAAGGTCAATGGGAGGTAAGCCAATGGGTTTTTCCCATTACTGACATGTATACTGAGTCATT
AGGGACTTTCCAATGGGTTTTGCCCAGTACATAAGGTCAATAGGGGTGAATCAACAGGAAAGTCCCATTGGAGCCAAGTACACTGAGTCAATAGGGACTTTCCATTG
GGTTTTGCCCAGTACAAAAGGTCAATAGGGGGTGAGTCAATGGGTTTTTCCCATTATTGGCACATACATAAGGTCAATAGGGGTGACTAGTGGAGAAGAGCATGCTT
GAGGGCTGAGTGCCCCTCAGTGGGCAGAGAGCACATGGCCCACAGTCCCTGAGAAGTTGGGGGGAGGGGTGGGCAATTGAACTGGTGCCTAGAGAAGGTGGGGC
TTGGGTAAACTGGGAAAGTGATGTGGTGTACTGGCTCCACCTTTTTCCCCAGGGTGGGGGAGAACCATATATAAGTGCAGTAGTCTCTGTGAACATTCAAGCTTCTG
CCTTCTCCCTCCTGTGAGTTTGgtaagtcactgactgtctatgcctgggaaagggtgggcaggagatggggcagtgcaggaaaagtggcactatgaacccTGCAGCCCTAGAcaattgtactaaccttct
tctctttcctctcctgacagGTTGGTAACCAAGCCACCATGGTTTCCAAAGGGGAAGAAGTCATCAAAGAGTTCATGAGGTTCAAAGTCAGAATGGAAGGCAGCATGAATGG
CCATGAGTTTGAGATTGAAGGAGAAGGAGAGGGCAGACCCTATGAGGGCACACAGACAGCCAAGCTGAAAGTGACCAAAGGTGGCCCTCTGCCTTTTGCCTGGGA
CATCCTGTCTCCACAGTTTATGTATGGCAGCAAGGCCTATGTGAAGCACCCTGCTGACATCCCTGACTACAAGAAGCTGAGCTTCCCAGAGGGCTTCAAGTGGGAGA
GAGTGATGAACTTTGAGGATGGTGGCCTGGTCACAGTGACCCAGGATAGCTCTCTCCAGGATGGCACCCTGATCTACAAAGTGAAGATGAGGGGCACAAACTTCCCT
CCAGATGGCCCTGTGATGCAGAAAAAGACCATGGGCTGGGAAGCCTCCACAGAGAGACTGTACCCTAGAGATGGGGTGCTGAAAGGGGAGATCCACCAGGCTCTG
AAGCTGAAGGATGGTGGACACTACCTGGTTGAGTTCAAGACCATCTACATGGCCAAGAAACCTGTGCAGCTGCCTGGCTACTACTATGTGGACACCAAGCTGGACAT
CACCAGCCACAATGAGGACTACACCATTGTGGAACAGTATGAGAGGAGTGAAGGCAGGCACCACCTGTTCCTTGGACATGGCACAGGCAGCACAGGCTCTGGCAGT
TCTGGAACAGCCAGCTCTGAGGACAACAACATGGCTGTGATCAAAGAGTTTATGAGATTCAAAGTTAGGATGGAAGGTTCCATGAATGGGCATGAATTTGAAATTGA
AGGAGAAGGAGAAGGCAGGCCTTATGAAGGGACCCAGACTGCTAAACTCAAAGTCACAAAAGGTGGACCACTTCCATTTGCTTGGGATATTCTGAGCCCTCAGTTTA
TGTATGGGTCCAAAGCCTATGTCAAACATCCAGCAGACATCCCAGATTATAAGAAACTGTCTTTTCCAGAGGGGTTTAAATGGGAAAGAGTCATGAATTTTGAAGAT
GGTGGACTTGTGACTGTCACCCAGGACAGCAGCCTGCAAGATGGAACACTCATCTACAAAGTCAAAATGAGAGGGACCAATTTTCCACCTGATGGGCCAGTGATGCA
AAAGAAAACAATGGGATGGGAAGCAAGCACTGAGAGGCTCTATCCCAGAGATGGTGTCCTCAAAGGGGAAATTCATCAGGCCCTCAAGCTCAAAGATGGTGGCCAT
TATCTTGTTGAGTTTAAAACAATCTATATGGCTAAAAAGCCAGTCCAGCTGCCAGGGTACTATTATGTTGATACAAAACTGGACATTACCTCTCACAATGAAGATTATA
CAATTGTGGAACAATATGAGAGGAGTGAAGGCAGACATCATCTGTTTCTGTATGGAATGGATGAGCTGTACAAGTGAAGATCTACTTCTGGCTAATAAAAGATCAGA
GCTCTAGTGATCTGTGTGTTGGTTTTTTGTGTCTGCATTCTAGCTCTAGTGATCAGCAGTTCAACCTGTTGATAGTATGTACTAAGCTCTCATGTTTAATGTACTAAGCT
CTCATGTTTAATGAACTAAACCCTCATGGCTAATGTACTAAGCTCTCATGGCTAATGTACTAAGCTCTCATGTTTCATGTACTAAGCTCTCATGTTTGAACAATAAAATT
AATATAAATCAGCAACTTAAATAGCCTCTAAGGTTTTAAGTTTTATAAGAAAAAAAAGAATATATAAGGCTTTTAAAGGTTTTAAGGTTTCCTAGGTTATCCTCATATG
AGCTCTTAGAAAAACTCATCCAGCATCAAATGAAACTGCAATTTATTCATATCAGGATTATCAATACCATATTTTTGAAAAAGTCTTTTCTGTAATGAAGGAGAAAACT
CACCCAGGCAGTTCCATAGGATGGCAAGATCCTGGTATCTGTCTGCAATTCCAACTCTTCCAACATCAATACAACCTATTAATTTCCCCTCATCAAAAATAAGGTTATCA
AGTGAGAAATCACCATGAGTGACCACTGAATCTGGTGAGAATGGCAAAAGATTATGCATTTCTTTCCAGACTTGTTCAACAGGCCAGCCATTTCTCTCATCATCAAAAT
CACTGGCATCAACCAAACCATTATTCATTCTTGATTGGGCCTGAGCCAGTCTAAATACTCTATCAGAGTTAAAAGGACAATTACAAACAGGAATGGAATGCAATCTTCT
CAGGAACACTGCCAGGGCATCAACAATATTTTCACCTGAATCAGGATATTCTTCCAATACCTGGAATGCTGTTTTCCCTGGGATGGCAGTGGTGAGTAACCATGCATC
ATCAGGAGTTCTGATAAAATGCTTGATGGTTGGAAGAGGCATAAATTCAGTCAGCCAGTTTAGTCTGACCATCTCATCTGTAACATCATTGGCAACAGAACCTTTGCC
ATGTTTCAGAAACAACTCTGGGGCATCTGGCTTCCCATACAATCTATAGATTGTGGCACCTGATTGCCCAACATTATCTCTAGCCCATTTATACCCATATAAATCAGCAT
CCATGTTGGAATTTAATCTTGGCCTGGAGCAAGAGGTTTCTCTTTGAATATGGCTCATACATGTGCACCTCCTATAGTGAGTTGTATTATACTATGCAGATATACTATG
CCAATGTTTAATTGTCAG

FIG. 20 p65 shB: NheΔhCMVΔhCMVRVp65 shB-TTTTT-XbaI-HindIII-Amp (SEQ ID NO:12)

GAATTCTCATAGCTAGCATGTTACATAACTTATGGTAAATGGCCTGCCTGGCTGACTGCCCAATGACCCCTGCCCAATGATGTCAATAATGATGTATGTTCCCATGT
AATGCCAATAGGGACTTTCCATTGATGTCAATGGGTGGAGTATTTATGGTAACTGCCCACTTGGCAGTACATCAAGTGTATCATATGCCAAGTATGCCCCCTATTG
ATGTCAATGATGGTAAATGGCCTGCCTGGCATTATGCCCAGTACATGACCTTATGGGACTTTCCTACTTGGCAGTACATCTATGTATTAGTCATTGCTATTACCATG
GTGATGGGTTTTGGCAGTACATCAATGGGTGTGGATAGTGGTTTGACCCATGGGGATTTCCAAGTCTCCACCCCATTGATGCCAATGGGAGTTTGTTTTGGCACCAAA
ATCAATGGGACTTTCCAAAATGTTGTAACAACTCTGCCCCATTGATGGAAATGGGTGGTAGGTGTGTGTGGTGGGAGGTCTATATAAGCAGAGCTTGTTTAGTGAAC
TGGATGCACCTACTAGATATCAGCGAATCCAGACCAACAATATCAAGAGTATTGTTGGTCTGGATTCGCTTTTTTTCTAGATACTAAGCTTGGCGTAA
TCATGGTCATAGCTGTTTCCTGTGTGAAATTGTTATCCGCTCACAATTCCACACAACATACGAGCCGGAAGCATAAAGTGTAAAGCCTGGGGTGCCTAATGAGTGAGC
TAACTCACATTAATTGCGTTGCGCTCACTGCCCGCTTTCCAGTCGGGAAACCTGTCGTGCCAGCTGCATTAATGAATCGGCCAACGCGCGGGGAGAGGCGGTTTGCG
TATTGGGCGCTCTTCCGCTTCCTCGCTCACTGACTCGCTGCGCTCGGTCGTTCGGCTGCGGCGAGCGGTATCAGCTCACTCAAAGGCGGTAATACGGTTATCCACAGA
ATCAGGGGATAACGCAGGAAAGAACATGTGAGCAAAAGGCCAGCAAAAGGCCAGGAACCGTAAAAAGGCCGCGTTGCTGGCGTTTTTCCATAGGCTCCGCCCCCCT
GACGAGCATCACAAAAATCGACGCTCAAGTCAGAGGTGGCGAAACCCGACAGGACTATAAAGATACCAGGCGTTTCCCCCTGGAAGCTCCCTCGTGCGCTCTCCTGT
TCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTGAAGTGGTGGCCTAACTACGGCTACACTAGAAGAACAGTATTTG
GTATCTGCGCTCTGCTGAAGCCAGTTACCTTCGGAAAAAGAGTTGGTAGCTCTTGATCCGGCAAACAAACCACCGCTGGTAGCGGTGGTTTTTTTGTTTGCAAGCAGC
AGATTACGCGCAGAAAAAAAGGATCTCAAGAAGATCCTTTGATCTTTTCTACGGGGTCTGACGCTCAGTGGAACGAAAACTCACGTTAAGGGATTTTGGTCATGAGA
TTATCAAAAAGGATCTTCACCTAGATCCTTTTAAATTAAAAATGAAGTTTTAAATCAATCTAAAGTATATATGAGTAAACTTGGTCTGACAGTTACCAATGCTTAATCAG
TGAGGCACCTATCTCAGCGATCTGTCTATTTCGTTCATCCATAGTTGCCTGACTCCCCGTCGTGTAGATAACTACGATACGGGAGGGCTTACCATCTGGCCCCAGTGCT
GCAATGATACCGCGAGACCCACGCTCACCGGCTCCAGATTTATCAGCAATAAACCAGCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGTTAATAGTTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTACATGATCCCCCATGTTGTGCAAAAAAGCGGTTAGCTCCTTCGGTCCTCCGATCGTTGTC
AGAAGTAAGTTGGCCGCAGTGTTATCACTCATGGTTATGGCAGCACTGCATAATTCTCTTACTGTCATGCCATCCGTAAGATGCTTTTCTGTGACTGGTGAGTACTCAA
CCAAGTCATTCTGAGAATAGTGTATGCGGCGACCGAGTTGCTCTTGCCCGGCGTCAATACGGGATAATACCGCGCCACATAGCAGAACTTTAAAAGTGCTCATCATTG
GAAAACGTTCTTCGGGGCGAAAACTCTCAAGGATCTTACCGCTGTTGAGATCCAGTTCGATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGGGAATAAGGGCGACACGGAAATGTTGAATACTCATACTCTTCCTTTTTCAATATTATT
GAAGCATTTATCAGGGTTATTGTCTCATGAGCGGATACATATTTGAATGTATTTAGAAAAATAAACAAATAGGGGTTCCGCGCACATTTCCCCGAAAAGTGCCACCTG
ACGTCTAAGAAACCATTATTATCATGACATTAACCTATAAAAATAGGCGTATCACGAGGCCCTTTCGTCTCGCGCGTTTCGGTGATGACGGTGAAAACCTCTGACACA
TGCAGCTCCCGGAGACGGTCACAGCTTGTCTGTAAGCGGATGCCGGGAGCAGACAAGCCCGTCAGGGCGCGTCAGCGGGTGTTGGCGGGTGTCGGGGCTGGCTTA
ACTATGCGGCATCAGAGCAGATTGTACTGAGAGTGCACCATATGCGGTGTGAAATACCGCACAGATGCGTAAGGAGAAAATACCGCATCAGGCGCCATTCGCCATTC
AGGCTGCGCAACTGTTGGGAAGGGCGATCGGTGCGGGCCTCTTCGCTATTACGCCAGCTGGCGAAAGGGGGATGTGCTGCAAGGCGATTAAGTTGGGTAACGCCA
GGGTTTTCCCAGTCACGACGTTGTAAAACGACGGCCAGTCCTTAATAGTTGCAGCCAAATCCTTCCTGTCAGATTTGGCTGCAACTATTAAGGTTTTT

FIG. 26 sv40-mCMV-EF1 : DraIIIRINhe-sv40-ΔmCMV-EF1-I126-BstEII-ΔGCSF-BglII-polyA-BV2 (SEQ ID NO:13)

CACTATGTGGACATGAATTCAATTGGCTAGCAGGGGCCTGAAATAACCTCTGAAAGAGGAACTTGGTTAGGTACCTTCTGAGGCTGAAAGAACCAGCTGTGGAATGT
GTGTCAGTTAGGGTGTGGAAAGTCCCCAGGCTCCCCAGCAGGCAGAAGTATGCAAAGCATGCATCTCAATTAGTCAGCAACCAGGTGTGGAAAGTCCCCAGGCTCC
CCAGCAGGCAGAAGTATGCAAAGCATGCATCTCAATTAGTCAGCAACCATAGTCCCAGTCTAGCAGGAGTCAATGGGAAAAACCCATTGGAGCCAAGTACACTGACT
CAATAGGGACTTTCCATTGGGTTTTGCCCAGTACATAAGGTCAATAGGGGGTGAGTCAACAGGAAAGTCCCATTGGAGCCAAGTACATTGAGTCAATAGGGACTTTC
CAATGGGTTTTGCCCAGTACATAAGGTCAATGGGAGGTAAGCCAATGGGTTTTTCCCATTACTGACATGTATACTGAGTCATTAGGGACTTTCCAATGGGTTTTGCCC
AGTACATAAGGTCAATAGGGGTGAATCAACAGGAAAGTCCCATTGGAGCCAAGTACACTGAGTCAATAGGGACTTTCCATTGGGTTTTGCCCAGTACAAAAGGTCAA
TAGGGGGTGAGTCAATGGGTTTTTCCCATTATTGGCACATACATAAGGTCAATAGGGGTGACTAGTGGAGAAGAGCATGCTTGAGGGCTGAGTGCCCCTCAGTGGG
CAGAGAGCACATGGCCCACAGTCCCTGAGAAGTTGGGGGGAGGGGTGGGCAATTGAACTGGTGCCTAGAGAAGGTGGGGCTTGGGTAAACTGGGAAAGTGATGT
GGTGTACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGTAA
GTCACTGACTGTCTATGCCTGGGAAAGGGTGGGCAGGAGATGGGGCAGTGCAGGAAAAGTGGCACTATGAACCCTGCAGCCCTAGACAATTGTACTAACCTTCTTC
TCTTTCCTCTCCTGACAGGTTGGTAACCAAGCTTTCCATGGCTGGACCTGCCACCCAGAGCCCCATGAAGCTGATGGCCCTGCAGCTGCTGCTGTGGCACAGTGCACT
CTGGACAGTGCAGGAAGCCACCCCCCTGGGCCCTGCCAGCTCCCTGCCCCAGAGCTTCCTGCTCAAGTGCTTAGAGCAAGTGAGGAAGATCCAGGGGGATGGGGCA
GCTCTCCAGGAGAAGCTGTGTGCCACCTACAAGCTGTGCCACCCTGAGGAGCTGGTGCTGCTGGGACACTCTCTGGGCATCCCCTGGGCTCCCCTGAGCAGCTGCCC
CAGCCAGGCCCTGCAGCTGGCAGGCTGCTTGAGCCAACTCCATAGTGGCCTTTTCCTCTACCAGGGGCTCCTGCAGGCCCTGGAAGGGATCTCCCCTGAGTTGGGTC
CCACCTTGGACACACTGCAGCTGGATGTTGCTGACTTTGCCACCACCATCTGGCAGCAGATGGAAGAACTGGGAATGGCCCCTGCCCTGCAGCCCACCCAGGGTGCC
ATGCCTGCCTTTGCCTCTGCTTTCCAGAGAAGGGCAGGAGGGGTCCTGGTTGCCTCCCATCTGCAGAGCTTCCTGGAGGTGTCCTACAGAGTTCTAAGACACCTTGCC
CAGCCCTGATAGATCTACTTCTGGCTAATAAAAGATCAGAGCTCTAGTGATCTGTGTGTTGGTTTTTTGTGTCTGCATTCTAGCTCTAGTGATCAGCAGTTCAACCTGTT
GATAGTATGTACTAAGCTCTCATGTTTAATGTACTAAGCTCTCATGTTTAATGAACTAAACCCTCATGGCTAATGTACTAAGCTCTCATGGCTAATGTACTAAGCTCTCA
TGTTTCATGTACTAAGCTCTCATGTTTGAACAATAAAATTAATATAAATCAGCAACTTAAATAGCCTCTAAGGTTTTAAGTTTTATAAGAAAAAAAAGAATATATAAGG
CTTTTAAAGGTTTTAAGGTTTCCTAGGTTATCCTCATATGAGCTCTTAGAAAAACTCATCCAGCATCAAATGAAACTGCAATTTATTCATATCAGGATTATCAATACCAT
ATTTTTGAAAAAGTCTTTTCTGTAATGAAGGAGAAAACTCACCCAGGCAGTTCCATAGGATGGCAAGATCCTGGTATCTGTCTGCAATTCCAACTCTTCCAACATCAAT
ACAACCTATTAATTTCCCCTCATCAAAAATAAGGTTATCAAGTGAGAAATCACCATGAGTGACCACTGAATCTGGTGAGAATGGCAAAAGATTATGCATTTCTTTCCAG
ACTTGTTCAACAGGCCAGCCATTTCTCTCATCATCAAAATCACTGGCATCAACCAAACCATTATTCATTCTTGATTGGGCCTGAGCCAGTCTAAATACTCTATCAGAGTT
AAAAGGACAATTACAAACAGGAATGGAATGCAATCTTCTCAGGAACACTGCCAGGGCATCAACAATATTTTCACCTGAATCAGGATATTCTTCCAATACCTGGAATGC
TGTTTTCCCTGGGATGGCAGTGGTGAGTAACCATGCATCATCAGGAGTTCTGATAAAATGCTTGATGGTTGGAAGAGGCATAAATTCAGTCAGCCAGTTTAGTCTGA
CCATCTCATCTGTAACATCATTGGCAACAGAACCTTTGCCATGTTTCAGAAACAACTCTGGGGCATCTGGCTTCCCATACAATCTATAGATTGTGGCACCTGATTGCCC
AACATTATCTCTAGCCCATTTATACCCATATAAATCAGCATCCATGTTGGAATTTAATCTTGGCCTGGAGCAAGAGGTTTCTCTTTGAATATGGCTCATACATGTGCACC
TCCTATAGTGAGTTGTATTATACTATGCAGATATACTATGCCAATGTTTAATTGTCAG

FIG. 27 mCMV-mCMV-EF1 : DraIIIRINhe-ΔmCMV -ΔmCMV-EF1-I126-BstEII-ΔGCSF-BglII-polyA-BV2
(SEQ ID NO:14)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGTCTAGCAGGAGTCAATGGGAAAAACCCATTGGAGCCAAGTACACTGACTCAATAGGGACTTTCCATTGGGTTTTGCCCAG
TACATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAAT
GGGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACA
GGAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTA
TTGGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGA
AGTTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGT
GGGGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGT
GGGCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAG
CTTTCCATGGCTGGACCTGCCACCCAGAGCCCCATGAAGCTGATGGCCCTGCAGCTGCTGCTGTGGCACAGTGCACTCTGGACAGTGCAGGAAGCCACCCCCCTGGG
CCCTGCCAGCTCCCTGCCCCAGAGCTTCCTGCTCAAGTGCTTAGAGCAAGTGAGGAAGATCCAGGGGGATGGGGCAGCTCTCCAGGAGAAGCTGTGTGCCACCTAC
AAGCTGTGCCACCCTGAGGAGCTGGTGCTGCTGGGACACTCTCTGGGCATCCCCTGGGCTCCCCTGAGCAGCTGCCCCAGCCAGGCCCTGCAGCTGGCAGGCTGCTT
GAGCCAACTCCATAGTGGCCTTTTCCTCTACCAGGGGCTCCTGCAGGCCCTGGAAGGGATCTCCCCTGAGTTGGGTCCCACCTTGGACACACTGCAGCTGGATGTTGC
TGACTTTGCCACCACCATCTGGCAGCAGATGGAAGAACTGGGAATGGCCCCTGCCCTGCAGCCCACCCAGGGTGCCATGCCTGCCTTTGCCTCTGCTTTCCAGAGAAG
GGCAGGAGGGGTCCTGGTTGCCTCCCATCTGCAGAGCTTCCTGGAGGTGTCCTACAGAGTTCTAAGACACCTTGCCCAGCCCTGATAGATCTACTTCTGGCTAATAAA
AGATCAGAGCTCTAGTGATCTGTGTGTTGGTTTTTTGTGTCTGCATTCTAGCTCTAGTGATCAGCAGTTCAACCTGTTGATAGTATGTACTAAGCTCTCATGTTTAATGT
ACTAAGCTCTCATGTTTAATGAACTAAACCCTCATGGCTAATGTACTAAGCTCTCATGGCTAATGTACTAAGCTCTCATGTTTCATGTACTAAGCTCTCATGTTTGAACA
ATAAAATTAATATAAATCAGCAACTTAAATAGCCTCTAAGGTTTTAAGTTTTATAAGAAAAAAAAGAATATATAAGGCTTTTAAAGGTTTTAAGGTTTCCTAGGTTATC
CTCATATGAGCTCTTAGAAAAACTCATCCAGCATCAAATGAAACTGCAATTTATTCATATCAGGATTATCAATACCATATTTTTGAAAAAGTCTTTTCTGTAATGAAGGA
GAAAACTCACCCAGGCAGTTCCATAGGATGGCAAGATCCTGGTATCTGTCTGCAATTCCAACTCTTCCAACATCAATACAACCTATTAATTTCCCCTCATCAAAAATAA
GGTTATCAAGTGAGAAATCACCATGAGTGACCACTGAATCTGGTGAGAATGGCAAAAGATTATGCATTTCTTTCCAGACTTGTTCAACAGGCCAGCCATTTCTCTCATC
ATCAAAATCACTGGCATCAACCAAACCATTATTCATTCTTGATTGGGCCTGAGCCAGTCTAAATACTCTATCAGAGTTAAAAGGACAATTACAAACAGGAATGGAATG
CAATCTTCTCAGGAACACTGCCAGGGCATCAACAATATTTTCACCTGAATCAGGATATTCTTCCAATACCTGGAATGCTGTTTTCCCTGGGATGGCAGTGGTGAGTAAC
CATGCATCATCAGGAGTTCTGATAAAATGCTTGATGGTTGGAAGAGGCATAAATTCAGTCAGCCAGTTTAGTCTGACCATCTCATCTGTAACATCATTGGCAACAGAA
CCTTTGCCATGTTTCAGAAACAACTCTGGGGCATCTGGCTTCCCATACAATCTATAGATTGTGGCACCTGATTGCCCAACATTATCTCTAGCCCATTTATACCCATATAA
ATCAGCATCCATGTTGGAATTTAATCTTGGCCTGGAGCAAGAGGTTTCTCTTTGAATATGGCTCATACATGTGCACCTCCTATAGTGAGTTGTATTATACTATGCAGAT
ATACTATGCCAATGTTTAATTGTCAG

FIG. 28 mCMV-hCMV-EF1 : DraIIIRINhe-ΔmCMV-ΔhCMV-EF1-I126-BstEII-ΔGCSF-BglII-polyA-BV2
(SEQ ID NO:15)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGTCTAGCatGTTACATAACTTATGGTAAATGGCCTGCCTGGCTGACTGCCCAATGACCCCTGCCCAATGATGTCAATAATG
ATGTATGTTCCCATGTAATGCCAATAGGGACTTTCCATTGATGTCAATGGGTGGAGTATTTATGGTAACTGCCCACTTGGCAGTACATCAAGTGTATCATATGCCAA
GTATGCCCCCTATTGATGTCAATGATGGTAAATGGCCTGCCTGGCATTATGCCCAGTACATGACCTTATGGGACTTTCCTACTTGGCAGTACATCTATGTATTAGTC
ATTGCTATTATCTAGCACTAGTGGAGAAGAGCATGCTTGAGGGCTGAGTGCCCCTCAGTGGGCAGAGAGCACATGGCCCACAGTCCCTGAGAAGTTGGGGGGAGG
GGTGGGCAATTGAACTGGTGCCTAGAGAAGGTGGGGCTTGGGTAAACTGGGAAAGTGATGTGGTGTACTGGCTCCACCTTTTTCCCCAGGGTGGGGGAGAACCAT
ATATAAGTGCAGTAGTCTCTGTGAACATTCAAGCTTCTGCCTTCTCCCTCCTGTGAGTTTGGTAAGTCACTGACTGTCTATGCCTGGGAAAGGGTGGGCAGGAGATGG
GGCAGTGCAGGAAAAGTGGCACTATGAACCCTGCAGCCCTAGACAATTGTACTAACCTTCTTCTCTTTCCTCTCCTGACAGGTTGGTAACCAAGCTTTCCATGGCTGG
ACCTGCCACCCAGAGCCCCATGAAGCTGATGGCCCTGCAGCTGCTGCTGTGGCACAGTGCACTCTGGACAGTGCAGGAAGCCACCCCCCTGGGCCCTGCCAGCTCCC
TGCCCCAGAGCTTCCTGCTCAAGTGCTTAGAGCAAGTGAGGAAGATCCAGGGGGATGGGGCAGCTCTCCAGGAGAAGCTGTGTGCCACCTACAAGCTGTGCCACCC
TGAGGAGCTGGTGCTGCTGGGACACTCTCTGGGCATCCCCTGGGCTCCCCTGAGCAGCTGCCCCAGCCAGGCCCTGCAGCTGGCAGGCTGCTTGAGCCAACTCCATA
GTGGCCTTTTCCTCTACCAGGGGCTCCTGCAGGCCCTGGAAGGGATCTCCCCTGAGTTGGGTCCCACCTTGGACACACTGCAGCTGGATGTTGCTGACTTTGCCACCA
CCATCTGGCAGCAGATGGAAGAACTGGGAATGGCCCCTGCCCTGCAGCCCACCCAGGGTGCCATGCCTGCCTTTGCCTCTGCTTTCCAGAGAAGGGCAGGAGGGGT
CCTGGTTGCCTCCCATCTGCAGAGCTTCCTGGAGGTGTCCTACAGAGTTCTAAGACACCTTGCCCAGCCCTGATAGATCTACTTCTGGCTAATAAAAGATCAGAGCTCT
AGTGATCTGTGTGTTGGTTTTTTGTGTCTGCATTCTAGCTCTAGTGATCAGCAGTTCAACCTGTTGATAGTATGTACTAAGCTCTCATGTTTAATGTACTAAGCTCTCAT
GTTTAATGAACTAAACCCTCATGGCTAATGTACTAAGCTCTCATGGCTAATGTACTAAGCTCTCATGTTTCATGTACTAAGCTCTCATGTTTGAACAATAAAATTAATAT
AAATCAGCAACTTAAATAGCCTCTAAGGTTTTAAGTTTTATAAGAAAAAAAAGAATATATAAGGCTTTTAAAGGTTTTAAGGTTTCCTAGGTTATCCTCATATGAGCTC
TTAGAAAAACTCATCCAGCATCAAATGAAACTGCAATTTATTCATATCAGGATTATCAATACCATATTTTTGAAAAAGTCTTTTCTGTAATGAAGGAGAAAACTCACCC
AGGCAGTTCCATAGGATGGCAAGATCCTGGTATCTGTCTGCAATTCCAACTCTTCCAACATCAATACAACCTATTAATTTCCCCTCATCAAAAATAAGGTTATCAAGTG
AGAAATCACCATGAGTGACCACTGAATCTGGTGAGAATGGCAAAAGATTATGCATTTCTTTCCAGACTTGTTCAACAGGCCAGCCATTTCTCTCATCATCAAAATCACT
GGCATCAACCAAACCATTATTCATTCTTGATTGGGCCTGAGCCAGTCTAAATACTCTATCAGAGTTAAAAGGACAATTACAAACAGGAATGGAATGCAATCTTCTCAG
GAACACTGCCAGGGCATCAACAATATTTTCACCTGAATCAGGATATTCTTCCAATACCTGGAATGCTGTTTTCCCTGGGATGGCAGTGGTGAGTAACCATGCATCATC
AGGAGTTCTGATAAAATGCTTGATGGTTGGAAGAGGCATAAATTCAGTCAGCCAGTTTAGTCTGACCATCTCATCTGTAACATCATTGGCAACAGAACCTTTGCCATG
TTTCAGAAACAACTCTGGGGCATCTGGCTTCCCATACAATCTATAGATTGTGGCACCTGATTGCCCAACATTATCTCTAGCCCATTTATACCCATATAAATCAGCATCCA
TGTTGGAATTTAATCTTGGCCTGGAGCAAGAGGTTTCTCTTTGAATATGGCTCATACATGTGCACCTCCTATAGTGAGTTGTATTATACTATGCAGATATACTATGCCA
ATGTTTAATTGTCAG

FIG. 29 mCMV- EF1 : DraIIIRINhe-ΔmCMV-EF1-I126-BstEII-ΔGCSF-BglII-polyA-BV2
(SEQ ID NO:16)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCTT
TCCATGGCTGGACCTGCCACCCAGAGCCCCATGAAGCTGATGGCCCTGCAGCTGCTGCTGTGGCACAGTGCACTCTGGACAGTGCAGGAAGCCACCCCCCTGGGCCC
TGCCAGCTCCCTGCCCCAGAGCTTCCTGCTCAAGTGCTTAGAGCAAGTGAGGAAGATCCAGGGGGATGGGGCAGCTCTCCAGGAGAAGCTGTGTGCCACCTACAAG
CTGTGCCACCCTGAGGAGCTGGTGCTGCTGGGACACTCTCTGGGCATCCCCTGGGCTCCCCTGAGCAGCTGCCCCAGCCAGGCCCTGCAGCTGGCAGGCTGCTTGAG
CCAACTCCATAGTGGCCTTTTCCTCTACCAGGGGCTCCTGCAGGCCCTGGAAGGGATCTCCCCTGAGTTGGGTCCCACCTTGGACACACTGCAGCTGGATGTTGCTGA
CTTTGCCACCACCATCTGGCAGCAGATGGAAGAACTGGGAATGGCCCCTGCCCTGCAGCCCACCCAGGGTGCCATGCCTGCCTTTGCCTCTGCTTTCCAGAGAAGGG
CAGGAGGGGTCCTGGTTGCCTCCCATCTGCAGAGCTTCCTGGAGGTGTCCTACAGAGTTCTAAGACACCTTGCCCAGCCCTGATAGATCTACTTCTGGCTAATAAAAG
ATCAGAGCTCTAGTGATCTGTGTGTTGGTTTTTTGTGTCTGCATTCTAGCTCTAGTGATCAGCAGTTCAACCTGTTGATAGTATGTACTAAGCTCTCATGTTTAATGTAC
TAAGCTCTCATGTTTAATGAACTAAACCCTCATGGCTAATGTACTAAGCTCTCATGGCTAATGTACTAAGCTCTCATGTTTCATGTACTAAGCTCTCATGTTTGAACAAT
AAAATTAATATAAATCAGCAACTTAAATAGCCTCTAAGGTTTTAAGTTTTATAAGAAAAAAAAGAATATATAAGGCTTTTAAAGGTTTTAAGGTTTCCTAGGTTATCCT
CATATGAGCTCTTAGAAAAACTCATCCAGCATCAAATGAAACTGCAATTTATTCATATCAGGATTATCAATACCATATTTTTGAAAAAGTCTTTTCTGTAATGAAGGAG
AAAACTCACCCAGGCAGTTCCATAGGATGGCAAGATCCTGGTATCTGTCTGCAATTCCAACTCTTCCAACATCAATACAACCTATTAATTTCCCCTCATCAAAAATAAG
GTTATCAAGTGAGAAATCACCATGAGTGACCACTGAATCTGGTGAGAATGGCAAAAGATTATGCATTTCTTTCCAGACTTGTTCAACAGGCCAGCCATTTCTCTCATCA
TCAAAATCACTGGCATCAACCAAACCATTATTCATTCTTGATTGGGCCTGAGCCAGTCTAAATACTCTATCAGAGTTAAAAGGACAATTACAAACAGGAATGGAATGC
AATCTTCTCAGGAACACTGCCAGGGCATCAACAATATTTTCACCTGAATCAGGATATTCTTCCAATACCTGGAATGCTGTTTTCCCTGGGATGGCAGTGGTGAGTAACC
ATGCATCATCAGGAGTTCTGATAAAATGCTTGATGGTTGGAAGAGGCATAAATTCAGTCAGCCAGTTTAGTCTGACCATCTCATCTGTAACATCATTGGCAACAGAAC
CTTTGCCATGTTTCAGAAACAACTCTGGGGCATCTGGCTTCCCATACAATCTATAGATTGTGGCACCTGATTGCCCAACATTATCTCTAGCCCATTTATACCCATATAAA
TCAGCATCCATGTTGGAATTTAATCTTGGCCTGGAGCAAGAGGTTTCTCTTTGAATATGGCTCATACATGTGCACCTCCTATAGTGAGTTGTATTATACTATGCAGATA
TACTATGCCAATGTTTAATTGTCAG

FIG. 31 hr3-mCMV-EF1-2 : DraIIIRINhe-hr3-ΔmCMV-EF1-I126-BstEII-ΔGCSF-BglII-polyA-BV2 (110716 #2 )
(SEQ ID NO:17)

CACTATGTGGACATGAATTCAATTGGCTAGCAAAACAAATGACATCATTCCTGATTATAATAATTTTAATTGTGCTTTACAAGTAGAATTCTACTTGTAAAGAGAGTTT
AATTTGAAAAACAAATTAGTCATTATTAAACATGTTAACAATTGTGTATAAAAATGACATCAGTTTAATGATGACATCATCTCTTGATTATGTTTTACAAGTAGAATTCT
ACTTGTAAAGCTGGTTCAGTTTTGAAAAACAAATGACATCATCTCTTGATTATGTTTTACAAGTAGAATTCTACTTGTAAAAGTGAGTTTAGTTTTAAAAAACAAATGA
CATCATTCAGTTTTGAAAAACAAATGACATCATCTCTTGATTGTGTTTTACAAGTAGAATTCTACTTGTAAAGTGAGTTCAGTTTTGAAAAACAAATGACCCTCTCATAC
AATTGTTGAACAATTTTAATAAATAATCTTTACAAGATTTCTAGCAGGAGTCAATGGGAAAAACCCATTGGAGCCAAGTACACTGACTCAATAGGGACTTTCCATTGG
GTTTTGCCCAGTACATAAGGTCAATAGGGGGTGAGTCAACAGGAAAGTCCCATTGGAGCCAAGTACATTGAGTCAATAGGGACTTTCCAATGGGTTTTGCCCAGTAC
ATAAGGTCAATGGGAGGTAAGCCAATGGGTTTTTCCCATTACTGACATGTATACTGAGTCATTAGGGACTTTCCAATGGGTTTTGCCCAGTACATAAGGTCAATAGGG
GTGAATCAACAGGAAAGTCCCATTGGAGCCAAGTACACTGAGTCAATAGGGACTTTCCATTGGGTTTTGCCCAGTACAAAAGGTCAATAGGGGGTGAGTCAATGGG
TTTTTCCCATTATTGGCACATACATAAGGTCAATAGGGGTGACTAGTGGAGAAGAGCATGCTTGAGGGCTGAGTGCCCCTCAGTGGGCAGAGAGCACATGGCCCAC
AGTCCCTGAGAAGTTGGGGGGAGGGGTGGGCAATTGAACTGGTGCCTAGAGAAGGTGGGGCTTGGGTAAACTGGGAAAGTGATGTGGTGTACTGGCTCCACCTTT
TTCCCCAGGGTGGGGGAGAACCATATATAAGTGCAGTAGTCTCTGTGAACATTCAAGCTTCTGCCTTCTCCCTCCTGTGAGTTTGGTAAGTCACTGACTGTCTATGCCT
GGGAAAGGGTGGGCAGGAGATGGGGCAGTGCAGGAAAAGTGGCACTATGAACCCTGCAGCCCTAGACAATTGTACTAACCTTCTTCTCTTTCCTCTCCTGACAGGTT
GGTAACCAAGCTTTCCATGGCTGGACCTGCCACCCAGAGCCCCATGAAGCTGATGGCCCTGCAGCTGCTGCTGTGGCACAGTGCACTCTGGACAGTGCAGGAAGCCA
CCCCCCTGGGCCCTGCCAGCTCCCTGCCCCAGAGCTTCCTGCTCAAGTGCTTAGAGCAAGTGAGGAAGATCCAGGGGGATGGGGCAGCTCTCCAGGAGAAGCTGTG
TGCCACCTACAAGCTGTGCCACCCTGAGGAGCTGGTGCTGCTGGGACACTCTCTGGGCATCCCCTGGGCTCCCCTGAGCAGCTGCCCCAGCCAGGCCCTGCAGCTGG
CAGGCTGCTTGAGCCAACTCCATAGTGGCCTTTTCCTCTACCAGGGGCTCCTGCAGGCCCTGGAAGGGATCTCCCCTGAGTTGGGTCCCACCTTGGACACACTGCAGC
TGGATGTTGCTGACTTTGCCACCACCATCTGGCAGCAGATGGAAGAACTGGGAATGGCCCCTGCCCTGCAGCCCACCCAGGGTGCCATGCCTGCCTTTGCCTCTGCTT
TCCAGAGAAGGGCAGGAGGGGTCCTGGTTGCCTCCCATCTGCAGAGCTTCCTGGAGGTGTCCTACAGAGTTCTAAGACACCTTGCCCAGCCCTGATAGATCTACTTCT
GGCTAATAAAAGATCAGAGCTCTAGTGATCTGTGTGTTGGTTTTTTGTGTCTGCATTCTAGCTCTAGTGATCAGCAGTTCAACCTGTTGATAGTATGTACTAAGCTCTC
ATGTTTAATGTACTAAGCTCTCATGTTTAATGAACTAAACCCTCATGGCTAATGTACTAAGCTCTCATGGCTAATGTACTAAGCTCTCATGTTTCATGTACTAAGCTCTC
ATGTTTGAACAATAAAATTAATATAAATCAGCAACTTAAATAGCCTCTAAGGTTTTAAGTTTTATAAGAAAAAAAAGAATATATAAGGCTTTTAAAGGTTTTAAGGTTT
CCTAGGTTATCCTCATATGAGCTCTTAGAAAAACTCATCCAGCATCAAATGAAACTGCAATTTATTCATATCAGGATTATCAATACCATATTTTTGAAAAAGTCTTTTCT
GTAATGAAGGAGAAAACTCACCCAGGCAGTTCCATAGGATGGCAAGATCCTGGTATCTGTCTGCAATTCCAACTCTTCCAACATCAATACAACCTATTAATTTCCCCTC
ATCAAAAATAAGGTTATCAAGTGAGAAATCACCATGAGTGACCACTGAATCTGGTGAGAATGGCAAAAGATTATGCATTTCTTTCCAGACTTGTTCAACAGGCCAGCC
ATTTCTCTCATCATCAAAATCACTGGCATCAACCAAACCATTATTCATTCTTGATTGGGCCTGAGCCAGTCTAAATACTCTATCAGAGTTAAAAGGACAATTACAAACA
GGAATGGAATGCAATCTTCTCAGGAACACTGCCAGGGCATCAACAATATTTTCACCTGAATCAGGATATTCTTCCAATACCTGGAATGCTGTTTTCCCTGGGATGGCA
GTGGTGAGTAACCATGCATCATCAGGAGTTCTGATAAAATGCTTGATGGTTGGAAGAGGCATAAATTCAGTCAGCCAGTTTAGTCTGACCATCTCATCTGTAACATCA
TTGGCAACAGAACCTTTGCCATGTTTCAGAAACAACTCTGGGGCATCTGGCTTCCCATACAATCTATAGATTGTGGCACCTGATTGCCCAACATTATCTCTAGCCCATTT
ATACCCATATAAATCAGCATCCATGTTGGAATTTAATCTTGGCCTGGAGCAAGAGGTTTCTCTTTGAATATGGCTCATACATGTGCACCTCCTATAGTGAGTTGTATTA
TACTATGCAGATATACTATGCCAATGTTTAATTGTCAG

FIG. 32 hr3-hCMV-hCMV-HTLV-5 : DraIIIRI-Δhr3-NheΔhCMVΔhCMVRVΔHTLV -BstEII-ΔhGCSF-BglII-MixpA/BV2 (110716 #5 : reverse hr3)

(SEQ ID NO:18)

CACTATGTGGACATGAATTCTCATAGCTAGAAATCTTGTAAAGATTATTTATTAAAATTGTTCAACAATTGTATGAGAGGGTCATTTGTTTTTCAAAACTGAACTCACTT
TACAAGTAGAATTCTACTTGTAAAACACAATCAAGAGATGATGTCATTTGTTTTTCAAAACTGAATGATGTCATTTGTTTTTTAAAACTAAACTCACTTTTACAAGTAGA
ATTCTACTTGTAAAACATAATCAAGAGATGATGTCATTTGTTTTTCAAAACTGAACCAGCTTTACAAGTAGAATTCTACTTGTAAAACATAATCAAGAGATGATGTCAT
CATTAAACTGATGTCATTTTTATACACAATTGTTAACATGTTTAATAATGACTAATTTGTTTTTCAAATTAAACTCTCTTTACAAGTAGAATTCTACTTGTAAAGCACAAT
TAAAATTATTATAATCAGGAATGATGTCATTTGTTTTGCTAGCTGTTACATAACTTATGGTAAATGGCCTGCCTGGCTGACTGCCCAATGACCCCTGCCCAATGATGT
CAATAATGATGTATGTTCCCATGTAATGCCAATAGGGACTTTCCATTGATGTCAATGGGTGGAGTATTTATGGTAACTGCCCACTTGGCAGTACATCAAGTGTATC
ATATGCCAAGTATGCCCCCTATTGATGTCAATGATGGTAAATGGCCTGCCTGGCATTATGCCCAGTACATGACCTTATGGGACTTTCCTACTTGGCAGTACATCTAT
GTATTAGTCATTGCTATTACCATGGTGATGGGTTTTGGCAGTACATCAATGGGTGTGGATAGTGGTTTGACCCATGGGGATTTCCAAGTCTCCACCCCATTGATGCCA
ATGGGAGTTTGTTTTGGCACCAAAATCAATGGGACTTTCCAAAATGTTGTAACAACTCTGCCCCATTGATGGAAATGGGTGGTAGGTGTGTGTGGTGGGAGGTCTAT
ATAAGCAGAGCTTGTTTAGTGAACTGGATGCACCTACTAGATATCCATATGGCTATCATCTCTCCTTCAATATCCATCATCCCTACCTGAGGCATCCATCCAATCATGTT
GAGTATATTTCTGCATCCTCCATCCTGTGGTGCCTCCTGAACTGATTCATCATTCTAGGTAAGTTTAAAGCTCAGGTATAGACATGGCCTTTGTCATGATCTCCCTTGGA
GCCTACCTAGACTCATCATGCTCTCCAATCTTTGCCTGACCCTGCTTGCTCAACTCTAATTCTTTGTTTATTTTTCTGTTCTGATCATTTACAGATCCAAGCTGTGACATGA
TCCCTACCATATGTTGGAGTGTAGGTAACCAAGCTTTCCATGGCTGGACCTGCCACCCAGAGCCCCATGAAGCTGATGGCCCTGCAGCTGCTGCTGTGGCACAGTGC
ACTCTGGACAGTGCAGGAAGCCACCCCCCTGGGCCCTGCCAGCTCCCTGCCCCAGAGCTTCCTGCTCAAGTGCTTAGAGCAAGTGAGGAAGATCCAGGGGGATGGG
GCAGCTCTCCAGGAGAAGCTGTGTGCCACCTACAAGCTGTGCCACCCTGAGGAGCTGGTGCTGCTGGGACACTCTCTGGGCATCCCCTGGGCTCCCCTGAGCAGCTG
CCCCAGCCAGGCCCTGCAGCTGGCAGGCTGCTTGAGCCAACTCCATAGTGGCCTTTTCCTCTACCAGGGGCTCCTGCAGGCCCTGGAAGGGATCTCCCCTGAGTTGG
GTCCCACCTTGGACACACTGCAGCTGGATGTTGCTGACTTTGCCACCACCATCTGGCAGCAGATGGAAGAACTGGGAATGGCCCCTGCCCTGCAGCCCACCCAGGGT
GCCATGCCTGCCTTTGCCTCTGCTTTCCAGAGAAGGGCAGGAGGGGTCCTGGTTGCCTCCCATCTGCAGAGCTTCCTGGAGGTGTCCTACAGAGTTCTAAGACACCTT
GCCCAGCCCTGATAGATCTACTTCTGGCTAATAAAAGATCAGAGCTCTAGTGATCTGTGTGTTGGTTTTTTGTGTCTGCATTCTAGCTCTAGTGATCAGCAGTTCAACC
TGTTGATAGTATGTACTAAGCTCTCATGTTTAATGTACTAAGCTCTCATGTTTAATGAACTAAACCCTCATGGCTAATGTACTAAGCTCTCATGGCTAATGTACTAAGCT
CTCATGTTTCATGTACTAAGCTCTCATGTTTGAACAATAAAATTAATATAAATCAGCAACTTAAATAGCCTCTAAGGTTTTAAGTTTTATAAGAAAAAAAAGAATATATA
AGGCTTTTAAAGGTTTTAAGGTTTCCTAGGTTATCCTCATATGAGCTCTTAGAAAAACTCATCCAGCATCAAATGAAACTGCAATTTATTCATATCAGGATTATCAATAC
CATATTTTTGAAAAAGTCTTTTCTGTAATGAAGGAGAAAACTCACCCAGGCAGTTCCATAGGATGGCAAGATCCTGGTATCTGTCTGCAATTCCAACTCTTCCAACATC
AATACAACCTATTAATTTCCCCTCATCAAAAATAAGGTTATCAAGTGAGAAATCACCATGAGTGACCACTGAATCTGGTGAGAATGGCAAAAGATTATGCATTTCTTTC
CAGACTTGTTCAACAGGCCAGCCATTTCTCTCATCATCAAAATCACTGGCATCAACCAAACCATTATTCATTCTTGATTGGGCCTGAGCCAGTCTAAATACTCTATCAGA
GTTAAAAGGACAATTACAAACAGGAATGGAATGCAATCTTCTCAGGAACACTGCCAGGGCATCAACAATATTTTCACCTGAATCAGGATATTCTTCCAATACCTGGAA
TGCTGTTTTCCCTGGGATGGCAGTGGTGAGTAACCATGCATCATCAGGAGTTCTGATAAAATGCTTGATGGTTGGAAGAGGCATAAATTCAGTCAGCCAGTTTAGTCT
GACCATCTCATCTGTAACATCATTGGCAACAGAACCTTTGCCATGTTTCAGAAACAACTCTGGGGCATCTGGCTTCCCATACAATCTATAGATTGTGGCACCTGATTGC
CCAACATTATCTCTAGCCCATTTATACCCATATAAATCAGCATCCATGTTGGAATTTAATCTTGGCCTGGAGCAAGAGGTTTCTCTTTGAATATGGCTCATACATGTGCA
CCTCCTATAGTGAGTTGTATTATACTATGCAGATATACTATGCCAATGTTTAATTGTCAG

FIG. 33 hr3- hCMV-hCMV-HTLV -8 : DraIIIRINhe-Δhr3-ΔhCMVΔhCMVRVΔHTLV -BstEII-ΔhGCSF-BglII-MixpA/BV2 (110716 #8)

(SEQ ID NO:19)

CACTATGTGGACATGAATTCTCATAGCTAGCAAAACAAATGACATCATTCCTGATTATAATAATTTTAATTGTGCTTTACAAGTAGAATTCTACTTGTAAAGAGAGTTTA
ATTTGAAAAACAAATTAGTCATTATTAAACATGTTAACAATTGTGTATAAAAATGACATCAGTTTAATGATGACATCATCTCTTGATTATGTTTTACAAGTAGAATTCTA
CTTGTAAAGCTGGTTCAGTTTTGAAAAACAAATGACATCATCTCTTGATTATGTTTTACAAGTAGAATTCTACTTGTAAAAGTGAGTTTAGTTTTAAAAAACAAATGAC
ATCATTCAGTTTTGAAAAACAAATGACATCATCTCTTGATTGTGTTTTACAAGTAGAATTCTACTTGTAAAGTGAGTTCAGTTTTGAAAAACAAATGACCCTCTCATACA
ATTGTTGAACAATTTTAATAAATAATCTTTACAAGATTTCTAGCTGTTACATAACTTATGGTAAATGGCCTGCCTGGCTGACTGCCCAATGACCCCTGCCCAATGATGT
CAATAATGATGTATGTTCCCATGTAATGCCAATAGGGACTTTCCATTGATGTCAATGGGTGGAGTATTTATGGTAACTGCCCACTTGGCAGTACATCAAGTGTATC
ATATGCCAAGTATGCCCCCTATTGATGTCAATGATGGTAAATGGCCTGCCTGGCATTATGCCCAGTACATGACCTTATGGGACTTTCCTACTTGGCAGTACATCTAT
GTATTAGTCATTGCTATTACCATGGTGATGGGTTTTGGCAGTACATCAATGGGTGTGGATAGTGGTTTGACCCATGGGGATTTCCAAGTCTCCACCCCATTGATGCCA
ATGGGAGTTTGTTTTGGCACCAAAATCAATGGGACTTTCCAAAATGTTGTAACAACTCTGCCCCATTGATGGAAATGGGTGGTAGGTGTGTGTGGTGGGAGGTCTAT
ATAAGCAGAGCTTGTTTAGTGAACTGGATGCACCTACTAGATATCCATATGGCTATCATCTCTCCTTCAATATCCATCATCCCTACCTGAGGCATCCATCCAATCATGTT
GAGTATATTTCTGCATCCTCCATCCTGTGGTGCCTCCTGAACTGATTCATCATTCTAGGTAAGTTTAAAGCTCAGGTATAGACATGGCCTTTGTCATGATCTCCCTTGGA
GCCTACCTAGACTCATCATGCTCTCCAATCTTTGCCTGACCCTGCTTGCTCAACTCTAATTCTTTGTTTATTTTTCTGTTCTGATCATTTACAGATCCAAGCTGTGACATGA
TCCCTACCATATGTTGGAGTGTAGGTAACCAAGCTTTCCATGGCTGGACCTGCCACCCAGAGCCCCATGAAGCTGATGGCCCTGCAGCTGCTGCTGTGGCACAGTGC
ACTCTGGACAGTGCAGGAAGCCACCCCCCTGGGCCCTGCCAGCTCCCTGCCCCAGAGCTTCCTGCTCAAGTGCTTAGAGCAAGTGAGGAAGATCCAGGGGGATGGG
GCAGCTCTCCAGGAGAAGCTGTGTGCCACCTACAAGCTGTGCCACCCTGAGGAGCTGGTGCTGCTGGGACACTCTCTGGGCATCCCCTGGGCTCCCCTGAGCAGCTG
CCCCAGCCAGGCCCTGCAGCTGGCAGGCTGCTTGAGCCAACTCCATAGTGGCCTTTTCCTCTACCAGGGGCTCCTGCAGGCCCTGGAAGGGATCTCCCCTGAGTTGG
GTCCCACCTTGGACACACTGCAGCTGGATGTTGCTGACTTTGCCACCACCATCTGGCAGCAGATGGAAGAACTGGGAATGGCCCCTGCCCTGCAGCCCACCCAGGGT
GCCATGCCTGCCTTTGCCTCTGCTTTCCAGAGAAGGGCAGGAGGGGTCCTGGTTGCCTCCCATCTGCAGAGCTTCCTGGAGGTGTCCTACAGAGTTCTAAGACACCTT
GCCCAGCCCTGATAGATCTACTTCTGGCTAATAAAAGATCAGAGCTCTAGTGATCTGTGTGTTGGTTTTTTGTGTCTGCATTCTAGCTCTAGTGATCAGCAGTTCAACC
TGTTGATAGTATGTACTAAGCTCTCATGTTTAATGTACTAAGCTCTCATGTTTAATGAACTAAACCCTCATGGCTAATGTACTAAGCTCTCATGGCTAATGTACTAAGCT
CTCATGTTTCATGTACTAAGCTCTCATGTTTGAACAATAAAATTAATATAAATCAGCAACTTAAATAGCCTCTAAGGTTTTAAGTTTTATAAGAAAAAAAAGAATATATA
AGGCTTTTAAAGGTTTTAAGGTTTCCTAGGTTATCCTCATATGAGCTCTTAGAAAAACTCATCCAGCATCAAATGAAACTGCAATTTATTCATATCAGGATTATCAATAC
CATATTTTTGAAAAAGTCTTTTCTGTAATGAAGGAGAAAACTCACCCAGGCAGTTCCATAGGATGGCAAGATCCTGGTATCTGTCTGCAATTCCAACTCTTCCAACATC
AATACAACCTATTAATTTCCCCTCATCAAAAATAAGGTTATCAAGTGAGAAATCACCATGAGTGACCACTGAATCTGGTGAGAATGGCAAAAGATTATGCATTTCTTTC
CAGACTTGTTCAACAGGCCAGCCATTTCTCTCATCATCAAAATCACTGGCATCAACCAAACCATTATTCATTCTTGATTGGGCCTGAGCCAGTCTAAATACTCTATCAGA
GTTAAAAGGACAATTACAAACAGGAATGGAATGCAATCTTCTCAGGAACACTGCCAGGGCATCAACAATATTTTCACCTGAATCAGGATATTCTTCCAATACCTGGAA
TGCTGTTTTCCCTGGGATGGCAGTGGTGAGTAACCATGCATCATCAGGAGTTCTGATAAAATGCTTGATGGTTGGAAGAGGCATAAATTCAGTCAGCCAGTTTAGTCT
GACCATCTCATCTGTAACATCATTGGCAACAGAACCTTTGCCATGTTTCAGAAACAACTCTGGGGCATCTGGCTTCCCATACAATCTATAGATTGTGGCACCTGATTGC
CCAACATTATCTCTAGCCCATTTATACCCATATAAATCAGCATCCATGTTGGAATTTAATCTTGGCCTGGAGCAAGAGGTTTCTCTTTGAATATGGCTCATACATGTGCA
CCTCCTATAGTGAGTTGTATTATACTATGCAGATATACTATGCCAATGTTTAATTGTCAG

FIG. 35

FIX Plasmid: DraIIIRINhe-ΔmCMV-EF1-I126-BstEII-ΔFIX-BgIII-polyA-BV2 (062316#4) (SEQ ID NO:20)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGCAGAGAGTGAATATGATCATGGCTGAGAGCCCTGGCCTGATCACCATCTGCCTGCTGGGCTACCTGCTGTCTGCTGAGTGCACAGTGTTTCTGGACCATGAG
AATGCCAACAAGATCCTGAACAGGCCCAAGAGGTACAACTCTGGCAAGCTGGAAGAGTTTGTGCAGGGCAACCTGGAAAGGGAATGCATGGAAGAGAAGTGCAGC
TTTGAAGAGGCCAGGGAAGTGTTTGAGAACACAGAGAGAACCACAGAGTTCTGGAAGCAGTATGTGGATGGGGACCAGTGTGAAAGCAACCCCTGCCTGAATGGG
GGCAGCTGCAAGGATGACATCAACAGCTATGAGTGCTGGTGCCCCTTTGGCTTTGAGGGCAAGAACTGTGAACTGGATGTGACCTGCAACATCAAGAATGGCAGAT
GTGAACAGTTCTGCAAGAACTCTGCTGACAACAAGGTTGTGTGCTCCTGCACAGAGGGCTACAGACTGGCTGAGAACCAGAAAAGCTGTGAACCTGCTGTGCCCTTC
CCATGTGGCAGAGTGTCTGTGTCCCAGACCAGCAAGCTGACCAGAGCTGAGACAGTGTTCCCTGATGTGGACTATGTGAACTCCACAGAGGCTGAAACCATCCTGGA
CAACATCACCCAGAGCACCCAGTCCTTCAATGACTTCACCAGAGTTGTGGGAGGGGAGGATGCCAAGCCTGGCCAGTTCCCATGGCAAGTGGTGCTGAATGGCAAA
GTGGATGCCTTCTGTGGGGGCTCCATTGTGAATGAGAAGTGGATTGTGACAGCTGCCCACTGTGTGGAAACTGGAGTGAAGATCACAGTGGTGGCTGGGGAGCAC
AACATTGAGGAAACAGAGCACACAGAGCAGAAAAGAAATGTGATCAGGATCATCCCCCACCACAACTACAATGCTGCCATCAACAAGTACAACCATGACATTGCCCT
GCTGGAACTGGATGAGCCCCTGGTGCTGAACAGCTATGTGACCCCCATCTGCATTGCTGACAAAGAGTACACCAACATCTTTCTGAAGTTTGGCTCTGGCTATGTGTC
TGGCTGGGGCAGGGTGTTCCACAAGGGAAGGAGTGCTCTGGTGCTGCAGTACCTGAGAGTGCCACTGGTGGACAGAGCCACCTGTCTGAGAAGCACCAAGTTCACC
ATCTACAACAACATGTTCTGTGCTGGCTTCCATGAGGGGGGCAGAGACTCCTGCCAGGGGGATTCTGGGGGCCCTCATGTGACAGAGGTGGAAGGCACCAGCTTTC
TGACAGGCATCATCAGCTGGGGAGAGGAATGTGCCATGAAGGGCAAATATGGCATCTACACCAAGGTGTCCAGATATGTGAATTGGATCAAAGAAAAGACCAAGCT
GACATGAAGATCTACTTCTGGCTAATAAAAGATCAGAGCTCTAGTGATCTGTGTGTTGGTTTTTTGTGTCTGCATTCTAGCTCTAGTGATCAGCAGTTCAACCTGTTGA
TAGTATGTACTAAGCTCTCATGTTTAATGTACTAAGCTCTCATGTTTAATGAACTAAACCCTCATGGCTAATGTACTAAGCTCTCATGGCTAATGTACTAAGCTCTCATG
TTTCATGTACTAAGCTCTCATGTTTGAACAATAAAATTAATATAAATCAGCAACTTAAATAGCCTCTAAGGTTTTAAGTTTTATAAGAAAAAAAAGAATATATAAGGCT
TTTAAAGGTTTTAAGGTTTCCTAGGTTATCCTCATATGAGCTCTTAGAAAAACTCATCCAGCATCAAATGAAACTGCAATTTATTCATATCAGGATTATCAATACCATAT
TTTTGAAAAAGTCTTTTCTGTAATGAAGGAGAAAACTCACCCAGGCAGTTCCATAGGATGGCAAGATCCTGGTATCTGTCTGCAATTCCAACTCTTCCAACATCAATAC
AACCTATTAATTTCCCCTCATCAAAAATAAGGTTATCAAGTGAGAAATCACCATGAGTGACCACTGAATCTGGTGAGAATGGCAAAAGATTATGCATTTCTTTCCAGAC
TTGTTCAACAGGCCAGCCATTTCTCTCATCATCAAAATCACTGGCATCAACCAAACCATTATTCATTCTTGATTGGGCCTGAGCCAGTCTAAATACTCTATCAGAGTTAA
AAGGACAATTACAAACAGGAATGGAATGCAATCTTCTCAGGAACACTGCCAGGGCATCAACAATATTTTCACCTGAATCAGGATATTCTTCCAATACCTGGAATGCTG
TTTTCCCTGGGATGGCAGTGGTGAGTAACCATGCATCATCAGGAGTTCTGATAAAATGCTTGATGGTTGGAAGAGGCATAAATTCAGTCAGCCAGTTTAGTCTGACC
ATCTCATCTGTAACATCATTGGCAACAGAACCTTTGCCATGTTTCAGAAACAACTCTGGGGCATCTGGCTTCCCATACAATCTATAGATTGTGGCACCTGATTGCCCAA
CATTATCTCTAGCCCATTTATACCCATATAAATCAGCATCCATGTTGGAATTTAATCTTGGCCTGGAGCAAGAGGTTTCTCTTTGAATATGGCTCATACATGTGCACCTC
CTATAGTGAGTTGTATTATACTATGCAGATATACTATGCCAATGTTTAATTGTCAG

FIG. 36

FIX R6K1: XbaRINhe-ΔmCMV-EF1-I126-BstEII-ΔFIX-BglII-R6K-Kan-polyA (121616 # 4) (SEQ ID NO:21)

TCTAGATGGACATGAATTCAATTGGCTAGCAGGAGTCAATGGGAAAAACCCATTGGAGCCAAGTACACTGACTCAATAGGGACTTTCCATTGGGTTTTGCCCAGTAC
ATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATGG
GAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAGG
AAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATTG
GCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAGT
TGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGGG
GGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGGG
CAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGCAGAGAGTGAATATGATCATGGCTGAGAGCCCTGGCCTGATCACCATCTGCCTGCTGGGCTACCTGCTGTCTGCTGAGTGCACAGTGTTTCTGGACCATGAG
AATGCCAACAAGATCCTGAACAGGCCCAAGAGGTACAACTCTGGCAAGCTGGAAGAGTTTGTGCAGGGCAACCTGGAAAGGGAATGCATGGAAGAGAAGTGCAGC
TTTGAAGAGGCCAGGGAAGTGTTTGAGAACACAGAGAGAACCACAGAGTTCTGGAAGCAGTATGTGGATGGGGACCAGTGTGAAAGCAACCCCTGCCTGAATGGG
GGCAGCTGCAAGGATGACATCAACAGCTATGAGTGCTGGTGCCCCTTTGGCTTTGAGGGCAAGAACTGTGAACTGGATGTGACCTGCAACATCAAGAATGGCAGAT
GTGAACAGTTCTGCAAGAACTCTGCTGACAACAAGGTTGTGTGCTCCTGCACAGAGGGCTACAGACTGGCTGAGAACCAGAAAAGCTGTGAACCTGCTGTGCCCTTC
CCATGTGGCAGAGTGTCTGTGTCCCAGACCAGCAAGCTGACCAGAGCTGAGACAGTGTTCCCTGATGTGGACTATGTGAACTCCACAGAGGCTGAAACCATCCTGGA
CAACATCACCCAGAGCACCCAGTCCTTCAATGACTTCACCAGAGTTGTGGGAGGGGAGGATGCCAAGCCTGGCCAGTTCCCATGGCAAGTGGTGCTGAATGGCAAA
GTGGATGCCTTCTGTGGGGGCTCCATTGTGAATGAGAAGTGGATTGTGACAGCTGCCCACTGTGTGGAAACTGGAGTGAAGATCACAGTGGTGGCTGGGGAGCAC
AACATTGAGGAAACAGAGCACACAGAGCAGAAAAGAAATGTGATCAGGATCATCCCCCACCACAACTACAATGCTGCCATCAACAAGTACAACCATGACATTGCCCT
GCTGGAACTGGATGAGCCCCTGGTGCTGAACAGCTATGTGACCCCCATCTGCATTGCTGACAAAGAGTACACCAACATCTTTCTGAAGTTTGGCTCTGGCTATGTGTC
TGGCTGGGGCAGGGTGTTCCACAAGGGAAGGAGTGCTCTGGTGCTGCAGTACCTGAGAGTGCCACTGGTGGACAGAGCCACCTGTCTGAGAAGCACCAAGTTCACC
ATCTACAACAACATGTTCTGTGCTGGCTTCCATGAGGGGGGCAGAGACTCCTGCCAGGGGGATTCTGGGGGCCCTCATGTGACAGAGGTGGAAGGCACCAGCTTTC
TGACAGGCATCATCAGCTGGGGAGAGGAATGTGCCATGAAGGGCAAATATGGCATCTACACCAAGGTGTCCAGATATGTGAATTGGATCAAAGAAAAGACCAAGCT
GACATGAAGATCTAGCTCTAGTGATCAGCAGTTCAACCTGTTGATAGTATGTACTAAGCTCTCATGTTTAATGTACTAAGCTCTCATGTTTAATGAACTAAACCCTCAT
GGCTAATGTACTAAGCTCTCATGGCTAATGTACTAAGCTCTCATGTTTCATGTACTAAGCTCTCATGTTTGAACAATAAAATTAATATAAATCAGCAACTTAAATAGCCT
CTAAGGTTTTAAGTTTTATAAGAAAAAAAAGAATATATAAGGCTTTTAAAGGTTTTAAGGTTTCCTAGGTTATCCTCATATGAGCTCTTAGAAAAACTCATCCAGCATC
AAATGAAACTGCAATTTATTCATATCAGGATTATCAATACCATATTTTTGAAAAAGTCTTTTCTGTAATGAAGGAGAAAACTCACCCAGGCAGTTCCATAGGATGGCAA
GATCCTGGTATCTGTCTGCAATTCCAACTCTTCCAACATCAATACAACCTATTAATTTCCCCTCATCAAAAATAAGGTTATCAAGTGAGAAATCACCATGAGTGACCACT
GAATCTGGTGAGAATGGCAAAAGATTATGCATTTCTTTCCAGACTTGTTCAACAGGCCAGCCATTTCTCTCATCATCAAAATCACTGGCATCAACCAAACCATTATTCA
TTCTTGATTGGGCCTGAGCCAGTCTAAATACTCTATCAGAGTTAAAAGGACAATTACAAACAGGAATGGAATGCAATCTTCTCAGGAACACTGCCAGGGCATCAACA
ATATTTTCACCTGAATCAGGATATTCTTCCAATACCTGGAATGCTGTTTTCCCTGGGATGGCAGTGGTGAGTAACCATGCATCATCAGGAGTTCTGATAAAATGCTTGA
TGGTTGGAAGAGGCATAAATTCAGTCAGCCAGTTTAGTCTGACCATCTCATCTGTAACATCATTGGCAACAGAACCTTTGCCATGTTTCAGAAACAACTCTGGGGCAT
CTGGCTTCCCATACAATCTATAGATTGTGGCACCTGATTGCCCAACATTATCTCTAGCCCATTTATACCCATATAAATCAGCATCCATGTTGGAATTTAATCTTGGCCTG
GAGCAAGAGGTTTCTCTTTGAATATGGCTCATACATGTGCACCTCCTATAGTGAGTTGTATTATACTATGCAGATATACTATGCCAATGTTTAATTGTCAGCTCTAGCA
CTTCTGGCTAATAAAAGATCAGAGCTCTAGTGATCTGTGTGTTGGTTTTTTGTGTCTGCAT

FIG. 37

FIX R6K1: DraIIIRINhe-ΔmCMV-EF1-RV-MIP-GA-R6K-Kan-MIP-BstEII-ΔFIX-BglII-polyA (121616 # 8) (SEQ ID NO:22)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGATGCACCTACTAGATATCattgggATCTTCacacagcag
GTaaggttgtgGGCTGGGCCTGGGCTGGGTCTGGGCTGGGGATCAGCAGTTCAACCTGTTGATAGTATGTACTAAGCTCTCATGTTTAATGTACTAAGCTCTCATGTTTA
ATGAACTAAACCCTCATGGCTAATGTACTAAGCTCTCATGGCTAATGTACTAAGCTCTCATGTTTCATGTACTAAGCTCTCATGTTTGAACAATAAAATTAATATAAATC
AGCAACTTAAATAGCCTCTAAGGTTTTAAGTTTTATAAGAAAAAAAAGAATATATAAGGCTTTTAAAGGTTTTAAGGTTTCCTAGGTTATCCTCATATGAGCTCTTAGA
AAAACTCATCCAGCATCAAATGAAACTGCAATTTATTCATATCAGGATTATCAATACCATATTTTTGAAAAAGTCTTTTCTGTAATGAAGGAGAAAACTCACCCAGGCA
GTTCCATAGGATGGCAAGATCCTGGTATCTGTCTGCAATTCCAACTCTTCCAACATCAATACAACCTATTAATTTCCCCTCATCAAAAATAAGGTTATCAAGTGAGAAA
TCACCATGAGTGACCACTGAATCTGGTGAGAATGGCAAAAGATTATGCATTTCTTTCCAGACTTGTTCAACAGGCCAGCCATTTCTCTCATCATCAAAATCACTGGCAT
CAACCAAACCATTATTCATTCTTGATTGGGCCTGAGCCAGTCTAAATACTCTATCAGAGTTAAAAGGACAATTACAAACAGGAATGGAATGCAATCTTCTCAGGAACA
CTGCCAGGGCATCAACAATATTTTCACCTGAATCAGGATATTCTTCCAATACCTGGAATGCTGTTTTCCCTGGGATGGCAGTGGTGAGTAACCATGCATCATCAGGAG
TTCTGATAAAATGCTTGATGGTTGGAAGAGGCATAAATTCAGTCAGCCAGTTTAGTCTGACCATCTCATCTGTAACATCATTGGCAACAGAACCTTTGCCATGTTTCAG
AAACAACTCTGGGGCATCTGGCTTCCCATACAATCTATAGATTGTGGCACCTGATTGCCCAACATTATCTCTAGCCCATTTATACCCATATAAATCAGCATCCATGTTGG
AATTTAATCTTGGCCTGGAGCAAGAGGTTTCTCTTTGAATATGGCTCATACATGTGCACCTCCTATAGTGAGTTGTATTATACTATGCAGATATACTATGCCAATGTTTA
ATTGTCAGctgcaCTGACccctggtgttgcTTTTTTTTTTTAGgctgcaagCTGAAGtgtgtccAGTTGGTAACCAAGCCACCATGCAGAGAGTGAATATGATCATGGCTGAGAGC
CCTGGCCTGATCACCATCTGCCTGCTGGGCTACCTGCTGTCTGCTGAGTGCACAGTGTTTCTGGACCATGAGAATGCCAACAAGATCCTGAACAGGCCCAAGAGGTA
CAACTCTGGCAAGCTGGAAGAGTTTGTGCAGGGCAACCTGGAAAGGGAATGCATGGAAGAGAAGTGCAGCTTTGAAGAGGCCAGGGAAGTGTTTGAGAACACAG
AGAGAACCACAGAGTTCTGGAAGCAGTATGTGGATGGGGACCAGTGTGAAAGCAACCCCTGCCTGAATGGGGGCAGCTGCAAGGATGACATCAACAGCTATGAGT
GCTGGTGCCCCTTTGGCTTTGAGGGCAAGAACTGTGAACTGGATGTGACCTGCAACATCAAGAATGGCAGATGTGAACAGTTCTGCAAGAACTCTGCTGACAACAAG
GTTGTGTGCTCCTGCACAGAGGGCTACAGACTGGCTGAGAACCAGAAAAGCTGTGAACCTGCTGTGCCCTTCCCATGTGGCAGAGTGTCTGTGTCCCAGACCAGCAA
GCTGACCAGAGCTGAGACAGTGTTCCCTGATGTGGACTATGTGAACTCCACAGAGGCTGAAACCATCCTGGACAACATCACCCAGAGCACCCAGTCCTTCAATGACTT
CACCAGAGTTGTGGGAGGGGAGGATGCCAAGCCTGGCCAGTTCCCATGGCAAGTGGTGCTGAATGGCAAAGTGGATGCCTTCTGTGGGGGCTCCATTGTGAATGA
GAAGTGGATTGTGACAGCTGCCCACTGTGTGGAAACTGGAGTGAAGATCACAGTGGTGGCTGGGGAGCACAACATTGAGGAAACAGAGCACACAGAGCAGAAAA
GAAATGTGATCAGGATCATCCCCCACCACAACTACAATGCTGCCATCAACAAGTACAACCATGACATTGCCCTGCTGGAACTGGATGAGCCCCTGGTGCTGAACAGCT
ATGTGACCCCCATCTGCATTGCTGACAAAGAGTACACCAACATCTTTCTGAAGTTTGGCTCTGGCTATGTGTCTGGCTGGGGCAGGGTGTTCCACAAGGGAAGGAGT
GCTCTGGTGCTGCAGTACCTGAGAGTGCCACTGGTGGACAGAGCCACCTGTCTGAGAAGCACCAAGTTCACCATCTACAACAACATGTTCTGTGCTGGCTTCCATGA
GGGGGGCAGAGACTCCTGCCAGGGGGATTCTGGGGGCCCTCATGTGACAGAGGTGGAAGGCACCAGCTTTCTGACAGGCATCATCAGCTGGGGAGAGGAATGTGC
CATGAAGGGCAAATATGGCATCTACACCAAGGTGTCCAGATATGTGAATTGGATCAAAGAAAAGACCAAGCTGACATGAAGATCTACTTCTGGCTAATAAAAGATCA
GAGCTCTAGTGATCTGTGTGTTGGTTTTTTGTGTCTGCATTCTAGCTCTAGTGATCAGCAGTTCAACCTGTTGATAGTATGTACTAAGCTCTCATGTTTAATGTACTAAG
CTCTCATGTTTAATGAACTAAACCCTCATGGCTAATGTACTAAGCTCTCATGGCTAATGTACTAAGCTCTCATGTTTCATGTACTAAGCTCTCATGTTTGAACAATAAAA
TTAATATAAATCAGCAACTTAAATAGCCTCTAAGGTTTTAAGTTTTATAAGAAAAAAAAGAATATATAAGGCTTTTAAAGGTTTTAAGGTTTCCTAGGTTATCCTCATAT
GAGCTCTTAGAAAAACTCATCCAGCATCAAATGAAACTGCAATTTATTCATATCAGGATTATCAATACCATATTTTTGAAAAAGTCTTTTCTGTAATGAAGGAGAAAAC
TCACCCAGGCAGTTCCATAGGATGGCAAGATCCTGGTATCTGTCTGCAATTCCAACTCTTCCAACATCAATACAACCTATTAATTTCCCCTCATCAAAAATAAGGTTATC
AAGTGAGAAATCACCATGAGTGACCACTGAATCTGGTGAGAATGGCAAAAGATTATGCATTTCTTTCCAGACTTGTTCAACAGGCCAGCCATTTCTCTCATCATCAAA
ATCACTGGCATCAACCAAACCATTATTCATTCTTGATTGGGCCTGAGCCAGTCTAAATACTCTATCAGAGTTAAAAGGACAATTACAAACAGGAATGGAATGCAATCT
TCTCAGGAACACTGCCAGGGCATCAACAATATTTTCACCTGAATCAGGATATTCTTCCAATACCTGGAATGCTGTTTTCCCTGGGATGGCAGTGGTGAGTAACCATGC
ATCATCAGGAGTTCTGATAAAATGCTTGATGGTTGGAAGAGGCATAAATTCAGTCAGCCAGTTTAGTCTGACCATCTCATCTGTAACATCATTGGCAACAGAACCTTT
GCCATGTTTCAGAAACAACTCTGGGGCATCTGGCTTCCCATACAATCTATAGATTGTGGCACCTGATTGCCCAACATTATCTCTAGCCCATTTATACCCATATAAATCAG
CATCCATGTTGGAATTTAATCTTGGCCTGGAGCAAGAGGTTTCTCTTTGAATATGGCTCATACATGTGCACCTCCTATAGTGAGTTGTATTATACTATGCAGATATACT
ATGCCAATGTTTAATTGTCAG

FIG. 38

FIX Superenh: DraIIIRINhe-SuperEnhancer-ΔmCMV-EF1-I126-BstEII-ΔFIX-BglII-polyA-BV2 (121616 # 12)

(SEQ ID NO:23)

CACTATGTGGACATGAATTCAATTGGCTAGCAAAACAAATGACATCATTCCTGATTATAATAATTTTAATTGTGCTTTACAAGTAGAATTCTACTTGTAAAGAGAGTTT
AATTTGAAAAACAAATTAGTCATTATTAAACATGTTAACAATTGTGTATAAAAATGACATCAGTTTAATGATGACATCATCTCTTGATTATGTTTTACAAGTAGAATTCT
ACTTGTAAAGCTGGTTCAGTTTTGAAAAACAAATGACATCATCTCTTGATTATGTTTTACAAGTAGAATTCTACTTGTAAAAGTGAGTTTAGTTTTAAAAAACAAATGA
CATCATTCAGTTTTGAAAAACAAATGACATCATCTCTTGATTGTGTTTTACAAGTAGAATTCTACTTGTAAAGTGAGTTCAGTTTTGAAAAACAAATGACCCTCTCATAC
AATTGTTGAACAATTTTAATAAATAATCTTTACAAGATTTCTAGCAGGAGTCAATGGGAAAAACCCATTGGAGCCAAGTACACTGACTCAATAGGGACTTTCCATTGG
GTTTTGCCCAGTACATAAGGTCAATAGGGGGTGAGTCAACAGGAAAGTCCCATTGGAGCCAAGTACATTGAGTCAATAGGGACTTTCCAATGGGTTTTGCCCAGTAC
ATAAGGTCAATGGGAGGTAAGCCAATGGGTTTTTCCCATTACTGACATGTATACTGAGTCATTAGGGACTTTCCAATGGGTTTTGCCCAGTACATAAGGTCAATAGGG
GTGAATCAACAGGAAAGTCCCATTGGAGCCAAGTACACTGAGTCAATAGGGACTTTCCATTGGGTTTTGCCCAGTACAAAAGGTCAATAGGGGGTGAGTCAATGGG
TTTTTCCCATTATTGGCACATACATAAGGTCAATAGGGGTGACTAGTGGAGAAGAGCATGCTTGAGGGCTGAGTGCCCCTCAGTGGGCAGAGAGCACATGGCCCAC
AGTCCCTGAGAAGTTGGGGGGAGGGGTGGGCAATTGAACTGGTGCCTAGAGAAGGTGGGGCTTGGGTAAACTGGGAAAGTGATGTGGTGTACTGGCTCCACCTTT
TTCCCCAGGGTGGGGGAGAACCATATATAAGTGCAGTAGTCTCTGTGAACATTCAAGCTTCTGCCTTCTCCCTCCTGTGAGTTTGGTAAGTCACTGACTGTCTATGCCT
GGGAAAGGGTGGGCAGGAGATGGGGCAGTGCAGGAAAAGTGGCACTATGAACCCTGCAGCCCTAGACAATTGTACTAACCTTCTTCTCTTTCCTCTCCTGACAGGTT
GGTAACCAAGCCACCATGCAGAGAGTGAATATGATCATGGCTGAGAGCCCTGGCCTGATCACCATCTGCCTGCTGGGCTACCTGCTGTCTGCTGAGTGCACAGTGTT
TCTGGACCATGAGAATGCCAACAAGATCCTGAACAGGCCCAAGAGGTACAACTCTGGCAAGCTGGAAGAGTTTGTGCAGGGCAACCTGGAAAGGGAATGCATGGA
AGAGAAGTGCAGCTTTGAAGAGGCCAGGGAAGTGTTTGAGAACACAGAGAGAACCACAGAGTTCTGGAAGCAGTATGTGGATGGGGACCAGTGTGAAAGCAACC
CCTGCCTGAATGGGGGCAGCTGCAAGGATGACATCAACAGCTATGAGTGCTGGTGCCCCTTTGGCTTTGAGGGCAAGAACTGTGAACTGGATGTGACCTGCAACAT
CAAGAATGGCAGATGTGAACAGTTCTGCAAGAACTCTGCTGACAACAAGGTTGTGTGCTCCTGCACAGAGGGCTACAGACTGGCTGAGAACCAGAAAAGCTGTGAA
CCTGCTGTGCCCTTCCCATGTGGCAGAGTGTCTGTGTCCCAGACCAGCAAGCTGACCAGAGCTGAGACAGTGTTCCCTGATGTGGACTATGTGAACTCCACAGAGGC
TGAAACCATCCTGGACAACATCACCCAGAGCACCCAGTCCTTCAATGACTTCACCAGAGTTGTGGGAGGGGAGGATGCCAAGCCTGGCCAGTTCCCATGGCAAGTGG
TGCTGAATGGCAAAGTGGATGCCTTCTGTGGGGGCTCCATTGTGAATGAGAAGTGGATTGTGACAGCTGCCCACTGTGTGGAAACTGGAGTGAAGATCACAGTGGT
GGCTGGGGAGCACAACATTGAGGAAACAGAGCACACAGAGCAGAAAAGAAATGTGATCAGGATCATCCCCCACCACAACTACAATGCTGCCATCAACAAGTACAAC
CATGACATTGCCCTGCTGGAACTGGATGAGCCCCTGGTGCTGAACAGCTATGTGACCCCCATCTGCATTGCTGACAAAGAGTACACCAACATCTTTCTGAAGTTTGGC
TCTGGCTATGTGTCTGGCTGGGGCAGGGTGTTCCACAAGGGAAGGAGTGCTCTGGTGCTGCAGTACCTGAGAGTGCCACTGGTGGACAGAGCCACCTGTCTGAGAA
GCACCAAGTTCACCATCTACAACAACATGTTCTGTGCTGGCTTCCATGAGGGGGGCAGAGACTCCTGCCAGGGGGATTCTGGGGGCCCTCATGTGACAGAGGTGGA
AGGCACCAGCTTTCTGACAGGCATCATCAGCTGGGGAGAGGAATGTGCCATGAAGGGCAAATATGGCATCTACACCAAGGTGTCCAGATATGTGAATTGGATCAAA
GAAAAGACCAAGCTGACATGAAGATCTACTTCTGGCTAATAAAAGATCAGAGCTCTAGTGATCTGTGTGTTGGTTTTTTGTGTCTGCATTCTAGCTCTAGTGATCAGC
AGTTCAACCTGTTGATAGTATGTACTAAGCTCTCATGTTTAATGTACTAAGCTCTCATGTTTAATGAACTAAACCCTCATGGCTAATGTACTAAGCTCTCATGGCTAATG
TACTAAGCTCTCATGTTTCATGTACTAAGCTCTCATGTTTGAACAATAAAATTAATATAAATCAGCAACTTAAATAGCCTCTAAGGTTTTAAGTTTTATAAGAAAAAAAA
GAATATATAAGGCTTTTAAAGGTTTTAAGGTTTCCTAGGTTATCCTCATATGAGCTCTTAGAAAAACTCATCCAGCATCAAATGAAACTGCAATTTATTCATATCAGGA
TTATCAATACCATATTTTTGAAAAAGTCTTTTCTGTAATGAAGGAGAAAACTCACCCAGGCAGTTCCATAGGATGGCAAGATCCTGGTATCTGTCTGCAATTCCAACTC
TTCCAACATCAATACAACCTATTAATTTCCCCTCATCAAAAATAAGGTTATCAAGTGAGAAATCACCATGAGTGACCACTGAATCTGGTGAGAATGGCAAAAGATTAT
GCATTTCTTTCCAGACTTGTTCAACAGGCCAGCCATTTCTCTCATCATCAAAATCACTGGCATCAACCAAACCATTATTCATTCTTGATTGGGCCTGAGCCAGTCTAAAT
ACTCTATCAGAGTTAAAAGGACAATTACAAACAGGAATGGAATGCAATCTTCTCAGGAACACTGCCAGGGCATCAACAATATTTTCACCTGAATCAGGATATTCTTCC
AATACCTGGAATGCTGTTTTCCCTGGGATGGCAGTGGTGAGTAACCATGCATCATCAGGAGTTCTGATAAAATGCTTGATGGTTGGAAGAGGCATAAATTCAGTCAG
CCAGTTTAGTCTGACCATCTCATCTGTAACATCATTGGCAACAGAACCTTTGCCATGTTTCAGAAACAACTCTGGGGCATCTGGCTTCCCATACAATCTATAGATTGTG
GCACCTGATTGCCCAACATTATCTCTAGCCCATTTATACCCATATAAATCAGCATCCATGTTGGAATTTAATCTTGGCCTGGAGCAAGAGGTTTCTCTTTGAATATGGCT
CATACATGTGCACCTCCTATAGTGAGTTGTATTATACTATGCAGATATACTATGCCAATGTTTAATTGTCAG

FIG. 39

FIX RNAout: NTC9385R-delta hFIX: Nature Technology (natx.com/): RNAout-cmv-ΔFIX (SEQ ID NO:24)

CCGCCTAATGAGCGGGCTTTTTTTTGGCTTGTTGTCCACAACCGTTAAACCTTAAAAGCTTTAAAAGCCTTATATATTCTTTTTTTTCTTATAAAACTTAAAACCTTAGAG
GCTATTTAAGTTGCTGATTTATATTAATTTTATTGTTCAAACATGAGAGCTTAGTACGTGAAACATGAGAGCTTAGTACGTTAGCCATGAGAGCTTAGTACGTTAGCCA
TGAGGGTTTAGTTCGTTAAACATGAGAGCTTAGTACGTTAAACATGAGAGCTTAGTACGTACTATCAACAGGTTGAACTGCTGATCCACGTTGTGGTAGAATTGGTAA
AGAGAGTCGTGTAAAATATCGAGTTCGCACATCTTGTTGTCTGATTATTGATTTTTGGCGAAACCATTTGATCATATGACAAGATGTGTATCTACCTTAACTTAATGATT
TTGATAAAAATCATTAGGTACCCCGGCTCTAGTTATTAATAGTAATCAATTACGGGGTCATTAGTTCATAGCCCATATATGGAGTTCCGCGTTACATAACTTACGGTAA
ATGGCCCGCCTGGCTGACCGCCCAACGACCCCCGCCCATTGACGTCAATAATGACGTATGTTCCCATAGTAACGCCAATAGGGACTTTCCATTGACGTCAATGGGTGG
AGTATTTACGGTAAACTGCCCACTTGGCAGTACATCAAGTGTATCATATGCCAAGTACGCCCCCTATTGACGTCAATGACGGTAAATGGCCCGCCTGGCATTATGCCC
AGTACATGACCTTATGGGACTTTCCTACTTGGCAGTACATCTACGTATTAGTCATCGCTATTACCATGGTGATGCGGTTTTGGCAGTACATCAATGGGCGTGGATAGC
GGTTTGACTCACGGGGATTTCCAAGTCTCCACCCCATTGACGTCAATGGGAGTTTGTTTTGGCACCAAAATCAACGGGACTTTCCAAAATGTCGTAACAACTCCGCCC
CATTGACGCAAATGGGCGGTAGGCGTGTACGGTGGGAGGTCTATATAAGCAGAGCTCGTTTAGTGAACCGTCAGATCGCCTGGAGACGCCATCCACGCTGTTTTGA
CCTCCATAGAAGACACCGGGACCGATCCAGCCTCCGCGGCTCGCATCTCTCCTTCACGCGCCCGCCGCCCTACCTGAGGCCGCCATCCACGCCGGTTGAGTCGCGTTC
TGCCGCCTCCCGCCTGTGGTGCCTCCTGAACTGCGTCCGCCGTCTAGGTAAGTTTAAAGCTCAGGTCGAGACCGGGCCTTTGTCCGGCGCTCCCTTGGAGCCTACCTA
GACTCAGCCGGCTCTCCACGCTTTGCCTGACCCTGCTTGCTCAACTCTAGTTCTCTCGTTAACTTAATGAGACAGATAGAAACTGGTCTTGTAGAAACAGAGTAGTCGC
CTGCTTTTCTGCCAGGTGCTGACTTCTCTCCCCTGGGCTTTTTTCTTTTTCTCAGGTTGAAAAGAAGAAGACGAAGAAGACGAAGAAGACAAACCGTCGTCGACGCTA
GGTAACCAAGCCACCATGCAGAGAGTGAATATGATCATGGCTGAGAGCCCTGGCCTGATCACCATCTGCCTGCTGGGCTACCTGCTGTCTGCTGAGTGCACAGTGTT
TCTGGACCATGAGAATGCCAACAAGATCCTGAACAGGCCCAAGAGGTACAACTCTGGCAAGCTGGAAGAGTTTGTGCAGGGCAACCTGGAAAGGGAATGCATGGA
AGAGAAGTGCAGCTTTGAAGAGGCCAGGGAAGTGTTTGAGAACACAGAGAGAACCACAGAGTTCTGGAAGCAGTATGTGGATGGGGACCAGTGTGAAAGCAACC
CCTGCCTGAATGGGGGCAGCTGCAAGGATGACATCAACAGCTATGAGTGCTGGTGCCCCTTTGGCTTTGAGGGCAAGAACTGTGAACTGGATGTGACCTGCAACAT
CAAGAATGGCAGATGTGAACAGTTCTGCAAGAACTCTGCTGACAACAAGGTTGTGTGCTCCTGCACAGAGGGCTACAGACTGGCTGAGAACCAGAAAAGCTGTGAA
CCTGCTGTGCCCTTCCCATGTGGCAGAGTGTCTGTGTCCCAGACCAGCAAGCTGACCAGAGCTGAGACAGTGTTCCCTGATGTGGACTATGTGAACTCCACAGAGGC
TGAAACCATCCTGGACAACATCACCCAGAGCACCCAGTCCTTCAATGACTTCACCAGAGTTGTGGGAGGGGAGGATGCCAAGCCTGGCCAGTTCCCATGGCAAGTGG
TGCTGAATGGCAAAGTGGATGCCTTCTGTGGGGGCTCCATTGTGAATGAGAAGTGGATTGTGACAGCTGCCCACTGTGTGGAAACTGGAGTGAAGATCACAGTGGT
GGCTGGGGAGCACAACATTGAGGAAACAGAGCACACAGAGCAGAAAAGAAATGTGATCAGGATCATCCCCCACCACAACTACAATGCTGCCATCAACAAGTACAAC
CATGACATTGCCCTGCTGGAACTGGATGAGCCCCTGGTGCTGAACAGCTATGTGACCCCCATCTGCATTGCTGACAAAGAGTACACCAACATCTTTCTGAAGTTTGGC
TCTGGCTATGTGTCTGGCTGGGGCAGGGTGTTCCACAAGGGAAGGAGTGCTCTGGTGCTGCAGTACCTGAGAGTGCCACTGGTGGACAGAGCCACCTGTCTGAGAA
GCACCAAGTTCACCATCTACAACAACATGTTCTGTGCTGGCTTCCATGAGGGGGGCAGAGACTCCTGCCAGGGGGATTCTGGGGGCCCTCATGTGACAGAGGTGGA
AGGCACCAGCTTTCTGACAGGCATCATCAGCTGGGGAGAGGAATGTGCCATGAAGGGCAAATATGGCATCTACACCAAGGTGTCCAGATATGTGAATTGGATCAAA
GAAAAGACCAAGCTGACATGAAGATCTTTTTCCCTCTGCCAAAAATTATGGGGACATCATGAAGCCCCTTGAGCATCTGACTTCTGGCTAATAAAGGAAATTTATTTTC
ATTGCAATAGTGTGTTGGAATTTTTTGTGTCTCTCACTCGGAAGGACATAAGGGCGGCCCTAGC

Ringers treated control

CRISPR/CAS9 anti-NFkB p65

FIG. 46

DNARx-31H4-2A

DraIIRINhe-ΔmCMVΔEF1I126-BstEII- Δ31H4-H-F3(RKRR)-P2A-Δ31H4-L-BglII-MixpA-BV2
(SEQ ID NO:25)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGGGATGGTCCCTGATCCTGCTGTT
TCTGGTGGCTGTGGCCACCAGAGTGCTGTCTGAAGTGCAGCTGGTGGAAAGTGGTGGTGGCCTGGTCAAGCCTGGTGGCTCTCTGAGACTGAGCTGTGCTGCCTCT
GGCTTCACCTTCAGCAGCTACAGCATGAACTGGGTCAGACAGGCCCCTGGCAAAGGCCTGGAATGGGTGTCCAGCATCAGCAGCAGCTCCAGCTACATCAGCTATGC
TGACTCTGTGAAGGGCAGATTCACCATCTCCAGAGACAATGCCAAGAACAGCCTGTACCTCCAGATGAACTCCCTGAGAGCTGAGGATACAGCTGTGTACTTCTGTG
CCAGGGACTATGACTTTTGGAGTGCCTACTATGATGCCTTTGATGTGTGGGGCCAGGGCACCATGGTCACAGTGTCCTCTGCTTCCACAAAGGGCCCCTCTGTGTTCC
CTCTGGCTCCTAGCAGCAAGAGCACCAGTGGTGGAACAGCTGCCCTGGGCTGTCTGGTCAAGGACTACTTTCCTGAGCCTGTGACAGTGTCTTGGAACTCTGGGGCC
CTGACATCTGGGGTGCACACATTTCCAGCTGTGCTCCAGTCCTCTGGCCTGTACTCCCTGTCCTCTGTGGTCACTGTGCCAAGCTCTAGCCTGGGCACCCAGACCTACA
TCTGCAATGTGAACCACAAGCCTAGCAACACCAAGGTGGACAAGAAGGCTGAGCCCAAGAGCTGTGACAAGACCCACACCTGTCCTCCATGTCCTGCTCCAGAGCTG
CTTGGAGGACCTTCTGTGTTTCTGTTCCCTCCAAAGCCAAAGGACACCCTGATGATCAGCAGAACCCCTGAAGTGACCTGTGTGGTGGTTGATGTGTCCCATGAGGAC
CCAGAAGTGAAGTTCAATTGGTATGTGGATGGTGTTGAGGTGCACAATGCTAAGACCAAGCCTAGAGAGGAACAGTACAACAGCACCTACAGGGTTGTGTCTGTGC
TGACAGTGCTGCACCAGGACTGGCTGAATGGCAAAGAGTACAAGTGCAAGGTGTCCAACAAGGCCCTGCCTGCTCCTATTGAAAAGACCATCAGCAAGGCCAAGGG
CCAGCCTAGGGAACCCCAGGTTTACACACTGCCACCTAGCAGAGATGAGCTGACCAAGAACCAGGTGTCCCTGACCTGTCTTGTGAAGGGATTCTACCCCTCTGACAT
TGCTGTGGAATGGGAGAGCAATGGCCAGCCTGAGAACAACTACAAGACAACCCCTCCTGTGCTGGACTCTGATGGCTCATTCTTCCTGTACAGCAAGCTGACTGTGG
ACAAGTCCAGATGGCAGCAGGGCAATGTGTTCAGCTGCTCTGTGATGCATGAGGCCCTGCACAACCACTACACACAGAAGTCCCTGTCTCTGAGCCCTGGCAAG*AGA*
*AAGAGAAGGAGTGGAAGTGGAGCTACTAACTTCAGCCTGCTGAAGCAGGCTGGAGATGTGGAGGAGAACCCTGGACCT*ATGGACTTCCAGGTGCAGATCATCAGCT
TTCTGCTGATCTCTGCCTCTGTGATCATGAGCAGAGGCCAGTCTGTGCTGACCCAGCCTCCATCTGTTAGTGGTGCCCCTGGCCAGAGAGTGACCATCAGCTGTACAG
GCAGCAGCAGCAACATTGGAGCTGGCTATGATGTGCACTGGTATCAGCAGCTGCCTGGCACAGCTCCCAAGCTGCTCATCTCTGGCAACAGCAACAGACCCTCTGGG
GTGCCAGACAGATTCTCTGGCAGCAAGTCTGGCACATCTGCCAGCCTGGCTATCACTGGACTCCAGGCTGAGGATGAGGCTGACTACTACTGCCAGAGCTATGACAG
CAGCCTGTCTGGCTCTGTGTTTGGTGGTGGCACCAAGCTGACAGTGCTGAGAACAGTGGCTGCCCCTTCTGTGTTCATCTTCCCACCATCTGATGAACAGCTGAAGAG
TGGCACAGCCTCTGTTGTGTGCCTGCTGAACAACTTCTACCCCAGAGAAGCCAAGGTGCAGTGGAAGGTGGACAATGCCCTCCAGTCTGGCAACTCCCAAGAGTCTG
TGACAGAGCAGGACAGCAAGGACTCCACCTACAGCCTGAGCAGCACCCTGACACTGAGCAAGGCAGACTATGAGAAGCACAAAGTCTATGCCTGTGAAGTGACCCA
CCAGGGCCTGTCTAGCCCTGTGACCAAGAGCTTCAACAGGGGAGAGAGCTGAAGATCTACTTCTGGCTAATAAAAGATCAGAGCTCTAGTGATCTGTGTGTTGGTTT
TTTGTGTCTGCATTCTAGCTCTAGTGATCAGCAGTTCAACCTGTTGATAGTATGTACTAAGCTCTCATGTTTAATGTACTAAGCTCTCATGTTTAATGAACTAAACCCTC
ATGGCTAATGTACTAAGCTCTCATGGCTAATGTACTAAGCTCTCATGTTTCATGTACTAAGCTCTCATGTTTGAACAATAAAATTAATATAAATCAGCAACTTAAATAGC
CTCTAAGGTTTTAAGTTTTATAAGAAAAAAAAGAATATATAAGGCTTTTAAAGGTTTTAAGGTTTCCTAGGTTATCCTCATATGAGCTCTTAGAAAAACTCATCCAGCA
TCAAATGAAACTGCAATTTATTCATATCAGGATTATCAATACCATATTTTTGAAAAAGTCTTTTCTGTAATGAAGGAGAAAACTCACCCAGGCAGTTCCATAGGATGGC
AAGATCCTGGTATCTGTCTGCAATTCCAACTCTTCCAACATCAATACAACCTATTAATTTCCCCTCATCAAAAATAAGGTTATCAAGTGAGAAATCACCATGAGTGACC
ACTGAATCTGGTGAGAATGGCAAAAGATTATGCATTTCTTTCCAGACTTGTTCAACAGGCCAGCCATTTCTCTCATCATCAAAATCACTGGCATCAACCAAACCATTAT
TCATTCTTGATTGGGCCTGAGCCAGTCTAAATACTCTATCAGAGTTAAAAGGACAATTACAAACAGGAATGGAATGCAATCTTCTCAGGAACACTGCCAGGGCATCAA
CAATATTTTCACCTGAATCAGGATATTCTTCCAATACCTGGAATGCTGTTTTCCCTGGGATGGCAGTGGTGAGTAACCATGCATCATCAGGAGTTCTGATAAAATGCTT
GATGGTTGGAAGAGGCATAAATTCAGTCAGCCAGTTTAGTCTGACCATCTCATCTGTAACATCATTGGCAACAGAACCTTTGCCATGTTTCAGAAACAACTCTGGGGC
ATCTGGCTTCCCATACAATCTATAGATTGTGGCACCTGATTGCCCAACATTATCTCTAGCCCATTTATACCCATATAAATCAGCATCCATGTTGGAATTTAATCTTGGCC
TGGAGCAAGAGGTTTCTCTTTGAATATGGCTCATACATGTGCACCTCCTATAGTGAGTTGTATTATACTATGCAGATATACTATGCCAATGTTTAATTGTCAG

FIG. 47

DNARx-31H4: Dual Cassette anti-PCSK9-31H4

DraIIRINhe- ΔmCMV-EF1-I126-BstEII-Δ31H4-H-BglII-polyA- ΔhCMV-EF1-I126-BstEII-Δ31H4-L -BglII-polyA BV2

(SEQ ID NO:26)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGATGGTCCCTGATCCTGCTGTTTCTGGTGGCTGTGGCCACCAGAGTGCTGTCTGAAGTGCAGCTGGTGGAAAGTGGTGGTGGCCTGGTCAAGCCTGGTGG
CTCTCTGAGACTGAGCTGTGCTGCCTCTGGCTTCACCTTCAGCAGCTACAGCATGAACTGGGTCAGACAGGCCCCTGGCAAAGGCCTGGAATGGGTGTCCAGCATCA
GCAGCAGCTCCAGCTACATCAGCTATGCTGACTCTGTGAAGGGCAGATTCACCATCTCCAGAGACAATGCCAAGAACAGCCTGTACCTCCAGATGAACTCCCTGAGA
GCTGAGGATACAGCTGTGTACTTCTGTGCCAGGGACTATGACTTTTGGAGTGCCTACTATGATGCCTTTGATGTGTGGGGCCAGGGCACCATGGTCACAGTGTCCTCT
GCTTCCACAAAGGGCCCCTCTGTGTTCCCTCTGGCTCCTAGCAGCAAGAGCACCAGTGGTGGAACAGCTGCCCTGGGCTGTCTGGTCAAGGACTACTTTCCTGAGCCT
GTGACAGTGTCTTGGAACTCTGGGGCCCTGACATCTGGGGTGCACACATTTCCAGCTGTGCTCCAGTCCTCTGGCCTGTACTCCCTGTCCTCTGTGGTCACTGTGCCAA
GCTCTAGCCTGGGCACCCAGACCTACATCTGCAATGTGAACCACAAGCCTAGCAACACCAAGGTGGACAAGAAGGCTGAGCCCAAGAGCTGTGACAAGACCCACAC
CTGTCCTCCATGTCCTGCTCCAGAGCTGCTTGGAGGACCTTCTGTGTTTCTGTTCCCTCCAAAGCCAAAGGACACCCTGATGATCAGCAGAACCCCTGAAGTGACCTGT
GTGGTGGTTGATGTGTCCCATGAGGACCCAGAAGTGAAGTTCAATTGGTATGTGGATGGTGTTGAGGTGCACAATGCTAAGACCAAGCCTAGAGAGGAACAGTACA
ACAGCACCTACAGGGTTGTGTCTGTGCTGACAGTGCTGCACCAGGACTGGCTGAATGGCAAAGAGTACAAGTGCAAGGTGTCCAACAAGGCCCTGCCTGCTCCTATT
GAAAAGACCATCAGCAAGGCCAAGGGCCAGCCTAGGGAACCCCAGGTTTACACACTGCCACCTAGCAGAGATGAGCTGACCAAGAACCAGGTGTCCCTGACCTGTC
TTGTGAAGGGATTCTACCCCTCTGACATTGCTGTGGAATGGGAGAGCAATGGCCAGCCTGAGAACAACTACAAGACAACCCCTCCTGTGCTGGACTCTGATGGCTCA
TTCTTCCTGTACAGCAAGCTGACTGTGGACAAGTCCAGATGGCAGCAGGGCAATGTGTTCAGCTGCTCTGTGATGCATGAGGCCCTGCACAACCACTACACACAGAA
GTCCCTGTCTCTGAGCCCTGGCAAGTGAAGATCTACTTCTGGCTAATAAAAGATCAGAGCTCTAGTGATCTGTGTGTTGGTTTTTTGTGTCTGCATTCTAGCATGTTAC
ATAACTTATGGTAAATGGCCTGCCTGGCTGACTGCCCAATGACCCCTGCCCAATGATGTCAATAATGATGTATGTTCCCATGTAATGCCAATAGGGACTTTCCATTGAT
GTCAATGGGTGGAGTATTTATGGTAACTGCCCACTTGGCAGTACATCAAGTGTATCATATGCCAAGTATGCCCCCTATTGATGTCAATGATGGTAAATGGCCTGCCTG
GCATTATGCCCAGTACATGACCTTATGGGACTTTCCTACTTGGCAGTACATCTATGTATTAGTCATTGCTATTACCATGGATTAGTGGAGAAGAGCATGCTTGAGGGCT
GAGTGCCCCTCAGTGGGCAGAGAGCACATGGCCCACAGTCCCTGAGAAGTTGGGGGGAGGGGTGGGCAATTGAACTGGTGCCTAGAGAAGGTGGGGCTTGGGTA
AACTGGGAAAGTGATGTGGTGTACTGGCTCCACCTTTTTCCCCAGGGTGGGGGAGAACCATATATAAGTGCAGTAGTCTCTGTGAACATTCAAGCTTCTGCCTTCTCC
CTCCTGTGAGTTTGGATGCACCTACTAGATATCTTGGTAAGTCACTGACTGTCTATGCCTGGGAAAGGGTGGGCAGGAGGTGGGGCAGTGCAGGAAAAGTGGCACT
GTGAACCCTGCAGCCCTAGACAATTGTACTAACCTTCTTCTCTTTCCTCTCCTGACAGGTTGGTAACCAAGCCACCATGGACTTCCAGGTGCAGATCATCAGCTTTCTGC
TGATCTCTGCCTCTGTGATCATGAGCAGAGGCCAGTCTGTGCTGACCCAGCCTCCATCTGTTAGTGGTGCCCCTGGCCAGAGAGTGACCATCAGCTGTACAGGCAGC
AGCAGCAACATTGGAGCTGGCTATGATGTGCACTGGTATCAGCAGCTGCCTGGCACAGCTCCCAAGCTGCTCATCTCTGGCAACAGCAACAGACCCTCTGGGGTGCC
AGACAGATTCTCTGGCAGCAAGTCTGGCACATCTGCCAGCCTGGCTATCACTGGACTCCAGGCTGAGGATGAGGCTGACTACTACTGCCAGAGCTATGACAGCAGCC
TGTCTGGCTCTGTGTTTGGTGGTGGCACCAAGCTGACAGTGCTGAGAACAGTGGCTGCCCCTTCTGTGTTCATCTTCCCACCATCTGATGAACAGCTGAAGAGTGGCA
CAGCCTCTGTTGTGTGCCTGCTGAACAACTTCTACCCCAGAGAAGCCAAGGTGCAGTGGAAGGTGGACAATGCCCTCCAGTCTGGCAACTCCCAAGAGTCTGTGACA
GAGCAGGACAGCAAGGACTCCACCTACAGCCTGAGCAGCACCCTGACACTGAGCAAGGCAGACTATGAGAAGCACAAAGTCTATGCCTGTGAAGTGACCCACCAGG
GCCTGTCTAGCCCTGTGACCAAGAGCTTCAACAGGGGAGAGAGCTGAAGATCTACTTCTGGCTAATAAAAGATCAGAGCTCTAGTGATCTGTGTGTTGGTTTTTTGTG
TCTGCATTCTAGCTCTAGTGATCAGCAGTTCAACCTGTTGATAGTATGTACTAAGCTCTCATGTTTAATGTACTAAGCTCTCATGTTTAATGAACTAAACCCTCATGGCT
AATGTACTAAGCTCTCATGGCTAATGTACTAAGCTCTCATGTTTCATGTACTAAGCTCTCATGTTTGAACAATAAAATTAATATAAATCAGCAACTTAAATAGCCTCTAA
GGTTTTAAGTTTTATAAGAAAAAAAAGAATATATAAGGCTTTTAAAGGTTTTAAGGTTTCCTAGGTTATCCTCATATGAGCTCTTAGAAAAACTCATCCAGCATCAAAT
GAAACTGCAATTTATTCATATCAGGATTATCAATACCATATTTTTGAAAAAGTCTTTTCTGTAATGAAGGAGAAAACTCACCCAGGCAGTTCCATAGGATGGCAAGATC
CTGGTATCTGTCTGCAATTCCAACTCTTCCAACATCAATACAACCTATTAATTTCCCCTCATCAAAAATAAGGTTATCAAGTGAGAAATCACCATGAGTGACCACTGAAT
CTGGTGAGAATGGCAAAAGATTATGCATTTCTTTCCAGACTTGTTCAACAGGCCAGCCATTTCTCTCATCATCAAAATCACTGGCATCAACCAAACCATTATTCATTCTT
GATTGGGCCTGAGCCAGTCTAAATACTCTATCAGAGTTAAAAGGACAATTACAAACAGGAATGGAATGCAATCTTCTCAGGAACACTGCCAGGGCATCAACAATATT
TTCACCTGAATCAGGATATTCTTCCAATACCTGGAATGCTGTTTTCCCTGGGATGGCAGTGGTGAGTAACCATGCATCATCAGGAGTTCTGATAAAATGCTTGATGGTT
GGAAGAGGCATAAATTCAGTCAGCCAGTTTAGTCTGACCATCTCATCTGTAACATCATTGGCAACAGAACCTTTGCCATGTTTCAGAAACAACTCTGGGGCATCTGGC
TTCCCATACAATCTATAGATTGTGGCACCTGATTGCCCAACATTATCTCTAGCCCATTTATACCCATATAAATCAGCATCCATGTTGGAATTTAATCTTGGCCTGGAGCA
AGAGGTTTCTCTTTGAATATGGCTCATACATGTGCACCTCCTATAGTGAGTTGTATTATACTATGCAGATATACTATGCCAATGTTTAATTGTCAG

FIG. 48

DNARx-21B12-2A

DraIIRINhe-ΔmCMVΔEF1I126-BstEII- Δ21B12-H-F3(RKRR)-P2A-Δ21B12-L-BglII-MixpA-BV2
(SEQ ID NO:27)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGGGATGGTCCCTGATCCTGCTGTT
TCTGGTGGCTGTGGCCACCAGAGTGCTGTCTCAGGTTCAGCTGGTGCAGTCTGGGGCTGAAGTGAAGAAACCTGGGGCCTCTGTGAAGGTGTCCTGCAAGGCTTCT
GGCTACACCCTGACCAGCTATGGCATCTCCTGGGTCAGACAGGCTCCTGGACAGGGCCTTGAATGGATGGGCTGGGTGTCCTTCTACAATGGCAACACCAACTATGC
CCAGAAGCTGCAAGGCAGAGGCACCATGACAACAGACCCCAGCACAAGCACAGCCTACATGGAACTGAGGAGTCTTAGGAGTGATGACACTGCTGTGTACTACTGT
GCCAGAGGCTATGGAATGGATGTGTGGGGCCAGGGCACCACAGTGACAGTGTCCTCTGCTTCCACAAAGGGCCCCTCTGTGTTCCCTCTGGCTCCTAGCAGCAAGAG
CACCAGTGGTGGAACAGCTGCCCTGGGCTGTCTGGTCAAGGACTACTTTCCTGAGCCTGTGACAGTGTCTTGGAACTCTGGGGCCCTGACATCTGGGGTGCACACAT
TTCCAGCTGTGCTCCAGTCCTCTGGCCTGTACTCCCTGTCCTCTGTGGTCACTGTGCCAAGCTCTAGCCTGGGCACCCAGACCTACATCTGCAATGTGAACCACAAGCC
TAGCAACACCAAGGTGGACAAGAAGGCTGAGCCCAAGAGCTGTGACAAGACCCACACCTGTCCTCCATGTCCTGCTCCAGAGCTGCTTGGAGGACCTTCTGTGTTTC
TGTTCCCTCCAAAGCCAAAGGACACCCTGATGATCAGCAGAACCCCTGAAGTGACCTGTGTGGTGGTTGATGTGTCCCATGAGGACCCAGAAGTGAAGTTCAATTGG
TATGTGGATGGTGTTGAGGTGCACAATGCTAAGACCAAGCCTAGAGAGGAACAGTACAACAGCACCTACAGGGTTGTGTCTGTGCTGACAGTGCTGCACCAGGACT
GGCTGAATGGCAAAGAGTACAAGTGCAAGGTGTCCAACAAGGCCCTGCCTGCTCCTATTGAAAAGACCATCAGCAAGGCCAAGGGCCAGCCTAGGGAACCCCAGGT
TTACACACTGCCACCTAGCAGAGATGAGCTGACCAAGAACCAGGTGTCCCTGACCTGTCTTGTGAAGGGATTCTACCCCTCTGACATTGCTGTGGAATGGGAGAGCA
ATGGCCAGCCTGAGAACAACTACAAGACAACCCCTCCTGTGCTGGACTCTGATGGCTCATTCTTCCTGTACAGCAAGCTGACTGTGGACAAGTCCAGATGGCAGCAG
GGCAATGTGTTCAGCTGCTCTGTGATGCATGAGGCCCTGCACAACCACTACACACAGAAGTCCCTGTCTCTGAGCCCTGGCAAG*AGAAAGAGAAGGAGTGGAAGTG*
*GAGCTACTAACTTCAGCCTGCTGAAGCAGGCTGGAGATGTGGAGGAGAACCCTGGACCT*ATGGACTTCCAGGTGCAGATCATCAGCTTTCTGCTGATCTCTGCCTCTG
TGATCATGAGCAGAGGCCAGTCTGCCCTGACACAGCCAGCATCTGTGTCTGGAAGCCCTGGCCAGAGCATCACCATCAGCTGTACAGGCACCAGCTCTGATGTTGGA
GGCTACAACTCTGTGTCCTGGTATCAGCAGCACCCTGGCAAGGCCCCTAAACTCATGATCTATGAGGTGTCCAACAGGCCCTCTGGGGTGTCCAATAGATTCTCTGGC
AGCAAGTCTGGCAACACTGCCAGCCTGACCATCAGTGGACTCCAGGCTGAGGATGAGGCTGACTACTACTGCAACAGCTACACCAGCACCAGCATGGTGTTTGGTGG
TGGCACCAAGCTGACAGTGCTGAGAACAGTGGCTGCCCCTTCTGTGTTCATCTTCCCACCATCTGATGAGCAGCTGAAGAGTGGCACAGCCTCTGTTGTGTGCCTGCT
GAACAACTTCTACCCCAGAGAAGCCAAGGTGCAGTGGAAGGTGGACAATGCCCTCCAGTCTGGAAACAGCCAAGAGTCTGTGACAGAGCAGGACAGCAAGGACTC
CACCTACAGCCTGAGCAGCACACTGACCCTGTCCAAGGCAGACTATGAGAAGCACAAAGTCTATGCCTGTGAAGTGACCCACCAGGGCCTGTCTAGCCCTGTGACCA
AGAGCTTCAACAGGGGAGAGAGCTGAAGATCTACTTCTGGCTAATAAAAGATCAGAGCTCTAGTGATCTGTGTGTTGGTTTTTTGTGTCTGCATTCTAGCTCTAGTGA
TCAGCAGTTCAACCTGTTGATAGTATGTACTAAGCTCTCATGTTTAATGTACTAAGCTCTCATGTTTAATGAACTAAACCCTCATGGCTAATGTACTAAGCTCTCATGGC
TAATGTACTAAGCTCTCATGTTTCATGTACTAAGCTCTCATGTTTGAACAATAAAATTAATATAAATCAGCAACTTAAATAGCCTCTAAGGTTTTAAGTTTTATAAGAAA
AAAAAGAATATATAAGGCTTTTAAAGGTTTTAAGGTTTCCTAGGTTATCCTCATATGAGCTCTTAGAAAAACTCATCCAGCATCAAATGAAACTGCAATTTATTCATAT
CAGGATTATCAATACCATATTTTTGAAAAAGTCTTTTCTGTAATGAAGGAGAAAACTCACCCAGGCAGTTCCATAGGATGGCAAGATCCTGGTATCTGTCTGCAATTCC
AACTCTTCCAACATCAATACAACCTATTAATTTCCCCTCATCAAAAATAAGGTTATCAAGTGAGAAATCACCATGAGTGACCACTGAATCTGGTGAGAATGGCAAAAG
ATTATGCATTTCTTTCCAGACTTGTTCAACAGGCCAGCCATTTCTCTCATCATCAAAATCACTGGCATCAACCAAACCATTATTCATTCTTGATTGGGCCTGAGCCAGTC
TAAATACTCTATCAGAGTTAAAAGGACAATTACAAACAGGAATGGAATGCAATCTTCTCAGGAACACTGCCAGGGCATCAACAATATTTTCACCTGAATCAGGATATT
CTTCCAATACCTGGAATGCTGTTTTCCCTGGGATGGCAGTGGTGAGTAACCATGCATCATCAGGAGTTCTGATAAAATGCTTGATGGTTGGAAGAGGCATAAATTCA
GTCAGCCAGTTTAGTCTGACCATCTCATCTGTAACATCATTGGCAACAGAACCTTTGCCATGTTTCAGAAACAACTCTGGGGCATCTGGCTTCCCATACAATCTATAGA
TTGTGGCACCTGATTGCCCAACATTATCTCTAGCCCATTTATACCCATATAAATCAGCATCCATGTTGGAATTTAATCTTGGCCTGGAGCAAGAGGTTTCTCTTTGAATA
TGGCTCATACATGTGCACCTCCTATAGTGAGTTGTATTATACTATGCAGATATACTATGCCAATGTTTAATTGTCAG

FIG. 49

DNARx-21B12: Dual Cassette anti-PCSK9-21B12

DraIIRINhe- ΔmCMV-EF1-I126-BstEII-Δ21B12-H-BglII-polyA- ΔhCMV-EF1-I126-BstEII-Δ21B12-L -BglII-polyA BV2
(SEQ ID NO:28)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGATGGTCCCTGATCCTGCTGTTTCTGGTGGCTGTGGCCACCAGAGTGCTGTCTCAGGTTCAGCTGGTGCAGTCTGGGGCTGAAGTGAAGAAACCTGGGGCC
TCTGTGAAGGTGTCCTGCAAGGCTTCTGGCTACACCCTGACCAGCTATGGCATCTCCTGGGTCAGACAGGCTCCTGGACAGGGCCTTGAATGGATGGGCTGGGTGTC
CTTCTACAATGGCAACACCAACTATGCCCAGAAGCTGCAAGGCAGAGGCACCATGACAACAGACCCCAGCACAAGCACAGCCTACATGGAACTGAGGAGTCTTAGG
AGTGATGACACTGCTGTGTACTACTGTGCCAGAGGCTATGGAATGGATGTGTGGGGCCAGGGCACCACAGTGACAGTGTCCTCTGCTTCCACAAAGGGCCCCTCTGT
GTTCCCTCTGGCTCCTAGCAGCAAGAGCACCAGTGGTGGAACAGCTGCCCTGGGCTGTCTGGTCAAGGACTACTTTCCTGAGCCTGTGACAGTGTCTTGGAACTCTG
GGGCCCTGACATCTGGGGTGCACACATTTCCAGCTGTGCTCCAGTCCTCTGGCCTGTACTCCCTGTCCTCTGTGGTCACTGTGCCAAGCTCTAGCCTGGGCACCCAGAC
CTACATCTGCAATGTGAACCACAAGCCTAGCAACACCAAGGTGGACAAGAAGGCTGAGCCCAAGAGCTGTGACAAGACCCACACCTGTCCTCCATGTCCTGCTCCAG
AGCTGCTTGGAGGACCTTCTGTGTTTCTGTTCCCTCCAAAGCCAAAGGACACCCTGATGATCAGCAGAACCCCTGAAGTGACCTGTGTGGTGGTTGATGTGTCCCATG
AGGACCCAGAAGTGAAGTTCAATTGGTATGTGGATGGTGTTGAGGTGCACAATGCTAAGACCAAGCCTAGAGAGGAACAGTACAACAGCACCTACAGGGTTGTGTC
TGTGCTGACAGTGCTGCACCAGGACTGGCTGAATGGCAAAGAGTACAAGTGCAAGGTGTCCAACAAGGCCCTGCCTGCTCCTATTGAAAAGACCATCAGCAAGGCC
AAGGGCCAGCCTAGGGAACCCCAGGTTTACACACTGCCACCTAGCAGAGATGAGCTGACCAAGAACCAGGTGTCCCTGACCTGTCTTGTGAAGGGATTCTACCCCTC
TGACATTGCTGTGGAATGGGAGAGCAATGGCCAGCCTGAGAACAACTACAAGACAACCCCTCCTGTGCTGGACTCTGATGGCTCATTCTTCCTGTACAGCAAGCTGA
CTGTGGACAAGTCCAGATGGCAGCAGGGCAATGTGTTCAGCTGCTCTGTGATGCATGAGGCCCTGCACAACCACTACACACAGAAGTCCCTGTCTCTGAGCCCTGGC
AAGTGAAGATCTACTTCTGGCTAATAAAAGATCAGAGCTCTAGTGATCTGTGTGTTGGTTTTTTGTGTCTGCATTCTAGCATGTTACATAACTTATGGTAAATGGCCTG
CCTGGCTGACTGCCCAATGACCCCTGCCCAATGATGTCAATAATGATGTATGTTCCCATGTAATGCCAATAGGGACTTTCCATTGATGTCAATGGGTGGAGTATTTATG
GTAACTGCCCACTTGGCAGTACATCAAGTGTATCATATGCCAAGTATGCCCCCTATTGATGTCAATGATGGTAAATGGCCTGCCTGGCATTATGCCCAGTACATGACCT
TATGGGACTTTCCTACTTGGCAGTACATCTATGTATTAGTCATTGCTATTACCATGGATTAGTGGAGAAGAGCATGCTTGAGGGCTGAGTGCCCCTCAGTGGGCAGAG
AGCACATGGCCCACAGTCCCTGAGAAGTTGGGGGGAGGGGTGGGCAATTGAACTGGTGCCTAGAGAAGGTGGGGCTTGGGTAAACTGGGAAAGTGATGTGGTGT
ACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGATGCACCT
ACTAGATATCTTGGTAAGTCACTGACTGTCTATGCCTGGGAAAGGGTGGCAGGAGGTGGGGCAGTGCAGGAAAAGTGGCACTGTGAACCCTGCAGCCCTAGACA
ATTGTACTAACCTTCTTCTCTTTCCTCTCCTGACAGGTTGGTAACCAAGCCACCATGGACTTCCAGGTGCAGATCATCAGCTTTCTGCTGATCTCTGCCTCTGTGATCAT
GAGCAGAGGCCAGTCTGCCCTGACACAGCCAGCATCTGTGTCTGGAAGCCCTGGCCAGAGCATCACCATCAGCTGTACAGGCACCAGCTCTGATGTTGGAGGCTACA
ACTCTGTGTCCTGGTATCAGCAGCACCCTGGCAAGGCCCCTAAACTCATGATCTATGAGGTGTCCAACAGGCCCTCTGGGGTGTCCAATAGATTCTCTGGCAGCAAGT
CTGGCAACACTGCCAGCCTGACCATCAGTGGACTCCAGGCTGAGGATGAGGCTGACTACTACTGCAACAGCTACACCAGCACCAGCATGGTGTTTGGTGGTGGCACC
AAGCTGACAGTGCTGAGAACAGTGGCTGCCCCTTCTGTGTTCATCTTCCCACCATCTGATGAGCAGCTGAAGAGTGGCACAGCCTCTGTTGTGTGCCTGCTGAACAAC
TTCTACCCCAGAGAAGCCAAGGTGCAGTGGAAGGTGGACAATGCCCTCCAGTCTGGAAACAGCCAAGAGTCTGTGACAGAGCAGGACAGCAAGGACTCCACCTACA
GCCTGAGCAGCACACTGACCCTGTCCAAGGCAGACTATGAGAAGCACAAAGTCTATGCCTGTGAAGTGACCCACCAGGGCCTGTCTAGCCCTGTGACCAAGAGCTTC
AACAGGGGAGAGAGCTGAAGATCTACTTCTGGCTAATAAAAGATCAGAGCTCTAGTGATCTGTGTGTTGGTTTTTTGTGTCTGCATTCTAGCTCTAGTGATCAGCAGT
TCAACCTGTTGATAGTATGTACTAAGCTCTCATGTTTAATGTACTAAGCTCTCATGTTTAATGAACTAAACCCTCATGGCTAATGTACTAAGCTCTCATGGCTAATGTAC
TAAGCTCTCATGTTTCATGTACTAAGCTCTCATGTTTGAACAATAAAATTAATATAAATCAGCAACTTAAATAGCCTCTAAGGTTTTAAGTTTTATAAGAAAAAAAAGA
ATATATAAGGCTTTTAAAGGTTTTAAGGTTTCCTAGGTTATCCTCATATGAGCTCTTAGAAAAACTCATCCAGCATCAAATGAAACTGCAATTTATTCATATCAGGATTA
TCAATACCATATTTTTGAAAAAGTCTTTTCTGTAATGAAGGAGAAAACTCACCCAGGCAGTTCCATAGGATGGCAAGATCCTGGTATCTGTCTGCAATTCCAACTCTTC
CAACATCAATACAACCTATTAATTTCCCCTCATCAAAAATAAGGTTATCAAGTGAGAAATCACCATGAGTGACCACTGAATCTGGTGAGAATGGCAAAAGATTATGCA
TTTCTTTCCAGACTTGTTCAACAGGCCAGCCATTTCTCTCATCATCAAAATCACTGGCATCAACCAAACCATTATTCATTCTTGATTGGGCCTGAGCCAGTCTAAATACT
CTATCAGAGTTAAAAGGACAATTACAAACAGGAATGGAATGCAATCTTCTCAGGAACACTGCCAGGGCATCAACAATATTTTCACCTGAATCAGGATATTCTTCCAAT
ACCTGGAATGCTGTTTTCCCTGGGATGGCAGTGGTGAGTAACCATGCATCATCAGGAGTTCTGATAAAATGCTTGATGGTTGGAAGAGGCATAAATTCAGTCAGCCA
GTTTAGTCTGACCATCTCATCTGTAACATCATTGGCAACAGAACCTTTGCCATGTTTCAGAAACAACTCTGGGGCATCTGGCTTCCCATACAATCTATAGATTGTGGCA
CCTGATTGCCCAACATTATCTCTAGCCCATTTATACCCATATAAATCAGCATCCATGTTGGAATTTAATCTTGGCCTGGAGCAAGAGGTTTCTCTTTGAATATGGCTCAT
ACATGTGCACCTCCTATAGTGAGTTGTATTATACTATGCAGATATACTATGCCAATGTTTAATTGTCAG

FIG. 50

DNARx-CD47-2A: aCD47-2A

DrallRINhe-ΔmCMVΔEF1l126-BstEII- ΔaCD47-H-F3(RKRR)-P2A-ΔaCD47-L-BglII-MixpA-BV2
(SEQ ID NO:29)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGGGCTGGTCCTGCATCATGTTCTT
TCTGGTGGCCACAGCCACAGGGGTGCACTCTCAGGTTCAGCTGCAACAGCCTGGTGCTGAGCTGGTTAAGCCTGGGGCCTCTGTGATGATGAGCTGCAAGGCCTCTG
GCTACACCTTCACCAACTACAACATGCACTGGGTCAAGCAGACCCCAGGCCAGGGCCTTGAGTGGATTGGCACAATCTACCCTGGCAATGATGACACCAGCTACAAC
CAGAAGTTCAAGGACAAGGCCACACTGACAGCTGACAAGAGCAGCTCTGCTGCCTACATGCAGCTGAGCAGCCTGACCTCTGAGGACTCTGCTGTGTACTACTGTGC
CAGAGGGGGCTACAGAGCCATGGATTACTGGGGCCAGGGCACCTCTGTGACAGTGTCATCTGCCAGCACAAAGGGCCCATCTGTGTTCCCTCTGGCACCCAGCAGC
AAGTCTACCAGTGGTGGAACAGCTGCCCTGGGCTGTCTGGTCAAGGACTACTTTCCTGAGCCAGTGACAGTGTCCTGGAACTCTGGGGCTCTGACATCTGGGGTGCA
CACATTCCCTGCTGTGCTCCAGTCCTCTGGCCTGTACAGCCTCAGCTCTGTGGTCACAGTGCCTAGCTCTAGCCTGGGCACCCAGACCTACATCTGCAATGTGAACCAC
AAGCCTAGCAACACCAAGGTGGACAAGAAGGCTGAGCCCAAGAGCTGTGACAAGACCCACACCTGTCCTCCATGTCCTGCTCCAGAGCTGCTTGGAGGACCTTCTGT
GTTTCTGTTCCCTCCAAAGCCAAAGGACACCCTGATGATCAGCAGAACCCCTGAAGTGACATGTGTGGTGGTTGATGTGTCCCATGAGGACCCAGAAGTGAAGTTCA
ATTGGTATGTGGATGGTGTTGAGGTGCACAATGCCAAGACCAAGCCTAGAGAGGAACAGTACAACAGCACCTACAGAGTGGTGTCTGTGCTGACAGTGCTGCATCA
GGACTGGCTGAATGGCAAAGAGTACAAGTGCAAGGTGTCCAACAAGGCCCTGCCTGCTCCTATTGAAAAGACCATCTCCAAGGCCAAGGGCCAGCCTAGGGAACCC
CAGGTTTACACACTGCCACCTAGCAGGGATGAGCTGACCAAGAACCAGGTGTCCCTGACCTGCCTGGTTAAGGGCTTCTACCCCTCTGACATTGCTGTGGAATGGGA
GAGCAATGGCCAGCCAGAGAACAACTACAAGACAACCCCTCCTGTGCTGGACTCTGATGGCTCATTCTTCCTGTACTCCAAGCTCACAGTGGACAAGTCCAGATGGC
AGCAAGGCAATGTGTTCAGCTGCTCTGTGATGCATGAGGCCCTGCACAACCACTACACACAGAAGTCCCTGAGCCTGTCTCCTGGCAAG*AGAAAGAGAAGGAGTGG*
*AAGTGGAGCTACTAACTTCAGCCTGCTGAAGCAGGCTGGAGATGTGGAGGAGAACCCTGGACCT*ATGAAGTTGCCTGTTAGGCTGTTGGTGCTGATGTTCTGGATTC
CTGGTTCCAGCAGTGATGTTTTGATGACCCAAACTCCACTCTCCCTGCCTGTCAGTCTTGGAGATCAAGCCTCCATCTCTTGCAGATCTAGTCAGAGCATTGTATATAG
TAATGGAAACACCTATTTAGGATGGTACCTGCAGAAACCAGGCCAGTCTCCAAAGCTCCTGATCTACAAAGTTTCCAACCGATTTTCTGGGGTCCCAGACAGGTTCAG
TGGCAGTGGATCAGGGACAGATTTCACACTCAAGATCAGCAGAGTGGAGGCTGAGGATCTGGGGGTTTATCACTGCTTTCAAGGTTCACATGTTCCGTACACGTTCG
GAGGGGGGACCAAGGTGGAAATAAAAAGAACAGTGGCTGCCCCTTCTGTGTTCATCTTCCCACCATCTGATGAACAGCTGAAGAGTGGCACAGCCTCTGTTGTGTGC
CTGCTGAACAACTTCTACCCCAGAGAAGCCAAGGTGCAGTGGAAGGTGGACAATGCCCTCCAGTCTGGCAACTCCCAAGAGTCTGTGACAGAGCAGGACAGCAAGG
ACTCCACCTACAGCCTGAGCAGCACCCTGACACTGAGCAAGGCAGACTATGAGAAGCACAAAGTCTATGCCTGTGAAGTGACCCACCAGGGCCTGTCTAGCCCTGTG
ACCAAGAGCTTCAACAGGGGAGAGAGCTGAAGATCTACTTCTGGCTAATAAAAGATCAGAGCTCTAGTGATCTGTGTGTTGGTTTTTTGTGTCTGCATTCTAGCTCTA
GTGATCAGCAGTTCAACCTGTTGATAGTATGTACTAAGCTCTCATGTTTAATGTACTAAGCTCTCATGTTTAATGAACTAAACCCTCATGGCTAATGTACTAAGCTCTCA
TGGCTAATGTACTAAGCTCTCATGTTTCATGTACTAAGCTCTCATGTTTGAACAATAAAATTAATATAAATCAGCAACTTAAATAGCCTCTAAGGTTTTAAGTTTTATAA
GAAAAAAAAGAATATATAAGGCTTTTAAAGGTTTTAAGGTTTCCTAGGTTATCCTCATATGAGCTCTTAGAAAAACTCATCCAGCATCAAATGAAACTGCAATTTATTC
ATATCAGGATTATCAATACCATATTTTTGAAAAAGTCTTTTCTGTAATGAAGGAGAAAACTCACCCAGGCAGTTCCATAGGATGGCAAGATCCTGGTATCTGTCTGCA
ATTCCAACTCTTCCAACATCAATACAACCTATTAATTTCCCCTCATCAAAAATAAGGTTATCAAGTGAGAAATCACCATGAGTGACCACTGAATCTGGTGAGAATGGCA
AAAGATTATGCATTTCTTTCCAGACTTGTTCAACAGGCCAGCCATTTCTCTCATCATCAAAATCACTGGCATCAACCAAACCATTATTCATTCTTGATTGGGCCTGAGCC
AGTCTAAATACTCTATCAGAGTTAAAAGGACAATTACAAACAGGAATGGAATGCAATCTTCTCAGGAACACTGCCAGGGCATCAACAATATTTTCACCTGAATCAGGA
TATTCTTCCAATACCTGGAATGCTGTTTTCCCTGGGATGGCAGTGGTGAGTAACCATGCATCATCAGGAGTTCTGATAAAATGCTTGATGGTTGGAAGAGGCATAAAT
TCAGTCAGCCAGTTTAGTCTGACCATCTCATCTGTAACATCATTGGCAACAGAACCTTTGCCATGTTTCAGAAACAACTCTGGGGCATCTGGCTTCCCATACAATCTAT
AGATTGTGGCACCTGATTGCCCAACATTATCTCTAGCCCATTTATACCCATATAAATCAGCATCCATGTTGGAATTTAATCTTGGCCTGGAGCAAGAGGTTTCTCTTTGA
ATATGGCTCATACATGTGCACCTCCTATAGTGAGTTGTATTATACTATGCAGATATACTATGCCAATGTTTAATTGTCAG

FIG. 51

DNARx-CD47: Dual Cassette aCD47

DraIIRINhe- ΔmCMV-EF1-I126-BstEII-ΔaCD47-H-BglII-polyA- ΔhCMV-EF1-I126-BstEII-ΔaCD47-L -BglII-polyA BV2
(SEQ ID NO:30)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGCTGGTCCTGCATCATGTTCTTTCTGGTGGCCACAGCCACAGGGGTGCACTCTCAGGTTCAGCTGCAACAGCCTGGTGCTGAGCTGGTTAAGCCTGGGGCC
TCTGTGATGATGAGCTGCAAGGCCTCTGGCTACACCTTCACCAACTACAACATGCACTGGGTCAAGCAGACCCCAGGCCAGGGCCTTGAGTGGATTGGCACAATCTA
CCCTGGCAATGATGACACCAGCTACAACCAGAAGTTCAAGGACAAGGCCACACTGACAGCTGACAAGAGCAGCTCTGCTGCCTACATGCAGCTGAGCAGCCTGACCT
CTGAGGACTCTGCTGTGTACTACTGTGCCAGAGGGGGCTACAGAGCCATGGATTACTGGGGCCAGGGCACCTCTGTGACAGTGTCATCTGCCAGCACAAAGGGCCC
ATCTGTGTTCCCTCTGGCACCCAGCAGCAAGTCTACCAGTGGTGGAACAGCTGCCCTGGGCTGTCTGGTCAAGGACTACTTTCCTGAGCCAGTGACAGTGTCCTGGAA
CTCTGGGGCTCTGACATCTGGGGTGCACACATTCCCTGCTGTGCTCCAGTCCTCTGGCCTGTACAGCCTCAGCTCTGTGGTCACAGTGCCTAGCTCTAGCCTGGGCAC
CCAGACCTACATCTGCAATGTGAACCACAAGCCTAGCAACACCAAGGTGGACAAGAAGGCTGAGCCCAAGAGCTGTGACAAGACCCACACCTGTCCTCCATGTCCTG
CTCCAGAGCTGCTTGGAGGACCTTCTGTGTTTCTGTTCCCTCCAAAGCCAAAGGACACCCTGATGATCAGCAGAACCCCTGAAGTGACATGTGTGGTGGTTGATGTGT
CCCATGAGGACCCAGAAGTGAAGTTCAATTGGTATGTGGATGGTGTTGAGGTGCACAATGCCAAGACCAAGCCTAGAGAGGAACAGTACAACAGCACCTACAGAGT
GGTGTCTGTGCTGACAGTGCTGCATCAGGACTGGCTGAATGGCAAAGAGTACAAGTGCAAGGTGTCCAACAAGGCCCTGCCTGCTCCTATTGAAAAGACCATCTCCA
AGGCCAAGGGCCAGCCTAGGGAACCCCAGGTTTACACACTGCCACCTAGCAGGGATGAGCTGACCAAGAACCAGGTGTCCCTGACCTGCCTGGTTAAGGGCTTCTA
CCCCTCTGACATTGCTGTGGAATGGGAGAGCAATGGCCAGCCAGAGAACAACTACAAGACAACCCCTCCTGTGCTGGACTCTGATGGCTCATTCTTCCTGTACTCCAA
GCTCACAGTGGACAAGTCCAGATGGCAGCAAGGCAATGTGTTCAGCTGCTCTGTGATGCATGAGGCCCTGCACAACCACTACACACAGAAGTCCCTGAGCCTGTCTC
CTGGCAAGTGAAGATCTACTTCTGGCTAATAAAAGATCAGAGCTCTAGTGATCTGTGTGTTGGTTTTTTGTGTCTGCATTCTAGCATGTTACATAACTTATGGTAAATG
GCCTGCCTGGCTGACTGCCCAATGACCCCTGCCCAATGATGTCAATAATGATGTATGTTCCCATGTAATGCCAATAGGGACTTTCCATTGATGTCAATGGGTGGAGTA
TTTATGGTAACTGCCCACTTGGCAGTACATCAAGTGTATCATATGCCAAGTATGCCCCCTATTGATGTCAATGATGGTAAATGGCCTGCCTGGCATTATGCCCAGTACA
TGACCTTATGGGACTTTCCTACTTGGCAGTACATCTATGTATTAGTCATTGCTATTACCATGGATTAGTGGAGAAGAGCATGCTTGAGGGCTGAGTGCCCCTCAGTGG
GCAGAGAGCACATGGCCCACAGTCCCTGAGAAGTTGGGGGGAGGGGTGGGCAATTGAACTGGTGCCTAGAGAAGGTGGGGCTTGGGTAAACTGGGAAAGTGATG
TGGTGTACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGAT
GCACCTACTAGATATCTTGGTAAGTCACTGACTGTCTATGCCTGGGAAAGGGTGGGCAGGAGGTGGGGCAGTGCAGGAAAAGTGGCACTGTGAACCCTGCAGCCCT
AGACAATTGTACTAACCTTCTTCTCTTTCCTCTCCTGACAGGTTGGTAACCAAGCCACCATGAAGTTGCCTGTTAGGCTGTTGGTGCTGATGTTCTGGATTCCTGGTTCC
AGCAGTGATGTTTTGATGACCCAAACTCCACTCTCCCTGCCTGTCAGTCTTGGAGATCAAGCCTCCATCTCTTGCAGATCTAGTCAGAGCATTGTATATAGTAATGGAA
ACACCTATTTAGGATGGTACCTGCAGAAACCAGGCCAGTCTCCAAAGCTCCTGATCTACAAAGTTTCCAACCGATTTTCTGGGGTCCCAGACAGGTTCAGTGGCAGTG
GATCAGGGACAGATTTCACACTCAAGATCAGCAGAGTGGAGGCTGAGGATCTGGGGGTTTATCACTGCTTTCAAGGTTCACATGTTCCGTACACGTTCGGAGGGGG
GACCAAGGTGGAAATAAAAAGAACAGTGGCTGCCCCTTCTGTGTTCATCTTCCCACCATCTGATGAACAGCTGAAGAGTGGCACAGCCTCTGTTGTGTGCCTGCTGA
ACAACTTCTACCCCAGAGAAGCCAAGGTGCAGTGGAAGGTGGACAATGCCCTCCAGTCTGGCAACTCCCAAGAGTCTGTGACAGAGCAGGACAGCAAGGACTCCAC
CTACAGCCTGAGCAGCACCCTGACACTGAGCAAGGCAGACTATGAGAAGCACAAAGTCTATGCCTGTGAAGTGACCCACCAGGGCCTGTCTAGCCCTGTGACCAAG
AGCTTCAACAGGGGAGAGAGCTGAAGATCTACTTCTGGCTAATAAAAGATCAGAGCTCTAGTGATCTGTGTGTTGGTTTTTTGTGTCTGCATTCTAGCTCTAGTGATC
AGCAGTTCAACCTGTTGATAGTATGTACTAAGCTCTCATGTTTAATGTACTAAGCTCTCATGTTTAATGAACTAAACCCTCATGGCTAATGTACTAAGCTCTCATGGCTA
ATGTACTAAGCTCTCATGTTTCATGTACTAAGCTCTCATGTTTGAACAATAAAATTAATATAAATCAGCAACTTAAATAGCCTCTAAGGTTTTAAGTTTTATAAGAAAAA
AAAGAATATATAAGGCTTTTAAAGGTTTTAAGGTTTCCTAGGTTATCCTCATATGAGCTCTTAGAAAAACTCATCCAGCATCAAATGAAACTGCAATTTATTCATATCA
GGATTATCAATACCATATTTTTGAAAAAGTCTTTTCTGTAATGAAGGAGAAAACTCACCCAGGCAGTTCCATAGGATGGCAAGATCCTGGTATCTGTCTGCAATTCCAA
CTCTTCCAACATCAATACAACCTATTAATTTCCCCTCATCAAAAATAAGGTTATCAAGTGAGAAATCACCATGAGTGACCACTGAATCTGGTGAGAATGGCAAAAGATT
ATGCATTTCTTTCCAGACTTGTTCAACAGGCCAGCCATTTCTCTCATCATCAAAATCACTGGCATCAACCAAACCATTATTCATTCTTGATTGGGCCTGAGCCAGTCTAA
ATACTCTATCAGAGTTAAAAGGACAATTACAAACAGGAATGGAATGCAATCTTCTCAGGAACACTGCCAGGGCATCAACAATATTTTCACCTGAATCAGGATATTCTT
CCAATACCTGGAATGCTGTTTTCCCTGGGATGGCAGTGGTGAGTAACCATGCATCATCAGGAGTTCTGATAAAATGCTTGATGGTTGGAAGAGGCATAAATTCAGTC
AGCCAGTTTAGTCTGACCATCTCATCTGTAACATCATTGGCAACAGAACCTTTGCCATGTTTCAGAAACAACTCTGGGGCATCTGGCTTCCCATACAATCTATAGATTG
TGGCACCTGATTGCCCAACATTATCTCTAGCCCATTTATACCCATATAAATCAGCATCCATGTTGGAATTTAATCTTGGCCTGGAGCAAGAGGTTTCTCTTTGAATATGG
CTCATACATGTGCACCTCCTATAGTGAGTTGTATTATACTATGCAGATATACTATGCCAATGTTTAATTGTCAG

FIG. 52

DNARx-D8-2A

DraIIRINhe-ΔmCMVΔEF1I126-BstEII- ΔD8-H-F3(RKRR)-P2A-ΔD8-L-BglII-MixpA-BV2
(SEQ ID NO:31)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGGGACTGGGACTCCAGTGGGTGT
TCTTTGTGGCCCTGCTGAAAGGGGTGCACTGTGAAGTCAGACTGCTGGAAAGTGGTGGTGGCCTGCAGGTTCAGCTGGTGCAGTCTGGGGCTGAAGTGAAGAAACC
TGGCAGCTCTGTGAAGGTGTCCTGCAAGGCTAGTGGTGGCACCTTCTCTGCCTATGCCTTCACCTGGGTCAGACAGGCTCCTGGACAGGGCCTTGAATGGATGGGAG
GCATCACAGGCATGTTTGGCACAGCCAACTATGCCCAGAAATTCCAGGGCAGAGTGACCATCACAGCTGATGAGCTGACCAGCACAGCCTACATGGAACTGAGCAG
CCTGACCTCTGAGGACACAGCCCTGTACTACTGTGCCAGAGGCCTGTACTATTATGAGTCTAGCCTGGACTACTGGGGCCAGGGCACACTGGTTACAGTGTCTAGTG
CCAGCACAAAGGGCCCATCTGTGTTCCCTCTGGCACCCAGCAGCAAGTCTACCAGTGGTGGAACAGCTGCCCTGGGCTGTCTGGTCAAGGACTACTTTCCTGAGCCA
GTGACAGTGTCCTGGAACTCTGGGGCTCTGACATCTGGGGTGCACACATTCCCTGCTGTGCTCCAGTCCTCTGGCCTGTACAGCCTCAGCTCTGTGGTCACAGTGCCT
AGCTCTAGCCTGGGCACCCAGACCTACATCTGCAATGTGAACCACAAGCCTAGCAACACCAAGGTGGACAAGAAGGCTGAGCCCAAGAGCTGTGACAAGACCCACA
CCTGTCCTCCATGTCCTGCTCCAGAGCTGCTTGGAGGACCTTCTGTGTTTCTGTTCCCTCCAAAGCCAAAGGACACCCTGATGATCAGCAGAACCCCTGAAGTGACATG
TGTGGTGGTTGATGTGTCCCATGAGGACCCAGAAGTGAAGTTCAATTGGTATGTGGATGGTGTTGAGGTGCACAATGCCAAGACCAAGCCTAGAGAGGAACAGTAC
AACAGCACCTACAGAGTGGTGTCTGTGCTGACAGTGCTGCATCAGGACTGGCTGAATGGCAAAGAGTACAAGTGCAAGGTGTCCAACAAGGCCCTGCCTGCTCCTAT
TGAAAAGACCATCTCCAAGGCCAAGGGCCAGCCTAGGGAACCCCAGGTTTACACACTGCCACCTAGCAGGGATGAGCTGACCAAGAACCAGGTGTCCCTGACCTGC
CTGGTTAAGGGCTTCTACCCCTCTGACATTGCTGTGGAATGGGAGAGCAATGGCCAGCCAGAGAACAACTACAAGACAACCCCTCCTGTGCTGGACTCTGATGGCTC
ATTCTTCCTGTACTCCAAGCTCACAGTGGACAAGTCCAGATGGCAGCAAGGCAATGTGTTCAGCTGCTCTGTGATGCATGAGGCCCTGCACAACCACTACACACAGAA
GTCCCTGAGCCTGTCTCCTGGCAAG*AGAAAGAGAAGGAGTGGAAGTGGAGCTACTAACTTCAGCCTGCTGAAGCAGGCTGGAGATGTGGAGGAGAACCCTGGACCT*
ATGGACTTCCAGGTGCAGATCATCAGCTTTCTGCTGATCTCTGCCTCTGTGATCATGAGCAGAGGCCAGTCTGTGCTGACCCAGCCTCCATCTGCATCTGGAAGCCCT
GGCCAGTCTGTGACCATCAGCTGTACAGGCACCAGCTCTGATGTTGGAGGCTACAACTCTGTGTCCTGGTATCAGCAGCACCCTGGCAAGGCCCCTAAGCTGATGAT
CTATGAAGTGACCAAGAGGCCCTCTGGGGTGCCAGACAGATTCTCTGCCAGCAAGTCTGGCAACACAGCCAGCCTGACAGTGTCTGGCCTGCAAGCTGAGGATGAG
GCTGACTACTTCTGCTGCTCCTATGCTGGCCACTCTGCCTATGTGTTTGGCACTGGCACCAAAGTGACAGTGCTGAGAACAGTGGCTGCCCCTTCTGTGTTCATCTTCC
CACCATCTGATGAGCAGCTGAAGTCTGGCACAGCCTCTGTTGTGTGCCTGCTGAACAACTTCTACCCTAGAGAAGCCAAGGTGCAGTGGAAGGTGGACAATGCCCTC
CAGTCTGGCAACTCCCAAGAGTCTGTGACAGAGCAGGACAGCAAGGACTCCACCTACAGCCTGAGCAGCACCCTGACACTGAGCAAGGCTGACTATGAGAAGCACA
AAGTCTATGCCTGTGAAGTGACCCACCAGGGCCTGTCTAGCCCTGTGACCAAGAGCTTCAACAGGGGAGAGAGCTGAAGATCTACTTCTGGCTAATAAAAGATCAGA
GCTCTAGTGATCTGTGTGTTGGTTTTTTGTGTCTGCATTCTAGCTCTAGTGATCAGCAGTTCAACCTGTTGATAGTATGTACTAAGCTCTCATGTTTAATGTACTAAGCT
CTCATGTTTAATGAACTAAACCCTCATGGCTAATGTACTAAGCTCTCATGGCTAATGTACTAAGCTCTCATGTTTCATGTACTAAGCTCTCATGTTTGAACAATAAAATT
AATATAAATCAGCAACTTAAATAGCCTCTAAGGTTTTAAGTTTTATAAGAAAAAAAAGAATATATAAGGCTTTTAAAGGTTTTAAGGTTTCCTAGGTTATCCTCATATG
AGCTCTTAGAAAAACTCATCCAGCATCAAATGAAACTGCAATTTATTCATATCAGGATTATCAATACCATATTTTTGAAAAAGTCTTTTCTGTAATGAAGGAGAAAACT
CACCCAGGCAGTTCCATAGGATGGCAAGATCCTGGTATCTGTCTGCAATTCCAACTCTTCCAACATCAATACAACCTATTAATTTCCCCTCATCAAAAATAAGGTTATCA
AGTGAGAAATCACCATGAGTGACCACTGAATCTGGTGAGAATGGCAAAAGATTATGCATTTCTTTCCAGACTTGTTCAACAGGCCAGCCATTTCTCTCATCATCAAAAT
CACTGGCATCAACCAAACCATTATTCATTCTTGATTGGGCCTGAGCCAGTCTAAATACTCTATCAGAGTTAAAAGGACAATTACAAACAGGAATGGAATGCAATCTTCT
CAGGAACACTGCCAGGGCATCAACAATATTTTCACCTGAATCAGGATATTCTTCCAATACCTGGAATGCTGTTTTCCCTGGGATGGCAGTGGTGAGTAACCATGCATC
ATCAGGAGTTCTGATAAAATGCTTGATGGTTGGAAGAGGCATAAATTCAGTCAGCCAGTTTAGTCTGACCATCTCATCTGTAACATCATTGGCAACAGAACCTTTGCC
ATGTTTCAGAAACAACTCTGGGGCATCTGGCTTCCCATACAATCTATAGATTGTGGCACCTGATTGCCCAACATTATCTCTAGCCCATTTATACCCATATAAATCAGCAT
CCATGTTGGAATTTAATCTTGGCCTGGAGCAAGAGGTTTCTCTTTGAATATGGCTCATACATGTGCACCTCCTATAGTGAGTTGTATTATACTATGCAGATATACTATG
CCAATGTTTAATTGTCAG

FIG. 53

DNARx-F10-2A

DraIIRINhe-ΔmCMVΔEF1I126-BstEII- ΔF10-H-F3(RKRR)-P2A-ΔF10-L-BglII-MixpA-BV2
(SEQ ID NO:32)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGGGACTGGGACTCCAGTGGGTGT
TCTTTGTGGCCCTGCTGAAAGGGGTGCACTGTGAAGTCAGACTGCTGGAAAGTGGTGGTGGCCTGCAGGTTCAGCTGGTGCAGTCTGGGGCTGAAGTGAAGAAACC
TGGCAGCTCTGTGAAGGTGTCCTGCACCTCCTCTGAAGTGACCTTCAGCAGCTTTGCCATCAGCTGGGTCAGACAGGCTCCTGGACAGGGCCTTGAATGGCTTGGAG
GCATCAGCCCCATGTTTGGCACCCCTAACTATGCCCAGAAATTCCAGGGCAGAGTGACCATCACAGCTGACCAGAGCACCAGAACAGCCTACATGGACCTGAGAAGT
CTTAGGAGTGAAGATACAGCTGTGTACTACTGTGCTAGAAGCCCCAGCTACATCTGCTCTGGTGGCACCTGTGTGTTTGACCACTGGGGCCAGGGAACCCTGGTCAC
AGTTTCTTCTGCCAGCACAAAGGGCCCATCTGTGTTCCCTCTGGCACCCAGCAGCAAGTCTACCAGTGGTGGAACAGCTGCCCTGGGCTGTCTGGTCAAGGACTACTT
TCCTGAGCCAGTGACAGTGTCCTGGAACTCTGGGGCTCTGACATCTGGGGTGCACACATTCCCTGCTGTGCTCCAGTCCTCTGGCCTGTACAGCCTCAGCTCTGTGGT
CACAGTGCCTAGCTCTAGCCTGGGCACCCAGACCTACATCTGCAATGTGAACCACAAGCCTAGCAACACCAAGGTGGACAAGAAGGCTGAGCCCAAGAGCTGTGAC
AAGACCCACACCTGTCCTCCATGTCCTGCTCCAGAGCTGCTTGGAGGACCTTCTGTGTTTCTGTTCCCTCCAAAGCCAAAGGACACCCTGATGATCAGCAGAACCCCTG
AAGTGACATGTGTGGTGGTTGATGTGTCCCATGAGGACCCAGAAGTGAAGTTCAATTGGTATGTGGATGGTGTTGAGGTGCACAATGCCAAGACCAAGCCTAGAGA
GGAACAGTACAACAGCACCTACAGAGTGGTGTCTGTGCTGACAGTGCTGCATCAGGACTGGCTGAATGGCAAAGAGTACAAGTGCAAGGTGTCCAACAAGGCCCTG
CCTGCTCCTATTGAAAAGACCATCTCCAAGGCCAAGGGCCAGCCTAGGGAACCCCAGGTTTACACACTGCCACCTAGCAGGGATGAGCTGACCAAGAACCAGGTGTC
CCTGACCTGCCTGGTTAAGGGCTTCTACCCCTCTGACATTGCTGTGGAATGGGAGAGCAATGGCCAGCCAGAGAACAACTACAAGACAACCCCTCCTGTGCTGGACT
CTGATGGCTCATTCTTCCTGTACTCCAAGCTCACAGTGGACAAGTCCAGATGGCAGCAAGGCAATGTGTTCAGCTGCTCTGTGATGCATGAGGCCCTGCACAACCACT
ACACACAGAAGTCCCTGAGCCTGTCTCCTGGCAAG*AGAAAGAGAAGGAGTGGAAGTGGAGCTACTAACTTCAGCCTGCTGAAGCAGGCTGGAGATGTGGAGGAGA*
*ACCCTGGACCT*ATGGACTTCCAGGTGCAGATCATCAGCTTTCTGCTGATCTCTGCCTCTGTGATCATGAGCAGAGGCCAGCCTGGACTGACACAGCCTCCATCTGTGTC
CAAGGGCCTGAGACAGACAGCCACACTGACCTGCACAGGCAACAGCAACAATGTGGGCAATCAAGGGGCTGCCTGGCTCCAGCAGCATCAGGGACATCCTCCAAAG
CTGCTGAGCTACAGAAACAATGACAGACCCTCTGGCATCTCTGAGAGATTCTCTGCCTCTAGGAGTGGCAACACAGCCAGCCTGACCATCACTGGACTCCAGCCAGA
GGATGAGGCTGACTACTACTGCTCCACCTGGGACAGCAGCCTGTCTGCTGTGGTTTTTGGTGGTGGCACCAAGCTGACAGTGCTGAGAACAGTGGCTGCCCCTTCTG
TGTTCATCTTCCCACCATCTGATGAGCAGCTGAAGTCTGGCACAGCCTCTGTTGTGTGCCTGCTGAACAACTTCTACCCTAGAGAAGCCAAGGTGCAGTGGAAGGTGG
ACAATGCCCTCCAGTCTGGCAACTCCCAAGAGTCTGTGACAGAGCAGGACAGCAAGGACTCCACCTACAGCCTGAGCAGCACCCTGACACTGAGCAAGGCTGACTAT
GAGAAGCACAAAGTCTATGCCTGTGAAGTGACCCACCAGGGCCTGTCTAGCCCTGTGACCAAGAGCTTCAACAGGGGAGAGAGCTGAAGATCTACTTCTGGCTAAT
AAAAGATCAGAGCTCTAGTGATCTGTGTGTTGGTTTTTTGTGTCTGCATTCTAGCTCTAGTGATCAGCAGTTCAACCTGTTGATAGTATGTACTAAGCTCTCATGTTTAA
TGTACTAAGCTCTCATGTTTAATGAACTAAACCCTCATGGCTAATGTACTAAGCTCTCATGGCTAATGTACTAAGCTCTCATGTTTCATGTACTAAGCTCTCATGTTTGA
ACAATAAAATTAATATAAATCAGCAACTTAAATAGCCTCTAAGGTTTTAAGTTTTATAAGAAAAAAAAGAATATATAAGGCTTTTAAAGGTTTTAAGGTTTCCTAGGTT
ATCCTCATATGAGCTCTTAGAAAAACTCATCCAGCATCAAATGAAACTGCAATTTATTCATATCAGGATTATCAATACCATATTTTTGAAAAAGTCTTTTCTGTAATGAA
GGAGAAAACTCACCCAGGCAGTTCCATAGGATGGCAAGATCCTGGTATCTGTCTGCAATTCCAACTCTTCCAACATCAATACAACCTATTAATTTCCCCTCATCAAAAA
TAAGGTTATCAAGTGAGAAATCACCATGAGTGACCACTGAATCTGGTGAGAATGGCAAAAGATTATGCATTTCTTTCCAGACTTGTTCAACAGGCCAGCCATTTCTCT
CATCATCAAAATCACTGGCATCAACCAAACCATTATTCATTCTTGATTGGGCCTGAGCCAGTCTAAATACTCTATCAGAGTTAAAAGGACAATTACAAACAGGAATGG
AATGCAATCTTCTCAGGAACACTGCCAGGGCATCAACAATATTTTCACCTGAATCAGGATATTCTTCCAATACCTGGAATGCTGTTTTCCCTGGGATGGCAGTGGTGA
GTAACCATGCATCATCAGGAGTTCTGATAAAATGCTTGATGGTTGGAAGAGGCATAAATTCAGTCAGCCAGTTTAGTCTGACCATCTCATCTGTAACATCATTGGCAA
CAGAACCTTTGCCATGTTTCAGAAACAACTCTGGGGCATCTGGCTTCCCATACAATCTATAGATTGTGGCACCTGATTGCCCAACATTATCTCTAGCCCATTTATACCCA
TATAAATCAGCATCCATGTTGGAATTTAATCTTGGCCTGGAGCAAGAGGTTTCTCTTTGAATATGGCTCATACATGTGCACCTCCTATAGTGAGTTGTATTATACTATG
CAGATATACTATGCCAATGTTTAATTGTCAG

FIG. 54

DNARx-A66-2A

DraIIRINhe-ΔmCMVΔEF1I126-BstEII- ΔA66-H-F3(RKRR)-P2A-ΔA66-L-BglII-MixpA-BV2
(SEQ ID NO:33)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGGGACTGGGACTCCAGTGGGTGT
TCTTTGTGGCCCTGCTGAAAGGGGTGCACTGTGAAGTCAGACTGCTGGAAAGTGGTGGTGGCCTGCAGGTTCAGCTGGTGCAGTCTGGGGCTGAAGTGAAGAAACC
TGGCAGCTCTGTGAAGGTGTCCTGCAAGGCTAGTGGTGGCCCCTTCAGCATGACAGCCTTCACCTGGCTGAGACAGGCTCCTGGACAGGGCCTTGAATGGATGGGA
GGCATCAGCCCCATCTTCAGAACCCCTAAGTATGCCCAGAAATTCCAGGGCAGAGTGACCATCACAGCTGATGAGAGCACCAACACAGCCAACATGGAACTGACCAG
CCTGAAGTCTGAGGACACTGCTGTGTACTACTGTGCCAGAACACTGAGCAGCTACCAGCCTAACAATGATGCCTTTGCCATCTGGGGCCAGGGCACCATGGTTACAG
TCAGCTCTGCCAGCACAAAGGGCCCATCTGTGTTCCCTCTGGCACCCAGCAGCAAGTCTACCAGTGGTGGAACAGCTGCCCTGGGCTGTCTGGTCAAGGACTACTTTC
CTGAGCCAGTGACAGTGTCCTGGAACTCTGGGGCTCTGACATCTGGGGTGCACACATTCCCTGCTGTGCTCCAGTCCTCTGGCCTGTACAGCCTCAGCTCTGTGGTCA
CAGTGCCTAGCTCTAGCCTGGGCACCCAGACCTACATCTGCAATGTGAACCACAAGCCTAGCAACACCAAGGTGGACAAGAAGGCTGAGCCCAAGAGCTGTGACAA
GACCCACACCTGTCCTCCATGTCCTGCTCCAGAGCTGCTTGGAGGACCTTCTGTGTTTCTGTTCCCTCCAAAGCCAAAGGACACCCTGATGATCAGCAGAACCCCTGAA
GTGACATGTGTGGTGGTTGATGTGTCCCATGAGGACCCAGAAGTGAAGTTCAATTGGTATGTGGATGGTGTTGAGGTGCACAATGCCAAGACCAAGCCTAGAGAGG
AACAGTACAACAGCACCTACAGAGTGGTGTCTGTGCTGACAGTGCTGCATCAGGACTGGCTGAATGGCAAAGAGTACAAGTGCAAGGTGTCCAACAAGGCCCTGCC
TGCTCCTATTGAAAAGACCATCTCCAAGGCCAAGGGCCAGCCTAGGGAACCCCAGGTTTACACACTGCCACCTAGCAGGGATGAGCTGACCAAGAACCAGGTGTCCC
TGACCTGCCTGGTTAAGGGCTTCTACCCCTCTGACATTGCTGTGGAATGGGAGAGCAATGGCCAGCCAGAGAACAACTACAAGACAACCCCTCCTGTGCTGGACTCT
GATGGCTCATTCTTCCTGTACTCCAAGCTCACAGTGGACAAGTCCAGATGGCAGCAAGGCAATGTGTTCAGCTGCTCTGTGATGCATGAGGCCCTGCACAACCACTAC
ACACAGAAGTCCCTGAGCCTGTCTCCTGGCAAG*AGAAAGAGAAGGAGTGGAAGTGGAGCTACTAACTTCAGCCTGCTGAAGCAGGCTGGAGATGTGGAGGAGAAC*
*CCTGGACCT*ATGGACTTCCAGGTGCAGATCATCAGCTTTCTGCTGATCTCTGCCTCTGTGATCATGAGCAGAGGCCGAGATTGTGCTGACACAGAGCCCTGCCACACT
GTCTCTTAGCCCTGGGGAGAGAGCCACACTGAGCTGTAGAGCCAGCCAGTCTGTGTCCTCTTACCTGGCCTGGTATCAGCAGAAGCCTGGACAGGCTCCCAGACTGC
TGATCTATGATGCCAGCAACAGAGCCACAGGCATCCCTGCCAGATTCAGTGGCTCTGGCAGTGGCACAGACTTCACCCTGACCATCAGCAGACTGGAACCAGAGGAC
TTTGCTGTGTACTTCTGCCAGCAGTATGGCAGCAGCCCTCAGTTTGGCCAGGGCACAAGACTGGAAATCAAGAGAACAGTGGCTGCCCCTTCTGTGTTCATCTTCCCA
CCATCTGATGAGCAGCTGAAGTCTGGCACAGCCTCTGTTGTGTGCCTGCTGAACAACTTCTACCCTAGAGAAGCCAAGGTGCAGTGGAAGGTGGACAATGCCCTCCA
GTCTGGCAACTCCCAAGAGTCTGTGACAGAGCAGGACAGCAAGGACTCCACCTACAGCCTGAGCAGCACCCTGACACTGAGCAAGGCTGACTATGAGAAGCACAAA
GTCTATGCCTGTGAAGTGACCCACCAGGGCCTGTCTAGCCCTGTGACCAAGAGCTTCAACAGGGGAGAGAGCTGAAGATCTACTTCTGGCTAATAAAAGATCAGAGC
TCTAGTGATCTGTGTGTTGGTTTTTTGTGTCTGCATTCTAGCTCTAGTGATCAGCAGTTCAACCTGTTGATAGTATGTACTAAGCTCTCATGTTTAATGTACTAAGCTCT
CATGTTTAATGAACTAAACCCTCATGGCTAATGTACTAAGCTCTCATGGCTAATGTACTAAGCTCTCATGTTTCATGTACTAAGCTCTCATGTTTGAACAATAAAATTAA
TATAAATCAGCAACTTAAATAGCCTCTAAGGTTTTAAGTTTTATAAGAAAAAAAAGAATATATAAGGCTTTTAAAGGTTTTAAGGTTTCCTAGGTTATCCTCATATGAG
CTCTTAGAAAAACTCATCCAGCATCAAATGAAACTGCAATTTATTCATATCAGGATTATCAATACCATATTTTTGAAAAAGTCTTTTCTGTAATGAAGGAGAAAACTCA
CCCAGGCAGTTCCATAGGATGGCAAGATCCTGGTATCTGTCTGCAATTCCAACTCTTCCAACATCAATACAACCTATTAATTTCCCCTCATCAAAAATAAGGTTATCAA
GTGAGAAATCACCATGAGTGACCACTGAATCTGGTGAGAATGGCAAAAGATTATGCATTTCTTTCCAGACTTGTTCAACAGGCCAGCCATTTCTCTCATCATCAAAATC
ACTGGCATCAACCAAACCATTATTCATTCTTGATTGGGCCTGAGCCAGTCTAAATACTCTATCAGAGTTAAAAGGACAATTACAAACAGGAATGGAATGCAATCTTCTC
AGGAACACTGCCAGGGCATCAACAATATTTTCACCTGAATCAGGATATTCTTCCAATACCTGGAATGCTGTTTTCCCTGGGATGGCAGTGGTGAGTAACCATGCATCA
TCAGGAGTTCTGATAAAATGCTTGATGGTTGGAAGAGGCATAAATTCAGTCAGCCAGTTTAGTCTGACCATCTCATCTGTAACATCATTGGCAACAGAACCTTTGCCA
TGTTTCAGAAACAACTCTGGGGCATCTGGCTTCCCATACAATCTATAGATTGTGGCACCTGATTGCCCAACATTATCTCTAGCCCATTTATACCCATATAAATCAGCATC
CATGTTGGAATTTAATCTTGGCCTGGAGCAAGAGGTTTCTCTTTGAATATGGCTCATACATGTGCACCTCCTATAGTGAGTTGTATTATACTATGCAGATATACTATGC
CAATGTTTAATTGTCAG

FIG. 55

DNARx-D8 : Dual Cassette anti-D8

DraIIRINhe- ΔmCMV-EF1-I126-BstEII-ΔD8-H-BglII-polyA- ΔhCMV-EF1-I126-BstEII-ΔD8-L -BglII-polyA BV2

(SEQ ID NO:34)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGACTGGGACTCCAGTGGGTGTTCTTTGTGGCCCTGCTGAAAGGGGTGCACTGTGAAGTCAGACTGCTGGAAAGTGGTGGTGGCCTGCAGGTTCAGCTGGT
GCAGTCTGGGGCTGAAGTGAAGAAACCTGGCAGCTCTGTGAAGGTGTCCTGCAAGGCTAGTGGTGGCACCTTCTCTGCCTATGCCTTCACCTGGGTCAGACAGGCTC
CTGGACAGGGCCTTGAATGGATGGGAGGCATCACAGGCATGTTTGGCACAGCCAACTATGCCCAGAAATTCCAGGGCAGAGTGACCATCACAGCTGATGAGCTGAC
CAGCACAGCCTACATGGAACTGAGCAGCCTGACCTCTGAGGACACAGCCCTGTACTACTGTGCCAGAGGCCTGTACTATTATGAGTCTAGCCTGGACTACTGGGGCC
AGGGCACACTGGTTACAGTGTCTAGTGCCAGCACAAAGGGCCCATCTGTGTTCCCTCTGGCACCCAGCAGCAAGTCTACCAGTGGTGGAACAGCTGCCCTGGGCTGT
CTGGTCAAGGACTACTTTCCTGAGCCAGTGACAGTGTCCTGGAACTCTGGGGCTCTGACATCTGGGGTGCACACATTCCCTGCTGTGCTCCAGTCCTCTGGCCTGTAC
AGCCTCAGCTCTGTGGTCACAGTGCCTAGCTCTAGCCTGGGCACCCAGACCTACATCTGCAATGTGAACCACAAGCCTAGCAACACCAAGGTGGACAAGAAGGCTGA
GCCCAAGAGCTGTGACAAGACCCACACCTGTCCTCCATGTCCTGCTCCAGAGCTGCTTGGAGGACCTTCTGTGTTTCTGTTCCCTCCAAAGCCAAAGGACACCCTGAT
GATCAGCAGAACCCCTGAAGTGACATGTGTGGTGGTTGATGTGTCCCATGAGGACCCAGAAGTGAAGTTCAATTGGTATGTGGATGGTGTTGAGGTGCACAATGCC
AAGACCAAGCCTAGAGAGGAACAGTACAACAGCACCTACAGAGTGGTGTCTGTGCTGACAGTGCTGCATCAGGACTGGCTGAATGGCAAAGAGTACAAGTGCAAG
GTGTCCAACAAGGCCCTGCCTGCTCCTATTGAAAAGACCATCTCCAAGGCCAAGGGCCAGCCTAGGGAACCCCAGGTTTACACACTGCCACCTAGCAGGGATGAGCT
GACCAAGAACCAGGTGTCCCTGACCTGCCTGGTTAAGGGCTTCTACCCCTCTGACATTGCTGTGGAATGGGAGAGCAATGGCCAGCCAGAGAACAACTACAAGACA
ACCCCTCCTGTGCTGGACTCTGATGGCTCATTCTTCCTGTACTCCAAGCTCACAGTGGACAAGTCCAGATGGCAGCAAGGCAATGTGTTCAGCTGCTCTGTGATGCAT
GAGGCCCTGCACAACCACTACACACAGAAGTCCCTGAGCCTGTCTCCTGGCAAGTGAAGATCTACTTCTGGCTAATAAAAGATCAGAGCTCTAGTGATCTGTGTGTTG
GTTTTTTGTGTCTGCATTCTAGCATGTTACATAACTTATGGTAAATGGCCTGCCTGGCTGACTGCCCAATGACCCCTGCCCAATGATGTCAATAATGATGTATGTTCCCA
TGTAATGCCAATAGGGACTTTCCATTGATGTCAATGGGTGGAGTATTTATGGTAACTGCCCACTTGGCAGTACATCAAGTGTATCATATGCCAAGTATGCCCCCTATTG
ATGTCAATGATGGTAAATGGCCTGCCTGGCATTATGCCCAGTACATGACCTTATGGGACTTTCCTACTTGGCAGTACATCTATGTATTAGTCATTGCTATTACCATGGA
TTAGTGGAGAAGAGCATGCTTGAGGGCTGAGTGCCCCTCAGTGGGCAGAGAGCACATGGCCCACAGTCCCTGAGAAGTTGGGGGGAGGGGTGGGCAATTGAACT
GGTGCCTAGAGAAGGTGGGGCTTGGGTAAACTGGGAAAGTGATGTGGTGTACTGGCTCCACCTTTTTCCCCAGGGTGGGGGAGAACCATATATAAGTGCAGTAGTC
TCTGTGAACATTCAAGCTTCTGCCTTCTCCCTCCTGTGAGTTTGGATGCACCTACTAGATATCTTGGTAAGTCACTGACTGTCTATGCCTGGGAAAGGGTGGGCAGGA
GGTGGGGCAGTGCAGGAAAAGTGGCACTGTGAACCCTGCAGCCCTAGACAATTGTACTAACCTTCTTCTCTTTCCTCTCCTGACAGGTTGGTAACCAAGCCACCATGG
ACTTCCAGGTGCAGATCATCAGCTTTCTGCTGATCTCTGCCTCTGTGATCATGAGCAGAGGCCAGTCTGTGCTGACCCAGCCTCCATCTGCATCTGGAAGCCCTGGCCA
GTCTGTGACCATCAGCTGTACAGGCACCAGCTCTGATGTTGGAGGCTACAACTCTGTGTCCTGGTATCAGCAGCACCCTGGCAAGGCCCCTAAGCTGATGATCTATGA
AGTGACCAAGAGGCCCTCTGGGGTGCCAGACAGATTCTCTGCCAGCAAGTCTGGCAACACAGCCAGCCTGACAGTGTCTGGCCTGCAAGCTGAGGATGAGGCTGAC
TACTTCTGCTGCTCCTATGCTGGCCACTCTGCCTATGTGTTTGGCACTGGCACCAAAGTGACAGTGCTGAGAACAGTGGCTGCCCCTTCTGTGTTCATCTTCCCACCATC
TGATGAGCAGCTGAAGTCTGGCACAGCCTCTGTTGTGTGCCTGCTGAACAACTTCTACCCTAGAGAAGCCAAGGTGCAGTGGAAGGTGGACAATGCCCTCCAGTCTG
GCAACTCCCAAGAGTCTGTGACAGAGCAGGACAGCAAGGACTCCACCTACAGCCTGAGCAGCACCCTGACACTGAGCAAGGCTGACTATGAGAAGCACAAAGTCTA
TGCCTGTGAAGTGACCCACCAGGGCCTGTCTAGCCCTGTGACCAAGAGCTTCAACAGGGGAGAGAGCTGAAGATCTACTTCTGGCTAATAAAAGATCAGAGCTCTAG
TGATCTGTGTGTTGGTTTTTTGTGTCTGCATTCTAGCTCTAGTGATCAGCAGTTCAACCTGTTGATAGTATGTACTAAGCTCTCATGTTTAATGTACTAAGCTCTCATGTT
TAATGAACTAAACCCTCATGGCTAATGTACTAAGCTCTCATGGCTAATGTACTAAGCTCTCATGTTTCATGTACTAAGCTCTCATGTTTGAACAATAAAATTAATATAAA
TCAGCAACTTAAATAGCCTCTAAGGTTTTAAGTTTTATAAGAAAAAAAAGAATATATAAGGCTTTTAAAGGTTTTAAGGTTTCCTAGGTTATCCTCATATGAGCTCTTA
GAAAAACTCATCCAGCATCAAATGAAACTGCAATTTATTCATATCAGGATTATCAATACCATATTTTTGAAAAAGTCTTTTCTGTAATGAAGGAGAAAACTCACCCAGG
CAGTTCCATAGGATGGCAAGATCCTGGTATCTGTCTGCAATTCCAACTCTTCCAACATCAATACAACCTATTAATTTCCCCTCATCAAAAATAAGGTTATCAAGTGAGA
AATCACCATGAGTGACCACTGAATCTGGTGAGAATGGCAAAAGATTATGCATTTCTTTCCAGACTTGTTCAACAGGCCAGCCATTTCTCTCATCATCAAAATCACTGGC
ATCAACCAAACCATTATTCATTCTTGATTGGGCCTGAGCCAGTCTAAATACTCTATCAGAGTTAAAAGGACAATTACAAACAGGAATGGAATGCAATCTTCTCAGGAA
CACTGCCAGGGCATCAACAATATTTTCACCTGAATCAGGATATTCTTCCAATACCTGGAATGCTGTTTTCCCTGGGATGGCAGTGGTGAGTAACCATGCATCATCAGG
AGTTCTGATAAAATGCTTGATGGTTGGAAGAGGCATAAATTCAGTCAGCCAGTTTAGTCTGACCATCTCATCTGTAACATCATTGGCAACAGAACCTTTGCCATGTTTC
AGAAACAACTCTGGGGCATCTGGCTTCCCATACAATCTATAGATTGTGGCACCTGATTGCCCAACATTATCTCTAGCCCATTTATACCCATATAAATCAGCATCCATGTT
GGAATTTAATCTTGGCCTGGAGCAAGAGGTTTCTCTTTGAATATGGCTCATACATGTGCACCTCCTATAGTGAGTTGTATTATACTATGCAGATATACTATGCCAATGT
TTAATTGTCAG

FIG. 56

DNARx-F10: Dual Cassette anti-F10

DraIIRINhe- ΔmCMV-EF1-I126-BstEII-ΔF10-H-BglII-polyA- ΔhCMV-EF1-I126-BstEII-ΔF10-L -BglII-polyA BV2

(SEQ ID NO:35)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGACTGGGACTCCAGTGGGTGTTCTTTGTGGCCCTGCTGAAAGGGGTGCACTGTGAAGTCAGACTGCTGGAAAGTGGTGGTGGCCTGCAGGTTCAGCTGGT
GCAGTCTGGGGCTGAAGTGAAGAAACCTGGCAGCTCTGTGAAGGTGTCCTGCACCTCCTCTGAAGTGACCTTCAGCAGCTTTGCCATCAGCTGGGTCAGACAGGCTC
CTGGACAGGGCCTTGAATGGCTTGGAGGCATCAGCCCCATGTTTGGCACCCCTAACTATGCCCAGAAATTCCAGGGCAGAGTGACCATCACAGCTGACCAGAGCACC
AGAACAGCCTACATGGACCTGAGAAGTCTTAGGAGTGAAGATACAGCTGTGTACTACTGTGCTAGAAGCCCCAGCTACATCTGCTCTGGTGGCACCTGTGTGTTTGA
CCACTGGGGCCAGGGAACCCTGGTCACAGTTTCTTCTGCCAGCACAAAGGGCCCATCTGTGTTCCCTCTGGCACCCAGCAGCAAGTCTACCAGTGGTGGAACAGCTG
CCCTGGGCTGTCTGGTCAAGGACTACTTTCCTGAGCCAGTGACAGTGTCCTGGAACTCTGGGGCTCTGACATCTGGGGTGCACACATTCCCTGCTGTGCTCCAGTCCT
CTGGCCTGTACAGCCTCAGCTCTGTGGTCACAGTGCCTAGCTCTAGCCTGGGCACCCAGACCTACATCTGCAATGTGAACCACAAGCCTAGCAACACCAAGGTGGAC
AAGAAGGCTGAGCCCAAGAGCTGTGACAAGACCCACACCTGTCCTCCATGTCCTGCTCCAGAGCTGCTTGGAGGACCTTCTGTGTTTCTGTTCCCTCCAAAGCCAAAG
GACACCCTGATGATCAGCAGAACCCCTGAAGTGACATGTGTGGTGGTTGATGTGTCCCATGAGGACCCAGAAGTGAAGTTCAATTGGTATGTGGATGGTGTTGAGG
TGCACAATGCCAAGACCAAGCCTAGAGAGGAACAGTACAACAGCACCTACAGAGTGGTGTCTGTGCTGACAGTGCTGCATCAGGACTGGCTGAATGGCAAAGAGTA
CAAGTGCAAGGTGTCCAACAAGGCCCTGCCTGCTCCTATTGAAAAGACCATCTCCAAGGCCAAGGGCCAGCCTAGGGAACCCCAGGTTTACACACTGCCACCTAGCA
GGGATGAGCTGACCAAGAACCAGGTGTCCCTGACCTGCCTGGTTAAGGGCTTCTACCCCTCTGACATTGCTGTGGAATGGGAGAGCAATGGCCAGCCAGAGAACAA
CTACAAGACAACCCCTCCTGTGCTGGACTCTGATGGCTCATTCTTCCTGTACTCCAAGCTCACAGTGGACAAGTCCAGATGGCAGCAAGGCAATGTGTTCAGCTGCTC
TGTGATGCATGAGGCCCTGCACAACCACTACACACAGAAGTCCCTGAGCCTGTCTCCTGGCAAGTGAAGATCTACTTCTGGCTAATAAAAGATCAGAGCTCTAGTGAT
CTGTGTGTTGGTTTTTTGTGTCTGCATTCTAGCATGTTACATAACTTATGGTAAATGGCCTGCCTGGCTGACTGCCCAATGACCCCTGCCCAATGATGTCAATAATGAT
GTATGTTCCCATGTAATGCCAATAGGGACTTTCCATTGATGTCAATGGGTGGAGTATTTATGGTAACTGCCCACTTGGCAGTACATCAAGTGTATCATATGCCAAGTAT
GCCCCCTATTGATGTCAATGATGGTAAATGGCCTGCCTGGCATTATGCCCAGTACATGACCTTATGGGACTTTCCTACTTGGCAGTACATCTATGTATTAGTCATTGCT
ATTACCATGGATTAGTGGAGAAGAGCATGCTTGAGGGCTGAGTGCCCCTCAGTGGGCAGAGAGCACATGGCCCACAGTCCCTGAGAAGTTGGGGGGAGGGGTGG
GCAATTGAACTGGTGCCTAGAGAAGGTGGGGCTTGGGTAAACTGGGAAAGTGATGTGGTGTACTGGCTCCACCTTTTTCCCCAGGGTGGGGGAGAACCATATATAA
GTGCAGTAGTCTCTGTGAACATTCAAGCTTCTGCCTTCTCCCTCCTGTGAGTTTGGATGCACCTACTAGATATCTTGGTAAGTCACTGACTGTCTATGCCTGGGAAAGG
GTGGGCAGGAGGTGGGGCAGTGCAGGAAAAGTGGCACTGTGAACCCTGCAGCCCTAGACAATTGTACTAACCTTCTTCTCTTTCCTCTCCTGACAGGTTGGTAACCA
AGCCACCATGGACTTCCAGGTGCAGATCATCAGCTTTCTGCTGATCTCTGCCTCTGTGATCATGAGCAGAGGCCAGCCTGGACTGACACAGCCTCCATCTGTGTCCAA
GGGCCTGAGACAGACAGCCACACTGACCTGCACAGGCAACAGCAACAATGTGGGCAATCAAGGGGCTGCCTGGCTCCAGCAGCATCAGGGACATCCTCCAAAGCTG
CTGAGCTACAGAAACAATGACAGACCCTCTGGCATCTCTGAGAGATTCTCTGCCTCTAGGAGTGGCAACACAGCCAGCCTGACCATCACTGGACTCCAGCCAGAGGA
TGAGGCTGACTACTACTGCTCCACCTGGGACAGCAGCCTGTCTGCTGTGGTTTTTGGTGGTGGCACCAAGCTGACAGTGCTGAGAACAGTGGCTGCCCCTTCTGTGTT
CATCTTCCCACCATCTGATGAGCAGCTGAAGTCTGGCACAGCCTCTGTTGTGTGCCTGCTGAACAACTTCTACCCTAGAGAAGCCAAGGTGCAGTGGAAGGTGGACA
ATGCCCTCCAGTCTGGCAACTCCCAAGAGTCTGTGACAGAGCAGGACAGCAAGGACTCCACCTACAGCCTGAGCAGCACCCTGACACTGAGCAAGGCTGACTATGA
GAAGCACAAAGTCTATGCCTGTGAAGTGACCCACCAGGGCCTGTCTAGCCCTGTGACCAAGAGCTTCAACAGGGGAGAGAGCTGAAGATCTACTTCTGGCTAATAAA
AGATCAGAGCTCTAGTGATCTGTGTGTTGGTTTTTTGTGTCTGCATTCTAGCTCTAGTGATCAGCAGTTCAACCTGTTGATAGTATGTACTAAGCTCTCATGTTTAATGT
ACTAAGCTCTCATGTTTAATGAACTAAACCCTCATGGCTAATGTACTAAGCTCTCATGGCTAATGTACTAAGCTCTCATGTTTCATGTACTAAGCTCTCATGTTTGAACA
ATAAAATTAATATAAATCAGCAACTTAAATAGCCTCTAAGGTTTTAAGTTTTATAAGAAAAAAAAGAATATATAAGGCTTTTAAAGGTTTTAAGGTTTCCTAGGTTATC
CTCATATGAGCTCTTAGAAAAACTCATCCAGCATCAAATGAAACTGCAATTTATTCATATCAGGATTATCAATACCATATTTTTGAAAAAGTCTTTTCTGTAATGAAGGA
GAAAACTCACCCAGGCAGTTCCATAGGATGGCAAGATCCTGGTATCTGTCTGCAATTCCAACTCTTCCAACATCAATACAACCTATTAATTTCCCCTCATCAAAAATAA
GGTTATCAAGTGAGAAATCACCATGAGTGACCACTGAATCTGGTGAGAATGGCAAAAGATTATGCATTTCTTTCCAGACTTGTTCAACAGGCCAGCCATTTCTCTCATC
ATCAAAATCACTGGCATCAACCAAACCATTATTCATTCTTGATTGGGCCTGAGCCAGTCTAAATACTCTATCAGAGTTAAAAGGACAATTACAAACAGGAATGGAATG
CAATCTTCTCAGGAACACTGCCAGGGCATCAACAATATTTTCACCTGAATCAGGATATTCTTCCAATACCTGGAATGCTGTTTTCCCTGGGATGGCAGTGGTGAGTAAC
CATGCATCATCAGGAGTTCTGATAAAATGCTTGATGGTTGGAAGAGGCATAAATTCAGTCAGCCAGTTTAGTCTGACCATCTCATCTGTAACATCATTGGCAACAGAA
CCTTTGCCATGTTTCAGAAACAACTCTGGGGCATCTGGCTTCCCATACAATCTATAGATTGTGGCACCTGATTGCCCAACATTATCTCTAGCCCATTTATACCCATATAA
ATCAGCATCCATGTTGGAATTTAATCTTGGCCTGGAGCAAGAGGTTTCTCTTTGAATATGGCTCATACATGTGCACCTCCTATAGTGAGTTGTATTATACTATGCAGAT
ATACTATGCCAATGTTTAATTGTCAG

FIG. 57

DNARx-A66: Dual Cassette anti-A66

DraIIRINhe- ΔmCMV-EF1-I126-BstEII-ΔA66-H-BglII-polyA- ΔhCMV-EF1-I126-BstEII-ΔA66-L -BglII-polyA BV2

(SEQ ID NO:36)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGACTGGGACTCCAGTGGGTGTTCTTTGTGGCCCTGCTGAAAGGGGTGCACTGTGAAGTCAGACTGCTGGAAAGTGGTGGTGGCCTGCAGGTTCAGCTGGT
GCAGTCTGGGGCTGAAGTGAAGAAACCTGGCAGCTCTGTGAAGGTGTCCTGCAAGGCTAGTGGTGGCCCCTTCAGCATGACAGCCTTCACCTGGCTGAGACAGGCT
CCTGGACAGGGCCTTGAATGGATGGGAGGCATCAGCCCCATCTTCAGAACCCCTAAGTATGCCCAGAAATTCCAGGGCAGAGTGACCATCACAGCTGATGAGAGCA
CCAACACAGCCAACATGGAACTGACCAGCCTGAAGTCTGAGGACACTGCTGTGTACTACTGTGCCAGAACACTGAGCAGCTACCAGCCTAACAATGATGCCTTTGCC
ATCTGGGGCCAGGGCACCATGGTTACAGTCAGCTCTGCCAGCACAAAGGGCCCATCTGTGTTCCCTCTGGCACCCAGCAGCAAGTCTACCAGTGGTGGAACAGCTGC
CCTGGGCTGTCTGGTCAAGGACTACTTTCCTGAGCCAGTGACAGTGTCCTGGAACTCTGGGGCTCTGACATCTGGGGTGCACACATTCCCTGCTGTGCTCCAGTCCTC
TGGCCTGTACAGCCTCAGCTCTGTGGTCACAGTGCCTAGCTCTAGCCTGGGCACCCAGACCTACATCTGCAATGTGAACCACAAGCCTAGCAACACCAAGGTGGACA
AGAAGGCTGAGCCCAAGAGCTGTGACAAGACCCACACCTGTCCTCCATGTCCTGCTCCAGAGCTGCTTGGAGGACCTTCTGTGTTTCTGTTCCCTCCAAAGCCAAAGG
ACACCCTGATGATCAGCAGAACCCCTGAAGTGACATGTGTGGTGGTTGATGTGTCCCATGAGGACCCAGAAGTGAAGTTCAATTGGTATGTGGATGGTGTTGAGGT
GCACAATGCCAAGACCAAGCCTAGAGAGGAACAGTACAACAGCACCTACAGAGTGGTGTCTGTGCTGACAGTGCTGCATCAGGACTGGCTGAATGGCAAAGAGTAC
AAGTGCAAGGTGTCCAACAAGGCCCTGCCTGCTCCTATTGAAAAGACCATCTCCAAGGCCAAGGGCCAGCCTAGGGAACCCCAGGTTTACACACTGCCACCTAGCAG
GGATGAGCTGACCAAGAACCAGGTGTCCCTGACCTGCCTGGTTAAGGGCTTCTACCCCTCTGACATTGCTGTGGAATGGGAGAGCAATGGCCAGCCAGAGAACAAC
TACAAGACAACCCCTCCTGTGCTGGACTCTGATGGCTCATTCTTCCTGTACTCCAAGCTCACAGTGGACAAGTCCAGATGGCAGCAAGGCAATGTGTTCAGCTGCTCT
GTGATGCATGAGGCCCTGCACAACCACTACACACAGAAGTCCCTGAGCCTGTCTCCTGGCAAGTGAAGATCTACTTCTGGCTAATAAAAGATCAGAGCTCTAGTGATC
TGTGTGTTGGTTTTTTGTGTCTGCATTCTAGCATGTTACATAACTTATGGTAAATGGCCTGCCTGGCTGACTGCCCAATGACCCCTGCCCAATGATGTCAATAATGATG
TATGTTCCCATGTAATGCCAATAGGGACTTTCCATTGATGTCAATGGGTGGAGTATTTATGGTAACTGCCCACTTGGCAGTACATCAAGTGTATCATATGCCAAGTATG
CCCCCTATTGATGTCAATGATGGTAAATGGCCTGCCTGGCATTATGCCCAGTACATGACCTTATGGGACTTTCCTACTTGGCAGTACATCTATGTATTAGTCATTGCTAT
TACCATGGATTAGTGGAGAAGAGCATGCTTGAGGGCTGAGTGCCCCTCAGTGGGCAGAGAGCACATGGCCCACAGTCCCTGAGAAGTTGGGGGGAGGGGTGGGC
AATTGAACTGGTGCCTAGAGAAGGTGGGGCTTGGGTAAACTGGGAAAGTGATGTGGTGTACTGGCTCCACCTTTTTCCCCAGGGTGGGGGAGAACCATATATAAGT
GCAGTAGTCTCTGTGAACATTCAAGCTTCTGCCTTCTCCCTCCTGTGAGTTTGGATGCACCTACTAGATATCTTGGTAAGTCACTGACTGTCTATGCCTGGGAAAGGGT
GGGCAGGAGGTGGGGCAGTGCAGGAAAAGTGGCACTGTGAACCCTGCAGCCCTAGACAATTGTACTAACCTTCTTCTCTTTCCTCTCCTGACAGGTTGGTAACCAAG
CCACCATGGACTTCCAGGTGCAGATCATCAGCTTTCTGCTGATCTCTGCCTCTGTGATCATGAGCAGAGGCCGAGATTGTGCTGACACAGAGCCCTGCCACACTGTCT
CTTAGCCCTGGGGAGAGAGCCACACTGAGCTGTAGAGCCAGCCAGTCTGTGTCCTCTTACCTGGCCTGGTATCAGCAGAAGCCTGGACAGGCTCCCAGACTGCTGAT
CTATGATGCCAGCAACAGAGCCACAGGCATCCCTGCCAGATTCAGTGGCTCTGGCAGTGGCACAGACTTCACCCTGACCATCAGCAGACTGGAACCAGAGGACTTTG
CTGTGTACTTCTGCCAGCAGTATGGCAGCAGCCCTCAGTTTGGCCAGGGCACAAGACTGGAAATCAAGAGAACAGTGGCTGCCCCTTCTGTGTTCATCTTCCCACCAT
CTGATGAGCAGCTGAAGTCTGGCACAGCCTCTGTTGTGTGCCTGCTGAACAACTTCTACCCTAGAGAAGCCAAGGTGCAGTGGAAGGTGGACAATGCCCTCCAGTCT
GGCAACTCCCAAGAGTCTGTGACAGAGCAGGACAGCAAGGACTCCACCTACAGCCTGAGCAGCACCCTGACACTGAGCAAGGCTGACTATGAGAAGCACAAAGTCT
ATGCCTGTGAAGTGACCCACCAGGGCCTGTCTAGCCCTGTGACCAAGAGCTTCAACAGGGGAGAGAGCTGAAGATCTACTTCTGGCTAATAAAAGATCAGAGCTCTA
GTGATCTGTGTGTTGGTTTTTTGTGTCTGCATTCTAGCTCTAGTGATCAGCAGTTCAACCTGTTGATAGTATGTACTAAGCTCTCATGTTTAATGTACTAAGCTCTCATG
TTTAATGAACTAAACCCTCATGGCTAATGTACTAAGCTCTCATGGCTAATGTACTAAGCTCTCATGTTTCATGTACTAAGCTCTCATGTTTGAACAATAAAATTAATATA
AATCAGCAACTTAAATAGCCTCTAAGGTTTTAAGTTTTATAAGAAAAAAAAGAATATATAAGGCTTTTAAAGGTTTTAAGGTTTCCTAGGTTATCCTCATATGAGCTCT
TAGAAAAACTCATCCAGCATCAAATGAAACTGCAATTTATTCATATCAGGATTATCAATACCATATTTTTGAAAAAGTCTTTTCTGTAATGAAGGAGAAAACTCACCCA
GGCAGTTCCATAGGATGGCAAGATCCTGGTATCTGTCTGCAATTCCAACTCTTCCAACATCAATACAACCTATTAATTTCCCCTCATCAAAAATAAGGTTATCAAGTGA
GAAATCACCATGAGTGACCACTGAATCTGGTGAGAATGGCAAAAGATTATGCATTTCTTTCCAGACTTGTTCAACAGGCCAGCCATTTCTCTCATCATCAAAATCACTG
GCATCAACCAAACCATTATTCATTCTTGATTGGGCCTGAGCCAGTCTAAATACTCTATCAGAGTTAAAAGGACAATTACAAACAGGAATGGAATGCAATCTTCTCAGG
AACACTGCCAGGGCATCAACAATATTTTCACCTGAATCAGGATATTCTTCCAATACCTGGAATGCTGTTTTCCCTGGGATGGCAGTGGTGAGTAACCATGCATCATCA
GGAGTTCTGATAAAATGCTTGATGGTTGGAAGAGGCATAAATTCAGTCAGCCAGTTTAGTCTGACCATCTCATCTGTAACATCATTGGCAACAGAACCTTTGCCATGT
TTCAGAAACAACTCTGGGGCATCTGGCTTCCCATACAATCTATAGATTGTGGCACCTGATTGCCCAACATTATCTCTAGCCCATTTATACCCATATAAATCAGCATCCAT
GTTGGAATTTAATCTTGGCCTGGAGCAAGAGGTTTCTCTTTGAATATGGCTCATACATGTGCACCTCCTATAGTGAGTTGTATTATACTATGCAGATATACTATGCCAA
TGTTTAATTGTCAG

FIG. 58

DNARx-HA-MITD

DraIIRINhe-ΔmCMVΔEF1I126-BstEII-HA-MITD-BglII-MixpA-BV2

(SEQ ID NO:37)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGAAGGCCAACCTGCTGGTGCTGC
TGTGTGCTCTGGCTGCTGCTGATGCTGACACCATCTGCATTGGCTACCATGCCAACAACAGCACAGACACAGTGGACACTGTGCTGGAAAAGAATGTGACAGTGACC
CACTCTGTCAACCTGCTTGAGGACAGCCACAATGGCAAGCTGTGCAGACTGAAGGGCATTGCCCCTCTGCAACTGGGCAAGTGCAACATTGCTGGATGGCTGCTGGG
CAACCCTGAGTGTGATCCTCTGCTGCCTGTCAGATCCTGGTCCTACATTGTGGAAACCCCTAGCTCTGAGAATGGCATCTGCTACCCTGGGGACTTCATTGACTATGAG
GAACTGAAAGAACAGCTGTCCTCTGTCAGCAGCTTTGAGAGATTTGAAATCTTCCCCAAAGAGAGCAGCTGGCCCAACCACAACACCAACAAAGGGGTCACAGCTGC
CTGTAGCCATGAGGGCAAGAGCAGCTTCTACAGAAACCTGCTGTGGCTGACTGAGAAAGAGGGCAGCTACCCCAAGCTGAAGAACTCCTATGTGAACAAGAAGGGC
AAAGAGGTCCTGGTTCTCTGGGGCATCCACCATCCTAGCAACAGCAAAGAGCAGCAGAACCTGTACCAGAATGAGAATGCCTATGTGTCTGTTGTGACCAGCAACTA
CAACAGAAGGTTCACCCCTGAGATTGCTGAGAGGCCCAAAGTGAAGGACCAGGCTGGCAGAATGAACTACTACTGGACCCTGCTGAAGCCTGGGGACACCATCATC
TTTGAGGCCAATGGCAACCTGATTGCCCCTATGTATGCCTTTGCTCTGAGCAGAGGCTTTGGCTCTGGCATCATCACCAGCAATGCCAGCATGCATGAGTGCAATACC
AAGTGTCAGACCCCTCTGGGAGCTATCAACAGCAGCCTGCCTTTCCAGAACATCCATCCTGTGACCATTGGAGAGTGCCCCAAATATGTTAGGAGTGCCAAGCTGAG
GATGGTCACTGGCCTGAGAAACATCCCCAGCATCCAGTCCAGAGGCCTGTTTGGAGCCATTGCTGGCTTCATTGAGGGAGGCTGGACAGGCATGATTGATGGATGG
TATGGCTACCACCATCAGAATGAGCAAGGCAGTGGCTATGCTGCTGACCAGAAAAGCACCCAGAATGCTGTGAATGGCATTACAAACAAAGTGAACACAGTGATTG
AGAAGATGAACATCCAGTTCACTGCTGTGGGGAAAGAGTTCAACAAGCTTGAGAAGAGGATGGAAAACCTGAACAAAAAAGTGGATGATGGCTTCCTGGACATCTG
GACCTACAATGCTGAGCTGCTGGTCCTCCTGGAAAATGAGAGAACCCTGGACTTCCATGACAGCAATGTGAAGAACCTCTATGAGAAAGTGAAGTCCCAGCTCAAGA
ACAATGCCAAAGAAATTGGCAATGGCTGCTTTGAGTTCTACCACAAGTGTGACAATGAGTGCATGGAATCTGTCAGAAATGGCACCTATGACTACCCTAAGTACTCTG
AGGAAAGCAAGCTGAACAGGGAAAAAGTTGATGGGGTCAAGCTGGAATCCATGGGCATCTACCAGATCATTGTGGGCATTGTGGCAGGCCTGGCTGTGCTGGCAG
TGGTGGTTATTGGAGCTGTGGTGGCAGCAGTGATGTGCAGAAGAAAGTCCTCTGGAGGCAAAGGTGGCAGCTACTCTCAGGCTGCCTGTTCTGATTCTGCCCAGGG
CTCTGATGTGTCCCTGACAGCTTAAAGATCTACTTCTGGCTAATAAAAGATCAGAGCTCTAGTGATCTGTGTGTTGGTTTTTTGTGTCTGCATTCTAGCTCTAGTGATCA
GCAGTTCAACCTGTTGATAGTATGTACTAAGCTCTCATGTTTAATGTACTAAGCTCTCATGTTTAATGAACTAAACCCTCATGGCTAATGTACTAAGCTCTCATGGCTAA
TGTACTAAGCTCTCATGTTTCATGTACTAAGCTCTCATGTTTGAACAATAAAATTAATATAAATCAGCAACTTAAATAGCCTCTAAGGTTTTAAGTTTTATAAGAAAAAA
AAGAATATATAAGGCTTTTAAAGGTTTTAAGGTTTCCTAGGTTATCCTCATATGAGCTCTTAGAAAAACTCATCCAGCATCAAATGAAACTGCAATTTATTCATATCAG
GATTATCAATACCATATTTTTGAAAAAGTCTTTTCTGTAATGAAGGAGAAAACTCACCCAGGCAGTTCCATAGGATGGCAAGATCCTGGTATCTGTCTGCAATTCCAAC
TCTTCCAACATCAATACAACCTATTAATTTCCCCTCATCAAAAATAAGGTTATCAAGTGAGAAATCACCATGAGTGACCACTGAATCTGGTGAGAATGGCAAAAGATT
ATGCATTTCTTTCCAGACTTGTTCAACAGGCCAGCCATTTCTCTCATCATCAAAATCACTGGCATCAACCAAACCATTATTCATTCTTGATTGGGCCTGAGCCAGTCTAA
ATACTCTATCAGAGTTAAAAGGACAATTACAAACAGGAATGGAATGCAATCTTCTCAGGAACACTGCCAGGGCATCAACAATATTTTCACCTGAATCAGGATATTCTT
CCAATACCTGGAATGCTGTTTTCCCTGGGATGGCAGTGGTGAGTAACCATGCATCATCAGGAGTTCTGATAAAATGCTTGATGGTTGGAAGAGGCATAAATTCAGTC
AGCCAGTTTAGTCTGACCATCTCATCTGTAACATCATTGGCAACAGAACCTTTGCCATGTTTCAGAAACAACTCTGGGGCATCTGGCTTCCCATACAATCTATAGATTG
TGGCACCTGATTGCCCAACATTATCTCTAGCCCATTTATACCCATATAAATCAGCATCCATGTTGGAATTTAATCTTGGCCTGGAGCAAGAGGTTTCTCTTTGAATATGG
CTCATACATGTGCACCTCCTATAGTGAGTTGTATTATACTATGCAGATATACTATGCCAATGTTTAATTGTCAG

FIG. 59

DNARx-SEC-partial HA-MITD

DraIIRINhe-ΔmCMVΔEF1I126-BstEII-SEC-partial HA-MITD-BglII-MixpA-BV2
(SEQ ID NO:38)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGAGAGTGACAGCCCCTAGAACAG
TCCTGCTGCTCCTGTCTGCTGCCCTGGCTCTGACAGAAACATGGGCTGGCTCCAGACTGAAGGGCATTGCTCCTCTGCAACTGGGCAAGTGCAACATTGCTGGCTGGC
TGCTGGGCAACCCTGAGTGTGATCCTCTGCTGCCTGTCAGATCCTGGTCCTACATTGTGGAAACCCCTAGCTCTGAGAATGGCATCTGCTACCCTGGGGACTTCATTG
ACTATGAGGAACTGAAAGAACAGCTGTCCTCTGTGTCCAGCTTTGAGAGATTTGAAATCTTCCCCAAAGAGAGCAGCTGGCCCAACCACAACACCAACAAAGGGGTC
ACAGCTGCCTGTAGCCATGAGGGCAAGAGCAGCTTCTACAGAAACCTGCTGTGGCTGACAGAGAAAGAGGGCAGCTACCCCAAGCTGAAGAACTCCTATGTGAACA
AGAAGGGCAAAGAGGTCCTGGTTCTCTGGGGCATCCACCATCCTAGCAACAGCAAAGAGCAGCAGAACCTGTACCAGAATGAGAATGCCTATGTGTCTGTGGTCAC
AAGCAACTACAACAGAAGGTTCACCCCTGAGATTGCTGAGAGGCCCAAAGTGAAGGACCAGGCTGGCAGAATGAACTACTACTGGACCCTGCTGAAGCCTGGGGAC
ACCATCATCTTTGAGGCCAATGGCAACCTGATTGCCCCTATGTATGCCTTTGCTCTGAGCAGAGGCTTTGGCTCTGGCATCATCACCTCTGTGGATGGGGTCAAGCTG
GAATCCATGGGCATCATTGTGGGCATTGTGGCAGGCCTGGCTGTGCTGGCAGTGGTGGTTATTGGAGCTGTGGTGGCTGCTGTGATGTGCAGAAGAAAGTCCTCTG
GAGGCAAAGGTGGCAGCTACTCTCAGGCTGCCTGTTCTGATTCTGCCCAGGGCTCTGATGTGTCCCTGACAGCTTAAAGATCTACTTCTGGCTAATAAAAGATCAGAG
CTCTAGTGATCTGTGTGTTGGTTTTTTGTGTCTGCATTCTAGCTCTAGTGATCAGCAGTTCAACCTGTTGATAGTATGTACTAAGCTCTCATGTTTAATGTACTAAGCTC
TCATGTTTAATGAACTAAACCCTCATGGCTAATGTACTAAGCTCTCATGGCTAATGTACTAAGCTCTCATGTTTCATGTACTAAGCTCTCATGTTTGAACAATAAAATTA
ATATAAATCAGCAACTTAAATAGCCTCTAAGGTTTTAAGTTTTATAAGAAAAAAAAGAATATATAAGGCTTTTAAAGGTTTTAAGGTTTCCTAGGTTATCCTCATATGA
GCTCTTAGAAAAACTCATCCAGCATCAAATGAAACTGCAATTTATTCATATCAGGATTATCAATACCATATTTTTGAAAAAGTCTTTTCTGTAATGAAGGAGAAAACTC
ACCCAGGCAGTTCCATAGGATGGCAAGATCCTGGTATCTGTCTGCAATTCCAACTCTTCCAACATCAATACAACCTATTAATTTCCCCTCATCAAAAATAAGGTTATCAA
GTGAGAAATCACCATGAGTGACCACTGAATCTGGTGAGAATGGCAAAAGATTATGCATTTCTTTCCAGACTTGTTCAACAGGCCAGCCATTTCTCTCATCATCAAAATC
ACTGGCATCAACCAAACCATTATTCATTCTTGATTGGGCCTGAGCCAGTCTAAATACTCTATCAGAGTTAAAAGGACAATTACAAACAGGAATGGAATGCAATCTTCTC
AGGAACACTGCCAGGGCATCAACAATATTTTCACCTGAATCAGGATATTCTTCCAATACCTGGAATGCTGTTTTCCCTGGGATGGCAGTGGTGAGTAACCATGCATCA
TCAGGAGTTCTGATAAAATGCTTGATGGTTGGAAGAGGCATAAATTCAGTCAGCCAGTTTAGTCTGACCATCTCATCTGTAACATCATTGGCAACAGAACCTTTGCCA
TGTTTCAGAAACAACTCTGGGGCATCTGGCTTCCCATACAATCTATAGATTGTGGCACCTGATTGCCCAACATTATCTCTAGCCCATTTATACCCATATAAATCAGCATC
CATGTTGGAATTTAATCTTGGCCTGGAGCAAGAGGTTTCTCTTTGAATATGGCTCATACATGTGCACCTCCTATAGTGAGTTGTATTATACTATGCAGATATACTATGC
CAATGTTTAATTGTCAG

FIG. 60

DNARx-D8-2A-HA-MITD : Dual Cassette anti-D8-2A-HA-MITD (SEQ ID NO:39)

DraIIRINhe- ΔmCMV-EF1-I126-BstEII-ΔD8H-2A-D8L-BglII-polyA-ΔhCMV-EF1-I126-BstEII-HA-MITD-BglII-polyA BV2

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGT
ACATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAAT
GGGAGGTAAGCCAATGGGTTTTTCCCATTACTGACATGTATACTGAGTCATTAGGGACTTTCCAATGGGTTTTGCCCAGTACATAAGGTCAATAGGGGTGAATCAA
CAGGAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCC
ATTATTGGCACATACATAAGGTCAATAGGGGTGACTAGTGGAGAAGAGCATGCTTGAGGGCTGAGTGCCCCTCAGTGGGCAGAGAGCACATGGCCCACAGTCCC
TGAGAAGTTGGGGGGAGGGGTGGGCAATTGAACTGGTGCCTAGAGAAGGTGGGGCTTGGGTAAACTGGGAAAGTGATGTGGTGTACTGGCTCCACCTTTTTCCC
CAGGGTGGGGGAGAACCATATATAAGTGCAGTAGTCTCTGTGAACATTCAAGCTTCTGCCTTCTCCCTCCTGTGAGTTTGGTAAGTCACTGACTGTCTATGCCTGG
GAAAGGGTGGGCAGGAGATGGGGCAGTGCAGGAAAAGTGGCACTATGAACCCTGCAGCCCTAGACAATTGTACTAACCTTCTTCTCTTTCCTCTCCTGACAGGTT
GGTAACCAAGCCACCATGGGACTGGGACTCCAGTGGGTGTTCTTTGTGGCCCTGCTGAAAGGGGTGCACTGTGAAGTCAGACTGCTGGAAAGTGGTGGTGGCCT
GCAGGTTCAGCTGGTGCAGTCTGGGGCTGAAGTGAAGAAACCTGGCAGCTCTGTGAAGGTGTCCTGCAAGGCTAGTGGTGGCACCTTCTCTGCCTATGCCTTCA
CCTGGGTCAGACAGGCTCCTGGACAGGGCCTTGAATGGATGGGAGGCATCACAGGCATGTTTGGCACAGCCAACTATGCCCAGAAATTCCAGGGCAGAGTGACC
ATCACAGCTGATGAGCTGACCAGCACAGCCTACATGGAACTGAGCAGCCTGACCTCTGAGGACACAGCCCTGTACTACTGTGCCAGAGGCCTGTACTATTATGAG
TCTAGCCTGGACTACTGGGGCCAGGGCACACTGGTTACAGTGTCTAGTGCCAGCACAAAGGGCCCATCTGTGTTCCCTCTGGCACCCAGCAGCAAGTCTACCAG
TGGTGGAACAGCTGCCCTGGGCTGTCTGGTCAAGGACTACTTTCCTGAGCCAGTGACAGTGTCCTGGAACTCTGGGGCTCTGACATCTGGGGTGCACACATTCC
CTGCTGTGCTCCAGTCCTCTGGCCTGTACAGCCTCAGCTCTGTGGTCACAGTGCCTAGCTCTAGCCTGGGCACCCAGACCTACATCTGCAATGTGAACCACAAGC
CTAGCAACACCAAGGTGGACAAGAAGGCTGAGCCCAAGAGCTGTGACAAGACCCACACCTGTCCTCCATGTCCTGCTCCAGAGCTGCTTGGAGGACCTTCTGTG
TTTCTGTTCCCTCCAAAGCCAAAGGACACCCTGATGATCAGCAGAACCCCTGAAGTGACATGTGTGGTGGTTGATGTGTCCCATGAGGACCCAGAAGTGAAGTTC
AATTGGTATGTGGATGGTGTTGAGGTGCACAATGCCAAGACCAAGCCTAGAGAGGAACAGTACAACAGCACCTACAGAGTGGTGTCTGTGCTGACAGTGCTGCAT
CAGGACTGGCTGAATGGCAAAGAGTACAAGTGCAAGGTGTCCAACAAGGCCCTGCCTGCTCCTATTGAAAAGACCATCTCCAAGGCCAAGGGCCAGCCTAGGGA
ACCCCAGGTTTACACACTGCCACCTAGCAGGGATGAGCTGACCAAGAACCAGGTGTCCCTGACCTGCCTGGTTAAGGGCTTCTACCCCTCTGACATTGCTGTGGA
ATGGGAGAGCAATGGCCAGCCAGAGAACAACTACAAGACAACCCCTCCTGTGCTGGACTCTGATGGCTCATTCTTCCTGTACTCCAAGCTCACAGTGGACAAGTC
CAGATGGCAGCAAGGCAATGTGTTCAGCTGCTCTGTGATGCATGAGGCCCTGCACAACCACTACACACAGAAGTCCCTGAGCCTGTCTCCTGGCAAGAGAAAGA
GAAGGAGTGGAAGTGGAGCTACTAACTTCAGCCTGCTGAAGCAGGCTGGAGATGTGGAGGAGAACCCTGGACCTATGGACTTCCAGGTGCAGATCATCAGCTTT
CTGCTGATCTCTGCCTCTGTGATCATGAGCAGAGGCCAGTCTGTGCTGACCCAGCCTCCATCTGCATCTGGAAGCCCTGGCCAGTCTGTGACCATCAGCTGTACA
GGCACCAGCTCTGATGTTGGAGGCTACAACTCTGTGTCCTGGTATCAGCAGCACCCTGGCAAGGCCCCTAAGCTGATGATCTATGAAGTGACCAAGAGGCCCTCT
GGGGTGCCAGACAGATTCTCTGCCAGCAAGTCTGGCAACACAGCCAGCCTGACAGTGTCTGGCCTGCAAGCTGAGGATGAGGCTGACTACTTCTGCTGCTCCTA
TGCTGGCCACTCTGCCTATGTGTTTGGCACTGGCACCAAAGTGACAGTGCTGAGAACAGTGGCTGCCCCTTCTGTGTTCATCTTCCCACCATCTGATGAGCAGCT
GAAGTCTGGCACAGCCTCTGTTGTGTGCCTGCTGAACAACTTCTACCCTAGAGAAGCCAAGGTGCAGTGGAAGGTGGACAATGCCCTCCAGTCTGGCAACTCCC
AAGAGTCTGTGACAGAGCAGGACAGCAAGGACTCCACCTACAGCCTGAGCAGCACCCTGACACTGAGCAAGGCTGACTATGAGAAGCACAAAGTCTATGCCTGT
GAAGTGACCCACCAGGGCCTGTCTAGCCCTGTGACCAAGAGCTTCAACAGGGGAGAGAGCTGAAGATCTACTTCTGGCTAATAAAAGATCAGAGCTCTAGTGATC
TGTGTGTTGGTTTTTTGTGTCTGCATTCTAGCATGTTACATAACTTATGGTAAATGGCCTGCCTGGCTGACTGCCCAATGACCCCTGCCCAATGATGTCAATAATGA
TGTATGTTCCCATGTAATGCCAATAGGGACTTTCCATTGATGTCAATGGGTGGAGTATTTATGGTAACTGCCCACTTGGCAGTACATCAAGTGTATCATATGCCAAG
TATGCCCCCTATTGATGTCAATGATGGTAAATGGCCTGCCTGGCATTATGCCCAGTACATGACCTTATGGGACTTTCCTACTTGGCAGTACATCTATGTATTAGTCA
TTGCTATTACCATGGATTAGTGGAGAAGAGCATGCTTGAGGGCTGAGTGCCCCTCAGTGGGCAGAGAGCACATGGCCCACAGTCCCTGAGAAGTTGGGGGGAG
GGGTGGGCAATTGAACTGGTGCCTAGAGAAGGTGGGGCTTGGGTAAACTGGGAAAGTGATGTGGTGTACTGGCTCCACCTTTTTCCCCAGGGTGGGGGAGAAC
CATATATAAGTGCAGTAGTCTCTGTGAACATTCAAGCTTCTGCCTTCTCCCTCCTGTGAGTTTGGATGCACCTACTAGATATCTTGGTAAGTCACTGACTGTCTATG
CCTGGGAAAGGGTGGGCAGGAGGTGGGGCAGTGCAGGAAAAGTGGCACTGTGAACCCTGCAGCCCTAGACAATTGTACTAACCTTCTTCTCTTTCCTCTCCTGA
CAGGTTGGTAACCAAGCCACCATGAAGGCCAACCTGCTGGTGCTGCTGTGTGCTCTGGCTGCTGCTGATGCTGACACCATCTGCATTGGCTACCATGCCAACAAC
AGCACAGACACAGTGGACACTGTGCTGGAAAAGAATGTGACAGTGACCCACTCTGTCAACCTGCTTGAGGACAGCCACAATGGCAAGCTGTGCAGACTGAAGGG
CATTGCCCCTCTGCAACTGGGCAAGTGCAACATTGCTGGATGGCTGCTGGGCAACCCTGAGTGTGATCCTCTGCTGCCTGTCAGATCCTGGTCCTACATTGTGGA
AACCCCTAGCTCTGAGAATGGCATCTGCTACCCTGGGGACTTCATTGACTATGAGGAACTGAAAGAACAGCTGTCCTCTGTCAGCAGCTTTGAGAGATTTGAAATC
TTCCCCAAAGAGAGCAGCTGGCCCAACCACAACACCAACAAAGGGGTCACAGCTGCCTGTAGCCATGAGGGCAAGAGCAGCTTCTACAGAAACCTGCTGTGGCT
GACTGAGAAAGAGGGCAGCTACCCCAAGCTGAAGAACTCCTATGTGAACAAGAAGGGCAAAGAGGTCCTGGTTCTCTGGGGCATCCACCATCCTAGCAACAGCA
AAGAGCAGCAGAACCTGTACCAGAATGAGAATGCCTATGTGTCTGTTGTGACCAGCAACTACAACAGAAGGTTCACCCCTGAGATTGCTGAGAGGCCCAAAGTGA
AGGACCAGGCTGGCAGAATGAACTACTACTGGACCCTGCTGAAGCCTGGGGACACCATCATCTTTGAGGCCAATGGCAACCTGATTGCCCCTATGTATGCCTTTG
CTCTGAGCAGAGGCTTTGGCTCTGGCATCATCACCAGCAATGCCAGCATGCATGAGTGCAATACCAAGTGTCAGACCCCTCTGGGAGCTATCAACAGCAGCCTGC
CTTTCCAGAACATCCATCCTGTGACCATTGGAGAGTGCCCCAAATATGTTAGGAGTGCCAAGCTGAGGATGGTCACTGGCCTGAGAAACATCCCCAGCATCCAGT
CCAGAGGCCTGTTTGGAGCCATTGCTGGCTTCATTGAGGGAGGCTGGACAGGCATGATTGATGGATGGTATGGCTACCACCATCAGAATGAGCAAGGCAGTGGC
TATGCTGCTGACCAGAAAAGCACCCAGAATGCTGTGAATGGCATTACAAACAAAGTGAACACAGTGATTGAGAAGATGAACATCCAGTTCACTGCTGTGGGGAAA
GAGTTCAACAAGCTTGAGAAGAGGATGGAAAACCTGAACAAAAAAGTGGATGATGGCTTCCTGGACATCTGGACCTACAATGCTGAGCTGCTGGTCCTCCTGGAA
AATGAGAGAACCCTGGACTTCCATGACAGCAATGTGAAGAACCTCTATGAGAAAGTGAAGTCCCAGCTCAAGAACAATGCCAAAGAAATTGGCAATGGCTGCTTTG
AGTTCTACCACAAGTGTGACAATGAGTGCATGGAATCTGTCAGAAATGGCACCTATGACTACCCTAAGTACTCTGAGGAAAGCAAGCTGAACAGGGAAAAAGTTGA
TGGGGTCAAGCTGGAATCCATGGGCATCTACCAGATCATTGTGGGCATTGTGGCAGGCCTGGCTGTGCTGGCAGTGGTGGTTATTGGAGCTGTGGTGGCAGCAG
TGATGTGCAGAAGAAAGTCCTCTGGAGGCAAAGGTGGCAGCTACTCTCAGGCTGCCTGTTCTGATTCTGCCCAGGGCTCTGATGTGTCCCTGACAGCTTAAAGAT
CTACTTCTGGCTAATAAAAGATCAGAGCTCTAGTGATCTGTGTGTTGGTTTTTTGTGTCTGCATTCTAGCTCTAGTGATCAGCAGTTCAACCTGTTGATAGTATGTAC
TAAGCTCTCATGTTTAATGTACTAAGCTCTCATGTTTAATGAACTAAACCCTCATGGCTAATGTACTAAGCTCTCATGGCTAATGTACTAAGCTCTCATGTTTCATGT
ACTAAGCTCTCATGTTTGAACAATAAAATTAATATAAATCAGCAACTTAAATAGCCTCTAAGGTTTTAAGTTTTATAAGAAAAAAAAGAATATATAAGGCTTTTAAAGG
TTTTAAGGTTTCCTAGGTTATCCTCATATGAGCTCTTAGAAAAACTCATCCAGCATCAAATGAAACTGCAATTTATTCATATCAGGATTATCAATACCATATTTTTGAA
AAAGTCTTTTCTGTAATGAAGGAGAAAACTCACCCAGGCAGTTCCATAGGATGGCAAGATCCTGGTATCTGTCTGCAATTCCAACTCTTCCAACATCAATACAACCT
ATTAATTTCCCCTCATCAAAAATAAGGTTATCAAGTGAGAAATCACCATGAGTGACCACTGAATCTGGTGAGAATGGCAAAAGATTATGCATTTCTTTCCAGACTTGT
TCAACAGGCCAGCCATTTCTCTCATCATCAAAATCACTGGCATCAACCAAACCATTATTCATTCTTGATTGGGCCTGAGCCAGTCTAAATACTCTATCAGAGTTAAAA
GGACAATTACAAACAGGAATGGAATGCAATCTTCTCAGGAACACTGCCAGGGCATCAACAATATTTTCACCTGAATCAGGATATTCTTCCAATACCTGGAATGCTGT
TTTCCCTGGGATGGCAGTGGTGAGTAACCATGCATCATCAGGAGTTCTGATAAAATGCTTGATGGTTGGAAGAGGCATAAATTCAGTCAGCCAGTTTAGTCTGACC
ATCTCATCTGTAACATCATTGGCAACAGAACCTTTGCCATGTTTCAGAAACAACTCTGGGGCATCTGGCTTCCCATACAATCTATAGATTGTGGCACCTGATTGCCC
AACATTATCTCTAGCCCATTTATACCCATATAAATCAGCATCCATGTTGGAATTTAATCTTGGCCTGGAGCAAGAGGTTTCTCTTTGAATATGGCTCATACATGTGCA
CCTCCTATAGTGAGTTGTATTATACTATGCAGATATACTATGCCAATGTTTAATTGTCAG

FIG. 61

DNARx-F10-2A-HA-MITD : Dual Cassette anti-F10-2A-HA-MITD (SEQ ID NO:40)

DraIIRINhe- ΔmCMV-EF1-I126-BstEII-ΔF10H-2A-F10L-BglII-polyA- ΔhCMV-EF1-I126-BstEII-HA-MITD-BglII-polyA BV2

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTACATAAGGTCAATAG
GGGGTGAGTCAACAGGAAAGTCCCATTGGAGCCAAGTACATTGAGTCAATAGGGACTTTCCAATGGGTTTTGCCCAGTACATAAGGTCAATGGGAGGTAAGCCAATGGGTTTTTCCCATTA
CTGACATGTATACTGAGTCATTAGGGACTTTCCAATGGGTTTTGCCCAGTACATAAGGTCAATAGGGGTGAATCAACAGGAAAGTCCCATTGGAGCCAAGTACACTGAGTCAATAGGGACT
TTCCATTGGGTTTTGCCCAGTACAAAAGGTCAATAGGGGGTGAGTCAATGGGTTTTTCCCATTATTGGCACATACATAAGGTCAATAGGGGTGACTAGTGGAGAAGAGCATGCTTGAGGGC
TGAGTGCCCCTCAGTGGGCAGAGAGCACATGGCCCACAGTCCCTGAGAAGTTGGGGGGAGGGGTGGGCAATTGAACTGGTGCCTAGAGAAGGTGGGGCTTGGGTAAACTGGGAAAGT
GATGTGGTGTACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCACTG
ACTGTCTATGCCTGGGAAAGGGTGGGCAGGAGATGGGGCAGTGCAGGAAAAGTGGCACTATGAACCCTGCAGCCCTAGACAATTGTACTAACCTTCTTCTCTTTCCTCTCCTGACAGGTT
GGTAACCAAGCCACCATGGGACTGGGACTCCAGTGGGTGTTCTTTGTGGCCCTGCTGAAAGGGGTGCACTGTGAAGTCAGACTGCTGGAAAGTGGTGGTGGCCTGCAGGTTCAGCTGG
TGCAGTCTGGGGCTGAAGTGAAGAAACCTGGCAGCTCTGTGAAGGTGTCCTGCACCTCCTCTGAAGTGACCTTCAGCAGCTTTGCCATCAGCTGGGTCAGACAGGCTCCTGGACAGGGC
CTTGAATGGCTTGGAGGCATCAGCCCCATGTTTGGCACCCCTAACTATGCCCAGAAATTCCAGGGCAGAGTGACCATCACAGCTGACCAGAGCACCAGAACAGCCTACATGGACCTGAG
AAGTCTTAGGAGTGAAGATACAGCTGTGTACTACTGTGCTAGAAGCCCCAGCTACATCTGCTCTGGTGGCACCTGTGTGTTTGACCACTGGGGCCAGGGAACCCTGGTCACAGTTTCTTC
TGCCAGCACAAAGGGCCCATCTGTGTTCCCTCTGGCACCCAGCAGCAAGTCTACCAGTGGTGGAACAGCTGCCCTGGGCTGTCTGGTCAAGGACTACTTTCCTGAGCCAGTGACAGTGT
CCTGGAACTCTGGGGCTCTGACATCTGGGGTGCACACATTCCCTGCTGTGCTCCAGTCCTCTGGCCTGTACAGCCTCAGCTCTGTGGTCACAGTGCCTAGCTCTAGCCTGGGCACCCAG
ACCTACATCTGCAATGTGAACCACAAGCCTAGCAACACCAAGGTGGACAAGAAGGCTGAGCCCAAGAGCTGTGACAAGACCCACACCTGTCCTCCATGTCCTGCTCCAGAGCTGCTTGGA
GGACCTTCTGTGTTTCTGTTCCCTCCAAAGCCAAAGGACACCCTGATGATCAGCAGAACCCCTGAAGTGACATGTGTGGTGGTTGATGTGTCCCATGAGGACCCAGAAGTGAAGTTCAATT
GGTATGTGGATGGTGTTGAGGTGCACAATGCCAAGACCAAGCCTAGAGAGGAACAGTACAACAGCACCTACAGAGTGGTGTCTGTGCTGACAGTGCTGCATCAGGACTGGCTGAATGGC
AAAGAGTACAAGTGCAAGGTGTCCAACAAGGCCCTGCCTGCTCCTATTGAAAAGACCATCTCCAAGGCCAAGGGCCAGCCTAGGGAACCCCAGGTTTACACACTGCCACCTAGCAGGGA
TGAGCTGACCAAGAACCAGGTGTCCCTGACCTGCCTGGTTAAGGGCTTCTACCCCTCTGACATTGCTGTGGAATGGGAGAGCAATGGCCAGCCAGAGAACAACTACAAGACAACCCCTC
CTGTGCTGGACTCTGATGGCTCATTCTTCCTGTACTCCAAGCTCACAGTGGACAAGTCCAGATGGCAGCAAGGCAATGTGTTCAGCTGCTCTGTGATGCATGAGGCCCTGCACAACCACT
ACACACAGAAGTCCCTGAGCCTGTCTCCTGGCAAGAGAAAGAGAAGGAGTGGAAGTGGAGCTACTAACTTCAGCCTGCTGAAGCAGGCTGGAGATGTGGAGGAGAACCCTGGACCTATG
GACTTCCAGGTGCAGATCATCAGCTTTCTGCTGATCTCTGCCTCTGTGATCATGAGCAGAGGCCAGCCTGGACTGACACAGCCTCCATCTGTGTCCAAGGGCCTGAGACAGACAGCCACA
CTGACCTGCACAGGCAACAGCAACAATGTGGGCAATCAAGGGGCTGCCTGGCTCCAGCAGCATCAGGGACATCCTCCAAAGCTGCTGAGCTACAGAAACAATGACAGACCCTCTGGCAT
CTCTGAGAGATTCTCTGCCTCTAGGAGTGGCAACACAGCCAGCCTGACCATCACTGGACTCCAGCCAGAGGATGAGGCTGACTACTACTGCTCCACCTGGGACAGCAGCCTGTCTGCTG
TGGTTTTTGGTGGTGGCACCAAGCTGACAGTGCTGAGAACAGTGGCTGCCCCTTCTGTGTTCATCTTCCCACCATCTGATGAGCAGCTGAAGTCTGGCACAGCCTCTGTTGTGTGCCTGC
TGAACAACTTCTACCCTAGAGAAGCCAAGGTGCAGTGGAAGGTGGACAATGCCCTCCAGTCTGGCAACTCCCAAGAGTCTGTGACAGAGCAGGACAGCAAGGACTCCACCTACAGCCTG
AGCAGCACCCTGACACTGAGCAAGGCTGACTATGAGAAGCACAAAGTCTATGCCTGTGAAGTGACCCACCAGGGCCTGTCTAGCCCTGTGACCAAGAGCTTCAACAGGGGAGAGAGCTG
AAGATCTACTTCTGGCTAATAAAAGATCAGAGCTCTAGTGATCTGTGTGTTGGTTTTTTGTGTCTGCATTCTAGCATGTTACATAACTTATGGTAAATGGCCTGCCTGGCTGACTGCCCAATG
ACCCCTGCCCAATGATGTCAATAATGATGTATGTTCCCATGTAATGCCAATAGGGACTTTCCATTGATGTCAATGGGTGGAGTATTTATGGTAACTGCCCACTTGGCAGTACATCAAGTGTA
TCATATGCCAAGTATGCCCCCTATTGATGTCAATGATGGTAAATGGCCTGCCTGGCATTATGCCCAGTACATGACCTTATGGGACTTTCCTACTTGGCAGTACATCTATGTATTAGTCATTG
CTATTACCATGGATTAGTGGAGAAGAGCATGCTTGAGGGCTGAGTGCCCCTCAGTGGGCAGAGAGCACATGGCCCACAGTCCCTGAGAAGTTGGGGGGAGGGGTGGGCAATTGAACTG
GTGCCTAGAGAAGGTGGGGCTTGGGTAAACTGGGAAAGTGATGTGGTGTACTGGCTCCACCTTTTTCCCCAGGGTGGGGGAGAACCATATATAAGTGCAGTAGTCTCTGTGAACATTCAA
GCTTCTGCCTTCTCCCTCCTGTGAGTTTGGATGCACCTACTAGATATCTTGGTAAGTCACTGACTGTCTATGCCTGGGAAAGGGTGGGCAGGAGGTGGGGCAGTGCAGGAAAAGTGGCA
CTGTGAACCCTGCAGCCCTAGACAATTGTACTAACCTTCTTCTCTTTCCTCTCCTGACAGGTTGGTAACCAAGCCACCATGAAGGCCAACCTGCTGGTGCTGCTGTGTGCTCTGGCTGCTG
CTGATGCTGACACCATCTGCATTGGCTACCATGCCAACAACAGCACAGACACAGTGGACACTGTGCTGGAAAAGAATGTGACAGTGACCCACTCTGTCAACCTGCTTGAGGACAGCCACA
ATGGCAAGCTGTGCAGACTGAAGGGCATTGCCCCTCTGCAACTGGGCAAGTGCAACATTGCTGGATGGCTGCTGGGCAACCCTGAGTGTGATCCTCTGCTGCCTGTCAGATCCTGGTCC
TACATTGTGGAAACCCCTAGCTCTGAGAATGGCATCTGCTACCCTGGGGACTTCATTGACTATGAGGAACTGAAAGAACAGCTGTCCTCTGTCAGCAGCTTTGAGAGATTTGAAATCTTCC
CCAAAGAGAGCAGCTGGCCCAACCACAACACCAACAAAGGGGTCACAGCTGCCTGTAGCCATGAGGGCAAGAGCAGCTTCTACAGAAACCTGCTGTGGCTGACTGAGAAAGAGGGCAG
CTACCCCAAGCTGAAGAACTCCTATGTGAACAAGAAGGGCAAAGAGGTCCTGGTTCTCTGGGGCATCCACCATCCTAGCAACAGCAAAGAGCAGCAGAACCTGTACCAGAATGAGAATGC
CTATGTGTCTGTTGTGACCAGCAACTACAACAGAAGGTTCACCCCTGAGATTGCTGAGAGGCCCAAAGTGAAGGACCAGGCTGGCAGAATGAACTACTACTGGACCCTGCTGAAGCCTGG
GGACACCATCATCTTTGAGGCCAATGGCAACCTGATTGCCCCTATGTATGCCTTTGCTCTGAGCAGAGGCTTTGGCTCTGGCATCATCACCAGCAATGCCAGCATGCATGAGTGCAATAC
CAAGTGTCAGACCCCTCTGGGAGCTATCAACAGCAGCCTGCCTTTCCAGAACATCCATCCTGTGACCATTGGAGAGTGCCCCAAATATGTTAGGAGTGCCAAGCTGAGGATGGTCACTGG
CCTGAGAAACATCCCCAGCATCCAGTCCAGAGGCCTGTTTGGAGCCATTGCTGGCTTCATTGAGGGAGGCTGGACAGGCATGATTGATGGATGGTATGGCTACCACCATCAGAATGAGC
AAGGCAGTGGCTATGCTGCTGACCAGAAAAGCACCCAGAATGCTGTGAATGGCATTACAAACAAAGTGAACACAGTGATTGAGAAGATGAACATCCAGTTCACTGCTGTGGGGAAAGAGT
TCAACAAGCTTGAGAAGAGGATGGAAAACCTGAACAAAAAAGTGGATGATGGCTTCCTGGACATCTGGACCTACAATGCTGAGCTGCTGGTCCTCCTGGAAAATGAGAGAACCCTGGACT
TCCATGACAGCAATGTGAAGAACCTCTATGAGAAAGTGAAGTCCCAGCTCAAGAACAATGCCAAAGAAATTGGCAATGGCTGCTTTGAGTTCTACCACAAGTGTGACAATGAGTGCATGGA
ATCTGTCAGAAATGGCACCTATGACTACCCTAAGTACTCTGAGGAAAGCAAGCTGAACAGGGAAAAAGTTGATGGGGTCAAGCTGGAATCCATGGGCATCTACCAGATCATTGTGGGCAT
TGTGGCAGGCCTGGCTGTGCTGGCAGTGGTGGTTATTGGAGCTGTGGTGGCAGCAGTGATGTGCAGAAGAAAGTCCTCTGGAGGCAAAGGTGGCAGCTACTCTCAGGCTGCCTGTTCT
GATTCTGCCCAGGGCTCTGATGTGTCCCTGACAGCTTAAAGATCTACTTCTGGCTAATAAAAGATCAGAGCTCTAGTGATCTGTGTGTTGGTTTTTTGTGTCTGCATTCTAGCTCTAGTGAT
CAGCAGTTCAACCTGTTGATAGTATGTACTAAGCTCTCATGTTTAATGTACTAAGCTCTCATGTTTAATGAACTAAACCCTCATGGCTAATGTACTAAGCTCTCATGGCTAATGTACTAAGCT
CTCATGTTTCATGTACTAAGCTCTCATGTTTGAACAATAAAATTAATATAAATCAGCAACTTAAATAGCCTCTAAGGTTTTAAGTTTTATAAGAAAAAAAAGAATATATAAGGCTTTTAAAGGTT
TTAAGGTTTCCTAGGTTATCCTCATATGAGCTCTTAGAAAAACTCATCCAGCATCAAATGAAACTGCAATTTATTCATATCAGGATTATCAATACCATATTTTTGAAAAAGTCTTTTCTGTAATG
AAGGAGAAAACTCACCCAGGCAGTTCCATAGGATGGCAAGATCCTGGTATCTGTCTGCAATTCCAACTCTTCCAACATCAATACAACCTATTAATTTCCCCTCATCAAAAATAAGGTTATCAA
GTGAGAAATCACCATGAGTGACCACTGAATCTGGTGAGAATGGCAAAAGATTATGCATTTCTTTCCAGACTTGTTCAACAGGCCAGCCATTTCTCTCATCATCAAAATCACTGGCATCAACC
AAACCATTATTCATTCTTGATTGGGCCTGAGCCAGTCTAAATACTCTATCAGAGTTAAAAGGACAATTACAAACAGGAATGGAATGCAATCTTCTCAGGAACACTGCCAGGGCATCAACAAT
ATTTTCACCTGAATCAGGATATTCTTCCAATACCTGGAATGCTGTTTTCCCTGGGATGGCAGTGGTGAGTAACCATGCATCATCAGGAGTTCTGATAAAATGCTTGATGGTTGGAAGAGGCA
TAAATTCAGTCAGCCAGTTTAGTCTGACCATCTCATCTGTAACATCATTGGCAACAGAACCTTTGCCATGTTTCAGAAACAACTCTGGGGCATCTGGCTTCCCATACAATCTATAGATTGTG
GCACCTGATTGCCCAACATTATCTCTAGCCCATTTATACCCATATAAATCAGCATCCATGTTGGAATTTAATCTTGGCCTGGAGCAAGAGGTTTCTCTTTGAATATGGCTCATACATGTGCAC
CTCCTATAGTGAGTTGTATTATACTATGCAGATATACTATGCCAATGTTTAATTGTCAG

FIG. 62

DNARx-A66-2A-HA-MITD : Dual Cassette anti-A66-2A-HA-MITD (SEQ ID NO:41)

DraIIRINhe- ΔmCMV-EF1-I126-BstEII-ΔA66H-2A-A66L-BglII-polyA- ΔhCMV-EF1-I126-BstEII-HA-MITD-BglII-polyA BV2

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTACATAAGGTCAATAGG
GGGTGAGTCAACAGGAAAGTCCCATTGGAGCCAAGTACATTGAGTCAATAGGGACTTTCCAATGGGTTTTGCCCAGTACATAAGGTCAATGGGAGGTAAGCCAATGGGTTTTTCCCATTACT
GACATGTATACTGAGTCATTAGGGACTTTCCAATGGGTTTTGCCCAGTACATAAGGTCAATAGGGGTGAATCAACAGGAAAGTCCCATTGGAGCCAAGTACACTGAGTCAATAGGGACTTTCC
ATTGGGTTTTGCCCAGTACAAAAGGTCAATAGGGGGTGAGTCAATGGGTTTTTCCCATTATTGGCACATACATAAGGTCAATAGGGGTGACTAGTGGAGAAGAGCATGCTTGAGGGCTGAGT
GCCCCTCAGTGGGCAGAGAGCACATGGCCCACAGTCCCTGAGAAGTTGGGGGGAGGGGTGGGCAATTGAACTGGTGCCTAGAGAAGGTGGGGCTTGGGTAAACTGGGAAAGTGATGTGG
TGTACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCACTGACTGTCTATGC
CTGGGAAAGGGTGGGCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGACTGGGACTCCAGTGGGTGTTCTTTGTGGCCCTGCTGAAAGGGGTGCACTGTGAAGTCAGACTGCTGGAAAGTGGTGGTGGCCTGCAGGTTCAGCTGGTGCAGTCTGGGGCTGA
AGTGAAGAAACCTGGCAGCTCTGTGAAGGTGTCCTGCAAGGCTAGTGGTGGCCCCTTCAGCATGACAGCCTTCACCTGGCTGAGACAGGCTCCTGGACAGGGCCTTGAATGGATGGGAGGC
ATCAGCCCCATCTTCAGAACCCCTAAGTATGCCCAGAAATTCCAGGGCAGAGTGACCATCACAGCTGATGAGAGCACCAACACAGCCAACATGGAACTGACCAGCCTGAAGTCTGAGGACAC
TGCTGTGTACTACTGTGCCAGAACACTGAGCAGCTACCAGCCTAACAATGATGCCTTTGCCATCTGGGGCCAGGGCACCATGGTTACAGTCAGCTCTGCCAGCACAAAGGGCCCATCTGTGTT
CCCTCTGGCACCCAGCAGCAAGTCTACCAGTGGTGGAACAGCTGCCCTGGGCTGTCTGGTCAAGGACTACTTCCCTGAGCCAGTGACAGTGTCCTGGAACTCTGGGGCTCTGACATCTGGGGT
GCACACATTCCCTGCTGTGCTCCAGTCCTCTGGCCTGTACAGCCTCAGCTCTGTGGTCACAGTGCCTAGCTCTAGCCTGGGCACCCAGACCTACATCTGCAATGTGAACCACAAGCCTAGCAAC
ACCAAGGTGGACAAGAAGGCTGAGCCCAAGAGCTGTGACAAGACCCACACCTGTCCTCCATGTCCTGCTCCAGAGCTGCTTGGAGGACCTTCTGTGTTTCTGTTCCCTCCAAAGCCAAAGGAC
ACCCTGATGATCAGCAGAACCCCTGAAGTGACATGTGTGGTGGTTGATGTGTCCCATGAGGACCCAGAAGTGAAGTTCAATTGGTATGTGGATGGTGTTGAGGTGCACAATGCCAAGACCAA
GCCTAGAGAGGAACAGTACAACAGCACCTACAGAGTGGTGTCTGTGCTGACAGTGCTGCATCAGGACTGGCTGAATGGCAAAGAGTACAAGTGCAAGGTGTCCAACAAGGCCCTGCCTGCT
CCTATTGAAAAGACCATCTCCAAGGCCAAGGGCCAGCCTAGGGAACCCCAGGTTTACACACTGCCACCTAGCAGGGATGAGCTGACCAAGAACCAGGTGTCCCTGACCTGCCTGGTTAAGGG
CTTCTACCCCTCTGACATTGCTGTGGAATGGGAGAGCAATGGCCAGCCAGAGAACAACTACAAGACAACCCCTCCTGTGCTGGACTCTGATGGCTCATTCTTCCTGTACTCCAAGCTCACAGTG
GACAAGTCCAGATGGCAGCAAGGCAATGTGTTCAGCTGCTCTGTGATGCATGAGGCCCTGCACAACCACTACACACAGAAGTCCCTGAGCCTGTCTCCTGGCAAG*AGAAAGAGAAGGAGTG*
*GAAGTGGAGCTACTAACTTCAGCCTGCTGAAGCAGGCTGGAGATGTGGAGGAGAACCCTGGACCT*ATGGACTTCCAGGTGCAGATCATCAGCTTTCTGCTGATCTCTGCCTCTGTGATCATGA
GCAGAGGCCGAGATTGTGCTGACACAGAGCCCTGCCACACTGTCTCTTAGCCCTGGGGAGAGAGCCACACTGAGCTGTAGAGCCAGCCAGTCTGTGTCCTCTTACCTGGCCTGGTATCAGCA
GAAGCCTGGACAGGCTCCCAGACTGCTGATCTATGATGCCAGCAACAGAGCCACAGGCATCCCTGCCAGATTCAGTGGCTCTGGCAGTGGCACAGACTTCACCCTGACCATCAGCAGACTGG
AACCAGAGGACTTTGCTGTGTACTTCTGCCAGCAGTATGGCAGCAGCCCTCAGTTTGGCCAGGGCACAAGACTGGAAATCAAGAGAACAGTGGCTGCCCCTTCTGTGTTCATCTTCCCACCAT
CTGATGAGCAGCTGAAGTCTGGCACAGCCTCTGTTGTGTGCCTGCTGAACAACTTCTACCCTAGAGAAGCCAAGGTGCAGTGGAAGGTGGACAATGCCCTCCAGTCTGGCAACTCCCAAGAG
TCTGTGACAGAGCAGGACAGCAAGGACTCCACCTACAGCCTGAGCAGCACCCTGACACTGAGCAAGGCTGACTATGAGAAGCACAAAGTCTATGCCTGTGAAGTGACCCACCAGGGCCTGTC
TAGCCCTGTGACCAAGAGCTTCAACAGGGGAGAGAGCTGAAGATCTACTTCTGGCTAATAAAAGATCAGAGCTCTAGTGATCTGTGTGTTGGTTTTTTGTGTCTGCATTCTAGCATGTTACATA
ACTTATGGTAAATGGCCTGCCTGGCTGACTGCCCAATGACCCCTGCCCAATGATGTCAATAATGATGTATGTTCCCATGTAATGCCAATAGGGACTTTCCATTGATGTCAATGGGTGGAGTATT
TATGGTAACTGCCCACTTGGCAGTACATCAAGTGTATCATATGCCAAGTATGCCCCCTATTGATGTCAATGATGGTAAATGGCCTGCCTGGCATTATGCCCAGTACATGACCTTATGGGACTTT
CCTACTTGGCAGTACATCTATGTATTAGTCATTGCTATTACCATGGATTAGTGGAGAAGAGCATGCTTGAGGGCTGAGTGCCCCTCAGTGGGCAGAGAGCACATGGCCCACAGTCCCTGAGA
AGTTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGGGGGAGAACCATAT
ATAAGTGCAGTAGTCTCTGTGAACATTCAAGCTTCTGCCTTCTCCCTCCTGTGAGTTTGGATGCACCTACTAGATATCTTGGTAAGTCACTGACTGTCTATGCCTGGGAAAGGGTGGGCAGGAG
GTGGGGCAGTGCAGGAAAAGTGGCACTGTGAACCCTGCAGCCCTAGACAATTGTACTAACCTTCTTCTCTTTCCTCTCCTGACAGGTTGGTAACCAAGCCACCATGAAGGCCAACCTGCTGGT
GCTGCTGTGTGCTCTGGCTGCTGCTGATGCTGACACCATCTGCATTGGCTACCATGCCAACAACAGCACAGACACAGTGGACACTGTGCTGGAAAAGAATGTGACAGTGACCCACTCTGTCAA
CCTGCTTGAGGACAGCCACAATGGCAAGCTGTGCAGACTGAAGGGCATTGCCCCTCTGCAACTGGGCAAGTGCAACATTGCTGGATGGCTGCTGGGCAACCCTGAGTGTGATCCTCTGCTGC
CTGTCAGATCCTGGTCCTACATTGTGGAAACCCCTAGCTCTGAGAATGGCATCTGCTACCCTGGGGACTTCATTGACTATGAGGAACTGAAAGAACAGCTGTCCTCTGTCAGCAGCTTTGAGA
GATTTGAAATCTTCCCCAAAGAGAGCAGCTGGCCCAACCACAACACCAACAAAGGGGTCACAGCTGCCTGTAGCCATGAGGGCAAGAGCAGCTTCTACAGAAACCTGCTGTGGCTGACTGAG
AAAGAGGGCAGCTACCCCAAGCTGAAGAACTCCTATGTGAACAAGAAGGGCAAAGAGGTCCTGGTTCTCTGGGGCATCCACCATCCTAGCAACAGCAAAGAGCAGCAGAACCTGTACCAGA
ATGAGAATGCCTATGTGTCTGTTGTGACCAGCAACTACAACAGAAGGTTCACCCCTGAGATTGCTGAGAGGCCCAAAGTGAAGGACCAGGCTGGCAGAATGAACTACTACTGGACCCTGCTG
AAGCCTGGGGACACCATCATCTTTGAGGCCAATGGCAACCTGATTGCCCCTATGTATGCCTTTGCTCTGAGCAGAGGCTTTGGCTCTGGCATCATCACCAGCAATGCCAGCATGCATGAGTGC
AATACCAAGTGTCAGACCCCTCTGGGAGCTATCAACAGCAGCCTGCCTTTCCAGAACATCCATCCTGTGACCATTGGAGAGTGCCCCAAATATGTTAGGAGTGCCAAGCTGAGGATGGTCACT
GGCCTGAGAAACATCCCCAGCATCCAGTCCAGAGGCCTGTTTGGAGCCATTGCTGGCTTCATTGAGGGAGGCTGGACAGGCATGATTGATGGATGGTATGGCTACCACCATCAGAATGAGCA
AGGCAGTGGCTATGCTGCTGACCAGAAAAGCACCCAGAATGCTGTGAATGGCATTACAAACAAAGTGAACACAGTGATTGAGAAGATGAACATCCAGTTCACTGCTGTGGGGAAAGAGTTC
AACAAGCTTGAGAAGAGGATGGAAAACCTGAACAAAAAAGTGGATGATGGCTTCCTGGACATCTGGACCTACAATGCTGAGCTGCTGGTCCTCCTGGAAAATGAGAGAACCCTGGACTTCCA
TGACAGCAATGTGAAGAACCTCTATGAGAAAGTGAAGTCCCAGCTCAAGAACAATGCCAAAGAAATTGGCAATGGCTGCTTTGAGTTCTACCACAAGTGTGACAATGAGTGCATGGAATCTG
TCAGAAATGGCACCTATGACTACCCTAAGTACTCTGAGGAAAGCAAGCTGAACAGGGAAAAAGTTGATGGGGTCAAGCTGGAATCCATGGGCATCTACCAGATCATTGTGGGCATTGTGGCA
GGCCTGGCTGTGCTGGCAGTGGTGGTTATTGGAGCTGTGGTGGCAGCAGTGATGTGCAGAAGAAAGTCCTCTGGAGGCAAAGGTGGCAGCTACTCTCAGGCTGCCTGTTCTGATTCTGCCCA
GGGCTCTGATGTGTCCCTGACAGCTTAAAGATCTACTTCTGGCTAATAAAAGATCAGAGCTCTAGTGATCTGTGTGTTGGTTTTTTGTGTCTGCATTCTAGCTCTAGTGATCAGCAGTTCAACCT
GTTGATAGTATGTACTAAGCTCTCATGTTTAATGTACTAAGCTCTCATGTTTAATGAACTAAACCCTCATGGCTAATGTACTAAGCTCTCATGGCTAATGTACTAAGCTCTCATGTTTCATGTACT
AAGCTCTCATGTTTGAACAATAAAATTAATATAAATCAGCAACTTAAATAGCCTCTAAGGTTTTAAGTTTTATAAGAAAAAAAAGAATATATAAGGCTTTTAAAGGTTTTAAGGTTTCCTAGGTT
ATCCTCATATGAGCTCTTAGAAAAACTCATCCAGCATCAAATGAAACTGCAATTTATTCATATCAGGATTATCAATACCATATTTTTGAAAAAGTCTTTTCTGTAATGAAGGAGAAAACTCACCC
AGGCAGTTCCATAGGATGGCAAGATCCTGGTATCTGTCTGCAATTCCAACTCTTCCAACATCAATACAACCTATTAATTTCCCCTCATCAAAAATAAGGTTATCAAGTGAGAAATCACCATGAGT
GACCACTGAATCTGGTGAGAATGGCAAAAGATTATGCATTTCTTTCCAGACTTGTTCAACAGGCCAGCCATTTCTCTCATCATCAAAATCACTGGCATCAACCAAACCATTATTCATTCTTGATT
GGGCCTGAGCCAGTCTAAATACTCTATCAGAGTTAAAAGGACAATTACAAACAGGAATGGAATGCAATCTTCTCAGGAACACTGCCAGGGCATCAACAATATTTTCACCTGAATCAGGATATT
CTTCCAATACCTGGAATGCTGTTTTCCCTGGGATGGCAGTGGTGAGTAACCATGCATCATCAGGAGTTCTGATAAAATGCTTGATGGTTGGAAGAGGCATAAATTCAGTCAGCCAGTTTAGTC
TGACCATCTCATCTGTAACATCATTGGCAACAGAACCTTTGCCATGTTTCAGAAACAACTCTGGGGCATCTGGCTTCCCATACAATCTATAGATTGTGGCACCTGATTGCCCAACATTATCTCTA
GCCCATTTATACCCATATAAATCAGCATCCATGTTGGAATTTAATCTTGGCCTGGAGCAAGAGGTTTCTCTTTGAATATGGCTCATACATGTGCACCTCCTATAGTGAGTTGTATTATACTATGC
AGATATACTATGCCAATGTTTAATTGTCAG

FIG. 63

DNARx-D8-2A-SEC-partial-HA-MITD : Dual Cassette anti-D8-2A-SEC-partial-HA-MITD (SEQ ID NO:42)

DraIIRINhe- ΔmCMV-EF1-I126-BstEII-ΔD8H-2A-D8L-BglII-polyA- ΔhCMV-EF1-I126-BstEII-SEC-partial-HA-MITD-BglII-polyA BV2

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGACTGGGACTCCAGTGGGTGTTCTTTGTGGCCCTGCTGAAAGGGGTGCACTGTGAAGTCAGACTGCTGGAAAGTGGTGGTGGCCTGCAGGTTCAGCTGGT
GCAGTCTGGGGCTGAAGTGAAGAAACCTGGCAGCTCTGTGAAGGTGTCCTGCAAGGCTAGTGGTGGCACCTTCTCTGCCTATGCCTTCACCTGGGTCAGACAGGCTC
CTGGACAGGGCCTTGAATGGATGGGAGGCATCACAGGCATGTTTGGCACAGCCAACTATGCCCAGAAATTCCAGGGCAGAGTGACCATCACAGCTGATGAGCTGAC
CAGCACAGCCTACATGGAACTGAGCAGCCTGACCTCTGAGGACACAGCCCTGTACTACTGTGCCAGAGGCCTGTACTATTATGAGTCTAGCCTGGACTACTGGGGCC
AGGGCACACTGGTTACAGTGTCTAGTGCCAGCACAAAGGGCCCATCTGTGTTCCCTCTGGCACCCAGCAGCAAGTCTACCAGTGGTGGAACAGCTGCCCTGGGCTGT
CTGGTCAAGGACTACTTTCCTGAGCCAGTGACAGTGTCCTGGAACTCTGGGGCTCTGACATCTGGGGTGCACACATTCCCTGCTGTGCTCCAGTCCTCTGGCCTGTAC
AGCCTCAGCTCTGTGGTCACAGTGCCTAGCTCTAGCCTGGGCACCCAGACCTACATCTGCAATGTGAACCACAAGCCTAGCAACACCAAGGTGGACAAGAAGGCTGA
GCCCAAGAGCTGTGACAAGACCCACACCTGTCCTCCATGTCCTGCTCCAGAGCTGCTTGGAGGACCTTCTGTGTTTCTGTTCCCTCCAAAGCCAAAGGACACCCTGAT
GATCAGCAGAACCCCTGAAGTGACATGTGTGGTGGTTGATGTGTCCCATGAGGACCCAGAAGTGAAGTTCAATTGGTATGTGGATGGTGTTGAGGTGCACAATGCC
AAGACCAAGCCTAGAGAGGAACAGTACAACAGCACCTACAGAGTGGTGTCTGTGCTGACAGTGCTGCATCAGGACTGGCTGAATGGCAAAGAGTACAAGTGCAAG
GTGTCCAACAAGGCCCTGCCTGCTCCTATTGAAAAGACCATCTCCAAGGCCAAGGGCCAGCCTAGGGAACCCCAGGTTTACACACTGCCACCTAGCAGGGATGAGCT
GACCAAGAACCAGGTGTCCCTGACCTGCCTGGTTAAGGGCTTCTACCCCTCTGACATTGCTGTGGAATGGGAGAGCAATGGCCAGCCAGAGAACAACTACAAGACA
ACCCCTCCTGTGCTGGACTCTGATGGCTCATTCTTCCTGTACTCCAAGCTCACAGTGGACAAGTCCAGATGGCAGCAAGGCAATGTGTTCAGCTGCTCTGTGATGCAT
GAGGCCCTGCACAACCACTACACACAGAAGTCCCTGAGCCTGTCTCCTGGCAAG*AGAAAGAGAAGGAGTGGAAGTGGAGCTACTAACTTCAGCCTGCTGAAGCAGG*
*CTGGAGATGTGGAGGAGAACCCTGGACCT*ATGGACTTCCAGGTGCAGATCATCAGCTTTCTGCTGATCTCTGCCTCTGTGATCATGAGCAGAGGCCAGTCTGTGCTG
ACCCAGCCTCCATCTGCATCTGGAAGCCCTGGCCAGTCTGTGACCATCAGCTGTACAGGCACCAGCTCTGATGTTGGAGGCTACAACTCTGTGTCCTGGTATCAGCAG
CACCCTGGCAAGGCCCCTAAGCTGATGATCTATGAAGTGACCAAGAGGCCCTCTGGGGTGCCAGACAGATTCTCTGCCAGCAAGTCTGGCAACACAGCCAGCCTGAC
AGTGTCTGGCCTGCAAGCTGAGGATGAGGCTGACTACTTCTGCTGCTCCTATGCTGGCCACTCTGCCTATGTGTTTGGCACTGGCACCAAAGTGACAGTGCTGAGAAC
AGTGGCTGCCCCTTCTGTGTTCATCTTCCCACCATCTGATGAGCAGCTGAAGTCTGGCACAGCCTCTGTTGTGTGCCTGCTGAACAACTTCTACCCTAGAGAAGCCAAG
GTGCAGTGGAAGGTGGACAATGCCCTCCAGTCTGGCAACTCCCAAGAGTCTGTGACAGAGCAGGACAGCAAGGACTCCACCTACAGCCTGAGCAGCACCCTGACAC
TGAGCAAGGCTGACTATGAGAAGCACAAAGTCTATGCCTGTGAAGTGACCCACCAGGGCCTGTCTAGCCCTGTGACCAAGAGCTTCAACAGGGGAGAGAGCTGAAG
ATCTACTTCTGGCTAATAAAAGATCAGAGCTCTAGTGATCTGTGTGTTGGTTTTTTGTGTCTGCATTCTAGCATGTTACATAACTTATGGTAAATGGCCTGCCTGGCTG
ACTGCCCAATGACCCCTGCCCAATGATGTCAATAATGATGTATGTTCCCATGTAATGCCAATAGGGACTTTCCATTGATGTCAATGGGTGGAGTATTTATGGTAACTGC
CCACTTGGCAGTACATCAAGTGTATCATATGCCAAGTATGCCCCCTATTGATGTCAATGATGGTAAATGGCCTGCCTGGCATTATGCCCAGTACATGACCTTATGGGA
CTTTCCTACTTGGCAGTACATCTATGTATTAGTCATTGCTATTACCATGGATTAGTGGAGAAGAGCATGCTTGAGGGCTGAGTGCCCCTCAGTGGGCAGAGAGCACAT
GGCCCACAGTCCCTGAGAAGTTGGGGGGAGGGGTGGGCAATTGAACTGGTGCCTAGAGAAGGTGGGGCTTGGGTAAACTGGGAAAGTGATGTGGTGTACTGGCT
CCACCTTTTTCCCCAGGGTGGGGGAGAACCATATATAAGTGCAGTAGTCTCTGTGAACATTCAAGCTTCTGCCTTCTCCCTCCTGTGAGTTTGGATGCACCTACTAGAT
ATCTTGGTAAGTCACTGACTGTCTATGCCTGGGAAAGGGTGGGCAGGAGGTGGGGCAGTGCAGGAAAAGTGGCACTGTGAACCCTGCAGCCCTAGACAATTGTACT
AACCTTCTTCTCTTTCCTCTCCTGACAGGTTGGTAACCAAGCCACCATGAGAGTGACAGCCCCTAGAACAGTCCTGCTGCTCCTGTCTGCTGCCCTGGCTCTGACAGAA
ACATGGGCTGGCTCCAGACTGAAGGGCATTGCTCCTCTGCAACTGGGCAAGTGCAACATTGCTGGCTGGCTGCTGGGCAACCCTGAGTGTGATCCTCTGCTGCCTGT
CAGATCCTGGTCCTACATTGTGGAAACCCCTAGCTCTGAGAATGGCATCTGCTACCCTGGGGACTTCATTGACTATGAGGAACTGAAAGAACAGCTGTCCTCTGTGTC
CAGCTTTGAGAGATTTGAAATCTTCCCCAAAGAGAGCAGCTGGCCCAACCACAACACCAACAAAGGGGTCACAGCTGCCTGTAGCCATGAGGGCAAGAGCAGCTTCT
ACAGAAACCTGCTGTGGCTGACAGAGAAAGAGGGCAGCTACCCCAAGCTGAAGAACTCCTATGTGAACAAGAAGGGCAAAGAGGTCCTGGTTCTCTGGGGCATCCA
CCATCCTAGCAACAGCAAAGAGCAGCAGAACCTGTACCAGAATGAGAATGCCTATGTGTCTGTGGTCACAAGCAACTACAACAGAAGGTTCACCCCTGAGATTGCTG
AGAGGCCCAAAGTGAAGGACCAGGCTGGCAGAATGAACTACTACTGGACCCTGCTGAAGCCTGGGGACACCATCATCTTTGAGGCCAATGGCAACCTGATTGCCCC
TATGTATGCCTTTGCTCTGAGCAGAGGCTTTGGCTCTGGCATCATCACCTCTGTGGATGGGGTCAAGCTGGAATCCATGGGCATCATTGTGGGCATTGTGGCAGGCCT
GGCTGTGCTGGCAGTGGTGGTTATTGGAGCTGTGGTGGCTGCTGTGATGTGCAGAAGAAAGTCCTCTGGAGGCAAAGGTGGCAGCTACTCTCAGGCTGCCTGTTCT
GATTCTGCCCAGGGCTCTGATGTGTCCCTGACAGCTTAAAGATCTACTTCTGGCTAATAAAAGATCAGAGCTCTAGTGATCTGTGTGTTGGTTTTTTGTGTCTGCATTC
TAGCTCTAGTGATCAGCAGTTCAACCTGTTGATAGTATGTACTAAGCTCTCATGTTTAATGTACTAAGCTCTCATGTTTAATGAACTAAACCCTCATGGCTAATGTACTA
AGCTCTCATGGCTAATGTACTAAGCTCTCATGTTTCATGTACTAAGCTCTCATGTTTGAACAATAAAATTAATATAAATCAGCAACTTAAATAGCCTCTAAGGTTTTAAG
TTTTATAAGAAAAAAAAGAATATATAAGGCTTTTAAAGGTTTTAAGGTTTCCTAGGTTATCCTCATATGAGCTCTTAGAAAAACTCATCCAGCATCAAATGAAACTGCA
ATTTATTCATATCAGGATTATCAATACCATATTTTTGAAAAAGTCTTTTCTGTAATGAAGGAGAAAACTCACCCAGGCAGTTCCATAGGATGGCAAGATCCTGGTATCT
GTCTGCAATTCCAACTCTTCCAACATCAATACAACCTATTAATTTCCCCTCATCAAAAATAAGGTTATCAAGTGAGAAATCACCATGAGTGACCACTGAATCTGGTGAG
AATGGCAAAAGATTATGCATTTCTTTCCAGACTTGTTCAACAGGCCAGCCATTTCTCTCATCATCAAAATCACTGGCATCAACCAAACCATTATTCATTCTTGATTGGGC
CTGAGCCAGTCTAAATACTCTATCAGAGTTAAAAGGACAATTACAAACAGGAATGGAATGCAATCTTCTCAGGAACACTGCCAGGGCATCAACAATATTTTCACCTGA
ATCAGGATATTCTTCCAATACCTGGAATGCTGTTTTCCCTGGGATGGCAGTGGTGAGTAACCATGCATCATCAGGAGTTCTGATAAAATGCTTGATGGTTGGAAGAG
GCATAAATTCAGTCAGCCAGTTTAGTCTGACCATCTCATCTGTAACATCATTGGCAACAGAACCTTTGCCATGTTTCAGAAACAACTCTGGGGCATCTGGCTTCCCATA
CAATCTATAGATTGTGGCACCTGATTGCCCAACATTATCTCTAGCCCATTTATACCCATATAAATCAGCATCCATGTTGGAATTTAATCTTGGCCTGGAGCAAGAGGTT
TCTCTTTGAATATGGCTCATACATGTGCACCTCCTATAGTGAGTTGTATTATACTATGCAGATATACTATGCCAATGTTTAATTGTCAG

FIG. 64

DNARx-F10-2A-SEC-partial-HA-MITD : Dual Cassette anti-F10-2A-SEC-partial-HA-MITD (SEQ ID NO:43)

DraIIRINhe- ΔmCMV-EF1-I126-BstEII-ΔF10H-2A-F10L-BgIII-polyA- ΔhCMV-EF1-I126-BstEII-SEC-partial-HA-MITD-BgIII-polyA BV2

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGACTGGGACTCCAGTGGGTGTTCTTTGTGGCCCTGCTGAAAGGGGTGCACTGTGAAGTCAGACTGCTGGAAAGTGGTGGTGGCCTGCAGGTTCAGCTGGT
GCAGTCTGGGGCTGAAGTGAAGAAACCTGGCAGCTCTGTGAAGGTGTCCTGCACCTCCTCTGAAGTGACCTTCAGCAGCTTTGCCATCAGCTGGGTCAGACAGGCTC
CTGGACAGGGCCTTGAATGGCTTGGAGGCATCAGCCCCATGTTTGGCACCCCTAACTATGCCCAGAAATTCCAGGGCAGAGTGACCATCACAGCTGACCAGAGCACC
AGAACAGCCTACATGGACCTGAGAAGTCTTAGGAGTGAAGATACAGCTGTGTACTACTGTGCTAGAAGCCCCAGCTACATCTGCTCTGGTGGCACCTGTGTGTTTGA
CCACTGGGGCCAGGGAACCCTGGTCACAGTTTCTTCTGCCAGCACAAAGGGCCCATCTGTGTTCCCTCTGGCACCCAGCAGCAAGTCTACCAGTGGTGGAACAGCTG
CCCTGGGCTGTCTGGTCAAGGACTACTTTCCTGAGCCAGTGACAGTGTCCTGGAACTCTGGGGCTCTGACATCTGGGGTGCACACATTCCCTGCTGTGCTCCAGTCCT
CTGGCCTGTACAGCCTCAGCTCTGTGGTCACAGTGCCTAGCTCTAGCCTGGGCACCCAGACCTACATCTGCAATGTGAACCACAAGCCTAGCAACACCAAGGTGGAC
AAGAAGGCTGAGCCCAAGAGCTGTGACAAGACCCACACCTGTCCTCCATGTCCTGCTCCAGAGCTGCTTGGAGGACCTTCTGTGTTTCTGTTCCCTCCAAAGCCAAAG
GACACCCTGATGATCAGCAGAACCCCTGAAGTGACATGTGTGGTGGTTGATGTGTCCCATGAGGACCCAGAAGTGAAGTTCAATTGGTATGTGGATGGTGTTGAGG
TGCACAATGCCAAGACCAAGCCTAGAGAGGAACAGTACAACAGCACCTACAGAGTGGTGTCTGTGCTGACAGTGCTGCATCAGGACTGGCTGAATGGCAAAGAGTA
CAAGTGCAAGGTGTCCAACAAGGCCCTGCCTGCTCCTATTGAAAAGACCATCTCCAAGGCCAAGGGCCAGCCTAGGGAACCCCAGGTTTACACACTGCCACCTAGCA
GGGATGAGCTGACCAAGAACCAGGTGTCCCTGACCTGCCTGGTTAAGGGCTTCTACCCCTCTGACATTGCTGTGGAATGGGAGAGCAATGGCCAGCCAGAGAACAA
CTACAAGACAACCCCTCCTGTGCTGGACTCTGATGGCTCATTCTTCCTGTACTCCAAGCTCACAGTGGACAAGTCCAGATGGCAGCAAGGCAATGTGTTCAGCTGCTC
TGTGATGCATGAGGCCCTGCACAACCACTACACACAGAAGTCCCTGAGCCTGTCTCCTGGCAAG*AGAAAGAGAAGGAGTGGAAGTGGAGCTACTAACTTCAGCCTG*
*CTGAAGCAGGCTGGAGATGTGGAGGAGAACCCTGGACCT*ATGGACTTCCAGGTGCAGATCATCAGCTTTCTGCTGATCTCTGCCTCTGTGATCATGAGCAGAGGCCA
GCCTGGACTGACACAGCCTCCATCTGTGTCCAAGGGCCTGAGACAGACAGCCACACTGACCTGCACAGGCAACAGCAACAATGTGGGCAATCAAGGGGCTGCCTGG
CTCCAGCAGCATCAGGGACATCCTCCAAAGCTGCTGAGCTACAGAAACAATGACAGACCCTCTGGCATCTCTGAGAGATTCTCTGCCTCTAGGAGTGGCAACACAGC
CAGCCTGACCATCACTGGACTCCAGCCAGAGGATGAGGCTGACTACTACTGCTCCACCTGGGACAGCAGCCTGTCTGCTGTGGTTTTTGGTGGTGGCACCAAGCTGA
CAGTGCTGAGAACAGTGGCTGCCCCTTCTGTGTTCATCTTCCCACCATCTGATGAGCAGCTGAAGTCTGGCACAGCCTCTGTTGTGTGCCTGCTGAACAACTTCTACCC
TAGAGAAGCCAAGGTGCAGTGGAAGGTGGACAATGCCCTCCAGTCTGGCAACTCCCAAGAGTCTGTGACAGAGCAGGACAGCAAGGACTCCACCTACAGCCTGAGC
AGCACCCTGACACTGAGCAAGGCTGACTATGAGAAGCACAAAGTCTATGCCTGTGAAGTGACCCACCAGGGCCTGTCTAGCCCTGTGACCAAGAGCTTCAACAGGG
GAGAGAGCTGAAGATCTACTTCTGGCTAATAAAAGATCAGAGCTCTAGTGATCTGTGTGTTGGTTTTTTGTGTCTGCATTCTAGCATGTTACATAACTTATGGTAAATG
GCCTGCCTGGCTGACTGCCCAATGACCCCTGCCCAATGATGTCAATAATGATGTATGTTCCCATGTAATGCCAATAGGGACTTTCCATTGATGTCAATGGGTGGAGTA
TTTATGGTAACTGCCCACTTGGCAGTACATCAAGTGTATCATATGCCAAGTATGCCCCCTATTGATGTCAATGATGGTAAATGGCCTGCCTGGCATTATGCCCAGTACA
TGACCTTATGGGACTTTCCTACTTGGCAGTACATCTATGTATTAGTCATTGCTATTACCATGGATTAGTGGAGAAGAGCATGCTTGAGGGCTGAGTGCCCCTCAGTGG
GCAGAGAGCACATGGCCCACAGTCCCTGAGAAGTTGGGGGGAGGGGTGGGCAATTGAACTGGTGCCTAGAGAAGGTGGGGCTTGGGTAAACTGGGAAAGTGATG
TGGTGTACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGAT
GCACCTACTAGATATCTTGGTAAGTCACTGACTGTCTATGCCTGGGAAAGGGTGGGCAGGAGGTGGGGCAGTGCAGGAAAAGTGGCACTGTGAACCCTGCAGCCCT
AGACAATTGTACTAACCTTCTTCTCTTTCCTCTCCTGACAGGTTGGTAACCAAGCCACCATGAGAGTGACAGCCCCTAGAACAGTCCTGCTGCTCCTGTCTGCTGCCCT
GGCTCTGACAGAAACATGGGCTGGCTCCAGACTGAAGGGCATTGCTCCTCTGCAACTGGGCAAGTGCAACATTGCTGGCTGGCTGCTGGGCAACCCTGAGTGTGAT
CCTCTGCTGCCTGTCAGATCCTGGTCCTACATTGTGGAAACCCCTAGCTCTGAGAATGGCATCTGCTACCCTGGGGACTTCATTGACTATGAGGAACTGAAAGAACAG
CTGTCCTCTGTGTCCAGCTTTGAGAGATTTGAAATCTTCCCCAAAGAGAGCAGCTGGCCCAACCACAACACCAACAAAGGGGTCACAGCTGCCTGTAGCCATGAGGG
CAAGAGCAGCTTCTACAGAAACCTGCTGTGGCTGACAGAGAAAGAGGGCAGCTACCCCAAGCTGAAGAACTCCTATGTGAACAAGAAGGGCAAAGAGGTCCTGGTT
CTCTGGGGCATCCACCATCCTAGCAACAGCAAAGAGCAGCAGAACCTGTACCAGAATGAGAATGCCTATGTGTCTGTGGTCACAAGCAACTACAACAGAAGGTTCAC
CCCTGAGATTGCTGAGAGGCCCAAAGTGAAGGACCAGGCTGGCAGAATGAACTACTACTGGACCCTGCTGAAGCCTGGGGACACCATCATCTTTGAGGCCAATGGC
AACCTGATTGCCCCTATGTATGCCTTTGCTCTGAGCAGAGGCTTTGGCTCTGGCATCATCACCTCTGTGGATGGGGTCAAGCTGGAATCCATGGGCATCATTGTGGGC
ATTGTGGCAGGCCTGGCTGTGCTGGCAGTGGTGGTTATTGGAGCTGTGGTGGCTGCTGTGATGTGCAGAAGAAAGTCCTCTGGAGGCAAAGGTGGCAGCTACTCTC
AGGCTGCCTGTTCTGATTCTGCCCAGGGCTCTGATGTGTCCCTGACAGCTTAAAGATCTACTTCTGGCTAATAAAAGATCAGAGCTCTAGTGATCTGTGTGTTGGTTTT
TTGTGTCTGCATTCTAGCTCTAGTGATCAGCAGTTCAACCTGTTGATAGTATGTACTAAGCTCTCATGTTTAATGTACTAAGCTCTCATGTTTAATGAACTAAACCCTCA
TGGCTAATGTACTAAGCTCTCATGGCTAATGTACTAAGCTCTCATGTTTCATGTACTAAGCTCTCATGTTTGAACAATAAAATTAATATAAATCAGCAACTTAAATAGCC
TCTAAGGTTTTAAGTTTTATAAGAAAAAAAAGAATATATAAGGCTTTTAAAGGTTTTAAGGTTTCCTAGGTTATCCTCATATGAGCTCTTAGAAAAACTCATCCAGCAT
CAAATGAAACTGCAATTTATTCATATCAGGATTATCAATACCATATTTTTGAAAAAGTCTTTTCTGTAATGAAGGAGAAAACTCACCCAGGCAGTTCCATAGGATGGCA
AGATCCTGGTATCTGTCTGCAATTCCAACTCTTCCAACATCAATACAACCTATTAATTTCCCCTCATCAAAAATAAGGTTATCAAGTGAGAAATCACCATGAGTGACCAC
TGAATCTGGTGAGAATGGCAAAAGATTATGCATTTCTTTCCAGACTTGTTCAACAGGCCAGCCATTTCTCTCATCATCAAAATCACTGGCATCAACCAAACCATTATTC
ATTCTTGATTGGGCCTGAGCCAGTCTAAATACTCTATCAGAGTTAAAAGGACAATTACAAACAGGAATGGAATGCAATCTTCTCAGGAACACTGCCAGGGCATCAAC
AATATTTTCACCTGAATCAGGATATTCTTCCAATACCTGGAATGCTGTTTTCCCTGGGATGGCAGTGGTGAGTAACCATGCATCATCAGGAGTTCTGATAAAATGCTTG
ATGGTTGGAAGAGGCATAAATTCAGTCAGCCAGTTTAGTCTGACCATCTCATCTGTAACATCATTGGCAACAGAACCTTTGCCATGTTTCAGAAACAACTCTGGGGCA
TCTGGCTTCCCATACAATCTATAGATTGTGGCACCTGATTGCCCAACATTATCTCTAGCCCATTTATACCCATATAAATCAGCATCCATGTTGGAATTTAATCTTGGCCT
GGAGCAAGAGGTTTCTCTTTGAATATGGCTCATACATGTGCACCTCCTATAGTGAGTTGTATTATACTATGCAGATATACTATGCCAATGTTTAATTGTCAG

FIG. 65

DNARx-A66-2A-SEC-partial-HA-MITD : Dual Cassette anti-A66-2A-SEC-partial-HA-MITD (SEQ ID NO:44)

DrallRINhe- ΔmCMV-EF1-I126-BstEII-ΔA66H-2A-A66L-BglII-polyA- ΔhCMV-EF1-I126-BstEII-SEC-partial-HA-MITD-BglII-polyA BV2

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGACTGGGACTCCAGTGGGTGTTCTTTGTGGCCCTGCTGAAAGGGGTGCACTGTGAAGTCAGACTGCTGGAAAGTGGTGGTGGCCTGCAGGTTCAGCTGGT
GCAGTCTGGGGCTGAAGTGAAGAAACCTGGCAGCTCTGTGAAGGTGTCCTGCAAGGCTAGTGGTGGCCCCTTCAGCATGACAGCCTTCACCTGGCTGAGACAGGCT
CCTGGACAGGGCCTTGAATGGATGGGAGGCATCAGCCCCATCTTCAGAACCCCTAAGTATGCCCAGAAATTCCAGGGCAGAGTGACCATCACAGCTGATGAGAGCA
CCAACACAGCCAACATGGAACTGACCAGCCTGAAGTCTGAGGACACTGCTGTGTACTACTGTGCCAGAACACTGAGCAGCTACCAGCCTAACAATGATGCCTTTGCC
ATCTGGGGCCAGGGCACCATGGTTACAGTCAGCTCTGCCAGCACAAAGGGCCCATCTGTGTTCCCTCTGGCACCCAGCAGCAAGTCTACCAGTGGTGGAACAGCTGC
CCTGGGCTGTCTGGTCAAGGACTACTTTCCTGAGCCAGTGACAGTGTCCTGGAACTCTGGGGCTCTGACATCTGGGGTGCACACATTCCCTGCTGTGCTCCAGTCCTC
TGGCCTGTACAGCCTCAGCTCTGTGGTCACAGTGCCTAGCTCTAGCCTGGGCACCCAGACCTACATCTGCAATGTGAACCACAAGCCTAGCAACACCAAGGTGGACA
AGAAGGCTGAGCCCAAGAGCTGTGACAAGACCCACACCTGTCCTCCATGTCCTGCTCCAGAGCTGCTTGGAGGACCTTCTGTGTTTCTGTTCCCTCCAAAGCCAAAGG
ACACCCTGATGATCAGCAGAACCCCTGAAGTGACATGTGTGGTGGTTGATGTGTCCCATGAGGACCCAGAAGTGAAGTTCAATTGGTATGTGGATGGTGTTGAGGT
GCACAATGCCAAGACCAAGCCTAGAGAGGAACAGTACAACAGCACCTACAGAGTGGTGTCTGTGCTGACAGTGCTGCATCAGGACTGGCTGAATGGCAAAGAGTAC
AAGTGCAAGGTGTCCAACAAGGCCCTGCCTGCTCCTATTGAAAAGACCATCTCCAAGGCCAAGGGCCAGCCTAGGGAACCCCAGGTTTACACACTGCCACCTAGCAG
GGATGAGCTGACCAAGAACCAGGTGTCCCTGACCTGCCTGGTTAAGGGCTTCTACCCCTCTGACATTGCTGTGGAATGGGAGAGCAATGGCCAGCCAGAGAACAAC
TACAAGACAACCCCTCCTGTGCTGGACTCTGATGGCTCATTCTTCCTGTACTCCAAGCTCACAGTGGACAAGTCCAGATGGCAGCAAGGCAATGTGTTCAGCTGCTCT
GTGATGCATGAGGCCCTGCACAACCACTACACACAGAAGTCCCTGAGCCTGTCTCCTGGCAAG*AGAAAGAGAAGGAGTGGAAGTGGAGCTACTAACTTCAGCCTGC*
*TGAAGCAGGCTGGAGATGTGGAGGAGAACCCTGGACCT*ATGGACTTCCAGGTGCAGATCATCAGCTTTCTGCTGATCTCTGCCTCTGTGATCATGAGCAGAGGCCGA
GATTGTGCTGACACAGAGCCCTGCCACACTGTCTCTTAGCCCTGGGGAGAGAGCCACACTGAGCTGTAGAGCCAGCCAGTCTGTGTCCTCTTACCTGGCCTGGTATCA
GCAGAAGCCTGGACAGGCTCCCAGACTGCTGATCTATGATGCCAGCAACAGAGCCACAGGCATCCCTGCCAGATTCAGTGGCTCTGGCAGTGGCACAGACTTCACCC
TGACCATCAGCAGACTGGAACCAGAGGACTTTGCTGTGTACTTCTGCCAGCAGTATGGCAGCAGCCCTCAGTTTGGCCAGGGCACAAGACTGGAAATCAAGAGAAC
AGTGGCTGCCCCTTCTGTGTTCATCTTCCCACCATCTGATGAGCAGCTGAAGTCTGGCACAGCCTCTGTTGTGTGCCTGCTGAACAACTTCTACCCTAGAGAAGCCAAG
GTGCAGTGGAAGGTGGACAATGCCCTCCAGTCTGGCAACTCCCAAGAGTCTGTGACAGAGCAGGACAGCAAGGACTCCACCTACAGCCTGAGCAGCACCCTGACAC
TGAGCAAGGCTGACTATGAGAAGCACAAAGTCTATGCCTGTGAAGTGACCCACCAGGGCCTGTCTAGCCCTGTGACCAAGAGCTTCAACAGGGGAGAGAGCTGAAG
ATCTACTTCTGGCTAATAAAAGATCAGAGCTCTAGTGATCTGTGTGTTGGTTTTTTGTGTCTGCATTCTAGCATGTTACATAACTTATGGTAAATGGCCTGCCTGGCTG
ACTGCCCAATGACCCCTGCCCAATGATGTCAATAATGATGTATGTTCCCATGTAATGCCAATAGGGACTTTCCATTGATGTCAATGGGTGGAGTATTTATGGTAACTGC
CCACTTGGCAGTACATCAAGTGTATCATATGCCAAGTATGCCCCCTATTGATGTCAATGATGGTAAATGGCCTGCCTGGCATTATGCCCAGTACATGACCTTATGGGA
CTTTCCTACTTGGCAGTACATCTATGTATTAGTCATTGCTATTACCATGGATTAGTGGAGAAGAGCATGCTTGAGGGCTGAGTGCCCCTCAGTGGGCAGAGAGCACAT
GGCCCACAGTCCCTGAGAAGTTGGGGGGAGGGGTGGGCAATTGAACTGGTGCCTAGAGAAGGTGGGGCTTGGGTAAACTGGGAAAGTGATGTGGTGTACTGGCT
CCACCTTTTTCCCCAGGGTGGGGGAGAACCATATATAAGTGCAGTAGTCTCTGTGAACATTCAAGCTTCTGCCTTCTCCCTCCTGTGAGTTTGGATGCACCTACTAGAT
ATCTTGGTAAGTCACTGACTGTCTATGCCTGGGAAAGGGTGGGCAGGAGGTGGGGCAGTGCAGGAAAAGTGGCACTGTGAACCCTGCAGCCCTAGACAATTGTACT
AACCTTCTTCTCTTTCCTCTCCTGACAGGTTGGTAACCAAGCCACCATGAGAGTGACAGCCCCTAGAACAGTCCTGCTGCTCCTGTCTGCTGCCCTGGCTCTGACAGAA
ACATGGGCTGGCTCCAGACTGAAGGGCATTGCTCCTCTGCAACTGGGCAAGTGCAACATTGCTGGCTGGCTGCTGGGCAACCCTGAGTGTGATCCTCTGCTGCCTGT
CAGATCCTGGTCCTACATTGTGGAAACCCCTAGCTCTGAGAATGGCATCTGCTACCCTGGGGACTTCATTGACTATGAGGAACTGAAAGAACAGCTGTCCTCTGTGTC
CAGCTTTGAGAGATTTGAAATCTTCCCCAAAGAGAGCAGCTGGCCCAACCACAACACCAACAAAGGGGTCACAGCTGCCTGTAGCCATGAGGGCAAGAGCAGCTTCT
ACAGAAACCTGCTGTGGCTGACAGAGAAAGAGGGCAGCTACCCCAAGCTGAAGAACTCCTATGTGAACAAGAAGGGCAAAGAGGTCCTGGTTCTCTGGGGCATCCA
CCATCCTAGCAACAGCAAAGAGCAGCAGAACCTGTACCAGAATGAGAATGCCTATGTGTCTGTGGTCACAAGCAACTACAACAGAAGGTTCACCCCTGAGATTGCTG
AGAGGCCCAAAGTGAAGGACCAGGCTGGCAGAATGAACTACTACTGGACCCTGCTGAAGCCTGGGGACACCATCATCTTTGAGGCCAATGGCAACCTGATTGCCCC
TATGTATGCCTTTGCTCTGAGCAGAGGCTTTGGCTCTGGCATCATCACCTCTGTGGATGGGGTCAAGCTGGAATCCATGGGCATCATTGTGGGCATTGTGGCAGGCCT
GGCTGTGCTGGCAGTGGTGGTTATTGGAGCTGTGGTGGCTGCTGTGATGTGCAGAAGAAAGTCCTCTGGAGGCAAAGGTGGCAGCTACTCTCAGGCTGCCTGTTCT
GATTCTGCCCAGGGCTCTGATGTGTCCCTGACAGCTTAAAGATCTACTTCTGGCTAATAAAAGATCAGAGCTCTAGTGATCTGTGTGTTGGTTTTTTGTGTCTGCATTC
TAGCTCTAGTGATCAGCAGTTCAACCTGTTGATAGTATGTACTAAGCTCTCATGTTTAATGTACTAAGCTCTCATGTTTAATGAACTAAACCCTCATGGCTAATGTACTA
AGCTCTCATGGCTAATGTACTAAGCTCTCATGTTTCATGTACTAAGCTCTCATGTTTGAACAATAAAATTAATATAAATCAGCAACTTAAATAGCCTCTAAGGTTTTAAG
TTTTATAAGAAAAAAAAGAATATATAAGGCTTTTAAAGGTTTTAAGGTTTCCTAGGTTATCCTCATATGAGCTCTTAGAAAAACTCATCCAGCATCAAATGAAACTGCA
ATTTATTCATATCAGGATTATCAATACCATATTTTTGAAAAAGTCTTTTCTGTAATGAAGGAGAAAACTCACCCAGGCAGTTCCATAGGATGGCAAGATCCTGGTATCT
GTCTGCAATTCCAACTCTTCCAACATCAATACAACCTATTAATTTCCCCTCATCAAAAATAAGGTTATCAAGTGAGAAATCACCATGAGTGACCACTGAATCTGGTGAG
AATGGCAAAAGATTATGCATTTCTTTCCAGACTTGTTCAACAGGCCAGCCATTTCTCTCATCATCAAAATCACTGGCATCAACCAAACCATTATTCATTCTTGATTGGGC
CTGAGCCAGTCTAAATACTCTATCAGAGTTAAAAGGACAATTACAAACAGGAATGGAATGCAATCTTCTCAGGAACACTGCCAGGGCATCAACAATATTTTCACCTGA
ATCAGGATATTCTTCCAATACCTGGAATGCTGTTTTCCCTGGGATGGCAGTGGTGAGTAACCATGCATCATCAGGAGTTCTGATAAAATGCTTGATGGTTGGAAGAG
GCATAAATTCAGTCAGCCAGTTTAGTCTGACCATCTCATCTGTAACATCATTGGCAACAGAACCTTTGCCATGTTTCAGAAACAACTCTGGGGCATCTGGCTTCCCATA
CAATCTATAGATTGTGGCACCTGATTGCCCAACATTATCTCTAGCCCATTTATACCCATATAAATCAGCATCCATGTTGGAATTTAATCTTGGCCTGGAGCAAGAGGTT
TCTCTTTGAATATGGCTCATACATGTGCACCTCCTATAGTGAGTTGTATTATACTATGCAGATATACTATGCCAATGTTTAATTGTCAG

FIG. 66

011215 # 7: βGlo-RINhe-ΔmCMVΔEF1I126-BstEII-hG-CSF-BglII-IFN S/MAR-MixpA/BV2: EF1-hGCSF (high expresser)

(SEQ ID NO:45)

CACTATGTGTTAATTAAAATTATCTCTAAGGCATGTGAACTGGCTGTCTTGGTTTTCATCTGTACTTCATCTGCTACCTCTGTGACCTGAAACATATTTATAATTCCATTA
AGCTGTGCATATGATAGATTTATCATATGTATTTTCCTTAAAGGATTTTTGTAAGAACTAATTGAATTGATACCTGTAAAGTCTTTATCACACTACCCAATAAATAATAA
ATCTCTTTGTTCAGCTCTCTGTTTCTATAAATATGTACCAGTTTTATTGTTTTTAGTGGTAGTGATTTTATTCTCTTTCTATATATATACACACACATGTGTGCATTCATAA
ATATATACAATTTTTATGAATAAAAAATTATTAGCAATCAATATTGAAAACCACTGATTTTTGTTTATGTGAGCAAACAGCAGATTAAAAGGAATTTCAATTGCCTGCA
GGACATGAATTCAATTGGCTAGCAGGAGTCAATGGGAAAAACCCATTGGAGCCAAGTACACTGACTCAATAGGGACTTTCCATTGGGTTTTGCCCAGTACATAAGGT
CAATAGGGGGTGAGTCAACAGGAAAGTCCCATTGGAGCCAAGTACATTGAGTCAATAGGGACTTTCCAATGGGTTTTGCCCAGTACATAAGGTCAATGGGAGGTAA
GCCAATGGGTTTTTCCCATTACTGACATGTATACTGAGTCATTAGGGACTTTCCAATGGGTTTTGCCCAGTACATAAGGTCAATAGGGGTGAATCAACAGGAAAGTCC
CATTGGAGCCAAGTACACTGAGTCAATAGGGACTTTCCATTGGGTTTTGCCCAGTACAAAAGGTCAATAGGGGGTGAGTCAATGGGTTTTTCCCATTATTGGCACATA
CATAAGGTCAATAGGGGTGACTAGTGGAGAAGAGCATGCTTGAGGGCTGAGTGCCCCTCAGTGGGCAGAGAGCACATGGCCCACAGTCCCTGAGAAGTTGGGGGG
AGGGGTGGGCAATTGAACTGGTGCCTAGAGAAGGTGGGGCTTGGGTAAACTGGGAAAGTGATGTGGTGTACTGGCTCCACCTTTTTCCCCAGGGTGGGGGAGAAC
CATATATAAGTGCAGTAGTCTCTGTGAACATTCAAGCTTCTGCCTTCTCCCTCCTGTGAGTTTGgtaagtcactgactgtctatgcctgggaaagggtgggcaggagatggggcagtgcag
gaaaagtggcactatgaacccTGCAGCCCTAGAcaattgtactaaccttcttctctttcctctcctgacagGTTGGTAACCAAGCTTTCCATGGCTGGACCTGCCACCCAGAGCCCCATGAA
GCTGATGGCCCTGCAGCTGCTGCTGTGGCACAGTGCACTCTGGACAGTGCAGGAAGCCACCCCCCTGGGCCCTGCCAGCTCCCTGCCCCAGAGCTTCCTGCTCAAGT
GCTTAGAGCAAGTGAGGAAGATCCAGGGGGATGGGGCAGCTCTCCAGGAGAAGCTGTGTGCCACCTACAAGCTGTGCCACCCTGAGGAGCTGGTGCTGCTGGGAC
ACTCTCTGGGCATCCCCTGGGCTCCCCTGAGCAGCTGCCCCAGCCAGGCCCTGCAGCTGGCAGGCTGCTTGAGCCAACTCCATAGTGGCCTTTTCCTCTACCAGGGGC
TCCTGCAGGCCCTGGAAGGGATCTCCCCTGAGTTGGGTCCCACCTTGGACACACTGCAGCTGGATGTTGCTGACTTTGCCACCACCATCTGGCAGCAGATGGAAGAA
CTGGGAATGGCCCCTGCCCTGCAGCCCACCCAGGGTGCCATGCCTGCCTTTGCCTCTGCTTTCCAGAGAAGGGCAGGAGGGGTCCTGGTTGCCTCCCATCTGCAGAG
CTTCCTGGAGGTGTCCTACAGAGTTCTAAGACACCTTGCCCAGCCCTGATAGATCTACTTCTGGCTAATAAAAGATCAGAGCTCTAGTGATCTGTGTGTTGGTTTTTTG
TGTCTGCATTCTAGCCTGCAGGAATTCAGTCAATATGTTCACCCCAAAAAAGCTGTTTGTTAACTTGTCAACCTCATTCTAAAATGTATATAGAAGCCCAAAAGACAAT
AACAAAAATATTCTTGTAGAACAAAATGGGAAAGAATGTTCCACTAAATATCAAGATTTAGAGCAAAGCATGAGATGTGTGGGGATAGACAGTGAGGCTGATAAAA
TAGAGTAGAGCTCAGAAACAGACCCATTGATATATGTAAGTGACCTATGAAAAAAATATGGCATTTTACAATGGGAAAATGATGGTCTTTTTCTTTTTTAGAAAAACA
GGGAAATATATTTATATGTAAAAAATAAAAGGGAACCCATATGTCATACCATACACACAAAAAAATTCCAGTGAATTATAAGTCTAAATGGAGAAGGCAAAACTTTA
AATCTTTTAGAAAATAATATAGAAGCATGCCATCAAGACTTCAGTGTAGAGAAAAATTTCTTATGACTCAAAGTCCTAACCACAAAGAAAAGATTGTTAATTAGATTG
CATGAATATTAAGACTTATTTTTAAAATTAAAAAACCATTAAGAAAAGTCAGGCCATAGAATGACAGAAAATATTTGCAACACCCCAGTAAAGAGAATTGTAATATGC
AGATTATAAAAAGAAGTCTTACAAATCAGTAAAAAATAAAACTAGACAAAAATTTGAACAGATGAAAGAGAAACTCTAAATAATCATTACACATGAGAAACTCAATCT
CAGAAATCAGAGAACTATCATTGCATATACACTAAATTAGAGAAATATTAAAAGGCTAAGTAACATCTGTGGCTTAATTAATCTAGTGATCAGCAGTTCAACCTGTTG
ATAGTATGTACTAAGCTCTCATGTTTAATGTACTAAGCTCTCATGTTTAATGAACTAAACCCTCATGGCTAATGTACTAAGCTCTCATGGCTAATGTACTAAGCTCTCAT
GTTTCATGTACTAAGCTCTCATGTTTGAACAATAAAATTAATATAAATCAGCAACTTAAATAGCCTCTAAGGTTTTAAGTTTTATAAGAAAAAAAAGAATATATAAGGC
TTTTAAAGGTTTTAAGGTTTCCTAGGTTATCCTCATATGAGCTCTTAGAAAAACTCATCCAGCATCAAATGAAACTGCAATTTATTCATATCAGGATTATCAATACCATA
TTTTTGAAAAAGTCTTTTCTGTAATGAAGGAGAAAACTCACCCAGGCAGTTCCATAGGATGGCAAGATCCTGGTATCTGTCTGCAATTCCAACTCTTCCAACATCAATA
CAACCTATTAATTTCCCCTCATCAAAAATAAGGTTATCAAGTGAGAAATCACCATGAGTGACCACTGAATCTGGTGAGAATGGCAAAAGATTATGCATTTCTTTCCAGA
CTTGTTCAACAGGCCAGCCATTTCTCTCATCATCAAAATCACTGGCATCAACCAAACCATTATTCATTCTTGATTGGGCCTGAGCCAGTCTAAATACTCTATCAGAGTTA
AAAGGACAATTACAAACAGGAATGGAATGCAATCTTCTCAGGAACACTGCCAGGGCATCAACAATATTTTCACCTGAATCAGGATATTCTTCCAATACCTGGAATGCT
GTTTTCCCTGGGATGGCAGTGGTGAGTAACCATGCATCATCAGGAGTTCTGATAAAATGCTTGATGGTTGGAAGAGGCATAAATTCAGTCAGCCAGTTTAGTCTGAC
CATCTCATCTGTAACATCATTGGCAACAGAACCTTTGCCATGTTTCAGAAACAACTCTGGGGCATCTGGCTTCCCATACAATCTATAGATTGTGGCACCTGATTGCCCA
ACATTATCTCTAGCCCATTTATACCCATATAAATCAGCATCCATGTTGGAATTTAATCTTGGCCTGGAGCAAGAGGTTTCTCTTTGAATATGGCTCATACATGTGCACCT
CCTATAGTGAGTTGTATTATACTATGCAGATATACTATGCCAATGTTTAATTGTCAG

FIG. 67

011315 #2: βGlo-RINhe-ΔhCMVΔCMVΔHTLV-BstEII-hG-CSF-BglII-IFN S/MAR-MixpA/BV2 : hCMV-hGCSF (low expresser)

(SEQ ID NO:46)

CACTATGTGTTAATTAAAATTATCTCTAAGGCATGTGAACTGGCTGTCTTGGTTTTCATCTGTACTTCATCTGCTACCTCTGTGACCTGAAACATATTTATAATTCCATTA
AGCTGTGCATATGATAGATTTATCATATGTATTTTCCTTAAAGGATTTTTGTAAGAACTAATTGAATTGATACCTGTAAAGTCTTTATCACACTACCCAATAAATAATAA
ATCTCTTTGTTCAGCTCTCTGTTTCTATAAATATGTACCAGTTTTATTGTTTTTAGTGGTAGTGATTTTATTCTCTTTCTATATATATACACACACATGTGTGCATTCATAA
ATATATACAATTTTTATGAATAAAAAATTATTAGCAATCAATATTGAAAACCACTGATTTTTGTTTATGTGAGCAAACAGCAGATTAAAAGGAATTTCAATTGCCTGCA
GGACATGAATTCTCATAGCTAGCATGTTACATAACTTATGGTAAATGGCCTGCCTGGCTGACTGCCCAATGACCCCTGCCCAATGATGTCAATAATGATGTATGTTC
CCATGTAATGCCAATAGGGACTTTCCATTGATGTCAATGGGTGGAGTATTTATGGTAACTGCCCACTTGGCAGTACATCAAGTGTATCATATGCCAAGTATGCCCC
CTATTGATGTCAATGATGGTAAATGGCCTGCCTGGCATTATGCCCAGTACATGACCTTATGGGACTTTCCTACTTGGCAGTACATCTATGTATTAGTCATTGCTATTA
CCATGGTGATGGGTTTTGGCAGTACATCAATGGGTGTGGATAGTGGTTTGACCCATGGGGATTTCCAAGTCTCCACCCCATTGATGCCAATGGGAGTTTGTTTTGGCA
CCAAAATCAATGGGACTTTCCAAAATGTTGTAACAACTCTGCCCCATTGATGGAAATGGGTGGTAGGTGTGTGTGGTGGGAGGTCTATATAAGCAGAGCTTGTTTAG
TGAACTGGATGCACCTACTAGATATCCATATGGCTATCATCTCTCCTTCAATATCCATCATCCCTACCTGAGGCATCCATCCAATCATGTTGAGTATATTTCTGCATCCTC
CATCCTGTGGTGCCTCCTGAACTGATTCATCATTCTAGGTAAGTTTAAAGCTCAGGTATAGACATGGCCTTTGTCATGATCTCCCTTGGAGCCTACCTAGACTCATCAT
GCTCTCCAATCTTTGCCTGACCCTGCTTGCTCAACTCTAATTCTTTGTTTATTTTTCTGTTCTGATCATTTACAGATCCAAGCTGTGACATGATCCCTACCATATGTTGGA
GTGTAGGTAACCAAGCTTTCCATGGCTGGACCTGCCACCCAGAGCCCCATGAAGCTGATGGCCCTGCAGCTGCTGCTGTGGCACAGTGCACTCTGGACAGTGCAGGA
AGCCACCCCCCTGGGCCCTGCCAGCTCCCTGCCCCAGAGCTTCCTGCTCAAGTGCTTAGAGCAAGTGAGGAAGATCCAGGGGGATGGGGCAGCTCTCCAGGAGAAG
CTGTGTGCCACCTACAAGCTGTGCCACCCTGAGGAGCTGGTGCTGCTGGGACACTCTCTGGGCATCCCCTGGGCTCCCCTGAGCAGCTGCCCCAGCCAGGCCCTGCA
GCTGGCAGGCTGCTTGAGCCAACTCCATAGTGGCCTTTTCCTCTACCAGGGGCTCCTGCAGGCCCTGGAAGGGATCTCCCCTGAGTTGGGTCCCACCTTGGACACACT
GCAGCTGGATGTTGCTGACTTTGCCACCACCATCTGGCAGCAGATGGAAGAACTGGGAATGGCCCCTGCCCTGCAGCCCACCCAGGGTGCCATGCCTGCCTTTGCCT
CTGCTTTCCAGAGAAGGGCAGGAGGGGTCCTGGTTGCCTCCCATCTGCAGAGCTTCCTGGAGGTGTCCTACAGAGTTCTAAGACACCTTGCCCAGCCCTGATAGATCT
ACTTCTGGCTAATAAAAGATCAGAGCTCTAGTGATCTGTGTGTTGGTTTTTTGTGTCTGCATTCTAGCCTGCAGGAATTCAGTCAATATGTTCACCCCAAAAAAGCTGT
TTGTTAACTTGTCAACCTCATTCTAAAATGTATATAGAAGCCCAAAAGACAATAACAAAAATATTCTTGTAGAACAAAATGGGAAAGAATGTTCCACTAAATATCAAG
ATTTAGAGCAAAGCATGAGATGTGTGGGGATAGACAGTGAGGCTGATAAAATAGAGTAGAGCTCAGAAACAGACCCATTGATATATGTAAGTGACCTATGAAAAAA
ATATGGCATTTTACAATGGGAAAATGATGGTCTTTTTCTTTTTTAGAAAAACAGGGAAATATATTTATATGTAAAAAATAAAAGGGAACCCATATGTCATACCATACAC
ACAAAAAAATTCCAGTGAATTATAAGTCTAAATGGAGAAGGCAAAACTTTAAATCTTTTAGAAAATAATATAGAAGCATGCCATCAAGACTTCAGTGTAGAGAAAAA
TTTCTTATGACTCAAAGTCCTAACCACAAAGAAAAGATTGTTAATTAGATTGCATGAATATTAAGACTTATTTTTAAAATTAAAAAACCATTAAGAAAAGTCAGGCCAT
AGAATGACAGAAAATATTTGCAACACCCCAGTAAAGAGAATTGTAATATGCAGATTATAAAAAGAAGTCTTACAAATCAGTAAAAAATAAAACTAGACAAAAATTTG
AACAGATGAAAGAGAAACTCTAAATAATCATTACACATGAGAAACTCAATCTCAGAAATCAGAGAACTATCATTGCATATACACTAAATTAGAGAAATATTAAAAGGC
TAAGTAACATCTGTGGCTTAATTAATCTAGTGATCAGCAGTTCAACCTGTTGATAGTATGTACTAAGCTCTCATGTTTAATGTACTAAGCTCTCATGTTTAATGAACTAA
ACCCTCATGGCTAATGTACTAAGCTCTCATGGCTAATGTACTAAGCTCTCATGTTTCATGTACTAAGCTCTCATGTTTGAACAATAAAATTAATATAAATCAGCAACTTA
AATAGCCTCTAAGGTTTTAAGTTTTATAAGAAAAAAAAGAATATATAAGGCTTTTAAAGGTTTTAAGGTTTCCTAGGTTATCCTCATATGAGCTCTTAGAAAAACTCAT
CCAGCATCAAATGAAACTGCAATTTATTCATATCAGGATTATCAATACCATATTTTTGAAAAAGTCTTTTCTGTAATGAAGGAGAAAACTCACCCAGGCAGTTCCATAG
GATGGCAAGATCCTGGTATCTGTCTGCAATTCCAACTCTTCCAACATCAATACAACCTATTAATTTCCCCTCATCAAAAATAAGGTTATCAAGTGAGAAATCACCATGA
GTGACCACTGAATCTGGTGAGAATGGCAAAAGATTATGCATTTCTTTCCAGACTTGTTCAACAGGCCAGCCATTTCTCTCATCATCAAAATCACTGGCATCAACCAAAC
CATTATTCATTCTTGATTGGGCCTGAGCCAGTCTAAATACTCTATCAGAGTTAAAAGGACAATTACAAACAGGAATGGAATGCAATCTTCTCAGGAACACTGCCAGGG
CATCAACAATATTTTCACCTGAATCAGGATATTCTTCCAATACCTGGAATGCTGTTTTCCCTGGGATGGCAGTGGTGAGTAACCATGCATCATCAGGAGTTCTGATAAA
ATGCTTGATGGTTGGAAGAGGCATAAATTCAGTCAGCCAGTTTAGTCTGACCATCTCATCTGTAACATCATTGGCAACAGAACCTTTGCCATGTTTCAGAAACAACTCT
GGGGCATCTGGCTTCCCATACAATCTATAGATTGTGGCACCTGATTGCCCAACATTATCTCTAGCCCATTTATACCCATATAAATCAGCATCCATGTTGGAATTTAATCT
TGGCCTGGAGCAAGAGGTTTCTCTTTGAATATGGCTCATACATGTGCACCTCCTATAGTGAGTTGTATTATACTATGCAGATATACTATGCCAATGTTTAATTGTCAG

FIG. 68

122014 # 235: βGlo-RINhe-ΔmCMVΔEF1I126-BstEII-soLux-BglII-IFN S/MAR-MixpA/BV2 : EF1-Luc
(SEQ ID NO:47)

CACTATGTGTTAATTAAAATTATCTCTAAGGCATGTGAACTGGCTGTCTTGGTTTTCATCTGTACTTCATCTGCTACCTCTGTGACCTGAAACATATTTATAATTCCATTA
AGCTGTGCATATGATAGATTTATCATATGTATTTTCCTTAAAGGATTTTTGTAAGAACTAATTGAATTGATACCTGTAAAGTCTTTATCACACTACCCAATAAATAATAA
ATCTCTTTGTTCAGCTCTCTGTTTCTATAAATATGTACCAGTTTTATTGTTTTTAGTGGTAGTGATTTTATTCTCTTTCTATATATATACACACACATGTGTGCATTCATAA
ATATATACAATTTTTATGAATAAAAAATTATTAGCAATCAATATTGAAAACCACTGATTTTTGTTTATGTGAGCAAACAGCAGATTAAAAGGAATTTCAATTGCCTGCA
GGACATGAATTCAATTGGCTAGCAGGAGTCAATGGGAAAAACCCATTGGAGCCAAGTACACTGACTCAATAGGGACTTTCCATTGGGTTTTGCCCAGTACATAAGGT
CAATAGGGGGTGAGTCAACAGGAAAGTCCCATTGGAGCCAAGTACATTGAGTCAATAGGGACTTTCCAATGGGTTTTGCCCAGTACATAAGGTCAATGGGAGGTAA
GCCAATGGGTTTTTCCCATTACTGACATGTATACTGAGTCATTAGGGACTTTCCAATGGGTTTTGCCCAGTACATAAGGTCAATAGGGGTGAATCAACAGGAAAGTCC
CATTGGAGCCAAGTACACTGAGTCAATAGGGACTTTCCATTGGGTTTTGCCCAGTACAAAAGGTCAATAGGGGGTGAGTCAATGGGTTTTTCCCATTATTGGCACATA
CATAAGGTCAATAGGGGTGACTAGTGGAGAAGAGCATGCTTGAGGGCTGAGTGCCCCTCAGTGGGCAGAGAGCACATGGCCCACAGTCCCTGAGAAGTTGGGGGG
AGGGGTGGGCAATTGAACTGGTGCCTAGAGAAGGTGGGGCTTGGGTAAACTGGGAAAGTGATGTGGTGTACTGGCTCCACCTTTTTCCCCAGGGTGGGGGAGAAC
CATATATAAGTGCAGTAGTCTCTGTGAACATTCAAGCTTCTGCCTTCTCCCTCCTGTGAGTTTGgtaagtcactgactgtctatgcctgggaaagggtgggcaggagatggggcagtgcag
gaaaagtggcactatgaacccTGCAGCCCTAGAcaattgtactaaccttcttctctttcctctcctgacagGTTGGTAACCAAGCTTTCCATGGAGGATGCTAAGAACATCAAGAAGGGGCC
TGCCCCCTTCTACCCCCTGGAGGATGGCACAGCTGGGGAGCAGCTGCACAAGGCTATGAAGAGATATGCCCTGGTGCCTGGCACTATTGCCTTCACAGATGCTCACA
TTGAAGTGGACATCACCTATGCTGAGTACTTTGAGATGTCAGTGAGGCTGGCTGAGGCTATGAAAAGATATGGGCTGAACACTAATCACAGGATTGTGGTGTGTTCA
GAGAACTCACTGCAGTTCTTCATGCCTGTGCTGGGAGCCCTGTTCATTGGAGTGGCTGTGGCCCCTGCTAATGACATCTACAATGAGAGGGAGCTGCTGAACTCTATG
GGCATCAGTCAGCCTACAGTGGTGTTTGTGTCTAAGAAGGGCCTGCAGAAAATCCTGAATGTGCAGAAGAAGCTGCCTATCATTCAGAAAATCATCATCATGGACTC
TAAGACAGACTATCAGGGCTTTCAGTCTATGTACACCTTTGTGACTAGTCACCTGCCCCCTGGCTTCAATGAGTATGACTTTGTGCCTGAGTCATTTGACAGGGACAAG
ACTATTGCCCTGATCATGAACTCATCAGGCTCTACAGGCCTGCCTAAGGGAGTGGCCCTGCCTCACAGGACAGCCTGTGTGAGATTCAGTCATGCTAGGGACCCTATC
TTTGGCAATCAGATCATCCCTGACACAGCTATCCTGTCAGTGGTGCCCTTTCATCATGGCTTTGGCATGTTCACTACCCTGGGCTACCTGATCTGTGGCTTCAGAGTGG
TGCTGATGTACAGATTTGAGGAGGAGCTGTTCCTGAGATCACTGCAGGACTACAAAATTCAGTCAGCCCTGCTGGTGCCTACCCTGTTCAGCTTCTTTGCTAAGTCTAC
CCTGATTGACAAGTATGACCTGTCTAACCTGCATGAGATTGCCTCAGGGGGAGCCCCCCTGTCTAAGGAAGTGGGGGAAGCTGTGGCTAAGAGATTTCACCTGCCTG
GCATCAGGCAGGGCTATGGCCTGACAGAGACTACCTCAGCTATTCTGATCACCCCTGAGGGGGATGACAAGCCTGGGGCTGTGGGCAAAGTGGTGCCTTTCTTTGA
GGCTAAAGTGGTGGACCTGGACACAGGCAAGACCCTGGGAGTGAATCAGAGGGGGGAGCTGTGTGTGAGAGGCCCTATGATCATGTCAGGCTATGTGAACAACCC
TGAGGCTACTAATGCCCTGATTGATAAGGATGGCTGGCTGCACTCAGGGGACATTGCCTACTGGGATGAGGATGAGCACTTCTTCATTGTGGACAGGCTGAAGTCAC
TCATCAAGTACAAGGGCTATCAAGTGGCCCCAGCTGAGTTAGAGTCAATCTTACTTCAGCACCCTAACATCTTTGATGCTGGAGTGGCAGGCTTACCTGATGATGATG
CTGGGGAGTTACCTGCTGCTGTGGTGGTGTTAGAGCATGGCAAGACTATGACAGAGAAAGAGATTGTGGATTATGTGGCTAGTCAAGTCACTACAGCTAAGAAGCT
CAGGGGGGGAGTGGTCTTTGTGGATGAAGTGCCTAAGGGCCTCACAGGCAAGTTAGATGCTAGGAAGATCAGGGAGATCCTCATCAAGGCTAAGAAGGGGGGCA
AGATTGCTGTTTAAAGATCTACTTCTGGCTAATAAAAGATCAGAGCTCTAGTGATCTGTGTGTTGGTTTTTTGTGTCTGCATTCTAGCCTGCAGGAATTCAGTCAATAT
GTTCACCCCAAAAAAGCTGTTTGTTAACTTGTCAACCTCATTCTAAAATGTATATAGAAGCCCAAAAGACAATAACAAAAATATTCTTGTAGAACAAAATGGGAAAGA
ATGTTCCACTAAATATCAAGATTTAGAGCAAAGCATGAGATGTGTGGGGATAGACAGTGAGGCTGATAAAATAGAGTAGAGCTCAGAAACAGACCCATTGATATAT
GTAAGTGACCTATGAAAAAAATATGGCATTTTACAATGGGAAAATGATGGTCTTTTTCTTTTTTAGAAAAACAGGGAAATATATTTATATGTAAAAAATAAAAGGGAA
CCCATATGTCATACCATACACACAAAAAAATTCCAGTGAATTATAAGTCTAAATGGAGAAGGCAAAACTTTAAATCTTTTAGAAAATAATATAGAAGCATGCCATCAA
GACTTCAGTGTAGAGAAAAATTTCTTATGACTCAAAGTCCTAACCACAAAGAAAAGATTGTTAATTAGATTGCATGAATATTAAGACTTATTTTTAAAATTAAAAAACC
ATTAAGAAAAGTCAGGCCATAGAATGACAGAAAATATTTGCAACACCCCAGTAAAGAGAATTGTAATATGCAGATTATAAAAAGAAGTCTTACAAATCAGTAAAAAA
TAAAACTAGACAAAAATTTGAACAGATGAAAGAGAAACTCTAAATAATCATTACACATGAGAAACTCAATCTCAGAAATCAGAGAACTATCATTGCATATACACTAAA
TTAGAGAAATATTAAAAGGCTAAGTAACATCTGTGGCTTAATTAATCTAGTGATCAGCAGTTCAACCTGTTGATAGTATGTACTAAGCTCTCATGTTTAATGTACTAAG
CTCTCATGTTTAATGAACTAAACCCTCATGGCTAATGTACTAAGCTCTCATGGCTAATGTACTAAGCTCTCATGTTTCATGTACTAAGCTCTCATGTTTGAACAATAAAA
TTAATATAAATCAGCAACTTAAATAGCCTCTAAGGTTTTAAGTTTTATAAGAAAAAAAAGAATATATAAGGCTTTTAAAGGTTTTAAGGTTTCCTAGGTTATCCTCATAT
GAGCTCTTAGAAAAACTCATCCAGCATCAAATGAAACTGCAATTTATTCATATCAGGATTATCAATACCATATTTTTGAAAAAGTCTTTTCTGTAATGAAGGAGAAAAC
TCACCCAGGCAGTTCCATAGGATGGCAAGATCCTGGTATCTGTCTGCAATTCCAACTCTTCCAACATCAATACAACCTATTAATTTCCCCTCATCAAAAATAAGGTTATC
AAGTGAGAAATCACCATGAGTGACCACTGAATCTGGTGAGAATGGCAAAAGATTATGCATTTCTTTCCAGACTTGTTCAACAGGCCAGCCATTTCTCTCATCATCAAA
ATCACTGGCATCAACCAAACCATTATTCATTCTTGATTGGGCCTGAGCCAGTCTAAATACTCTATCAGAGTTAAAAGGACAATTACAAACAGGAATGGAATGCAATCT
TCTCAGGAACACTGCCAGGGCATCAACAATATTTTCACCTGAATCAGGATATTCTTCCAATACCTGGAATGCTGTTTTCCCTGGGATGGCAGTGGTGAGTAACCATGC
ATCATCAGGAGTTCTGATAAAATGCTTGATGGTTGGAAGAGGCATAAATTCAGTCAGCCAGTTTAGTCTGACCATCTCATCTGTAACATCATTGGCAACAGAACCTTT
GCCATGTTTCAGAAACAACTCTGGGGCATCTGGCTTCCCATACAATCTATAGATTGTGGCACCTGATTGCCCAACATTATCTCTAGCCCATTTATACCCATATAAATCAG
CATCCATGTTGGAATTTAATCTTGGCCTGGAGCAAGAGGTTTCTCTTTGAATATGGCTCATACATGTGCACCTCCTATAGTGAGTTGTATTATACTATGCAGATATACT
ATGCCAATGTTTAATTGTCAG

FIG. 69

DNARx-PD1-2A

DraIIRINhe-ΔmCMVΔEF1I126-BstEII- ΔPD1-H-F3(RKRR)-P2A-ΔPD1-L-BglII-MixpA-BV2
(SEQ ID NO:48)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGGGACTGGGACTCCAGTGGGTGT
TCTTTGTGGCCCTGCTGAAAGGGGTGCACTGTGAAGTCAGACTGCTGGAAAGTGGTGGTGGCCTGGTCAAGCCAGAGGGCTCTCTGAAGCTGAGCTGTGTGGCTTC
TGGCTTCACCTTCTCTGACTACTTCATGAGCTGGGTCAGACAGGCCCCTGGCAAAGGCCTTGAATGGGTTGCCCACATCTACACCAAGAGCTACAACTATGCCACCTA
CTACTCTGGCTCTGTGAAGGGCAGATTCACCATCAGCAGAGATGACAGCAGATCCATGGTGTACCTCCAGATGAACAACCTGAGAACAGAGGACACAGCCACCTATT
ACTGCACCAGAGATGGCTCTGGCTACCCCAGCCTGGATTTTTGGGGCCAGGGCACCCAAGTGACAGTCAGCTCTGCCACAACCACAGCTCCCTCTGTGTACCCACTGG
CTCCAGCCTGTGACAGCACCACAAAGTCTGCCAGCACAAAGGGCCCATCTGTGTTCCCTCTGGCACCCAGCAGCAAGTCTACCAGTGGTGGAACAGCTGCCCTGGGC
TGTCTGGTCAAGGACTACTTTCCTGAGCCAGTGACAGTGTCCTGGAACTCTGGGGCTCTGACATCTGGGGTGCACACATTCCCTGCTGTGCTCCAGTCCTCTGGCCTG
TACAGCCTCAGCTCTGTGGTCACAGTGCCTAGCTCTAGCCTGGGCACCCAGACCTACATCTGCAATGTGAACCACAAGCCTAGCAACACCAAGGTGGACAAGAAGGC
TGAGCCCAAGAGCTGTGACAAGACCCACACCTGTCCTCCATGTCCTGCTCCAGAGCTGCTTGGAGGACCTTCTGTGTTTCTGTTCCCTCCAAAGCCAAAGGACACCCT
GATGATCAGCAGAACCCCTGAAGTGACATGTGTGGTGGTTGATGTGTCCCATGAGGACCCAGAAGTGAAGTTCAATTGGTATGTGGATGGTGTTGAGGTGCACAAT
GCCAAGACCAAGCCTAGAGAGGAACAGTACAACAGCACCTACAGAGTGGTGTCTGTGCTGACAGTGCTGCATCAGGACTGGCTGAATGGCAAAGAGTACAAGTGC
AAGGTGTCCAACAAGGCCCTGCCTGCTCCTATTGAAAAGACCATCTCCAAGGCCAAGGGCCAGCCTAGGGAACCCCAGGTTTACACACTGCCACCTAGCAGGGATGA
GCTGACCAAGAACCAGGTGTCCCTGACCTGCCTGGTTAAGGGCTTCTACCCCTCTGACATTGCTGTGGAATGGGAGAGCAATGGCCAGCCAGAGAACAACTACAAGA
CAACCCCTCCTGTGCTGGACTCTGATGGCTCATTCTTCCTGTACTCCAAGCTCACAGTGGACAAGTCCAGATGGCAGCAAGGCAATGTGTTCAGCTGCTCTGTGATGC
ATGAGGCCCTGCACAACCACTACACACAGAAGTCCCTGAGCCTGTCTCCTGGCAAG*AGAAAGAGAAGGAGTGGAAGTGGAGCTACTAACTTCAGCCTGCTGAAGCA*
*GGCTGGAGATGTGGAGGAGAACCCTGGACCT*ATGGACTTCCAGGTGCAGATCATCAGCTTTCTGCTGATCTCTGCCTCTGTGATCATGAGCAGAGGCTATGAGCTGA
CCCAGCCTCCTTCTGCTTCTGTGAATGTGGGAGAAGCTGTGAAGATCACCTGTTCTGGGGACCAGCTGCCTAAGTACTTTGCTGACTGGTTCCACCAGAGGAGTGACC
AGACCATCCTGCAAGTGATCTATGATGACAACAAGAGGCCCTCTGGCATCCCTGAGAGAATCTCTGGCAGCAGCTCTGGCACCACAGCCACACTGACCATCAGAGAT
GTCAGAGCTGAGGATGAAGGGGACTACTACTGCTTCTCTGGCTATGTGGACTCTGACAGCAAGCTGTATGTGTTTGGCAGTGGCACCCAGCTGACAGTGCTTGGAG
GACCCAAGAGCAGAACAGTGGCTGCCCCTTCTGTGTTCATCTTCCCACCATCTGATGAGCAGCTGAAGTCTGGCACAGCCTCTGTTGTGTGCCTGCTGAACAACTTCT
ACCCTAGAGAAGCCAAGGTGCAGTGGAAGGTGGACAATGCCCTCCAGTCTGGCAACTCCCAAGAGTCTGTGACAGAGCAGGACAGCAAGGACTCCACCTACAGCCT
GAGCAGCACCCTGACACTGAGCAAGGCTGACTATGAGAAGCACAAAGTCTATGCCTGTGAAGTGACCCACCAGGGCCTGTCTAGCCCTGTGACCAAGAGCTTCAACA
GGGGAGAGAGCTGAAGATCTACTTCTGGCTAATAAAAGATCAGAGCTCTAGTGATCTGTGTGTTGGTTTTTTGTGTCTGCATTCTAGCTCTAGTGATCAGCAGTTCAA
CCTGTTGATAGTATGTACTAAGCTCTCATGTTTAATGTACTAAGCTCTCATGTTTAATGAACTAAACCCTCATGGCTAATGTACTAAGCTCTCATGGCTAATGTACTAAG
CTCTCATGTTTCATGTACTAAGCTCTCATGTTTGAACAATAAAATTAATATAAATCAGCAACTTAAATAGCCTCTAAGGTTTTAAGTTTTATAAGAAAAAAAAGAATATA
TAAGGCTTTTAAAGGTTTTAAGGTTTCCTAGGTTATCCTCATATGAGCTCTTAGAAAAACTCATCCAGCATCAAATGAAACTGCAATTTATTCATATCAGGATTATCAAT
ACCATATTTTTGAAAAAGTCTTTTCTGTAATGAAGGAGAAAACTCACCCAGGCAGTTCCATAGGATGGCAAGATCCTGGTATCTGTCTGCAATTCCAACTCTTCCAACA
TCAATACAACCTATTAATTTCCCCTCATCAAAAATAAGGTTATCAAGTGAGAAATCACCATGAGTGACCACTGAATCTGGTGAGAATGGCAAAAGATTATGCATTTCTT
TCCAGACTTGTTCAACAGGCCAGCCATTTCTCTCATCATCAAAATCACTGGCATCAACCAAACCATTATTCATTCTTGATTGGGCCTGAGCCAGTCTAAATACTCTATCA
GAGTTAAAAGGACAATTACAAACAGGAATGGAATGCAATCTTCTCAGGAACACTGCCAGGGCATCAACAATATTTTCACCTGAATCAGGATATTCTTCCAATACCTGG
AATGCTGTTTTCCCTGGGATGGCAGTGGTGAGTAACCATGCATCATCAGGAGTTCTGATAAAATGCTTGATGGTTGGAAGAGGCATAAATTCAGTCAGCCAGTTTAG
TCTGACCATCTCATCTGTAACATCATTGGCAACAGAACCTTTGCCATGTTTCAGAAACAACTCTGGGGCATCTGGCTTCCCATACAATCTATAGATTGTGGCACCTGAT
TGCCCAACATTATCTCTAGCCCATTTATACCCATATAAATCAGCATCCATGTTGGAATTTAATCTTGGCCTGGAGCAAGAGGTTTCTCTTTGAATATGGCTCATACATGT
GCACCTCCTATAGTGAGTTGTATTATACTATGCAGATATACTATGCCAATGTTTAATTGTCAG

FIG. 70

DNARx-SEC-OVA-MITD

DraIIRINhe-ΔmCMVΔEF1I126-BstEII- SEC-OVA-MITD-BglII-MixpA-BV2
(SEQ ID NO:49)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGAGAGTGACAGCCCCTAGAACAG
TCCTGCTGCTCCTGTCTGCTGCCCTGGCTCTGACAGAAACATGGGCTGGCAGCAGCATCATCAACTTTGAGAAGCTGATTGTGGGCATTGTGGCTGGCCTGGCTGTGC
TGGCAGTGGTGGTTATTGGAGCTGTGGTGGCTGCTGTGATGTGCAGAAGAAAGTCCTCTGGAGGCAAAGGTGGCAGCTACTCCCAGGCTGCCTGTTCTGATTCTGCC
CAGGGCTCTGATGTGTCCCTGACAGCTTAAAGATCTACTTCTGGCTAATAAAAGATCAGAGCTCTAGTGATCTGTGTGTTGGTTTTTTGTGTCTGCATTCTAGCTCTAG
TGATCAGCAGTTCAACCTGTTGATAGTATGTACTAAGCTCTCATGTTTAATGTACTAAGCTCTCATGTTTAATGAACTAAACCCTCATGGCTAATGTACTAAGCTCTCAT
GGCTAATGTACTAAGCTCTCATGTTTCATGTACTAAGCTCTCATGTTTGAACAATAAAATTAATATAAATCAGCAACTTAAATAGCCTCTAAGGTTTTAAGTTTTATAAG
AAAAAAAAGAATATATAAGGCTTTTAAAGGTTTTAAGGTTTCCTAGGTTATCCTCATATGAGCTCTTAGAAAAACTCATCCAGCATCAAATGAAACTGCAATTTATTCA
TATCAGGATTATCAATACCATATTTTTGAAAAAGTCTTTTCTGTAATGAAGGAGAAAACTCACCCAGGCAGTTCCATAGGATGGCAAGATCCTGGTATCTGTCTGCAAT
TCCAACTCTTCCAACATCAATACAACCTATTAATTTCCCCTCATCAAAAATAAGGTTATCAAGTGAGAAATCACCATGAGTGACCACTGAATCTGGTGAGAATGGCAAA
AGATTATGCATTTCTTTCCAGACTTGTTCAACAGGCCAGCCATTTCTCTCATCATCAAAATCACTGGCATCAACCAAACCATTATTCATTCTTGATTGGGCCTGAGCCAG
TCTAAATACTCTATCAGAGTTAAAAGGACAATTACAAACAGGAATGGAATGCAATCTTCTCAGGAACACTGCCAGGGCATCAACAATATTTTCACCTGAATCAGGATA
TTCTTCCAATACCTGGAATGCTGTTTTCCCTGGGATGGCAGTGGTGAGTAACCATGCATCATCAGGAGTTCTGATAAAATGCTTGATGGTTGGAAGAGGCATAAATTC
AGTCAGCCAGTTTAGTCTGACCATCTCATCTGTAACATCATTGGCAACAGAACCTTTGCCATGTTTCAGAAACAACTCTGGGGCATCTGGCTTCCCATACAATCTATAG
ATTGTGGCACCTGATTGCCCAACATTATCTCTAGCCCATTTATACCCATATAAATCAGCATCCATGTTGGAATTTAATCTTGGCCTGGAGCAAGAGGTTTCTCTTTGAAT
ATGGCTCATACATGTGCACCTCCTATAGTGAGTTGTATTATACTATGCAGATATACTATGCCAATGTTTAATTGTCAG

FIG. 71

DNARx-SEC-gp70-MITD

DraIIRINhe-ΔmCMVΔEF1I126-BstEII- SEC-gp70-MITD-BglII-MixpA-BV2
(SEQ ID NO:50)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCAAGCCACCATGAGAGTGACAGCCCCTAGAACAG
TCCTGCTGCTCCTGTCTGCTGCCCTGGCTCTGACAGAAACATGGGCTGGCAGCAGCCCCAGCTATGCCTACCACCAGTTCATTGTGGGCATTGTGGCTGGCCTGGCTG
TGCTGGCAGTGGTGGTTATTGGAGCTGTGGTGGCTGCTGTGATGTGCAGAAGAAAGTCCTCTGGAGGCAAAGGTGGCAGCTACTCCCAGGCTGCCTGTTCTGATTCT
GCCCAGGGCTCTGATGTGTCCCTGACAGCTTAAAGATCTACTTCTGGCTAATAAAAGATCAGAGCTCTAGTGATCTGTGTGTTGGTTTTTTGTGTCTGCATTCTAGCTC
TAGTGATCAGCAGTTCAACCTGTTGATAGTATGTACTAAGCTCTCATGTTTAATGTACTAAGCTCTCATGTTTAATGAACTAAACCCTCATGGCTAATGTACTAAGCTCT
CATGGCTAATGTACTAAGCTCTCATGTTTCATGTACTAAGCTCTCATGTTTGAACAATAAAATTAATATAAATCAGCAACTTAAATAGCCTCTAAGGTTTTAAGTTTTAT
AAGAAAAAAAAGAATATATAAGGCTTTTAAAGGTTTTAAGGTTTCCTAGGTTATCCTCATATGAGCTCTTAGAAAAACTCATCCAGCATCAAATGAAACTGCAATTTAT
TCATATCAGGATTATCAATACCATATTTTTGAAAAAGTCTTTTCTGTAATGAAGGAGAAAACTCACCCAGGCAGTTCCATAGGATGGCAAGATCCTGGTATCTGTCTGC
AATTCCAACTCTTCCAACATCAATACAACCTATTAATTTCCCCTCATCAAAAATAAGGTTATCAAGTGAGAAATCACCATGAGTGACCACTGAATCTGGTGAGAATGGC
AAAAGATTATGCATTTCTTTCCAGACTTGTTCAACAGGCCAGCCATTTCTCTCATCATCAAAATCACTGGCATCAACCAAACCATTATTCATTCTTGATTGGGCCTGAGC
CAGTCTAAATACTCTATCAGAGTTAAAAGGACAATTACAAACAGGAATGGAATGCAATCTTCTCAGGAACACTGCCAGGGCATCAACAATATTTTCACCTGAATCAGG
ATATTCTTCCAATACCTGGAATGCTGTTTTCCCTGGGATGGCAGTGGTGAGTAACCATGCATCATCAGGAGTTCTGATAAAATGCTTGATGGTTGGAAGAGGCATAAA
TTCAGTCAGCCAGTTTAGTCTGACCATCTCATCTGTAACATCATTGGCAACAGAACCTTTGCCATGTTTCAGAAACAACTCTGGGGCATCTGGCTTCCCATACAATCTAT
AGATTGTGGCACCTGATTGCCCAACATTATCTCTAGCCCATTTATACCCATATAAATCAGCATCCATGTTGGAATTTAATCTTGGCCTGGAGCAAGAGGTTTCTCTTTGA
ATATGGCTCATACATGTGCACCTCCTATAGTGAGTTGTATTATACTATGCAGATATACTATGCCAATGTTTAATTGTCAG

FIG. 72

DNARx-PD1-2A-OVA: Dual Cassette anti-PD1-2A and antiOVA

DraIIRINhe-ΔmCMV-EF1-I126BstEII-ΔPD1-H-2A-ΔPD1-LBglIIpolyA-ΔhCMV-EF1-I126BstEII-SEC-OVA-MITDBglIIpolyA BV2

(SEQ ID NO:51)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGACTGGGACTCCAGTGGGTGTTCTTTGTGGCCCTGCTGAAAGGGGTGCACTGTGAAGTCAGACTGCTGGAAAGTGGTGGTGGCCTGGTCAAGCCAGAGG
GCTCTCTGAAGCTGAGCTGTGTGGCTTCTGGCTTCACCTTCTCTGACTACTTCATGAGCTGGGTCAGACAGGCCCCTGGCAAAGGCCTTGAATGGGTTGCCCACATCT
ACACCAAGAGCTACAACTATGCCACCTACTACTCTGGCTCTGTGAAGGGCAGATTCACCATCAGCAGAGATGACAGCAGATCCATGGTGTACCTCCAGATGAACAAC
CTGAGAACAGAGGACACAGCCACCTATTACTGCACCAGAGATGGCTCTGGCTACCCCAGCCTGGATTTTTGGGGCCAGGGCACCCAAGTGACAGTCAGCTCTGCCAC
AACCACAGCTCCCTCTGTGTACCCACTGGCTCCAGCCTGTGACAGCACCACAAAGTCTGCCAGCACAAAGGGCCCATCTGTGTTCCCTCTGGCACCCAGCAGCAAGTC
TACCAGTGGTGGAACAGCTGCCCTGGGCTGTCTGGTCAAGGACTACTTTCCTGAGCCAGTGACAGTGTCCTGGAACTCTGGGGCTCTGACATCTGGGGTGCACACAT
TCCCTGCTGTGCTCCAGTCCTCTGGCCTGTACAGCCTCAGCTCTGTGGTCACAGTGCCTAGCTCTAGCCTGGGCACCCAGACCTACATCTGCAATGTGAACCACAAGCC
TAGCAACACCAAGGTGGACAAGAAGGCTGAGCCCAAGAGCTGTGACAAGACCCACACCTGTCCTCCATGTCCTGCTCCAGAGCTGCTTGGAGGACCTTCTGTGTTTC
TGTTCCCTCCAAAGCCAAAGGACACCCTGATGATCAGCAGAACCCCTGAAGTGACATGTGTGGTGGTTGATGTGTCCCATGAGGACCCAGAAGTGAAGTTCAATTGG
TATGTGGATGGTGTTGAGGTGCACAATGCCAAGACCAAGCCTAGAGAGGAACAGTACAACAGCACCTACAGAGTGGTGTCTGTGCTGACAGTGCTGCATCAGGACT
GGCTGAATGGCAAAGAGTACAAGTGCAAGGTGTCCAACAAGGCCCTGCCTGCTCCTATTGAAAAGACCATCTCCAAGGCCAAGGGCCAGCCTAGGGAACCCCAGGT
TTACACACTGCCACCTAGCAGGGATGAGCTGACCAAGAACCAGGTGTCCCTGACCTGCCTGGTTAAGGGCTTCTACCCCTCTGACATTGCTGTGGAATGGGAGAGCA
ATGGCCAGCCAGAGAACAACTACAAGACAACCCCTCCTGTGCTGGACTCTGATGGCTCATTCTTCCTGTACTCCAAGCTCACAGTGGACAAGTCCAGATGGCAGCAA
GGCAATGTGTTCAGCTGCTCTGTGATGCATGAGGCCCTGCACAACCACTACACACAGAAGTCCCTGAGCCTGTCTCCTGGCAAG*AGAAAGAGAAGGAGTGGAAGTG*
*GAGCTACTAACTTCAGCCTGCTGAAGCAGGCTGGAGATGTGGAGGAGAACCCTGGACCT*ATGGACTTCCAGGTGCAGATCATCAGCTTTCTGCTGATCTCTGCCTCTG
TGATCATGAGCAGAGGCTATGAGCTGACCCAGCCTCCTTCTGCTTCTGTGAATGTGGGAGAAGCTGTGAAGATCACCTGTTCTGGGGACCAGCTGCCTAAGTACTTT
GCTGACTGGTTCCACCAGAGGAGTGACCAGACCATCCTGCAAGTGATCTATGATGACAACAAGAGGCCCTCTGGCATCCCTGAGAGAATCTCTGGCAGCAGCTCTGG
CACCACAGCCACACTGACCATCAGAGATGTCAGAGCTGAGGATGAAGGGGACTACTACTGCTTCTCTGGCTATGTGGACTCTGACAGCAAGCTGTATGTGTTTGGCA
GTGGCACCCAGCTGACAGTGCTTGGAGGACCCAAGAGCAGAACAGTGGCTGCCCCTTCTGTGTTCATCTTCCCACCATCTGATGAGCAGCTGAAGTCTGGCACAGCC
TCTGTTGTGTGCCTGCTGAACAACTTCTACCCTAGAGAAGCCAAGGTGCAGTGGAAGGTGGACAATGCCCTCCAGTCTGGCAACTCCCAAGAGTCTGTGACAGAGCA
GGACAGCAAGGACTCCACCTACAGCCTGAGCAGCACCCTGACACTGAGCAAGGCTGACTATGAGAAGCACAAAGTCTATGCCTGTGAAGTGACCCACCAGGGCCTG
TCTAGCCCTGTGACCAAGAGCTTCAACAGGGGAGAGAGCTGAAGATCTACTTCTGGCTAATAAAAGATCAGAGCTCTAGTGATCTGTGTGTTGGTTTTTTGTGTCTGC
ATTCTAGCATGTTACATAACTTATGGTAAATGGCCTGCCTGGCTGACTGCCCAATGACCCCTGCCCAATGATGTCAATAATGATGTATGTTCCCATGTAATGCCAATAG
GGACTTTCCATTGATGTCAATGGGTGGAGTATTTATGGTAACTGCCCACTTGGCAGTACATCAAGTGTATCATATGCCAAGTATGCCCCCTATTGATGTCAATGATGGT
AAATGGCCTGCCTGGCATTATGCCCAGTACATGACCTTATGGGACTTTCCTACTTGGCAGTACATCTATGTATTAGTCATTGCTATTACCATGGATTAGTGGAGAAGAG
CATGCTTGAGGGCTGAGTGCCCCTCAGTGGGCAGAGAGCACATGGCCCACAGTCCCTGAGAAGTTGGGGGGAGGGGTGGGCAATTGAACTGGTGCCTAGAGAAG
GTGGGGCTTGGGTAAACTGGGAAAGTGATGTGGTGTACTGGCTCCACCTTTTTCCCCAGGGTGGGGGAGAACCATATATAAGTGCAGTAGTCTCTGTGAACATTCAA
GCTTCTGCCTTCTCCCTCCTGTGAGTTTGGATGCACCTACTAGATATCTTGGTAAGTCACTGACTGTCTATGCCTGGGAAAGGGTGGGCAGGAGGTGGGGCAGTGCA
GGAAAAGTGGCACTGTGAACCCTGCAGCCCTAGACAATTGTACTAACCTTCTTCTCTTTCCTCTCCTGACAGGTTGGTAACCAAGCCACCATGAGAGTGACAGCCCCT
AGAACAGTCCTGCTGCTCCTGTCTGCTGCCCTGGCTCTGACAGAAACATGGGCTGGCAGCAGCCCCAGCTATGCCTACCACCAGTTCATTGTGGGCATTGTGGCTGGC
CTGGCTGTGCTGGCAGTGGTGGTTATTGGAGCTGTGGTGGCTGCTGTGATGTGCAGAAGAAAGTCCTCTGGAGGCAAAGGTGGCAGCTACTCCCAGGCTGCCTGTT
CTGATTCTGCCCAGGGCTCTGATGTGTCCCTGACAGCTTAAAGATCTACTTCTGGCTAATAAAAGATCAGAGCTCTAGTGATCTGTGTGTTGGTTTTTTGTGTCTGCAT
TCTAGCTCTAGTGATCAGCAGTTCAACCTGTTGATAGTATGTACTAAGCTCTCATGTTTAATGTACTAAGCTCTCATGTTTAATGAACTAAACCCTCATGGCTAATGTAC
TAAGCTCTCATGGCTAATGTACTAAGCTCTCATGTTTCATGTACTAAGCTCTCATGTTTGAACAATAAAATTAATATAAATCAGCAACTTAAATAGCCTCTAAGGTTTTA
AGTTTTATAAGAAAAAAAAGAATATATAAGGCTTTTAAAGGTTTTAAGGTTTCCTAGGTTATCCTCATATGAGCTCTTAGAAAAACTCATCCAGCATCAAATGAAACTG
CAATTTATTCATATCAGGATTATCAATACCATATTTTTGAAAAAGTCTTTTCTGTAATGAAGGAGAAAACTCACCCAGGCAGTTCCATAGGATGGCAAGATCCTGGTAT
CTGTCTGCAATTCCAACTCTTCCAACATCAATACAACCTATTAATTTCCCCTCATCAAAAATAAGGTTATCAAGTGAGAAATCACCATGAGTGACCACTGAATCTGGTG
AGAATGGCAAAAGATTATGCATTTCTTTCCAGACTTGTTCAACAGGCCAGCCATTTCTCTCATCATCAAAATCACTGGCATCAACCAAACCATTATTCATTCTTGATTGG
GCCTGAGCCAGTCTAAATACTCTATCAGAGTTAAAAGGACAATTACAAACAGGAATGGAATGCAATCTTCTCAGGAACACTGCCAGGGCATCAACAATATTTTCACCT
GAATCAGGATATTCTTCCAATACCTGGAATGCTGTTTTCCCTGGGATGGCAGTGGTGAGTAACCATGCATCATCAGGAGTTCTGATAAAATGCTTGATGGTTGGAAGA
GGCATAAATTCAGTCAGCCAGTTTAGTCTGACCATCTCATCTGTAACATCATTGGCAACAGAACCTTTGCCATGTTTCAGAAACAACTCTGGGGCATCTGGCTTCCCAT
ACAATCTATAGATTGTGGCACCTGATTGCCCAACATTATCTCTAGCCCATTTATACCCATATAAATCAGCATCCATGTTGGAATTTAATCTTGGCCTGGAGCAAGAGGT
TTCTCTTTGAATATGGCTCATACATGTGCACCTCCTATAGTGAGTTGTATTATACTATGCAGATATACTATGCCAATGTTTAATTGTCAG

FIG. 73

DNARx-PD1-2A-gp70: Dual Cassette anti-PD1-2A and gp70

DraIIRINhe-ΔmCMV-EF1-I126BstEII-ΔPD1-H-2A-ΔPD1-LBglIIpolyA-ΔhCMV-EF1-I126BstEII-SEC-gp70-MITDBglIIpolyA BV2

(SEQ ID NO:52)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGACTGGGACTCCAGTGGGTGTTCTTTGTGGCCCTGCTGAAAGGGGTGCACTGTGAAGTCAGACTGCTGGAAAGTGGTGGTGGCCTGGTCAAGCCAGAGG
GCTCTCTGAAGCTGAGCTGTGTGGCTTCTGGCTTCACCTTCTCTGACTACTTCATGAGCTGGGTCAGACAGGCCCCTGGCAAAGGCCTTGAATGGGTTGCCCACATCT
ACACCAAGAGCTACAACTATGCCACCTACTACTCTGGCTCTGTGAAGGGCAGATTCACCATCAGCAGAGATGACAGCAGATCCATGGTGTACCTCCAGATGAACAAC
CTGAGAACAGAGGACACAGCCACCTATTACTGCACCAGAGATGGCTCTGGCTACCCCAGCCTGGATTTTTGGGGCCAGGGCACCCAAGTGACAGTCAGCTCTGCCAC
AACCACAGCTCCCTCTGTGTACCCACTGGCTCCAGCCTGTGACAGCACCACAAAGTCTGCCAGCACAAAGGGCCCATCTGTGTTCCCTCTGGCACCCAGCAGCAAGTC
TACCAGTGGTGGAACAGCTGCCCTGGGCTGTCTGGTCAAGGACTACTTTCCTGAGCCAGTGACAGTGTCCTGGAACTCTGGGGCTCTGACATCTGGGGTGCACACAT
TCCCTGCTGTGCTCCAGTCCTCTGGCCTGTACAGCCTCAGCTCTGTGGTCACAGTGCCTAGCTCTAGCCTGGGCACCCAGACCTACATCTGCAATGTGAACCACAAGCC
TAGCAACACCAAGGTGGACAAGAAGGCTGAGCCCAAGAGCTGTGACAAGACCCACACCTGTCCTCCATGTCCTGCTCCAGAGCTGCTTGGAGGACCTTCTGTGTTTC
TGTTCCCTCCAAAGCCAAAGGACACCCTGATGATCAGCAGAACCCCTGAAGTGACATGTGTGGTGGTTGATGTGTCCCATGAGGACCCAGAAGTGAAGTTCAATTGG
TATGTGGATGGTGTTGAGGTGCACAATGCCAAGACCAAGCCTAGAGAGGAACAGTACAACAGCACCTACAGAGTGGTGTCTGTGCTGACAGTGCTGCATCAGGACT
GGCTGAATGGCAAAGAGTACAAGTGCAAGGTGTCCAACAAGGCCCTGCCTGCTCCTATTGAAAAGACCATCTCCAAGGCCAAGGGCCAGCCTAGGGAACCCCAGGT
TTACACACTGCCACCTAGCAGGGATGAGCTGACCAAGAACCAGGTGTCCCTGACCTGCCTGGTTAAGGGCTTCTACCCCTCTGACATTGCTGTGGAATGGGAGAGCA
ATGGCCAGCCAGAGAACAACTACAAGACAACCCCTCCTGTGCTGGACTCTGATGGCTCATTCTTCCTGTACTCCAAGCTCACAGTGGACAAGTCCAGATGGCAGCAA
GGCAATGTGTTCAGCTGCTCTGTGATGCATGAGGCCCTGCACAACCACTACACACAGAAGTCCCTGAGCCTGTCTCCTGGCAAG*AGAAAGAGAAGGAGTGGAAGTG*
*GAGCTACTAACTTCAGCCTGCTGAAGCAGGCTGGAGATGTGGAGGAGAACCCTGGACCT*ATGGACTTCCAGGTGCAGATCATCAGCTTTCTGCTGATCTCTGCCTCTG
TGATCATGAGCAGAGGCTATGAGCTGACCCAGCCTCCTTCTGCTTCTGTGAATGTGGGAGAAGCTGTGAAGATCACCTGTTCTGGGGACCAGCTGCCTAAGTACTTT
GCTGACTGGTTCCACCAGAGGAGTGACCAGACCATCCTGCAAGTGATCTATGATGACAACAAGAGGCCCTCTGGCATCCCTGAGAGAATCTCTGGCAGCAGCTCTGG
CACCACAGCCACACTGACCATCAGAGATGTCAGAGCTGAGGATGAAGGGGACTACTACTGCTTCTCTGGCTATGTGGACTCTGACAGCAAGCTGTATGTGTTTGGCA
GTGGCACCCAGCTGACAGTGCTTGGAGGACCCAAGAGCAGAACAGTGGCTGCCCCTTCTGTGTTCATCTTCCCACCATCTGATGAGCAGCTGAAGTCTGGCACAGCC
TCTGTTGTGTGCCTGCTGAACAACTTCTACCCTAGAGAAGCCAAGGTGCAGTGGAAGGTGGACAATGCCCTCCAGTCTGGCAACTCCCAAGAGTCTGTGACAGAGCA
GGACAGCAAGGACTCCACCTACAGCCTGAGCAGCACCCTGACACTGAGCAAGGCTGACTATGAGAAGCACAAAGTCTATGCCTGTGAAGTGACCCACCAGGGCCTG
TCTAGCCCTGTGACCAAGAGCTTCAACAGGGGAGAGAGCTGAAGATCTACTTCTGGCTAATAAAAGATCAGAGCTCTAGTGATCTGTGTGTTGGTTTTTTGTGTCTGC
ATTCTAGCATGTTACATAACTTATGGTAAATGGCCTGCCTGGCTGACTGCCCAATGACCCCTGCCCAATGATGTCAATAATGATGTATGTTCCCATGTAATGCCAATAG
GGACTTTCCATTGATGTCAATGGGTGGAGTATTTATGGTAACTGCCCACTTGGCAGTACATCAAGTGTATCATATGCCAAGTATGCCCCCTATTGATGTCAATGATGGT
AAATGGCCTGCCTGGCATTATGCCCAGTACATGACCTTATGGGACTTTCCTACTTGGCAGTACATCTATGTATTAGTCATTGCTATTACCATGGATTAGTGGAGAAGAG
CATGCTTGAGGGCTGAGTGCCCCTCAGTGGGCAGAGAGCACATGGCCCACAGTCCCTGAGAAGTTGGGGGGAGGGGTGGGCAATTGAACTGGTGCCTAGAGAAG
GTGGGGCTTGGGTAAACTGGGAAAGTGATGTGGTGTACTGGCTCCACCTTTTTCCCCAGGGTGGGGGAGAACCATATATAAGTGCAGTAGTCTCTGTGAACATTCAA
GCTTCTGCCTTCTCCCTCCTGTGAGTTTGGATGCACCTACTAGATATCTTGGTAAGTCACTGACTGTCTATGCCTGGGAAAGGGTGGCAGGAGGTGGGGCAGTGCA
GGAAAAGTGGCACTGTGAACCCTGCAGCCCTAGACAATTGTACTAACCTTCTTCTCTTTCCTCTCCTGACAGGTTGGTAACCAAGCCACCATGAGAGTGACAGCCCCT
AGAACAGTCCTGCTGCTCCTGTCTGCTGCCCTGGCTCTGACAGAAACATGGGCTGGCAGCAGCATCATCAACTTTGAGAAGCTGATTGTGGGCATTGTGGCTGGCCT
GGCTGTGCTGGCAGTGGTGGTTATTGGAGCTGTGGTGGCTGCTGTGATGTGCAGAAGAAAGTCCTCTGGAGGCAAAGGTGGCAGCTACTCCCAGGCTGCCTGTTCT
GATTCTGCCCAGGGCTCTGATGTGTCCCTGACAGCTTAAAGATCTACTTCTGGCTAATAAAAGATCAGAGCTCTAGTGATCTGTGTGTTGGTTTTTTGTGTCTGCATTC
TAGCTCTAGTGATCAGCAGTTCAACCTGTTGATAGTATGTACTAAGCTCTCATGTTTAATGTACTAAGCTCTCATGTTTAATGAACTAAACCCTCATGGCTAATGTACTA
AGCTCTCATGGCTAATGTACTAAGCTCTCATGTTTCATGTACTAAGCTCTCATGTTTGAACAATAAAATTAATATAAATCAGCAACTTAAATAGCCTCTAAGGTTTTAAG
TTTTATAAGAAAAAAAAGAATATATAAGGCTTTTAAAGGTTTTAAGGTTTCCTAGGTTATCCTCATATGAGCTCTTAGAAAAACTCATCCAGCATCAAATGAAACTGCA
ATTTATTCATATCAGGATTATCAATACCATATTTTTGAAAAAGTCTTTTCTGTAATGAAGGAGAAAACTCACCCAGGCAGTTCCATAGGATGGCAAGATCCTGGTATCT
GTCTGCAATTCCAACTCTTCCAACATCAATACAACCTATTAATTTCCCCTCATCAAAAATAAGGTTATCAAGTGAGAAATCACCATGAGTGACCACTGAATCTGGTGAG
AATGGCAAAAGATTATGCATTTCTTTCCAGACTTGTTCAACAGGCCAGCCATTTCTCTCATCATCAAAATCACTGGCATCAACCAAACCATTATTCATTCTTGATTGGGC
CTGAGCCAGTCTAAATACTCTATCAGAGTTAAAAGGACAATTACAAACAGGAATGGAATGCAATCTTCTCAGGAACACTGCCAGGGCATCAACAATATTTTCACCTGA
ATCAGGATATTCTTCCAATACCTGGAATGCTGTTTTCCCTGGGATGGCAGTGGTGAGTAACCATGCATCATCAGGAGTTCTGATAAAATGCTTGATGGTTGGAAGAG
GCATAAATTCAGTCAGCCAGTTTAGTCTGACCATCTCATCTGTAACATCATTGGCAACAGAACCTTTGCCATGTTTCAGAAACAACTCTGGGGCATCTGGCTTCCCATA
CAATCTATAGATTGTGGCACCTGATTGCCCAACATTATCTCTAGCCCATTTATACCCATATAAATCAGCATCCATGTTGGAATTTAATCTTGGCCTGGAGCAAGAGGTT
TCTCTTTGAATATGGCTCATACATGTGCACCTCCTATAGTGAGTTGTATTATACTATGCAGATATACTATGCCAATGTTTAATTGTCAG

FIG. 74

DNARx-CD20-2A CAS9: Dual Cassette anti-CD20-2A and CAS9 (SEQ ID NO:53)

DraIIRINhe- ΔmCMV-EF1-I126-BstEII-ΔaCD20H-2A-aCD20L-BglII-polyA- ΔhCMV-hFerH-HTLVBstEII-CAS9-BglII-polyA BV2

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTACATAAGGTCAATAG
GGGGTGAGTCAACAGGAAAGTCCCATTGGAGCCAAGTACATTGAGTCAATAGGGACTTTCCAATGGGTTTTGCCCAGTACATAAGGTCAATGGGAGGTAAGCCAATGGGTTTTTCCCATTA
CTGACATGTATACTGAGTCATTAGGGACTTTCCAATGGGTTTTGCCCAGTACATAAGGTCAATAGGGGTGAATCAACAGGAAAGTCCCATTGGAGCCAAGTACACTGAGTCAATAGGGACT
TTCCATTGGGTTTTGCCCAGTACAAAAGGTCAATAGGGGGTGAGTCAATGGGTTTTTCCCATTATTGGCACATACATAAGGTCAATAGGGGTGACTAGTGGAGAAGAGCATGCTTGAGGGC
TGAGTGCCCCTCAGTGGGCAGAGAGCACATGGCCCACAGTCCCTGAGAAGTTGGGGGGAGGGGTGGGCAATTGAACTGGTGCCTAGAGAAGGTGGGGCTTGGGTAAACTGGGAAAGT
GATGTGGTGTACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCACTG
ACTGTCTATGCCTGGGAAAGGGTGGGCAGGAGATGGGGCAGTGCAGGAAAAGTGGCACTATGAACCCTGCAGCCCTAGACAATTGTACTAACCTTCTTCTCTTTCCTCTCCTGACAGGTT
GGTAACCAAGCCACCATGGGCTGGTCCCTGATCCTGCTGTTCCTGGTGGCTGTGGCCACCAGAGTGCTGAGCCAGGTGCAGCTGCAGCAGCCTGGGGCTGAGCTTGTGAAACCTGGGG
CCTCTGTGAAGATGAGCTGCAAGGCCTCTGGCTACACCTTCACCAGCTACAACATGCACTGGGTCAAGCAGACCCCTGGCAGAGGCCTGGAATGGATTGGAGCCATCTACCCTGGCAAT
GGGGACACCTCCTACAACCAGAAGTTCAAGGGCAAGGCCACCCTGACAGCTGACAAGAGCAGCAGCACAGCCTACATGCAGCTGTCCAGCCTGACCTCTGAGGACTCTGCTGTGTACTA
CTGTGCCAGGTCCACCTACTATGGGGGAGACTGGTACTTCAATGTGTGGGGAGCTGGCACCACAGTGACAGTGTCTGCTGCCAGCACCAAGGGCCCCTCTGTGTTTCCTCTGGCCCCCA
GCAGCAAGAGCACCTCTGGGGGAACAGCTGCCCTGGGCTGCCTTGTGAAGGACTACTTCCCTGAGCCTGTGACTGTGTCCTGGAACTCTGGGGCCCTGACATCTGGGGTGCACACCTTC
CCTGCAGTGCTGCAGTCCAGTGGCCTGTACTCCCTGTCCTCTGTTGTGACAGTGCCCAGCTCCAGCCTGGGCACCCAGACCTACATCTGCAATGTGAACCACAAGCCCAGCAACACCAA
GGTGGACAAGAAGGCTGAGCCCAAGAGCTGTGACAAGACCCACACCTGTCCCCCCTGTCCTGCCCCTGAACTGCTGGGAGGACCTTCTGTGTTCCTGTTCCCACCCAAGCCCAAGGATA
CCCTGATGATCAGCAGAACCCCTGAAGTGACCTGTGTGGTGGTGGATGTGTCCCATGAGGACCCAGAAGTGAAGTTCAATTGGTATGTGGATGGGGTGGAAGTGCACAATGCCAAGACC
AAGCCCAGAGAGGAACAGTACAACAGCACCTACAGAGTGGTGTCTGTGCTGACTGTGCTGCACCAGGACTGGCTGAATGGCAAAGAGTACAAGTGCAAGGTGTCCAACAAGGCCCTGCC
AGCCCCCATTGAGAAAACCATCAGCAAGGCCAAGGGCCAGCCTAGAGAACCCCAGGTGTACACACTGCCCCCTAGCAGGGATGAGCTGACCAAGAACCAGGTGTCCCTGACATGCCTTG
TGAAAGGCTTCTACCCCTCTGACATTGCTGTGGAATGGGAGAGCAATGGACAGCCTGAGAACAACTACAAGACCACCCCCCCTGTGCTGGACTCTGATGGCTCATTCTTCCTGTACAGCA
AGCTGACAGTGGACAAGTCCAGATGGCAGCAGGGCAATGTGTTCAGCTGCTCTGTGATGCATGAGGCCCTGCACAACCACTACACCCAGAAAAGCCTGTCCCTGTCCCCTGGCAAGAGA
GCAAAGAGGGGAAGTGGAGCTACTAACTTCAGCCTGCTGAAGCAGGCTGGAGATGTGGAGGAGAACCCTGGACCTATGGACTTCCAGGTGCAGATCATCAGCTTTCTGCTGATCTCTGC
CTCTGTGATCATGAGCAGAGGCCAGATTGTGCTGAGCCAGAGCCCTGCCATCCTGTCTGCAAGCCCTGGGGAGAAAGTGACCATGACCTGCAGAGCCAGCAGCTCTGTGTCCTACATCC
ACTGGTTCCAGCAGAAGCCTGGCAGCAGCCCCAAGCCTTGGATCTATGCCACCAGCAACCTGGCATCTGGGGTGCCAGTCAGATTCTCTGGCTCTGGATCTGGCACCAGCTACAGCCTG
ACCATCAGCAGAGTGGAAGCTGAGGATGCTGCCACCTACTACTGCCAGCAGTGGACCAGCAATCCCCCCACCTTTGGAGGGGGCACCAAGCTGGAAATCAAGAGAACAGTGGCTGCCC
CCTCTGTGTTCATCTTCCCACCCTCTGATGAGCAGCTGAAGTCTGGAACAGCCTCTGTTGTGTGCCTGCTGAACAACTTCTACCCCAGAGAAGCCAAGGTGCAGTGGAAGGTGGACAATG
CCCTGCAGTCTGGCAACTCCCAGGAATCTGTGACAGAGCAGGACAGCAAGGACTCCACCTACTCCCTGAGCAGCACCCTGACCCTGAGCAAGGCTGACTATGAGAAGCACAAAGTGTAT
GCCTGTGAAGTGACCCACCAGGGCCTGTCCAGCCCTGTGACCAAGAGCTTCAACAGAGGGGAGAGCTGAAGATCTACTTCTGGCTAATAAAAGATCAGAGCTCTAGTGATCTGTGTGTTG
GTTTTTTGTGTCTGCATTCTAGCATGTTACATAACTTATGGTAAATGGCCTGCCTGGCTGACTGCCCAATGACCCCTGCCCAATGATGTCAATAATGATGTATGTTCCCATGTAATGCCAATA
GGGACTTTCCATTGATGTCAATGGGTGGAGTATTTATGGTAACTGCCCACTTGGCAGTACATCAAGTGTATCATATGCCAAGTATGCCCCCTATTGATGTCAATGATGGTAAATGGCCTGCC
TGGCATTATGCCCAGTACATGACCTTATGGGACTTTCCTACTTGGCAGTACATCTATGTATTAGTCATTGCTATTATCTAGCTTCTGCCAGAGTGTGTGAGGGCCTCCAGTGGCTGCCCCTC
CCCCACAGCAGGGGTGGGGTCCTGTGCCCACTGGAAGGAGTGGGCTTGGGGTGGGTGGTGCTGATTGGCTGGGGTGGGCCTGATGCTGATGTGGCTATAAGAGACCACAAGTGACCT
GCAGGGCCAGATGTTCTTTGCTGAAGATGCACCTACTAGATATCCATATGGCTATCATCTCTCCTTCAATATCCATCATCCCTACCTGAGGCATCCATCCAATCATGTTGAGTATATTTCTGC
ATCCTCCATCCTGTGGTGCCTCCTGAACTGATTCATCATTCTAGGTAAGTTTAAAGCTCAGGTATAGACATGGCCTTTGTCATGATCTCCCTTGGAGCCTACCTAGACTCAGCATGCTCTCC
AATCTTTGCCTGACCCTGCTTGCTCAACTCTAATTCTTTGTTTATTTTTCTGTTCTGATCATTTACAGATCCAAGCTGTGACATGATCCTACCATAGGTTGGAGTGTAGGTAACCAAGCCACC
ATGGACTACAAGGACCATGATGGGGATTATAAGGATCATGACATTGATTACAAGGATGATGATGACAAGATGGCCCCTAAGAAGAAGAGGAAAGTTGGCATCCATGGGGTGCCAGCTGCT
GACAAGAAGTACAGCATTGGCCTGGACATTGGCACCAACTCTGTTGGCTGGGCTGTGATCACTGATGAGTACAAGGTGCCCAGCAAGAAGTTCAAGGTCCTGGGCAACACAGACAGGCA
CAGCATCAAGAAGAACCTGATTGGAGCCCTGCTGTTTGACTCTGGGGAGACAGCTGAGGCCACCAGACTGAAGAGAACAGCCAGAAGAAGATACACAAGAAGAAAGAACAGGATCTGCT
ACCTGCAAGAAATCTTCAGCAATGAGATGGCCAAAGTGGATGACAGCTTCTTCCACAGACTGGAAGAGTCCTTCCTGGTGGAAGAGGACAAGAAACATGAGAGACACCCCATCTTTGGCA
ACATTGTGGATGAGGTGGCCTACCATGAGAAGTACCCCACCATCTACCACCTGAGAAAGAAACTGGTGGACAGCACAGACAAGGCTGACCTGAGACTGATCTACCTGGCTCTGGCCCAC
ATGATCAAGTTCAGAGGCCACTTCCTGATTGAAGGGGATCTGAACCCTGACAACTCTGATGTGGACAAGCTGTTTATCCAGCTGGTGCAGACCTACAACCAGCTGTTTGAGGAAAACCCCA
TCAATGCCAGTGGTGTTGATGCCAAGGCCATCCTGTCTGCCAGACTGAGCAAGAGCAGAAGGCTGGAAAATCTGATTGCCCAGCTGCCTGGGGAGAAGAAGAATGGCCTGTTTGGCAAC
CTCATTGCCCTGAGCCTGGGCCTGACACCTAACTTCAAGAGCAACTTTGACCTGGCTGAGGATGCCAAGCTCCAGCTGTCCAAGGACACCTATGATGATGATCTGGACAACCTGCTGGCC
CAGATTGGGGACCAGTATGCTGACCTGTTCCTGGCTGCCAAGAACCTGTCTGATGCCATCCTGCTGTCTGACATCCTGAGAGTGAACACAGAGATCACAAAGGCCCCTCTGTCTGCCTCT
ATGATCAAGAGATATGATGAGCACCACCAGGACCTGACACTGCTGAAGGCTCTTGTTAGACAGCAGCTGCCAGAGAAGTACAAAGAGATTTTCTTTGACCAGAGCAAGAATGGCTATGCT
GGCTACATTGATGGTGGTGCCTCTCAAGAAGAGTTCTACAAGTTCATCAAGCCCATCCTGGAAAAGATGGATGGCACAGAGGAACTGCTGGTCAAGCTGAACAGAGAGGACCTGCTGAGA
AAGCAGAGGACCTTTGACAATGGCAGCATCCCTCACCAGATCCACCTGGGAGAGCTGCATGCTATCCTGAGAAGGCAAGAGGATTTCTACCCATTCCTGAAGGACAACAGAGAGAAGATT
GAGAAGATCCTGACCTTCAGAATCCCCTACTATGTGGGCCCTCTGGCTAGAGGCAACAGCAGATTTGCCTGGATGACCAGAAAGTCTGAGGAAACCATCACACCCTGGAACTTTGAGGAA
GTGGTGGACAAAGGGGCCTCTGCTCAGAGCTTCATTGAGAGAATGACAAACTTTGACAAGAATCTGCCCAATGAGAAGGTGCTGCCCAAGCACAGCCTGCTGTATGAGTACTTCACAGTG
TACAATGAGCTGACAAAAGTGAAATATGTGACAGAGGGAATGAGAAAGCCTGCCTTCCTGTCTGGGGAGCAGAAAAAGGCCATTGTGGACCTGCTTTTCAAGACCAACAGAAAAGTGACA
GTGAAGCAGCTGAAAGAGGACTACTTCAAGAAAATTGAGTGCTTTGATTCTGTGGAAATCTCTGGTGTTGAGGACAGGTTCAATGCCTCTCTGGGCACATACCATGACCTGCTCAAGATTA
TCAAGGACAAGGACTTCCTGGACAATGAGGAAAATGAGGACATCCTTGAGGACATTGTGCTGACACTGACCCTGTTTGAAGATAGGGGAAATGATTGAGGAAAGGCTCAAGACATATGCCC
ACCTGTTTGATGACAAAGTGATGAAGCAACTCAAGAGAAGAAGATATACAGGCTGGGGCAGACTGTCCAGAAAGCTGATCAATGGAATCAGGGACAAGCAGAGTGGCAAGACAATCCTGG
ATTTCCTGAAGTCTGATGGCTTTGCCAATAGGAACTTCATGCAGCTCATCCATGATGACAGCCTCACCTTCAAAGAGGACATTCAGAAGGCCCAAGTCTCTGGCCAAGGGGACAGCCTGC
ATGAGCACATTGCTAACCTGGCTGGCAGCCCTGCTATCAAGAAGGGCATCCTCCAGACTGTGAAGGTGGTGGATGAGCTTGTGAAAGTGATGGGCAGACACAAGCCTGAGAACATTGTG
ATTGAGATGGCTAGAGAGAACCAGACCACACAGAAGGGACAGAAGAACAGCAGAGAAAGGATGAAGAGGATTGAAGAGGGCATCAAAGAGCTGGGCAGCCAGATCCTGAAAGAGCACC
CTGTTGAGAACACCCAGCTCCAGAATGAGAAGCTGTACCTGTACTACTTGCAGAATGGCAGGGATATGTATGTGGACCAAGAGCTGGACATCAACAGACTGTCTGACTATGATGTGGATC
ATATTGTGCCCCAGAGCTTTCTGAAGGATGACTCCATTGACAACAAGGTGCTGACTAGGAGTGACAAGAACAGGGGCAAGTCTGACAATGTGCCCTCTGAAGAGGTGGTCAAGAAGATGA
AGAACTATTGGAGGCAGCTCCTGAATGCCAAACTGATCACCCAGAGGAAGTTTGACAACCTGACCAAGGCTGAGAGAGGTGGACTCTCTGAACTGGATAAGGCTGGCTTCATCAAGAGGC
AGCTTGTGGAAACCAGACAGATCACCAAACATGTGGCTCAGATCCTGGACAGCAGAATGAACACTAAGTATGATGAGAATGATAAGCTCATCAGGGAAGTGAAAGTCATCACCCTGAAGTC
CAAGCTGGTGTCTGACTTTAGGAAAGACTTCCAGTTTTACAAAGTCAGAGAGATCAACAACTACCACCATGCTCATGATGCCTACCTGAATGCTGTTGTGGGCACAGCCCTGATCAAAAAG
TACCCTAAGCTGGAATCTGAGTTTGTGTATGGGGACTACAAAGTGTATGATGTCAGAAAGATGATTGCCAAGTCTGAACAAGAGATTGGCAAGGCTACAGCCAAGTACTTCTTCTACAGCA
ACATCATGAATTTCTTCAAGACTGAGATCACCCTGGCTAATGGGGAGATCAGAAAGAGGCCACTGATTGAGACAAATGGAGAGACTGGGGAGATTGTGTGGGACAAGGGCAGAGACTTTG
CCACAGTCAGAAAGGTGCTGTCTATGCCCCAAGTGAACATTGTCAAGAAAACAGAGGTGCAGACTGGTGGCTTCTCCAAAGAGAGCATCCTGCCTAAGAGGAACAGTGACAAGCTGATTG
CCAGAAAGAAGGACTGGGACCCCAAGAAGTATGGAGGCTTTGACAGCCCCACAGTGGCCTACTCTGTGCTGGTGGTGGCCAAGGTGGAAAAGGGCAAGAGCAAAAAGCTCAAGAGTGT
GAAAGAGCTGCTGGGCATCACCATCATGGAAAGGTCCAGCTTTGAGAAGAACCCTATTGACTTCCTTGAGGCCAAGGGCTACAAAGAAGTGAAAAAGGACCTGATCATCAAGCTCCCCAA
GTACTCTCTGTTTGAACTGGAAAATGGGAGAAAGAGGATGCTGGCTTCTGCTGGGGAACTCCAGAAAGGCAATGAACTGGCCCTGCCTAGCAAATATGTCAACTTCCTGTACCTGGCCAG
CCACTATGAGAAACTGAAGGGCAGCCCAGAGGATAATGAGCAAAAGCAGCTTTTTGTGGAACAGCACAAGCACTACCTGGATGAGATCATTGAGCAAATCTCTGAGTTCAGCAAGAGGGT
CATCCTGGCAGATGCCAACCTGGACAAAGTGCTGAGTGCCTACAACAAGCACAGGGACAAACCCATCAGAGAGCAGGCAGAGAACATCATCCACCTGTTCACCCTGACCAACCTGGGAG
CCCCTGCTGCCTTCAAGTACTTTGACACCACCATTGATAGGAAGAGGTACACCAGCACCAAAGAGGTCCTGGATGCTACCCTGATCCACCAGAGCATCACTGGCCTGTATGAGACAAGAA
TTGACCTGTCTCAGCTTGGAGGGGACAAGAGGCCTGCTGCCACAAAGAAAGCAGGCCAGGCCAAAAAGAAGAAGTGAAGATCTACTTCTGGCTAATAAAAGATCAGAGCTCTAGTGATCT
GTGTGTTGGTTTTTTGTGTCTGCATTCTAGCTCTAGTGATCAGCAGTTCAACCTGTTGATAGTATGTACTAAGCTCTCATGTTTAATGTACTAAGCTCTCATGTTTAATGAACTAAACCCTCAT
GGCTAATGTACTAAGCTCTCATGGCTAATGTACTAAGCTCTCATGTTTCATGTACTAAGCTCTCATGTTTGAACAATAAAATTAATATAAATCAGCAACTTAAATAGCCTCTAAGGTTTTAAGT
TTTATAAGAAAAAAAAGAATATATAAGGCTTTTAAAGCTTTTAAGGTTTCCTAGGTTATCCTCATATGAGCTCTTAGAAAAACTCATCCAGCATCAAATGAAACTGCAATTTATTCATATCAGG
ATTATCAATACCATATTTTTGAAAAAGTCTTTTCTGTAATGAAGGAGAAAACTCACCCAGGCAGTTCCATAGGATGGCAAGATCCTGGTATCTGTCTGCAATTCCAACTCTTCCAACATCAAT
ACAACCTATTAATTTCCCCTCATCAAAAATAAGGTTATCAAGTGAGAAATCACCATGAGTGACGACTGAATCTGGTGAGAATGGCAAAAGATTATGCATTTCTTTCCAGACTTGTTCAACAGG
CCAGCCATTTCTCTCATCATCAAAATCACTGGCATCAACCAAACCATTATTCATTCTTGATTGGGCCTGAGCCAGTCTAAATACTCTATCAGAGTTAAAAGGACAATTACAAACAGGAATGGA
ATGCAATCTTCTCAGGAACACTGCCAGGGCATCAACAATATTTTCACCTGAATCAGGATATTCTTCCAATACCTGGAATGCTGTTTTCCCTGGGATGGCAGTGGTGAGTAACCATGCATCAT
CAGGAGTTCTGATAAAATGCTTGATGGTTGGAAGAGGCATAAATTCAGTCAGCCAGTTTAGTCTGACCATCTCATCTGTAACATCATTGGCAACAGAACCTTTGCCATGTTTCAGAAACAAC
TCTGGGGCATCTGGCTTCCCATACAATCTATAGATTGTGGCACCTGATTGCCCAACATTATCTCTAGCCCATTTATACCCATATAAATCAGCATCCATGTTGGAATTTAATCTTGGCCTGGAG
CAAGAGGTTTCTCTTTGAATATGGCTCATAACATGTGCACCTCCTATAGTGAGTTGTATTATACTATGCAGATATACTATGCCAATGTTTAATTGTCAG

FIG. 75

DNARx-CD20-2A HG-CSF: Dual Cassette anti-CD20-2A and HG-CSF (SEQ ID NO:54)

DraIIRINhe- ΔmCMV-EF1-I126-BstEII-ΔaCD20H-2A-aCD20L-BglII-polyA- ΔhCMV-hFerH-HTLVBstEII-HG-CSF-BglII-polyA BV2

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGG
GCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCA
CCATGGGCTGGTCCCTGATCCTGCTGTTCCTGGTGGCTGTGGCCACCAGAGTGCTGAGCCAGGTGCAGCTGCAGCAGCCTGGGGCTGAGCTTGTGAAACCTGGGGC
CTCTGTGAAGATGAGCTGCAAGGCCTCTGGCTACACCTTCACCAGCTACAACATGCACTGGGTCAAGCAGACCCCTGGCAGAGGCCTGGAATGGATTGGAGCCATCT
ACCCTGGCAATGGGGACACCTCCTACAACCAGAAGTTCAAGGGCAAGGCCACCCTGACAGCTGACAAGAGCAGCAGCACAGCCTACATGCAGCTGTCCAGCCTGAC
CTCTGAGGACTCTGCTGTGTACTACTGTGCCAGGTCCACCTACTATGGGGGAGACTGGTACTTCAATGTGTGGGGAGCTGGCACCACAGTGACAGTGTCTGCTGCCA
GCACCAAGGGCCCCTCTGTGTTTCCTCTGGCCCCCAGCAGCAAGAGCACCTCTGGGGGAACAGCTGCCCTGGGCTGCCTTGTGAAGGACTACTTCCCTGAGCCTGTG
ACTGTGTCCTGGAACTCTGGGGCCCTGACATCTGGGGTGCACACCTTCCCTGCAGTGCTGCAGTCCAGTGGCCTGTACTCCCTGTCCTCTGTTGTGACAGTGCCCAGC
TCCAGCCTGGGCACCCAGACCTACATCTGCAATGTGAACCACAAGCCCAGCAACACCAAGGTGGACAAGAAGGCTGAGCCCAAGAGCTGTGACAAGACCCACACCT
GTCCCCCCTGTCCTGCCCCTGAACTGCTGGGAGGACCTTCTGTGTTCCTGTTCCCACCCAAGCCCAAGGATACCCTGATGATCAGCAGAACCCCTGAAGTGACCTGTG
TGGTGGTGGATGTGTCCCATGAGGACCCAGAAGTGAAGTTCAATTGGTATGTGGATGGGGTGGAAGTGCACAATGCCAAGACCAAGCCCAGAGAGGAACAGTACA
ACAGCACCTACAGAGTGGTGTCTGTGCTGACTGTGCTGCACCAGGACTGGCTGAATGGCAAAGAGTACAAGTGCAAGGTGTCCAACAAGGCCCTGCCAGCCCCCATT
GAGAAAACCATCAGCAAGGCCAAGGGCCAGCCTAGAGAACCCCAGGTGTACACACTGCCCCCTAGCAGGGATGAGCTGACCAAGAACCAGGTGTCCCTGACATGCC
TTGTGAAAGGCTTCTACCCCTCTGACATTGCTGTGGAATGGGAGAGCAATGGACAGCCTGAGAACAACTACAAGACCACCCCCCCTGTGCTGGACTCTGATGGCTCA
TTCTTCCTGTACAGCAAGCTGACAGTGGACAAGTCCAGATGGCAGCAGGGCAATGTGTTCAGCTGCTCTGTGATGCATGAGGCCCTGCACAACCACTACACCCAGAA
AAGCCTGTCCCTGTCCCCTGGCAAG*AGAGCAAAGAGGGGAAGTGGAGCTACTAACTTCAGCCTGCTGAAGCAGGCTGGAGATGTGGAGGAGAACCCTGGACCT*ATG
GACTTCCAGGTGCAGATCATCAGCTTTCTGCTGATCTCTGCCTCTGTGATCATGAGCAGAGGCCAGATTGTGCTGAGCCAGAGCCCTGCCATCCTGTCTGCAAGCCCT
GGGGAGAAAGTGACCATGACCTGCAGAGCCAGCAGCTCTGTGTCCTACATCCACTGGTTCCAGCAGAAGCCTGGCAGCAGCCCCAAGCCTTGGATCTATGCCACCAG
CAACCTGGCATCTGGGGTGCCAGTCAGATTCTCTGGCTCTGGATCTGGCACCAGCTACAGCCTGACCATCAGCAGAGTGGAAGCTGAGGATGCTGCCACCTACTACT
GCCAGCAGTGGACCAGCAATCCCCCCACCTTTGGAGGGGGCACCAAGCTGGAAATCAAGAGAACAGTGGCTGCCCCCTCTGTGTTCATCTTCCCACCCTCTGATGAG
CAGCTGAAGTCTGGAACAGCCTCTGTTGTGTGCCTGCTGAACAACTTCTACCCCAGAGAAGCCAAGGTGCAGTGGAAGGTGGACAATGCCCTGCAGTCTGGCAACTC
CCAGGAATCTGTGACAGAGCAGGACAGCAAGGACTCCACCTACTCCCTGAGCAGCACCCTGACCCTGAGCAAGGCTGACTATGAGAAGCACAAAGTGTATGCCTGT
GAAGTGACCCACCAGGGCCTGTCCAGCCCTGTGACCAAGAGCTTCAACAGAGGGGAGAGCTGAAGATCTACTTCTGGCTAATAAAAGATCAGAGCTCTAGTGATCT
GTGTGTTGGTTTTTTGTGTCTGCATTCTAGCATGTTACATAACTTATGGTAAATGGCCTGCCTGGCTGACTGCCCAATGACCCCTGCCCAATGATGTCAATAATGATGT
ATGTTCCCATGTAATGCCAATAGGGACTTTCCATTGATGTCAATGGGTGGAGTATTTATGGTAACTGCCCACTTGGCAGTACATCAAGTGTATCATATGCCAAGTATG
CCCCCTATTGATGTCAATGATGGTAAATGGCCTGCCTGGCATTATGCCCAGTACATGACCTTATGGGACTTTCCTACTTGGCAGTACATCTATGTATTAGTCATTGCTAT
TATCTAGCTTCTGCCAGAGTGTGTGAGGGCCTCCAGTGGCTGCCCCTCCCCCACAGCAGGGGTGGGGTCCTGTGCCCACTGGAAGGAGTGGGCTTGGGGTGGGTGG
TGCTGATTGGCTGGGGTGGGCCTGATGCTGATGTGGCTATAAGAGACCACAAGTGACCTGCAGGGCCAGATGTTCTTTGCTGAAGATGCACCTACTAGATATCCATA
TGGCTATCATCTCTCCTTCAATATCCATCATCCCTACCTGAGGCATCCATCCAATCATGTTGAGTATATTTCTGCATCCTCCATCCTGTGGTGCCTCCTGAACTGATTCAT
CATTCTAGGTAAGTTTAAAGCTCAGGTATAGACATGGCCTTTGTCATGATCTCCCTTGGAGCCTACCTAGACTCAGCATGCTCTCCAATCTTTGCCTGACCCTGCTTGCT
CAACTCTAATTCTTTGTTTATTTTTCTGTTCTGATCATTTACAGATCCAAGCTGTGACATGATCCTACCATAGGTTGGAGTGTAGGTAACCAAGCTTTCCATGGCTGGAC
CTGCCACCCAGAGCCCCATGAAGCTGATGGCCCTGCAGCTGCTGCTGTGGCACAGTGCACTCTGGACAGTGCAGGAAGCCACCCCCCTGGGCCCTGCCAGCTCCCTG
CCCCAGAGCTTCCTGCTCAAGTGCTTAGAGCAAGTGAGGAAGATCCAGGGGGATGGGGCAGCTCTCCAGGAGAAGCTGTGTGCCACCTACAAGCTGTGCCACCCTG
AGGAGCTGGTGCTGCTGGGACACTCTCTGGGCATCCCCTGGGCTCCCCTGAGCAGCTGCCCCAGCCAGGCCCTGCAGCTGGCAGGCTGCTTGAGCCAACTCCATAGT
GGCCTTTTCCTCTACCAGGGGCTCCTGCAGGCCCTGGAAGGGATCTCCCCTGAGTTGGGTCCCACCTTGGACACACTGCAGCTGGATGTTGCTGACTTTGCCACCACC
ATCTGGCAGCAGATGGAAGAACTGGGAATGGCCCCTGCCCTGCAGCCCACCCAGGGTGCCATGCCTGCCTTTGCCTCTGCTTTCCAGAGAAGGGCAGGAGGGGTCC
TGGTTGCCTCCCATCTGCAGAGCTTCCTGGAGGTGTCCTACAGAGTTCTAAGACACCTTGCCCAGCCCTGATAGATCTACTTCTGGCTAATAAAAGATCAGAGCTCTA
GTGATCTGTGTGTTGGTTTTTTGTGTCTGCATTCTAGCTCTAGTGATCAGCAGTTCAACCTGTTGATAGTATGTACTAAGCTCTCATGTTTAATGTACTAAGCTCTCATG
TTTAATGAACTAAACCCTCATGGCTAATGTACTAAGCTCTCATGGCTAATGTACTAAGCTCTCATGTTTCATGTACTAAGCTCTCATGTTTGAACAATAAAATTAATATA
AATCAGCAACTTAAATAGCCTCTAAGGTTTTAAGTTTTATAAGAAAAAAAAGAATATATAAGGCTTTTAAAGGTTTTAAGGTTTCCTAGGTTATCCTCATATGAGCTCT
TAGAAAAACTCATCCAGCATCAAATGAAACTGCAATTTATTCATATCAGGATTATCAATACCATATTTTTGAAAAAGTCTTTTCTGTAATGAAGGAGAAAACTCACCCA
GGCAGTTCCATAGGATGGCAAGATCCTGGTATCTGTCTGCAATTCCAACTCTTCCAACATCAATACAACCTATTAATTTCCCCTCATCAAAAATAAGGTTATCAAGTGA
GAAATCACCATGAGTGACCACTGAATCTGGTGAGAATGGCAAAAGATTATGCATTTCTTTCCAGACTTGTTCAACAGGCCAGCCATTTCTCTCATCATCAAAATCACTG
GCATCAACCAAACCATTATTCATTCTTGATTGGGCCTGAGCCAGTCTAAATACTCTATCAGAGTTAAAAGGACAATTACAAACAGGAATGGAATGCAATCTTCTCAGG
AACACTGCCAGGGCATCAACAATATTTTCACCTGAATCAGGATATTCTTCCAATACCTGGAATGCTGTTTTCCCTGGGATGGCAGTGGTGAGTAACCATGCATCATCA
GGAGTTCTGATAAAATGCTTGATGGTTGGAAGAGGCATAAATTCAGTCAGCCAGTTTAGTCTGACCATCTCATCTGTAACATCATTGGCAACAGAACCTTTGCCATGT
TTCAGAAACAACTCTGGGGCATCTGGCTTCCCATACAATCTATAGATTGTGGCACCTGATTGCCCAACATTATCTCTAGCCCATTTATACCCATATAAATCAGCATCCAT
GTTGGAATTTAATCTTGGCCTGGAGCAAGAGGTTTCTCTTTGAATATGGCTCATACATGTGCACCTCCTATAGTGAGTTGTATTATACTATGCAGATATACTATGCCAA
TGTTTAATTGTCAG

FIG. 76 p65 shA2: NheΔhCMVΔhCMVRVp65 shA2-TTTTT-XbaI-HindIII-Amp
(SEQ ID NO:55)

GAATTCTCATAGCTAGCATGTTACATAACTTATGGTAAATGGCCTGCCTGGCTGACTGCCCAATGACCCCTGCCCAATGATGTCAATAATGATGTATGTTCCCATGT
AATGCCAATAGGGACTTTCCATTGATGTCAATGGGTGGAGTATTTATGGTAACTGCCCACTTGGCAGTACATCAAGTGTATCATATGCCAAGTATGCCCCCTATTG
ATGTCAATGATGGTAAATGGCCTGCCTGGCATTATGCCCAGTACATGACCTTATGGGACTTTCCTACTTGGCAGTACATCTATGTATTAGTCATTGCTATTACCATG
GTGATGGGTTTTGGCAGTACATCAATGGGTGTGGATAGTGGTTTGACCCATGGGGATTTCCAAGTCTCCACCCCATTGATGCCAATGGGAGTTTGTTTTGGCACCAAA
ATCAATGGGACTTTCCAAAATGTTGTAACAACTCTGCCCCATTGATGGAAATGGGTGGTAGGTGTGTGTGGTGGGAGGTCTATATAAGCAGAGCTTGTTTAGTGAAC
TGGATGCACCTACTAGATATCAGACATTGAGGTGTATTTCACTCAAGAGGTGAAATACACCTCAATGTCTTTTTTTTCTAGATACTAAGCTTGGCGTAA
TCATGGTCATAGCTGTTTCCTGTGTGAAATTGTTATCCGCTCACAATTCCACACAACATACGAGCCGGAAGCATAAAGTGTAAAGCCTGGGGTGCCTAATGAGTGAGC
TAACTCACATTAATTGCGTTGCGCTCACTGCCCGCTTTCCAGTCGGGAAACCTGTCGTGCCAGCTGCATTAATGAATCGGCCAACGCGCGGGGAGAGGCGGTTTGCG
TATTGGGCGCTCTTCCGCTTCCTCGCTCACTGACTCGCTGCGCTCGGTCGTTCGGCTGCGGCGAGCGGTATCAGCTCACTCAAAGGCGGTAATACGGTTATCCACAGA
ATCAGGGGATAACGCAGGAAAGAACATGTGAGCAAAAGGCCAGCAAAAGGCCAGGAACCGTAAAAAGGCCGCGTTGCTGGCGTTTTTCCATAGGCTCCGCCCCCCT
GACGAGCATCACAAAAATCGACGCTCAAGTCAGAGGTGGCGAAACCCGACAGGACTATAAAGATACCAGGCGTTTCCCCCTGGAAGCTCCCTCGTGCGCTCTCCTGT
TCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTGAAGTGGTGGCCTAACTACGGCTACACTAGAAGAACAGTATTTG
GTATCTGCGCTCTGCTGAAGCCAGTTACCTTCGGAAAAAGAGTTGGTAGCTCTTGATCCGGCAAACAAACCACCGCTGGTAGCGGTGGTTTTTTTGTTTGCAAGCAGC
AGATTACGCGCAGAAAAAAAGGATCTCAAGAAGATCCTTTGATCTTTTCTACGGGGTCTGACGCTCAGTGGAACGAAAACTCACGTTAAGGGATTTTGGTCATGAGA
TTATCAAAAAGGATCTTCACCTAGATCCTTTTAAATTAAAAATGAAGTTTTAAATCAATCTAAAGTATATATGAGTAAACTTGGTCTGACAGTTACCAATGCTTAATCAG
TGAGGCACCTATCTCAGCGATCTGTCTATTTCGTTCATCCATAGTTGCCTGACTCCCCGTCGTGTAGATAACTACGATACGGGAGGGCTTACCATCTGGCCCCAGTGCT
GCAATGATACCGCGAGACCCACGCTCACCGGCTCCAGATTTATCAGCAATAAACCAGCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGTTAATAGTTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTACATGATCCCCCATGTTGTGCAAAAAAGCGGTTAGCTCCTTCGGTCCTCCGATCGTTGTC
AGAAGTAAGTTGGCCGCAGTGTTATCACTCATGGTTATGGCAGCACTGCATAATTCTCTTACTGTCATGCCATCCGTAAGATGCTTTTCTGTGACTGGTGAGTACTCAA
CCAAGTCATTCTGAGAATAGTGTATGCGGCGACCGAGTTGCTCTTGCCCGGCGTCAATACGGGATAATACCGCGCCACATAGCAGAACTTTAAAAGTGCTCATCATTG
GAAAACGTTCTTCGGGGCGAAAACTCTCAAGGATCTTACCGCTGTTGAGATCCAGTTCGATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGGGAATAAGGGCGACACGGAAATGTTGAATACTCATACTCTTCCTTTTTCAATATTATT
GAAGCATTTATCAGGGTTATTGTCTCATGAGCGGATACATATTTGAATGTATTTAGAAAAATAAACAAATAGGGGTTCCGCGCACATTTCCCCGAAAAGTGCCACCTG
ACGTCTAAGAAACCATTATTATCATGACATTAACCTATAAAAATAGGCGTATCACGAGGCCCTTTCGTCTCGCGCGTTTCGGTGATGACGGTGAAAACCTCTGACACA
TGCAGCTCCCGGAGACGGTCACAGCTTGTCTGTAAGCGGATGCCGGGAGCAGACAAGCCCGTCAGGGCGCGTCAGCGGGTGTTGGCGGGTGTCGGGGCTGGCTTA
ACTATGCGGCATCAGAGCAGATTGTACTGAGAGTGCACCATATGCGGTGTGAAATACCGCACAGATGCGTAAGGAGAAAATACCGCATCAGGCGCCATTCGCCATTC
AGGCTGCGCAACTGTTGGGAAGGGCGATCGGTGCGGGCCTCTTCGCTATTACGCCAGCTGGCGAAAGGGGGATGTGCTGCAAGGCGATTAAGTTGGGTAACGCCA
GGGTTTTCCCAGTCACGACGTTGTAAAACGACGGCCAGT

FIG. 77

PECAM shControl: NheΔhCMVΔhCMVRVD3PECAM sh-TTTTT-XbaI-HindIII-Amp
(SEQ ID NO:56)

GAATTCTCATAGCTAGCATGTTACATAACTTATGGTAAATGGCCTGCCTGGCTGACTGCCCAATGACCCCTGCCCAATGATGTCAATAATGATGTATGTTCCCATGT
AATGCCAATAGGGACTTTCCATTGATGTCAATGGGTGGAGTATTTATGGTAACTGCCCACTTGGCAGTACATCAAGTGTATCATATGCCAAGTATGCCCCCTATTG
ATGTCAATGATGGTAAATGGCCTGCCTGGCATTATGCCCAGTACATGACCTTATGGGACTTTCCTACTTGGCAGTACATCTATGTATTAGTCATTGCTATTACCATG
GTGATGGGTTTTGGCAGTACATCAATGGGTGTGGATAGTGGTTTGACCCATGGGGATTTCCAAGTCTCCACCCCATTGATGCCAATGGGAGTTTGTTTTGGCACCAAA
ATCAATGGGACTTTCCAAAATGTTGTAACAACTCTGCCCCATTGATGGAAATGGGTGGTAGGTGTGTGTGGTGGGAGGTCTATATAAGCAGAGCTTGTTTAGTGAAC
TGGATGCACCTACTAGATATCCCTTAATAGTTGCAGCCAAATCCTTCCTGTCAGATTTGGCTGCAACTATTAAGGTTTTTTCTAGATACTAAGC
TTGGCGTAATCATGGTCATAGCTGTTTCCTGTGTGAAATTGTTATCCGCTCACAATTCCACACAACATACGAGCCGGAAGCATAAAGTGTAAAGCCTGGGGTGCCTAA
TGAGTGAGCTAACTCACATTAATTGCGTTGCGCTCACTGCCCGCTTTCCAGTCGGGAAACCTGTCGTGCCAGCTGCATTAATGAATCGGCCAACGCGCGGGGAGAGG
CGGTTTGCGTATTGGGCGCTCTTCCGCTTCCTCGCTCACTGACTCGCTGCGCTCGGTCGTTCGGCTGCGGCGAGCGGTATCAGCTCACTCAAAGGCGGTAATACGGTT
ATCCACAGAATCAGGGGATAACGCAGGAAAGAACATGTGAGCAAAAGGCCAGCAAAAGGCCAGGAACCGTAAAAAGGCCGCGTTGCTGGCGTTTTTCCATAGGCT
CCGCCCCCCTGACGAGCATCACAAAAATCGACGCTCAAGTCAGAGGTGGCGAAACCCGACAGGACTATAAAGATACCAGGCGTTTCCCCCTGGAAGCTCCCTCGTGC
GCTCTCCTGTTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGACACGACTT
ATCGCCACTGGCAGCAGCCACTGGTAACAGGATTAGCAGAGCGAGGTATGTAGGCGGTGCTACAGAGTTCTTGAAGTGGTGGCCTAACTACGGCTACACTAGAAGA
ACAGTATTTGGTATCTGCGCTCTGCTGAAGCCAGTTACCTTCGGAAAAAGAGTTGGTAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTTGATCTTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGAAGTTTTAAATCAATCTAAAGTATATATGAGTAAACTTGGTCTGACAGTTACCAA
TGCTTAATCAGTGAGGCACCTATCTCAGCGATCTGTCTATTTCGTTCATCCATAGTTGCCTGACTCCCCGTCGTGTAGATAACTACGATACGGGAGGGCTTACCATCTG
GCCCCAGTGCTGCAATGATACCGCGAGACCCACGCTCACCGGCTCCAGATTTATCAGCAATAAACCAGCCAGCCGGAAGGGCCGAGCGCAGAAGTGGTCCTGCAAC
TTTATCCGCCTCCATCCAGTCTATTAATTGTTGCCGGGAAGCTAGAGTAAGTAGTTCGCCAGTTAATAGTTTGCGCAACGTTGTTGCCATTGCTACAGGCATCGTGGTG
TCACGCTCGTCGTTTGGTATGGCTTCATTCAGCTCCGGTTCCCAACGATCAAGGCGAGTTACATGATCCCCCATGTTGTGCAAAAAAGCGGTTAGCTCCTTCGGTCCTC
CGATCGTTGTCAGAAGTAAGTTGGCCGCAGTGTTATCACTCATGGTTATGGCAGCACTGCATAATTCTCTTACTGTCATGCCATCCGTAAGATGCTTTTCTGTGACTGG
TGAGTACTCAACCAAGTCATTCTGAGAATAGTGTATGCGGCGACCGAGTTGCTCTTGCCCGGCGTCAATACGGGATAATACCGCGCCACATAGCAGAACTTTAAAAG
TGCTCATCATTGGAAAACGTTCTTCGGGGCGAAAACTCTCAAGGATCTTACCGCTGTTGAGATCCAGTTCGATGTAACCCACTCGTGCACCCAACTGATCTTCAGCATC
TTTTACTTTCACCAGCGTTTCTGGGTGAGCAAAAACAGGAAGGCAAAATGCCGCAAAAAAGGGAATAAGGGCGACACGGAAATGTTGAATACTCATACTCTTCCTTT
TTCAATATTATTGAAGCATTTATCAGGGTTATTGTCTCATGAGCGGATACATATTTGAATGTATTTAGAAAAATAAACAAATAGGGGTTCCGCGCACATTTCCCCGAAA
AGTGCCACCTGACGTCTAAGAAACCATTATTATCATGACATTAACCTATAAAAATAGGCGTATCACGAGGCCCTTTCGTCTCGCGCGTTTCGGTGATGACGGTGAAAA
CCTCTGACACATGCAGCTCCCGGAGACGGTCACAGCTTGTCTGTAAGCGGATGCCGGGAGCAGACAAGCCCGTCAGGGCGCGTCAGCGGGTGTTGGCGGGTGTCG
GGGCTGGCTTAACTATGCGGCATCAGAGCAGATTGTACTGAGAGTGCACCATATGCGGTGTGAAATACCGCACAGATGCGTAAGGAGAAAATACCGCATCAGGCGC
CATTCGCCATTCAGGCTGCGCAACTGTTGGGAAGGGCGATCGGTGCGGGCCTCTTCGCTATTACGCCAGCTGGCGAAAGGGGGATGTGCTGCAAGGCGATTAAGTT
GGGTAACGCCAGGGTTTTCCCAGTCACGACGTTGTAAAACGACGGCCAGT

FIG. 79

020117 # 5 : RINhe-ΔmCMVΔEFI126-BstEII-spCas9-BglII-MixpA-U6- rel 1-gRNA scaffold-TTTTTT-extra bases-BV2 (SEQ ID NO:57)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTACATAAGGTCAATAG
GGGGTGAGTCAACAGGAAAGTCCCATTGGAGCCAAGTACATTGAGTCAATAGGGACTTTCCAATGGGTTTTGCCCAGTACATAAGGTCAATGGGAGGTAAGCCAATGGGTTTTTCCCATTA
CTGACATGTATACTGAGTCATTAGGGACTTTCCAATGGGTTTTGCCCAGTACATAAGGTCAATAGGGGTGAATCAACAGGAAAGTCCCATTGGAGCCAAGTACACTGAGTCAATAGGGACT
TTCCATTGGGTTTTGCCCAGTACAAAAGGTCAATAGGGGGTGAGTCAATGGGTTTTTCCCATTATTGGCACATACATAAGGTCAATAGGGGTGACTAGTGGAGAAGAGCATGCTTGAGGGC
TGAGTGCCCCTCAGTGGGCAGAGAGCACATGGCCCACAGTCCCTGAGAAGTTGGGGGGAGGGGTGGGCAATTGAACTGGTGCCTAGAGAAGGTGGGGCTTGGGTAAACTGGGAAAGT
GATGTGGTGTACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCACTG
ACTGTCTATGCCTGGGAAAGGGTGGGCAGGAGATGGGGCAGTGCAGGAAAAGTGGCACTATGAACCCTGCAGCCCTAGACAATTGTACTAACCTTCTTCTCTTTCCTCTCCTGACAGGTT
GGTAACCAAGCCACCATGGACTACAAGGACCATGATGGGGATTATAAGGATCATGACATTGATTACAAGGATGATGATGACAAGATGGCCCCTAAGAAGAAGAGGAAAGTTGGCATCCAT
GGGGTGCCAGCTGCTGACAAGAAGTACAGCATTGGCCTGGACATTGGCACCAACTCTGTTGGCTGGGCTGTGATCACTGATGAGTACAAGGTGCCCAGCAAGAAGTTCAAGGTCCTGGG
CAACACAGACAGGCACAGCATCAAGAAGAACCTGATTGGAGCCCTGCTGTTTGACTCTGGGGAGACAGCTGAGGCCACCAGACTGAAGAGAACAGCCAGAAGAAGATACACAAGAAGAA
AGAACAGGATCTGCTACCTGCAAGAAATCTTCAGCAATGAGATGGCCAAAGTGGATGACAGCTTCTTCCACAGACTGGAAGAGTCCTTCCTGGTGGAAGAGGACAAGAAACATGAGAGAC
ACCCCATCTTTGGCAACATTGTGGATGAGGTGGCCTACCATGAGAAGTACCCCACCATCTACCACCTGAGAAAGAAACTGGTGGACAGCACAGACAAGGCTGACCTGAGACTGATCTACC
TGGCTCTGGCCCACATGATCAAGTTCAGAGGCCACTTCCTGATTGAAGGGGATCTGAACCCTGACAACTCTGATGTGGACAAGCTGTTTATCCAGCTGGTGCAGACCTACAACCAGCTGT
TTGAGGAAAACCCCATCAATGCCAGTGGTGTTGATGCCAAGGCCATCCTGTCTGCCAGACTGAGCAAGAGCAGAAGGCTGGAAAATCTGATTGCCCAGCTGCCTGGGGAGAAGAAGAAT
GGCCTGTTTGGCAACCTCATTGCCCTGAGCCTGGGCCTGACACCTAACTTCAAGAGCAACTTTGACCTGGCTGAGGATGCCAAGCTCCAGCTGTCCAAGGACACCTATGATGATGATCTG
GACAACCTGCTGGCCCAGATTGGGGACCAGTATGCTGACCTGTTCCTGGCTGCCAAGAACCTGTCTGATGCCATCCTGCTGTCTGACATCCTGAGAGTGAACACAGAGATCACAAAGGCC
CCTCTGTCTGCCTCTATGATCAAGAGATATGATGAGCACCACCAGGACCTGACACTGCTGAAGGCTCTTGTTAGACAGCAGCTGCCAGAGAAGTACAAAGAGATTTTCTTTGACCAGAGCA
AGAATGGCTATGCTGGCTACATTGATGGTGGTGCCTCTCAAGAAGAGTTCTACAAGTTCATCAAGCCCATCCTGGAAAAGATGGATGGCACAGAGGAACTGCTGGTCAAGCTGAACAGAG
AGGACCTGCTGAGAAAGCAGAGGACCTTTGACAATGGCAGCATCCCTCACCAGATCCACCTGGGAGAGCTGCATGCTATCCTGAGAAGGCAAGAGGATTTCTACCCATTCCTGAAGGACA
ACAGAGAGAAGATTGAGAAGATCCTGACCTTCAGAATCCCCTACTATGTGGGCCCTCTGGCTAGAGGCAACAGCAGATTTGCCTGGATGACCAGAAAGTCTGAGGAAACCATCACACCCT
GGAACTTTGAGGAAGTGGTGGACAAAGGGGCCTCTGCTCAGAGCTTCATTGAGAGAATGACAAACTTTGACAAGAATCTGCCCAATGAGAAGGTGCTGCCCAAGCACAGCCTGCTGTATG
AGTACTTCACAGTGTACAATGAGCTGACAAAAGTGAAATATGTGACAGAGGGAATGAGAAAGCCTGCCTTCCTGTCTGGGGAGCAGAAAAAGGCCATTGTGGACCTGCTTTTCAAGACCA
ACAGAAAAGTGACAGTGAAGCAGCTGAAAGAGGACTACTTCAAGAAAATTGAGTGCTTTGATTCTGTGGAAATCTCTGGTGTTGAGGACAGGTTCAATGCCTCTCTGGGCACATACCATGA
CCTGCTCAAGATTATCAAGGACAAGGACTTCCTGGACAATGAGGAAAATGAGGACATCCTTGAGGACATTGTGCTGACACTGACCCTGTTTGAAGATAGGGAAATGATTGAGGAAAGGCT
CAAGACATATGCCCACCTGTTTGATGACAAAGTGATGAAGCAACTCAAGAGAAGAAGATATACAGGCTGGGGCAGACTGTCCAGAAAGCTGATCAATGGAATCAGGGACAAGCAGAGTGG
CAAGACAATCCTGGATTTCCTGAAGTCTGATGGCTTTGCCAATAGGAACTTCATGCAGCTGATCCATGATGACAGCCTCACCTTCAAAGAGGACATTCAGAAGGCCCAAGTCTCTGGCCAA
GGGGACAGCCTGCATGAGCACATTGCTAACCTGGCTGGCAGCCCTGCTATCAAGAAGGGCATCCTCCAGACTGTGAAGGTGGTGGATGAGCTTGTGAAAGTGATGGGCAGACACAAGCC
TGAGAACATTGTGATTGAGATGGCTAGAGAGAACCAGACCACACAGAAGGGACAGAAGAACAGCAGAGAAAGGATGAAGAGGATTGAAGAGGGCATCAAAGAGCTGGGCAGCCAGATCC
TGAAAGAGCACCCTGTTGAGAACACCCAGCTCCAGAATGAGAAGCTGTACCTGTACTACTTGCAGAATGGCAGGGATATGTATGTGGACCAAGAGCTGGACATCAACAGACTGTCTGACT
ATGATGTGGATCATATTGTGCCCCAGAGCTTTCTGAAGGATGACTCCATTGACAACAAGGTGCTGACTAGGAGTGACAAGAACAGGGGCAAGTCTGACAATGTGCCCTCTGAAGAGGTGG
TCAAGAAGATGAAGAACTATTGGAGGCAGCTCCTGAATGCCAAACTGATCACCCAGAGGAAGTTTGACAACCTGACCAAGGCTGAGAGAGGTGGACTCTCTGAACTGGATAAGGCTGGCT
TCATCAAGAGGCAGCTTGTGGAAACCAGACAGATCACCAAACATGTGGCTCAGATCCTGGACAGCAGAATGAACACTAAGTATGATGAGAATGATAAGCTCATCAGGGAAGTGAAAGTCAT
CACCCTGAAGTCCAAGCTGGTGTCTGACTTTAGGAAAGACTTCCAGTTTTACAAAGTCAGAGAGATCAACAACTACCACCATGCTCATGATGCCTACCTGAATGCTGTTGTGGGCACAGCC
CTGATCAAAAAGTACCCTAAGCTGGAATCTGAGTTTGTGTATGGGGACTACAAAGTGTATGATGTCAGAAAGATGATTGCCAAGTCTGAACAAGAGATTGGCAAGGCTACAGCCAAGTACT
TCTTCTACAGCAACATCATGAATTTCTTCAAGACTGAGATCACCCTGGCTAATGGGGAGATCAGAAAGAGGCCACTGATTGAGACAAATGGAGAGACTGGGGAGATTGTGTGGGACAAGG
GCAGAGACTTTGCCACAGTCAGAAAGGTGCTGTCTATGCCCCAAGTGAACATTGTCAAGAAAACAGAGGTGCAGACTGGTGGCTTCTCCAAAGAGAGCATCCTGCCTAAGAGGAACAGTG
ACAAGCTGATTGCCAGAAAGAAGGACTGGGACCCCAAGAAGTATGGAGGCTTTGACAGCCCCACAGTGGCCTACTCTGTGCTGGTGGTGGCCAAGGTGGAAAAGGGCAAGAGCAAAAA
GCTCAAGAGTGTGAAAGAGCTGCTGGGCATCACCATCATGGAAAGGTCCAGCTTTGAGAAGAACCCTATTGACTTCCTTGAGGCCAAGGGCTACAAAGAAGTGAAAAAGGACCTGATCAT
CAAGCTCCCCAAGTACTCTCTGTTTGAACTGGAAAATGGGAGAAAGAGGATGCTGGCTTCTGCTGGGGAACTCCAGAAAGGCAATGAACTGGCCCTGCCTAGCAAATATGTCAACTTCCT
GTACCTGGCCAGCCACTATGAGAAACTGAAGGGCAGCCCAGAGGATAATGAGCAAAAGCAGCTTTTTGTGGAACAGCACAAGCACTACCTGGATGAGATCATTGAGCAAATCTCTGAGTT
CAGCAAGAGGGTCATCCTGGCAGATGCCAACCTGGACAAAGTGCTGAGTGCCTACAACAAGCACAGGGACAAACCCATCAGAGAGCAGGCAGAGAACATCATCCACCTGTTCACCCTGA
CCAACCTGGGAGCCCCTGCTGCCTTCAAGTACTTTGACACCACCATTGATAGGAAGAGGTACACCAGCACCAAAGAGGTCCTGGATGCTACCCTGATCCACCAGAGCATCACTGGCCTGT
ATGAGACAAGAATTGACCTGTCTCAGCTTGGAGGGGACAAGAGGCCTGCTGCCACAAAGAAAGCAGGCCAGGCCAAAAAGAAGAAGTGAAGATCTACTTCTGGCTAATAAAAGATCAGAG
CTCTAGTGATCTGTGTGTTGGTTTTTTGTGTCTGCATTCTAGCATGAGGGCCTATTTCCCATGATTCCTTCATATTTGCATATACGATACAAGGCTGTTAGAGAGATAATTGGAATTAATTTGA
CTGTAAACACAAAGATATTAGTACAAAATACGTGACGTAGAAAGTAATAATTTCTTGGGTAGTTTGCAGTTTTAAAATTATGTTTTAAAATGGACTATCATATGCTTACCGTAACTTGAAAGTA
TTTCGATTTCTTGGCTTTATATATCTTGTGGAAAGGACGAAACACCGGCGATTCCGCTATAAATGCGGTTTTAGAGCTAGAAATAGCAAGTTAAAATAAGGCTAGTCCGTTATCAACTTGAAA
AAGTGGCACCGAGTCGGTGCTTTTTTGTTTTAGAGCTAGAAATAGCAAGTTAAAATAAGGCTAGTCCGTTTTTAGCGCGTGCGCCAATTCTAGCTCTAGTGATCAGCAGTTCAACCTGTTGA
TAGTATGTACTAAGCTCTCATGTTTAATGTACTAAGCTCTCATGTTTAATGAACTAAACCCTCATGGCTAATGTACTAAGCTCTCATGGCTAATGTACTAAGCTCTCATGTTTCATGTACTAAG
CTCTCATGTTTGAACAATAAAATTAATATAAATCAGCAACTTAAATAGCCTCTAAGGTTTTAAGTTTTATAAGAAAAAAAAGAATATATAAGGCTTTTAAAGGTTTTAAGGTTTCCTAGGTTATC
CTCATATGAGCTCTTAGAAAAACTCATCCAGCATCAAATGAAACTGCAATTTATTCATATCAGGATTATCAATACCATATTTTTGAAAAAGTCTTTTCTGTAATGAAGGAGAAAACTCACCCAG
GCAGTTCCATAGGATGGCAAGATCCTGGTATCTGTCTGCAATTCCAACTCTTCCAACATCAATACAACCTATTAATTTCCCCTCATCAAAAATAAGGTTATCAAGTGAGAAATCACCATGAGT
GACCACTGAATCTGGTGAGAATGGCAAAAGATTATGCATTTCTTTCCAGACTTGTTCAACAGGCCAGCCATTTCTCTCATCATCAAAATCACTGGCATCAACCAAACCATTATTCATTCTTGA
TTGGGCCTGAGCCAGTCTAAATACTCTATCAGAGTTAAAAGGACAATTACAAACAGGAATGGAATGCAATCTTCTCAGGAACACTGCCAGGGCATCAACAATATTTTCACCTGAATCAGGAT
ATTCTTCCAATACCTGGAATGCTGTTTTCCCTGGGATGGCAGTGGTGAGTAACCATGCATCATCAGGAGTTCTGATAAAATGCTTGATGGTTGGAAGAGGCATAAATTCAGTCAGCCAGTTT
AGTCTGACCATCTCATCTGTAACATCATTGGCAACAGAACCTTTGCCATGTTTCAGAAACAACTCTGGGGCATCTGGCTTCCCATACAATCTATAGATTGTGGCACCTGATTGCCCAACATT
ATCTCTAGCCCATTTATACCCATATAAATCAGCATCCATGTTGGAATTTAATCTTGGCCTGGAGCAAGAGGTTTCTCTTTGAATATGGCTCATACATGTGCACCTCCTATAGTGAGTTGTATT
ATACTATGCAGATATACTATGCCAATGTTTAATTGTCAG

FIG. 80

020117 # 8 : RINhe-ΔmCMVΔEFI126-BstEII-spCas9-BglII-MixpA-U6- rel 4-gRNA scaffold-TTTTTT-extra bases-BV2 (SEQ ID NO:58)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTACATAAGGTCAATAG
GGGGTGAGTCAACAGGAAAGTCCCATTGGAGCCAAGTACATTGAGTCAATAGGGACTTTCCAATGGGTTTTGCCCAGTACATAAGGTCAATGGGAGGTAAGCCAATGGGTTTTTCCCATTA
CTGACATGTATACTGAGTCATTAGGGACTTTCCAATGGGTTTTGCCCAGTACATAAGGTCAATAGGGGTGAATCAACAGGAAAGTCCCATTGGAGCCAAGTACACTGAGTCAATAGGGACT
TTCCATTGGGTTTTGCCCAGTACAAAAGGTCAATAGGGGGTGAGTCAATGGGTTTTTCCCATTATTGGCACATACATAAGGTCAATAGGGGTGACTAGTGGAGAAGAGCATGCTTGAGGGC
TGAGTGCCCCTCAGTGGGCAGAGAGCACATGGCCCACAGTCCCTGAGAAGTTGGGGGGAGGGGTGGGCAATTGAACTGGTGCCTAGAGAAGGTGGGGCTTGGGTAAACTGGGAAAGT
GATGTGGTGTACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCACTG
ACTGTCTATGCCTGGGAAAGGGTGGGCAGGAGATGGGGCAGTGCAGGAAAAGTGGCACTATGAACCCTGCAGCCCTAGACAATTGTACTAACCTTCTTCTCTTTCCTCTCCTGACAGGTT
GGTAACCAAGCCACCATGGACTACAAGGACCATGATGGGGATTATAAGGATCATGACATTGATTACAAGGATGATGATGACAAGATGGCCCCTAAGAAGAAGAGGAAAGTTGGCATCCAT
GGGGTGCCAGCTGCTGACAAGAAGTACAGCATTGGCCTGGACATTGGCACCAACTCTGTTGGCTGGGCTGTGATCACTGATGAGTACAAGGTGCCCAGCAAGAAGTTCAAGGTCCTGGG
CAACACAGACAGGCACAGCATCAAGAAGAACCTGATTGGAGCCCTGCTGTTTGACTCTGGGGAGACAGCTGAGGCCACCAGACTGAAGAGAACAGCCAGAAGAAGATACACAAGAAGAA
AGAACAGGATCTGCTACCTGCAAGAAATCTTCAGCAATGAGATGGCCAAAGTGGATGACAGCTTCTTCCACAGACTGGAAGAGTCCTTCCTGGTGGAAGAGGACAAGAAACATGAGAGAC
ACCCCATCTTTGGCAACATTGTGGATGAGGTGGCCTACCATGAGAAGTACCCCACCATCTACCACCTGAGAAAGAAACTGGTGGACAGCACAGACAAGGCTGACCTGAGACTGATCTACC
TGGCTCTGGCCCACATGATCAAGTTCAGAGGCCACTTCCTGATTGAAGGGGATCTGAACCCTGACAACTCTGATGTGGACAAGCTGTTTATCCAGCTGGTGCAGACCTACAACCAGCTGT
TTGAGGAAAACCCCATCAATGCCAGTGGTGTTGATGCCAAGGCCATCCTGTCTGCCAGACTGAGCAAGAGCAGAAGGCTGGAAAATCTGATTGCCCAGCTGCCTGGGGAGAAGAAGAAT
GGCCTGTTTGGCAACCTCATTGCCCTGAGCCTGGGCCTGACACCTAACTTCAAGAGCAACTTTGACCTGGCTGAGGATGCCAAGCTCCAGCTGTCCAAGGACACCTATGATGATGATCTG
GACAACCTGCTGGCCCAGATTGGGGACCAGTATGCTGACCTGTTCCTGGCTGCCAAGAACCTGTCTGATGCCATCCTGCTGTCTGACATCCTGAGAGTGAACACAGAGATCACAAAGGCC
CCTCTGTCTGCCTCTATGATCAAGAGATATGATGAGCACCACCAGGACCTGACACTGCTGAAGGCTCTTGTTAGACAGCAGCTGCCAGAGAAGTACAAAGAGATTTTCTTTGACCAGAGCA
AGAATGGCTATGCTGGCTACATTGATGGTGGTGCCTCTCAAGAAGAGTTCTACAAGTTCATCAAGCCCATCCTGGAAAAGATGGATGGCACAGAGGAACTGCTGGTCAAGCTGAACAGAG
AGGACCTGCTGAGAAAGCAGAGGACCTTTGACAATGGCAGCATCCCTCACCAGATCCACCTGGGAGAGCTGCATGCTATCCTGAGAAGGCAAGAGGATTTCTACCCATTCCTGAAGGACA
ACAGAGAGAAGATTGAGAAGATCCTGACCTTCAGAATCCCCTACTATGTGGGCCCTCTGGCTAGAGGCAACAGCAGATTTGCCTGGATGACCAGAAAGTCTGAGGAAACCATCACACCCT
GGAACTTTGAGGAAGTGGTGGACAAAGGGGCCTCTGCTCAGAGCTTCATTGAGAGAATGACAAACTTTGACAAGAATCTGCCCAATGAGAAGGTGCTGCCCAAGCACAGCCTGCTGTATG
AGTACTTCACAGTGTACAATGAGCTGACAAAAGTGAAATATGTGACAGAGGGAATGAGAAAGCCTGCCTTCCTGTCTGGGGAGCAGAAAAAGGCCATTGTGGACCTGCTTTTCAAGACCA
ACAGAAAAGTGACAGTGAAGCAGCTGAAAGAGGACTACTTCAAGAAAATTGAGTGCTTTGATTCTGTGGAAATCTCTGGTGTTGAGGACAGGTTCAATGCCTCTCTGGGCACATACCATGA
CCTGCTCAAGATTATCAAGGACAAGGACTTCCTGGACAATGAGGAAAATGAGGACATCCTTGAGGACATTGTGCTGACACTGACCCTGTTTGAAGATAGGGAAATGATTGAGGAAAGGCT
CAAGACATATGCCCACCTGTTTGATGACAAAGTGATGAAGCAACTCAAGAGAAGAAGATATACAGGCTGGGGCAGACTGTCCAGAAAGCTGATCAATGGAATCAGGGACAAGCAGAGTGG
CAAGACAATCCTGGATTTCCTGAAGTCTGATGGCTTTGCCAATAGGAACTTCATGCAGCTGATCCATGATGACAGCCTCACCTTCAAAGAGGACATTCAGAAGGCCCAAGTCTCTGGCCAA
GGGGACAGCCTGCATGAGCACATTGCTAACCTGGCTGGCAGCCCTGCTATCAAGAAGGGCATCCTCCAGACTGTGAAGGTGGTGGATGAGCTTGTGAAAGTGATGGGCAGACACAAGCC
TGAGAACATTGTGATTGAGATGGCTAGAGAGAACCAGACCACACAGAAGGGACAGAAGAACAGCAGAGAAAGGATGAAGAGGATTGAAGAGGGCATCAAAGAGCTGGGCAGCCAGATCC
TGAAAGAGCACCCTGTTGAGAACACCCAGCTCCAGAATGAGAAGCTGTACCTGTACTACTTGCAGAATGGCAGGGATATGTATGTGGACCAAGAGCTGGACATCAACAGACTGTCTGACT
ATGATGTGGATCATATTGTGCCCCAGAGCTTTCTGAAGGATGACTCCATTGACAACAAGGTGCTGACTAGGAGTGACAAGAACAGGGGCAAGTCTGACAATGTGCCCTCTGAAGAGGTGG
TCAAGAAGATGAAGAACTATTGGAGGCAGCTCCTGAATGCCAAACTGATCACCCAGAGGAAGTTTGACAACCTGACCAAGGCTGAGAGAGGTGGACTCTCTGAACTGGATAAGGCTGGCT
TCATCAAGAGGCAGCTTGTGGAAACCAGACAGATCACCAAACATGTGGCTCAGATCCTGGACAGCAGAATGAACACTAAGTATGATGAGAATGATAAGCTCATCAGGGAAGTGAAAGTCAT
CACCCTGAAGTCCAAGCTGGTGTCTGACTTTAGGAAAGACTTCCAGTTTTACAAAGTCAGAGAGATCAACAACTACCACCATGCTCATGATGCCTACCTGAATGCTGTTGTGGGCACAGCC
CTGATCAAAAAGTACCCTAAGCTGGAATCTGAGTTTGTGTATGGGGACTACAAAGTGTATGATGTCAGAAAGATGATTGCCAAGTCTGAACAAGAGATTGGCAAGGCTACAGCCAAGTACT
TCTTCTACAGCAACATCATGAATTTCTTCAAGACTGAGATCACCCTGGCTAATGGGGAGATCAGAAAGAGGCCACTGATTGAGACAAATGGAGAGACTGGGGAGATTGTGTGGGACAAGG
GCAGAGACTTTGCCACAGTCAGAAAGGTGCTGTCTATGCCCCAAGTGAACATTGTCAAGAAAACAGAGGTGCAGACTGGTGGCTTCTCCAAAGAGAGCATCCTGCCTAAGAGGAACAGTG
ACAAGCTGATTGCCAGAAAGAAGGACTGGGACCCCAAGAAGTATGGAGGCTTTGACAGCCCCACAGTGGCCTACTCTGTGCTGGTGGTGGCCAAGGTGGAAAAGGGCAAGAGCAAAAA
GCTCAAGAGTGTGAAAGAGCTGCTGGGCATCACCATCATGGAAAGGTCCAGCTTTGAGAAGAACCCTATTGACTTCCTTGAGGCCAAGGGCTACAAAGAAGTGAAAAAGGACCTGATCAT
CAAGCTCCCCAAGTACTCTCTGTTTGAACTGGAAAATGGGAGAAAGAGGATGCTGGCTTCTGCTGGGGAACTCCAGAAAGGCAATGAACTGGCCCTGCCTAGCAAATATGTCAACTTCCT
GTACCTGGCCAGCCACTATGAGAAACTGAAGGGCAGCCCAGAGGATAATGAGCAAAAGCAGCTTTTTGTGGAACAGCACAAGCACTACCTGGATGAGATCATTGAGCAAATCTCTGAGTT
CAGCAAGAGGGTCATCCTGGCAGATGCCAACCTGGACAAAGTGCTGAGTGCCTACAACAAGCACAGGGACAAACCCATCAGAGAGCAGGCAGAGAACATCATCCACCTGTTCACCCTGA
CCAACCTGGGAGCCCCTGCTGCCTTCAAGTACTTTGACACCACCATTGATAGGAAGAGGTACACCAGCACCAAAGAGGTCCTGGATGCTACCCTGATCCACCAGAGCATCACTGGCCTGT
ATGAGACAAGAATTGACCTGTCTCAGCTTGGAGGGGACAAGAGGCCTGCTGCCACAAAGAAAGCAGGCCAGGCCAAAAAGAAGAAGTGAAGATCTACTTCTGGCTAATAAAAGATCAGAG
CTCTAGTGATCTGTGTGTTGGTTTTTTGTGTCTGCATTCTAGCATGAGGGCCTATTTCCCATGATTCCTTCATATTTGCATATACGATACAAGGCTGTTAGAGAGATAATTGGAATTAATTTGA
CTGTAAACACAAAGATATTAGTACAAAATACGTGACGTAGAAAGTAATAATTTCTTGGGTAGTTTGCAGTTTTAAAATTATGTTTTAAAATGGACTATCATATGCTTACCGTAACTTGAAAGTA
TTTCGATTTCTTGGCTTTATATATCTTGTGGAAAGGACGAAACACCGCTGCCGGGATGGCTACTATGGTTTTAGAGCTAGAAATAGCAAGTTAAAATAAGGCTAGTCCGTTATCAACTTGAA
AAAGTGGCACCGAGTCGGTGCTTTTTTGTTTTAGAGCTAGAAATAGCAAGTTAAAATAAGGCTAGTCCGTTTTTAGCGCGTGCGCCAATTCTAGCTCTAGTGATCAGCAGTTCAACCTGTTG
ATAGTATGTACTAAGCTCTCATGTTTAATGTACTAAGCTCTCATGTTTAATGAACTAAACCCTCATGGCTAATGTACTAAGCTCTCATGGCTAATGTACTAAGCTCTCATGTTTCATGTACTAA
GCTCTCATGTTTGAACAATAAAATTAATATAAATCAGCAACTTAAATAGCCTCTAAGGTTTTAAGTTTTATAAGAAAAAAAAGAATATATAAGGCTTTTAAAGGTTTTAAGGTTTCCTAGGTTAT
CCTCATATGAGCTCTTAGAAAAACTCATCCAGCATCAAATGAAACTGCAATTTATTCATATCAGGATTATCAATACCATATTTTTGAAAAAGTCTTTTCTGTAATGAAGGAGAAAACTCACCCA
GGCAGTTCCATAGGATGGCAAGATCCTGGTATCTGTCTGCAATTCCAACTCTTCCAACATCAATACAACCTATTAATTTCCCCTCATCAAAAATAAGGTTATCAAGTGAGAAATCACCATGAG
TGACCACTGAATCTGGTGAGAATGGCAAAAGATTATGCATTTCTTTCCAGACTTGTTCAACAGGCCAGCCATTTCTCTCATCATCAAAATCACTGGCATCAACCAAACCATTATTCATTCTTG
ATTGGGCCTGAGCCAGTCTAAATACTCTATCAGAGTTAAAAGGACAATTACAAACAGGAATGGAATGCAATCTTCTCAGGAACACTGCCAGGGCATCAACAATATTTTCACCTGAATCAGGA
TATTCTTCCAATACCTGGAATGCTGTTTTCCCTGGGATGGCAGTGGTGAGTAACCATGCATCATCAGGAGTTCTGATAAAATGCTTGATGGTTGGAAGAGGCATAAATTCAGTCAGCCAGTT
TAGTCTGACCATCTCATCTGTAACATCATTGGCAACAGAACCTTTGCCATGTTTCAGAAACAACTCTGGGGCATCTGGCTTCCCATACAATCTATAGATTGTGGCACCTGATTGCCCAACAT
TATCTCTAGCCCATTTATACCCATATAAATCAGCATCCATGTTGGAATTTAATCTTGGCCTGGAGCAAGAGGTTTCTCTTTGAATATGGCTCATACATGTGCACCTCCTATAGTGAGTTGTAT
TATACTATGCAGATATACTATGCCAATGTTTAATTGTCAG

FIG. 81

021417 # 3 : RINhe- U1-rel 1-gRNA scaffold-BglII-3'Box -ΔmCMVΔEFI126-BstEII-spCas9-BglII-MixpA-U6- rel 1-gRNA scaffold-TTTTTT-extra bases-BV2 (triple cassette) (SEQ ID NO:59)

CACTATGTGGACATGAATTCAATTGGCTAGCAGACTAGTCCCACCGAAAGGTTGCTCCTTAACACAGGCTAAGGACCAGCTTCTTTGGGAGAGAACAGACGCAGGGGCGGGAGGGAAAAAG
GGAGAGGCAGACGTCACTTCCCCTTGGCGGCTCTGGCAGCAGATTGGTCGGTTGAGTGGCAGAAAGGCAGACGGGGACTGGGCAAGGCACTGTCGGTGACATCACGGACAGGGCGACTTC
TATGTAGATGAGGCAGCGCAGAGGCTGCTGCTTCGCCACTTGCTGCTTCGCCACGAAGGAGTTCCCGTGCCCTGGGAGCGGGTTCAGGACCGCGGATCGGAAGTGAGAATCCCAGCTGTGT
GTCAGGGCTGGAAAGGGCTCGGGAGTGCGCGGGGCAAGTGACCGTGTGTGTAAAGAGTGAGGCGTATGAGGCTGTGTCGGGGCAGAGCCCGAAGATCCAGTTTGGCGATTCCGCTATAAA
TGCGGTTTTAGAGCTAGAAATAGCAAGTTAAAATAAGGCTAGTCCGTTATCAACTTGAAAAAGTGGCACCGAGTCGGTGCAGATCTGGAGGAGTTTCAAAAACAGACCTGGCAGCATCTAGC
AGGAGTCAATGGGAAAAACCCATTGGAGCCAAGTACACTGACTCAATAGGGACTTTCCATTGGGTTTTGCCCAGTACATAAGGTCAATAGGGGGTGAGTCAACAGGAAAGTCCCATTGGAGC
CAAGTACATTGAGTCAATAGGGACTTTCCAATGGGTTTTGCCCAGTACATAAGGTCAATGGGAGGTAAGCCAATGGGTTTTTCCCATTACTGACATGTATACTGAGTCATTAGGGACTTTCCAA
TGGGTTTTGCCCAGTACATAAGGTCAATAGGGGTGAATCAACAGGAAAGTCCCATTGGAGCCAAGTACACTGAGTCAATAGGGACTTTCCATTGGGTTTTGCCCAGTACAAAAGGTCAATAG
GGGGTGAGTCAATGGGTTTTTCCCATTATTGGCACATACATAAGGTCAATAGGGGTGACTAGTGGAGAAGAGCATGCTTGAGGGCTGAGTGCCCCTCAGTGGGCAGAGAGCACATGGCCCA
CAGTCCCTGAGAAGTTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGGG
GGAGAACCATATATAAGTGCAGTAGTCTCTGTGAACATTCAAGCTTCTGCCTTCTCCCTCCTGTGAGTTTGGTAAGTCACTGACTGTCTATGCCTGGGAAAGGGTGGGCAGGAGATGGGGCA
GTGCAGGAAAAGTGGCACTATGAACCCTGCAGCCCTAGACAATTGTACTAACCTTCTTCTCTTTCCTCTCCTGACAGGTTGGTAACCAAGCCACCATGGACTACAAGGACCATGATGGGGATT
ATAAGGATCATGACATTGATTACAAGGATGATGATGACAAGATGGCCCCTAAGAAGAAGAGGAAAGTTGGCATCCATGGGGTGCCAGCTGCTGACAAGAAGTACAGCATTGGCCTGGACAT
TGGCACCAACTCTGTTGGCTGGGCTGTGATCACTGATGAGTACAAGGTGCCCAGCAAGAAGTTCAAGGTCCTGGGCAACACAGACAGGCACAGCATCAAGAAGAACCTGATTGGAGCCCTG
CTGTTTGACTCTGGGGAGACAGCTGAGGCCACCAGACTGAAGAGAACAGCCAGAAGAAGATACACAAGAAGAAAGAACAGGATCTGCTACCTGCAAGAAATCTTCAGCAATGAGATGGCCA
AAGTGGATGACAGCTTCTTCCACAGACTGGAAGAGTCCTTCCTGGTGGAAGAGGACAAGAAACATGAGAGACACCCCATCTTTGGCAACATTGTGGATGAGGTGGCCTACCATGAGAAGTAC
CCCACCATCTACCACCTGAGAAAGAAACTGGTGGACAGCACAGACAAGGCTGACCTGAGACTGATCTACCTGGCTCTGGCCCACATGATCAAGTTCAGAGGCCACTTCCTGATTGAAGGGGA
TCTGAACCCTGACAACTCTGATGTGGACAAGCTGTTTATCCAGCTGGTGCAGACCTACAACCAGCTGTTTGAGGAAAACCCCATCAATGCCAGTGGTGTTGATGCCAAGGCCATCCTGTCTGC
CAGACTGAGCAAGAGCAGAAGGCTGGAAAATCTGATTGCCCAGCTGCCTGGGGAGAAGAAGAATGGCCTGTTTGGCAACCTCATTGCCCTGAGCCTGGGCCTGACACCTAACTTCAAGAGC
AACTTTGACCTGGCTGAGGATGCCAAGCTCCAGCTGTCCAAGGACACCTATGATGATGATCTGGACAACCTGCTGGCCCAGATTGGGGACCAGTATGCTGACCTGTTCCTGGCTGCCAAGAAC
CTGTCTGATGCCATCCTGCTGTCTGACATCCTGAGAGTGAACACAGAGATCACAAAGGCCCCTCTGTCTGCCTCTATGATCAAGAGATATGATGAGCACCACCAGGACCTGACACTGCTGAAG
GCTCTTGTTAGACAGCAGCTGCCAGAGAAGTACAAAGAGATTTTCTTTGACCAGAGCAAGAATGGCTATGCTGGCTACATTGATGGTGGTGCCTCTCAAGAAGAGTTCTACAAGTTCATCAAG
CCCATCCTGGAAAAGATGGATGGCACAGAGGAACTGCTGGTCAAGCTGAACAGAGAGGACCTGCTGAGAAAGCAGAGGACCTTTGACAATGGCAGCATCCCTCACCAGATCCACCTGGGAG
AGCTGCATGCTATCCTGAGAAGGCAAGAGGATTTCTACCCATTCCTGAAGGACAACAGAGAGAAGATTGAGAAGATCCTGACCTTCAGAATCCCCTACTATGTGGGCCCTCTGGCTAGAGGC
AACAGCAGATTTGCCTGGATGACCAGAAAGTCTGAGGAAACCATCACACCCTGGAACTTTGAGGAAGTGGTGGACAAAGGGGCCTCTGCTCAGAGCTTCATTGAGAGAATGACAAACTTTGA
CAAGAATCTGCCCAATGAGAAGGTGCTGCCCAAGCACAGCCTGCTGTATGAGTACTTCACAGTGTACAATGAGCTGACAAAAGTGAAATATGTGACAGAGGGAATGAGAAAGCCTGCCTTCC
TGTCTGGGGAGCAGAAAAAGGCCATTGTGGACCTGCTTTTCAAGACCAACAGAAAAGTGACAGTGAAGCAGCTGAAAGAGGACTACTTCAAGAAAATTGAGTGCTTTGATTCTGTGGAAATC
TCTGGTGTTGAGGACAGGTTCAATGCCTCTCTGGGCACATACCATGACCTGCTCAAGATTATCAAGGACAAGGACTTCCTGGACAATGAGGAAAATGAGGACATCCTTGAGGACATTGTGCT
GACACTGACCCTGTTTGAAGATAGGGAAATGATTGAGGAAAGGCTCAAGACATATGCCCACCTGTTTGATGACAAAGTGATGAAGCAACTCAAGAGAAGAAGATATACAGGCTGGGGCAGA
CTGTCCAGAAAGCTGATCAATGGAATCAGGGACAAGCAGAGTGGCAAGACAATCCTGGATTTCCTGAAGTCTGATGGCTTTGCCAATAGGAACTTCATGCAGCTGATCCATGATGACAGCCT
CACCTTCAAAGAGGACATTCAGAAGGCCCAAGTCTCTGGCCAAGGGGACAGCCTGCATGAGCACATTGCTAACCTGGCTGGCAGCCCTGCTATCAAGAAGGGCATCCTCCAGACTGTGAAGG
TGGTGGATGAGCTTGTGAAAGTGATGGGCAGACACAAGCCTGAGAACATTGTGATTGAGATGGCTAGAGAGAACCAGACCACACAGAAGGGACAGAAGAACAGCAGAGAAAGGATGAAG
AGGATTGAAGAGGGCATCAAAGAGCTGGGCAGCCAGATCCTGAAAGAGCACCCTGTTGAGAACACCCAGCTCCAGAATGAGAAGCTGTACCTGTACTACTTGCAGAATGGCAGGGATATGT
ATGTGGACCAAGAGCTGGACATCAACAGACTGTCTGACTATGATGTGGATCATATTGTGCCCCAGAGCTTTCTGAAGGATGACTCCATTGACAACAAGGTGCTGACTAGGAGTGACAAGAAC
AGGGGCAAGTCTGACAATGTGCCCTCTGAAGAGGTGGTCAAGAAGATGAAGAACTATTGGAGGCAGCTCCTGAATGCCAAACTGATCACCCAGAGGAAGTTTGACAACCTGACCAAGGCTG
AGAGAGGTGGACTCTCTGAACTGGATAAGGCTGGCTTCATCAAGAGGCAGCTTGTGGAAACCAGACAGATCACCAAACATGTGGCTCAGATCCTGGACAGCAGAATGAACACTAAGTATGA
TGAGAATGATAAGCTCATCAGGGAAGTGAAAGTCATCACCCTGAAGTCCAAGCTGGTGTCTGACTTTAGGAAAGACTTCCAGTTTTACAAAGTCAGAGAGATCAACAACTACCACCATGCTCA
TGATGCCTACCTGAATGCTGTTGTGGGCACAGCCCTGATCAAAAAGTACCCTAAGCTGGAATCTGAGTTTGTGTATGGGGACTACAAAGTGTATGATGTCAGAAAGATGATTGCCAAGTCTGA
ACAAGAGATTGGCAAGGCTACAGCCAAGTACTTCTTCTACAGCAACATCATGAATTTCTTCAAGACTGAGATCACCCTGGCTAATGGGGAGATCAGAAAGAGGCCACTGATTGAGACAAATG
GAGAGACTGGGGAGATTGTGTGGGACAAGGGCAGAGACTTTGCCACAGTCAGAAAGGTGCTGTCTATGCCCCAAGTGAACATTGTCAAGAAAACAGAGGTGCAGACTGGTGGCTTCTCCAA
AGAGAGCATCCTGCCTAAGAGGAACAGTGACAAGCTGATTGCCAGAAAGAAGGACTGGGACCCCAAGAAGTATGGAGGCTTTGACAGCCCCACAGTGGCCTACTCTGTGCTGGTGGTGGCC
AAGGTGGAAAAGGGCAAGAGCAAAAAGCTCAAGAGTGTGAAAGAGCTGCTGGGCATCACCATCATGGAAAGGTCCAGCTTTGAGAAGAACCCTATTGACTTCCTTGAGGCCAAGGGCTACA
AAGAAGTGAAAAAGGACCTGATCATCAAGCTCCCCAAGTACTCTCTGTTTGAACTGGAAAATGGGAGAAAGAGGATGCTGGCTTCTGCTGGGGAACTCCAGAAAGGCAATGAACTGGCCCT
GCCTAGCAAATATGTCAACTTCCTGTACCTGGCCAGCCACTATGAGAAACTGAAGGGCAGCCCAGAGGATAATGAGCAAAAGCAGCTTTTTGTGGAACAGCACAAGCACTACCTGGATGAGA
TCATTGAGCAAATCTCTGAGTTCAGCAAGAGGGTCATCCTGGCAGATGCCAACCTGGACAAAGTGCTGAGTGCCTACAACAAGCACAGGGACAAACCCATCAGAGAGCAGGCAGAGAACAT
CATCCACCTGTTCACCCTGACCAACCTGGGAGCCCCTGCTGCCTTCAAGTACTTTGACACCACCATTGATAGGAAGAGGTACACCAGCACCAAAGAGGTCCTGGATGCTACCCTGATCCACCAG
AGCATCACTGGCCTGTATGAGACAAGAATTGACCTGTCTCAGCTTGGAGGGGACAAGAGGCCTGCTGCCACAAAGAAAGCAGGCCAGGCCAAAAAGAAGAAGTGAAGATCTACTTCTGGCT
AATAAAAGATCAGAGCTCTAGTGATCTGTGTGTTGGTTTTTTGTGTCTGCATTCTAGCATGAGGGCCTATTTCCCATGATTCCTTCATATTTGCATATACGATACAAGGCTGTTAGAGAGATAAT
TGGAATTAATTTGACTGTAAACACAAAGATATTAGTACAAAATACGTGACGTAGAAAGTAATAATTTCTTGGGTAGTTTGCAGTTTTAAAATTATGTTTTAAAATGGACTATCATATGCTTACCG
TAACTTGAAAGTATTTCGATTTCTTGGCTTTATATATCTTGTGGAAAGGACGAAACACCGGCGATTCCGCTATAAATGCGGTTTTAGAGCTAGAAATAGCAAGTTAAAATAAGGCTAGTCCGTT
ATCAACTTGAAAAAGTGGCACCGAGTCGGTGCTTTTTTGTTTTAGAGCTAGAAATAGCAAGTTAAAATAAGGCTAGTCCGTTTTTAGCGCGTGCGCCAATTCTAGCTCTAGTGATCAGCAGTTC
AACCTGTTGATAGTATGTACTAAGCTCTCATGTTTAATGTACTAAGCTCTCATGTTTAATGAACTAAACCCTCATGGCTAATGTACTAAGCTCTCATGGCTAATGTACTAAGCTCTCATGTTTCAT
GTACTAAGCTCTCATGTTTGAACAATAAAATTAATATAAATCAGCAACTTAAATAGCCTCTAAGGTTTTAAGTTTTATAAGAAAAAAAAGAATATATAAGGCTTTTAAAGGTTTTAAGGTTTCCT
AGGTTATCCTCATATGAGCTCTTAGAAAAACTCATCCAGCATCAAATGAAACTGCAATTTATTCATATCAGGATTATCAATACCATATTTTTGAAAAAGTCTTTTCTGTAATGAAGGAGAAAACT
CACCCAGGCAGTTCCATAGGATGGCAAGATCCTGGTATCTGTCTGCAATTCCAACTCTTCCAACATCAATACAACCTATTAATTTCCCCTCATCAAAAATAAGGTTATCAAGTGAGAAATCACCA
TGAGTGACCACTGAATCTGGTGAGAATGGCAAAAGATTATGCATTTCTTTCCAGACTTGTTCAACAGGCCAGCCATTTCTCTCATCATCAAAATCACTGGCATCAACCAAACCATTATTCATTCT
TGATTGGGCCTGAGCCAGTCTAAATACTCTATCAGAGTTAAAAGGACAATTACAAACAGGAATGGAATGCAATCTTCTCAGGAACACTGCCAGGGCATCAACAATATTTTCACCTGAATCAGG
ATATTCTTCCAATACCTGGAATGCTGTTTTCCCTGGGATGGCAGTGGTGAGTAACCATGCATCATCAGGAGTTCTGATAAAATGCTTGATGGTTGGAAGAGGCATAAATTCAGTCAGCCAGTTT
AGTCTGACCATCTCATCTGTAACATCATTGGCAACAGAACCTTTGCCATGTTTCAGAAACAACTCTGGGGCATCTGGCTTCCCATACAATCTATAGATTGTGGCACCTGATTGCCCAACATTATC
TCTAGCCCATTTATACCCATATAAATCAGCATCCATGTTGGAATTTAATCTTGGCCTGGAGCAAGAGGTTTCTCTTTGAATATGGCTCATACATGTGCACCTCCTATAGTGAGTTGTATTATACTA
TGCAGATATACTATGCCAATGTTTAATTGTCAG

FIG. 85

062817 # 8: DraIIRINhe-ΔmCMVΔEF1I126-BstEII-syn21-ΔaCD20-H-*F3(RKRR)-P2A-2*-ΔaCD20-L-BglII-Δp10-pA/BV2 (SEQ ID NO:82)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTA
CATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATG
GGAGGTAAGCCAATGGGTTTTTCCCATTACTGACATGTATACTGAGTCATTAGGGACTTTCCAATGGGTTTTGCCCAGTACATAAGGTCAATAGGGGTGAATCAACAG
GAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATT
GGCACATACATAAGGTCAATAGGGGTGACTAGTGGAGAAGAGCATGCTTGAGGGCTGAGTGCCCCTCAGTGGGCAGAGAGCACATGGCCCACAGTCCCTGAGAAG
TTGGGGGGAGGGGTGGGCAATTGAACTGGTGCCTAGAGAAGGTGGGGCTTGGGTAAACTGGGAAAGTGATGTGGTGTACTGGCTCCACCTTTTTCCCCAGGGTGG
GGGAGAACCATATATAAGTGCAGTAGTCTCTGTGAACATTCAAGCTTCTGCCTTCTCCCTCCTGTGAGTTTGgtaagtcactgactgtctatgcctgggaaagggtgggcaggagatgg
ggcagtgcaggaaaagtggcactatgaacccTGCAGCCCTAGAcaattgtactaaccttcttctctttcctctcctgacagGTTGGTAACCGCGGCCGCGGCTCGAGGGTACCAACTTAAAAA
AAAAAATCAAAATGGGCTGGTCCCTGATCCTGCTGTTCCTGGTGGCTGTGGCCACCAGAGTGCTGAGCCAGGTGCAGCTGCAGCAGCCTGGGGCTGAGCTTGTGAA
ACCTGGGGCCTCTGTGAAGATGAGCTGCAAGGCCTCTGGCTACACCTTCACCAGCTACAACATGCACTGGGTCAAGCAGACCCCTGGCAGAGGCCTGGAATGGATTG
GAGCCATCTACCCTGGCAATGGGGACACCTCCTACAACCAGAAGTTCAAGGGCAAGGCCACCCTGACAGCTGACAAGAGCAGCAGCACAGCCTACATGCAGCTGTC
CAGCCTGACCTCTGAGGACTCTGCTGTGTACTACTGTGCCAGGTCCACCTACTATGGGGGAGACTGGTACTTCAATGTGTGGGGAGCTGGCACCACAGTGACAGTGT
CTGCTGCCAGCACCAAGGGCCCCTCTGTGTTTCCTCTGGCCCCCAGCAGCAAGAGCACCTCTGGGGGAACAGCTGCCCTGGGCTGCCTTGTGAAGGACTACTTCCCTG
AGCCTGTGACTGTGTCCTGGAACTCTGGGGCCCTGACATCTGGGGTGCACACCTTCCCTGCAGTGCTGCAGTCCAGTGGCCTGTACTCCCTGTCCTCTGTTGTGACAG
TGCCCAGCTCCAGCCTGGGCACCCAGACCTACATCTGCAATGTGAACCACAAGCCCAGCAACACCAAGGTGGACAAGAAGGCTGAGCCCAAGAGCTGTGACAAGAC
CCACACCTGTCCCCCCTGTCCTGCCCCTGAACTGCTGGGAGGACCTTCTGTGTTCCTGTTCCCACCCAAGCCCAAGGATACCCTGATGATCAGCAGAACCCCTGAAGTG
ACCTGTGTGGTGGTGGATGTGTCCCATGAGGACCCAGAAGTGAAGTTCAATTGGTATGTGGATGGGGTGGAAGTGCACAATGCCAAGACCAAGCCCAGAGAGGAA
CAGTACAACAGCACCTACAGAGTGGTGTCTGTGCTGACTGTGCTGCACCAGGACTGGCTGAATGGCAAAGAGTACAAGTGCAAGGTGTCCAACAAGGCCCTGCCAG
CCCCCATTGAGAAAACCATCAGCAAGGCCAAGGGCCAGCCTAGAGAACCCCAGGTGTACACACTGCCCCCTAGCAGGGATGAGCTGACCAAGAACCAGGTGTCCCT
GACATGCCTTGTGAAAGGCTTCTACCCCTCTGACATTGCTGTGGAATGGGAGAGCAATGGACAGCCTGAGAACAACTACAAGACCACCCCCCCTGTGCTGGACTCTG
ATGGCTCATTCTTCCTGTACAGCAAGCTGACAGTGGACAAGTCCAGATGGCAGCAGGGCAATGTGTTCAGCTGCTCTGTGATGCATGAGGCCCTGCACAACCACTAC
ACCCAGAAAAGCCTGTCCCTGTCCCCTGGCAAGAGAAAGAGAAGGAGTGGAAGTGGAGCTACTAACTTCAGCCTGCTGAAGCAGGCTGGAGATGTGGAGGAGAA
CCCTGGACCTATGGACTTCCAGGTGCAGATCATCAGCTTTCTGCTGATCTCTGCCTCTGTGATCATGAGCAGAGGCCAGATTGTGCTGAGCCAGAGCCCTGCCATCCT
GTCTGCAAGCCCTGGGGAGAAAGTGACCATGACCTGCAGAGCCAGCAGCTCTGTGTCCTACATCCACTGGTTCCAGCAGAAGCCTGGCAGCAGCCCCAAGCCTTGGA
TCTATGCCACCAGCAACCTGGCATCTGGGGTGCCAGTCAGATTCTCTGGCTCTGGATCTGGCACCAGCTACAGCCTGACCATCAGCAGAGTGGAAGCTGAGGATGCT
GCCACCTACTACTGCCAGCAGTGGACCAGCAATCCCCCCACCTTTGGAGGGGGCACCAAGCTGGAAATCAAGAGAACAGTGGCTGCCCCCTCTGTGTTCATCTTCCCA
CCCTCTGATGAGCAGCTGAAGTCTGGAACAGCCTCTGTTGTGTGCCTGCTGAACAACTTCTACCCCAGAGAAGCCAAGGTGCAGTGGAAGGTGGACAATGCCCTGCA
GTCTGGCAACTCCCAGGAATCTGTGACAGAGCAGGACAGCAAGGACTCCACCTACTCCCTGAGCAGCACCCTGACCCTGAGCAAGGCTGACTATGAGAAGCACAAA
GTGTATGCCTGTGAAGTGACCCACCAGGGCCTGTCCAGCCCTGTGACCAAGAGCTTCAACAGAGGGGAGAGCTGAAGATCTAAATAACAAATCAATTGTTTTATAA
TATTCTTACTATTCTTTGATTATGTAATAAAATGTGATCATTAGGAAGATTACTAAAAATATAAAAAATATGAGTTCTGTGTGTATAACAAATGCTGTAAACTCCAC
AATTGTGTTTGTTGCAAATAAACCCATGATTATTTGATTAAAATTGTTGTTTTCTTTGTTCATAGACAATAGTGTGTTTTGCCTAAACTTGTACTGCATAAACTCCAT
GCTAGTGTATAGCAAGCTAGTGGCTAACTCTTGCCCCACCAAAGTAGATTCTTCAAAATCCTCAATTTCATCACCCTCCTCCAAGTTTAACATTTGGCCTTCTGAATT
AACTTCTAAAGATGCCACATAATCTAATAAATGAAATAGAGATTCAAACTTGGCTTCATCTTCCTTTTCTACCATTTCCTAAAAGAACTCTGGCATAAACTCTATGAT
TTCTCTGGACTTGGTGTTGTCTAAACTCTCAAAGTACTCAGTCAGGAACTTGCTCTACATGTCTTCTGGAAACTCTCTCTGAAACATGTTGTTGTAACCTAACTGGTC
CCATAGCTCCAAAACCAAATCTGCCAGCTTCAATAGAATGAGCACTATGCCTACAATGGAGCTGGCTTGGATAGCTATTCTAGTTAACTGCCTGCCTTTTAAACTAA
TTCTTGAAGACTAAAGGGCCTCTTGATACTCCTATTTTTATAGGTTAATGTCATGATAATAATGGTTTCTTATCTAGTACTTCTGGCTAATAAAAGATCAGAGCTCTA
GTGATCTGTGTGTTGGTTTTTTGTGTCTGCATTCTAGCTCTAGTGATCAGCAGTTCAACCTGTTGATAGTATGTACTAAGCTCTCATGTTTAATGTACTAAGCTCTCATG
TTTAATGAACTAAACCCTCATGGCTAATGTACTAAGCTCTCATGGCTAATGTACTAAGCTCTCATGTTTCATGTACTAAGCTCTCATGTTTGAACAATAAAATTAATATA
AATCAGCAACTTAAATAGCCTCTAAGGTTTTAAGTTTTATAAGAAAAAAAAGAATATATAAGGCTTTTAAAGGTTTTAAGGTTTCCTAGGTTATCCTCATATGAGCTCT
TAGAAAAACTCATCCAGCATCAAATGAAACTGCAATTTATTCATATCAGGATTATCAATACCATATTTTTGAAAAAGTCTTTTCTGTAATGAAGGAGAAAACTCACCCA
GGCAGTTCCATAGGATGGCAAGATCCTGGTATCTGTCTGCAATTCCAACTCTTCCAACATCAATACAACCTATTAATTTCCCCTCATCAAAAATAAGGTTATCAAGTGA
GAAATCACCATGAGTGACCACTGAATCTGGTGAGAATGGCAAAAGATTATGCATTTCTTTCCAGACTTGTTCAACAGGCCAGCCATTTCTCTCATCATCAAAATCACTG
GCATCAACCAAACCATTATTCATTCTTGATTGGGCCTGAGCCAGTCTAAATACTCTATCAGAGTTAAAAGGACAATTACAAACAGGAATGGAATGCAATCTTCTCAGG
AACACTGCCAGGGCATCAACAATATTTTCACCTGAATCAGGATATTCTTCCAATACCTGGAATGCTGTTTTCCCTGGGATGGCAGTGGTGAGTAACCATGCATCATCA
GGAGTTCTGATAAAATGCTTGATGGTTGGAAGAGGCATAAATTCAGTCAGCCAGTTTAGTCTGACCATCTCATCTGTAACATCATTGGCAACAGAACCTTTGCCATGT
TTCAGAAACAACTCTGGGGCATCTGGCTTCCCATACAATCTATAGATTGTGGCACCTGATTGCCCAACATTATCTCTAGCCCATTTATACCCATATAAATCAGCATCCAT
GTTGGAATTTAATCTTGGCCTGGAGCAAGAGGTTTCTCTTTGAATATGGCTCATACATGTGCACCTCCTATAGTGAGTTGTATTATACTATGCAGATATACTATGCCAA
TGTTTAATTGTCAG

FIG. 90

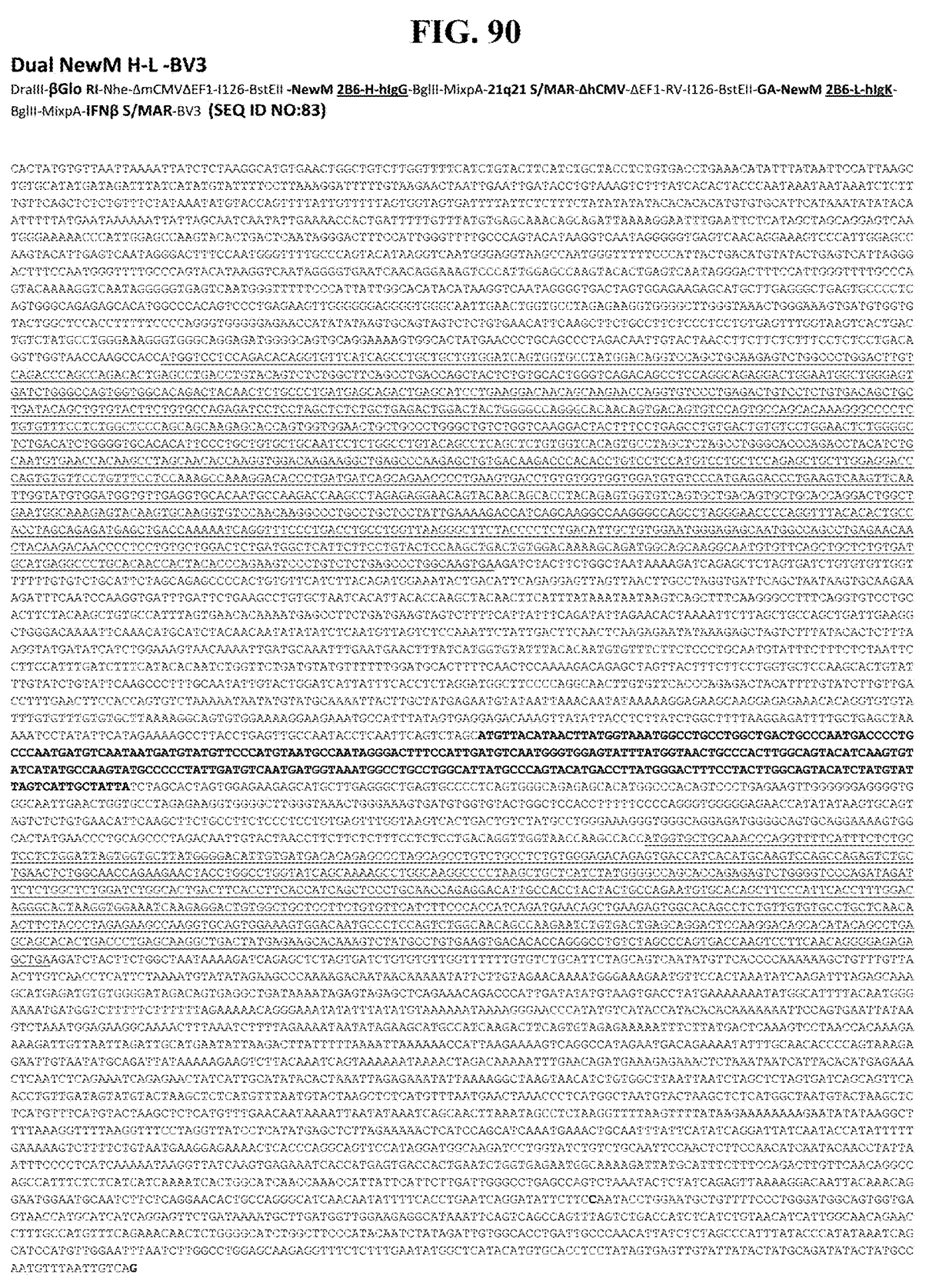

Dual NewM H-L -BV3

DraIII-βGlo RI-Nhe-ΔmCMVΔEF1-I126-BstEII -NewM 2B6-H-hIgG-BglII-MixpA-21q21 S/MAR-ΔhCMV-ΔEF1-RV-I126-BstEII-GA-NewM 2B6-L-hIgK-BglII-MixpA-IFNβ S/MAR-BV3 (SEQ ID NO:83)

CACTATGTGTTAATTAAAATTATCTCTAAGGCATGTGAACTGGCTGTCTTGGTTTTCATCTGTACTTCATCTGCTACCTCTGTGACCTGAAACATATTTATAATTCCATTAAGC
TGTGCATATGATAGATTTATCATATGTATTTTCCTTAAAGGATTTTTGTAAGAACTAATTGAATTGATACCTGTAAAGTCTTTATCACACTACCCAATAAATAATAAATCTCTT
TGTTCAGCTCTCTGTTTCTATAAATATGTACCAGTTTTATTGTTTTTAGTGGTAGTGATTTTATTCTCTTTCTATATATATACACACACATGTGTGCATTCATAAATATATACA
ATTTTTATGAATAAAAAATTATTAGCAATCAATATTGAAAACCACTGATTTTTGTTTATGTGAGCAAACAGCAGATTAAAAGGAATTTGAATTCTCATAGCTAGCAGGAGTCAA
TGGGAAAAACCCATTGGAGCCAAGTACACTGACTCAATAGGGACTTTCCATTGGGTTTTGCCCAGTACATAAGGTCAATAGGGGGTGAGTCAACAGGAAAGTCCCATTGGAGCC
AAGTACATTGAGTCAATAGGGACTTTCCAATGGGTTTTGCCCAGTACATAAGGTCAATGGGAGGTAAGCCAATGGGTTTTTCCCATTACTGACATGTATACTGAGTCATTAGGG
ACTTTCCAATGGGTTTTGCCCAGTACATAAGGTCAATAGGGGTGAATCAACAGGAAAGTCCCATTGGAGCCAAGTACACTGAGTCAATAGGGACTTTCCATTGGGTTTTGCCCA
GTACAAAAGGTCAATAGGGGGTGAGTCAATGGGTTTTTCCCATTATTGGCACATACATAAGGTCAATAGGGGTGACTAGTGGAGAAGAGCATGCTTGAGGGCTGAGTGCCCCTC
AGTGGGCAGAGAGCACATGGCCCACAGTCCCTGAGAAGTTGGGGGGAGGGGTGGGCAATTGAACTGGTGCCTAGAGAAGGTGGGGCTTGGGTAAACTGGGAAAGTGATGTGGTG
TACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCACTGAC
TGTCTATGCCTGGGAAAGGGTGGGCAGGAGATGGGGCAGTGCAGGAAAAGTGGCACTATGAACCCTGCAGCCCTAGACAATTGTACTAACCTTCTTCTCTTTCCTCTCCTGACA
GGTTGGTAACCAAGCCACCATGGTCCTCCAGACACAGGTGTTCATCAGCCTGCTGCTGTGGATCAGTGGTGCCTATGGACAGGTCCAGCTGCAAGAGTCTGGCCCTGGACTTGT
CAGACCCAGCCAGACACTGAGCCTGACCTGTACAGTCTCTGGCTTCAGCCTGACCAGCTACTCTGTGCACTGGGTCAGACAGCCTCCAGGCAGAGGACTGGAATGGCTGGGAGT
GATCTGGGCCAGTGGTGGCACAGACTACAACTCTGCCCTGATGAGCAGACTGAGCATCCTGAAGGACAACAGCAAGAACCAGGTGTCCCTGAGACTGTCCTCTGTGACAGCTGC
TGATACAGCTGTGTACTTCTGTGCCAGAGATCCTCCTAGCTCTCTGCTGAGACTGGACTACTGGGGCCAGGGCACAACAGTGACAGTGTCCAGTGCCAGCACAAAGGGCCCCTC
TGTGTTTCCTCTGGCTCCCAGCAGCAAGAGCACCAGTGGTGGAACTGCTGCCCTGGGCTGTCTGGTCAAGGACTACTTTCCTGAGCCTGTGACTGTGTCCTGGAACTCTGGGGC
TCTGACATCTGGGGTGCACACATTCCCTGCTGTGCTGCAATCCTCTGGCCTGTACAGCCTCAGCTCTGTGGTCACAGTGCCTAGCTCTAGCCTGGGCACCCAGACCTACATCTG
CAATGTGAACCACAAGCCTAGCAACACCAAGGTGGACAAGAAGGCTGAGCCCAAGAGCTGTGACAAGACCCACACCTGTCCTCCATGTCCTGCTCCAGAGCTGCTTGGAGGACC
CAGTGTGTTCCTGTTTCCTCCAAAGCCAAAGGACACCCTGATGATCAGCAGAACCCCTGAAGTGACCTGTGTGGTGGTGGATGTGTCCCATGAGGACCCTGAAGTCAAGTTCAA
TTGGTATGTGGATGGTGTTGAGGTGCACAATGCCAAGACCAAGCCTAGAGAGGAACAGTACAACAGCACCTACAGAGTGGTGTCAGTGCTGACAGTGCTGCACCAGGACTGGCT
GAATGGCAAAGAGTACAAGTGCAAGGTGTCCAACAAGGCCCTGCCTGCTCCTATTGAAAAGACCATCAGCAAGGCCAAGGGCCAGCCTAGGGAACCCCAGGTTTACACACTGCC
ACCTAGCAGAGATGAGCTGACCAAAAATCAGGTTTCCCTGACCTGCCTGGTTAAGGGCTTCTACCCCTCTGACATTGCTGTGGAATGGGAGAGCAATGGCCAGCCTGAGAACAA
CTACAAGACAACCCCTCCTGTGCTGGACTCTGATGGCTCATTCTTCCTGTACTCCAAGCTGACTGTGGACAAAAGCAGATGGCAGCAAGGCAATGTGTTCAGCTGCTCTGTGAT
GCATGAGGCCCTGCACAACCACTACACCCAGAAGTCCCTGTCTCTGAGCCCTGGCAAGTGAAGATCTACTTCTGGCTAATAAAAGATCAGAGCTCTAGTGATCTGTGTGTTGGT
TTTTTGTGTCTGCATTCTAGCAGAGCCCCACTGTGTTCATCTTACAGATGGAAATACTGACATTCAGAGGAGTTAGTTAACTTGCCTAGGTGATTCAGCTAATAAGTGCAAGAA
AGATTTCAATCCAAGGTGATTTGATTCTGAAGCCTGTGCTAATCACATTACACCAAGCTACAACTTCATTTATAAATAATAAGTCAGCTTTCAAGGGCCTTTCAGGTGTCCTGC
ACTTCTACAAGCTGTGCCATTTAGTGAACACAAAATGAGCCTTCTGATGAAGTAGTCTTTTCATTATTTCAGATATTAGAACACTAAAATTCTTAGCTGCCAGCTGATTGAAGG
CTGGGACAAAATTCAAACATGCATCTACAACAATATATATCTCAATGTTAGTCTCCAAATTCTATTGACTTCAACTCAAGAGAATATAAAGAGCTAGTCTTTATACACTCTTTA
AGGTATGATATCATCTGGAAAGTAACAAAATTGATGCAAATTTGAATGAACTTTATCATGGTGTATTTACACAATGTGTTTCTTCTCCCTGCAATGTATTTCTTTCTCTAATTC
CTTCCATTTGATCTTTCATACACAATCTGGTTCTGATGTATGTTTTTTGGATGCACTTTTCAACTCCAAAAGACAGAGCTAGTTACTTTCTTCCTGGTGCTCCAAGCACTGTAT
TTGTATCTGTATTCAAGCCCTTTGCAATATTGTACTGGATCATTATTTCACCTCTAGGATGGCTTCCCCAGGCAACTTGTGTTCACCCAGAGACTACATTTTGTATCTTGTTGA
CCTTTGAACTTCCACCAGTGTCTAAAAATAATATGTATGCAAAATTACTTGCTATGAGAATGTATAATTAAACAATATAAAAAGGAGAAGCAAGGAGAGAAACACAGGTGTGTA
TTTGTGTTTGTGTGCTTAAAAGGCAGTGTGGAAAAGGAAGAAATGCCATTTATAGTGAGGAGACAAAGTTATATTACCTCTTATCTGGCTTTTAAGGAGATTTTGCTGAGCTAA
AAATCCTATATTCATAGAAAAGCCTTACCTGAGTTGCCAATACCTCAATTCAGTCTAGCATGTTACATAACTTATGGTAAATGGCCTGCCTGGCTGACTGCCCAATGACCCCTG
CCCAATGATGTCAATAATGATGTATGTTCCCATGTAATGCCAATAGGGACTTTCCATTGATGTCAATGGGTGGAGTATTTATGGTAACTGCCCACTTGGCAGTACATCAAGTGT
ATCATATGCCAAGTATGCCCCCTATTGATGTCAATGATGGTAAATGGCCTGCCTGGCATTATGCCCAGTACATGACCTTATGGGACTTTCCTACTTGGCAGTACATCTATGTAT
TAGTCATTGCTATTATCTAGCACTAGTGGAGAAGAGCATGCTTGAGGGCTGAGTGCCCCTCAGTGGGCAGAGAGCACATGGCCCACAGTCCCTGAGAAGTTGGGGGGAGGGGTG
GGCAATTGAACTGGTGCCTAGAGAAGGTGGGGCTTGGGTAAACTGGGAAAGTGATGTGGTGTACTGGCTCCACCTTTTTCCCCAGGGTGGGGGAGAACCATATATAAGTGCAGT
AGTCTCTGTGAACATTCAAGCTTCTGCCTTCTCCCTCCTGTGAGTTTGGTAAGTCACTGACTGTCTATGCCTGGGAAAGGGTGGGCAGGAGATGGGGCAGTGCAGGAAAAGTGG
CACTATGAACCCTGCAGCCCTAGACAATTGTACTAACCTTCTTCTCTTTCCTCTCCTGACAGGTTGGTAACCAAGCCACCATGGTGCTGCAAACCCAGGTTTTCATTTCTCTGC
TCCTCTGGATTAGTGGTGCTTATGGGGACATTGTGATGACACAGAGCCCTAGCAGCCTGTCTGCCTCTGTGGGAGACAGAGTGACCATCACATGCAAGTCCAGCCAGAGTCTGC
TGAACTCTGGCAACCAGAAGAACTACCTGGCCTGGTATCAGCAAAAGCCTGGCAAGGCCCCTAAGCTGCTCATCTATGGGGCCAGCACCAGAGAGTCTGGGGTCCCAGATAGAT
TCTCTGGCTCTGGATCTGGCACTGACTTCACCTTCACCATCAGCTCCCTGCAACCAGAGGACATTGCCACCTACTACTGCCAGAATGTGCACAGCTTCCCATTCACCTTTGGAC
AGGGCACTAAGGTGGAAATCAAGAGGACTGTGGCTGCTCCTTCTGTGTTCATCTTCCCACCATCAGATGAACAGCTGAAGAGTGGCACAGCCTCTGTTGTGTGCCTGCTCAACA
ACTTCTACCCTAGAGAAGCCAAGGTGCAGTGGAAAGTGGACAATGCCCTCCAGTCTGGCAACAGCCAAGAATCTGTGACTGAGCAGGACTCCAAGGACAGCACATACAGCCTGA
GCAGCACACTGACCCTGAGCAAGGCTGACTATGAGAAGCACAAAGTCTATGCCTGTGAAGTGACACACCAGGGCCTGTCTAGCCCAGTGACCAAGTCCTTCAACAGGGGAGAGA
GCTGAAGATCTACTTCTGGCTAATAAAAGATCAGAGCTCTAGTGATCTGTGTGTTGGTTTTTTGTGTCTGCATTCTAGCAGTCAATATGTTCACCCCAAAAAAGCTGTTTGTTA
ACTTGTCAACCTCATTCTAAAATGTATATAGAAGCCCAAAAGACAATAACAAAAATATTCTTGTAGAACAAAATGGGAAAGAATGTTCCACTAAATATCAAGATTTAGAGCAAA
GCATGAGATGTGTGGGGATAGACAGTGAGGCTGATAAAATAGAGTAGAGCTCAGAAACAGACCCATTGATATATGTAAGTGACCTATGAAAAAAATATGGCATTTTACAATGGG
AAAATGATGGTCTTTTTCTTTTTTAGAAAAACAGGGAAATATATTTATATGTAAAAAATAAAAGGGAACCCATATGTCATACCATACACACAAAAAAATTCCAGTGAATTATAA
GTCTAAATGGAGAAGGCAAAACTTTAAATCTTTTAGAAAATAATATAGAAGCATGCCATCAAGACTTCAGTGTAGAGAAAAATTTCTTATGACTCAAAGTCCTAACCACAAAGA
AAAGATTGTTAATTAGATTGCATGAATATTAAGACTTATTTTTAAAATTAAAAAACCATTAAGAAAAGTCAGGCCATAGAATGACAGAAAATATTTGCAACACCCCAGTAAAGA
GAATTGTAATATGCAGATTATAAAAAGAAGTCTTACAAATCAGTAAAAAATAAAACTAGACAAAAATTTGAACAGATGAAAGAGAAACTCTAAATAATCATTACACATGAGAAA
CTCAATCTCAGAAATCAGAGAACTATCATTGCATATACACTAAATTAGAGAAATATTAAAAGGCTAAGTAACATCTGTGGCTTAATTAATCTAGCTCTAGTGATCAGCAGTTCA
ACCTGTTGATAGTATGTACTAAGCTCTCATGTTTAATGTACTAAGCTCTCATGTTTAATGAACTAAACCCTCATGGCTAATGTACTAAGCTCTCATGGCTAATGTACTAAGCTC
TCATGTTTCATGTACTAAGCTCTCATGTTTGAACAATAAAATTAATATAAATCAGCAACTTAAATAGCCTCTAAGGTTTTAAGTTTTATAAGAAAAAAAAGAATATATAAGGCT
TTTAAAGGTTTTAAGGTTTCCTAGGTTATCCTCATATGAGCTCTTAGAAAAACTCATCCAGCATCAAATGAAACTGCAATTTATTCATATCAGGATTATCAATACCATATTTTT
GAAAAAGTCTTTTCTGTAATGAAGGAGAAAACTCACCCAGGCAGTTCCATAGGATGGCAAGATCCTGGTATCTGTCTGCAATTCCAACTCTTCCAACATCAATACAACCTATTA
ATTTCCCCTCATCAAAAATAAGGTTATCAAGTGAGAAATCACCATGAGTGACCACTGAATCTGGTGAGAATGGCAAAAGATTATGCATTTCTTTCCAGACTTGTTCAACAGGCC
AGCCATTTCTCTCATCATCAAAATCACTGGCATCAACCAAACCATTATTCATTCTTGATTGGGCCTGAGCCAGTCTAAATACTCTATCAGAGTTAAAAGGACAATTACAAACAG
GAATGGAATGCAATCTTCTCAGGAACACTGCCAGGGCATCAACAATATTTTCACCTGAATCAGGATATTCTTCCAATACCTGGAATGCTGTTTTCCCTGGGATGGCAGTGGTGA
GTAACCATGCATCATCAGGAGTTCTGATAAAATGCTTGATGGTTGGAAGAGGCATAAATTCAGTCAGCCAGTTTAGTCTGACCATCTCATCTGTAACATCATTGGCAACAGAAC
CTTTGCCATGTTTCAGAAACAACTCTGGGGCATCTGGCTTCCCATACAATCTATAGATTGTGGCACCTGATTGCCCAACATTATCTCTAGCCCATTTATACCCATATAAATCAG
CATCCATGTTGGAATTTAATCTTGGCCTGGAGCAAGAGGTTTCTCTTTGAATATGGCTCATACATGTGCACCTCCTATAGTGAGTTGTATTATACTATGCAGATATACTATGCC
AATGTTTAATTGTCAG

FIG. 92

Dual 5J8 H-L -BV3

DraIII-βGlo RI-Nhe-ΔmCMVΔEF1-I126-BstEII-5J8H-hIgG-BglII-MixpA-21q21 S/MAR-ΔhCMV-ΔEF1-RV-I126-BstEII-5J8L-hIgL-BglII-MixpA-IFNβ S/MAR-BV3 (SEQ ID NO:84)

CACTATGTGTTAATTAAAATTATCTCTAAGGCATGTGAACTGGCTGTCTTGGTTTTCATCTGTACTTCATCTGCTACCTCTGTGACCTGAAACATATTTATAATTCCATTAAGCTGTGCATATG
ATAGATTTATCATATGTATTTTCCTTAAAGGATTTTTGTAAGAACTAATTGAATTGATACCTGTAAAGTCTTTATCACACTACCCAATAAATAATAAATCTCTTTGTTCAGCTCTCTGTTTCTAT
AAATATGTACCAGTTTTATTGTTTTTAGTGGTAGTGATTTTATTCTCTTTCTATATATATACACACACATGTGTGCATTCATAAATATATACAATTTTTATGAATAAAAAATTATTAGCAATCA
ATATTGAAAACCACTGATTTTTGTTTATGTGAGCAAACAGCAGATTAAAAGGAATTTGAATTCTCATAGCTAGCAGGAGTCAATGGGAAAAACCCATTGGAGCCAAGTACACTGACTCAA
TAGGGACTTTCCATTGGGTTTTGCCCAGTACATAAGGTCAATAGGGGGTGAGTCAACAGGAAAGTCCCATTGGAGCCAAGTACATTGAGTCAATAGGGACTTTCCAATGGGTTTTGCCCA
GTACATAAGGTCAATGGGAGGTAAGCCAATGGGTTTTTCCCATTACTGACATGTATACTGAGTCATTAGGGACTTTCCAATGGGTTTTGCCCAGTACATAAGGTCAATAGGGGTGAATCAA
CAGGAAAGTCCCATTGGAGCCAAGTACACTGAGTCAATAGGGACTTTCCATTGGGTTTTGCCCAGTACAAAAGGTCAATAGGGGGTGAGTCAATGGGTTTTTCCCATTATTGGCACATACA
TAAGGTCAATAGGGGTGACTAGTGGAGAAGAGCATGCTTGAGGGCTGAGTGCCCCTCAGTGGGCAGAGAGCACATGGCCCACAGTCCCTGAGAAGTTGGGGGGAGGGGTGGGCAATT
GAACTGGTGCCTAGAGAAGGTGGGGCTTGGGTAAACTGGGAAAGTGATGTGGTGTACTGGCTCCACCTTTTTCCCCAGGGTGGGGGAGAACCATATATAAGTGCAGTAGTCTCTGTGAA
CATTCAAGCTTCTGCCTTCTCCCTCCTGTGAGTTTGGTAAGTCACTGACTGTCTATGCCTGGGAAAGGGTGGGCAGGAGATGGGGCAGTGCAGGAAAAGTGGCACTATGAACCCTGCAGC
CCTAGACAATTGTACTAACCTTCTTCTCTTTCCTCTCCTGACAGGTTGGTAACCAAGCCACCATGGGATGGTCCCTGATCCTGCTGTTTCTGGTGGCTGTGGCCACCAGAGTGCTGTCTGAAG
TGCAGCTGGTGGAATCTGGCCCTGGCCTGGTTAAGCCCTCTGACATCCTGAGCCTGACCTGTGCTGTGTCTGGCTACAGCATCAGCAGCAACTACTACTGGGGCTGGATCAGACAGCCTCC
TGGCAAAGGCCTGGAATGGATTGGCAGCATCTACCACTCTGGCTCCACCTACTACAAGCCCAGCCTGGAAAGCAGACTGGGCATCTCTGTGGACACCAGCAAGAACCAGTTCAGCCTGAA
GCTGAGCTTTGTGTCTGCTGCTGACACTGCTGTGTACTACTGTGCCAGACATGTTAGGAGTGGCTACCCTGACACAGCCTACTACTTTGATAAGTGGGGCCAGGGCACCCTGGTCACAGTG
TCTGCTTCTACAAAGGGCCCCTCTGTGTTCCCACTGGCTCCTAGCAGCAAGAGCACCAGTGGTGGAACAGCTGCCCTGGGCTGTCTGGTCAAGGACTACTTTCCTGAGCCAGTGACAGTGTC
CTGGAACTCTGGGGCTCTGACTTCTGGGGTGCACACATTCCCTGCTGTGCTCCAGTCCTCTGGCCTGTACAGCCTGTCCTCTGTGGTCACTGTGCCAAGCTCTAGCCTGGGCACCCAGACCTA
CATCTGCAATGTGAACCACAAGCCTAGCAACACCAAGGTGGACAAGAAGGCTGAGCCCAAGAGCTGTGACAAGACCCACACCTGTCCTCCATGTCCTGCTCCAGAGCTGCTTGGAGGACC
TTCTGTGTTTCTGTTCCCTCCAAAGCCAAAGGACACCCTGATGATCAGCAGAACCCCTGAAGTGACCTGTGTGGTGGTGGATGTGTCCCATGAGGACCCAGAAGTGAAGTTCAATTGGTAT
GTGGATGGTGTTGAGGTGCACAATGCCAAGACCAAGCCTAGAGAGGAACAGTACAACAGCACCTACAGGGTTGTGTCAGTGCTGACTGTGCTGCACCAGGACTGGCTGAATGGCAAAG
AGTACAAGTGCAAGGTGTCCAACAAGGCCCTGCCTGCTCCTATTGAAAAGACCATCAGCAAGGCCAAGGGACAGCCTAGGGAACCCCAGGTGTACACACTGCCACCTAGCAGAGATGAG
CTGACCAAGAATCAGGTGTCCCTGACATGCCTTGTGAAGGGCTTCTACCCTTCTGACATTGCAGTGGAATGGGAGAGCAATGGCCAGCCTGAGAACAACTACAAGACAACCCCTCCTGTGC
TGGACTCTGATGGCTCATTCTTCCTGTACTCCAAGCTGACAGTGGACAAGTCCAGATGGCAGCAAGGCAATGTGTTCAGCTGCTCTGTGATGCATGAGGCCCTGCACAACCACTACACACA
GAAGTCCCTGTCTCTGAGCCCTGGCAAGTGAAGATCTACTTCTGGCTAATAAAAGATCAGAGCTCTAGTGATCTGTGTGTTGGTTTTTTGTGTCTGCATTCTAGCAGAGCCCCACTGTGTTC
ATCTTACAGATGGAAATACTGACATTCAGAGGAGTTAGTTAACTTGCCTAGGTGATTCAGCTAATAAGTGCAAGAAAGATTTCAATCCAAGGTGATTTGATTCTGAAGCCTGTGCTAATCA
CATTACACCAAGCTACAACTTCATTTATAAATAATAAGTCAGCTTTCAAGGGCCTTTCAGGTGTCCTGCACTTCTACAAGCTGTGCCATTTAGTGAACACAAAATGAGCCTTCTGATGAAGT
AGTCTTTTCATTATTTCAGATATTAGAACACTAAAATTCTTAGCTGCCAGCTGATTGAAGGCTGGGACAAAATTCAAACATGCATCTACAACAATATATATCTCAATGTTAGTCTCCAAATTC
TATTGACTTCAACTCAAGAGAATATAAAGAGCTAGTCTTTATACACTCTTTAAGGTATGATATCATCTGGAAAGTAACAAAATTGATGCAAATTTGAATGAACTTTATCATGGTGTATTTAC
ACAATGTGTTTCTTCTCCCTGCAATGTATTTCTTTCTCTAATTCCTTCCATTTGATCTTTCATACACAATCTGGTTCTGATGTATGTTTTTTGGATGCACTTTTCAACTCCAAAAGACAGAGCTA
GTTACTTTCTTCCTGGTGCTCCAAGCACTGTATTTGTATCTGTATTCAAGCCCTTTGCAATATTGTACTGGATCATTATTTCACCTCTAGGATGGCTTCCCCAGGCAACTTGTGTTCACCCAGA
GACTACATTTTGTATCTTGTTGACCTTTGAACTTCCACCAGTGTCTAAAAATAATATGTATGCAAAATTACTTGCTATGAGAATGTATAATTAAACAATATAAAAAGGAGAAGCAAGGAGA
GAAACACAGGTGTGTATTTGTGTTTGTGTGCTTAAAAGGCAGTGTGGAAAAGGAAGAAATGCCATTTATAGTGAGGAGACAAAGTTATATTACCTCTTATCTGGCTTTTAAGGAGATTTT
GCTGAGCTAAAAATCCTATATTCATAGAAAAGCCTTACCTGAGTTGCCAATACCTCAATTCAGTCTAGCATGTTACATAACTTATGGTAAATGGCCTGCCTGGCTGACTGCCCAATGACCCC
TGCCCAATGATGTCAATAATGATGTATGTTCCCATGTAATGCCAATAGGGACTTTCCATTGATGTCAATGGGTGGAGTATTTATGGTAACTGCCCACTTGGCAGTACATCAAGTGTATCATA
TGCCAAGTATGCCCCCTATTGATGTCAATGATGGTAAATGGCCTGCCTGGCATTATGCCCAGTACATGACCTTATGGGACTTTCCTACTTGGCAGTACATCTATGTATTAGTCATTGCTATTA
TCTAGCACTAGTGGAGAAGAGCATGCTTGAGGGCTGAGTGCCCCTCAGTGGGCAGAGAGCACATGGCCCACAGTCCCTGAGAAGTTGGGGGGAGGGGTGGGCAATTGAACTGGTGCCT
AGAGAAGGTGGGGCTTGGGTAAACTGGGAAAGTGATGTGGTGTACTGGCTCCACCTTTTTCCCCAGGGTGGGGGAGAACCATATATAAGTGCAGTAGTCTCTGTGAACATTCAAGCTTCT
GCCTTCTCCCTCCTGTGAGTTTGGTAAGTCACTGACTGTCTATGCCTGGGAAAGGGTGGGCAGGAGATGGGGCAGTGCAGGAAAAGTGGCACTATGAACCCTGCAGCCCTAGACAATTGT
ACTAACCTTCTTCTCTTTCCTCTCCTGACAGGTTGGTAACCAAGCCACCATGGCCTGGGCTCTGCTGCTTCTGGGACTGCTGTCTCACTGCACAGGCAGTGTGACCAGCTATGTGCTGA
CCCAGCCTCCATCTGTGTCTGTGGCTCCAGGGGAGACAGCCAGAATCAGCTGTGGTGGCAACAACATTGGCACAAAGGTGCTGCACTGGTATCAGCAGACTCCAGGACAGGCAC
CAGTGCTGGTGGTGTATGATGACTCTGACAGACCCTCTGGCATCCCAGAGAGGTTCTCTGGCAGCAACTCTGGCAACACAGCCACACTGACCATCTCCAGAGTGGAAGTTGGAG
ATGAGGCTGATTACTACTGCCAAGTGTGGGACATCAGCACAGACCAGGCTGTGTTTGGTGGTGGCACCAAGCTCACTGTGCTGGGCCAACCTAAAGCTGCCCCTTCTGTGACAC
TGTTCCCACCTAGCTCTGAGGAACTCCAGGCTAACAAGGCCACACTTGTGTGCCTGATCAGTGACTTCTACCCAGGGGCTGTGACTGTGGCCTGGAAGGCTGATAGCAGCCCTG
TGAAGGCTGGGGTTGAGACAACCACACCTAGCAAGCAGAGCAACAACAAATATGCTGCCAGCAGCTACCTGAGTCTGACCCCTGAGCAGTGGAAGTCCCACAGATCCTACAGCT
GTCAAGTGACCCATGAGGGCTCCACAGTGGAAAAGACAGTGGCCCCTACAGAGTGCTCCTGAAGATCTACTTCTGGCTAATAAAAGATCAGAGCTCTAGTGATCTGTGTGTTGGTTTT
TTGTGTCTGCATTCTAGCAGTCAATATGTTCACCCCAAAAAAGCTGTTTGTTAACTTGTCAACCTCATTCTAAAATGTATATAGAAGCCCAAAAGACAATAACAAAAATATTCTTGTAGAAC
AAAATGGGAAAGAATGTTCCACTAAATATCAAGATTTAGAGCAAAGCATGAGATGTGTGGGGATAGACAGTGAGGCTGATAAAATAGAGTAGAGCTCAGAAACAGACCCATTGATATA
TGTAAGTGACCTATGAAAAAAATATGGCATTTTACAATGGGAAAATGATGGTCTTTTTCTTTTTTAGAAAAACAGGGAAATATATTTATATGTAAAAAATAAAAGGGAACCCATATGTCAT
ACCATACACACAAAAAAATTCCAGTGAATTATAAGTCTAAATGGAGAAGGCAAAACTTTAAATCTTTTAGAAAATAATATAGAAGCATGCCATCAAGACTTCAGTGTAGAGAAAAATTTC
TTATGACTCAAAGTCCTAACCACAAAGAAAAGATTGTTAATTAGATTGCATGAATATTAAGACTTATTTTTAAAATTAAAAAACCATTAAGAAAAGTCAGGCCATAGAATGACAGAAAAT
ATTTGCAACACCCCAGTAAAGAGAATTGTAATATGCAGATTATAAAAAGAAGTCTTACAAATCAGTAAAAAATAAAACTAGACAAAAAATTTGAACAGATGAAAGAGAAACTCTAAATAA
TCATTACACATGAGAAACTCAATCTCAGAAATCAGAGAACTATCATTGCATATACACTAAATTAGAGAAATATTAAAAGGCTAAGTAACATCTGTGGCTTAATTAATCTAGCTCTAGTGAT
CAGCAGTTCAACCTGTTGATAGTATGTACTAAGCTCTCATGTTTAATGTACTAAGCTCTCATGTTTAATGAACTAAACCCTCATGGCTAATGTACTAAGCTCTCATGGCTAATGTACTAAGCT
CTCATGTTTCATGTACTAAGCTCTCATGTTTGAACAATAAAATTAATATAAATCAGCAACTTAAATAGCCTCTAAGGTTTTAAGTTTTATAAGAAAAAAAAGAATATATATAAGGCTTTTAAAG
GTTTTAAGGTTTCCTAGGTTATCCTCATATGAGCTCTTAGAAAAACTCATCCAGCATCAAATGAAACTGCAATTTATTCATATCAGGATTATCAATACCATATTTTTGAAAAAGTCTTTTCTGT
AATGAAGGAGAAAACTCACCCAGGCAGTTCCATAGGATGGCAAGATCCTGGTATCTGTCTGCAATTCCAACTCTTCCAACATCAATACAACCTATTAATTTCCCCTCATCAAAAATAAGGTT
ATCAAGTGAGAAATCACCATGAGTGACCACTGAATCTGGTGAGAATGGCAAAAGATTATGCATTTCTTTCCAGACTTGTTCAACAGGCCAGCCATTTCTCTCATCATCAAAATCACTGGCAT
CAACCAAACCATTATTCATTCTTGATTGGGCCTGAGCCAGTCTAAATACTCTATCAGAGTTAAAAGGACAATTACAAACAGGAATGGAATGCAATCTTCTCAGGAACACTGCCAGGGCATC
AACAATATTTTCACCTGAATCAGGATATTCTTCCAATACCTGGAATGCTGTTTTCCCTGGGATGGCAGTGGTGAGTAACCATGCATCATCAGGAGTTCTGATAAAATGCTTGATGGTTGGAA
GAGGCATAAATTCAGTCAGCCAGTTTAGTCTGACCATCTCATCTGTAACATCATTGGCAACAGAACCTTTGCCATGTTTCAGAAACAACTCTGGGGCATCTGGCTTCCCATACAATCTATAG
ATTGTGGCACCTGATTGCCCAACATTATCTCTAGCCCATTTATACCCATATAAATCAGCATCCATGTTGGAATTTAATCTTGGCCTGGAGCAAGAGGTTTCTCTTTGAATATGGCTCATACAT
GTGCACCTCCTATAGTGAGTTGTATTATACTATGCAGATATACTATGCCAATGTTTAATTGTCAG

FIG. 94

101217 # 6 : NewM-G-BV3 DraIII-βGlo RI-Nhe-ΔmCMVΔEF1I126-BstEII **-NewM 2B6-H-*F3P2A*-L-BglII-MixpA-21q21 S/MAR-ΔmCMV -ΔEF1I126-BstEII-ΔhGCSF-BglII-MixpA-IFNβ S/MAR-BV3 (SEQ ID NO:85)**

CACTATGTGTTAATTAAAATTATCTCTAAGGCATGTGAACTGGCTGTCTTGGTTTTCATCTGTACTTCATCTGCTACCTCTGTGACCTGAAACATATTTATAATTCCATTAAGCTGTGCATATGATAGAT
TTATCATATGTATTTTCCTTAAAGGATTTTTGTAAGAACTAATTGAATTGATACCTGTAAAGTCTTTATCACACTACCCAATAAATAATAAATCTCTTTGTTCAGCTCTCTGTTTCTATAAATATGTACCA
GTTTTATTGTTTTTAGTGGTAGTGATTTTATTCTCTTTCTATATATATACACACACATGTGTGCATTCATAAATATATACAATTTTTATGAATAAAAAATTATTAGCAATCAATATTGAAAACCACTGATT
TTTGTTTATGTGAGCAAACAGCAGATTAAAAGGAATTTGAATTCTCATAGCTAGCAGGAGTCAATGGGAAAAACCCATTGGAGCCAAGTACACTGACTCAATAGGGACTTTCCATTGGGTTTTGCCC
AGTACATAAGGTCAATAGGGGGTGAGTCAACAGGAAAGTCCCATTGGAGCCAAGTACATTGAGTCAATAGGGACTTTCCAATGGGTTTTGCCCAGTACATAAGGTCAATGGGAGGTAAGCCAATG
GGTTTTTCCCATTACTGACATGTATACTGAGTCATTAGGGACTTTCCAATGGGTTTTGCCCAGTACATAAGGTCAATAGGGGTGAATCAACAGGAAAGTCCCATTGGAGCCAAGTACACTGAGTCAA
TAGGGACTTTCCATTGGGTTTTGCCCAGTACAAAAGGTCAATAGGGGGTGAGTCAATGGGTTTTTCCCATTATTGGCACATACATAAGGTCAATAGGGGTGACTAGTGGAGAAGAGCATGCTTGAG
GGCTGAGTGCCCCTCAGTGGGCAGAGAGCACATGGCCCACAGTCCCTGAGAAGTTGGGGGGAGGGGTGGGCAATTGAACTGGTGCCTAGAGAAGGTGGGGCTTGGGTAAACTGGGAAAGTGAT
GTGGTGTACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCACTGACTGTCTATG
CCTGGGAAAGGGTGGGCAGGAGATGGGGCAGTGCAGGAAAAGTGGCACTATGAACCCTGCAGCCCTAGACAATTGTACTAACCTTCTTCTCTTTCCTCTCCTGACAGGTTGGTAACCAAGCCACCA
TGGTCCTCCAGACACAGGTGTTCATCAGCCTGCTGCTGTGGATCAGTGGTGCCTATGGACAGGTCCAGCTGCAAGAGTCTGGCCCTGGACTTGTCAGACCCAGCCAGACACTGAGCCTGACCTGTA
CAGTCTCTGGCTTCAGCCTGACCAGCTACTCTGTGCACTGGGTCAGACAGCCTCCAGGCAGAGGACTGGAATGGCTGGGAGTGATCTGGGCCAGTGGTGGCACAGACTACAACTCTGCCCTGATG
AGCAGACTGAGCATCCTGAAGGACAACAGCAAGAACCAGGTGTCCCTGAGACTGTCCTCTGTGACAGCTGCTGATACAGCTGTGTACTTCTGTGCCAGAGATCCTCCTAGCTCTCTGCTGAGACTGG
ACTACTGGGGCCAGGGCACAACAGTGACAGTGTCCAGTGCCAGCACAAAGGGCCCCTCTGTGTTTCCTCTGGCTCCCAGCAGCAAGAGCACCAGTGGTGGAACTGCTGCCCTGGGCTGTCTGGTCA
AGGACTACTTTCCTGAGCCTGTGACTGTGTCCTGGAACTCTGGGGCTCTGACATCTGGGGTGCACACATTCCCTGCTGTGCTGCAATCCTCTGGCCTGTACAGCCTCAGCTCTGTGGTCACAGTGCCT
AGCTCTAGCCTGGGCACCCAGACCTACATCTGCAATGTGAACCACAAGCCTAGCAACACCAAGGTGGACAAGAAGGCTGAGCCCAAGAGCTGTGACAAGACCCACACCTGTCCTCCATGTCCTGCT
CCAGAGCTGCTTGGAGGACCCAGTGTGTTCCTGTTTCCTCCAAAGCCAAAGGACACCCTGATGATCAGCAGAACCCCTGAAGTGACCTGTGTGGTGGTGGATGTGTCCCATGAGGACCCTGAAGTC
AAGTTCAATTGGTATGTGGATGGTGTTGAGGTGCACAATGCCAAGACCAAGCCTAGAGAGGAACAGTACAACAGCACCTACAGAGTGGTGTCAGTGCTGACAGTGCTGCACCAGGACTGGCTGAA
TGGCAAAGAGTACAAGTGCAAGGTGTCCAACAAGGCCCTGCCTGCTCCTATTGAAAAGACCATCAGCAAGGCCAAGGGCCAGCCTAGGGAACCCCAGGTTTACACACTGCCACCTAGCAGAGATG
AGCTGACCAAAAATCAGGTTTCCCTGACCTGCCTGGTTAAGGGCTTCTACCCCTCTGACATTGCTGTGGAATGGGAGAGCAATGGCCAGCCTGAGAACAACTACAAGACAACCCCTCCTGTGCTGG
ACTCTGATGGCTCATTCTTCCTGTACTCCAAGCTGACTGTGGACAAAAGCAGATGGCAGCAAGGCAATGTGTTCAGCTGCTCTGTGATGCATGAGGCCCTGCACAACCACTACACCCAGAAGTCCCT
GTCTCTGAGCCCTGGCAAG*AGAAAGAGAAGGAGTGGCTCTGGGGCCACCAACTTTAGCCTGCTGAAACAGGCTGGGGATGTTGAAGAGAACCCTGGACCT*ATGGTGCTGCAAACCCAGGTTTTCA
TTTCTCTGCTCCTCTGGATTAGTGGTGCTTATGGGGACATTGTGATGACACAGAGCCCTAGCAGCCTGTCTGCCTCTGTGGGAGACAGAGTGACCATCACATGCAAGTCCAGCCAGAGTCTGCTGAA
CTCTGGCAACCAGAAGAACTACCTGGCCTGGTATCAGCAAAAGCCTGGCAAGGCCCCTAAGCTGCTCATCTATGGGGCCAGCACCAGAGAGTCTGGGGTCCCAGATAGATTCTCTGGCTCTGGATC
TGGCACTGACTTCACCTTCACCATCAGCTCCCTGCAACCAGAGGACATTGCCACCTACTACTGCCAGAATGTGCACAGCTTCCCATTCACCTTTGGACAGGGCACTAAGGTGGAAATCAAGAGGACT
GTGGCTGCTCCTTCTGTGTTCATCTTCCCACCATCAGATGAACAGCTGAAGAGTGGCACAGCCTCTGTTGTGTGCCTGCTCAACAACTTCTACCCTAGAGAAGCCAAGGTGCAGTGGAAAGTGGACA
ATGCCCTCCAGTCTGGCAACAGCCAAGAATCTGTGACTGAGCAGGACTCCAAGGACAGCACATACAGCCTGAGCAGCACACTGACCCTGAGCAAGGCTGACTATGAGAAGCACAAAGTCTATGCCT
GTGAAGTGACACACCAGGGCCTGTCTAGCCCAGTGACCAAGTCCTTCAACAGGGGAGAGAGCTGAAGATCTACTTCTGGCTAATAAAAGATCAGAGCTCTAGTGATCTGTGTGTTGGTTTT
TTGTGTCTGCATTCTAGCAGAGCCCCACTGTGTTCATCTTACAGATGGAAATACTGACATTCAGAGGAGTTAGTTAACTTGCCTAGGTGATTCAGCTAATAAGTGCAAGAAAGATTTC
AATCCAAGGTGATTTGATTCTGAAGCCTGTGCTAATCACATTACACCAAGCTACAACTTCATTTATAAATAATAAGTCAGCTTTCAAGGGCCTTTCAGGTGTCCTGCACTTCTACAAG
CTGTGCCATTTAGTGAACACAAAATGAGCCTTCTGATGAAGTAGTCTTTTCATTATTTCAGATATTAGAACACTAAAATTCTTAGCTGCCAGCTGATTGAAGGCTGGGACAAAATTCA
AACATGCATCTACAACAATATATATCTCAATGTTAGTCTCCAAATTCTATTGACTTCAACTCAAGAGAATATAAAGAGCTAGTCTTTATACACTCTTTAAGGTATGATATCATCTGGA
AAGTAACAAAATTGATGCAAATTTGAATGAACTTTATCATGGTGTATTTACACAATGTGTTTCTTCTCCCTGCAATGTATTTCTTTCTCTAATTCCTTCCATTTGATCTTTCATACAC
AATCTGGTTCTGATGTATGTTTTTTGGATGCACTTTTCAACTCCAAAAGACAGAGCTAGTTACTTTCTTCCTGGTGCTCCAAGCACTGTATTTGTATCTGTATTCAAGCCCTTTGCAA
TATTGTACTGGATCATTATTTCACCTCTAGGATGGCTTCCCCAGGCAACTTGTGTTCACCCAGAGACTACATTTTGTATCTTGTTGACCTTTGAACTTCCACCAGTGTCTAAAAATAA
TATGTATGCAAAATTACTTGCTATGAGAATGTATAATTAAACAATATAAAAAGGAGAAGCAAGGAGAGAAACACAGGTGTGTATTTGTGTTTGTGTGCTTAAAAGGCAGTGTGGAAAA
GGAAGAAATGCCATTTATAGTGAGGAGACAAAGTTATATTACCTCTTATCTGGCTTTTAAGGAGATTTTGCTGAGCTAAAAATCCTATATTCATAGAAAAGCCTTACCTGAGTTGCCA
ATACCTCAATTCAGTCTAGCAGGAGTCAATGGGAAAAACCCATTGGAGCCAAGTACACTGACTCAATAGGGACTTTCCATTGGGTTTTGCCCAGTACATAAGGTCAATAGGGGGTGAG
TCAACAGGAAAGTCCCATTGGAGCCAAGTACATTGAGTCAATAGGGACTTTCCAATGGGTTTTGCCCAGTACATAAGGTCAATGGGAGGTAAGCCAATGGGTTTTTCCCATTACTGAC
ATGTATACTGAGTCATTAGGGACTTTCCAATGGGTTTTGCCCAGTACATAAGGTCAATAGGGGTGAATCAACAGGAAAGTCCCATTGGAGCCAAGTACACTGAGTCAATAGGGACTTT
CCATTGGGTTTTGCCCAGTACAAAAGGTCAATAGGGGGTGAGTCAATGGGTTTTTCCCATTATTGGCACATACATAAGGTCAATAGGGGTGACTAGTGGAGAAGAGCATGCTTGAGGG
CTGAGTGCCCCTCAGTGGGCAGAGAGCACATGGCCCACAGTCCCTGAGAAGTTGGGGGGAGGGGTGGGCAATTGAACTGGTGCCTAGAGAAGGTGGGGCTTGGGTAAACTGGGAAAGT
GATGTGGTGTACTGGCTCCACCTTTTTCCCCAGGGTGGGGGAGAACCATATATAAGTGCAGTAGTCTCTGTGAACATTCAAGCTTCTGCCTTCTCCCTCCTGTGAGTTTGGTAAGTCA
CTGACTGTCTATGCCTGGGAAAGGGTGGGCAGGAGATGGGGCAGTGCAGGAAAAGTGGCACTATGAACCCTGCAGCCCTAGACAATTGTACTAACCTTCTTCTCTTTCCTCTCCTGAC
AGGTTGGTAACCAAGCTTTCCATGGCTGGACCTGCCACCCAGAGCCCCATGAAGCTGATGGCCCTGCAGCTGCTGCTGTGGCACAGTGCACTCTGGACAGTGCAGGAAGCCACCCCCCT
GGGCCCTGCCAGCTCCCTGCCCCAGAGCTTCCTGCTCAAGTGCTTAGAGCAAGTGAGGAAGATCCAGGGGGATGGGCAGCTCTCCAGGAGAAGCTGTGTGCCACCTACAAGCTGTGC
CACCCTGAGGAGCTGGTGCTGCTGGGACACTCTCTGGGCATCCCCTGGGCTCCCCTGAGCAGCTGCCCCAGCCAGGCCCTGCAGCTGGCAGGCTGCTTGAGCCAACTCCATAGTGGCC
TTTTCCTCTACCAGGGGCTCCTGCAGGCCCTGGAAGGGATCTCCCCTGAGTTGGGTCCCACCTTGGACACACTGCAGCTGGATGTTGCTGACTTTGCCACCACCATCTGGCAGCAGAT
GGAAGAACTGGGAATGGCCCCTGCCCTGCAGCCCACCCAGGGTGCCATGCCTGCCTTTGCCTCTGCTTTCCAGAGAAGGGCAGGAGGGGTCCTGGTTGCCTCCCATCTGCAGAGCTTC
CTGGAGGTGTCCTACAGAGTTCTAAGACACCTTGCCCAGCCCTGATAGATCTACTTCTGGCTAATAAAAGATCAGAGCTCTAGTGATCTGTGTGTTGGTTTTTTGTGTCTGCATTCTAGCAGTCA
ATATGTTCACCCCAAAAAAGCTGTTTGTTAACTTGTCAACCTCATTCTAAAATGTATATAGAAGCCCAAAAGACAATAACAAAAATATTCTTGTAGAACAAAATGGGAAAGAATGTTCCACTAAATAT
CAAGATTTAGAGCAAAGCATGAGATGTGTGGGGATAGACAGTGAGGCTGATAAAATAGAGTAGAGCTCAGAAACAGACCCATTGATATATGTAAGTGACCTATGAAAAAAATATGGCATTTTACA
ATGGGAAAATGATGGTCTTTTTCTTTTTTAGAAAAACAGGGAAATATATTTATATGTAAAAAATAAAAGGGAACCCATATGTCATACCATACACACAAAAAAATTCCAGTGAATTATAAGTCTAAATG
GAGAAGGCAAAACTTTAAATCTTTTAGAAAATAATATAGAAGCATGCCATCAAGACTTCAGTGTAGAGAAAAATTTCTTATGACTCAAAGTCCTAACCACAAAGAAAAGATTGTTAATTAGATTGCA
TGAATATTAAGACTTATTTTTAAAATTAAAAAACCATTAAGAAAAGTCAGGCCATAGAATGACAGAAAATATTTGCAACACCCCAGTAAAGAGAATTGTAATATGCAGATTATAAAAAGAAGTCTTA
CAAATCAGTAAAAAATAAAACTAGACAAAAATTTGAACAGATGAAAGAGAAACTCTAAATAATCATTACACATGAGAAACTCAATCTCAGAAATCAGAGAACTATCATTGCATATACACTAAATTAG
AGAAATATTAAAAGGCTAAGTAACATCTGTGGCTTAATTAATCTAGCTCTAGTGATCAGCAGTTCAACCTGTTGATAGTATGTACTAAGCTCTCATGTTTAATGTACTAAGCTCTCATGTTTAATGAAC
TAAACCCTCATGGCTAATGTACTAAGCTCTCATGGCTAATGTACTAAGCTCTCATGTTTCATGTACTAAGCTCTCATGTTTGAACAATAAAATTAATATAAATCAGCAACTTAAATAGCCTCTAAGGTT
TTAAGTTTTATAAGAAAAAAAAGAATATATAAGGCTTTTAAAGGTTTTAAGGTTTCCTAGGTTATCCTCATATGAGCTCTTAGAAAAACTCATCCAGCATCAAATGAAACTGCAATTTATTCATATCAG
GATTATCAATACCATATTTTTGAAAAAGTCTTTTCTGTAATGAAGGAGAAAACTCACCCAGGCAGTTCCATAGGATGGCAAGATCCTGGTATCTGTCTGCAATTCCAACTCTTCCAACATCAATACAA
CCTATTAATTTCCCCTCATCAAAAATAAGGTTATCAAGTGAGAAATCACCATGAGTGACCACTGAATCTGGTGAGAATGGCAAAAGATTATGCATTTCTTTCCAGACTTGTTCAACAGGCCAGCCATT
TCTCTCATCATCAAAATCACTGGCATCAACCAAACCATTATTCATTCTTGATTGGGCCTGAGCCAGTCTAAATACTCTATCAGAGTTAAAAGGACAATTACAAACAGGAATGGAATGCAATCTTCTCA
GGAACACTGCCAGGGCATCAACAATATTTTCACCTGAATCAGGATATTCTTCCAATACCTGGAATGCTGTTTTCCCTGGGATGGCAGTGGTGAGTAACCATGCATCATCAGGAGTTCTGATAAAATG
CTTGATGGTTGGAAGAGGCATAAATTCAGTCAGCCAGTTTAGTCTGACCATCTCATCTGTAACATCATTGGCAACAGAACCTTTGCCATGTTTCAGAAACAACTCTGGGGCATCTGGCTTCCCATACA
ATCTATAGATTGTGGCACCTGATTGCCCAACATTATCTCTAGCCCATTTATACCCATATAAATCAGCATCCATGTTGGAATTTAATCTTGGCCTGGAGCAAGAGGTTTCTCTTTGAATATGGCTCATAC
ATGTGCACCTCCTATAGTGAGTTGTATTATACTATGCAGATATACTATGCCAATGTTTAATTGTCAG

FIG. 108 p53: RINhe-ΔmCMVΔEF1I126-BstEII-p53-BglII-MixpA/BV2 (SEQ ID NO:86)

CACTATGTGGACATGAATTCAATTGGCTAGCAGGAGTCAATGGGAAAAACCCATTGGAGCCAAGTACACTGACTCAATAGGGACTTTCCATTGGGTTTTGCCCAGTACATA
AGGTCAATAGGGGGTGAGTCAACAGGAAAGTCCCATTGGAGCCAAGTACATTGAGTCAATAGGGACTTTCCAATGGGTTTTGCCCAGTACATAAGGTCAATGGGAGGTA
AGCCAATGGGTTTTTCCCATTACTGACATGTATACTGAGTCATTAGGGACTTTCCAATGGGTTTTGCCCAGTACATAAGGTCAATAGGGGTGAATCAACAGGAAAGTCCCA
TTGGAGCCAAGTACACTGAGTCAATAGGGACTTTCCATTGGGTTTTGCCCAGTACAAAAGGTCAATAGGGGGTGAGTCAATGGGTTTTTCCCATTATTGGCACATACATAA
GGTCAATAGGGGTGACTAGTGGAGAAGAGCATGCTTGAGGGCTGAGTGCCCCTCAGTGGGCAGAGAGCACATGGCCCACAGTCCCTGAGAAGTTGGGGGGAGGGGTG
GGCAATTGAACTGGTGCCTAGAGAAGGTGGGGCTTGGGTAAACTGGGAAAGTGATGTGGTGTACTGGCTCCACCTTTTTCCCCAGGGTGGGGGAGAACCATATATAAGT
GCAGTAGTCTCTGTGAACATTCAAGCTTCTGCCTTCTCCCTCCTGTGAGTTTGgtaagtcactgactgtctatgcctgggaaagggtgggcaggagatggggcagtgcaggaaaagtggcactatgaa
cccTGCAGCCCTAGAcaattgtactaaccttcttctctttcctctcctgacagGTTGGTAACCAAGCCACCATGGAAGAACCCCAGTCTGACCCCTCTGTGGAACCTCCTCTGAGCCAAGAG
ACATTCTCTGACCTGTGGAAGCTGCTGCCTGAGAACAATGTGCTGAGCCCTCTGCCTAGCCAGGCCATGGATGATCTGATGCTGTCCCCTGATGACATTGAGCAGTGGTTC
ACAGAGGACCCTGGACCTGATGAGGCCCCTAGAATGCCTGAAGCTGCCCCTAGAGTTGCCCCTGCTCCTGCTGCTCCTACACCAGCTGCTCCAGCTCCAGCACCTTCTTGG
CCTCTGTCTAGCTCTGTGCCCAGCCAGAAAACCTACCAGGGCAGCTATGGCTTCAGGCTGGGCTTTCTGCACTCTGGCACAGCCAAGTCTGTGACCTGCACATACAGCCCT
GCTCTGAACAAGATGTTCTGTCAGCTGGCCAAGACCTGTCCTGTGCAGCTGTGGGTTGACAGCACACCTCCTCCAGGCACAAGAGTCAGAGCCATGGCCATCTACAAGCA
GAGCCAGCACATGACAGAGGTTGTCAGAAGATGCCCTCACCATGAGAGGTGCTCTGATTCTGATGGACTGGCCCCTCCTCAGCACCTGATCAGAGTGGAAGGCAACCTGA
GAGTGGAATACCTGGATGACAGAAACACCTTCAGGCACTCTGTGGTGGTGCCCTATGAGCCTCCTGAAGTGGGCTCTGATTGCACCACCATCCACTACAACTACATGTGCA
ACAGCAGCTGCATGGGAGGCATGAACAGAAGGCCCATCCTGACCATCATCACCCTGGAAGATAGCTCTGGCAACCTGCTGGGCAGAAACAGCTTTGAAGTCAGAGTGTG
TGCCTGTCCAGGCAGAGACAGAAGAACTGAGGAAGAGAACCTGAGAAAGAAAGGGGAGCCACACCATGAGCTGCCACCTGGCTCTACCAAAAGAGCCCTGCCTAACAA
CACCAGCAGCAGCCCTCAGCCTAAGAAAAAGCCCCTGGATGGGGAGTACTTCACACTCCAGATCAGAGGCAGGGAAAGATTTGAGATGTTCAGGGAACTGAATGAGGCC
CTGGAACTGAAGGATGCCCAGGCTGGAAAAGAGCCTGGAGGCAGCAGAGCCCATAGCAGCCACCTGAAGTCTAAGAAGGGCCAGAGCACCAGCAGACACAAGAAACTG
ATGTTCAAGACAGAGGGCCCTGACTCTGACTGAAGATCTACTTCTGGCTAATAAAAGATCAGAGCTCTAGTGATCTGTGTGTTGGTTTTTTGTGTCTGCATTCTAGCTCTAG
TGATCAGCAGTTCAACCTGTTGATAGTATGTACTAAGCTCTCATGTTTAATGTACTAAGCTCTCATGTTTAATGAACTAAACCCTCATGGCTAATGTACTAAGCTCTCATGGC
TAATGTACTAAGCTCTCATGTTTCATGTACTAAGCTCTCATGTTTGAACAATAAAATTAATATAAATCAGCAACTTAAATAGCCTCTAAGGTTTTAAGTTTTATAAGAAAAAA
AAGAATATATAAGGCTTTTAAAGGTTTTAAGGTTTCCTAGGTTATCCTCATATGAGCTCTTAGAAAAACTCATCCAGCATCAAATGAAACTGCAATTTATTCATATCAGGATT
ATCAATACCATATTTTTGAAAAAGTCTTTTCTGTAATGAAGGAGAAAACTCACCCAGGCAGTTCCATAGGATGGCAAGATCCTGGTATCTGTCTGCAATTCCAACTCTTCCA
ACATCAATACAACCTATTAATTTCCCCTCATCAAAAATAAGGTTATCAAGTGAGAAATCACCATGAGTGACCACTGAATCTGGTGAGAATGGCAAAAGATTATGCATTTCTT
TCCAGACTTGTTCAACAGGCCAGCCATTTCTCTCATCATCAAAATCACTGGCATCAACCAAACCATTATTCATTCTTGATTGGGCCTGAGCCAGTCTAAATACTCTATCAGAG
TTAAAAGGACAATTACAAACAGGAATGGAATGCAATCTTCTCAGGAACACTGCCAGGGCATCAACAATATTTTCACCTGAATCAGGATATTCTTCCAATACCTGGAATGCT
GTTTTCCCTGGGATGGCAGTGGTGAGTAACCATGCATCATCAGGAGTTCTGATAAAATGCTTGATGGTTGGAAGAGGCATAAATTCAGTCAGCCAGTTTAGTCTGACCATC
TCATCTGTAACATCATTGGCAACAGAACCTTTGCCATGTTTCAGAAACAACTCTGGGGCATCTGGCTTCCCATACAATCTATAGATTGTGGCACCTGATTGCCCAACATTATC
TCTAGCCCATTTATACCCATATAAATCAGCATCCATGTTGGAATTTAATCTTGGCCTGGAGCAAGAGGTTTCTCTTTGAATATGGCTCATACATGTGCACCTCCTATAGTGAG
TTGTATTATACTATGCAGATATACTATGCCAATGTTTAATTGTCAG

SEQUENCE LISTING

```
<160> NUMBER OF SEQ ID NOS: 86

<210> SEQ ID NO 1
<211> LENGTH: 615
<212> TYPE: DNA
<213> ORGANISM: Artificial sequence
<220> FEATURE:
<223> OTHER INFORMATION: Synthetic

<400> SEQUENCE: 1

atggctggac ctgccaccca gagccccatg aagctgatgg ccctgcagct gctgctgtgg     60

cacagtgcac tctggacagt gcaggaagcc acccccctgg gccctgccag ctccctgccc    120

cagagcttcc tgctcaagtg cttagagcaa gtgaggaaga tccaggggga tggggcagct    180

ctccaggaga agctgtgtgc cacctacaag ctgtgccacc ctgaggagct ggtgctgctg    240

ggacactctc tgggcatccc ctgggctccc ctgagcagct gccccagcca ggccctgcag    300

ctggcaggct gcttgagcca actccatagt ggccttttcc tctaccaggg gctcctgcag    360

gccctggaag ggatctcccc tgagttgggt cccaccttgg acacactgca gctggatgtt    420

gctgactttg ccaccaccat ctggcagcag atggaagaac tgggaatggc ccctgccctg    480

cagcccaccc agggtgccat gcctgccttt gcctctgctt tccagagaag ggcaggaggg    540

gtcctggttg cctcccatct gcagagcttc ctggaggtgt cctacagagt tctaagacac    600

cttgcccagc cctga                                                     615


<210> SEQ ID NO 2
<211> LENGTH: 207
<212> TYPE: PRT
<213> ORGANISM: Homo sapiens

<400> SEQUENCE: 2
```

-continued

```
Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205
```

<210> SEQ ID NO 3
<211> LENGTH: 4302
<212> TYPE: DNA
<213> ORGANISM: Artificial sequence
<220> FEATURE:
<223> OTHER INFORMATION: Synthetic

<400> SEQUENCE: 3

```
cactatgtgg acatgaattc aattggctag caggagtcaa tgggaaaaac ccattggagc     60

caagtacact gactcaatag ggactttcca ttgggttttg cccagtacat aaggtcaata    120

gggggtgagt caacaggaaa gtcccattgg agccaagtac attgagtcaa tagggacttt    180

ccaatgggtt ttgcccagta cataaggtca atgggaggta agccaatggg tttttcccat    240

tactgacatg tatactgagt cattagggac tttccaatgg gttttgccca gtacataagg    300

tcaatagggg tgaatcaaca ggaaagtccc attggagcca agtacactga gtcaataggg    360

actttccatt gggttttgcc cagtacaaaa ggtcaatagg gggtgagtca atgggttttt    420

cccattattg gcacatacat aaggtcaata ggggtgacta gtggagaaga gcatgcttga    480

gggctgagtg cccctcagtg ggcagagagc acatggccca cagtccctga gaagttgggg    540

ggaggggtgg gcaattgaac tggtgcctag agaaggtggg gcttgggtaa actgggaaag    600

tgatgtggtg tactggctcc acctttttcc ccagggtggg ggagaaccat atataagtgc    660

agtagtctct gtgaacattc aagcttctgc cttctccctc ctgtgagttt ggtaagtcac    720

tgactgtcta tgcctgggaa agggtgggca ggagatgggg cagtgcagga aaagtggcac    780

tatgaaccct gcagccctag acaattgtac taaccttctt ctctttcctc tcctgacagg    840

ttggtaacca agccaccatg ggctggtccc tgatcctgct gttcctggtg gctgtggcca    900
```

-continued

```
ccagagtgct gagccaggtg cagctgcagc agcctggggc tgagcttgtg aaacctgggg    960
cctctgtgaa gatgagctgc aaggcctctg gctacacctt caccagctac aacatgcact   1020
gggtcaagca gacccctggc agaggcctgg aatggattgg agccatctac cctggcaatg   1080
gggacacctc ctacaaccag aagttcaagg gcaaggccac cctgacagct gacaagagca   1140
gcagcacagc ctacatgcag ctgtccagcc tgacctctga ggactctgct gtgtactact   1200
gtgccaggtc cacctactat gggggagact ggtacttcaa tgtgtgggga gctggcacca   1260
cagtgacagt gtctgctgcc agcaccaagg gcccctctgt gtttcctctg gcccccagca   1320
gcaagagcac ctctgggggga acagctgccc tgggctgcct tgtgaaggac tacttccctg   1380
agcctgtgac tgtgtcctgg aactctgggg ccctgacatc tggggtgcac accttccctg   1440
cagtgctgca gtccagtggc ctgtactccc tgtcctctgt tgtgacagtg cccagctcca   1500
gcctgggcac ccagacctac atctgcaatg tgaaccacaa gcccagcaac accaaggtgg   1560
acaagaaggc tgagcccaag agctgtgaca agacccacac ctgtccccc tgtcctgccc   1620
ctgaactgct gggaggacct tctgtgttcc tgttcccacc caagcccaag gataccctga   1680
tgatcagcag aacccctgaa gtgacctgtg tggtggtgga tgtgtcccat gaggacccag   1740
aagtgaagtt caattggtat gtggatgggg tggaagtgca caatgccaag accaagccca   1800
gagaggaaca gtacaacagc acctacagag tggtgtctgt gctgactgtg ctgcaccagg   1860
actggctgaa tggcaaagag tacaagtgca aggtgtccaa caaggccctg ccagcccca   1920
ttgagaaaac catcagcaag gccaagggcc agcctagaga accccaggtg tacacactgc   1980
cccctagcag ggatgagctg accaagaacc aggtgtccct gacatgcctt gtgaaaggct   2040
tctacccctc tgacattgct gtggaatggg agagcaatgg acagcctgag aacaactaca   2100
agaccacccc ccctgtgctg gactctgatg gctcattctt cctgtacagc aagctgacag   2160
tggacaagtc cagatggcag cagggcaatg tgttcagctg ctctgtgatg catgaggccc   2220
tgcacaacca ctacacccag aaaagcctgt ccctgtcccc tggcaagaga gcaaagaggg   2280
gaagtggagc tactaacttc agcctgctga agcaggctgg agatgtggag gagaaccctg   2340
gacctatgga cttccaggtg cagatcatca gctttctgct gatctctgcc tctgtgatca   2400
tgagcagagg ccagattgtg ctgagccaga gccctgccat cctgtctgca agccctgggg   2460
agaaagtgac catgacctgc agagccagca gctctgtgtc ctacatccac tggttccagc   2520
agaagcctgg cagcagcccc aagccttgga tctatgccac cagcaacctg gcatctgggg   2580
tgccagtcag attctctggc tctggatctg gcaccagcta cagcctgacc atcagcagag   2640
tggaagctga ggatgctgcc acctactact gccagcagtg gaccagcaat cccccacct   2700
ttggaggggg caccaagctg gaaatcaaga gaacagtggc tgccccctct gtgttcatct   2760
tcccaccctc tgatgagcag ctgaagtctg gaacagcctc tgttgtgtgc ctgctgaaca   2820
acttctaccc cagagaagcc aaggtgcagt ggaaggtgga caatgccctg cagtctggca   2880
actcccagga atctgtgaca gagcaggaca gcaaggactc cacctactcc ctgagcagca   2940
ccctgaccct gagcaaggct gactatgaga agcacaaagt gtatgcctgt gaagtgaccc   3000
accagggcct gtccagccct gtgaccaaga gcttcaacag aggggagagc tgaagatcta   3060
cttctggcta ataaaagatc agagctctag tgatctgtgt gttggttttt tgtgtctgca   3120
ttctagctct agtgatcagc agttcaacct gttgatagta tgtactaagc tctcatgttt   3180
aatgtactaa gctctcatgt ttaatgaact aaaccctcat ggctaatgta ctaagctctc   3240
atggctaatg tactaagctc tcatgtttca tgtactaagc tctcatgttt gaacaataaa   3300
```

```
attaatataa atcagcaact taaatagcct ctaaggtttt aagttttata agaaaaaaaa   3360
gaatatataa ggcttttaaa ggttttaagg tttcctaggt tatcctcata tgagctctta   3420
gaaaaactca tccagcatca aatgaaactg caatttattc atatcaggat tatcaatacc   3480
atatttttga aaaagtcttt tctgtaatga aggagaaaac tcacccaggc agttccatag   3540
gatggcaaga tcctggtatc tgtctgcaat tccaactctt ccaacatcaa tacaacctat   3600
taatttcccc tcatcaaaaa taaggttatc aagtgagaaa tcaccatgag tgaccactga   3660
atctggtgag aatggcaaaa gattatgcat ttctttccag acttgttcaa caggccagcc   3720
atttctctca tcatcaaaat cactggcatc aaccaaacca ttattcattc ttgattgggc   3780
ctgagccagt ctaaatactc tatcagagtt aaaaggacaa ttacaaacag gaatggaatg   3840
caatcttctc aggaacactg ccagggcatc aacaatattt tcacctgaat caggatattc   3900
ttccaatacc tggaatgctg ttttccctgg gatggcagtg gtgagtaacc atgcatcatc   3960
aggagttctg ataaaatgct tgatggttgg aagaggcata aattcagtca gccagtttag   4020
tctgaccatc tcatctgtaa catcattggc aacagaacct ttgccatgtt tcagaaacaa   4080
ctctggggca tctggcttcc catacaatct atagattgtg gcacctgatt gcccaacatt   4140
atctctagcc catttatacc catataaatc agcatccatg ttggaattta atcttggcct   4200
ggagcaagag gtttctcttt gaatatggct catacatgtg cacctcctat agtgagttgt   4260
attatactat gcagatatac tatgccaatg tttaattgtc ag                      4302
```

<210> SEQ ID NO 4
<211> LENGTH: 5027
<212> TYPE: DNA
<213> ORGANISM: Artificial sequence
<220> FEATURE:
<223> OTHER INFORMATION: Synthetic

<400> SEQUENCE: 4

```
cactatgtgg acatgaattc aattggctag caggagtcaa tgggaaaaac ccattggagc     60
caagtacact gactcaatag ggactttcca ttgggttttg cccagtacat aaggtcaata    120
gggggtgagt caacaggaaa gtcccattgg agccaagtac attgagtcaa tagggacttt    180
ccaatgggtt ttgcccagta cataaggtca atgggaggta agccaatggg tttttcccat    240
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc acctttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg ggctggtccc tgatcctgct gttcctggtg gctgtggcca    900
ccagagtgct gagccaggtg cagctgcagc agcctggggc tgagcttgtg aaacctgggg    960
cctctgtgaa gatgagctgc aaggcctctg gctacacctt caccagctac aacatgcact   1020
```

-continued

```
gggtcaagca gacccctggc agaggcctgg aatggattgg agccatctac cctggcaatg   1080
gggacacctc ctacaaccag aagttcaagg gcaaggccac cctgacagct gacaagagca   1140
gcagcacagc ctacatgcag ctgtccagcc tgacctctga ggactctgct gtgtactact   1200
gtgccaggtc cacctactat gggggagact ggtacttcaa tgtgtgggga gctggcacca   1260
cagtgacagt gtctgctgcc agcaccaagg gcccctctgt gtttcctctg gcccccagca   1320
gcaagagcac ctctgggggga acagctgccc tgggctgcct tgtgaaggac tacttccctg   1380
agcctgtgac tgtgtcctgg aactctgggg ccctgacatc tggggtgcac accttccctg   1440
cagtgctgca gtccagtggc ctgtactccc tgtcctctgt tgtgacagtg cccagctcca   1500
gcctgggcac ccagacctac atctgcaatg tgaaccacaa gcccagcaac accaaggtgg   1560
acaagaaggc tgagcccaag agctgtgaca agacccacac ctgtcccccc tgtcctgccc   1620
ctgaactgct gggaggacct tctgtgttcc tgttcccacc caagcccaag gataccctga   1680
tgatcagcag aacccctgaa gtgacctgtg tggtggtgga tgtgtcccat gaggacccag   1740
aagtgaagtt caattggtat gtggatgggg tggaagtgca caatgccaag accaagccca   1800
gagaggaaca gtacaacagc acctacagag tggtgtctgt gctgactgtg ctgcaccagg   1860
actggctgaa tggcaaagag tacaagtgca aggtgtccaa caaggccctg ccagcccccca   1920
ttgagaaaac catcagcaag gccaagggcc agcctagaga accccaggtg tacacactgc   1980
cccctagcag ggatgagctg accaagaacc aggtgtccct gacatgcctt gtgaaaggct   2040
tctacccctc tgacattgct gtggaatggg agagcaatgg acagcctgag aacaactaca   2100
agaccacccc ccctgtgctg gactctgatg gctcattctt cctgtacagc aagctgacag   2160
tggacaagtc cagatggcag cagggcaatg tgttcagctg ctctgtgatg catgaggccc   2220
tgcacaacca ctacacccag aaaagcctgt ccctgtcccc tggcaagtga agatctactt   2280
ctggctaata aaagatcaga gctctagtga tctgtgtgtt ggtttttttgt gtctgcattc   2340
tagctgttac ataacttatg gtaaatggcc tgcctggctg actgcccaat gacccctgcc   2400
caatgatgtc aataatgatg tatgttccca tgtaatgcca atagggactt tccattgatg   2460
tcaatgggtg gagtatttat ggtaactgcc cacttggcag tacatcaagt gtatcatatg   2520
ccaagtatgc cccctattga tgtcaatgat ggtaaatggc ctgcctggca ttatgcccag   2580
tacatgacct tatgggactt tcctacttgg cagtacatct atgtattagt cattgctatt   2640
accatggatt agtggagaag agcatgcttg agggctgagt gcccctcagt gggcagagag   2700
cacatggccc acagtccctg agaagttggg gggagggggtg ggcaattgaa ctggtgccta   2760
gagaaggtgg ggcttgggta aactgggaaa gtgatgtggt gtactggctc caccttttttc   2820
cccagggtgg gggagaacca tatataagtg cagtagtctc tgtgaacatt caagcttctg   2880
ccttctccct cctgtgagtt tggatgcacc tactagatat cttggtaagt cactgactgt   2940
ctatgcctgg gaaagggtgg gcaggaggtg gggcagtgca ggaaaagtgg cactgtgaac   3000
cctgcagccc tagacaattg tactaacctt cttctctttc ctctcctgac aggttggtaa   3060
ccaagccacc atggacttcc aggtgcagat catcagcttt ctgctgatct ctgcctctgt   3120
gatcatgagc agaggccaga ttgtgctgag ccagagccct gccatcctgt ctgcaagccc   3180
tggggagaaa gtgaccatga cctgcagagc cagcagctct gtgtcctaca tccactggtt   3240
ccagcagaag cctggcagca gccccaagcc ttggatctat gccaccagca acctggcatc   3300
tggggtgcca gtcagattct ctggctctgg atctggcacc agctacagcc tgaccatcag   3360
cagagtggaa gctgaggatg ctgccaccta ctactgccag cagtggacca gcaatccccc   3420
```

cacctttgga gggggcacca agctggaaat caagagaaca gtggctgccc cctctgtgtt 3480
catcttccca ccctctgatg agcagctgaa gtctggaaca gcctctgttg tgtgcctgct 3540
gaacaacttc taccccagag aagccaaggt gcagtggaag gtggacaatg ccctgcagtc 3600
tggcaactcc caggaatctg tgacagagca ggacagcaag gactccacct actccctgag 3660
cagcaccctg accctgagca aggctgacta tgagaagcac aaagtgtatg cctgtgaagt 3720
gacccaccag ggcctgtcca gccctgtgac caagagcttc aacagagggg agagctgaag 3780
atctacttct ggctaataaa agatcagagc tctagtgatc tgtgtgttgg ttttttgtgt 3840
ctgcattcta gctctagtga tcagcagttc aacctgttga tagtatgtac taagctctca 3900
tgtttaatgt actaagctct catgtttaat gaactaaacc ctcatggcta atgtactaag 3960
ctctcatggc taatgtacta agctctcatg tttcatgtac taagctctca tgtttgaaca 4020
ataaaattaa tataaatcag caacttaaat agcctctaag gttttaagtt ttataagaaa 4080
aaaaagaata tataaggctt ttaaaggttt taaggtttcc taggttatcc tcatatgagc 4140
tcttagaaaa actcatccag catcaaatga aactgcaatt tattcatatc aggattatca 4200
ataccatatt tttgaaaaag tcttttctgt aatgaaggag aaaactcacc caggcagttc 4260
cataggatgg caagatcctg gtatctgtct gcaattccaa ctcttccaac atcaatacaa 4320
cctattaatt tcccctcatc aaaaataagg ttatcaagtg agaaatcacc atgagtgacc 4380
actgaatctg gtgagaatgg caaaagatta tgcatttctt tccagacttg ttcaacaggc 4440
cagccatttc tctcatcatc aaaatcactg gcatcaacca aaccattatt cattcttgat 4500
tgggcctgag ccagtctaaa tactctatca gagttaaaag gacaattaca aacaggaatg 4560
gaatgcaatc ttctcaggaa cactgccagg gcatcaacaa tattttcacc tgaatcagga 4620
tattcttcca atacctggaa tgctgttttc cctgggatgg cagtggtgag taaccatgca 4680
tcatcaggag ttctgataaa atgcttgatg gttggaagag gcataaattc agtcagccag 4740
tttagtctga ccatctcatc tgtaacatca ttggcaacag aacctttgcc atgtttcaga 4800
aacaactctg gggcatctgg cttcccatac aatctataga ttgtggcacc tgattgccca 4860
acattatctc tagcccattt atacccatat aaatcagcat ccatgttgga atttaatctt 4920
ggcctggagc aagaggtttc tctttgaata tggctcatac atgtgcacct cctatagtga 4980
gttgtattat actatgcaga tatactatgc caatgtttaa ttgtcag 5027

<210> SEQ ID NO 5
<211> LENGTH: 4305
<212> TYPE: DNA
<213> ORGANISM: Artificial sequence
<220> FEATURE:
<223> OTHER INFORMATION: Synthetic

<400> SEQUENCE: 5
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420

-continued

```
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc accttttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg ggctggtccc tgatcctgct gttcctggtg gctgtggcca    900
ccagagtgct gagccaggtg cagctgcagc agcctggggc tgagcttgtg aaacctgggg    960
cctctgtgaa gatgagctgc aaggcctctg gctacacctt caccagctac aacatgcact   1020
gggtcaagca gacccctggc agaggcctgg aatggattgg agccatctac cctggcaatg   1080
gggacacctc ctacaaccag aagttcaagg gcaaggccac cctgacagct gacaagagca   1140
gcagcacagc ctacatgcag ctgtccagcc tgacctctga ggactctgct gtgtactact   1200
gtgccaggtc cacctactat gggggagact ggtacttcaa tgtgtgggga gctggcacca   1260
cagtgacagt gtctgctgcc agcaccaagg gcccctctgt gtttcctctg gcccccagca   1320
gcaagagcac ctctgggggga acagctgccc tgggctgcct tgtgaaggac tacttccctg   1380
agcctgtgac tgtgtcctgg aactctgggg ccctgacatc tggggtgcac accttccctg   1440
cagtgctgca gtccagtggc ctgtactccc tgtcctctgt tgtgacagtg cccagctcca   1500
gcctgggcac ccagacctac atctgcaatg tgaaccacaa gcccagcaac accaaggtgg   1560
acaagaaggc tgagcccaag agctgtgaca agacccacac ctgtccccccc tgtcctgccc   1620
ctgaactgct gggaggacct tctgtgttcc tgttcccacc caagcccaag gataccctga   1680
tgatcagcag aacccctgaa gtgacctgtg tggtggtgga tgtgtcccat gaggacccag   1740
aagtgaagtt caattggtat gtggatgggg tggaagtgca caatgccaag accaagccca   1800
gagaggaaca gtacaacagc acctacagag tggtgtctgt gctgactgtg ctgcaccagg   1860
actggctgaa tggcaaagag tacaagtgca aggtgtccaa caaggccctg ccagccccca   1920
ttgagaaaac catcagcaag gccaagggcc agcctagaga accccaggtg tacacactgc   1980
cccctagcag ggatgagctg accaagaacc aggtgtccct gacatgcctt gtgaaaggct   2040
tctacccctc tgacattgct gtggaatggg agagcaatgg acagcctgag aacaactaca   2100
agaccacccc ccctgtgctg gactctgatg gctcattctt cctgtacagc aagctgacag   2160
tggacaagtc cagatggcag cagggcaatg tgttcagctg ctctgtgatg catgaggccc   2220
tgcacaacca ctacacccag aaaagcctgt ccctgtcccc tggcaagaga aagagaagga   2280
gtggaagtgg agctactaac ttcagcctgc tgaagcaggc tggagatgtg gaggagaacc   2340
ctggacctat ggacttccag gtgcagatca tcagcttttct gctgatctct gcctctgtga   2400
tcatgagcag aggccagatt gtgctgagcc agagccctgc catcctgtct gcaagccctg   2460
gggagaaagt gaccatgacc tgcagagcca gcagctctgt gtcctacatc cactggttcc   2520
agcagaagcc tggcagcagc cccaagcctt ggatctatgc caccagcaac ctggcatctg   2580
gggtgccagt cagattctct ggctctggat ctggcaccag ctacagcctg accatcagca   2640
gagtggaagc tgaggatgct gccacctact actgccagca gtggaccagc aatcccccca   2700
cctttggagg gggcaccaag ctggaaatca agagaacagt ggctgccccc tctgtgttca   2760
tcttcccacc ctctgatgag cagctgaagt ctggaacagc ctctgttgtg tgcctgctga   2820
```

acaacttcta ccccagagaa gccaaggtgc agtggaaggt ggacaatgcc ctgcagtctg 2880
gcaactccca ggaatctgtg acagagcagg acagcaagga ctccacctac tccctgagca 2940
gcaccctgac cctgagcaag gctgactatg agaagcacaa agtgtatgcc tgtgaagtga 3000
cccaccaggg cctgtccagc cctgtgacca agagcttcaa cagaggggag agctgaagat 3060
ctacttctgg ctaataaaag atcagagctc tagtgatctg tgtgttggtt ttttgtgtct 3120
gcattctagc tctagtgatc agcagttcaa cctgttgata gtatgtacta agctctcatg 3180
tttaatgtac taagctctca tgtttaatga actaaaccct catggctaat gtactaagct 3240
ctcatggcta atgtactaag ctctcatgtt tcatgtacta agctctcatg tttgaacaat 3300
aaaattaata taaatcagca acttaaatag cctctaaggt tttaagtttt ataagaaaaa 3360
aaagaatata taaggctttt aaaggtttta aggtttccta ggttatcctc atatgagctc 3420
ttagaaaaac tcatccagca tcaaatgaaa ctgcaattta ttcatatcag gattatcaat 3480
accatatttt tgaaaaagtc ttttctgtaa tgaaggagaa aactcaccca ggcagttcca 3540
taggatggca agatcctggt atctgtctgc aattccaact cttccaacat caatacaacc 3600
tattaatttc ccctcatcaa aaataaggtt atcaagtgag aaatcaccat gagtgaccac 3660
tgaatctggt gagaatggca aaagattatg catttctttc cagacttgtt caacaggcca 3720
gccatttctc tcatcatcaa aatcactggc atcaaccaaa ccattattca ttcttgattg 3780
ggcctgagcc agtctaaata ctctatcaga gttaaaagga caattacaaa caggaatgga 3840
atgcaatctt ctcaggaaca ctgccagggc atcaacaata ttttcacctg aatcaggata 3900
ttcttccaat acctggaatg ctgttttccc tgggatggca gtggtgagta accatgcatc 3960
atcaggagtt ctgataaaat gcttgatggt tggaagaggc ataaattcag tcagccagtt 4020
tagtctgacc atctcatctg taacatcatt ggcaacagaa cctttgccat gtttcagaaa 4080
caactctggg gcatctggct tcccatacaa tctatagatt gtggcacctg attgcccaac 4140
attatctcta gcccatttat acccatataa atcagcatcc atgttggaat ttaatcttgg 4200
cctggagcaa gaggtttctc tttgaatatg gctcatacat gtgcacctcc tatagtgagt 4260
tgtattatac tatgcagata tactatgcca atgtttaatt gtcag 4305

<210> SEQ ID NO 6
<211> LENGTH: 5931
<212> TYPE: DNA
<213> ORGANISM: Artificial sequence
<220> FEATURE:
<223> OTHER INFORMATION: Synthetic

<400> SEQUENCE: 6
cactatgtgg acatgaattc aattggctag caaaacaaat gacatcattc ctgattataa 60
taattttaat tgtgctttac aagtagaatt ctacttgtaa agagagttta atttgaaaaa 120
caaattagtc attattaaac atgttaacaa ttgtgtataa aaatgacatc agtttaatga 180
tgacatcatc tcttgattat gttttacaag tagaattcta cttgtaaagc tggttcagtt 240
ttgaaaaaca aatgacatca tctcttgatt atgttttaca agtagaattc tacttgtaaa 300
agtgagttta gttttaaaaa acaaatgaca tcattcagtt ttgaaaaaca aatgacatca 360
tctcttgatt gtgttttaca agtagaattc tacttgtaaa gtgagttcag ttttgaaaaa 420
caaatgaccc tctcatacaa ttgttgaaca attttaataa ataatcttta caagatttct 480
agcaggagtc aatgggaaaa acccattgga gccaagtaca ctgactcaat agggactttc 540

-continued

```
cattgggttt tgcccagtac ataaggtcaa tagggggtga gtcaacagga aagtcccatt    600
ggagccaagt acattgagtc aatagggact ttccaatggg ttttgcccag tacataaggt    660
caatgggagg taagccaatg ggtttttccc attactgaca tgtatactga gtcattaggg    720
actttccaat gggttttgcc cagtacataa ggtcaatagg ggtgaatcaa caggaaagtc    780
ccattggagc caagtacact gagtcaatag ggactttcca ttgggttttg cccagtacaa    840
aaggtcaata gggggtgagt caatgggttt ttcccattat tggcacatac ataaggtcaa    900
taggggtgac tagtggagaa gagcatgctt gagggctgag tgcccctcag tgggcagaga    960
gcacatggcc cacagtccct gagaagttgg ggggaggggt gggcaattga actggtgcct   1020
agagaaggtg gggcttgggt aaactgggaa agtgatgtgg tgtactggct ccaccttttt   1080
ccccagggtg gggggagaacc atatataagt gcagtagtct ctgtgaacat tcaagcttct   1140
gccttctccc tcctgtgagt ttggtaagtc actgactgtc tatgcctggg aaagggtggg   1200
caggagatgg ggcagtgcag gaaaagtggc actatgaacc ctgcagccct agacaattgt   1260
actaaccttc ttctctttcc tctcctgaca ggttggtaac caagccacca tgggctggtc   1320
cctgatcctg ctgttcctgg tggctgtggc caccagagtg ctgagccagg tgcagctgca   1380
gcagcctggg gctgagcttg tgaaacctgg ggcctctgtg aagatgagct gcaaggcctc   1440
tggctacacc ttcaccagct acaacatgca ctgggtcaag cagacccctg gcagaggcct   1500
ggaatggatt ggagccatct accctggcaa tggggacacc tcctacaacc agaagttcaa   1560
gggcaaggcc accctgacag ctgacaagag cagcagcaca gcctacatgc agctgtccag   1620
cctgacctct gaggactctg ctgtgtacta ctgtgccagg tccacctact atgggggaga   1680
ctggtacttc aatgtgtggg gagctggcac cacagtgaca gtgtctgctg ccagcaccaa   1740
gggcccctct gtgtttcctc tggcccccag cagcaagagc acctctgggg gaacagctgc   1800
cctgggctgc cttgtgaagg actacttccc tgagcctgtg actgtgtcct ggaactctgg   1860
ggccctgaca tctggggtgc acaccttccc tgcagtgctg cagtccagtg gcctgtactc   1920
cctgtcctct gttgtgacag tgcccagctc cagcctgggc acccagacct acatctgcaa   1980
tgtgaaccac aagcccagca acaccaaggt ggacaagaag gctgagccca agagctgtga   2040
caagacccac acctgtcccc cctgtcctgc ccctgaactg ctgggaggac cttctgtgtt   2100
cctgttccca cccaagccca aggataccct gatgatcagc agaacccctg aagtgacctg   2160
tgtggtggtg gatgtgtccc atgaggaccc agaagtgaag ttcaattggt atgtggatgg   2220
ggtggaagtg cacaatgcca agaccaagcc cagagaggaa cagtacaaca gcacctacag   2280
agtggtgtct gtgctgactg tgctgcacca ggactggctg aatggcaaag agtacaagtg   2340
caaggtgtcc aacaaggccc tgccagcccc cattgagaaa accatcagca aggccaaggg   2400
ccagcctaga gaaccccagg tgtacacact gccccctagc agggatgagc tgaccaagaa   2460
ccaggtgtcc ctgacatgcc ttgtgaaagg cttctacccc tctgacattg ctgtggaatg   2520
ggagagcaat ggacagcctg agaacaacta caagaccacc ccccctgtgc tggactctga   2580
tggctcattc ttcctgtaca gcaagctgac agtggacaag tccagatggc agcagggcaa   2640
tgtgttcagc tgctctgtga tgcatgaggc cctgcacaac cactacaccc agaaaagcct   2700
gtccctgtcc cctggcaagt gaagatctac ttctggctaa taaaagatca gagctctagt   2760
gatctgtgtg ttggtttttt gtgtctgcat tctagcaaaa caaatgacat cattcctgat   2820
tataataatt ttaattgtgc tttacaagta gaattctact tgtaaagaga gtttaatttg   2880
aaaaacaaat tagtcattat taaacatgtt aacaattgtg tataaaaatg acatcagttt   2940
```

```
aatgatgaca tcatctcttg attatgtttt acaagtagaa ttctacttgt aaagctggtt   3000

cagttttgaa aaacaaatga catcatctct tgattatgtt ttacaagtag aattctactt   3060

gtaaaagtga gtttagtttt aaaaaacaaa tgacatcatt cagttttgaa aaacaaatga   3120

catcatctct tgattgtgtt ttacaagtag aattctactt gtaaagtgag ttcagttttg   3180

aaaaacaaat gaccctctca tacaattgtt gaacaatttt aataaataat ctttacaaga   3240

tttctagctg ttacataact tatggtaaat ggcctgcctg gctgactgcc caatgacccc   3300

tgcccaatga tgtcaataat gatgtatgtt cccatgtaat gccaataggg actttccatt   3360

gatgtcaatg ggtggagtat ttatggtaac tgcccacttg gcagtacatc aagtgtatca   3420

tatgccaagt atgcccccta ttgatgtcaa tgatggtaaa tggcctgcct ggcattatgc   3480

ccagtacatg accttatggg actttcctac ttggcagtac atctatgtat tagtcattgc   3540

tattaccatg gattagtgga gaagagcatg cttgagggct gagtgcccct cagtgggcag   3600

agagcacatg gcccacagtc cctgagaagt tgggggggagg ggtgggcaat tgaactggtg   3660

cctagagaag gtggggcttg ggtaaactgg gaaagtgatg tggtgtactg gctccacctt   3720

tttccccagg gtgggggaga accatatata agtgcagtag tctctgtgaa cattcaagct   3780

tctgccttct ccctcctgtg agtttggatg cacctactag atatcttggt aagtcactga   3840

ctgtctatgc ctgggaaagg gtgggcagga ggtggggcag tgcaggaaaa gtggcactgt   3900

gaaccctgca gccctagaca attgtactaa ccttcttctc tttcctctcc tgacaggttg   3960

gtaaccaagc caccatggac ttccaggtgc agatcatcag ctttctgctg atctctgcct   4020

ctgtgatcat gagcagaggc cagattgtgc tgagccagag ccctgccatc ctgtctgcaa   4080

gccctgggga gaaagtgacc atgacctgca gagccagcag ctctgtgtcc tacatccact   4140

ggttccagca gaagcctggc agcagcccca agccttggat ctatgccacc agcaacctgg   4200

catctggggt gccagtcaga ttctctggct ctggatctgg caccagctac agcctgacca   4260

tcagcagagt ggaagctgag gatgctgcca cctactactg ccagcagtgg accagcaatc   4320

cccccacctt tggagggggc accaagctgg aaatcaagag aacagtggct gccccctctg   4380

tgttcatctt cccaccctct gatgagcagc tgaagtctgg aacagcctct gttgtgtgcc   4440

tgctgaacaa cttctacccc agagaagcca aggtgcagtg gaaggtggac aatgccctgc   4500

agtctggcaa ctcccaggaa tctgtgacag agcaggacag caaggactcc acctactccc   4560

tgagcagcac cctgaccctg agcaaggctg actatgagaa gcacaaagtg tatgcctgtg   4620

aagtgaccca ccagggcctg tccagccctg tgaccaagag cttcaacaga ggggagagct   4680

gaagatctac ttctggctaa taaaagatca gagctctagt gatctgtgtg ttggtttttt   4740

gtgtctgcat tctagctcta gtgatcagca gttcaacctg ttgatagtat gtactaagct   4800

ctcatgttta atgtactaag ctctcatgtt taatgaacta aaccctcatg gctaatgtac   4860

taagctctca tggctaatgt actaagctct catgtttcat gtactaagct ctcatgtttg   4920

aacaataaaa ttaatataaa tcagcaactt aaatagcctc taaggtttta agttttataa   4980

gaaaaaaaag aatatataag gcttttaaag gttttaaggt ttcctaggtt atcctcatat   5040

gagctcttag aaaaactcat ccagcatcaa atgaaactgc aatttattca tatcaggatt   5100

atcaatacca tatttttgaa aaagtctttt ctgtaatgaa ggagaaaact cacccaggca   5160

gttccatagg atggcaagat cctggtatct gtctgcaatt ccaactcttc caacatcaat   5220

acaacctatt aatttcccct catcaaaaat aaggttatca agtgagaaat caccatgagt   5280
```

```
gaccactgaa tctggtgaga atggcaaaag attatgcatt tctttccaga cttgttcaac   5340

aggccagcca tttctctcat catcaaaatc actggcatca accaaaccat tattcattct   5400

tgattgggcc tgagccagtc taaatactct atcagagtta aaaggacaat tacaaacagg   5460

aatggaatgc aatcttctca ggaacactgc cagggcatca acaatatttt cacctgaatc   5520

aggatattct tccaatacct ggaatgctgt tttccctggg atggcagtgg tgagtaacca   5580

tgcatcatca ggagttctga taaaatgctt gatggttgga agaggcataa attcagtcag   5640

ccagtttagt ctgaccatct catctgtaac atcattggca acagaacctt tgccatgttt   5700

cagaaacaac tctggggcat ctggcttccc atacaatcta tagattgtgg cacctgattg   5760

cccaacatta tctctagccc atttataccc atataaatca gcatccatgt tggaatttaa   5820

tcttggcctg gagcaagagg tttctctttg aatatggctc atacatgtgc acctcctata   5880

gtgagttgta ttatactatg cagatatact atgccaatgt ttaattgtca g            5931
```

```
<210> SEQ ID NO 7
<211> LENGTH: 2142
<212> TYPE: DNA
<213> ORGANISM: Artificial sequence
<220> FEATURE:
<223> OTHER INFORMATION: Synthetic

<400> SEQUENCE: 7

cactatgtgg acatgaattc aattggctag caggagtcaa tgggaaaaac ccattggagc     60

caagtacact gactcaatag ggactttcca ttgggttttg cccagtacat aaggtcaata    120

gggggtgagt caacaggaaa gtcccattgg agccaagtac attgagtcaa tagggacttt    180

ccaatgggtt ttgcccagta cataaggtca atgggaggta agccaatggg tttttcccat    240

tactgacatg tatactgagt cattagggac tttccaatgg gttttgccca gtacataagg    300

tcaatagggg tgaatcaaca ggaaagtccc attggagcca agtacactga gtcaataggg    360

actttccatt gggttttgcc cagtacaaaa ggtcaatagg gggtgagtca atgggttttt    420

cccattattg gcacatacat aaggtcaata ggggtgacta gtggagaaga gcatgcttga    480

gggctgagtg cccctcagtg ggcagagagc acatggccca cagtccctga gaagttgggg    540

ggaggggtgg gcaattgaac tggtgcctag agaaggtggg gcttgggtaa actgggaaag    600

tgatgtggtg tactggctcc accttttttcc ccagggtggg ggagaaccat atataagtgc   660

agtagtctct gtgaacattc aagcttctgc cttctccctc ctgtgagttt ggtaagtcac    720

tgactgtcta tgcctgggaa agggtgggca ggagatgggg cagtgcagga aaagtggcac    780

tatgaaccct gcagccctag acaattgtac taaccttctt ctctttcctc tcctgacagg    840

ttggtaacca agctttccgt gaaactgatg agtccgtgag gacgaaacac ctcagatcta    900

cttctggcta ataaaagatc agagctctag tgatctgtgt gttggttttt tgtgtctgca    960

ttctagctct agtgatcagc agttcaacct gttgatagta tgtactaagc tctcatgttt   1020

aatgtactaa gctctcatgt ttaatgaact aaaccctcat ggctaatgta ctaagctctc   1080

atggctaatg tactaagctc tcatgtttca tgtactaagc tctcatgttt gaacaataaa   1140

attaatataa atcagcaact taaatagcct ctaaggtttt aagttttata agaaaaaaaa   1200

gaatatataa ggcttttaaa ggttttaagg tttcctaggt tatcctcata tgagctctta   1260

gaaaaactca tccagcatca aatgaaactg caatttattc atatcaggat tatcaatacc   1320

atatttttga aaaagtcttt tctgtaatga aggagaaaac tcacccaggc agttccatag   1380

gatggcaaga tcctggtatc tgtctgcaat tccaactctt ccaacatcaa tacaacctat   1440
```

```
taatttcccc tcatcaaaaa taaggttatc aagtgagaaa tcaccatgag tgaccactga   1500

atctggtgag aatggcaaaa gattatgcat ttctttccag acttgttcaa caggccagcc   1560

atttctctca tcatcaaaat cactggcatc aaccaaacca ttattcattc ttgattgggc   1620

ctgagccagt ctaaatactc tatcagagtt aaaaggacaa ttacaaacag gaatggaatg   1680

caatcttctc aggaacactg ccagggcatc aacaatattt tcacctgaat caggatattc   1740

ttccaatacc tggaatgctg ttttccctgg gatggcagtg gtgagtaacc atgcatcatc   1800

aggagttctg ataaaatgct tgatggttgg aagaggcata aattcagtca gccagtttag   1860

tctgaccatc tcatctgtaa catcattggc aacagaacct ttgccatgtt tcagaaacaa   1920

ctctggggca tctggcttcc catacaatct atagattgtg gcacctgatt gcccaacatt   1980

atctctagcc catttatacc catataaatc agcatccatg ttggaattta atcttggcct   2040

ggagcaagag gtttctcttt gaatatggct catacatgtg cacctcctat agtgagttgt   2100

attatactat gcagatatac tatgccaatg tttaattgtc ag                      2142
```

<210> SEQ ID NO 8
<211> LENGTH: 9290
<212> TYPE: DNA
<213> ORGANISM: Artificial sequence
<220> FEATURE:
<223> OTHER INFORMATION: Synthetic

<400> SEQUENCE: 8

```
gagggcctat ttcccatgat tccttcatat ttgcatatac gatacaaggc tgttagagag     60

ataattggaa ttaatttgac tgtaaacaca aagatattag tacaaaatac gtgacgtaga    120

aagtaataat ttcttgggta gtttgcagtt ttaaaattat gttttaaaat ggactatcat    180

atgcttaccg taacttgaaa gtatttcgat ttcttggctt tatatatctt gtggaaagga    240

cgaaacaccg cgattccgct ataaatgcgg ttttagagct agaaatagca agttaaaata    300

aggctagtcc gttatcaact tgaaaaagtg gcaccgagtc ggtgcttttt tgttttagag    360

ctagaaatag caagttaaaa taaggctagt ccgtttttag cgcgtgcgcc aattctgcag    420

acaaatggct ctagaggtac ccgttacata acttacggta aatggcccgc ctggctgacc    480

gcccaacgac ccccgcccat tgacgtcaat agtaacgcca atagggactt tccattgacg    540

tcaatgggtg gagtatttac ggtaaactgc ccacttggca gtacatcaag tgtatcatat    600

gccaagtacg ccccctattg acgtcaatga cggtaaatgg cccgcctggc attgtgccca    660

gtacatgacc ttatgggact ttcctacttg gcagtacatc tacgtattag tcatcgctat    720

taccatggtc gaggtgagcc ccacgttctg cttcactctc cccatctccc ccccctcccc    780

acccccaatt ttgtatttat ttatttttta attattttgt gcagcgatgg gggcgggggg    840

gggggggggg cgcgcgccag gcggggcggg gcggggcgag gggcggggcg gggcgaggcg    900

gagaggtgcg gcggcagcca atcagagcgg cgcgctccga aagtttcctt ttatggcgag    960

gcggcggcgg cggcggccct ataaaaagcg aagcgcgcgg cgggcgggag tcgctgcgcg   1020

ctgccttcgc cccgtgcccc gctccgccgc cgcctcgcgc cgcccgcccc ggctctgact   1080

gaccgcgtta ctcccacagg tgagcgggcg ggacggccct tctcctccgg gctgtaatta   1140

gctgagcaag aggtaagggt ttaagggatg gttggttggt ggggtattaa tgtttaatta   1200

cctggagcac ctgcctgaaa tcactttttt tcaggttgga ccggtgccac catggactat   1260

aaggaccacg acggagacta caaggatcat gatattgatt acaaagacga tgacgataag   1320
```

-continued

```
atggccccaa agaagaagcg gaaggtcggt atccacggag tcccagcagc cgacaagaag   1380
tacagcatcg gcctggacat cggcaccaac tctgtgggct gggccgtgat caccgacgag   1440
tacaaggtgc ccagcaagaa attcaaggtg ctgggcaaca ccgaccggca cagcatcaag   1500
aagaacctga tcggagccct gctgttcgac agcggcgaaa cagccgaggc cacccggctg   1560
aagagaaccg ccagaagaag atacaccaga cggaagaacc ggatctgcta tctgcaagag   1620
atcttcagca acgagatggc caaggtggac gacagcttct tccacagact ggaagagtcc   1680
ttcctggtgg aagaggataa gaagcacgag cggcacccca tcttcggcaa catcgtggac   1740
gaggtggcct accacgagaa gtaccccacc atctaccacc tgagaaagaa actggtggac   1800
agcaccgaca aggccgacct gcggctgatc tatctggccc tggcccacat gatcaagttc   1860
cggggccact tcctgatcga gggcgacctg aaccccgaca acagcgacgt ggacaagctg   1920
ttcatccagc tggtgcagac ctacaaccag ctgttcgagg aaaaccccat caacgccagc   1980
ggcgtggacg ccaaggccat cctgtctgcc agactgagca agagcagacg gctggaaaat   2040
ctgatcgccc agctgcccgg cgagaagaag aatggcctgt tcggaaacct gattgccctg   2100
agcctgggcc tgacccccaa cttcaagagc aacttcgacc tggccgagga tgccaaactg   2160
cagctgagca aggacaccta cgacgacgac ctggacaacc tgctggccca gatcggcgac   2220
cagtacgccg acctgtttct ggccgccaag aacctgtccg acgccatcct gctgagcgac   2280
atcctgagag tgaacaccga gatcaccaag gccccccctga gcgcctctat gatcaagaga   2340
tacgacgagc accaccagga cctgaccctg ctgaaagctc tcgtgcggca gcagctgcct   2400
gagaagtaca aagagatttt cttcgaccag agcaagaacg gctacgccgg ctacattgac   2460
ggcggagcca gccaggaaga gttctacaag ttcatcaagc ccatcctgga aaagatggac   2520
ggcaccgagg aactgctcgt gaagctgaac agagaggacc tgctgcggaa gcagcggacc   2580
ttcgacaacg gcagcatccc ccaccagatc cacctgggag agctgcacgc cattctgcgg   2640
cggcaggaag atttttaccc attcctgaag gacaaccggg aaaagatcga gaagatcctg   2700
accttccgca tcccctacta cgtgggccct ctggccaggg gaaacagcag attcgcctgg   2760
atgaccagaa agagcgagga aaccatcacc ccctggaact tcgaggaagt ggtggacaag   2820
ggcgcttccg cccagagctt catcgagcgg atgaccaact tcgataagaa cctgcccaac   2880
gagaaggtgc tgcccaagca cagcctgctg tacgagtact tcaccgtgta taacgagctg   2940
accaaagtga aatacgtgac cgagggaatg agaaagcccg ccttcctgag cggcgagcag   3000
aaaaaggcca tcgtggacct gctgttcaag accaaccgga aagtgaccgt gaagcagctg   3060
aaagaggact acttcaagaa aatcgagtgc ttcgactccg tggaaatctc cggcgtggaa   3120
gatcggttca acgcctccct gggcacatac cacgatctgc tgaaaattat caaggacaag   3180
gacttcctgg acaatgagga aaacgaggac attctggaag atatcgtgct gaccctgaca   3240
ctgtttgagg acagagagat gatcgaggaa cggctgaaaa cctatgccca cctgttcgac   3300
gacaaagtga tgaagcagct gaagcggcgg agatacaccg gctggggcag gctgagccgg   3360
aagctgatca acggcatccg ggacaagcag tccggcaaga caatcctgga tttcctgaag   3420
tccgacggct tcgccaacag aaacttcatg cagctgatcc acgacgacag cctgaccttt   3480
aaagaggaca tccagaaagc ccaggtgtcc ggccagggcg atagcctgca cgagcacatt   3540
gccaatctgg ccggcagccc cgccattaag aagggcatcc tgcagacagt gaaggtggtg   3600
gacgagctcg tgaaagtgat gggccggcac aagcccgaga acatcgtgat cgaaatggcc   3660
agagagaacc agaccaccca gaagggacag aagaacagcc gcgagagaat gaagcggatc   3720
```

gaagagggca tcaaagagct gggcagccag atcctgaaag aacaccccgt ggaaaacacc 3780
cagctgcaga acgagaagct gtacctgtac tacctgcaga atgggcggga tatgtacgtg 3840
gaccaggaac tggacatcaa ccggctgtcc gactacgatg tggaccatat cgtgcctcag 3900
agctttctga aggacgactc catcgacaac aaggtgctga ccagaagcga caagaaccgg 3960
ggcaagagcg acaacgtgcc ctccgaagag gtcgtgaaga agatgaagaa ctactggcgg 4020
cagctgctga acgccaagct gattacccag agaaagttcg acaatctgac caaggccgag 4080
agaggcggcc tgagcgaact ggataaggcc ggcttcatca agagacagct ggtggaaacc 4140
cggcagatca caaagcacgt ggcacagatc ctggactccc ggatgaacac taagtacgac 4200
gagaatgaca agctgatccg ggaagtgaaa gtgatcaccc tgaagtccaa gctggtgtcc 4260
gatttccgga aggatttcca gttttacaaa gtgcgcgaga tcaacaacta ccaccacgcc 4320
cacgacgcct acctgaacgc cgtcgtggga accgccctga tcaaaaagta ccctaagctg 4380
gaaagcgagt tcgtgtacgg cgactacaag gtgtacgacg tgcggaagat gatcgccaag 4440
agcgagcagg aaatcggcaa ggctaccgcc aagtacttct tctacagcaa catcatgaac 4500
tttttcaaga ccgagattac cctggccaac ggcgagatcc ggaagcggcc tctgatcgag 4560
acaaacggcg aaaccgggga gatcgtgtgg gataagggcc gggattttgc caccgtgcgg 4620
aaagtgctga gcatgcccca agtgaatatc gtgaaaaaga ccgaggtgca gacaggcggc 4680
ttcagcaaag agtctatcct gcccaagagg aacagcgata agctgatcgc cagaaagaag 4740
gactgggacc ctaagaagta cggcggcttc gacagcccca ccgtggccta ttctgtgctg 4800
gtggtggcca aagtggaaaa gggcaagtcc aagaaactga agagtgtgaa agagctgctg 4860
gggatcacca tcatggaaag aagcagcttc gagaagaatc ccatcgactt tctggaagcc 4920
aagggctaca aagaagtgaa aaaggacctg atcatcaagc tgcctaagta ctccctgttc 4980
gagctggaaa acggccggaa gagaatgctg gcctctgccg gcgaactgca gaagggaaac 5040
gaactggccc tgccctccaa atatgtgaac ttcctgtacc tggccagcca ctatgagaag 5100
ctgaagggct cccccgagga taatgagcag aaacagctgt ttgtggaaca gcacaagcac 5160
tacctggacg agatcatcga gcagatcagc gagttctcca agagagtgat cctggccgac 5220
gctaatctgg acaaagtgct gtccgcctac aacaagcacc gggataagcc catcagagag 5280
caggccgaga atatcatcca cctgtttacc ctgaccaatc tgggagcccc tgccgccttc 5340
aagtactttg acaccaccat cgaccggaag aggtacacca gcaccaaaga ggtgctggac 5400
gccaccctga tccaccagag catcaccggc ctgtacgaga cacggatcga cctgtctcag 5460
ctgggaggcg acaaaaggcc ggcggccacg aaaaaggccg gccaggcaaa aaagaaaaag 5520
gaattcggca gtggagaggg cagaggaagt ctgctaacat gcggtgacgt cgaggagaat 5580
cctggcccag tgagcaaggg cgaggagctg ttcaccgggg tggtgcccat cctggtcgag 5640
ctggacggcg acgtaaacgg ccacaagttc agcgtgtccg gcgagggcga gggcgatgcc 5700
acctacggca agctgaccct gaagttcatc tgcaccaccg gcaagctgcc cgtgccctgg 5760
cccaccctcg tgaccaccct gacctacggc gtgcagtgct tcagccgcta ccccgaccac 5820
atgaagcagc acgacttctt caagtccgcc atgcccgaag gctacgtcca ggagcgcacc 5880
atcttcttca aggacgacgg caactacaag acccgcgccg aggtgaagtt cgagggcgac 5940
accctggtga accgcatcga gctgaagggc atcgacttca aggaggacgg caacatcctg 6000
gggcacaagc tggagtacaa ctacaacagc cacaacgtct atatcatggc cgacaagcag 6060

-continued aagaacggca tcaaggtgaa cttcaagatc cgccacaaca tcgaggacgg cagcgtgcag 6120
ctcgccgacc actaccagca gaacaccccc atcggcgacg gccccgtgct gctgcccgac 6180
aaccactacc tgagcaccca gtccgccctg agcaaagacc ccaacgagaa gcgcgatcac 6240
atggtcctgc tggagttcgt gaccgccgcc gggatcactc tcggcatgga cgagctgtac 6300
aaggaattct aactagagct cgctgatcag cctcgactgt gccttctagt tgccagccat 6360
ctgttgtttg cccctccccc gtgccttcct tgaccctgga aggtgccact cccactgtcc 6420
tttcctaata aaatgaggaa attgcatcgc attgtctgag taggtgtcat tctattctgg 6480
ggggtggggt ggggcaggac agcaaggggg aggattggga agagaatagc aggcatgctg 6540
gggagcggcc gcaggaaccc ctagtgatgg agttggccac tccctctctg cgcgctcgct 6600
cgctcactga ggccgggcga ccaaaggtcg cccgacgccc gggctttgcc cgggcggcct 6660
cagtgagcga gcgagcgcgc agctgcctgc aggggcgcct gatgcggtat tttctcctta 6720
cgcatctgtg cggtatttca caccgcatac gtcaaagcaa ccatagtacg cgccctgtag 6780
cggcgcatta agcgcggcgg gtgtggtggt tacgcgcagc gtgaccgcta cacttgccag 6840
cgccttagcg cccgctcctt tcgctttctt cccttccttt ctcgccacgt tcgccggctt 6900
tccccgtcaa gctctaaatc gggggctccc tttagggttc cgatttagtg ctttacggca 6960
cctcgacccc aaaaaacttg atttgggtga tggttcacgt agtgggccat cgccctgata 7020
gacggttttt cgccctttga cgttggagtc cacgttcttt aatagtggac tcttgttcca 7080
aactggaaca acactcaact ctatctcggg ctattctttt gatttataag ggattttgcc 7140
gatttcggtc tattggttaa aaaatgagct gatttaacaa aaatttaacg cgaattttaa 7200
caaaatatta acgtttacaa ttttatggtg cactctcagt acaatctgct ctgatgccgc 7260
atagttaagc cagccccgac acccgccaac acccgctgac gcgccctgac gggcttgtct 7320
gctcccggca tccgcttaca gacaagctgt gaccgtctcc gggagctgca tgtgtcagag 7380
gttttcaccg tcatcaccga aacgcgcgag acgaaagggc ctcgtgatac gcctattttt 7440
ataggttaat gtcatgataa taatggtttc ttagacgtca ggtggcactt ttcggggaaa 7500
tgtgcgcgga acccctattt gtttattttt ctaaatacat tcaaatatgt atccgctcat 7560
gagacaataa ccctgataaa tgcttcaata atattgaaaa aggaagagta tgagtattca 7620
acatttccgt gtcgccctta ttcccttttt tgcggcattt tgccttcctg tttttgctca 7680
cccagaaacg ctggtgaaag taaaagatgc tgaagatcag ttgggtgcac gagtgggtta 7740
catcgaactg gatctcaaca gcggtaagat ccttgagagt tttcgccccg aagaacgttt 7800
tccaatgatg agcactttta aagttctgct atgtggcgcg gtattatccc gtattgacgc 7860
cgggcaagag caactcggtc gccgcataca ctattctcag aatgacttgg ttgagtactc 7920
accagtcaca gaaaagcatc ttacggatgg catgacagta agagaattat gcagtgctgc 7980
cataaccatg agtgataaca ctgcggccaa cttacttctg acaacgatcg gaggaccgaa 8040
ggagctaacc gcttttttgc acaacatggg ggatcatgta actcgccttg atcgttggga 8100
accggagctg aatgaagcca taccaaacga cgagcgtgac accacgatgc ctgtagcaat 8160
ggcaacaacg ttgcgcaaac tattaactgg cgaactactt actctagctt cccggcaaca 8220
attaatagac tggatggagg cggataaagt tgcaggacca cttctgcgct cggcccttcc 8280
ggctggctgg tttattgctg ataaatctgg agccggtgag cgtggaagcc gcggtatcat 8340
tgcagcactg gggccagatg gtaagccctc ccgtatcgta gttatctaca cgacggggag 8400
tcaggcaact atggatgaac gaaatagaca gatcgctgag ataggtgcct cactgattaa 8460

```
gcattggtaa ctgtcagacc aagtttactc atatatactt tagattgatt taaaacttca   8520

tttttaattt aaaaggatct aggtgaagat cctttttgat aatctcatga ccaaaatccc   8580

ttaacgtgag ttttcgttcc actgagcgtc agaccccgta gaaaagatca aaggatcttc   8640

ttgagatcct ttttttctgc gcgtaatctg ctgcttgcaa acaaaaaaac caccgctacc   8700

agcggtggtt tgtttgccgg atcaagagct accaactctt tttccgaagg taactggctt   8760

cagcagagcg cagataccaa atactgttct tctagtgtag ccgtagttag gccaccactt   8820

caagaactct gtagcaccgc ctacatacct cgctctgcta atcctgttac cagtggctgc   8880

tgccagtggc gataagtcgt gtcttaccgg gttggactca agacgatagt taccggataa   8940

ggcgcagcgg tcgggctgaa cggggggttc gtgcacacag cccagcttgg agcgaacgac   9000

ctacaccgaa ctgagatacc tacagcgtga gctatgagaa agcgccacgc ttcccgaagg   9060

gagaaaggcg gacaggtatc cggtaagcgg cagggtcgga acaggagagc gcacgaggga   9120

gcttccaggg ggaaacgcct ggtatcttta tagtcctgtc gggtttcgcc acctctgact   9180

tgagcgtcga tttttgtgat gctcgtcagg ggggcggagc ctatggaaaa acgccagcaa   9240

cgcggccttt ttacggttcc tggccttttg ctggcctttt gctcacatgt              9290
```

<210> SEQ ID NO 9
<211> LENGTH: 9290
<212> TYPE: DNA
<213> ORGANISM: Artificial sequence
<220> FEATURE:
<223> OTHER INFORMATION: Synthetic

<400> SEQUENCE: 9

```
gagggcctat ttcccatgat tccttcatat ttgcatatac gatacaaggc tgttagagag     60

ataattggaa ttaatttgac tgtaaacaca aagatattag tacaaaatac gtgacgtaga    120

aagtaataat ttcttgggta gtttgcagtt ttaaaattat gttttaaaat ggactatcat    180

atgcttaccg taacttgaaa gtatttcgat ttcttggctt tatatatctt gtggaaagga    240

cgaaacaccc tgccgggatg gctactatgg ttttagagct agaaatagca agttaaaata    300

aggctagtcc gttatcaact tgaaaaagtg gcaccgagtc ggtgcttttt tgttttagag    360

ctagaaatag caagttaaaa taaggctagt ccgtttttag cgcgtgcgcc aattctgcag    420

acaaatggct ctagaggtac ccgttacata acttacggta aatggcccgc ctggctgacc    480

gcccaacgac ccccgcccat tgacgtcaat agtaacgcca atagggactt tccattgacg    540

tcaatgggtg gagtatttac ggtaaactgc ccacttggca gtacatcaag tgtatcatat    600

gccaagtacg ccccctattg acgtcaatga cggtaaatgg cccgcctggc attgtgccca    660

gtacatgacc ttatgggact ttcctacttg gcagtacatc tacgtattag tcatcgctat    720

taccatggtc gaggtgagcc ccacgttctg cttcactctc cccatctccc ccccctcccc    780

acccccaatt ttgtatttat ttatttttta attattttgt gcagcgatgg gggcgggggg    840

gggggggggg cgcgcgccag gcggggcggg gcggggcgag gggcggggcg gggcgaggcg    900

gagaggtgcg gcggcagcca atcagagcgg cgcgctccga aagtttcctt ttatggcgag    960

gcggcggcgg cggcggccct ataaaaagcg aagcgcgcgg cgggcgggag tcgctgcgcg   1020

ctgccttcgc cccgtgcccc gctccgccgc cgcctcgcgc cgcccgcccc ggctctgact   1080

gaccgcgtta ctcccacagg tgagcgggcg ggacggccct tctcctccgg gctgtaatta   1140

gctgagcaag aggtaagggt ttaagggatg gttggttggt ggggtattaa tgtttaatta   1200
```

```
cctggagcac ctgcctgaaa tcactttttt tcaggttgga ccggtgccac catggactat   1260
aaggaccacg acggagacta caaggatcat gatattgatt acaaagacga tgacgataag   1320
atggccccaa agaagaagcg gaaggtcggt atccacggag tcccagcagc cgacaagaag   1380
tacagcatcg gcctggacat cggcaccaac tctgtgggct gggccgtgat caccgacgag   1440
tacaaggtgc ccagcaagaa attcaaggtg ctgggcaaca ccgaccggca cagcatcaag   1500
aagaacctga tcggagccct gctgttcgac agcggcgaaa cagccgaggc cacccggctg   1560
aagagaaccg ccagaagaag atacaccaga cggaagaacc ggatctgcta tctgcaagag   1620
atcttcagca acgagatggc caaggtggac gacagcttct tccacagact ggaagagtcc   1680
ttcctggtgg aagaggataa gaagcacgag cggcacccca tcttcggcaa catcgtggac   1740
gaggtggcct accacgagaa gtaccccacc atctaccacc tgagaaagaa actggtggac   1800
agcaccgaca aggccgacct gcggctgatc tatctggccc tggcccacat gatcaagttc   1860
cggggccact tcctgatcga gggcgacctg aaccccgaca acagcgacgt ggacaagctg   1920
ttcatccagc tggtgcagac ctacaaccag ctgttcgagg aaaaccccat caacgccagc   1980
ggcgtggacg ccaaggccat cctgtctgcc agactgagca agagcagacg gctggaaaat   2040
ctgatcgccc agctgcccgg cgagaagaag aatggcctgt tcggaaacct gattgccctg   2100
agcctgggcc tgacccccaa cttcaagagc aacttcgacc tggccgagga tgccaaactg   2160
cagctgagca aggacaccta cgacgacgac ctggacaacc tgctggccca gatcggcgac   2220
cagtacgccg acctgtttct ggccgccaag aacctgtccg acgccatcct gctgagcgac   2280
atcctgagag tgaacaccga gatcaccaag gccccccctga gcgcctctat gatcaagaga   2340
tacgacgagc accaccagga cctgaccctg ctgaaagctc tcgtgcggca gcagctgcct   2400
gagaagtaca aagagatttt cttcgaccag agcaagaacg gctacgccgg ctacattgac   2460
ggcggagcca gccaggaaga gttctacaag ttcatcaagc ccatcctgga aaagatggac   2520
ggcaccgagg aactgctcgt gaagctgaac agagaggacc tgctgcggaa gcagcggacc   2580
ttcgacaacg gcagcatccc ccaccagatc cacctgggag agctgcacgc cattctgcgg   2640
cggcaggaag atttttaccc attcctgaag gacaaccggg aaaagatcga gaagatcctg   2700
accttccgca tcccctacta cgtgggccct ctggccaggg gaaacagcag attcgcctgg   2760
atgaccagaa agagcgagga aaccatcacc ccctggaact tcgaggaagt ggtggacaag   2820
ggcgcttccg cccagagctt catcgagcgg atgaccaact tcgataagaa cctgcccaac   2880
gagaaggtgc tgcccaagca cagcctgctg tacgagtact tcaccgtgta taacgagctg   2940
accaaagtga aatacgtgac cgagggaatg agaaagcccg ccttcctgag cggcgagcag   3000
aaaaaggcca tcgtggacct gctgttcaag accaaccgga aagtgaccgt gaagcagctg   3060
aaagaggact acttcaagaa aatcgagtgc ttcgactccg tggaaatctc cggcgtggaa   3120
gatcggttca acgcctccct gggcacatac cacgatctgc tgaaaattat caaggacaag   3180
gacttcctgg acaatgagga aaacgaggac attctggaag atatcgtgct gaccctgaca   3240
ctgtttgagg acagagagat gatcgaggaa cggctgaaaa cctatgccca cctgttcgac   3300
gacaaagtga tgaagcagct gaagcggcgg agatacaccg gctggggcag gctgagccgg   3360
aagctgatca acggcatccg ggacaagcag tccggcaaga caatcctgga tttcctgaag   3420
tccgacggct tcgccaacag aaacttcatg cagctgatcc acgacgacag cctgaccttt   3480
aaagaggaca tccagaaagc ccaggtgtcc ggccagggcg atagcctgca cgagcacatt   3540
gccaatctgg ccggcagccc cgccattaag aagggcatcc tgcagacagt gaaggtggtg   3600
```

gacgagctcg tgaaagtgat gggccggcac aagcccgaga acatcgtgat cgaaatggcc 3660
agagagaacc agaccaccca gaagggacag aagaacagcc gcgagagaat gaagcggatc 3720
gaagagggca tcaaagagct gggcagccag atcctgaaag aacaccccgt ggaaaacacc 3780
cagctgcaga acgagaagct gtacctgtac tacctgcaga atgggcggga tatgtacgtg 3840
gaccaggaac tggacatcaa ccggctgtcc gactacgatg tggaccatat cgtgcctcag 3900
agctttctga aggacgactc catcgacaac aaggtgctga ccagaagcga caagaaccgg 3960
ggcaagagcg acaacgtgcc ctccgaagag gtcgtgaaga agatgaagaa ctactggcgg 4020
cagctgctga acgccaagct gattacccag agaaagttcg acaatctgac caaggccgag 4080
agaggcggcc tgagcgaact ggataaggcc ggcttcatca agagacagct ggtggaaacc 4140
cggcagatca caaagcacgt ggcacagatc ctggactccc ggatgaacac taagtacgac 4200
gagaatgaca agctgatccg ggaagtgaaa gtgatcaccc tgaagtccaa gctggtgtcc 4260
gatttccgga aggatttcca gttttacaaa gtgcgcgaga tcaacaacta ccaccacgcc 4320
cacgacgcct acctgaacgc cgtcgtggga accgccctga tcaaaaagta ccctaagctg 4380
gaaagcgagt tcgtgtacgg cgactacaag gtgtacgacg tgcggaagat gatcgccaag 4440
agcgagcagg aaatcggcaa ggctaccgcc aagtacttct tctacagcaa catcatgaac 4500
tttttcaaga ccgagattac cctggccaac ggcgagatcc ggaagcggcc tctgatcgag 4560
acaaacggcg aaaccgggga gatcgtgtgg gataagggcc gggattttgc caccgtgcgg 4620
aaagtgctga gcatgcccca agtgaatatc gtgaaaaaga ccgaggtgca gacaggcggc 4680
ttcagcaaag agtctatcct gcccaagagg aacagcgata agctgatcgc cagaaagaag 4740
gactgggacc ctaagaagta cggcggcttc gacagcccca ccgtggccta ttctgtgctg 4800
gtggtggcca aagtggaaaa gggcaagtcc aagaaactga agagtgtgaa agagctgctg 4860
gggatcacca tcatggaaag aagcagcttc gagaagaatc ccatcgactt tctggaagcc 4920
aagggctaca aagaagtgaa aaaggacctg atcatcaagc tgcctaagta ctccctgttc 4980
gagctggaaa acggccggaa gagaatgctg gcctctgccg gcgaactgca gaagggaaac 5040
gaactggccc tgccctccaa atatgtgaac ttcctgtacc tggccagcca ctatgagaag 5100
ctgaagggct cccccgagga taatgagcag aaacagctgt ttgtggaaca gcacaagcac 5160
tacctggacg agatcatcga gcagatcagc gagttctcca agagagtgat cctggccgac 5220
gctaatctgg acaaagtgct gtccgcctac aacaagcacc gggataagcc catcagagag 5280
caggccgaga atatcatcca cctgtttacc ctgaccaatc tgggagcccc tgccgccttc 5340
aagtactttg acaccaccat cgaccggaag aggtacacca gcaccaaaga ggtgctggac 5400
gccaccctga tccaccagag catcaccggc ctgtacgaga cacggatcga cctgtctcag 5460
ctgggaggcg acaaaaggcc ggcggccacg aaaaaggccg gccaggcaaa aaagaaaaag 5520
gaattcggca gtggagaggg cagaggaagt ctgctaacat gcggtgacgt cgaggagaat 5580
cctggcccag tgagcaaggg cgaggagctg ttcaccgggg tggtgcccat cctggtcgag 5640
ctggacggcg acgtaaacgg ccacaagttc agcgtgtccg gcgagggcga gggcgatgcc 5700
acctacggca agctgaccct gaagttcatc tgcaccaccg gcaagctgcc cgtgccctgg 5760
cccaccctcg tgaccaccct gacctacggc gtgcagtgct tcagccgcta ccccgaccac 5820
atgaagcagc acgacttctt caagtccgcc atgcccgaag gctacgtcca ggagcgcacc 5880
atcttcttca aggacgacgg caactacaag acccgcgccg aggtgaagtt cgagggcgac 5940

-continued

```
accctggtga accgcatcga gctgaagggc atcgacttca aggaggacgg caacatcctg   6000
gggcacaagc tggagtacaa ctacaacagc cacaacgtct atatcatggc cgacaagcag   6060
aagaacggca tcaaggtgaa cttcaagatc cgccacaaca tcgaggacgg cagcgtgcag   6120
ctcgccgacc actaccagca gaacaccccc atcggcgacg gccccgtgct gctgcccgac   6180
aaccactacc tgagcaccca gtccgccctg agcaaagacc ccaacgagaa gcgcgatcac   6240
atggtcctgc tggagttcgt gaccgccgcc gggatcactc tcggcatgga cgagctgtac   6300
aaggaattct aactagagct cgctgatcag cctcgactgt gccttctagt tgccagccat   6360
ctgttgtttg cccctccccc gtgccttcct tgaccctgga aggtgccact cccactgtcc   6420
tttcctaata aaatgaggaa attgcatcgc attgtctgag taggtgtcat tctattctgg   6480
ggggtggggt ggggcaggac agcaaggggg aggattggga agagaatagc aggcatgctg   6540
gggagcggcc gcaggaaccc ctagtgatgg agttggccac tccctctctg cgcgctcgct   6600
cgctcactga ggccgggcga ccaaaggtcg cccgacgccc gggctttgcc cgggcggcct   6660
cagtgagcga gcgagcgcgc agctgcctgc aggggcgcct gatgcggtat tttctcctta   6720
cgcatctgtg cggtatttca caccgcatac gtcaaagcaa ccatagtacg cgccctgtag   6780
cggcgcatta agcgcggcgg gtgtggtggt tacgcgcagc gtgaccgcta cacttgccag   6840
cgccttagcg cccgctcctt tcgctttctt cccttccttt ctcgccacgt tcgccggctt   6900
tccccgtcaa gctctaaatc gggggctccc tttagggttc cgatttagtg ctttacggca   6960
cctcgacccc aaaaaacttg atttgggtga tggttcacgt agtgggccat cgccctgata   7020
gacggttttt cgccctttga cgttggagtc cacgttcttt aatagtggac tcttgttcca   7080
aactggaaca acactcaact ctatctcggg ctattctttt gatttataag ggattttgcc   7140
gatttcggtc tattggttaa aaaatgagct gatttaacaa aaatttaacg cgaattttaa   7200
caaaatatta acgtttacaa ttttatggtg cactctcagt acaatctgct ctgatgccgc   7260
atagttaagc cagccccgac acccgccaac acccgctgac gcgccctgac gggcttgtct   7320
gctcccggca tccgcttaca gacaagctgt gaccgtctcc gggagctgca tgtgtcagag   7380
gttttcaccg tcatcaccga aacgcgcgag acgaaagggc ctcgtgatac gcctattttt   7440
ataggttaat gtcatgataa taatggtttc ttagacgtca ggtggcactt ttcggggaaa   7500
tgtgcgcgga acccctattt gtttattttt ctaaatacat tcaaatatgt atccgctcat   7560
gagacaataa ccctgataaa tgcttcaata atattgaaaa aggaagagta tgagtattca   7620
acatttccgt gtcgccctta ttcccttttt tgcggcattt tgccttcctg tttttgctca   7680
cccagaaacg ctggtgaaag taaaagatgc tgaagatcag ttgggtgcac gagtgggtta   7740
catcgaactg gatctcaaca gcggtaagat ccttgagagt tttcgccccg aagaacgttt   7800
tccaatgatg agcactttta aagttctgct atgtggcgcg gtattatccc gtattgacgc   7860
cgggcaagag caactcggtc gccgcataca ctattctcag aatgacttgg ttgagtactc   7920
accagtcaca gaaaagcatc ttacggatgg catgacagta agagaattat gcagtgctgc   7980
cataaccatg agtgataaca ctgcggccaa cttacttctg acaacgatcg gaggaccgaa   8040
ggagctaacc gcttttttgc acaacatggg ggatcatgta actcgccttg atcgttggga   8100
accggagctg aatgaagcca taccaaacga cgagcgtgac accacgatgc ctgtagcaat   8160
ggcaacaacg ttgcgcaaac tattaactgg cgaactactt actctagctt cccggcaaca   8220
attaatagac tggatggagg cggataaagt tgcaggacca cttctgcgct cggcccttcc   8280
ggctggctgg tttattgctg ataaatctgg agccggtgag cgtggaagcc gcggtatcat   8340
```

```
tgcagcactg gggccagatg gtaagccctc ccgtatcgta gttatctaca cgacggggag   8400
tcaggcaact atggatgaac gaaatagaca gatcgctgag ataggtgcct cactgattaa   8460
gcattggtaa ctgtcagacc aagtttactc atatatactt tagattgatt taaaacttca   8520
tttttaattt aaaaggatct aggtgaagat cctttttgat aatctcatga ccaaaatccc   8580
ttaacgtgag ttttcgttcc actgagcgtc agaccccgta gaaaagatca aaggatcttc   8640
ttgagatcct ttttttctgc gcgtaatctg ctgcttgcaa acaaaaaaac caccgctacc   8700
agcggtggtt tgtttgccgg atcaagagct accaactctt tttccgaagg taactggctt   8760
cagcagagcg cagataccaa atactgttct tctagtgtag ccgtagttag gccaccactt   8820
caagaactct gtagcaccgc ctacatacct cgctctgcta atcctgttac cagtggctgc   8880
tgccagtggc gataagtcgt gtcttaccgg gttggactca agacgatagt taccggataa   8940
ggcgcagcgg tcgggctgaa cggggggttc gtgcacacag cccagcttgg agcgaacgac   9000
ctacaccgaa ctgagatacc tacagcgtga gctatgagaa agcgccacgc ttcccgaagg   9060
gagaaaggcg gacaggtatc cggtaagcgg cagggtcgga acaggagagc gcacgaggga   9120
gcttccaggg ggaaacgcct ggtatcttta tagtcctgtc gggtttcgcc acctctgact   9180
tgagcgtcga tttttgtgat gctcgtcagg ggggcggagc ctatggaaaa acgccagcaa   9240
cgcggccttt ttacggttcc tggccttttg ctggcctttt gctcacatgt              9290
```

```
<210> SEQ ID NO 10
<211> LENGTH: 9290
<212> TYPE: DNA
<213> ORGANISM: Artificial sequence
<220> FEATURE:
<223> OTHER INFORMATION: Synthetic

<400> SEQUENCE: 10
```

```
gagggcctat ttcccatgat tccttcatat ttgcatatac gatacaaggc tgttagagag     60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccc ctgtccggat tcaaattgcg ttttagagct agaaatagca agttaaaata    300
aggctagtcc gttatcaact tgaaaaagtg gcaccgagtc ggtgcttttt tgttttagag    360
ctagaaatag caagttaaaa taaggctagt ccgtttttag cgcgtgcgcc aattctgcag    420
acaaatggct ctagaggtac ccgttacata acttacggta aatggcccgc ctggctgacc    480
gcccaacgac ccccgcccat tgacgtcaat agtaacgcca atagggactt tccattgacg    540
tcaatgggtg gagtatttac ggtaaactgc ccacttggca gtacatcaag tgtatcatat    600
gccaagtacg ccccctattg acgtcaatga cggtaaatgg cccgcctggc attgtgccca    660
gtacatgacc ttatgggact ttcctacttg gcagtacatc tacgtattag tcatcgctat    720
taccatggtc gaggtgagcc ccacgttctg cttcactctc cccatctccc ccccctcccc    780
acccccaatt ttgtatttat ttatttttta attattttgt gcagcgatgg gggcgggggg    840
gggggggggg cgcgcgccag gcggggcggg gcggggcgag gggcggggcg gggcgaggcg    900
gagaggtgcg gcggcagcca atcagagcgg cgcgctccga aagtttcctt ttatggcgag    960
gcggcggcgg cggcggccct ataaaaagcg aagcgcgcgg cgggcgggag tcgctgcgcg   1020
ctgccttcgc cccgtgcccc gctccgccgc cgcctcgcgc cgcccgcccc ggctctgact   1080
```

-continued

```
gaccgcgtta ctcccacagg tgagcgggcg ggacggccct tctcctccgg gctgtaatta   1140
gctgagcaag aggtaagggt ttaagggatg gttggttggt ggggtattaa tgtttaatta   1200
cctggagcac ctgcctgaaa tcactttttt tcaggttgga ccggtgccac catggactat   1260
aaggaccacg acggagacta caaggatcat gatattgatt acaaagacga tgacgataag   1320
atggccccaa agaagaagcg gaaggtcggt atccacggag tcccagcagc cgacaagaag   1380
tacagcatcg gcctggacat cggcaccaac tctgtgggct gggccgtgat caccgacgag   1440
tacaaggtgc ccagcaagaa attcaaggtg ctgggcaaca ccgaccggca cagcatcaag   1500
aagaacctga tcggagccct gctgttcgac agcggcgaaa cagccgaggc cacccggctg   1560
aagagaaccg ccagaagaag atacaccaga cggaagaacc ggatctgcta tctgcaagag   1620
atcttcagca acgagatggc caaggtggac gacagcttct tccacagact ggaagagtcc   1680
ttcctggtgg aagaggataa gaagcacgag cggcacccca tcttcggcaa catcgtggac   1740
gaggtggcct accacgagaa gtaccccacc atctaccacc tgagaaagaa actggtggac   1800
agcaccgaca aggccgacct gcggctgatc tatctggccc tggcccacat gatcaagttc   1860
cggggccact tcctgatcga gggcgacctg aaccccgaca acagcgacgt ggacaagctg   1920
ttcatccagc tggtgcagac ctacaaccag ctgttcgagg aaaaccccat caacgccagc   1980
ggcgtggacg ccaaggccat cctgtctgcc agactgagca agagcagacg gctggaaaat   2040
ctgatcgccc agctgcccgg cgagaagaag aatggcctgt tcggaaacct gattgccctg   2100
agcctgggcc tgacccccaa cttcaagagc aacttcgacc tggccgagga tgccaaactg   2160
cagctgagca aggacaccta cgacgacgac ctggacaacc tgctggccca gatcggcgac   2220
cagtacgccg acctgtttct ggccgccaag aacctgtccg acgccatcct gctgagcgac   2280
atcctgagag tgaacaccga gatcaccaag gccccccctga gcgcctctat gatcaagaga   2340
tacgacgagc accaccagga cctgaccctg ctgaaagctc tcgtgcggca gcagctgcct   2400
gagaagtaca aagagatttt cttcgaccag agcaagaacg gctacgccgg ctacattgac   2460
ggcggagcca gccaggaaga gttctacaag ttcatcaagc ccatcctgga aaagatggac   2520
ggcaccgagg aactgctcgt gaagctgaac agagaggacc tgctgcggaa gcagcggacc   2580
ttcgacaacg gcagcatccc ccaccagatc cacctgggag agctgcacgc cattctgcgg   2640
cggcaggaag atttttaccc attcctgaag gacaaccggg aaaagatcga gaagatcctg   2700
accttccgca tcccctacta cgtgggccct ctggccaggg gaaacagcag attcgcctgg   2760
atgaccagaa agagcgagga aaccatcacc ccctggaact tcgaggaagt ggtggacaag   2820
ggcgcttccg cccagagctt catcgagcgg atgaccaact tcgataagaa cctgcccaac   2880
gagaaggtgc tgcccaagca cagcctgctg tacgagtact tcaccgtgta taacgagctg   2940
accaaagtga aatacgtgac cgagggaatg agaaagcccg ccttcctgag cggcgagcag   3000
aaaaaggcca tcgtggacct gctgttcaag accaaccgga aagtgaccgt gaagcagctg   3060
aaagaggact acttcaagaa aatcgagtgc ttcgactccg tggaaatctc cggcgtggaa   3120
gatcggttca acgcctccct gggcacatac cacgatctgc tgaaaattat caaggacaag   3180
gacttcctgg acaatgagga aaacgaggac attctggaag atatcgtgct gaccctgaca   3240
ctgtttgagg acagagagat gatcgaggaa cggctgaaaa cctatgccca cctgttcgac   3300
gacaaagtga tgaagcagct gaagcggcgg agatacaccg gctggggcag gctgagccgg   3360
aagctgatca acggcatccg ggacaagcag tccggcaaga caatcctgga tttcctgaag   3420
tccgacggct tcgccaacag aaacttcatg cagctgatcc acgacgacag cctgaccttt   3480
```

aaagaggaca tccagaaagc ccaggtgtcc ggccagggcg atagcctgca cgagcacatt 3540
gccaatctgg ccggcagccc cgccattaag aagggcatcc tgcagacagt gaaggtggtg 3600
gacgagctcg tgaaagtgat gggccggcac aagcccgaga acatcgtgat cgaaatggcc 3660
agagagaacc agaccaccca gaagggacag aagaacagcc gcgagagaat gaagcggatc 3720
gaagagggca tcaaagagct gggcagccag atcctgaaag aacaccccgt ggaaaacacc 3780
cagctgcaga acgagaagct gtacctgtac tacctgcaga atgggcggga tatgtacgtg 3840
gaccaggaac tggacatcaa ccggctgtcc gactacgatg tggaccatat cgtgcctcag 3900
agctttctga aggacgactc catcgacaac aaggtgctga ccagaagcga caagaaccgg 3960
ggcaagagcg acaacgtgcc ctccgaagag gtcgtgaaga agatgaagaa ctactggcgg 4020
cagctgctga acgccaagct gattacccag agaaagttcg acaatctgac caaggccgag 4080
agaggcggcc tgagcgaact ggataaggcc ggcttcatca agagacagct ggtggaaacc 4140
cggcagatca caaagcacgt ggcacagatc ctggactccc ggatgaacac taagtacgac 4200
gagaatgaca agctgatccg ggaagtgaaa gtgatcaccc tgaagtccaa gctggtgtcc 4260
gatttccgga aggatttcca gttttacaaa gtgcgcgaga tcaacaacta ccaccacgcc 4320
cacgacgcct acctgaacgc cgtcgtggga accgccctga tcaaaaagta ccctaagctg 4380
gaaagcgagt tcgtgtacgg cgactacaag gtgtacgacg tgcggaagat gatcgccaag 4440
agcgagcagg aaatcggcaa ggctaccgcc aagtacttct tctacagcaa catcatgaac 4500
tttttcaaga ccgagattac cctggccaac ggcgagatcc ggaagcggcc tctgatcgag 4560
acaaacggcg aaaccgggga gatcgtgtgg gataagggcc gggattttgc caccgtgcgg 4620
aaagtgctga gcatgcccca agtgaatatc gtgaaaaaga ccgaggtgca gacaggcggc 4680
ttcagcaaag agtctatcct gcccaagagg aacagcgata agctgatcgc cagaaagaag 4740
gactgggacc ctaagaagta cggcggcttc gacagcccca ccgtggccta ttctgtgctg 4800
gtggtggcca aagtggaaaa gggcaagtcc aagaaactga agagtgtgaa agagctgctg 4860
gggatcacca tcatggaaag aagcagcttc gagaagaatc ccatcgactt tctggaagcc 4920
aagggctaca aagaagtgaa aaaggacctg atcatcaagc tgcctaagta ctccctgttc 4980
gagctggaaa acggccggaa gagaatgctg gcctctgccg gcgaactgca gaagggaaac 5040
gaactggccc tgccctccaa atatgtgaac ttcctgtacc tggccagcca ctatgagaag 5100
ctgaagggct cccccgagga taatgagcag aaacagctgt ttgtggaaca gcacaagcac 5160
tacctggacg agatcatcga gcagatcagc gagttctcca agagagtgat cctggccgac 5220
gctaatctgg acaaagtgct gtccgcctac aacaagcacc gggataagcc catcagagag 5280
caggccgaga atatcatcca cctgtttacc ctgaccaatc tgggagcccc tgccgccttc 5340
aagtactttg acaccaccat cgaccggaag aggtacacca gcaccaaaga ggtgctggac 5400
gccaccctga tccaccagag catcaccggc ctgtacgaga cacggatcga cctgtctcag 5460
ctgggaggcg acaaaaggcc ggcggccacg aaaaaggccg gccaggcaaa aaagaaaaag 5520
gaattcggca gtggagaggg cagaggaagt ctgctaacat gcggtgacgt cgaggagaat 5580
cctggcccag tgagcaaggg cgaggagctg ttcaccgggg tggtgcccat cctggtcgag 5640
ctggacggcg acgtaaacgg ccacaagttc agcgtgtccg gcgagggcga gggcgatgcc 5700
acctacggca agctgaccct gaagttcatc tgcaccaccg gcaagctgcc cgtgccctgg 5760
cccaccctcg tgaccaccct gacctacggc gtgcagtgct tcagccgcta ccccgaccac 5820

-continued

```
atgaagcagc acgacttctt caagtccgcc atgcccgaag gctacgtcca ggagcgcacc   5880
atcttcttca aggacgacgg caactacaag acccgcgccg aggtgaagtt cgagggcgac   5940
accctggtga accgcatcga gctgaagggc atcgacttca aggaggacgg caacatcctg   6000
gggcacaagc tggagtacaa ctacaacagc cacaacgtct atatcatggc cgacaagcag   6060
aagaacggca tcaaggtgaa cttcaagatc cgccacaaca tcgaggacgg cagcgtgcag   6120
ctcgccgacc actaccagca gaacaccccc atcggcgacg gccccgtgct gctgcccgac   6180
aaccactacc tgagcaccca gtccgccctg agcaaagacc ccaacgagaa gcgcgatcac   6240
atggtcctgc tggagttcgt gaccgccgcc gggatcactc tcggcatgga cgagctgtac   6300
aaggaattct aactagagct cgctgatcag cctcgactgt gccttctagt tgccagccat   6360
ctgttgtttg cccctccccc gtgccttcct tgaccctgga aggtgccact cccactgtcc   6420
tttcctaata aaatgaggaa attgcatcgc attgtctgag taggtgtcat tctattctgg   6480
ggggtggggt ggggcaggac agcaaggggg aggattggga agagaatagc aggcatgctg   6540
gggagcggcc gcaggaaccc ctagtgatgg agttggccac tccctctctg cgcgctcgct   6600
cgctcactga ggccgggcga ccaaaggtcg cccgacgccc gggctttgcc cgggcggcct   6660
cagtgagcga gcgagcgcgc agctgcctgc aggggcgcct gatgcggtat tttctcctta   6720
cgcatctgtg cggtatttca caccgcatac gtcaaagcaa ccatagtacg cgccctgtag   6780
cggcgcatta agcgcggcgg gtgtggtggt tacgcgcagc gtgaccgcta cacttgccag   6840
cgccttagcg cccgctcctt tcgctttctt cccttccttt ctcgccacgt tcgccggctt   6900
tccccgtcaa gctctaaatc gggggctccc tttagggttc cgatttagtg ctttacggca   6960
cctcgacccc aaaaaacttg atttgggtga tggttcacgt agtgggccat cgccctgata   7020
gacggttttt cgccctttga cgttggagtc cacgttcttt aatagtggac tcttgttcca   7080
aactggaaca acactcaact ctatctcggg ctattctttt gatttataag ggattttgcc   7140
gatttcggtc tattggttaa aaaatgagct gatttaacaa aaatttaacg cgaattttaa   7200
caaaatatta acgtttacaa ttttatggtg cactctcagt acaatctgct ctgatgccgc   7260
atagttaagc cagccccgac acccgccaac acccgctgac gcgccctgac gggcttgtct   7320
gctcccggca tccgcttaca gacaagctgt gaccgtctcc gggagctgca tgtgtcagag   7380
gttttcaccg tcatcaccga aacgcgcgag acgaaagggc ctcgtgatac gcctattttt   7440
ataggttaat gtcatgataa taatggtttc ttagacgtca ggtggcactt ttcggggaaa   7500
tgtgcgcgga acccctattt gtttattttt ctaaatacat tcaaatatgt atccgctcat   7560
gagacaataa ccctgataaa tgcttcaata atattgaaaa aggaagagta tgagtattca   7620
acatttccgt gtcgccctta ttcccttttt tgcggcattt tgccttcctg tttttgctca   7680
cccagaaacg ctggtgaaag taaaagatgc tgaagatcag ttgggtgcac gagtgggtta   7740
catcgaactg gatctcaaca gcggtaagat ccttgagagt tttcgccccg aagaacgttt   7800
tccaatgatg agcactttta aagttctgct atgtggcgcg gtattatccc gtattgacgc   7860
cgggcaagag caactcggtc gccgcataca ctattctcag aatgacttgg ttgagtactc   7920
accagtcaca gaaaagcatc ttacggatgg catgacagta agagaattat gcagtgctgc   7980
cataaccatg agtgataaca ctgcggccaa cttacttctg acaacgatcg gaggaccgaa   8040
ggagctaacc gcttttttgc acaacatggg ggatcatgta actcgccttg atcgttggga   8100
accggagctg aatgaagcca taccaaacga cgagcgtgac accacgatgc ctgtagcaat   8160
ggcaacaacg ttgcgcaaac tattaactgg cgaactactt actctagctt cccggcaaca   8220
```

```
attaatagac tggatggagg cggataaagt tgcaggacca cttctgcgct cggcccttcc   8280
ggctggctgg tttattgctg ataaatctgg agccggtgag cgtggaagcc gcggtatcat   8340
tgcagcactg gggccagatg gtaagccctc ccgtatcgta gttatctaca cgacggggag   8400
tcaggcaact atggatgaac gaaatagaca gatcgctgag ataggtgcct cactgattaa   8460
gcattggtaa ctgtcagacc aagtttactc atatatactt tagattgatt taaaacttca   8520
tttttaattt aaaaggatct aggtgaagat cctttttgat aatctcatga ccaaaatccc   8580
ttaacgtgag ttttcgttcc actgagcgtc agaccccgta gaaaagatca aaggatcttc   8640
ttgagatcct ttttttctgc gcgtaatctg ctgcttgcaa acaaaaaaac caccgctacc   8700
agcggtggtt tgtttgccgg atcaagagct accaactctt tttccgaagg taactggctt   8760
cagcagagcg cagataccaa atactgttct tctagtgtag ccgtagttag gccaccactt   8820
caagaactct gtagcaccgc ctacatacct cgctctgcta atcctgttac cagtggctgc   8880
tgccagtggc gataagtcgt gtcttaccgg gttggactca agacgatagt taccggataa   8940
ggcgcagcgg tcgggctgaa cggggggttc gtgcacacag cccagcttgg agcgaacgac   9000
ctacaccgaa ctgagatacc tacagcgtga gctatgagaa agcgccacgc ttcccgaagg   9060
gagaaaggcg gacaggtatc cggtaagcgg cagggtcgga acaggagagc gcacgaggga   9120
gcttccaggg ggaaacgcct ggtatcttta tagtcctgtc gggtttcgcc acctctgact   9180
tgagcgtcga tttttgtgat gctcgtcagg ggggcggagc ctatggaaaa acgccagcaa   9240
cgcggccttt ttacggttcc tggccttttg ctggcctttt gctcacatgt              9290
```

```
<210> SEQ ID NO 11
<211> LENGTH: 4242
<212> TYPE: DNA
<213> ORGANISM: Artificial sequence
<220> FEATURE:
<223> OTHER INFORMATION: Synthetic

<400> SEQUENCE: 11
```

```
cagcactatg tggacatgaa ttcaattggc tagcaggagt caatgggaaa aacccattgg     60
agccaagtac actgactcaa tagggacttt ccattgggtt ttgcccagta cataaggtca    120
atagggggtg agtcaacagg aaagtcccat tggagccaag tacattgagt caatagggac    180
tttccaatgg gttttgccca gtacataagg tcaatgggag gtaagccaat gggtttttcc    240
cattactgac atgtatactg agtcattagg gactttccaa tgggttttgc ccagtacata    300
aggtcaatag ggtgaatca acaggaaagt cccattggag ccaagtacac tgagtcaata    360
gggactttcc attgggtttt gcccagtaca aaaggtcaat agggggtgag tcaatgggtt    420
tttcccatta ttggcacata cataaggtca ataggggtga ctagtgctgc agtatttagc    480
atgccccacc catctgcaag gcattctgga tagtgtcaaa acagctggaa atcaagtctg    540
tttatctcaa actttagcat tttgggaata aatgatattt gctatgctgg ttaaattaga    600
ttttagttaa atttcctgct gaagctctag tatgataagt aacttgacct aagtgtaaag    660
ttgagatttc cttcaggttt atatagtccc tatcagtgat agagacctca gatatcgtga    720
aatacacctc tctagcagga gtcaatggga aaaacccatt ggagccaagt acactgactc    780
aatagggact ttccattggg ttttgcccag tacataaggt caataggggg tgagtcaaca    840
ggaaagtccc attggagcca agtacattga gtcaataggg actttccaat gggttttgcc    900
cagtacataa ggtcaatggg aggtaagcca atgggttttt cccattactg acatgtatac    960
```

-continued tgagtcatta gggactttcc aatgggtttt gcccagtaca taaggtcaat aggggtgaat 1020
caacaggaaa gtcccattgg agccaagtac actgagtcaa tagggacttt ccattgggtt 1080
ttgcccagta caaaaggtca ataggggggtg agtcaatggg tttttcccat tattggcaca 1140
tacataaggt caataggggt gactagtgga gaagagcatg cttgagggct gagtgcccct 1200
cagtgggcag agagcacatg gcccacagtc cctgagaagt tggggggagg ggtgggcaat 1260
tgaactggtg cctagagaag gtggggcttg ggtaaactgg gaaagtgatg tggtgtactg 1320
gctccacctt tttccccagg gtgggggaga accatatata agtgcagtag tctctgtgaa 1380
cattcaagct tctgccttct ccctcctgtg agtttggtaa gtcactgact gtctatgcct 1440
gggaaagggt gggcaggaga tggggcagtg caggaaaagt ggcactatga accctgcagc 1500
cctagacaat tgtactaacc ttcttctctt tcctctcctg acaggttggt aaccaagcca 1560
ccatggtttc caaaggggaa gaagtcatca aagagttcat gaggttcaaa gtcagaatgg 1620
aaggcagcat gaatggccat gagtttgaga ttgaaggaga aggagagggc agaccctatg 1680
agggcacaca gacagccaag ctgaaagtga ccaaaggtgg ccctctgcct tttgcctggg 1740
acatcctgtc tccacagttt atgtatggca gcaaggccta tgtgaagcac cctgctgaca 1800
tccctgacta caagaagctg agcttcccag agggcttcaa gtgggagaga gtgatgaact 1860
ttgaggatgg tggcctggtc acagtgaccc aggatagctc tctccaggat ggcaccctga 1920
tctacaaagt gaagatgagg ggcacaaact tccctccaga tggccctgtg atgcagaaaa 1980
agaccatggg ctgggaagcc tccacagaga gactgtaccc tagagatggg gtgctgaaag 2040
gggagatcca ccaggctctg aagctgaagg atggtggaca ctacctggtt gagttcaaga 2100
ccatctacat ggccaagaaa cctgtgcagc tgcctggcta ctactatgtg gacaccaagc 2160
tggacatcac cagccacaat gaggactaca ccattgtgga acagtatgag aggagtgaag 2220
gcaggcacca cctgttcctt ggacatggca caggcagcac aggctctggc agttctggaa 2280
cagccagctc tgaggacaac aacatggctg tgatcaaaga gtttatgaga ttcaaagtta 2340
ggatggaagg ttccatgaat gggcatgaat ttgaaattga aggagaagga gaaggcaggc 2400
cttatgaagg gacccagact gctaaactca aagtcacaaa aggtggacca cttccatttg 2460
cttgggatat tctgagccct cagtttatgt atgggtccaa agcctatgtc aaacatccag 2520
cagacatccc agattataag aaactgtctt ttccagaggg gtttaaatgg gaaagagtca 2580
tgaattttga agatggtgga cttgtgactg tcacccagga cagcagcctg caagatggaa 2640
cactcatcta caaagtcaaa atgagaggga ccaattttcc acctgatggg ccagtgatgc 2700
aaaagaaaac aatgggatgg gaagcaagca ctgagaggct ctatcccaga gatggtgtcc 2760
tcaaagggga aattcatcag gccctcaagc tcaaagatgg tggccattat cttgttgagt 2820
ttaaaacaat ctatatggct aaaaagccag tccagctgcc agggtactat tatgttgata 2880
caaaactgga cattacctct cacaatgaag attatacaat tgtggaacaa tatgagagga 2940
gtgaaggcag acatcatctg tttctgtatg gaatggatga gctgtacaag tgaagatcta 3000
cttctggcta ataaaagatc agagctctag tgatctgtgt gttggttttt tgtgtctgca 3060
ttctagctct agtgatcagc agttcaacct gttgatagta tgtactaagc tctcatgttt 3120
aatgtactaa gctctcatgt ttaatgaact aaaccctcat ggctaatgta ctaagctctc 3180
atggctaatg tactaagctc tcatgtttca tgtactaagc tctcatgttt gaacaataaa 3240
attaatataa atcagcaact taaatagcct ctaaggtttt aagttttata agaaaaaaaa 3300
gaatatataa ggcttttaaa ggttttaagg tttcctaggt tatcctcata tgagctctta 3360
gaaaaactca tccagcatca aatgaaactg caatttattc atatcaggat tatcaatacc 3420
atatttttga aaaagtcttt tctgtaatga aggagaaaac tcacccaggc agttccatag 3480
gatggcaaga tcctggtatc tgtctgcaat tccaactctt ccaacatcaa tacaacctat 3540
taatttcccc tcatcaaaaa taaggttatc aagtgagaaa tcaccatgag tgaccactga 3600
atctggtgag aatggcaaaa gattatgcat ttctttccag acttgttcaa caggccagcc 3660
atttctctca tcatcaaaat cactggcatc aaccaaacca ttattcattc ttgattgggc 3720
ctgagccagt ctaaatactc tatcagagtt aaaaggacaa ttacaaacag gaatggaatg 3780
caatcttctc aggaacactg ccagggcatc aacaatattt tcacctgaat caggatattc 3840
ttccaatacc tggaatgctg ttttccctgg gatggcagtg gtgagtaacc atgcatcatc 3900
aggagttctg ataaaatgct tgatggttgg aagaggcata aattcagtca gccagtttag 3960
tctgaccatc tcatctgtaa catcattggc aacagaacct ttgccatgtt tcagaaacaa 4020
ctctggggca tctggcttcc catacaatct atagattgtg gcacctgatt gcccaacatt 4080
atctctagcc catttatacc catataaatc agcatccatg ttggaattta atcttggcct 4140
ggagcaagag gtttctcttt gaatatggct catacatgtg cacctcctat agtgagttgt 4200
attatactat gcagatatac tatgccaatg tttaattgtc ag 4242

<210> SEQ ID NO 12
<211> LENGTH: 3314
<212> TYPE: DNA
<213> ORGANISM: Artificial sequence
<220> FEATURE:
<223> OTHER INFORMATION: Synthetic

<400> SEQUENCE: 12
gaattctcat agctagcatg ttacataact tatggtaaat ggcctgcctg gctgactgcc 60
caatgacccc tgcccaatga tgtcaataat gatgtatgtt cccatgtaat gccaataggg 120
actttccatt gatgtcaatg ggtggagtat ttatggtaac tgcccacttg gcagtacatc 180
aagtgtatca tatgccaagt atgcccccta ttgatgtcaa tgatggtaaa tggcctgcct 240
ggcattatgc ccagtacatg accttatggg actttcctac ttggcagtac atctatgtat 300
tagtcattgc tattaccatg gtgatgggtt ttggcagtac atcaatgggt gtggatagtg 360
gtttgaccca tggggatttc caagtctcca ccccattgat gccaatggga gtttgttttg 420
gcaccaaaat caatgggact ttccaaaatg ttgtaacaac tctgccccat tgatggaaat 480
gggtggtagg tgtgtgtggt gggaggtcta tataagcaga gcttgtttag tgaactggat 540
gcacctacta gatatcagcg aatccagacc aacaatatca agagtattgt tggtctggat 600
tcgctttttt tctagatact aagcttggcg taatcatggt catagctgtt tcctgtgtga 660
aattgttatc cgctcacaat tccacacaac atacgagccg gaagcataaa gtgtaaagcc 720
tggggtgcct aatgagtgag ctaactcaca ttaattgcgt tgcgctcact gcccgctttc 780
cagtcgggaa acctgtcgtg ccagctgcat taatgaatcg gccaacgcgc ggggagaggc 840
ggtttgcgta ttgggcgctc ttccgcttcc tcgctcactg actcgctgcg ctcggtcgtt 900
cggctgcggc gagcggtatc agctcactca aaggcggtaa tacggttatc cacagaatca 960
ggggataacg caggaaagaa catgtgagca aaaggccagc aaaaggccag gaaccgtaaa 1020
aaggccgcgt tgctggcgtt tttccatagg ctccgccccc ctgacgagca tcacaaaaat 1080
cgacgctcaa gtcagaggtg gcgaaacccg acaggactat aaagatacca ggcgtttccc 1140

-continued

```
cctggaagct ccctcgtgcg ctctcctgtt ccgaccctgc cgcttaccgg atacctgtcc   1200

gcctttctcc cttcgggaag cgtggcgctt tctcatagct cacgctgtag gtatctcagt   1260

tcggtgtagg tcgttcgctc caagctgggc tgtgtgcacg aaccccccgt tcagcccgac   1320

cgctgcgcct tatccggtaa ctatcgtctt gagtccaacc cggtaagaca cgacttatcg   1380

ccactggcag cagccactgg taacaggatt agcagagcga ggtatgtagg cggtgctaca   1440

gagttcttga agtggtggcc taactacggc tacactagaa gaacagtatt tggtatctgc   1500

gctctgctga agccagttac cttcggaaaa agagttggta gctcttgatc cggcaaacaa   1560

accaccgctg gtagcggtgg tttttttgtt tgcaagcagc agattacgcg cagaaaaaaa   1620

ggatctcaag aagatccttt gatcttttct acggggtctg acgctcagtg gaacgaaaac   1680

tcacgttaag ggattttggt catgagatta tcaaaaagga tcttcaccta gatcctttta   1740

aattaaaaat gaagttttaa atcaatctaa agtatatatg agtaaacttg gtctgacagt   1800

taccaatgct taatcagtga ggcacctatc tcagcgatct gtctatttcg ttcatccata   1860

gttgcctgac tccccgtcgt gtagataact acgatacggg agggcttacc atctggcccc   1920

agtgctgcaa tgataccgcg agacccacgc tcaccggctc cagatttatc agcaataaac   1980

cagccagccg gaagggccga gcgcagaagt ggtcctgcaa ctttatccgc ctccatccag   2040

tctattaatt gttgccggga agctagagta agtagttcgc cagttaatag tttgcgcaac   2100

gttgttgcca ttgctacagg catcgtggtg tcacgctcgt cgtttggtat ggcttcattc   2160

agctccggtt cccaacgatc aaggcgagtt acatgatccc ccatgttgtg caaaaaagcg   2220

gttagctcct tcggtcctcc gatcgttgtc agaagtaagt tggccgcagt gttatcactc   2280

atggttatgg cagcactgca taattctctt actgtcatgc catccgtaag atgcttttct   2340

gtgactggtg agtactcaac caagtcattc tgagaatagt gtatgcggcg accgagttgc   2400

tcttgcccgg cgtcaatacg ggataatacc gcgccacata gcagaacttt aaaagtgctc   2460

atcattggaa aacgttcttc ggggcgaaaa ctctcaagga tcttaccgct gttgagatcc   2520

agttcgatgt aacccactcg tgcacccaac tgatcttcag catcttttac tttcaccagc   2580

gtttctgggt gagcaaaaac aggaaggcaa aatgccgcaa aaaagggaat aagggcgaca   2640

cggaaatgtt gaatactcat actcttcctt tttcaatatt attgaagcat ttatcagggt   2700

tattgtctca tgagcggata catatttgaa tgtatttaga aaaataaaca aataggggtt   2760

ccgcgcacat ttccccgaaa agtgccacct gacgtctaag aaaccattat tatcatgaca   2820

ttaacctata aaaataggcg tatcacgagg ccctttcgtc tcgcgcgttt cggtgatgac   2880

ggtgaaaacc tctgacacat gcagctcccg gagacggtca cagcttgtct gtaagcggat   2940

gccgggagca gacaagcccg tcagggcgcg tcagcgggtg ttggcgggtg tcggggctgg   3000

cttaactatg cggcatcaga gcagattgta ctgagagtgc accatatgcg gtgtgaaata   3060

ccgcacagat gcgtaaggag aaaataccgc atcaggcgcc attcgccatt caggctgcgc   3120

aactgttggg aagggcgatc ggtgcgggcc tcttcgctat tacgccagct ggcgaaaggg   3180

ggatgtgctg caaggcgatt aagttgggta acgccagggt tttcccagtc acgacgttgt   3240

aaaacgacgg ccagtcctta atagttgcag ccaaatcctt cctgtcagat ttggctgcaa   3300

ctattaaggt tttt                                                      3314
```

<210> SEQ ID NO 13
<211> LENGTH: 2969
<212> TYPE: DNA
<213> ORGANISM: Artificial sequence
<220> FEATURE:
<223> OTHER INFORMATION: Synthetic

<400> SEQUENCE: 13
cactatgtgg acatgaattc aattggctag caggggcctg aaataacctc tgaaagagga 60
acttggttag gtaccttctg aggctgaaag aaccagctgt ggaatgtgtg tcagttaggg 120
tgtggaaagt ccccaggctc cccagcaggc agaagtatgc aaagcatgca tctcaattag 180
tcagcaacca ggtgtggaaa gtccccaggc tccccagcag gcagaagtat gcaaagcatg 240
catctcaatt agtcagcaac catagtccca gtctagcagg agtcaatggg aaaaacccat 300
tggagccaag tacactgact caatagggac tttccattgg gttttgccca gtacataagg 360
tcaatagggg gtgagtcaac aggaaagtcc cattggagcc aagtacattg agtcaatagg 420
gactttccaa tgggttttgc ccagtacata aggtcaatgg gaggtaagcc aatgggtttt 480
tcccattact gacatgtata ctgagtcatt agggactttc caatgggttt tgcccagtac 540
ataaggtcaa taggggtgaa tcaacaggaa agtcccattg gagccaagta cactgagtca 600
atagggactt tccattgggt tttgcccagt acaaaaggtc aataggggt gagtcaatgg 660 gtttttccca ttattggcac atacataagg tcaatagggg tgactagtgg agaagagcat 720
gcttgagggc tgagtgcccc tcagtgggca gagagcacat ggcccacagt ccctgagaag 780 ttgggggag gggtgggcaa ttgaactggt gcctagagaa ggtggggctt gggtaaactg 840
ggaaagtgat gtggtgtact ggctccacct ttttccccag ggtgggggag aaccatatat 900
aagtgcagta gtctctgtga acattcaagc ttctgccttc tccctcctgt gagtttggta 960
agtcactgac tgtctatgcc tgggaaaggg tgggcaggag atggggcagt gcaggaaaag 1020
tggcactatg aaccctgcag ccctagacaa ttgtactaac cttcttctct ttcctctcct 1080
gacaggttgg taaccaagct ttccatggct ggacctgcca cccagagccc catgaagctg 1140
atggccctgc agctgctgct gtggcacagt gcactctgga cagtgcagga agccaccccc 1200
ctgggccctg ccagctccct gccccagagc ttcctgctca agtgcttaga gcaagtgagg 1260
aagatccagg gggatggggc agctctccag gagaagctgt gtgccaccta caagctgtgc 1320
caccctgagg agctggtgct gctgggacac tctctgggca tcccctgggc tcccctgagc 1380
agctgcccca gccaggccct gcagctggca ggctgcttga gccaactcca tagtggcctt 1440
ttcctctacc aggggctcct gcaggccctg gaagggatct cccctgagtt gggtcccacc 1500
ttggacacac tgcagctgga tgttgctgac tttgccacca ccatctggca gcagatggaa 1560
gaactgggaa tggcccctgc cctgcagccc acccagggtg ccatgcctgc ctttgcctct 1620
gctttccaga gaagggcagg aggggtcctg gttgcctccc atctgcagag cttcctggag 1680
gtgtcctaca gagttctaag acaccttgcc cagccctgat agatctactt ctggctaata 1740
aaagatcaga gctctagtga tctgtgtgtt ggttttttgt gtctgcattc tagctctagt 1800
gatcagcagt tcaacctgtt gatagtatgt actaagctct catgtttaat gtactaagct 1860
ctcatgttta atgaactaaa ccctcatggc taatgtacta agctctcatg gctaatgtac 1920
taagctctca tgtttcatgt actaagctct catgtttgaa caataaaatt aatataaatc 1980
agcaacttaa atagcctcta aggttttaag ttttataaga aaaaaaagaa tatataaggc 2040
ttttaaaggt tttaaggttt cctaggttat cctcatatga gctcttagaa aaactcatcc 2100
agcatcaaat gaaactgcaa tttattcata tcaggattat caataccata tttttgaaaa 2160
agtcttttct gtaatgaagg agaaaactca cccaggcagt tccataggat ggcaagatcc 2220
tggtatctgt ctgcaattcc aactcttcca acatcaatac aacctattaa tttcccctca 2280
tcaaaaataa ggttatcaag tgagaaatca ccatgagtga ccactgaatc tggtgagaat 2340
ggcaaaagat tatgcatttc tttccagact tgttcaacag gccagccatt tctctcatca 2400
tcaaaatcac tggcatcaac caaaccatta ttcattcttg attgggcctg agccagtcta 2460
aatactctat cagagttaaa aggacaatta caaacaggaa tggaatgcaa tcttctcagg 2520
aacactgcca gggcatcaac aatattttca cctgaatcag gatattcttc caatacctgg 2580
aatgctgttt tccctgggat ggcagtggtg agtaaccatg catcatcagg agttctgata 2640
aaatgcttga tggttggaag aggcataaat tcagtcagcc agtttagtct gaccatctca 2700
tctgtaacat cattggcaac agaacctttg ccatgtttca gaaacaactc tggggcatct 2760
ggcttcccat acaatctata gattgtggca cctgattgcc caacattatc tctagcccat 2820
ttatacccat ataaatcagc atccatgttg gaatttaatc ttggcctgga gcaagaggtt 2880
tctctttgaa tatggctcat acatgtgcac ctcctatagt gagttgtatt atactatgca 2940
gatatactat gccaatgttt aattgtcag 2969

<210> SEQ ID NO 14
<211> LENGTH: 3154
<212> TYPE: DNA
<213> ORGANISM: Artificial sequence
<220> FEATURE:
<223> OTHER INFORMATION: Synthetic

<400> SEQUENCE: 14
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgtcta gcaggagtca atgggaaaaa 480
cccattggag ccaagtacac tgactcaata gggactttcc attgggtttt gcccagtaca 540
taaggtcaat agggggtgag tcaacaggaa agtcccattg gagccaagta cattgagtca 600
atagggactt tccaatgggt tttgcccagt acataaggtc aatgggaggt aagccaatgg 660
gtttttccca ttactgacat gtatactgag tcattaggga ctttccaatg ggttttgccc 720
agtacataag gtcaataggg gtgaatcaac aggaaagtcc cattggagcc aagtacactg 780
agtcaatagg gactttccat tgggttttgc ccagtacaaa aggtcaatag ggggtgagtc 840
aatgggtttt tcccattatt ggcacataca taaggtcaat aggggtgact agtggagaag 900
agcatgcttg agggctgagt gcccctcagt gggcagagag cacatggccc acagtccctg 960
agaagttggg gggagggggtg ggcaattgaa ctggtgccta gagaaggtgg ggcttgggta 1020
aactgggaaa gtgatgtggt gtactggctc cacctttttc cccagggtgg gggagaacca 1080
tatataagtg cagtagtctc tgtgaacatt caagcttctg ccttctccct cctgtgagtt 1140
tggtaagtca ctgactgtct atgcctggga aagggtgggc aggagatggg gcagtgcagg 1200
aaaagtggca ctatgaaccc tgcagcccta gacaattgta ctaaccttct tctctttcct 1260
ctcctgacag gttggtaacc aagctttcca tggctggacc tgccacccag agccccatga 1320
agctgatggc cctgcagctg ctgctgtggc acagtgcact ctggacagtg caggaagcca 1380 ccccccctggg ccctgccagc tccctgcccc agagcttcct gctcaagtgc ttagagcaag 1440
tgaggaagat ccagggggat ggggcagctc tccaggagaa gctgtgtgcc acctacaagc 1500
tgtgccaccc tgaggagctg gtgctgctgg gacactctct gggcatcccc tgggctcccc 1560
tgagcagctg ccccagccag gccctgcagc tggcaggctg cttgagccaa ctccatagtg 1620
gccttttcct ctaccagggg ctcctgcagg ccctggaagg gatctcccct gagttgggtc 1680
ccaccttgga cacactgcag ctggatgttg ctgactttgc caccaccatc tggcagcaga 1740
tggaagaact gggaatggcc cctgccctgc agcccaccca gggtgccatg cctgcctttg 1800
cctctgcttt ccagagaagg gcaggagggg tcctggttgc ctcccatctg cagagcttcc 1860
tggaggtgtc ctacagagtt ctaagacacc ttgcccagcc ctgatagatc tacttctggc 1920
taataaaaga tcagagctct agtgatctgt gtgttggttt tttgtgtctg cattctagct 1980
ctagtgatca gcagttcaac ctgttgatag tatgtactaa gctctcatgt ttaatgtact 2040
aagctctcat gtttaatgaa ctaaaccctc atggctaatg tactaagctc tcatggctaa 2100
tgtactaagc tctcatgttt catgtactaa gctctcatgt ttgaacaata aaattaatat 2160
aaatcagcaa cttaaatagc ctctaaggtt ttaagtttta taagaaaaaa aagaatatat 2220
aaggctttta aaggttttaa ggtttcctag gttatcctca tatgagctct tagaaaaact 2280
catccagcat caaatgaaac tgcaatttat tcatatcagg attatcaata ccatattttt 2340
gaaaaagtct ttctgtaat gaaggagaaa actcacccag gcagttccat aggatggcaa 2400
gatcctggta tctgtctgca attccaactc ttccaacatc aatacaacct attaatttcc 2460
cctcatcaaa aataaggtta tcaagtgaga aatcaccatg agtgaccact gaatctggtg 2520
agaatggcaa aagattatgc atttctttcc agacttgttc aacaggccag ccatttctct 2580
catcatcaaa atcactggca tcaaccaaac cattattcat tcttgattgg gcctgagcca 2640
gtctaaatac tctatcagag ttaaaaggac aattacaaac aggaatggaa tgcaatcttc 2700
tcaggaacac tgccagggca tcaacaatat tttcacctga atcaggatat tcttccaata 2760
cctggaatgc tgttttccct gggatggcag tggtgagtaa ccatgcatca tcaggagttc 2820
tgataaaatg cttgatggtt ggaagaggca taaattcagt cagccagttt agtctgacca 2880
tctcatctgt aacatcattg gcaacagaac ctttgccatg tttcagaaac aactctgggg 2940
catctggctt cccatacaat ctatagattg tggcacctga ttgcccaaca ttatctctag 3000
cccatttata cccatataaa tcagcatcca tgttggaatt taatcttggc ctggagcaag 3060
aggtttctct ttgaatatgg ctcatacatg tgcacctcct atagtgagtt gtattatact 3120
atgcagatat actatgccaa tgtttaattg tcag 3154

<210> SEQ ID NO 15
<211> LENGTH: 3033
<212> TYPE: DNA
<213> ORGANISM: Artificial sequence
<220> FEATURE:
<223> OTHER INFORMATION: Synthetic

<400> SEQUENCE: 15
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180

-continued

```
ccaatgggtt ttgcccagta cataaggtca atgggaggta agccaatggg tttttcccat    240
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgtcta gcatgttaca taacttatgg    480
taaatggcct gcctggctga ctgcccaatg acccctgccc aatgatgtca ataatgatgt    540
atgttcccat gtaatgccaa tagggacttt ccattgatgt caatgggtgg agtatttatg    600
gtaactgccc acttggcagt acatcaagtg tatcatatgc caagtatgcc ccctattgat    660
gtcaatgatg gtaaatggcc tgcctggcat tatgcccagt acatgacctt atgggacttt    720
cctacttggc agtacatcta tgtattagtc attgctatta tctagcacta gtggagaaga    780
gcatgcttga gggctgagtg cccctcagtg ggcagagagc acatggccca cagtccctga    840
gaagttgggg ggaggggtgg gcaattgaac tggtgcctag agaaggtggg gcttgggtaa    900
actgggaaag tgatgtggtg tactggctcc accttttttcc ccagggtggg ggagaaccat    960
atataagtgc agtagtctct gtgaacattc aagcttctgc cttctccctc ctgtgagttt   1020
ggtaagtcac tgactgtcta tgcctgggaa agggtgggca ggagatgggg cagtgcagga   1080
aaagtggcac tatgaaccct gcagccctag acaattgtac taaccttctt ctctttcctc   1140
tcctgacagg ttggtaacca agctttccat ggctggacct gccacccaga gccccatgaa   1200
gctgatggcc ctgcagctgc tgctgtggca cagtgcactc tggacagtgc aggaagccac   1260
cccccctgggc cctgccagct ccctgcccca gagcttcctg ctcaagtgct tagagcaagt   1320
gaggaagatc caggggggatg ggcagctctt ccaggagaag ctgtgtgcca cctacaagct   1380
gtgccaccct gaggagctgg tgctgctggg acactctctg ggcatcccct gggctcccct   1440
gagcagctgc cccagccagg ccctgcagct ggcaggctgc ttgagccaac tccatagtgg   1500
ccttttcctc taccaggggc tcctgcaggc cctggaaggg atctcccctg agttgggtcc   1560
caccttggac acactgcagc tggatgttgc tgactttgcc accaccatct ggcagcagat   1620
ggaagaactg ggaatggccc ctgccctgca gcccacccag ggtgccatgc ctgcctttgc   1680
ctctgctttc cagagaaggg caggaggggt cctggttgcc tcccatctgc agagcttcct   1740
ggaggtgtcc tacagagttc taagacacct tgcccagccc tgatagatct acttctggct   1800
aataaaagat cagagctcta gtgatctgtg tgttggtttt ttgtgtctgc attctagctc   1860
tagtgatcag cagttcaacc tgttgatagt atgtactaag ctctcatgtt taatgtacta   1920
agctctcatg tttaatgaac taaaccctca tggctaatgt actaagctct catggctaat   1980
gtactaagct ctcatgtttc atgtactaag ctctcatgtt tgaacaataa aattaatata   2040
aatcagcaac ttaaatagcc tctaaggttt taagttttat aagaaaaaaa agaatatata   2100
aggcttttaa aggttttaag gtttcctagg ttatcctcat atgagctctt agaaaaactc   2160
atccagcatc aaatgaaact gcaatttatt catatcagga ttatcaatac catatttttg   2220
aaaaagtctt ttctgtaatg aaggagaaaa ctcacccagg cagttccata ggatggcaag   2280
atcctggtat ctgtctgcaa ttccaactct tccaacatca atacaaccta ttaatttccc   2340
ctcatcaaaa ataaggttat caagtgagaa atcaccatga gtgaccactg aatctggtga   2400
gaatggcaaa agattatgca tttctttcca gacttgttca acaggccagc catttctctc   2460
atcatcaaaa tcactggcat caaccaaacc attattcatt cttgattggg cctgagccag   2520
tctaaatact ctatcagagt taaaaggaca attacaaaca ggaatggaat gcaatcttct   2580
```

```
caggaacact gccagggcat caacaatatt ttcacctgaa tcaggatatt cttccaatac   2640
ctggaatgct gttttccctg ggatggcagt ggtgagtaac catgcatcat caggagttct   2700
gataaaatgc ttgatggttg gaagaggcat aaattcagtc agccagttta gtctgaccat   2760
ctcatctgta acatcattgg caacagaacc tttgccatgt ttcagaaaca actctggggc   2820
atctggcttc ccatacaatc tatagattgt ggcacctgat tgcccaacat tatctctagc   2880
ccatttatac ccatataaat cagcatccat gttggaattt aatcttggcc tggagcaaga   2940
ggtttctctt tgaatatggc tcatacatgt gcacctccta tagtgagttg tattatacta   3000
tgcagatata ctatgccaat gtttaattgt cag                                3033
```

<210> SEQ ID NO 16
<211> LENGTH: 2723
<212> TYPE: DNA
<213> ORGANISM: Artificial sequence
<220> FEATURE:
<223> OTHER INFORMATION: Synthetic

<400> SEQUENCE: 16

```
cactatgtgg acatgaattc aattggctag caggagtcaa tgggaaaaac ccattggagc     60
caagtacact gactcaatag ggactttcca ttgggttttg cccagtacat aaggtcaata    120
gggggtgagt caacaggaaa gtcccattgg agccaagtac attgagtcaa tagggacttt    180
ccaatgggtt ttgcccagta cataaggtca atgggaggta agccaatggg tttttcccat    240
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc accttttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agctttccat ggctggacct gccacccaga gccccatgaa gctgatggcc    900
ctgcagctgc tgctgtggca cagtgcactc tggacagtgc aggaagccac ccccctgggc    960
cctgccagct ccctgcccca gagcttcctg ctcaagtgct tagagcaagt gaggaagatc   1020
caggggggatg ggcagctctt ccaggagaag ctgtgtgcca cctacaagct gtgccaccct   1080
gaggagctgg tgctgctggg acactctctg ggcatcccct gggctcccct gagcagctgc   1140
cccagccagg ccctgcagct ggcaggctgc ttgagccaac tccatagtgg cctttttcctc   1200
taccaggggc tcctgcaggc cctggaaggg atctcccctg agttgggtcc caccttggac   1260
acactgcagc tggatgttgc tgactttgcc accaccatct ggcagcagat ggaagaactg   1320
ggaatggccc ctgccctgca gcccacccag ggtgccatgc ctgcctttgc ctctgctttc   1380
cagagaaggg caggaggggt cctggttgcc tcccatctgc agagcttcct ggaggtgtcc   1440
tacagagttc taagacacct tgcccagccc tgatagatct acttctggct aataaaagat   1500
cagagctcta gtgatctgtg tgttggtttt ttgtgtctgc attctagctc tagtgatcag   1560
```

-continued

```
cagttcaacc tgttgatagt atgtactaag ctctcatgtt taatgtacta agctctcatg   1620

tttaatgaac taaaccctca tggctaatgt actaagctct catggctaat gtactaagct   1680

ctcatgtttc atgtactaag ctctcatgtt tgaacaataa aattaatata aatcagcaac   1740

ttaaatagcc tctaaggttt taagttttat aagaaaaaaa agaatatata aggcttttaa   1800

aggttttaag gtttcctagg ttatcctcat atgagctctt agaaaaactc atccagcatc   1860

aaatgaaact gcaatttatt catatcagga ttatcaatac catatttttg aaaaagtctt   1920

ttctgtaatg aaggagaaaa ctcacccagg cagttccata ggatggcaag atcctggtat   1980

ctgtctgcaa ttccaactct tccaacatca atacaaccta ttaatttccc ctcatcaaaa   2040

ataaggttat caagtgagaa atcaccatga gtgaccactg aatctggtga gaatggcaaa   2100

agattatgca tttctttcca gacttgttca acaggccagc catttctctc atcatcaaaa   2160

tcactggcat caaccaaacc attattcatt cttgattggg cctgagccag tctaaatact   2220

ctatcagagt taaaaggaca attacaaaca ggaatggaat gcaatcttct caggaacact   2280

gccagggcat caacaatatt ttcacctgaa tcaggatatt cttccaatac ctggaatgct   2340

gttttccctg ggatggcagt ggtgagtaac catgcatcat caggagttct gataaaatgc   2400

ttgatggttg gaagaggcat aaattcagtc agccagttta gtctgaccat ctcatctgta   2460

acatcattgg caacagaacc tttgccatgt ttcagaaaca actctggggc atctggcttc   2520

ccatacaatc tatagattgt ggcacctgat tgcccaacat tatctctagc ccatttatac   2580

ccatataaat cagcatccat gttggaattt aatcttggcc tggagcaaga ggtttctctt   2640

tgaatatggc tcatacatgt gcacctccta tagtgagttg tattatacta tgcagatata   2700

ctatgccaat gtttaattgt cag                                           2723
```

<210> SEQ ID NO 17
<211> LENGTH: 3175
<212> TYPE: DNA
<213> ORGANISM: Artificial sequence
<220> FEATURE:
<223> OTHER INFORMATION: Synthetic

<400> SEQUENCE: 17

```
cactatgtgg acatgaattc aattggctag caaaacaaat gacatcattc ctgattataa     60

taattttaat tgtgctttac aagtagaatt ctacttgtaa agagagttta atttgaaaaa    120

caaattagtc attattaaac atgttaacaa ttgtgtataa aaatgacatc agtttaatga    180

tgacatcatc tcttgattat gttttacaag tagaattcta cttgtaaagc tggttcagtt    240

ttgaaaaaca aatgacatca tctcttgatt atgttttaca agtagaattc tacttgtaaa    300

agtgagttta gttttaaaaa acaaatgaca tcattcagtt ttgaaaaaca aatgacatca    360

tctcttgatt gtgttttaca agtagaattc tacttgtaaa gtgagttcag ttttgaaaaa    420

caaatgaccc tctcatacaa ttgttgaaca attttaataa ataatcttta caagatttct    480

agcaggagtc aatgggaaaa acccattgga gccaagtaca ctgactcaat agggactttc    540

cattgggttt tgcccagtac ataaggtcaa taggggggtga gtcaacagga aagtcccatt    600

ggagccaagt acattgagtc aatagggact ttccaatggg ttttgcccag tacataaggt    660

caatgggagg taagccaatg ggtttttccc attactgaca tgtatactga gtcattaggg    720

actttccaat gggttttgcc cagtacataa ggtcaatagg ggtgaatcaa caggaaagtc    780

ccattggagc caagtacact gagtcaatag ggactttcca ttgggttttg cccagtacaa    840

aaggtcaata gggggtgagt caatgggttt ttcccattat tggcacatac ataaggtcaa    900
```

-continued

```
tagggggtgac tagtggagaa gagcatgctt gagggctgag tgcccctcag tgggcagaga    960
gcacatggcc cacagtccct gagaagttgg ggggaggggt gggcaattga actggtgcct   1020
agagaaggtg gggcttgggt aaactgggaa agtgatgtgg tgtactggct ccacctttt   1080
ccccaggggtg ggggagaacc atatataagt gcagtagtct ctgtgaacat tcaagcttct   1140
gccttctccc tcctgtgagt ttggtaagtc actgactgtc tatgcctggg aaagggtggg   1200
caggagatgg ggcagtgcag gaaaagtggc actatgaacc ctgcagccct agacaattgt   1260
actaaccttc ttctctttcc tctcctgaca ggttggtaac caagctttcc atggctggac   1320
ctgccaccca gagccccatg aagctgatgg ccctgcagct gctgctgtgg cacagtgcac   1380
tctggacagt gcaggaagcc accccctgg gccctgccag ctccctgccc cagagcttcc   1440
tgctcaagtg cttagagcaa gtgaggaaga tccaggggga tggggcagct ctccaggaga   1500
agctgtgtgc cacctacaag ctgtgccacc ctgaggagct ggtgctgctg ggacactctc   1560
tgggcatccc ctgggctccc ctgagcagct gccccagcca ggccctgcag ctggcaggct   1620
gcttgagcca actccatagt ggcctttcc tctaccaggg gctcctgcag gccctggaag   1680
ggatctcccc tgagttgggt cccaccttgg acacactgca gctggatgtt gctgactttg   1740
ccaccaccat ctgcagcag atggaagaac tgggaatggc ccctgccctg cagcccaccc   1800
agggtgccat gcctgccttt gcctctgctt tccagagaag ggcaggaggg gtcctggttg   1860
cctcccatct gcagagcttc ctggaggtgt cctacagagt tctaagacac cttgcccagc   1920
cctgatagat ctacttctgg ctaataaaag atcagagctc tagtgatctg tgtgttggtt   1980
ttttgtgtct gcattctagc tctagtgatc agcagttcaa cctgttgata gtatgtacta   2040
agctctcatg tttaatgtac taagctctca tgtttaatga actaaaccct catggctaat   2100
gtactaagct ctcatggcta atgtactaag ctctcatgtt tcatgtacta agctctcatg   2160
tttgaacaat aaaattaata taaatcagca acttaaatag cctctaaggt tttaagtttt   2220
ataagaaaaa aaagaatata taaggctttt aaaggtttta aggtttccta ggttatcctc   2280
atatgagctc ttagaaaaac tcatccagca tcaaatgaaa ctgcaattta ttcatatcag   2340
gattatcaat accatatttt tgaaaaagtc ttttctgtaa tgaaggagaa aactcaccca   2400
ggcagttcca taggatggca agatcctggt atctgtctgc aattccaact cttccaacat   2460
caatacaacc tattaatttc ccctcatcaa aaataaggtt atcaagtgag aaatcaccat   2520
gagtgaccac tgaatctggt gagaatggca aaagattatg catttctttc cagacttgtt   2580
caacaggcca gccatttctc tcatcatcaa aatcactggc atcaaccaaa ccattattca   2640
ttcttgattg ggcctgagcc agtctaaata ctctatcaga gttaaaagga caattacaaa   2700
caggaatgga atgcaatctt ctcaggaaca ctgccagggc atcaacaata ttttcacctg   2760
aatcaggata ttcttccaat acctggaatg ctgttttccc tgggatggca gtggtgagta   2820
accatgcatc atcaggagtt ctgataaaat gcttgatggt tggaagaggc ataaattcag   2880
tcagccagtt tagtctgacc atctcatctg taacatcatt ggcaacagaa cctttgccat   2940
gtttcagaaa caactctggg gcatctggct tccatacaa tctatagatt gtggcacctg   3000
attgcccaac attatctcta gcccatttat acccatataa atcagcatcc atgttggaat   3060
ttaatcttgg cctggagcaa gaggtttctc tttgaatatg gctcatacat gtgcacctcc   3120
tatagtgagt tgtattatac tatgcagata tactatgcca atgtttaatt gtcag        3175
```

<210> SEQ ID NO 18

<211> LENGTH: 3212
<212> TYPE: DNA
<213> ORGANISM: Artificial sequence
<220> FEATURE:
<223> OTHER INFORMATION: Synthetic

<400> SEQUENCE: 18
cactatgtgg acatgaattc tcatagctag aaatcttgta aagattattt attaaaattg 60
ttcaacaatt gtatgagagg gtcatttgtt tttcaaaact gaactcactt tacaagtaga 120
attctacttg taaaacacaa tcaagagatg atgtcatttg tttttcaaaa ctgaatgatg 180
tcatttgttt tttaaaacta aactcacttt tacaagtaga attctacttg taaaacataa 240
tcaagagatg atgtcatttg tttttcaaaa ctgaaccagc tttacaagta gaattctact 300
tgtaaaacat aatcaagaga tgatgtcatc attaaactga tgtcattttt atacacaatt 360
gttaacatgt ttaataatga ctaatttgtt tttcaaatta aactctcttt acaagtagaa 420
ttctacttgt aaagcacaat taaaattatt ataatcagga atgatgtcat ttgttttgct 480
agctgttaca taacttatgg taaatggcct gcctggctga ctgcccaatg acccctgccc 540
aatgatgtca ataatgatgt atgttcccat gtaatgccaa tagggacttt ccattgatgt 600
caatgggtgg agtatttatg gtaactgccc acttggcagt acatcaagtg tatcatatgc 660
caagtatgcc ccctattgat gtcaatgatg gtaaatggcc tgcctggcat tatgcccagt 720
acatgacctt atgggacttt cctacttggc agtacatcta tgtattagtc attgctatta 780
ccatggtgat gggttttggc agtacatcaa tgggtgtgga tagtggtttg acccatgggg 840
atttccaagt ctccacccca ttgatgccaa tgggagtttg ttttggcacc aaaatcaatg 900
ggactttcca aaatgttgta acaactctgc cccattgatg gaaatgggtg gtaggtgtgt 960
gtggtgggag gtctatataa gcagagcttg tttagtgaac tggatgcacc tactagatat 1020
ccatatggct atcatctctc cttcaatatc catcatccct acctgaggca tccatccaat 1080
catgttgagt atatttctgc atcctccatc ctgtggtgcc tcctgaactg attcatcatt 1140
ctaggtaagt ttaaagctca ggtatagaca tggcctttgt catgatctcc cttggagcct 1200
acctagactc atcatgctct ccaatctttg cctgaccctg cttgctcaac tctaattctt 1260
tgtttatttt tctgttctga tcatttacag atccaagctg tgacatgatc cctaccatat 1320
gttggagtgt aggtaaccaa gctttccatg gctggacctg ccacccagag ccccatgaag 1380
ctgatggccc tgcagctgct gctgtggcac agtgcactct ggacagtgca ggaagccacc 1440
cccctgggcc ctgccagctc cctgccccag agcttcctgc tcaagtgctt agagcaagtg 1500
aggaagatcc agggggatgg ggcagctctc caggagaagc tgtgtgccac ctacaagctg 1560
tgccaccctg aggagctggt gctgctggga cactctctgg gcatcccctg ggctcccctg 1620
agcagctgcc ccagccaggc cctgcagctg gcaggctgct tgagccaact ccatagtggc 1680
cttttcctct accaggggct cctgcaggcc ctggaaggga tctcccctga gttgggtccc 1740
accttggaca cactgcagct ggatgttgct gactttgcca ccaccatctg gcagcagatg 1800
gaagaactgg gaatggcccc tgccctgcag cccacccagg gtgccatgcc tgcctttgcc 1860
tctgctttcc agagaagggc aggaggggtc ctggttgcct cccatctgca gagcttcctg 1920
gaggtgtcct acagagttct aagacacctt gcccagccct gatagatcta cttctggcta 1980
ataaaagatc agagctctag tgatctgtgt gttggttttt tgtgtctgca ttctagctct 2040
agtgatcagc agttcaacct gttgatagta tgtactaagc tctcatgttt aatgtactaa 2100
gctctcatgt ttaatgaact aaaccctcat ggctaatgta ctaagctctc atggctaatg 2160

```
tactaagctc tcatgtttca tgtactaagc tctcatgttt gaacaataaa attaatataa   2220
atcagcaact taaatagcct ctaaggtttt aagttttata agaaaaaaaa gaatatataa   2280
ggcttttaaa ggttttaagg tttcctaggt tatcctcata tgagctctta gaaaaactca   2340
tccagcatca aatgaaactg caatttattc atatcaggat tatcaatacc atatttttga   2400
aaaagtcttt tctgtaatga aggagaaaac tcacccaggc agttccatag gatggcaaga   2460
tcctggtatc tgtctgcaat tccaactctt ccaacatcaa tacaacctat taatttcccc   2520
tcatcaaaaa taaggttatc aagtgagaaa tcaccatgag tgaccactga atctggtgag   2580
aatggcaaaa gattatgcat ttctttccag acttgttcaa caggccagcc atttctctca   2640
tcatcaaaat cactggcatc aaccaaacca ttattcattc ttgattgggc ctgagccagt   2700
ctaaatactc tatcagagtt aaaaggacaa ttacaaacag gaatggaatg caatcttctc   2760
aggaacactg ccagggcatc aacaatattt tcacctgaat caggatattc ttccaatacc   2820
tggaatgctg ttttccctgg gatggcagtg gtgagtaacc atgcatcatc aggagttctg   2880
ataaaatgct tgatggttgg aagaggcata aattcagtca gccagtttag tctgaccatc   2940
tcatctgtaa catcattggc aacagaacct ttgccatgtt tcagaaacaa ctctggggca   3000
tctggcttcc catacaatct atagattgtg gcacctgatt gcccaacatt atctctagcc   3060
catttatacc catataaatc agcatccatg ttggaattta atcttggcct ggagcaagag   3120
gtttctcttt gaatatggct catacatgtg cacctcctat agtgagttgt attatactat   3180
gcagatatac tatgccaatg tttaattgtc ag                                  3212
```

<210> SEQ ID NO 19
<211> LENGTH: 3212
<212> TYPE: DNA
<213> ORGANISM: Artificial sequence
<220> FEATURE:
<223> OTHER INFORMATION: Synthetic

<400> SEQUENCE: 19

```
cactatgtgg acatgaattc tcatagctag caaaacaaat gacatcattc ctgattataa     60
taattttaat tgtgctttac aagtagaatt ctacttgtaa agagagttta atttgaaaaa    120
caaattagtc attattaaac atgttaacaa ttgtgtataa aaatgacatc agtttaatga    180
tgacatcatc tcttgattat gttttacaag tagaattcta cttgtaaagc tggttcagtt    240
ttgaaaaaca aatgacatca tctcttgatt atgttttaca agtagaattc tacttgtaaa    300
agtgagttta gttttaaaaa acaaatgaca tcattcagtt ttgaaaaaca aatgacatca    360
tctcttgatt gtgttttaca agtagaattc tacttgtaaa gtgagttcag ttttgaaaaa    420
caaatgaccc tctcatacaa ttgttgaaca attttaataa ataatcttta caagatttct    480
agctgttaca taacttatgg taaatggcct gcctggctga ctgcccaatg acccctgccc    540
aatgatgtca ataatgatgt atgttcccat gtaatgccaa tagggacttt ccattgatgt    600
caatgggtgg agtatttatg gtaactgccc acttggcagt acatcaagtg tatcatatgc    660
caagtatgcc ccctattgat gtcaatgatg gtaaatggcc tgcctggcat tatgcccagt    720
acatgacctt atgggacttt cctacttggc agtacatcta tgtattagtc attgctatta    780
ccatggtgat gggttttggc agtacatcaa tgggtgtgga tagtggtttg acccatgggg    840
atttccaagt ctccacccca ttgatgccaa tgggagtttg ttttggcacc aaaatcaatg    900
ggactttcca aaatgttgta acaactctgc cccattgatg gaaatgggtg gtaggtgtgt    960
```

-continued

```
gtggtgggag gtctatataa gcagagcttg tttagtgaac tggatgcacc tactagatat   1020
ccatatggct atcatctctc cttcaatatc catcatccct acctgaggca tccatccaat   1080
catgttgagt atatttctgc atcctccatc ctgtggtgcc tcctgaactg attcatcatt   1140
ctaggtaagt ttaaagctca ggtatagaca tggcctttgt catgatctcc cttggagcct   1200
acctagactc atcatgctct ccaatctttg cctgaccctg cttgctcaac tctaattctt   1260
tgtttatttt tctgttctga tcatttacag atccaagctg tgacatgatc cctaccatat   1320
gttggagtgt aggtaaccaa gctttccatg gctggacctg ccacccagag ccccatgaag   1380
ctgatggccc tgcagctgct gctgtggcac agtgcactct ggacagtgca ggaagccacc   1440
cccctgggcc ctgccagctc cctgccccag agcttcctgc tcaagtgctt agagcaagtg   1500
aggaagatcc agggggatgg ggcagctctc caggagaagc tgtgtgccac ctacaagctg   1560
tgccaccctg aggagctggt gctgctggga cactctctgg gcatcccctg ggctcccctg   1620
agcagctgcc ccagccaggc cctgcagctg gcaggctgct tgagccaact ccatagtggc   1680
cttttcctct accaggggct cctgcaggcc ctggaaggga tctcccctga gttgggtccc   1740
accttggaca cactgcagct ggatgttgct gactttgcca ccaccatctg gcagcagatg   1800
gaagaactgg gaatggcccc tgccctgcag cccacccagg gtgccatgcc tgcctttgcc   1860
tctgctttcc agagaagggc aggaggggtc ctggttgcct cccatctgca gagcttcctg   1920
gaggtgtcct acagagttct aagacacctt gcccagccct gatagatcta cttctggcta   1980
ataaaagatc agagctctag tgatctgtgt gttggttttt tgtgtctgca ttctagctct   2040
agtgatcagc agttcaacct gttgatagta tgtactaagc tctcatgttt aatgtactaa   2100
gctctcatgt ttaatgaact aaaccctcat ggctaatgta ctaagctctc atggctaatg   2160
tactaagctc tcatgtttca tgtactaagc tctcatgttt gaacaataaa attaatataa   2220
atcagcaact taaatagcct ctaaggtttt aagttttata agaaaaaaaa gaatatataa   2280
ggcttttaaa ggttttaagg tttcctaggt tatcctcata tgagctctta gaaaaactca   2340
tccagcatca aatgaaactg caatttattc atatcaggat tatcaatacc atatttttga   2400
aaaagtcttt tctgtaatga aggagaaaac tcacccaggc agttccatag gatggcaaga   2460
tcctggtatc tgtctgcaat tccaactctt ccaacatcaa tacaacctat taatttcccc   2520
tcatcaaaaa taaggttatc aagtgagaaa tcaccatgag tgaccactga atctggtgag   2580
aatggcaaaa gattatgcat ttctttccag acttgttcaa caggccagcc atttctctca   2640
tcatcaaaat cactggcatc aaccaaacca ttattcattc ttgattgggc ctgagccagt   2700
ctaaatactc tatcagagtt aaaaggacaa ttacaaacag gaatggaatg caatcttctc   2760
aggaacactg ccagggcatc aacaatattt tcacctgaat caggatattc ttccaatacc   2820
tggaatgctg ttttccctgg gatggcagtg gtgagtaacc atgcatcatc aggagttctg   2880
ataaaatgct tgatggttgg aagaggcata aattcagtca gccagtttag tctgaccatc   2940
tcatctgtaa catcattggc aacagaacct ttgccatgtt tcagaaacaa ctctggggca   3000
tctggcttcc catacaatct atagattgtg gcacctgatt gcccaacatt atctctagcc   3060
catttatacc catataaatc agcatccatg ttggaattta atcttggcct ggagcaagag   3120
gtttctcttt gaatatggct catacatgtg cacctcctat agtgagttgt attatactat   3180
gcagatatac tatgccaatg tttaattgtc ag                                 3212
```

<210> SEQ ID NO 20
<211> LENGTH: 3492

<212> TYPE: DNA
<213> ORGANISM: Artificial sequence
<220> FEATURE:
<223> OTHER INFORMATION: Synthetic

<400> SEQUENCE: 20
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg cagagagtga atatgatcat ggctgagagc cctggcctga 900
tcaccatctg cctgctgggc tacctgctgt ctgctgagtg cacagtgttt ctggaccatg 960
agaatgccaa caagatcctg aacaggccca agaggtacaa ctctggcaag ctggaagagt 1020
ttgtgcaggg caacctggaa agggaatgca tggaagagaa gtgcagcttt gaagaggcca 1080
gggaagtgtt tgagaacaca gagagaacca cagagttctg gaagcagtat gtggatgggg 1140
accagtgtga aagcaacccc tgcctgaatg gggcagctg caaggatgac atcaacagct 1200
atgagtgctg gtgccccttt ggctttgagg gcaagaactg tgaactggat gtgacctgca 1260
acatcaagaa tggcagatgt gaacagttct gcaagaactc tgctgacaac aaggttgtgt 1320
gctcctgcac agagggctac agactggctg agaaccagaa aagctgtgaa cctgctgtgc 1380
ccttcccatg tggcagagtg tctgtgtccc agaccagcaa gctgaccaga gctgagacag 1440
tgttccctga tgtggactat gtgaactcca cagaggctga aaccatcctg gacaacatca 1500
cccagagcac ccagtccttc aatgacttca ccagagttgt gggaggggag gatgccaagc 1560
ctggccagtt cccatggcaa gtggtgctga atggcaaagt ggatgccttc tgtgggggct 1620
ccattgtgaa tgagaagtgg attgtgacag ctgcccactg tgtggaaact ggagtgaaga 1680
tcacagtggt ggctggggag cacaacattg aggaaacaga gcacacagag cagaaaagaa 1740
atgtgatcag gatcatcccc caccacaact acaatgctgc catcaacaag tacaaccatg 1800
acattgccct gctggaactg gatgagcccc tggtgctgaa cagctatgtg acccccatct 1860
gcattgctga caaagagtac accaacatct ttctgaagtt tggctctggc tatgtgtctg 1920
gctggggcag ggtgttccac aagggaagga gtgctctggt gctgcagtac ctgagagtgc 1980
cactggtgga cagagccacc tgtctgagaa gcaccaagtt caccatctac aacaacatgt 2040
tctgtgctgg cttccatgag ggggcagag actcctgcca gggggattct gggggccctc 2100
atgtgacaga ggtggaaggc accagctttc tgacaggcat catcagctgg ggagaggaat 2160

```
gtgccatgaa gggcaaatat ggcatctaca ccaaggtgtc cagatatgtg aattggatca   2220

aagaaaagac caagctgaca tgaagatcta cttctggcta ataaaagatc agagctctag   2280

tgatctgtgt gttggttttt tgtgtctgca ttctagctct agtgatcagc agttcaacct   2340

gttgatagta tgtactaagc tctcatgttt aatgtactaa gctctcatgt ttaatgaact   2400

aaaccctcat ggctaatgta ctaagctctc atggctaatg tactaagctc tcatgtttca   2460

tgtactaagc tctcatgttt gaacaataaa attaatataa atcagcaact taaatagcct   2520

ctaaggtttt aagttttata agaaaaaaaa gaatatataa ggcttttaaa ggttttaagg   2580

tttcctaggt tatcctcata tgagctctta gaaaaactca tccagcatca aatgaaactg   2640

caatttattc atatcaggat tatcaatacc atatttttga aaaagtcttt tctgtaatga   2700

aggagaaaac tcacccaggc agttccatag gatggcaaga tcctggtatc tgtctgcaat   2760

tccaactctt ccaacatcaa tacaacctat taatttcccc tcatcaaaaa taaggttatc   2820

aagtgagaaa tcaccatgag tgaccactga atctggtgag aatggcaaaa gattatgcat   2880

ttctttccag acttgttcaa caggccagcc atttctctca tcatcaaaat cactggcatc   2940

aaccaaacca ttattcattc ttgattgggc ctgagccagt ctaaatactc tatcagagtt   3000

aaaaggacaa ttacaaacag gaatggaatg caatcttctc aggaacactg ccagggcatc   3060

aacaatattt tcacctgaat caggatattc ttccaatacc tggaatgctg ttttccctgg   3120

gatggcagtg gtgagtaacc atgcatcatc aggagttctg ataaaatgct tgatggttgg   3180

aagaggcata aattcagtca gccagtttag tctgaccatc tcatctgtaa catcattggc   3240

aacagaacct ttgccatgtt tcagaaacaa ctctggggca tctggcttcc catacaatct   3300

atagattgtg gcacctgatt gcccaacatt atctctagcc catttatacc catataaatc   3360

agcatccatg ttggaattta atcttggcct ggagcaagag gtttctcttt gaatatggct   3420

catacatgtg cacctcctat agtgagttgt attatactat gcagatatac tatgccaatg   3480

tttaattgtc ag                                                       3492
```

<210> SEQ ID NO 21
<211> LENGTH: 3495
<212> TYPE: DNA
<213> ORGANISM: Artificial sequence
<220> FEATURE:
<223> OTHER INFORMATION: Synthetic

<400> SEQUENCE: 21

```
tctagatgga catgaattca attggctagc aggagtcaat gggaaaaacc cattggagcc     60

aagtacactg actcaatagg gactttccat tgggttttgc ccagtacata aggtcaatag    120

ggggtgagtc aacaggaaag tcccattgga gccaagtaca ttgagtcaat agggactttc    180

caatgggttt tgcccagtac ataaggtcaa tgggaggtaa gccaatgggt ttttcccatt    240

actgacatgt atactgagtc attagggact ttccaatggg ttttgcccag tacataaggt    300

caataggggt gaatcaacag gaaagtccca ttggagccaa gtacactgag tcaataggga    360

ctttccattg ggttttgccc agtacaaaag gtcaataggg ggtgagtcaa tgggtttttc    420

ccattattgg cacatacata aggtcaatag ggtgactag tggagaagag catgcttgag    480

ggctgagtgc ccctcagtgg gcagagagca catggcccac agtccctgag aagttggggg    540

gaggggtggg caattgaact ggtgcctaga gaaggtgggg cttgggtaaa ctgggaaagt    600

gatgtggtgt actggctcca cctttttccc cagggtgggg gagaaccata tataagtgca    660

gtagtctctg tgaacattca agcttctgcc ttctccctcc tgtgagtttg gtaagtcact    720
```

-continued

```
gactgtctat gcctgggaaa gggtgggcag gagatggggc agtgcaggaa aagtggcact    780
atgaaccctg cagccctaga caattgtact aaccttcttc tctttcctct cctgacaggt    840
tggtaaccaa gccaccatgc agagagtgaa tatgatcatg gctgagagcc ctggcctgat    900
caccatctgc ctgctgggct acctgctgtc tgctgagtgc acagtgtttc tggaccatga    960
gaatgccaac aagatcctga acaggcccaa gaggtacaac tctggcaagc tggaagagtt   1020
tgtgcagggc aacctggaaa gggaatgcat ggaagagaag tgcagctttg aagaggccag   1080
ggaagtgttt gagaacacag agagaaccac agagttctgg aagcagtatg tggatgggga   1140
ccagtgtgaa agcaacccct gcctgaatgg gggcagctgc aaggatgaca tcaacagcta   1200
tgagtgctgg tgcccctttg gctttgaggg caagaactgt gaactggatg tgacctgcaa   1260
catcaagaat ggcagatgtg aacagttctg caagaactct gctgacaaca aggttgtgtg   1320
ctcctgcaca gagggctaca gactggctga gaaccagaaa agctgtgaac ctgctgtgcc   1380
cttcccatgt ggcagagtgt ctgtgtccca gaccagcaag ctgaccagag ctgagacagt   1440
gttccctgat gtggactatg tgaactccac agaggctgaa accatcctgg acaacatcac   1500
ccagagcacc cagtccttca atgacttcac cagagttgtg ggaggggagg atgccaagcc   1560
tggccagttc ccatggcaag tggtgctgaa tggcaaagtg gatgccttct gtgggggctc   1620
cattgtgaat gagaagtgga ttgtgacagc tgcccactgt gtggaaactg gagtgaagat   1680
cacagtggtg gctggggagc acaacattga ggaaacagag cacacagagc agaaaagaaa   1740
tgtgatcagg atcatccccc accacaacta caatgctgcc atcaacaagt acaaccatga   1800
cattgccctg ctggaactgg atgagcccct ggtgctgaac agctatgtga cccccatctg   1860
cattgctgac aaagagtaca ccaacatctt tctgaagttt ggctctggct atgtgtctgg   1920
ctggggcagg gtgttccaca agggaaggag tgctctggtg ctgcagtacc tgagagtgcc   1980
actggtggac agagccacct gtctgagaag caccaagttc accatctaca acaacatgtt   2040
ctgtgctggc ttccatgagg ggggcagaga ctcctgccag ggggattctg gggggccctca  2100
tgtgacagag gtggaaggca ccagctttct gacaggcatc atcagctggg gagaggaatg   2160
tgccatgaag ggcaaatatg gcatctacac caaggtgtcc agatatgtga attggatcaa   2220
agaaaagacc aagctgacat gaagatctag ctctagtgat cagcagttca acctgttgat   2280
agtatgtact aagctctcat gtttaatgta ctaagctctc atgtttaatg aactaaaccc   2340
tcatggctaa tgtactaagc tctcatggct aatgtactaa gctctcatgt ttcatgtact   2400
aagctctcat gtttgaacaa taaaattaat ataaatcagc aacttaaata gcctctaagg   2460
ttttaagttt tataagaaaa aaaagaatat ataaggcttt taaaggtttt aaggtttcct   2520
aggttatcct catatgagct cttagaaaaa ctcatccagc atcaaatgaa actgcaattt   2580
attcatatca ggattatcaa taccatattt ttgaaaaagt cttttctgta atgaaggaga   2640
aaactcaccc aggcagttcc ataggatggc aagatcctgg tatctgtctg caattccaac   2700
tcttccaaca tcaatacaac ctattaattt cccctcatca aaaataaggt tatcaagtga   2760
gaaatcacca tgagtgacca ctgaatctgg tgagaatggc aaaagattat gcatttcttt   2820
ccagacttgt tcaacaggcc agccatttct ctcatcatca aaatcactgg catcaaccaa   2880
accattattc attcttgatt gggcctgagc cagtctaaat actctatcag agttaaaagg   2940
acaattacaa acaggaatgg aatgcaatct tctcaggaac actgccaggg catcaacaat   3000
attttcacct gaatcaggat attcttccaa tacctggaat gctgttttcc ctgggatggc   3060
```

```
agtggtgagt aaccatgcat catcaggagt tctgataaaa tgcttgatgg ttggaagagg   3120

cataaattca gtcagccagt ttagtctgac catctcatct gtaacatcat tggcaacaga   3180

acctttgcca tgtttcagaa acaactctgg ggcatctggc ttcccataca atctatagat   3240

tgtggcacct gattgcccaa cattatctct agcccattta tacccatata aatcagcatc   3300

catgttggaa tttaatcttg gcctggagca agaggtttct ctttgaatat ggctcataca   3360

tgtgcacctc ctatagtgag ttgtattata ctatgcagat atactatgcc aatgtttaat   3420

tgtcagctct agcacttctg gctaataaaa gatcagagct ctagtgatct gtgtgttggt   3480

tttttgtgtc tgcat                                                    3495
```

<210> SEQ ID NO 22
<211> LENGTH: 4670
<212> TYPE: DNA
<213> ORGANISM: Artificial sequence
<220> FEATURE:
<223> OTHER INFORMATION: Synthetic

<400> SEQUENCE: 22

```
cactatgtgg acatgaattc aattggctag caggagtcaa tgggaaaaac ccattggagc     60

caagtacact gactcaatag ggactttcca ttgggttttg cccagtacat aaggtcaata    120

gggggtgagt caacaggaaa gtcccattgg agccaagtac attgagtcaa tagggacttt    180

ccaatgggtt ttgcccagta cataaggtca atgggaggta agccaatggg tttttcccat    240

tactgacatg tatactgagt cattagggac tttccaatgg gttttgccca gtacataagg    300

tcaatagggg tgaatcaaca ggaaagtccc attggagcca agtacactga gtcaataggg    360

actttccatt gggttttgcc cagtacaaaa ggtcaatagg gggtgagtca atgggttttt    420

cccattattg gcacatacat aaggtcaata ggggtgacta gtggagaaga gcatgcttga    480

gggctgagtg cccctcagtg ggcagagagc acatggccca cagtccctga gaagttgggg    540

ggaggggtgg gcaattgaac tggtgcctag agaaggtggg gcttgggtaa actgggaaag    600

tgatgtggtg tactggctcc accttttttcc ccagggtggg ggagaaccat atataagtgc    660

agtagtctct gtgaacattc aagcttctgc cttctccctc ctgtgagttt ggatgcacct    720

actagatatc attgggatct tcacacagca ggtaaggttg tgggctgggc ctgggctggg    780

tctgggctgg ggatcagcag ttcaacctgt tgatagtatg tactaagctc tcatgtttaa    840

tgtactaagc tctcatgttt aatgaactaa accctcatgg ctaatgtact aagctctcat    900

ggctaatgta ctaagctctc atgtttcatg tactaagctc tcatgtttga acaataaaat    960

taatataaat cagcaactta aatagcctct aaggttttaa gttttataag aaaaaaaaga   1020

atatataagg cttttaaagg ttttaaggtt tcctaggtta tcctcatatg agctcttaga   1080

aaaactcatc cagcatcaaa tgaaactgca atttattcat atcaggatta tcaataccat   1140

atttttgaaa aagtcttttc tgtaatgaag gagaaaactc acccaggcag ttccatagga   1200

tggcaagatc ctggtatctg tctgcaattc caactcttcc aacatcaata caacctatta   1260

atttcccctc atcaaaaata aggttatcaa gtgagaaatc accatgagtg accactgaat   1320

ctggtgagaa tggcaaaaga ttatgcattt ctttccagac ttgttcaaca ggccagccat   1380

ttctctcatc atcaaaatca ctggcatcaa ccaaaccatt attcattctt gattgggcct   1440

gagccagtct aaatactcta tcagagttaa aaggacaatt acaaacagga atggaatgca   1500

atcttctcag gaacactgcc agggcatcaa caatattttc acctgaatca ggatattctt   1560

ccaatacctg gaatgctgtt ttccctggga tggcagtggt gagtaaccat gcatcatcag   1620
```

gagttctgat aaaatgcttg atggttggaa gaggcataaa ttcagtcagc cagtttagtc 1680
tgaccatctc atctgtaaca tcattggcaa cagaaccttt gccatgtttc agaaacaact 1740
ctggggcatc tggcttccca tacaatctat agattgtggc acctgattgc ccaacattat 1800
ctctagccca tttataccca tataaatcag catccatgtt ggaatttaat cttggcctgg 1860
agcaagaggt ttctctttga atatggctca tacatgtgca cctcctatag tgagttgtat 1920
tatactatgc agatatacta tgccaatgtt taattgtcag ctgcactgac ccctggtgtt 1980
gcttttttttt tttaggctgc aagctgaagt gtgtccagtt ggtaaccaag ccaccatgca 2040
gagagtgaat atgatcatgg ctgagagccc tggcctgatc accatctgcc tgctgggcta 2100
cctgctgtct gctgagtgca cagtgtttct ggaccatgag aatgccaaca agatcctgaa 2160
caggcccaag aggtacaact ctggcaagct ggaagagttt gtgcagggca acctggaaag 2220
ggaatgcatg gaagagaagt gcagctttga agaggccagg gaagtgtttg agaacacaga 2280
gagaaccaca gagttctgga agcagtatgt ggatggggac cagtgtgaaa gcaacccctg 2340
cctgaatggg ggcagctgca aggatgacat caacagctat gagtgctggt gcccctttgg 2400
ctttgagggc aagaactgtg aactggatgt gacctgcaac atcaagaatg gcagatgtga 2460
acagttctgc aagaactctg ctgacaacaa ggttgtgtgc tcctgcacag agggctacag 2520
actggctgag aaccagaaaa gctgtgaacc tgctgtgccc ttcccatgtg gcagagtgtc 2580
tgtgtcccag accagcaagc tgaccagagc tgagacagtg ttccctgatg tggactatgt 2640
gaactccaca gaggctgaaa ccatcctgga caacatcacc cagagcaccc agtccttcaa 2700
tgacttcacc agagttgtgg gaggggagga tgccaagcct ggccagttcc catggcaagt 2760
ggtgctgaat ggcaaagtgg atgccttctg tgggggctcc attgtgaatg agaagtggat 2820
tgtgacagct gcccactgtg tggaaactgg agtgaagatc acagtggtgg ctggggagca 2880
caacattgag gaaacagagc acacagagca gaaaagaaat gtgatcagga tcatccccca 2940
ccacaactac aatgctgcca tcaacaagta caaccatgac attgccctgc tggaactgga 3000
tgagcccctg gtgctgaaca gctatgtgac ccccatctgc attgctgaca aagagtacac 3060
caacatcttt ctgaagtttg gctctggcta tgtgtctggc tggggcaggg tgttccacaa 3120
gggaaggagt gctctggtgc tgcagtacct gagagtgcca ctggtggaca gagccacctg 3180
tctgagaagc accaagttca ccatctacaa caacatgttc tgtgctggct tccatgaggg 3240
gggcagagac tcctgccagg gggattctgg gggccctcat gtgacagagg tggaaggcac 3300
cagctttctg acaggcatca tcagctgggg agaggaatgt gccatgaagg gcaaatatgg 3360
catctacacc aaggtgtcca gatatgtgaa ttggatcaaa gaaaagacca agctgacatg 3420
aagatctact tctggctaat aaaagatcag agctctagtg atctgtgtgt tggtttttttg 3480
tgtctgcatt ctagctctag tgatcagcag ttcaacctgt tgatagtatg tactaagctc 3540
tcatgtttaa tgtactaagc tctcatgttt aatgaactaa accctcatgg ctaatgtact 3600
aagctctcat ggctaatgta ctaagctctc atgtttcatg tactaagctc tcatgtttga 3660
acaataaaat taatataaat cagcaactta aatagcctct aaggttttaa gttttataag 3720
aaaaaaaaga atatataagg cttttaaagg ttttaaggtt tcctaggtta tcctcatatg 3780
agctcttaga aaaactcatc cagcatcaaa tgaaactgca atttattcat atcaggatta 3840
tcaataccat atttttgaaa aagtcttttc tgtaatgaag gagaaaactc acccaggcag 3900
ttccatagga tggcaagatc ctggtatctg tctgcaattc caactcttcc aacatcaata 3960

```
caacctatta atttcccctc atcaaaaata aggttatcaa gtgagaaatc accatgagtg   4020
accactgaat ctggtgagaa tggcaaaaga ttatgcattt ctttccagac ttgttcaaca   4080
ggccagccat ttctctcatc atcaaaatca ctggcatcaa ccaaaccatt attcattctt   4140
gattgggcct gagccagtct aaatactcta tcagagttaa aaggacaatt acaaacagga   4200
atggaatgca atcttctcag gaacactgcc agggcatcaa caatattttc acctgaatca   4260
ggatattctt ccaatacctg gaatgctgtt ttccctggga tggcagtggt gagtaaccat   4320
gcatcatcag gagttctgat aaaatgcttg atggttggaa gaggcataaa ttcagtcagc   4380
cagtttagtc tgaccatctc atctgtaaca tcattggcaa cagaaccttt gccatgtttc   4440
agaaacaact ctggggcatc tggcttccca tacaatctat agattgtggc acctgattgc   4500
ccaacattat ctctagccca tttataccca tataaatcag catccatgtt ggaatttaat   4560
cttggcctgg agcaagaggt ttctctttga atatggctca tacatgtgca cctcctatag   4620
tgagttgtat tatactatgc agatatacta tgccaatgtt taattgtcag              4670
```

<210> SEQ ID NO 23
<211> LENGTH: 3944
<212> TYPE: DNA
<213> ORGANISM: Artificial sequence
<220> FEATURE:
<223> OTHER INFORMATION: Synthetic

<400> SEQUENCE: 23

```
cactatgtgg acatgaattc aattggctag caaaacaaat gacatcattc ctgattataa     60
taattttaat tgtgctttac aagtagaatt ctacttgtaa agagagttta atttgaaaaa    120
caaattagtc attattaaac atgttaacaa ttgtgtataa aaatgacatc agtttaatga    180
tgacatcatc tcttgattat gttttacaag tagaattcta cttgtaaagc tggttcagtt    240
ttgaaaaaca aatgacatca tctcttgatt atgttttaca agtagaattc tacttgtaaa    300
agtgagttta gttttaaaaa acaaatgaca tcattcagtt ttgaaaaaca aatgacatca    360
tctcttgatt gtgttttaca agtagaattc tacttgtaaa gtgagttcag ttttgaaaaa    420
caaatgaccc tctcatacaa ttgttgaaca attttaataa ataatcttta caagatttct    480
agcaggagtc aatgggaaaa acccattgga gccaagtaca ctgactcaat agggactttc    540
cattgggttt tgcccagtac ataaggtcaa taggggtgga gtcaacagga aagtcccatt    600
ggagccaagt acattgagtc aatagggact ttccaatggg ttttgcccag tacataaggt    660
caatgggagg taagccaatg ggtttttccc attactgaca tgtatactga gtcattaggg    720
actttccaat gggttttgcc cagtacataa ggtcaatagg ggtgaatcaa caggaaagtc    780
ccattggagc caagtacact gagtcaatag ggactttcca ttgggttttg cccagtacaa    840
aaggtcaata gggggtgagt caatgggttt ttcccattat tggcacatac ataaggtcaa    900
taggggtgac tagtggagaa gagcatgctt gagggctgag tgcccctcag tgggcagaga    960
gcacatggcc cacagtccct gagaagttgg ggggaggggt gggcaattga actggtgcct   1020
agagaaggtg gggcttgggt aaactgggaa agtgatgtgg tgtactggct ccaccttttt   1080
ccccagggtg ggggagaacc atatataagt gcagtagtct ctgtgaacat tcaagcttct   1140
gccttctccc tcctgtgagt ttggtaagtc actgactgtc tatgcctggg aaagggtggg   1200
caggagatgg ggcagtgcag gaaaagtggc actatgaacc ctgcagccct agacaattgt   1260
actaaccttc ttctctttcc tctcctgaca ggttggtaac caagccacca tgcagagagt   1320
gaatatgatc atggctgaga gccctggcct gatcaccatc tgcctgctgg gctacctgct   1380
```

```
gtctgctgag tgcacagtgt ttctggacca tgagaatgcc aacaagatcc tgaacaggcc   1440
caagaggtac aactctggca agctggaaga gtttgtgcag ggcaacctgg aaagggaatg   1500
catggaagag aagtgcagct ttgaagaggc cagggaagtg tttgagaaca cagagagaac   1560
cacagagttc tggaagcagt atgtggatgg ggaccagtgt gaaagcaacc cctgcctgaa   1620
tgggggcagc tgcaaggatg acatcaacag ctatgagtgc tggtgcccct ttggctttga   1680
gggcaagaac tgtgaactgg atgtgacctg caacatcaag aatggcagat gtgaacagtt   1740
ctgcaagaac tctgctgaca acaaggttgt gtgctcctgc acagagggct acagactggc   1800
tgagaaccag aaaagctgtg aacctgctgt gcccttccca tgtggcagag tgtctgtgtc   1860
ccagaccagc aagctgacca gagctgagac agtgttccct gatgtggact atgtgaactc   1920
cacagaggct gaaaccatcc tggacaacat cacccagagc acccagtcct tcaatgactt   1980
caccagagtt gtgggagggg aggatgccaa gcctggccag ttcccatggc aagtggtgct   2040
gaatggcaaa gtggatgcct tctgtggggg ctccattgtg aatgagaagt ggattgtgac   2100
agctgcccac tgtgtggaaa ctggagtgaa gatcacagtg gtggctgggg agcacaacat   2160
tgaggaaaca gagcacacag agcagaaaag aaatgtgatc aggatcatcc cccaccacaa   2220
ctacaatgct gccatcaaca agtacaacca tgacattgcc ctgctggaac tggatgagcc   2280
cctggtgctg aacagctatg tgacccccat ctgcattgct gacaaagagt acaccaacat   2340
ctttctgaag tttggctctg gctatgtgtc tggctggggc agggtgttcc acaagggaag   2400
gagtgctctg gtgctgcagt acctgagagt gccactggtg gacagagcca cctgtctgag   2460
aagcaccaag ttcaccatct acaacaacat gttctgtgct ggcttccatg agggggggcag  2520
agactcctgc caggggggatt ctgggggccc tcatgtgaca gaggtggaag gcaccagctt  2580
tctgacaggc atcatcagct ggggagagga atgtgccatg aagggcaaat atggcatcta   2640
caccaaggtg tccagatatg tgaattggat caaagaaaag accaagctga catgaagatc   2700
tacttctggc taataaaaga tcagagctct agtgatctgt gtgttggttt tttgtgtctg   2760
cattctagct ctagtgatca gcagttcaac ctgttgatag tatgtactaa gctctcatgt   2820
ttaatgtact aagctctcat gtttaatgaa ctaaaccctc atggctaatg tactaagctc   2880
tcatggctaa tgtactaagc tctcatgttt catgtactaa gctctcatgt ttgaacaata   2940
aaattaatat aaatcagcaa cttaaatagc ctctaaggtt ttaagtttta taagaaaaaa   3000
aagaatatat aaggctttta aaggttttaa ggtttcctag gttatcctca tatgagctct   3060
tagaaaaact catccagcat caaatgaaac tgcaatttat tcatatcagg attatcaata   3120
ccatattttt gaaaaagtct tttctgtaat gaaggagaaa actcacccag gcagttccat   3180
aggatggcaa gatcctggta tctgtctgca attccaactc ttccaacatc aatacaacct   3240
attaatttcc cctcatcaaa aataaggtta tcaagtgaga aatcaccatg agtgaccact   3300
gaatctggtg agaatggcaa aagattatgc atttctttcc agacttgttc aacaggccag   3360
ccatttctct catcatcaaa atcactggca tcaaccaaac cattattcat tcttgattgg   3420
gcctgagcca gtctaaatac tctatcagag ttaaaaggac aattacaaac aggaatggaa   3480
tgcaatcttc tcaggaacac tgccagggca tcaacaatat tttcacctga atcaggatat   3540
tcttccaata cctggaatgc tgttttccct gggatggcag tggtgagtaa ccatgcatca   3600
tcaggagttc tgataaaatg cttgatggtt ggaagaggca taaattcagt cagccagttt   3660
agtctgacca tctcatctgt aacatcattg gcaacagaac ctttgccatg tttcagaaac   3720
```

aactctgggg catctggctt cccatacaat ctatagattg tggcacctga ttgcccaaca 3780
ttatctctag cccatttata cccatataaa tcagcatcca tgttggaatt taatcttggc 3840
ctggagcaag aggtttctct ttgaatatgg ctcatacatg tgcacctcct atagtgagtt 3900
gtattatact atgcagatat actatgccaa tgtttaattg tcag 3944

<210> SEQ ID NO 24
<211> LENGTH: 3071
<212> TYPE: DNA
<213> ORGANISM: Artificial sequence
<220> FEATURE:
<223> OTHER INFORMATION: Synthetic

<400> SEQUENCE: 24
ccgcctaatg agcgggcttt tttttggctt gttgtccaca accgttaaac cttaaaagct 60
ttaaaagcct tatatattct ttttttctt ataaaactta aaaccttaga ggctatttaa 120
gttgctgatt tatattaatt ttattgttca aacatgagag cttagtacgt gaaacatgag 180
agcttagtac gttagccatg agagcttagt acgttagcca tgagggttta gttcgttaaa 240
catgagagct tagtacgtta aacatgagag cttagtacgt actatcaaca ggttgaactg 300
ctgatccacg ttgtggtaga attggtaaag agagtcgtgt aaaatatcga gttcgcacat 360
cttgttgtct gattattgat ttttggcgaa accatttgat catatgacaa gatgtgtatc 420
taccttaact taatgatttt gataaaaatc attaggtacc ccggctctag ttattaatag 480
taatcaatta cggggtcatt agttcatagc ccatatatgg agttccgcgt tacataactt 540
acggtaaatg gcccgcctgg ctgaccgccc aacgaccccc gcccattgac gtcaataatg 600
acgtatgttc ccatagtaac gccaataggg actttccatt gacgtcaatg ggtggagtat 660
ttacggtaaa ctgcccactt ggcagtacat caagtgtatc atatgccaag tacgccccct 720
attgacgtca atgacggtaa atggcccgcc tggcattatg cccagtacat gaccttatgg 780
gactttccta cttggcagta catctacgta ttagtcatcg ctattaccat ggtgatgcgg 840
ttttggcagt acatcaatgg gcgtggatag cggtttgact cacggggatt tccaagtctc 900
caccccattg acgtcaatgg gagtttgttt tggcaccaaa atcaacggga ctttccaaaa 960
tgtcgtaaca actccgcccc attgacgcaa atgggcggta ggcgtgtacg gtgggaggtc 1020
tatataagca gagctcgttt agtgaaccgt cagatcgcct ggagacgcca tccacgctgt 1080
tttgacctcc atagaagaca ccgggaccga tccagcctcc gcggctcgca tctctccttc 1140
acgcgcccgc cgccctacct gaggccgcca tccacgccgg ttgagtcgcg ttctgccgcc 1200
tcccgcctgt ggtgcctcct gaactgcgtc cgccgtctag gtaagtttaa agctcaggtc 1260
gagaccgggc ctttgtccgg cgctcccttg gagcctacct agactcagcc ggctctccac 1320
gctttgcctg accctgcttg ctcaactcta gttctctcgt taacttaatg agacagatag 1380
aaactggtct tgtagaaaca gagtagtcgc ctgcttttct gccaggtgct gacttctctc 1440
ccctgggctt ttttcttttt ctcaggttga aaagaagaag acgaagaaga cgaagaagac 1500
aaaccgtcgt cgacgctagg taaccaagcc accatgcaga gagtgaatat gatcatggct 1560
gagagccctg gcctgatcac catctgcctg ctgggctacc tgctgtctgc tgagtgcaca 1620
gtgtttctgg accatgagaa tgccaacaag atcctgaaca ggcccaagag gtacaactct 1680
ggcaagctgg aagagtttgt gcagggcaac ctggaaaggg aatgcatgga agagaagtgc 1740
agctttgaag aggccaggga agtgtttgag aacacagaga gaaccacaga gttctggaag 1800
cagtatgtgg atggggacca gtgtgaaagc aacccctgcc tgaatggggg cagctgcaag 1860
gatgacatca acagctatga gtgctggtgc ccctttggct ttgagggcaa gaactgtgaa 1920
ctggatgtga cctgcaacat caagaatggc agatgtgaac agttctgcaa gaactctgct 1980
gacaacaagg ttgtgtgctc ctgcacagag ggctacagac tggctgagaa ccagaaaagc 2040
tgtgaacctg ctgtgccctt cccatgtggc agagtgtctg tgtcccagac cagcaagctg 2100
accagagctg agacagtgtt ccctgatgtg gactatgtga actccacaga ggctgaaacc 2160
atcctggaca acatcaccca gagcacccag tccttcaatg acttcaccag agttgtggga 2220
ggggaggatg ccaagcctgg ccagttccca tggcaagtgg tgctgaatgg caaagtggat 2280
gccttctgtg ggggctccat tgtgaatgag aagtggattg tgacagctgc ccactgtgtg 2340
gaaactggag tgaagatcac agtggtggct ggggagcaca acattgagga aacagagcac 2400
acagagcaga aaagaaatgt gatcaggatc atcccccacc acaactacaa tgctgccatc 2460
aacaagtaca accatgacat tgccctgctg gaactggatg agcccctggt gctgaacagc 2520
tatgtgaccc ccatctgcat tgctgacaaa gagtacacca acatctttct gaagtttggc 2580
tctggctatg tgtctggctg gggcagggtg ttccacaagg gaaggagtgc tctggtgctg 2640
cagtacctga gagtgccact ggtggacaga gccacctgtc tgagaagcac caagttcacc 2700
atctacaaca acatgttctg tgctggcttc catgaggggg gcagagactc ctgccagggg 2760
gattctgggg gccctcatgt gacagaggtg gaaggcacca gctttctgac aggcatcatc 2820
agctggggag aggaatgtgc catgaagggc aaatatggca tctacaccaa ggtgtccaga 2880
tatgtgaatt ggatcaaaga aaagaccaag ctgacatgaa gatctttttc cctctgccaa 2940
aaattatggg gacatcatga agccccttga gcatctgact tctggctaat aaaggaaatt 3000
tattttcatt gcaatagtgt gttggaattt tttgtgtctc tcactcggaa ggacataagg 3060
gcggccctag c 3071

<210> SEQ ID NO 25
<211> LENGTH: 4326
<212> TYPE: DNA
<213> ORGANISM: Artificial sequence
<220> FEATURE:
<223> OTHER INFORMATION: Synthetic

<400> SEQUENCE: 25
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780

-continued

```
tatgaaccct gcagccctag acaattgtac taaccttctt ctctttcctc tcctgacagg    840
ttggtaacca agccaccatg ggatggtccc tgatcctgct gtttctggtg gctgtggcca    900
ccagagtgct gtctgaagtg cagctggtgg aaagtggtgg tggcctggtc aagcctggtg    960
gctctctgag actgagctgt gctgcctctg gcttcacctt cagcagctac agcatgaact   1020
gggtcagaca ggcccctggc aaaggcctgg aatgggtgtc cagcatcagc agcagctcca   1080
gctacatcag ctatgctgac tctgtgaagg gcagattcac catctccaga gacaatgcca   1140
agaacagcct gtacctccag atgaactccc tgagagctga ggatacagct gtgtacttct   1200
gtgccaggga ctatgacttt tggagtgcct actatgatgc ctttgatgtg tggggccagg   1260
gcaccatggt cacagtgtcc tctgcttcca caaagggccc ctctgtgttc cctctggctc   1320
ctagcagcaa gagcaccagt ggtggaacag ctgccctggg ctgtctggtc aaggactact   1380
ttcctgagcc tgtgacagtg tcttggaact ctggggccct gacatctggg gtgcacacat   1440
ttccagctgt gctccagtcc tctggcctgt actccctgtc ctctgtggtc actgtgccaa   1500
gctctagcct gggcacccag acctacatct gcaatgtgaa ccacaagcct agcaacacca   1560
aggtggacaa gaaggctgag cccaagagct gtgacaagac ccacacctgt cctccatgtc   1620
ctgctccaga gctgcttgga ggaccttctg tgtttctgtt ccctccaaag ccaaaggaca   1680
ccctgatgat cagcagaacc cctgaagtga cctgtgtggt ggttgatgtg tcccatgagg   1740
acccagaagt gaagttcaat tggtatgtgg atggtgttga ggtgcacaat gctaagacca   1800
agcctagaga ggaacagtac aacagcacct acagggttgt gtctgtgctg acagtgctgc   1860
accaggactg gctgaatggc aaagagtaca agtgcaaggt gtccaacaag gccctgcctg   1920
ctcctattga aaagaccatc agcaaggcca agggccagcc tagggaaccc caggtttaca   1980
cactgccacc tagcagagat gagctgacca agaaccaggt gtccctgacc tgtcttgtga   2040
agggattcta cccctctgac attgctgtgg aatgggagag caatggccag cctgagaaca   2100
actacaagac aacccctcct gtgctggact ctgatggctc attcttcctg tacagcaagc   2160
tgactgtgga caagtccaga tggcagcagg gcaatgtgtt cagctgctct gtgatgcatg   2220
aggccctgca caaccactac acacagaagt ccctgtctct gagccctggc aagagaaaga   2280
gaaggagtgg aagtggagct actaacttca gcctgctgaa gcaggctgga gatgtggagg   2340
agaaccctgg acctatggac ttccaggtgc agatcatcag ctttctgctg atctctgcct   2400
ctgtgatcat gagcagaggc cagtctgtgc tgacccagcc tccatctgtt agtggtgccc   2460
ctggccagag agtgaccatc agctgtacag gcagcagcag caacattgga gctggctatg   2520
atgtgcactg gtatcagcag ctgcctggca cagctcccaa gctgctcatc tctggcaaca   2580
gcaacagacc ctctggggtg ccagacagat tctctggcag caagtctggc acatctgcca   2640
gcctggctat cactggactc caggctgagg atgaggctga ctactactgc cagagctatg   2700
acagcagcct gtctggctct gtgtttggtg gtggcaccaa gctgacagtg ctgagaacag   2760
tggctgcccc ttctgtgttc atcttcccac catctgatga acagctgaag agtggcacag   2820
cctctgttgt gtgcctgctg aacaacttct accccagaga agccaaggtg cagtggaagg   2880
tggacaatgc cctccagtct ggcaactccc aagagtctgt gacagagcag gacagcaagg   2940
actccaccta cagcctgagc agcaccctga cactgagcaa ggcagactat gagaagcaca   3000
aagtctatgc ctgtgaagtg acccaccagg gcctgtctag ccctgtgacc aagagcttca   3060
acaggggaga gagctgaaga tctacttctg gctaataaaa gatcagagct ctagtgatct   3120
gtgtgttggt tttttgtgtc tgcattctag ctctagtgat cagcagttca acctgttgat   3180
```

agtatgtact aagctctcat gtttaatgta ctaagctctc atgtttaatg aactaaaccc 3240
tcatggctaa tgtactaagc tctcatggct aatgtactaa gctctcatgt ttcatgtact 3300
aagctctcat gtttgaacaa taaaattaat ataaatcagc aacttaaata gcctctaagg 3360
ttttaagttt tataagaaaa aaaagaatat ataaggcttt taaaggtttt aaggtttcct 3420
aggttatcct catatgagct cttagaaaaa ctcatccagc atcaaatgaa actgcaattt 3480
attcatatca ggattatcaa taccatattt ttgaaaaagt cttttctgta atgaaggaga 3540
aaactcaccc aggcagttcc ataggatggc aagatcctgg tatctgtctg caattccaac 3600
tcttccaaca tcaatacaac ctattaattt cccctcatca aaaataaggt tatcaagtga 3660
gaaatcacca tgagtgacca ctgaatctgg tgagaatggc aaaagattat gcatttcttt 3720
ccagacttgt tcaacaggcc agccatttct ctcatcatca aaatcactgg catcaaccaa 3780
accattattc attcttgatt gggcctgagc cagtctaaat actctatcag agttaaaagg 3840
acaattacaa acaggaatgg aatgcaatct tctcaggaac actgccaggg catcaacaat 3900
attttcacct gaatcaggat attcttccaa tacctggaat gctgttttcc ctgggatggc 3960
agtggtgagt aaccatgcat catcaggagt tctgataaaa tgcttgatgg ttggaagagg 4020
cataaattca gtcagccagt ttagtctgac catctcatct gtaacatcat tggcaacaga 4080
acctttgcca tgtttcagaa acaactctgg ggcatctggc ttcccataca atctatagat 4140
tgtggcacct gattgcccaa cattatctct agcccattta tacccatata aatcagcatc 4200
catgttggaa tttaatcttg gcctggagca agaggtttct ctttgaatat ggctcataca 4260
tgtgcacctc ctatagtgag ttgtattata ctatgcagat atactatgcc aatgtttaat 4320
tgtcag 4326

<210> SEQ ID NO 26
<211> LENGTH: 5049
<212> TYPE: DNA
<213> ORGANISM: Artificial sequence
<220> FEATURE:
<223> OTHER INFORMATION: Synthetic

<400> SEQUENCE: 26
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840

-continued

```
ttggtaacca agccaccatg ggatggtccc tgatcctgct gtttctggtg gctgtggcca    900
ccagagtgct gtctgaagtg cagctggtgg aaagtggtgg tggcctggtc aagcctggtg    960
gctctctgag actgagctgt gctgcctctg gcttcacctt cagcagctac agcatgaact   1020
gggtcagaca ggcccctggc aaaggcctgg aatgggtgtc cagcatcagc agcagctcca   1080
gctacatcag ctatgctgac tctgtgaagg gcagattcac catctccaga gacaatgcca   1140
agaacagcct gtacctccag atgaactccc tgagagctga ggatacagct gtgtacttct   1200
gtgccaggga ctatgacttt tggagtgcct actatgatgc ctttgatgtg tggggccagg   1260
gcaccatggt cacagtgtcc tctgcttcca caaagggccc ctctgtgttc cctctggctc   1320
ctagcagcaa gagcaccagt ggtggaacag ctgccctggg ctgtctggtc aaggactact   1380
ttcctgagcc tgtgacagtg tcttggaact ctggggccct gacatctggg gtgcacacat   1440
ttccagctgt gctccagtcc tctggcctgt actccctgtc ctctgtggtc actgtgccaa   1500
gctctagcct gggcacccag acctacatct gcaatgtgaa ccacaagcct agcaacacca   1560
aggtggacaa gaaggctgag cccaagagct gtgacaagac ccacacctgt cctccatgtc   1620
ctgctccaga gctgcttgga ggaccttctg tgtttctgtt ccctccaaag ccaaaggaca   1680
ccctgatgat cagcagaacc cctgaagtga cctgtgtggt ggttgatgtg tcccatgagg   1740
acccagaagt gaagttcaat tggtatgtgg atggtgttga ggtgcacaat gctaagacca   1800
agcctagaga ggaacagtac aacagcacct acagggttgt gtctgtgctg acagtgctgc   1860
accaggactg gctgaatggc aaagagtaca agtgcaaggt gtccaacaag gccctgcctg   1920
ctcctattga aaagaccatc agcaaggcca agggccagcc tagggaaccc caggtttaca   1980
cactgccacc tagcagagat gagctgacca agaaccaggt gtccctgacc tgtcttgtga   2040
agggattcta cccctctgac attgctgtgg aatgggagag caatggccag cctgagaaca   2100
actacaagac aacccctcct gtgctggact ctgatggctc attcttcctg tacagcaagc   2160
tgactgtgga caagtccaga tggcagcagg gcaatgtgtt cagctgctct gtgatgcatg   2220
aggccctgca caaccactac acacagaagt ccctgtctct gagccctggc aagtgaagat   2280
ctacttctgg ctaataaaag atcagagctc tagtgatctg tgtgttggtt ttttgtgtct   2340
gcattctagc atgttacata acttatggta aatggcctgc ctggctgact gcccaatgac   2400
ccctgcccaa tgatgtcaat aatgatgtat gttcccatgt aatgccaata gggactttcc   2460
attgatgtca atgggtggag tatttatggt aactgcccac ttggcagtac atcaagtgta   2520
tcatatgcca agtatgcccc ctattgatgt caatgatggt aaatggcctg cctggcatta   2580
tgcccagtac atgaccttat gggactttcc tacttggcag tacatctatg tattagtcat   2640
tgctattacc atggattagt ggagaagagc atgcttgagg gctgagtgcc cctcagtggg   2700
cagagagcac atggcccaca gtccctgaga agttgggggg aggggtgggc aattgaactg   2760
gtgcctagag aaggtggggc ttgggtaaac tgggaaagtg atgtggtgta ctggctccac   2820
ctttttcccc agggtggggg agaaccatat ataagtgcag tagtctctgt gaacattcaa   2880
gcttctgcct tctccctcct gtgagtttgg atgcacctac tagatatctt ggtaagtcac   2940
tgactgtcta tgcctgggaa agggtgggca ggaggtgggg cagtgcagga aaagtggcac   3000
tgtgaaccct gcagccctag acaattgtac taaccttctt ctctttcctc tcctgacagg   3060
ttggtaacca agccaccatg gacttccagg tgcagatcat cagctttctg ctgatctctg   3120
cctctgtgat catgagcaga ggccagtctg tgctgaccca gcctccatct gttagtggtg   3180
cccctggcca gagagtgacc atcagctgta caggcagcag cagcaacatt ggagctggct   3240
```

-continued

```
atgatgtgca ctggtatcag cagctgcctg gcacagctcc caagctgctc atctctggca   3300

acagcaacag accctctggg gtgccagaca gattctctgg cagcaagtct ggcacatctg   3360

ccagcctggc tatcactgga ctccaggctg aggatgaggc tgactactac tgccagagct   3420

atgacagcag cctgtctggc tctgtgtttg gtggtggcac caagctgaca gtgctgagaa   3480

cagtggctgc cccttctgtg ttcatcttcc caccatctga tgaacagctg aagagtggca   3540

cagcctctgt tgtgtgcctg ctgaacaact tctaccccag agaagccaag gtgcagtgga   3600

aggtggacaa tgccctccag tctggcaact cccaagagtc tgtgacagag caggacagca   3660

aggactccac ctacagcctg agcagcaccc tgacactgag caaggcagac tatgagaagc   3720

acaaagtcta tgcctgtgaa gtgacccacc agggcctgtc tagccctgtg accaagagct   3780

tcaacagggg agagagctga agatctactt ctggctaata aaagatcaga gctctagtga   3840

tctgtgtgtt ggtttttgt gtctgcattc tagctctagt gatcagcagt tcaacctgtt   3900

gatagtatgt actaagctct catgtttaat gtactaagct ctcatgttta atgaactaaa   3960

ccctcatggc taatgtacta agctctcatg gctaatgtac taagctctca tgtttcatgt   4020

actaagctct catgtttgaa caataaaatt aatataaatc agcaacttaa atagcctcta   4080

aggttttaag ttttataaga aaaaaaagaa tatataaggc ttttaaaggt tttaaggttt   4140

cctaggttat cctcatatga gctcttagaa aaactcatcc agcatcaaat gaaactgcaa   4200

tttattcata tcaggattat caataccata tttttgaaaa agtcttttct gtaatgaagg   4260

agaaaactca cccaggcagt tccataggat ggcaagatcc tggtatctgt ctgcaattcc   4320

aactcttcca acatcaatac aacctattaa tttcccctca tcaaaaataa ggttatcaag   4380

tgagaaatca ccatgagtga ccactgaatc tggtgagaat ggcaaaagat tatgcatttc   4440

tttccagact tgttcaacag gccagccatt tctctcatca tcaaaatcac tggcatcaac   4500

caaaccatta ttcattcttg attgggcctg agccagtcta aatactctat cagagttaaa   4560

aggacaatta caaacaggaa tggaatgcaa tcttctcagg aacactgcca gggcatcaac   4620

aatattttca cctgaatcag gatattcttc caatacctgg aatgctgttt tccctgggat   4680

ggcagtggtg agtaaccatg catcatcagg agttctgata aaatgcttga tggttggaag   4740

aggcataaat tcagtcagcc agtttagtct gaccatctca tctgtaacat cattggcaac   4800

agaacctttg ccatgtttca gaaacaactc tggggcatct ggcttcccat acaatctata   4860

gattgtggca cctgattgcc caacattatc tctagcccat ttatacccat ataaatcagc   4920

atccatgttg gaatttaatc ttggcctgga gcaagaggtt tctctttgaa tatggctcat   4980

acatgtgcac ctcctatagt gagttgtatt atactatgca gatatactat gccaatgttt   5040

aattgtcag                                                           5049
```

<210> SEQ ID NO 27
<211> LENGTH: 4296
<212> TYPE: DNA
<213> ORGANISM: Artificial sequence
<220> FEATURE:
<223> OTHER INFORMATION: Synthetic

<400> SEQUENCE: 27

```
cactatgtgg acatgaattc aattggctag caggagtcaa tgggaaaaac ccattggagc     60

caagtacact gactcaatag ggactttcca ttgggttttg cccagtacat aaggtcaata    120

gggggtgagt caacaggaaa gtcccattgg agccaagtac attgagtcaa tagggacttt    180
```

```
ccaatgggtt ttgcccagta cataaggtca atgggaggta agccaatggg tttttcccat    240
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc accttttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg ggatggtccc tgatcctgct gtttctggtg gctgtggcca    900
ccagagtgct gtctcaggtt cagctggtgc agtctggggc tgaagtgaag aaacctgggg    960
cctctgtgaa ggtgtcctgc aaggcttctg gctacaccct gaccagctat ggcatctcct   1020
gggtcagaca ggctcctgga cagggccttg aatggatggg ctgggtgtcc ttctacaatg   1080
gcaacaccaa ctatgcccag aagctgcaag gcagaggcac catgacaaca gaccccagca   1140
caagcacagc ctacatggaa ctgaggagtc ttaggagtga tgacactgct gtgtactact   1200
gtgccagagg ctatggaatg gatgtgtggg gccagggcac cacagtgaca gtgtcctctg   1260
cttccacaaa gggcccctct gtgttccctc tggctcctag cagcaagagc accagtggtg   1320
gaacagctgc cctgggctgt ctggtcaagg actactttcc tgagcctgtg acagtgtctt   1380
ggaactctgg ggccctgaca tctggggtgc acacatttcc agctgtgctc cagtcctctg   1440
gcctgtactc cctgtcctct gtggtcactg tgccaagctc tagcctgggc acccagacct   1500
acatctgcaa tgtgaaccac aagcctagca acaccaaggt ggacaagaag gctgagccca   1560
agagctgtga caagacccac acctgtcctc catgtcctgc tccagagctg cttggaggac   1620
cttctgtgtt tctgttccct ccaaagccaa aggacaccct gatgatcagc agaacccctg   1680
aagtgacctg tgtggtggtt gatgtgtccc atgaggaccc agaagtgaag ttcaattggt   1740
atgtggatgg tgttgaggtg cacaatgcta agaccaagcc tagagaggaa cagtacaaca   1800
gcacctacag ggttgtgtct gtgctgacag tgctgcacca ggactggctg aatggcaaag   1860
agtacaagtg caaggtgtcc aacaaggccc tgcctgctcc tattgaaaag accatcagca   1920
aggccaaggg ccagcctagg gaaccccagg tttacacact gccacctagc agagatgagc   1980
tgaccaagaa ccaggtgtcc ctgacctgtc ttgtgaaggg attctacccc tctgacattg   2040
ctgtggaatg ggagagcaat ggccagcctg agaacaacta caagacaacc cctcctgtgc   2100
tggactctga tggctcattc ttcctgtaca gcaagctgac tgtggacaag tccagatggc   2160
agcagggcaa tgtgttcagc tgctctgtga tgcatgaggc cctgcacaac cactacacac   2220
agaagtccct gtctctgagc cctggcaaga gaaagagaag gagtggaagt ggagctacta   2280
acttcagcct gctgaagcag gctggagatg tggaggagaa ccctggacct atggacttcc   2340
aggtgcagat catcagcttt ctgctgatct ctgcctctgt gatcatgagc agaggccagt   2400
ctgccctgac acagccagca tctgtgtctg gaagccctgg ccagagcatc accatcagct   2460
gtacaggcac cagctctgat gttggaggct acaactctgt gtcctggtat cagcagcacc   2520
ctggcaaggc ccctaaactc atgatctatg aggtgtccaa caggccctct ggggtgtcca   2580
```

atagattctc tggcagcaag tctggcaaca ctgccagcct gaccatcagt ggactccagg 2640
ctgaggatga ggctgactac tactgcaaca gctacaccag caccagcatg gtgtttggtg 2700
gtggcaccaa gctgacagtg ctgagaacag tggctgcccc ttctgtgttc atcttcccac 2760
catctgatga gcagctgaag agtggcacag cctctgttgt gtgcctgctg aacaacttct 2820
accccagaga agccaaggtg cagtggaagg tggacaatgc cctccagtct ggaaacagcc 2880
aagagtctgt gacagagcag gacagcaagg actccaccta cagcctgagc agcacactga 2940
ccctgtccaa ggcagactat gagaagcaca aagtctatgc ctgtgaagtg acccaccagg 3000
gcctgtctag ccctgtgacc aagagcttca acaggggaga gagctgaaga tctacttctg 3060
gctaataaaa gatcagagct ctagtgatct gtgtgttggt tttttgtgtc tgcattctag 3120
ctctagtgat cagcagttca acctgttgat agtatgtact aagctctcat gtttaatgta 3180
ctaagctctc atgtttaatg aactaaaccc tcatggctaa tgtactaagc tctcatggct 3240
aatgtactaa gctctcatgt ttcatgtact aagctctcat gtttgaacaa taaaattaat 3300
ataaatcagc aacttaaata gcctctaagg ttttaagttt tataagaaaa aaaagaatat 3360
ataaggcttt taaaggtttt aaggtttcct aggttatcct catatgagct cttagaaaaa 3420
ctcatccagc atcaaatgaa actgcaattt attcatatca ggattatcaa taccatattt 3480
ttgaaaaagt cttttctgta atgaaggaga aaactcaccc aggcagttcc ataggatggc 3540
aagatcctgg tatctgtctg caattccaac tcttccaaca tcaatacaac ctattaattt 3600
cccctcatca aaaataaggt tatcaagtga gaaatcacca tgagtgacca ctgaatctgg 3660
tgagaatggc aaaagattat gcatttcttt ccagacttgt tcaacaggcc agccatttct 3720
ctcatcatca aaatcactgg catcaaccaa accattattc attcttgatt gggcctgagc 3780
cagtctaaat actctatcag agttaaaagg acaattacaa acaggaatgg aatgcaatct 3840
tctcaggaac actgccaggg catcaacaat attttcacct gaatcaggat attcttccaa 3900
tacctggaat gctgttttcc ctgggatggc agtggtgagt aaccatgcat catcaggagt 3960
tctgataaaa tgcttgatgg ttggaagagg cataaattca gtcagccagt ttagtctgac 4020
catctcatct gtaacatcat tggcaacaga acctttgcca tgtttcagaa acaactctgg 4080
ggcatctggc ttcccataca atctatagat tgtggcacct gattgcccaa cattatctct 4140
agcccattta tacccatata aatcagcatc catgttggaa tttaatcttg gcctggagca 4200
agaggtttct ctttgaatat ggctcataca tgtgcacctc ctatagtgag ttgtattata 4260
ctatgcagat atactatgcc aatgtttaat tgtcag 4296

<210> SEQ ID NO 28
<211> LENGTH: 5019
<212> TYPE: DNA
<213> ORGANISM: Artificial sequence
<220> FEATURE:
<223> OTHER INFORMATION: Synthetic

<400> SEQUENCE: 28
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300

```
tcaataggggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc acctttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg ggatggtccc tgatcctgct gtttctggtg gctgtggcca    900
ccagagtgct gtctcaggtt cagctggtgc agtctggggc tgaagtgaag aaacctgggg    960
cctctgtgaa ggtgtcctgc aaggcttctg gctacaccct gaccagctat ggcatctcct   1020
gggtcagaca ggctcctgga cagggccttg aatggatggg ctgggtgtcc ttctacaatg   1080
gcaacaccaa ctatgcccag aagctgcaag gcagaggcac catgacaaca gaccccagca   1140
caagcacagc ctacatggaa ctgaggagtc ttaggagtga tgacactgct gtgtactact   1200
gtgccagagg ctatggaatg gatgtgtggg gccagggcac cacagtgaca gtgtcctctg   1260
cttccacaaa gggcccctct gtgttccctc tggctcctag cagcaagagc accagtggtg   1320
gaacagctgc cctgggctgt ctggtcaagg actactttcc tgagcctgtg acagtgtctt   1380
ggaactctgg ggccctgaca tctggggtgc acacatttcc agctgtgctc cagtcctctg   1440
gcctgtactc cctgtcctct gtggtcactg tgccaagctc tagcctgggc acccagacct   1500
acatctgcaa tgtgaaccac aagcctagca acaccaaggt ggacaagaag gctgagccca   1560
agagctgtga caagacccac acctgtcctc catgtcctgc tccagagctg cttggaggac   1620
cttctgtgtt tctgttccct ccaaagccaa aggacaccct gatgatcagc agaacccctg   1680
aagtgacctg tgtggtggtt gatgtgtccc atgaggaccc agaagtgaag ttcaattggt   1740
atgtggatgg tgttgaggtg cacaatgcta agaccaagcc tagagaggaa cagtacaaca   1800
gcacctacag ggttgtgtct gtgctgacag tgctgcacca ggactggctg aatggcaaag   1860
agtacaagtg caaggtgtcc aacaaggccc tgcctgctcc tattgaaaag accatcagca   1920
aggccaaggg ccagcctagg gaaccccagg tttacacact gccacctagc agagatgagc   1980
tgaccaagaa ccaggtgtcc ctgacctgtc ttgtgaaggg attctacccc tctgacattg   2040
ctgtggaatg ggagagcaat ggccagcctg agaacaacta caagacaacc cctcctgtgc   2100
tggactctga tggctcattc ttcctgtaca gcaagctgac tgtggacaag tccagatggc   2160
agcagggcaa tgtgttcagc tgctctgtga tgcatgaggc cctgcacaac cactacacac   2220
agaagtccct gtctctgagc cctggcaagt gaagatctac ttctggctaa taaaagatca   2280
gagctctagt gatctgtgtg ttggtttttt gtgtctgcat tctagcatgt tacataactt   2340
atggtaaatg gcctgcctgg ctgactgccc aatgacccct gcccaatgat gtcaataatg   2400
atgtatgttc ccatgtaatg ccaataggga ctttccattg atgtcaatgg gtggagtatt   2460
tatggtaact gcccacttgg cagtacatca agtgtatcat atgccaagta tgccccctat   2520
tgatgtcaat gatggtaaat ggcctgcctg gcattatgcc cagtacatga ccttatggga   2580
ctttcctact tggcagtaca tctatgtatt agtcattgct attaccatgg attagtggag   2640
aagagcatgc ttgagggctg agtgcccctc agtgggcaga gagcacatgg cccacagtcc   2700
```

ctgagaagtt ggggggaggg gtgggcaatt gaactggtgc ctagagaagg tggggcttgg 2760
gtaaactggg aaagtgatgt ggtgtactgg ctccaccttt ttccccaggg tgggggagaa 2820
ccatatataa gtgcagtagt ctctgtgaac attcaagctt ctgccttctc cctcctgtga 2880
gtttggatgc acctactaga tatcttggta agtcactgac tgtctatgcc tgggaaaggg 2940
tgggcaggag gtggggcagt gcaggaaaag tggcactgtg aaccctgcag ccctagacaa 3000
ttgtactaac cttcttctct ttcctctcct gacaggttgg taaccaagcc accatggact 3060
tccaggtgca gatcatcagc tttctgctga tctctgcctc tgtgatcatg agcagaggcc 3120
agtctgccct gacacagcca gcatctgtgt ctggaagccc tggccagagc atcaccatca 3180
gctgtacagg caccagctct gatgttggag gctacaactc tgtgtcctgg tatcagcagc 3240
accctggcaa ggcccctaaa ctcatgatct atgaggtgtc caacaggccc tctggggtgt 3300
ccaatagatt ctctggcagc aagtctggca acactgccag cctgaccatc agtggactcc 3360
aggctgagga tgaggctgac tactactgca acagctacac cagcaccagc atggtgtttg 3420
gtggtggcac caagctgaca gtgctgagaa cagtggctgc cccttctgtg ttcatcttcc 3480
caccatctga tgagcagctg aagagtggca cagcctctgt tgtgtgcctg ctgaacaact 3540
tctaccccag agaagccaag gtgcagtgga aggtggacaa tgccctccag tctggaaaca 3600
gccaagagtc tgtgacagag caggacagca aggactccac ctacagcctg agcagcacac 3660
tgaccctgtc caaggcagac tatgagaagc acaaagtcta tgcctgtgaa gtgacccacc 3720
agggcctgtc tagccctgtg accaagagct tcaacagggg agagagctga agatctactt 3780
ctggctaata aaagatcaga gctctagtga tctgtgtgtt ggttttttgt gtctgcattc 3840
tagctctagt gatcagcagt tcaacctgtt gatagtatgt actaagctct catgtttaat 3900
gtactaagct ctcatgttta atgaactaaa ccctcatggc taatgtacta agctctcatg 3960
gctaatgtac taagctctca tgtttcatgt actaagctct catgtttgaa caataaaatt 4020
aatataaatc agcaacttaa atagcctcta aggttttaag ttttataaga aaaaaaagaa 4080
tatataaggc ttttaaaggt tttaaggttt cctaggttat cctcatatga gctcttagaa 4140
aaactcatcc agcatcaaat gaaactgcaa tttattcata tcaggattat caataccata 4200
tttttgaaaa agtcttttct gtaatgaagg agaaaactca cccaggcagt tccataggat 4260
ggcaagatcc tggtatctgt ctgcaattcc aactcttcca acatcaatac aacctattaa 4320
tttcccctca tcaaaaataa ggttatcaag tgagaaatca ccatgagtga ccactgaatc 4380
tggtgagaat ggcaaaagat tatgcatttc tttccagact tgttcaacag gccagccatt 4440
tctctcatca tcaaaatcac tggcatcaac caaaccatta ttcattcttg attgggcctg 4500
agccagtcta aatactctat cagagttaaa aggacaatta caaacaggaa tggaatgcaa 4560
tcttctcagg aacactgcca gggcatcaac aatattttca cctgaatcag gatattcttc 4620
caatacctgg aatgctgttt tccctgggat ggcagtggtg agtaaccatg catcatcagg 4680
agttctgata aaatgcttga tggttggaag aggcataaat tcagtcagcc agtttagtct 4740
gaccatctca tctgtaacat cattggcaac agaacctttg ccatgtttca gaaacaactc 4800
tggggcatct ggcttcccat acaatctata gattgtggca cctgattgcc caacattatc 4860
tctagcccat ttatacccat ataaatcagc atccatgttg gaatttaatc ttggcctgga 4920
gcaagaggtt tctctttgaa tatggctcat acatgtgcac ctcctatagt gagttgtatt 4980
atactatgca gatatactat gccaatgttt aattgtcag 5019

<210> SEQ ID NO 29
<211> LENGTH: 4302
<212> TYPE: DNA
<213> ORGANISM: Artificial sequence
<220> FEATURE:
<223> OTHER INFORMATION: Synthetic

<400> SEQUENCE: 29

```
cactatgtgg acatgaattc aattggctag caggagtcaa tgggaaaaac ccattggagc     60
caagtacact gactcaatag ggactttcca ttgggttttg cccagtacat aaggtcaata    120
gggggtgagt caacaggaaa gtcccattgg agccaagtac attgagtcaa tagggacttt    180
ccaatgggtt ttgcccagta cataaggtca atgggaggta agccaatggg tttttcccat    240
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc acctttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg ggctggtcct gcatcatgtt ctttctggtg gccacagcca    900
caggggtgca ctctcaggtt cagctgcaac agcctggtgc tgagctggtt aagcctgggg    960
cctctgtgat gatgagctgc aaggcctctg gctacacctt caccaactac aacatgcact   1020
gggtcaagca gacccccaggc cagggccttg agtggattgg cacaatctac cctggcaatg   1080
atgacaccag ctacaaccag aagttcaagg acaaggccac actgacagct gacaagagca   1140
gctctgctgc ctacatgcag ctgagcagcc tgacctctga ggactctgct gtgtactact   1200
gtgccagagg gggctacaga gccatggatt actggggcca gggcacctct gtgacagtgt   1260
catctgccag cacaaagggc ccatctgtgt tccctctggc acccagcagc aagtctacca   1320
gtggtggaac agctgccctg ggctgtctgg tcaaggacta ctttcctgag ccagtgacag   1380
tgtcctggaa ctctggggct ctgacatctg gggtgcacac attccctgct gtgctccagt   1440
cctctggcct gtacagcctc agctctgtgg tcacagtgcc tagctctagc ctgggcaccc   1500
agacctacat ctgcaatgtg aaccacaagc ctagcaacac caaggtggac aagaaggctg   1560
agcccaagag ctgtgacaag acccacacct gtcctccatg tcctgctcca gagctgcttg   1620
gaggaccttc tgtgtttctg ttccctccaa agccaaagga caccctgatg atcagcagaa   1680
cccctgaagt gacatgtgtg gtggttgatg tgtcccatga ggacccagaa gtgaagttca   1740
attggtatgt ggatggtgtt gaggtgcaca atgccaagac caagcctaga gaggaacagt   1800
acaacagcac ctacagagtg gtgtctgtgc tgacagtgct gcatcaggac tggctgaatg   1860
gcaaagagta caagtgcaag gtgtccaaca aggccctgcc tgctcctatt gaaaagacca   1920
tctccaaggc caagggccag cctagggaac cccaggttta cacactgcca cctagcaggg   1980
atgagctgac caagaaccag gtgtccctga cctgcctggt taagggcttc tacccctctg   2040
acattgctgt ggaatgggag agcaatggcc agccagagaa caactacaag acaacccctc   2100
```

ctgtgctgga ctctgatggc tcattcttcc tgtactccaa gctcacagtg gacaagtcca 2160
gatggcagca aggcaatgtg ttcagctgct ctgtgatgca tgaggccctg cacaaccact 2220
acacacagaa gtccctgagc ctgtctcctg gcaagagaaa gagaaggagt ggaagtggag 2280
ctactaactt cagcctgctg aagcaggctg gagatgtgga ggagaaccct ggacctatga 2340
agttgcctgt taggctgttg gtgctgatgt tctggattcc tggttccagc agtgatgttt 2400
tgatgaccca aactccactc tccctgcctg tcagtcttgg agatcaagcc tccatctctt 2460
gcagatctag tcagagcatt gtatatagta atggaaacac ctatttagga tggtacctgc 2520
agaaaccagg ccagtctcca aagctcctga tctacaaagt ttccaaccga ttttctgggg 2580
tcccagacag gttcagtggc agtggatcag ggacagattt cacactcaag atcagcagag 2640
tggaggctga ggatctgggg gtttatcact gctttcaagg ttcacatgtt ccgtacacgt 2700
tcggaggggg gaccaaggtg gaaataaaaa gaacagtggc tgccccttct gtgttcatct 2760
tcccaccatc tgatgaacag ctgaagagtg gcacagcctc tgttgtgtgc ctgctgaaca 2820
acttctaccc cagagaagcc aaggtgcagt ggaaggtgga caatgccctc cagtctggca 2880
actcccaaga gtctgtgaca gagcaggaca gcaaggactc cacctacagc ctgagcagca 2940
ccctgacact gagcaaggca gactatgaga agcacaaagt ctatgcctgt gaagtgaccc 3000
accagggcct gtctagccct gtgaccaaga gcttcaacag gggagagagc tgaagatcta 3060
cttctggcta ataaaagatc agagctctag tgatctgtgt gttggttttt tgtgtctgca 3120
ttctagctct agtgatcagc agttcaacct gttgatagta tgtactaagc tctcatgttt 3180
aatgtactaa gctctcatgt ttaatgaact aaaccctcat ggctaatgta ctaagctctc 3240
atggctaatg tactaagctc tcatgtttca tgtactaagc tctcatgttt gaacaataaa 3300
attaatataa atcagcaact taaatagcct ctaaggtttt aagttttata agaaaaaaaa 3360
gaatatataa ggcttttaaa ggttttaagg tttcctaggt tatcctcata tgagctctta 3420
gaaaaactca tccagcatca aatgaaactg caatttattc atatcaggat tatcaatacc 3480
atatttttga aaaagtcttt tctgtaatga aggagaaaac tcacccaggc agttccatag 3540
gatggcaaga tcctggtatc tgtctgcaat tccaactctt ccaacatcaa tacaacctat 3600
taatttcccc tcatcaaaaa taaggttatc aagtgagaaa tcaccatgag tgaccactga 3660
atctggtgag aatggcaaaa gattatgcat ttctttccag acttgttcaa caggccagcc 3720
atttctctca tcatcaaaat cactggcatc aaccaaacca ttattcattc ttgattgggc 3780
ctgagccagt ctaaatactc tatcagagtt aaaaggacaa ttacaaacag gaatggaatg 3840
caatcttctc aggaacactg ccagggcatc aacaatattt tcacctgaat caggatattc 3900
ttccaatacc tggaatgctg ttttccctgg gatggcagtg gtgagtaacc atgcatcatc 3960
aggagttctg ataaaatgct tgatggttgg aagaggcata aattcagtca gccagtttag 4020
tctgaccatc tcatctgtaa catcattggc aacagaacct ttgccatgtt tcagaaacaa 4080
ctctggggca tctggcttcc catacaatct atagattgtg gcacctgatt gcccaacatt 4140
atctctagcc catttatacc catataaatc agcatccatg ttggaattta atcttggcct 4200
ggagcaagag gtttctcttt gaatatggct catacatgtg cacctcctat agtgagttgt 4260
attatactat gcagatatac tatgccaatg tttaattgtc ag 4302

<210> SEQ ID NO 30
<211> LENGTH: 5025
<212> TYPE: DNA

<213> ORGANISM: Artificial sequence
<220> FEATURE:
<223> OTHER INFORMATION: Synthetic

<400> SEQUENCE: 30

```
cactatgtgg acatgaattc aattggctag caggagtcaa tgggaaaaac ccattggagc     60
caagtacact gactcaatag ggactttcca ttgggttttg cccagtacat aaggtcaata    120
gggggtgagt caacaggaaa gtcccattgg agccaagtac attgagtcaa tagggacttt    180
ccaatgggtt ttgcccagta cataaggtca atgggaggta agccaatggg tttttcccat    240
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc acctttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg ggctggtcct gcatcatgtt ctttctggtg gccacagcca    900
caggggtgca ctctcaggtt cagctgcaac agcctggtgc tgagctggtt aagcctgggg    960
cctctgtgat gatgagctgc aaggcctctg gctacacctt caccaactac aacatgcact   1020
gggtcaagca gaccccaggc cagggccttg agtggattgg cacaatctac cctggcaatg   1080
atgacaccag ctacaaccag aagttcaagg acaaggccac actgacagct gacaagagca   1140
gctctgctgc ctacatgcag ctgagcagcc tgacctctga ggactctgct gtgtactact   1200
gtgccagagg gggctacaga gccatggatt actggggcca gggcacctct gtgacagtgt   1260
catctgccag cacaaagggc ccatctgtgt tccctctggc acccagcagc aagtctacca   1320
gtggtggaac agctgccctg ggctgtctgg tcaaggacta ctttcctgag ccagtgacag   1380
tgtcctggaa ctctggggct ctgacatctg gggtgcacac attccctgct gtgctccagt   1440
cctctggcct gtacagcctc agctctgtgg tcacagtgcc tagctctagc ctgggcaccc   1500
agacctacat ctgcaatgtg aaccacaagc ctagcaacac caaggtggac aagaaggctg   1560
agcccaagag ctgtgacaag acccacacct gtcctccatg tcctgctcca gagctgcttg   1620
gaggaccttc tgtgtttctg ttccctccaa agccaaagga caccctgatg atcagcagaa   1680
cccctgaagt gacatgtgtg gtggttgatg tgtcccatga ggacccagaa gtgaagttca   1740
attggtatgt ggatggtgtt gaggtgcaca atgccaagac caagcctaga gaggaacagt   1800
acaacagcac ctacagagtg gtgtctgtgc tgacagtgct gcatcaggac tggctgaatg   1860
gcaaagagta caagtgcaag gtgtccaaca aggccctgcc tgctcctatt gaaaagacca   1920
tctccaaggc caagggccag cctagggaac cccaggttta cacactgcca cctagcaggg   1980
atgagctgac caagaaccag gtgtccctga cctgcctggt taagggcttc taccccctctg  2040
acattgctgt ggaatgggag agcaatggcc agccagagaa caactacaag acaacccctc   2100
ctgtgctgga ctctgatggc tcattcttcc tgtactccaa gctcacagtg gacaagtcca   2160
gatggcagca aggcaatgtg ttcagctgct ctgtgatgca tgaggccctg cacaaccact   2220
```

-continued

```
acacacagaa gtccctgagc ctgtctcctg gcaagtgaag atctacttct ggctaataaa   2280
agatcagagc tctagtgatc tgtgtgttgg ttttttgtgt ctgcattcta gcatgttaca   2340
taacttatgg taaatggcct gcctggctga ctgcccaatg acccctgccc aatgatgtca   2400
ataatgatgt atgttcccat gtaatgccaa tagggacttt ccattgatgt caatgggtgg   2460
agtatttatg gtaactgccc acttggcagt acatcaagtg tatcatatgc caagtatgcc   2520
ccctattgat gtcaatgatg gtaaatggcc tgcctggcat tatgcccagt acatgacctt   2580
atgggacttt cctacttggc agtacatcta tgtattagtc attgctatta ccatggatta   2640
gtggagaaga gcatgcttga gggctgagtg cccctcagtg ggcagagagc acatggccca   2700
cagtccctga gaagttgggg ggaggggtgg gcaattgaac tggtgcctag agaaggtggg   2760
gcttgggtaa actgggaaag tgatgtggtg tactggctcc acctttttcc ccagggtggg   2820
ggagaaccat atataagtgc agtagtctct gtgaacattc aagcttctgc cttctccctc   2880
ctgtgagttt ggatgcacct actagatatc ttggtaagtc actgactgtc tatgcctggg   2940
aaagggtggg caggaggtgg ggcagtgcag gaaaagtggc actgtgaacc ctgcagccct   3000
agacaattgt actaaccttc ttctctttcc tctcctgaca ggttggtaac caagccacca   3060
tgaagttgcc tgttaggctg ttggtgctga tgttctggat tcctggttcc agcagtgatg   3120
ttttgatgac ccaaactcca ctctccctgc ctgtcagtct tggagatcaa gcctccatct   3180
cttgcagatc tagtcagagc attgtatata gtaatggaaa cacctattta ggatggtacc   3240
tgcagaaacc aggccagtct ccaaagctcc tgatctacaa agtttccaac cgattttctg   3300
gggtcccaga caggttcagt ggcagtggat cagggacaga tttcacactc aagatcagca   3360
gagtggaggc tgaggatctg gggtttatc actgctttca aggttcacat gttccgtaca   3420
cgttcggagg ggggaccaag gtggaaataa aaagaacagt ggctgcccct tctgtgttca   3480
tcttcccacc atctgatgaa cagctgaaga gtggcacagc ctctgttgtg tgcctgctga   3540
acaacttcta ccccagagaa gccaaggtgc agtggaaggt ggacaatgcc ctccagtctg   3600
gcaactccca agagtctgtg acagagcagg acagcaagga ctccacctac agcctgagca   3660
gcaccctgac actgagcaag gcagactatg agaagcacaa agtctatgcc tgtgaagtga   3720
cccaccaggg cctgtctagc cctgtgacca agagcttcaa caggggagag agctgaagat   3780
ctacttctgg ctaataaaag atcagagctc tagtgatctg tgtgttggtt ttttgtgtct   3840
gcattctagc tctagtgatc agcagttcaa cctgttgata gtatgtacta agctctcatg   3900
tttaatgtac taagctctca tgtttaatga actaaaccct catggctaat gtactaagct   3960
ctcatggcta atgtactaag ctctcatgtt tcatgtacta agctctcatg tttgaacaat   4020
aaaattaata taaatcagca acttaaatag cctctaaggt tttaagtttt ataagaaaaa   4080
aaagaatata taaggctttt aaaggtttta aggtttccta ggttatcctc atatgagctc   4140
ttagaaaaac tcatccagca tcaaatgaaa ctgcaattta ttcatatcag gattatcaat   4200
accatatttt tgaaaaagtc ttttctgtaa tgaaggagaa aactcaccca ggcagttcca   4260
taggatggca agatcctggt atctgtctgc aattccaact cttccaacat caatacaacc   4320
tattaatttc ccctcatcaa aaataaggtt atcaagtgag aaatcaccat gagtgaccac   4380
tgaatctggt gagaatggca aaagattatg catttctttc cagacttgtt caacaggcca   4440
gccatttctc tcatcatcaa aatcactggc atcaaccaaa ccattattca ttcttgattg   4500
ggcctgagcc agtctaaata ctctatcaga gttaaaagga caattacaaa caggaatgga   4560
```

-continued

```
atgcaatctt ctcaggaaca ctgccagggc atcaacaata ttttcacctg aatcaggata   4620

ttcttccaat acctggaatg ctgttttccc tgggatggca gtggtgagta accatgcatc   4680

atcaggagtt ctgataaaat gcttgatggt tggaagaggc ataaattcag tcagccagtt   4740

tagtctgacc atctcatctg taacatcatt ggcaacagaa cctttgccat gtttcagaaa   4800

caactctggg gcatctggct tcccatacaa tctatagatt gtggcacctg attgcccaac   4860

attatctcta gcccatttat acccatataa atcagcatcc atgttggaat ttaatcttgg   4920

cctggagcaa gaggtttctc tttgaatatg gctcatacat gtgcacctcc tatagtgagt   4980

tgtattatac tatgcagata tactatgcca atgtttaatt gtcag                   5025
```

<210> SEQ ID NO 31
<211> LENGTH: 4347
<212> TYPE: DNA
<213> ORGANISM: Artificial sequence
<220> FEATURE:
<223> OTHER INFORMATION: Synthetic

<400> SEQUENCE: 31

```
cactatgtgg acatgaattc aattggctag caggagtcaa tgggaaaaac ccattggagc     60

caagtacact gactcaatag ggactttcca ttgggttttg cccagtacat aaggtcaata    120

gggggtgagt caacaggaaa gtcccattgg agccaagtac attgagtcaa tagggacttt    180

ccaatgggtt ttgcccagta cataaggtca atgggaggta agccaatggg tttttcccat    240

tactgacatg tatactgagt cattagggac tttccaatgg gttttgccca gtacataagg    300

tcaatagggg tgaatcaaca ggaaagtccc attggagcca agtacactga gtcaataggg    360

actttccatt gggttttgcc cagtacaaaa ggtcaatagg gggtgagtca atgggttttt    420

cccattattg gcacatacat aaggtcaata ggggtgacta gtggagaaga gcatgcttga    480

gggctgagtg cccctcagtg ggcagagagc acatggccca cagtccctga gaagttgggg    540

ggaggggtgg gcaattgaac tggtgcctag agaaggtggg gcttgggtaa actgggaaag    600

tgatgtggtg tactggctcc acctttttcc ccagggtggg ggagaaccat atataagtgc    660

agtagtctct gtgaacattc aagcttctgc cttctccctc ctgtgagttt ggtaagtcac    720

tgactgtcta tgcctgggaa agggtgggca ggagatgggg cagtgcagga aaagtggcac    780

tatgaaccct gcagccctag acaattgtac taaccttctt ctctttcctc tcctgacagg    840

ttggtaacca agccaccatg ggactgggac tccagtgggt gttctttgtg gccctgctga    900

aaggggtgca ctgtgaagtc agactgctgg aaagtggtgg tggcctgcag gttcagctgg    960

tgcagtctgg ggctgaagtg aagaaacctg gcagctctgt gaaggtgtcc tgcaaggcta   1020

gtggtggcac cttctctgcc tatgccttca cctgggtcag acaggctcct ggacagggcc   1080

ttgaatggat gggaggcatc acaggcatgt ttggcacagc caactatgcc cagaaattcc   1140

agggcagagt gaccatcaca gctgatgagc tgaccagcac agcctacatg gaactgagca   1200

gcctgacctc tgaggacaca gccctgtact actgtgccag aggcctgtac tattatgagt   1260

ctagcctgga ctactggggc cagggcacac tggttacagt gtctagtgcc agcacaaagg   1320

gcccatctgt gttccctctg gcacccagca gcaagtctac cagtggtgga acagctgccc   1380

tgggctgtct ggtcaaggac tactttcctg agccagtgac agtgtcctgg aactctgggg   1440

ctctgacatc tggggtgcac acattccctg ctgtgctcca gtcctctggc ctgtacagcc   1500

tcagctctgt ggtcacagtg cctagctcta gcctgggcac ccagacctac atctgcaatg   1560

tgaaccacaa gcctagcaac accaaggtgg acaagaaggc tgagcccaag agctgtgaca   1620
```

```
agacccacac ctgtcctcca tgtcctgctc cagagctgct tggaggacct tctgtgtttc   1680
tgttccctcc aaagccaaag gacaccctga tgatcagcag aacccctgaa gtgacatgtg   1740
tggtggttga tgtgtcccat gaggacccag aagtgaagtt caattggtat gtggatggtg   1800
ttgaggtgca caatgccaag accaagccta gagaggaaca gtacaacagc acctacagag   1860
tggtgtctgt gctgacagtg ctgcatcagg actggctgaa tggcaaagag tacaagtgca   1920
aggtgtccaa caaggccctg cctgctccta ttgaaaagac catctccaag gccaagggcc   1980
agcctaggga accccaggtt tacacactgc cacctagcag ggatgagctg accaagaacc   2040
aggtgtccct gacctgcctg gttaagggct tctacccctc tgacattgct gtggaatggg   2100
agagcaatgg ccagccagag aacaactaca agacaacccc tcctgtgctg gactctgatg   2160
gctcattctt cctgtactcc aagctcacag tggacaagtc cagatggcag caaggcaatg   2220
tgttcagctg ctctgtgatg catgaggccc tgcacaacca ctacacacag aagtccctga   2280
gcctgtctcc tggcaagaga aagagaagga gtggaagtgg agctactaac ttcagcctgc   2340
tgaagcaggc tggagatgtg gaggagaacc ctggacctat ggacttccag gtgcagatca   2400
tcagctttct gctgatctct gcctctgtga tcatgagcag aggccagtct gtgctgaccc   2460
agcctccatc tgcatctgga agccctggcc agtctgtgac catcagctgt acaggcacca   2520
gctctgatgt tggaggctac aactctgtgt cctggtatca gcagcaccct ggcaaggccc   2580
ctaagctgat gatctatgaa gtgaccaaga ggccctctgg ggtgccagac agattctctg   2640
ccagcaagtc tggcaacaca gccagcctga cagtgtctgg cctgcaagct gaggatgagg   2700
ctgactactt ctgctgctcc tatgctggcc actctgccta tgtgtttggc actggcacca   2760
aagtgacagt gctgagaaca gtggctgccc cttctgtgtt catcttccca ccatctgatg   2820
agcagctgaa gtctggcaca gcctctgttg tgtgcctgct gaacaacttc taccctagag   2880
aagccaaggt gcagtggaag gtggacaatg ccctccagtc tggcaactcc caagagtctg   2940
tgacagagca ggacagcaag gactccacct acagcctgag cagcaccctg acactgagca   3000
aggctgacta tgagaagcac aaagtctatg cctgtgaagt gacccaccag ggcctgtcta   3060
gccctgtgac caagagcttc aacaggggag agagctgaag atctacttct ggctaataaa   3120
agatcagagc tctagtgatc tgtgtgttgg ttttttgtgt ctgcattcta gctctagtga   3180
tcagcagttc aacctgttga tagtatgtac taagctctca tgtttaatgt actaagctct   3240
catgtttaat gaactaaacc ctcatggcta atgtactaag ctctcatggc taatgtacta   3300
agctctcatg tttcatgtac taagctctca tgtttgaaca ataaaattaa tataaatcag   3360
caacttaaat agcctctaag gttttaagtt ttataagaaa aaaaagaata tataaggctt   3420
ttaaaggttt taaggtttcc taggttatcc tcatatgagc tcttagaaaa actcatccag   3480
catcaaatga aactgcaatt tattcatatc aggattatca ataccatatt tttgaaaaag   3540
tcttttctgt aatgaaggag aaaactcacc caggcagttc cataggatgg caagatcctg   3600
gtatctgtct gcaattccaa ctcttccaac atcaatacaa cctattaatt tcccctcatc   3660
aaaaataagg ttatcaagtg agaaatcacc atgagtgacc actgaatctg gtgagaatgg   3720
caaaagatta tgcatttctt tccagacttg ttcaacaggc cagccatttc tctcatcatc   3780
aaaatcactg gcatcaacca aaccattatt cattcttgat tgggcctgag ccagtctaaa   3840
tactctatca gagttaaaag gacaattaca aacaggaatg gaatgcaatc ttctcaggaa   3900
cactgccagg gcatcaacaa tattttcacc tgaatcagga tattcttcca atacctggaa   3960
```

-continued

```
tgctgttttc cctgggatgg cagtggtgag taaccatgca tcatcaggag ttctgataaa   4020

atgcttgatg gttggaagag gcataaattc agtcagccag tttagtctga ccatctcatc   4080

tgtaacatca ttggcaacag aacctttgcc atgtttcaga aacaactctg ggcatctgg    4140

cttcccatac aatctataga ttgtggcacc tgattgccca acattatctc tagcccattt   4200

atacccatat aaatcagcat ccatgttgga atttaatctt ggcctggagc aagaggtttc   4260

tctttgaata tggctcatac atgtgcacct cctatagtga gttgtattat actatgcaga   4320

tatactatgc caatgtttaa ttgtcag                                       4347
```

<210> SEQ ID NO 32
<211> LENGTH: 4359
<212> TYPE: DNA
<213> ORGANISM: Artificial sequence
<220> FEATURE:
<223> OTHER INFORMATION: Synthetic

<400> SEQUENCE: 32

```
cactatgtgg acatgaattc aattggctag caggagtcaa tgggaaaaac ccattggagc     60

caagtacact gactcaatag ggactttcca ttgggttttg cccagtacat aaggtcaata    120

gggggtgagt caacaggaaa gtcccattgg agccaagtac attgagtcaa tagggacttt    180

ccaatgggtt ttgcccagta cataaggtca atgggaggta agccaatggg tttttcccat    240

tactgacatg tatactgagt cattagggac tttccaatgg gttttgccca gtacataagg    300

tcaatagggg tgaatcaaca ggaaagtccc attggagcca agtacactga gtcaataggg    360

actttccatt gggttttgcc cagtacaaaa ggtcaatagg gggtgagtca atgggttttt    420

cccattattg gcacatacat aaggtcaata ggggtgacta gtggagaaga gcatgcttga    480

gggctgagtg cccctcagtg ggcagagagc acatggccca cagtccctga gaagttgggg    540

ggaggggtgg gcaattgaac tggtgcctag agaaggtggg gcttgggtaa actgggaaag    600

tgatgtggtg tactggctcc accttttcc ccagggtggg ggagaaccat atataagtgc     660

agtagtctct gtgaacattc aagcttctgc cttctccctc ctgtgagttt ggtaagtcac    720

tgactgtcta tgcctgggaa agggtgggca ggagatgggg cagtgcagga aaagtggcac    780

tatgaaccct gcagccctag acaattgtac taaccttctt ctctttcctc tcctgacagg    840

ttggtaacca agccaccatg ggactgggac tccagtgggt gttctttgtg gccctgctga    900

aaggggtgca ctgtgaagtc agactgctgg aaagtggtgg tggcctgcag gttcagctgg    960

tgcagtctgg ggctgaagtg aagaaacctg gcagctctgt gaaggtgtcc tgcacctcct   1020

ctgaagtgac cttcagcagc tttgccatca gctgggtcag acaggctcct ggacagggcc   1080

ttgaatggct tggaggcatc agccccatgt ttggcacccc taactatgcc cagaaattcc   1140

agggcagagt gaccatcaca gctgaccaga gcaccagaac agcctacatg gacctgagaa   1200

gtcttaggag tgaagataca gctgtgtact actgtgctag aagccccagc tacatctgct   1260

ctggtggcac ctgtgtgttt gaccactggg gccagggaac cctggtcaca gtttcttctg   1320

ccagcacaaa gggcccatct gtgttccctc tggcacccag cagcaagtct accagtggtg   1380

gaacagctgc cctgggctgt ctggtcaagg actactttcc tgagccagtg acagtgtcct   1440

ggaactctgg ggctctgaca tctggggtgc acacattccc tgctgtgctc cagtcctctg   1500

gcctgtacag cctcagctct gtggtcacag tgcctagctc tagcctgggc acccagacct   1560

acatctgcaa tgtgaaccac aagcctagca acaccaaggt ggacaagaag gctgagccca   1620

agagctgtga caagacccac acctgtcctc catgtcctgc tccagagctg cttggaggac   1680
```

-continued

```
cttctgtgtt tctgttccct ccaaagccaa aggacaccct gatgatcagc agaacccctg   1740
aagtgacatg tgtggtggtt gatgtgtccc atgaggaccc agaagtgaag ttcaattggt   1800
atgtggatgg tgttgaggtg cacaatgcca agaccaagcc tagagaggaa cagtacaaca   1860
gcacctacag agtggtgtct gtgctgacag tgctgcatca ggactggctg aatggcaaag   1920
agtacaagtg caaggtgtcc aacaaggccc tgcctgctcc tattgaaaag accatctcca   1980
aggccaaggg ccagcctagg gaaccccagg tttacacact gccacctagc agggatgagc   2040
tgaccaagaa ccaggtgtcc ctgacctgcc tggttaaggg cttctacccc tctgacattg   2100
ctgtggaatg ggagagcaat ggccagccag agaacaacta caagacaacc cctcctgtgc   2160
tggactctga tggctcattc ttcctgtact ccaagctcac agtggacaag tccagatggc   2220
agcaaggcaa tgtgttcagc tgctctgtga tgcatgaggc cctgcacaac cactacacac   2280
agaagtccct gagcctgtct cctggcaaga gaaagagaag gagtggaagt ggagctacta   2340
acttcagcct gctgaagcag gctggagatg tggaggagaa ccctggacct atggacttcc   2400
aggtgcagat catcagcttt ctgctgatct ctgcctctgt gatcatgagc agaggccagc   2460
ctggactgac acagcctcca tctgtgtcca agggcctgag acagacagcc acactgacct   2520
gcacaggcaa cagcaacaat gtgggcaatc aaggggctgc ctggctccag cagcatcagg   2580
gacatcctcc aaagctgctg agctacagaa acaatgacag accctctggc atctctgaga   2640
gattctctgc ctctaggagt ggcaacacag ccagcctgac catcactgga ctccagccag   2700
aggatgaggc tgactactac tgctccacct gggacagcag cctgtctgct gtggtttttg   2760
gtggtggcac caagctgaca gtgctgagaa cagtggctgc cccttctgtg ttcatcttcc   2820
caccatctga tgagcagctg aagtctggca cagcctctgt tgtgtgcctg ctgaacaact   2880
tctaccctag agaagccaag gtgcagtgga aggtggacaa tgccctccag tctggcaact   2940
cccaagagtc tgtgacagag caggacagca aggactccac ctacagcctg agcagcaccc   3000
tgacactgag caaggctgac tatgagaagc acaaagtcta tgcctgtgaa gtgacccacc   3060
agggcctgtc tagccctgtg accaagagct tcaacagggg agagagctga agatctactt   3120
ctggctaata aaagatcaga gctctagtga tctgtgtgtt ggtttttgt gtctgcattc    3180
tagctctagt gatcagcagt tcaacctgtt gatagtatgt actaagctct catgtttaat   3240
gtactaagct ctcatgttta atgaactaaa ccctcatggc taatgtacta agctctcatg   3300
gctaatgtac taagctctca tgtttcatgt actaagctct catgtttgaa caataaaatt   3360
aatataaatc agcaacttaa atagcctcta aggttttaag ttttataaga aaaaaaagaa   3420
tatataaggc ttttaaaggt tttaaggttt cctaggttat cctcatatga gctcttagaa   3480
aaactcatcc agcatcaaat gaaactgcaa tttattcata tcaggattat caataccata   3540
tttttgaaaa agtcttttct gtaatgaagg agaaaactca cccaggcagt tccataggat   3600
ggcaagatcc tggtatctgt ctgcaattcc aactcttcca acatcaatac aacctattaa   3660
tttcccctca tcaaaaataa ggttatcaag tgagaaatca ccatgagtga ccactgaatc   3720
tggtgagaat ggcaaaagat tatgcatttc tttccagact tgttcaacag gccagccatt   3780
tctctcatca tcaaaatcac tggcatcaac caaaccatta ttcattcttg attgggcctg   3840
agccagtcta aatactctat cagagttaaa aggacaatta caaacaggaa tggaatgcaa   3900
tcttctcagg aacactgcca gggcatcaac aatattttca cctgaatcag gatattcttc   3960
caatacctgg aatgctgttt tccctgggat ggcagtggtg agtaaccatg catcatcagg   4020
```

agttctgata aaatgcttga tggttggaag aggcataaat tcagtcagcc agtttagtct 4080
gaccatctca tctgtaacat cattggcaac agaacctttg ccatgtttca gaaacaactc 4140
tggggcatct ggcttcccat acaatctata gattgtggca cctgattgcc caacattatc 4200
tctagcccat ttatacccat ataaatcagc atccatgttg gaatttaatc ttggcctgga 4260
gcaagaggtt tctctttgaa tatggctcat acatgtgcac ctcctatagt gagttgtatt 4320
atactatgca gatatactat gccaatgttt aattgtcag 4359

<210> SEQ ID NO 33
<211> LENGTH: 4345
<212> TYPE: DNA
<213> ORGANISM: Artificial sequence
<220> FEATURE:
<223> OTHER INFORMATION: Synthetic

<400> SEQUENCE: 33
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg ggactgggac tccagtgggt gttctttgtg gccctgctga 900
aaggggtgca ctgtgaagtc agactgctgg aaagtggtgg tggcctgcag gttcagctgg 960
tgcagtctgg ggctgaagtg aagaaacctg gcagctctgt gaaggtgtcc tgcaaggcta 1020
gtggtggccc cttcagcatg acagccttca cctggctgag acaggctcct ggacagggcc 1080
ttgaatggat gggaggcatc agccccatct tcagaacccc taagtatgcc cagaaattcc 1140
agggcagagt gaccatcaca gctgatgaga gcaccaacac agccaacatg gaactgacca 1200
gcctgaagtc tgaggacact gctgtgtact actgtgccag aacactgagc agctaccagc 1260
ctaacaatga tgcctttgcc atctggggcc agggcaccat ggttacagtc agctctgcca 1320
gcacaaaggg cccatctgtg ttccctctgg cacccagcag caagtctacc agtggtggaa 1380
cagctgccct gggctgtctg gtcaaggact actttcctga gccagtgaca gtgtcctgga 1440
actctggggc tctgacatct ggggtgcaca cattccctgc tgtgctccag tcctctggcc 1500
tgtacagcct cagctctgtg gtcacagtgc ctagctctag cctgggcacc cagacctaca 1560
tctgcaatgt gaaccacaag cctagcaaca ccaaggtgga caagaaggct gagcccaaga 1620
gctgtgacaa gacccacacc tgtcctccat gtcctgctcc agagctgctt ggaggacctt 1680
ctgtgtttct gttccctcca aagccaaagg acaccctgat gatcagcaga acccctgaag 1740

```
tgacatgtgt ggtggttgat gtgtcccatg aggacccaga agtgaagttc aattggtatg   1800
tggatggtgt tgaggtgcac aatgccaaga ccaagcctag agaggaacag tacaacagca   1860
cctacagagt ggtgtctgtg ctgacagtgc tgcatcagga ctggctgaat ggcaaagagt   1920
acaagtgcaa ggtgtccaac aaggccctgc ctgctcctat tgaaaagacc atctccaagg   1980
ccaagggcca gcctagggaa ccccaggttt acacactgcc acctagcagg gatgagctga   2040
ccaagaacca ggtgtccctg acctgcctgg ttaagggctt ctacccctct gacattgctg   2100
tggaatggga gagcaatggc cagccagaga acaactacaa gacaacccct cctgtgctgg   2160
actctgatgg ctcattcttc ctgtactcca agctcacagt ggacaagtcc agatggcagc   2220
aaggcaatgt gttcagctgc tctgtgatgc atgaggccct gcacaaccac tacacacaga   2280
agtccctgag cctgtctcct ggcaagagaa agagaaggag tggaagtgga gctactaact   2340
tcagcctgct gaagcaggct ggagatgtgg aggagaaccc tggacctatg gacttccagg   2400
tgcagatcat cagctttctg ctgatctctg cctctgtgat catgagcaga ggccgagatt   2460
gtgctgacac agagccctgc cacactgtct cttagccctg gggagagagc cacactgagc   2520
tgtagagcca gccagtctgt gtcctcttac ctggcctggt atcagcagaa gcctggacag   2580
gctcccagac tgctgatcta tgatgccagc aacagagcca caggcatccc tgccagattc   2640
agtggctctg gcagtggcac agacttcacc ctgaccatca gcagactgga accagaggac   2700
tttgctgtgt acttctgcca gcagtatggc agcagccctc agtttggcca gggcacaaga   2760
ctggaaatca agagaacagt ggctgcccct tctgtgttca tcttcccacc atctgatgag   2820
cagctgaagt ctggcacagc ctctgttgtg tgcctgctga acaacttcta ccctagagaa   2880
gccaaggtgc agtggaaggt ggacaatgcc ctccagtctg gcaactccca agagtctgtg   2940
acagagcagg acagcaagga ctccacctac agcctgagca gcaccctgac actgagcaag   3000
gctgactatg agaagcacaa agtctatgcc tgtgaagtga cccaccaggg cctgtctagc   3060
cctgtgacca agagcttcaa caggggagag agctgaagat ctacttctgg ctaataaaag   3120
atcagagctc tagtgatctg tgtgttggtt ttttgtgtct gcattctagc tctagtgatc   3180
agcagttcaa cctgttgata gtatgtacta agctctcatg tttaatgtac taagctctca   3240
tgtttaatga actaaaccct catggctaat gtactaagct ctcatggcta atgtactaag   3300
ctctcatgtt tcatgtacta agctctcatg tttgaacaat aaaattaata taaatcagca   3360
acttaaatag cctctaaggt tttaagtttt ataagaaaaa aaagaatata taaggctttt   3420
aaaggtttta aggtttccta ggttatcctc atatgagctc ttagaaaaac tcatccagca   3480
tcaaatgaaa ctgcaattta ttcatatcag gattatcaat accatatttt tgaaaaagtc   3540
ttttctgtaa tgaaggagaa aactcaccca ggcagttcca taggatggca agatcctggt   3600
atctgtctgc aattccaact cttccaacat caatacaacc tattaatttc ccctcatcaa   3660
aaataaggtt atcaagtgag aaatcaccat gagtgaccac tgaatctggt gagaatggca   3720
aaagattatg catttctttc cagacttgtt caacaggcca gccatttctc tcatcatcaa   3780
aatcactggc atcaaccaaa ccattattca ttcttgattg ggcctgagcc agtctaaata   3840
ctctatcaga gttaaaagga caattacaaa caggaatgga atgcaatctt ctcaggaaca   3900
ctgccagggc atcaacaata ttttcacctg aatcaggata ttcttccaat acctggaatg   3960
ctgttttccc tgggatggca gtggtgagta accatgcatc atcaggagtt ctgataaaat   4020
gcttgatggt tggaagaggc ataaattcag tcagccagtt tagtctgacc atctcatctg   4080
```

```
taacatcatt ggcaacagaa cctttgccat gtttcagaaa caactctggg gcatctggct   4140

tcccatacaa tctatagatt gtggcacctg attgcccaac attatctcta gcccatttat   4200

acccatataa atcagcatcc atgttggaat ttaatcttgg cctggagcaa gaggtttctc   4260

tttgaatatg gctcatacat gtgcacctcc tatagtgagt tgtattatac tatgcagata   4320

tactatgcca atgtttaatt gtcag                                         4345


<210> SEQ ID NO 34
<211> LENGTH: 5070
<212> TYPE: DNA
<213> ORGANISM: Artificial sequence
<220> FEATURE:
<223> OTHER INFORMATION: Synthetic

<400> SEQUENCE: 34

cactatgtgg acatgaattc aattggctag caggagtcaa tgggaaaaac ccattggagc     60

caagtacact gactcaatag ggactttcca ttgggttttg cccagtacat aaggtcaata    120

gggggtgagt caacaggaaa gtcccattgg agccaagtac attgagtcaa tagggacttt    180

ccaatgggtt ttgcccagta cataaggtca atgggaggta agccaatggg tttttcccat    240

tactgacatg tatactgagt cattagggac tttccaatgg gttttgccca gtacataagg    300

tcaatagggg tgaatcaaca ggaaagtccc attggagcca agtacactga gtcaataggg    360

actttccatt gggttttgcc cagtacaaaa ggtcaatagg gggtgagtca atgggttttt    420

cccattattg gcacatacat aaggtcaata ggggtgacta gtggagaaga gcatgcttga    480

gggctgagtg cccctcagtg ggcagagagc acatggccca cagtccctga gaagttgggg    540

ggaggggtgg gcaattgaac tggtgcctag agaaggtggg gcttgggtaa actgggaaag    600

tgatgtggtg tactggctcc accttttttcc ccagggtggg ggagaaccat atataagtgc   660

agtagtctct gtgaacattc aagcttctgc cttctccctc ctgtgagttt ggtaagtcac    720

tgactgtcta tgcctgggaa agggtgggca ggagatgggg cagtgcagga aaagtggcac    780

tatgaaccct gcagccctag acaattgtac taaccttctt ctctttcctc tcctgacagg    840

ttggtaacca agccaccatg ggactgggac tccagtgggt gttctttgtg gccctgctga    900

aaggggtgca ctgtgaagtc agactgctgg aaagtggtgg tggcctgcag gttcagctgg    960

tgcagtctgg ggctgaagtg aagaaacctg gcagctctgt gaaggtgtcc tgcaaggcta   1020

gtggtggcac cttctctgcc tatgccttca cctgggtcag acaggctcct ggacagggcc   1080

ttgaatggat gggaggcatc acaggcatgt ttggcacagc caactatgcc cagaaattcc   1140

agggcagagt gaccatcaca gctgatgagc tgaccagcac agcctacatg gaactgagca   1200

gcctgacctc tgaggacaca gccctgtact actgtgccag aggcctgtac tattatgagt   1260

ctagcctgga ctactggggc cagggcacac tggttacagt gtctagtgcc agcacaaagg   1320

gcccatctgt gttccctctg gcacccagca gcaagtctac cagtggtgga acagctgccc   1380

tgggctgtct ggtcaaggac tactttcctg agccagtgac agtgtcctgg aactctgggg   1440

ctctgacatc tggggtgcac acattccctg ctgtgctcca gtcctctggc ctgtacagcc   1500

tcagctctgt ggtcacagtg cctagctcta gcctgggcac ccagacctac atctgcaatg   1560

tgaaccacaa gcctagcaac accaaggtgg acaagaaggc tgagcccaag agctgtgaca   1620

agacccacac ctgtcctcca tgtcctgctc cagagctgct tggaggacct tctgtgtttc   1680

tgttccctcc aaagccaaag gacaccctga tgatcagcag aacccctgaa gtgacatgtg   1740

tggtggttga tgtgtcccat gaggacccag aagtgaagtt caattggtat gtggatggtg   1800
```

```
ttgaggtgca caatgccaag accaagccta gagaggaaca gtacaacagc acctacagag   1860
tggtgtctgt gctgacagtg ctgcatcagg actggctgaa tggcaaagag tacaagtgca   1920
aggtgtccaa caaggccctg cctgctccta ttgaaaagac catctccaag gccaagggcc   1980
agcctaggga accccaggtt tacacactgc cacctagcag ggatgagctg accaagaacc   2040
aggtgtccct gacctgcctg gttaagggct tctacccctc tgacattgct gtggaatggg   2100
agagcaatgg ccagccagag aacaactaca agacaacccc tcctgtgctg gactctgatg   2160
gctcattctt cctgtactcc aagctcacag tggacaagtc cagatggcag caaggcaatg   2220
tgttcagctg ctctgtgatg catgaggccc tgcacaacca ctacacacag aagtccctga   2280
gcctgtctcc tggcaagtga agatctactt ctggctaata aaagatcaga gctctagtga   2340
tctgtgtgtt ggtttttgt gtctgcattc tagcatgtta cataacttat ggtaaatggc   2400
ctgcctggct gactgcccaa tgacccctgc ccaatgatgt caataatgat gtatgttccc   2460
atgtaatgcc aatagggact ttccattgat gtcaatgggt ggagtattta tggtaactgc   2520
ccacttggca gtacatcaag tgtatcatat gccaagtatg ccccctattg atgtcaatga   2580
tggtaaatgg cctgcctggc attatgccca gtacatgacc ttatgggact ttcctacttg   2640
gcagtacatc tatgtattag tcattgctat taccatggat tagtggagaa gagcatgctt   2700
gagggctgag tgcccctcag tgggcagaga gcacatggcc cacagtccct gagaagttgg   2760
ggggaggggt gggcaattga actggtgcct agagaaggtg gggcttgggt aaactgggaa   2820
agtgatgtgg tgtactggct ccaccttttt ccccagggtg ggggagaacc atatataagt   2880
gcagtagtct ctgtgaacat tcaagcttct gccttctccc tcctgtgagt ttggatgcac   2940
ctactagata tcttggtaag tcactgactg tctatgcctg ggaaagggtg ggcaggaggt   3000
ggggcagtgc aggaaaagtg gcactgtgaa ccctgcagcc ctagacaatt gtactaacct   3060
tcttctcttt cctctcctga caggttggta accaagccac catggacttc caggtgcaga   3120
tcatcagctt tctgctgatc tctgcctctg tgatcatgag cagaggccag tctgtgctga   3180
cccagcctcc atctgcatct ggaagccctg gccagtctgt gaccatcagc tgtacaggca   3240
ccagctctga tgttggaggc tacaactctg tgtcctggta tcagcagcac cctggcaagg   3300
cccctaagct gatgatctat gaagtgacca agaggccctc tggggtgcca gacagattct   3360
ctgccagcaa gtctggcaac acagccagcc tgacagtgtc tggcctgcaa gctgaggatg   3420
aggctgacta cttctgctgc tcctatgctg gccactctgc ctatgtgttt ggcactggca   3480
ccaaagtgac agtgctgaga acagtggctg ccccttctgt gttcatcttc ccaccatctg   3540
atgagcagct gaagtctggc acagcctctg ttgtgtgcct gctgaacaac ttctacccta   3600
gagaagccaa ggtgcagtgg aaggtggaca atgccctcca gtctggcaac tcccaagagt   3660
ctgtgacaga gcaggacagc aaggactcca cctacagcct gagcagcacc ctgacactga   3720
gcaaggctga ctatgagaag cacaaagtct atgcctgtga agtgacccac cagggcctgt   3780
ctagccctgt gaccaagagc ttcaacaggg gagagagctg aagatctact tctggctaat   3840
aaaagatcag agctctagtg atctgtgtgt tggtttttg tgtctgcatt ctagctctag   3900
tgatcagcag ttcaacctgt tgatagtatg tactaagctc tcatgtttaa tgtactaagc   3960
tctcatgttt aatgaactaa accctcatgg ctaatgtact aagctctcat ggctaatgta   4020
ctaagctctc atgtttcatg tactaagctc tcatgtttga acaataaaat taatataaat   4080
cagcaactta aatagcctct aaggttttaa gttttataag aaaaaaaaga atatataagg   4140
```

-continued

```
cttttaaagg ttttaaggtt tcctaggtta tcctcatatg agctcttaga aaaactcatc   4200

cagcatcaaa tgaaactgca atttattcat atcaggatta tcaataccat atttttgaaa   4260

aagtcttttc tgtaatgaag gagaaaactc acccaggcag ttccatagga tggcaagatc   4320

ctggtatctg tctgcaattc caactcttcc aacatcaata caacctatta atttcccctc   4380

atcaaaaata aggttatcaa gtgagaaatc accatgagtg accactgaat ctggtgagaa   4440

tggcaaaaga ttatgcattt ctttccagac ttgttcaaca ggccagccat ttctctcatc   4500

atcaaaatca ctggcatcaa ccaaaccatt attcattctt gattgggcct gagccagtct   4560

aaatactcta tcagagttaa aaggacaatt acaaacagga atggaatgca atcttctcag   4620

gaacactgcc agggcatcaa caatattttc acctgaatca ggatattctt ccaatacctg   4680

gaatgctgtt ttccctggga tggcagtggt gagtaaccat gcatcatcag gagttctgat   4740

aaaatgcttg atggttggaa gaggcataaa ttcagtcagc cagtttagtc tgaccatctc   4800

atctgtaaca tcattggcaa cagaaccttt gccatgtttc agaaacaact ctggggcatc   4860

tggcttccca tacaatctat agattgtggc acctgattgc ccaacattat ctctagccca   4920

tttataccca tataaatcag catccatgtt ggaatttaat cttggcctgg agcaagaggt   4980

ttctctttga atatggctca tacatgtgca cctcctatag tgagttgtat tatactatgc   5040

agatatacta tgccaatgtt taattgtcag                                    5070
```

<210> SEQ ID NO 35
<211> LENGTH: 5082
<212> TYPE: DNA
<213> ORGANISM: Artificial sequence
<220> FEATURE:
<223> OTHER INFORMATION: Synthetic

<400> SEQUENCE: 35

```
cactatgtgg acatgaattc aattggctag caggagtcaa tgggaaaaac ccattggagc     60

caagtacact gactcaatag ggactttcca ttgggttttg cccagtacat aaggtcaata    120

gggggtgagt caacaggaaa gtcccattgg agccaagtac attgagtcaa tagggacttt    180

ccaatgggtt ttgcccagta cataaggtca atgggaggta agccaatggg tttttcccat    240

tactgacatg tatactgagt cattagggac tttccaatgg gttttgccca gtacataagg    300

tcaatagggg tgaatcaaca ggaaagtccc attggagcca agtacactga gtcaataggg    360

actttccatt gggttttgcc cagtacaaaa ggtcaatagg gggtgagtca atgggttttt    420

cccattattg gcacatacat aaggtcaata ggggtgacta gtggagaaga gcatgcttga    480

gggctgagtg cccctcagtg ggcagagagc acatggccca cagtccctga gaagttgggg    540

ggaggggtgg gcaattgaac tggtgcctag agaaggtggg gcttgggtaa actgggaaag    600

tgatgtggtg tactggctcc accttttttcc ccagggtggg ggagaaccat atataagtgc    660

agtagtctct gtgaacattc aagcttctgc cttctccctc ctgtgagttt ggtaagtcac    720

tgactgtcta tgcctgggaa agggtgggca ggagatgggg cagtgcagga aaagtggcac    780

tatgaaccct gcagccctag acaattgtac taaccttctt ctctttcctc tcctgacagg    840

ttggtaacca agccaccatg ggactgggac tccagtgggt gttctttgtg gccctgctga    900

aaggggtgca ctgtgaagtc agactgctgg aaagtggtgg tggcctgcag gttcagctgg    960

tgcagtctgg ggctgaagtg aagaaacctg gcagctctgt gaaggtgtcc tgcacctcct   1020

ctgaagtgac cttcagcagc tttgccatca gctgggtcag acaggctcct ggacagggcc   1080

ttgaatggct tggaggcatc agccccatgt ttggcacccc taactatgcc cagaaattcc   1140
```

-continued

```
agggcagagt gaccatcaca gctgaccaga gcaccagaac agcctacatg gacctgagaa   1200
gtcttaggag tgaagataca gctgtgtact actgtgctag aagccccagc tacatctgct   1260
ctggtggcac ctgtgtgttt gaccactggg gccagggaac cctggtcaca gtttcttctg   1320
ccagcacaaa gggcccatct gtgttccctc tggcacccag cagcaagtct accagtggtg   1380
gaacagctgc cctgggctgt ctggtcaagg actactttcc tgagccagtg acagtgtcct   1440
ggaactctgg ggctctgaca tctggggtgc acacattccc tgctgtgctc cagtcctctg   1500
gcctgtacag cctcagctct gtggtcacag tgcctagctc tagcctgggc acccagacct   1560
acatctgcaa tgtgaaccac aagcctagca acaccaaggt ggacaagaag gctgagccca   1620
agagctgtga caagacccac acctgtcctc catgtcctgc tccagagctg cttggaggac   1680
cttctgtgtt tctgttccct ccaaagccaa aggacaccct gatgatcagc agaacccctg   1740
aagtgacatg tgtggtggtt gatgtgtccc atgaggaccc agaagtgaag ttcaattggt   1800
atgtggatgg tgttgaggtg cacaatgcca agaccaagcc tagagaggaa cagtacaaca   1860
gcacctacag agtggtgtct gtgctgacag tgctgcatca ggactggctg aatggcaaag   1920
agtacaagtg caaggtgtcc aacaaggccc tgcctgctcc tattgaaaag accatctcca   1980
aggccaaggg ccagcctagg gaaccccagg tttacacact gccacctagc agggatgagc   2040
tgaccaagaa ccaggtgtcc ctgacctgcc tggttaaggg cttctacccc tctgacattg   2100
ctgtggaatg ggagagcaat ggccagccag agaacaacta caagacaacc cctcctgtgc   2160
tggactctga tggctcattc ttcctgtact ccaagctcac agtggacaag tccagatggc   2220
agcaaggcaa tgtgttcagc tgctctgtga tgcatgaggc cctgcacaac cactacacac   2280
agaagtccct gagcctgtct cctggcaagt gaagatctac ttctggctaa taaaagatca   2340
gagctctagt gatctgtgtg ttggtttttt gtgtctgcat tctagcatgt tacataactt   2400
atggtaaatg gcctgcctgg ctgactgccc aatgacccct gcccaatgat gtcaataatg   2460
atgtatgttc ccatgtaatg ccaataggga ctttccattg atgtcaatgg gtggagtatt   2520
tatggtaact gcccacttgg cagtacatca agtgtatcat atgccaagta tgccccctat   2580
tgatgtcaat gatggtaaat ggcctgcctg gcattatgcc cagtacatga ccttatggga   2640
ctttcctact tggcagtaca tctatgtatt agtcattgct attaccatgg attagtggag   2700
aagagcatgc ttgagggctg agtgcccctc agtgggcaga gagcacatgg cccacagtcc   2760
ctgagaagtt ggggggaggg gtgggcaatt gaactggtgc ctagagaagg tggggcttgg   2820
gtaaactggg aaagtgatgt ggtgtactgg ctccaccttt ttccccaggg tgggggagaa   2880
ccatatataa gtgcagtagt ctctgtgaac attcaagctt ctgccttctc cctcctgtga   2940
gtttggatgc acctactaga tatcttggta agtcactgac tgtctatgcc tgggaaaggg   3000
tgggcaggag gtggggcagt gcaggaaaag tggcactgtg aaccctgcag ccctagacaa   3060
ttgtactaac cttcttctct ttcctctcct gacaggttgg taaccaagcc accatggact   3120
tccaggtgca gatcatcagc tttctgctga tctctgcctc tgtgatcatg agcagaggcc   3180
agcctggact gacacagcct ccatctgtgt ccaagggcct gagacagaca gccacactga   3240
cctgcacagg caacagcaac aatgtgggca atcaaggggc tgcctggctc cagcagcatc   3300
agggacatcc tccaaagctg ctgagctaca gaaacaatga cagaccctct ggcatctctg   3360
agagattctc tgcctctagg agtggcaaca cagccagcct gaccatcact ggactccagc   3420
cagaggatga ggctgactac tactgctcca cctgggacag cagcctgtct gctgtggttt   3480
```

ttggtggtgg caccaagctg acagtgctga gaacagtggc tgccccttct gtgttcatct 3540
tcccaccatc tgatgagcag ctgaagtctg gcacagcctc tgttgtgtgc ctgctgaaca 3600
acttctaccc tagagaagcc aaggtgcagt ggaaggtgga caatgccctc cagtctggca 3660
actcccaaga gtctgtgaca gagcaggaca gcaaggactc cacctacagc ctgagcagca 3720
ccctgacact gagcaaggct gactatgaga agcacaaagt ctatgcctgt gaagtgaccc 3780
accagggcct gtctagccct gtgaccaaga gcttcaacag gggagagagc tgaagatcta 3840
cttctggcta ataaaagatc agagctctag tgatctgtgt gttggttttt tgtgtctgca 3900
ttctagctct agtgatcagc agttcaacct gttgatagta tgtactaagc tctcatgttt 3960
aatgtactaa gctctcatgt ttaatgaact aaaccctcat ggctaatgta ctaagctctc 4020
atggctaatg tactaagctc tcatgtttca tgtactaagc tctcatgttt gaacaataaa 4080
attaatataa atcagcaact taaatagcct ctaaggtttt aagttttata agaaaaaaaa 4140
gaatatataa ggcttttaaa ggttttaagg tttcctaggt tatcctcata tgagctctta 4200
gaaaaactca tccagcatca aatgaaactg caatttattc atatcaggat tatcaatacc 4260
atatttttga aaaagtcttt tctgtaatga aggagaaaac tcacccaggc agttccatag 4320
gatggcaaga tcctggtatc tgtctgcaat tccaactctt ccaacatcaa tacaacctat 4380
taatttcccc tcatcaaaaa taaggttatc aagtgagaaa tcaccatgag tgaccactga 4440
atctggtgag aatggcaaaa gattatgcat ttctttccag acttgttcaa caggccagcc 4500
atttctctca tcatcaaaat cactggcatc aaccaaacca ttattcattc ttgattgggc 4560
ctgagccagt ctaaatactc tatcagagtt aaaaggacaa ttacaaacag gaatggaatg 4620
caatcttctc aggaacactg ccagggcatc aacaatattt tcacctgaat caggatattc 4680
ttccaatacc tggaatgctg ttttccctgg gatggcagtg gtgagtaacc atgcatcatc 4740
aggagttctg ataaaatgct tgatggttgg aagaggcata aattcagtca gccagtttag 4800
tctgaccatc tcatctgtaa catcattggc aacagaacct ttgccatgtt tcagaaacaa 4860
ctctggggca tctggcttcc catacaatct atagattgtg gcacctgatt gcccaacatt 4920
atctctagcc catttatacc catataaatc agcatccatg ttggaattta atcttggcct 4980
ggagcaagag gtttctcttt gaatatggct catacatgtg cacctcctat agtgagttgt 5040
attatactat gcagatatac tatgccaatg tttaattgtc ag 5082

<210> SEQ ID NO 36
<211> LENGTH: 5068
<212> TYPE: DNA
<213> ORGANISM: Artificial sequence
<220> FEATURE:
<223> OTHER INFORMATION: Synthetic

<400> SEQUENCE: 36
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480

```
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc accttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg ggactgggac tccagtgggt gttctttgtg gccctgctga    900
aaggggtgca ctgtgaagtc agactgctgg aaagtggtgg tggcctgcag gttcagctgg    960
tgcagtctgg ggctgaagtg aagaaacctg gcagctctgt gaaggtgtcc tgcaaggcta   1020
gtggtggccc cttcagcatg acagccttca cctggctgag acaggctcct ggacagggcc   1080
ttgaatggat gggaggcatc agccccatct tcagaacccc taagtatgcc cagaaattcc   1140
agggcagagt gaccatcaca gctgatgaga gcaccaacac agccaacatg gaactgacca   1200
gcctgaagtc tgaggacact gctgtgtact actgtgccag aacactgagc agctaccagc   1260
ctaacaatga tgcctttgcc atctggggcc agggcaccat ggttacagtc agctctgcca   1320
gcacaaaggg cccatctgtg ttccctctgg cacccagcag caagtctacc agtggtggaa   1380
cagctgccct gggctgtctg gtcaaggact actttcctga gccagtgaca gtgtcctgga   1440
actctggggc tctgacatct ggggtgcaca cattccctgc tgtgctccag tcctctggcc   1500
tgtacagcct cagctctgtg gtcacagtgc ctagctctag cctgggcacc cagacctaca   1560
tctgcaatgt gaaccacaag cctagcaaca ccaaggtgga caagaaggct gagcccaaga   1620
gctgtgacaa gacccacacc tgtcctccat gtcctgctcc agagctgctt ggaggacctt   1680
ctgtgtttct gttccctcca aagccaaagg acaccctgat gatcagcaga acccctgaag   1740
tgacatgtgt ggtggttgat gtgtcccatg aggacccaga agtgaagttc aattggtatg   1800
tggatggtgt tgaggtgcac aatgccaaga ccaagcctag agaggaacag tacaacagca   1860
cctacagagt ggtgtctgtg ctgacagtgc tgcatcagga ctggctgaat ggcaaagagt   1920
acaagtgcaa ggtgtccaac aaggccctgc ctgctcctat tgaaaagacc atctccaagg   1980
ccaagggcca gcctagggaa ccccaggttt acacactgcc acctagcagg gatgagctga   2040
ccaagaacca ggtgtccctg acctgcctgg ttaagggctt ctacccctct gacattgctg   2100
tggaatggga gagcaatggc cagccagaga acaactacaa gacaacccct cctgtgctgg   2160
actctgatgg ctcattcttc ctgtactcca agctcacagt ggacaagtcc agatggcagc   2220
aaggcaatgt gttcagctgc tctgtgatgc atgaggccct gcacaaccac tacacacaga   2280
agtccctgag cctgtctcct ggcaagtgaa gatctacttc tggctaataa aagatcagag   2340
ctctagtgat ctgtgtgttg gttttttgtg tctgcattct agcatgttac ataacttatg   2400
gtaaatggcc tgcctggctg actgcccaat gacccctgcc caatgatgtc aataatgatg   2460
tatgttccca tgtaatgcca atagggactt tccattgatg tcaatgggtg gagtatttat   2520
ggtaactgcc cacttggcag tacatcaagt gtatcatatg ccaagtatgc cccctattga   2580
tgtcaatgat ggtaaatggc ctgcctggca ttatgcccag tacatgacct tatgggactt   2640
tcctacttgg cagtacatct atgtattagt cattgctatt accatggatt agtggagaag   2700
agcatgcttg agggctgagt gcccctcagt gggcagagag cacatggccc acagtccctg   2760
agaagttggg gggaggggtg ggcaattgaa ctggtgccta gagaaggtgg ggcttgggta   2820
```

aactgggaaa gtgatgtggt gtactggctc caccttttc cccagggtgg gggagaacca 2880
tatataagtg cagtagtctc tgtgaacatt caagcttctg ccttctccct cctgtgagtt 2940
tggatgcacc tactagatat cttggtaagt cactgactgt ctatgcctgg gaaagggtgg 3000
gcaggaggtg gggcagtgca ggaaaagtgg cactgtgaac cctgcagccc tagacaattg 3060
tactaacctt cttctctttc ctctcctgac aggttggtaa ccaagccacc atggacttcc 3120
aggtgcagat catcagcttt ctgctgatct ctgcctctgt gatcatgagc agaggccgag 3180
attgtgctga cacagagccc tgccacactg tctcttagcc ctggggagag agccacactg 3240
agctgtagag ccagccagtc tgtgtcctct tacctggcct ggtatcagca gaagcctgga 3300
caggctccca gactgctgat ctatgatgcc agcaacagag ccacaggcat ccctgccaga 3360
ttcagtggct ctggcagtgg cacagacttc accctgacca tcagcagact ggaaccagag 3420
gactttgctg tgtacttctg ccagcagtat ggcagcagcc ctcagtttgg ccagggcaca 3480
agactggaaa tcaagagaac agtggctgcc ccttctgtgt tcatcttccc accatctgat 3540
gagcagctga agtctggcac agcctctgtt gtgtgcctgc tgaacaactt ctaccctaga 3600
gaagccaagg tgcagtggaa ggtggacaat gccctccagt ctggcaactc ccaagagtct 3660
gtgacagagc aggacagcaa ggactccacc tacagcctga gcagcaccct gacactgagc 3720
aaggctgact atgagaagca caaagtctat gcctgtgaag tgacccacca gggcctgtct 3780
agccctgtga ccaagagctt caacagggga gagagctgaa gatctacttc tggctaataa 3840
aagatcagag ctctagtgat ctgtgtgttg gttttttgtg tctgcattct agctctagtg 3900
atcagcagtt caacctgttg atagtatgta ctaagctctc atgtttaatg tactaagctc 3960
tcatgtttaa tgaactaaac cctcatggct aatgtactaa gctctcatgg ctaatgtact 4020
aagctctcat gtttcatgta ctaagctctc atgtttgaac aataaaatta atataaatca 4080
gcaacttaaa tagcctctaa ggttttaagt tttataagaa aaaaaagaat atataaggct 4140
tttaaaggtt ttaaggtttc ctaggttatc ctcatatgag ctcttagaaa aactcatcca 4200
gcatcaaatg aaactgcaat ttattcatat caggattatc aataccatat ttttgaaaaa 4260
gtcttttctg taatgaagga gaaaactcac ccaggcagtt ccataggatg gcaagatcct 4320
ggtatctgtc tgcaattcca actcttccaa catcaataca acctattaat ttcccctcat 4380
caaaaataag gttatcaagt gagaaatcac catgagtgac cactgaatct ggtgagaatg 4440
gcaaaagatt atgcatttct ttccagactt gttcaacagg ccagccattt ctctcatcat 4500
caaaatcact ggcatcaacc aaaccattat tcattcttga ttgggcctga gccagtctaa 4560
atactctatc agagttaaaa ggacaattac aaacaggaat ggaatgcaat cttctcagga 4620
acactgccag ggcatcaaca atattttcac ctgaatcagg atattcttcc aatacctgga 4680
atgctgtttt ccctgggatg gcagtggtga gtaaccatgc atcatcagga gttctgataa 4740
aatgcttgat ggttggaaga ggcataaatt cagtcagcca gtttagtctg accatctcat 4800
ctgtaacatc attggcaaca gaacctttgc catgtttcag aaacaactct ggggcatctg 4860
gcttcccata caatctatag attgtggcac ctgattgccc aacattatct ctagcccatt 4920
tatacccata taaatcagca tccatgttgg aatttaatct tggcctggag caagaggttt 4980
ctctttgaat atggctcata catgtgcacc tcctatagtg agttgtatta tactatgcag 5040
atatactatg ccaatgttta attgtcag 5068

<210> SEQ ID NO 37
<211> LENGTH: 3864

<212> TYPE: DNA
<213> ORGANISM: Artificial sequence
<220> FEATURE:
<223> OTHER INFORMATION: Synthetic

<400> SEQUENCE: 37
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc acctttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg aaggccaacc tgctggtgct gctgtgtgct ctggctgctg 900
ctgatgctga caccatctgc attggctacc atgccaacaa cagcacagac acagtggaca 960
ctgtgctgga aaagaatgtg acagtgaccc actctgtcaa cctgcttgag gacagccaca 1020
atggcaagct gtgcagactg aagggcattg cccctctgca actgggcaag tgcaacattg 1080
ctggatggct gctgggcaac cctgagtgtg atcctctgct gcctgtcaga tcctggtcct 1140
acattgtgga aacccctagc tctgagaatg gcatctgcta ccctggggac ttcattgact 1200
atgaggaact gaaagaacag ctgtcctctg tcagcagctt tgagagattt gaaatcttcc 1260
ccaaagagag cagctggccc aaccacaaca ccaacaaagg ggtcacagct gcctgtagcc 1320
atgagggcaa gagcagcttc tacagaaacc tgctgtggct gactgagaaa gagggcagct 1380
accccaagct gaagaactcc tatgtgaaca agaagggcaa agaggtcctg gttctctggg 1440
gcatccacca tcctagcaac agcaaagagc agcagaacct gtaccagaat gagaatgcct 1500
atgtgtctgt tgtgaccagc aactacaaca gaaggttcac ccctgagatt gctgagaggc 1560
ccaaagtgaa ggaccaggct ggcagaatga actactactg gaccctgctg aagcctgggg 1620
acaccatcat ctttgaggcc aatggcaacc tgattgcccc tatgtatgcc tttgctctga 1680
gcagaggctt tggctctggc atcatcacca gcaatgccag catgcatgag tgcaatacca 1740
agtgtcagac ccctctggga gctatcaaca gcagcctgcc tttccagaac atccatcctg 1800
tgaccattgg agagtgcccc aaatatgtta ggagtgccaa gctgaggatg gtcactggcc 1860
tgagaaacat ccccagcatc cagtccagag gcctgtttgg agccattgct ggcttcattg 1920
agggaggctg gacaggcatg attgatggat ggtatggcta ccaccatcag aatgagcaag 1980
gcagtggcta tgctgctgac cagaaaagca cccagaatgc tgtgaatggc attacaaaca 2040
aagtgaacac agtgattgag aagatgaaca tccagttcac tgctgtgggg aaagagttca 2100
acaagcttga gaagaggatg gaaaacctga acaaaaaagt ggatgatggc ttcctggaca 2160

-continued

```
tctggaccta caatgctgag ctgctggtcc tcctggaaaa tgagagaacc ctggacttcc   2220

atgacagcaa tgtgaagaac ctctatgaga aagtgaagtc ccagctcaag aacaatgcca   2280

aagaaattgg caatggctgc tttgagttct accacaagtg tgacaatgag tgcatggaat   2340

ctgtcagaaa tggcacctat gactacccta agtactctga ggaaagcaag ctgaacaggg   2400

aaaaagttga tggggtcaag ctggaatcca tgggcatcta ccagatcatt gtgggcattg   2460

tggcaggcct ggctgtgctg gcagtggtgg ttattggagc tgtggtggca gcagtgatgt   2520

gcagaagaaa gtcctctgga ggcaaaggtg gcagctactc tcaggctgcc tgttctgatt   2580

ctgcccaggg ctctgatgtg tccctgacag cttaaagatc tacttctggc taataaaaga   2640

tcagagctct agtgatctgt gtgttggttt tttgtgtctg cattctagct ctagtgatca   2700

gcagttcaac ctgttgatag tatgtactaa gctctcatgt ttaatgtact aagctctcat   2760

gtttaatgaa ctaaaccctc atggctaatg tactaagctc tcatggctaa tgtactaagc   2820

tctcatgttt catgtactaa gctctcatgt ttgaacaata aaattaatat aaatcagcaa   2880

cttaaatagc ctctaaggtt ttaagtttta taagaaaaaa aagaatatat aaggctttta   2940

aaggttttaa ggtttcctag gttatcctca tatgagctct tagaaaaact catccagcat   3000

caaatgaaac tgcaatttat tcatatcagg attatcaata ccatattttt gaaaaagtct   3060

tttctgtaat gaaggagaaa actcacccag gcagttccat aggatggcaa gatcctggta   3120

tctgtctgca attccaactc ttccaacatc aatacaacct attaatttcc cctcatcaaa   3180

aataaggtta tcaagtgaga aatcaccatg agtgaccact gaatctggtg agaatggcaa   3240

aagattatgc atttctttcc agacttgttc aacaggccag ccatttctct catcatcaaa   3300

atcactggca tcaaccaaac cattattcat tcttgattgg gcctgagcca gtctaaatac   3360

tctatcagag ttaaaaggac aattacaaac aggaatggaa tgcaatcttc tcaggaacac   3420

tgccagggca tcaacaatat tttcacctga atcaggatat tcttccaata cctggaatgc   3480

tgttttccct gggatggcag tggtgagtaa ccatgcatca tcaggagttc tgataaaatg   3540

cttgatggtt ggaagaggca taaattcagt cagccagttt agtctgacca tctcatctgt   3600

aacatcattg gcaacagaac ctttgccatg tttcagaaac aactctgggg catctggctt   3660

cccatacaat ctatagattg tggcacctga ttgcccaaca ttatctctag cccatttata   3720

cccatataaa tcagcatcca tgttggaatt taatcttggc ctggagcaag aggtttctct   3780

ttgaatatgg ctcatacatg tgcacctcct atagtgagtt gtattatact atgcagatat   3840

actatgccaa tgtttaattg tcag                                          3864
```

<210> SEQ ID NO 38
<211> LENGTH: 3063
<212> TYPE: DNA
<213> ORGANISM: Artificial sequence
<220> FEATURE:
<223> OTHER INFORMATION: Synthetic

<400> SEQUENCE: 38

```
cactatgtgg acatgaattc aattggctag caggagtcaa tgggaaaaac ccattggagc     60

caagtacact gactcaatag ggactttcca ttgggttttg cccagtacat aaggtcaata    120

gggggtgagt caacaggaaa gtcccattgg agccaagtac attgagtcaa tagggacttt    180

ccaatgggtt ttgcccagta cataaggtca atgggaggta agccaatggg tttttcccat    240

tactgacatg tatactgagt cattagggac tttccaatgg gttttgccca gtacataagg    300

tcaatagggg tgaatcaaca ggaaagtccc attggagcca agtacactga gtcaataggg    360
```

-continued

```
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc accttttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg agagtgacag cccctagaac agtcctgctg ctcctgtctg    900
ctgccctggc tctgacagaa acatgggctg gctccagact gaagggcatt gctcctctgc    960
aactgggcaa gtgcaacatt gctggctggc tgctgggcaa ccctgagtgt gatcctctgc   1020
tgcctgtcag atcctggtcc tacattgtgg aaacccctag ctctgagaat ggcatctgct   1080
accctgggga cttcattgac tatgaggaac tgaaagaaca gctgtcctct gtgtccagct   1140
ttgagagatt tgaaatcttc cccaaagaga gcagctggcc caaccacaac accaacaaag   1200
gggtcacagc tgcctgtagc catgagggca agagcagctt ctacagaaac ctgctgtggc   1260
tgacagagaa agagggcagc taccccaagc tgaagaactc ctatgtgaac aagaagggca   1320
aagaggtcct ggttctctgg ggcatccacc atcctagcaa cagcaaagag cagcagaacc   1380
tgtaccagaa tgagaatgcc tatgtgtctg tggtcacaag caactacaac agaaggttca   1440
cccctgagat tgctgagagg cccaaagtga aggaccaggc tggcagaatg aactactact   1500
ggaccctgct gaagcctggg gacaccatca tctttgaggc caatggcaac ctgattgccc   1560
ctatgtatgc ctttgctctg agcagaggct ttggctctgg catcatcacc tctgtggatg   1620
gggtcaagct ggaatccatg ggcatcattg tgggcattgt ggcaggcctg gctgtgctgg   1680
cagtggtggt tattggagct gtggtggctg ctgtgatgtg cagaagaaag tcctctggag   1740
gcaaaggtgg cagctactct caggctgcct gttctgattc tgcccagggc tctgatgtgt   1800
ccctgacagc ttaaagatct acttctggct aataaaagat cagagctcta gtgatctgtg   1860
tgttggtttt ttgtgtctgc attctagctc tagtgatcag cagttcaacc tgttgatagt   1920
atgtactaag ctctcatgtt taatgtacta agctctcatg tttaatgaac taaaccctca   1980
tggctaatgt actaagctct catggctaat gtactaagct ctcatgtttc atgtactaag   2040
ctctcatgtt tgaacaataa aattaatata aatcagcaac ttaaatagcc tctaaggttt   2100
taagttttat aagaaaaaaa agaatatata aggcttttaa aggttttaag gtttcctagg   2160
ttatcctcat atgagctctt agaaaaactc atccagcatc aaatgaaact gcaatttatt   2220
catatcagga ttatcaatac catatttttg aaaaagtctt ttctgtaatg aaggagaaaa   2280
ctcacccagg cagttccata ggatggcaag atcctggtat ctgtctgcaa ttccaactct   2340
tccaacatca atacaaccta ttaatttccc ctcatcaaaa ataaggttat caagtgagaa   2400
atcaccatga gtgaccactg aatctggtga gaatggcaaa agattatgca tttctttcca   2460
gacttgttca acaggccagc catttctctc atcatcaaaa tcactggcat caaccaaacc   2520
attattcatt cttgattggg cctgagccag tctaaatact ctatcagagt taaaaggaca   2580
attacaaaca ggaatggaat gcaatcttct caggaacact gccagggcat caacaatatt   2640
ttcacctgaa tcaggatatt cttccaatac ctggaatgct gttttccctg ggatggcagt   2700
```

ggtgagtaac catgcatcat caggagttct gataaaatgc ttgatggttg gaagaggcat 2760
aaattcagtc agccagttta gtctgaccat ctcatctgta acatcattgg caacagaacc 2820
tttgccatgt ttcagaaaca actctggggc atctggcttc ccatacaatc tatagattgt 2880
ggcacctgat tgcccaacat tatctctagc ccatttatac ccatataaat cagcatccat 2940
gttggaattt aatcttggcc tggagcaaga ggtttctctt tgaatatggc tcatacatgt 3000
gcacctccta tagtgagttg tattatacta tgcagatata ctatgccaat gtttaattgt 3060
cag 3063

<210> SEQ ID NO 39
<211> LENGTH: 6906
<212> TYPE: DNA
<213> ORGANISM: Artificial sequence
<220> FEATURE:
<223> OTHER INFORMATION: Synthetic

<400> SEQUENCE: 39
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg ggactgggac tccagtgggt gttctttgtg gccctgctga 900
aaggggtgca ctgtgaagtc agactgctgg aaagtggtgg tggcctgcag gttcagctgg 960
tgcagtctgg ggctgaagtg aagaaacctg gcagctctgt gaaggtgtcc tgcaaggcta 1020
gtggtggcac cttctctgcc tatgccttca cctgggtcag acaggctcct ggacagggcc 1080
ttgaatggat gggaggcatc acaggcatgt ttggcacagc caactatgcc cagaaattcc 1140
agggcagagt gaccatcaca gctgatgagc tgaccagcac agcctacatg gaactgagca 1200
gcctgacctc tgaggacaca gccctgtact actgtgccag aggcctgtac tattatgagt 1260
ctagcctgga ctactggggc cagggcacac tggttacagt gtctagtgcc agcacaaagg 1320
gcccatctgt gttccctctg gcacccagca gcaagtctac cagtggtgga acagctgccc 1380
tgggctgtct ggtcaaggac tactttcctg agccagtgac agtgtcctgg aactctgggg 1440
ctctgacatc tggggtgcac acattccctg ctgtgctcca gtcctctggc ctgtacagcc 1500
tcagctctgt ggtcacagtg cctagctcta gcctgggcac ccagacctac atctgcaatg 1560
tgaaccacaa gcctagcaac accaaggtgg acaagaaggc tgagcccaag agctgtgaca 1620
agacccacac ctgtcctcca tgtcctgctc cagagctgct tggaggacct tctgtgtttc 1680

```
tgttccctcc aaagccaaag gacaccctga tgatcagcag aacccctgaa gtgacatgtg   1740
tggtggttga tgtgtcccat gaggacccag aagtgaagtt caattggtat gtggatggtg   1800
ttgaggtgca caatgccaag accaagccta gagaggaaca gtacaacagc acctacagag   1860
tggtgtctgt gctgacagtg ctgcatcagg actggctgaa tggcaaagag tacaagtgca   1920
aggtgtccaa caaggccctg cctgctccta ttgaaaagac catctccaag gccaagggcc   1980
agcctaggga accccaggtt tacacactgc cacctagcag ggatgagctg accaagaacc   2040
aggtgtccct gacctgcctg gttaagggct tctacccctc tgacattgct gtggaatggg   2100
agagcaatgg ccagccagag aacaactaca agacaacccc tcctgtgctg gactctgatg   2160
gctcattctt cctgtactcc aagctcacag tggacaagtc cagatggcag caaggcaatg   2220
tgttcagctg ctctgtgatg catgaggccc tgcacaacca ctacacacag aagtccctga   2280
gcctgtctcc tggcaagaga aagagaagga gtggaagtgg agctactaac ttcagcctgc   2340
tgaagcaggc tggagatgtg gaggagaacc ctggacctat ggacttccag gtgcagatca   2400
tcagctttct gctgatctct gcctctgtga tcatgagcag aggccagtct gtgctgaccc   2460
agcctccatc tgcatctgga agccctggcc agtctgtgac catcagctgt acaggcacca   2520
gctctgatgt tggaggctac aactctgtgt cctggtatca gcagcaccct ggcaaggccc   2580
ctaagctgat gatctatgaa gtgaccaaga ggccctctgg ggtgccagac agattctctg   2640
ccagcaagtc tggcaacaca gccagcctga cagtgtctgg cctgcaagct gaggatgagg   2700
ctgactactt ctgctgctcc tatgctggcc actctgccta tgtgtttggc actggcacca   2760
aagtgacagt gctgagaaca gtggctgccc cttctgtgtt catcttccca ccatctgatg   2820
agcagctgaa gtctggcaca gcctctgttg tgtgcctgct gaacaacttc taccctagag   2880
aagccaaggt gcagtggaag gtggacaatg ccctccagtc tggcaactcc caagagtctg   2940
tgacagagca ggacagcaag gactccacct acagcctgag cagcaccctg acactgagca   3000
aggctgacta tgagaagcac aaagtctatg cctgtgaagt gacccaccag ggcctgtcta   3060
gccctgtgac caagagcttc aacaggggag agagctgaag atctacttct ggctaataaa   3120
agatcagagc tctagtgatc tgtgtgttgg tttttgtgt ctgcattcta gcatgttaca   3180
taacttatgg taaatggcct gcctggctga ctgcccaatg acccctgccc aatgatgtca   3240
ataatgatgt atgttcccat gtaatgccaa tagggacttt ccattgatgt caatgggtgg   3300
agtatttatg gtaactgccc acttggcagt acatcaagtg tatcatatgc caagtatgcc   3360
ccctattgat gtcaatgatg gtaaatggcc tgcctggcat tatgcccagt acatgacctt   3420
atgggacttt cctacttggc agtacatcta tgtattagtc attgctatta ccatggatta   3480
gtggagaaga gcatgcttga gggctgagtg cccctcagtg ggcagagagc acatggccca   3540
cagtccctga gaagttgggg ggaggggtgg gcaattgaac tggtgcctag agaaggtggg   3600
gcttgggtaa actgggaaag tgatgtggtg tactggctcc accttttcc ccagggtggg   3660
ggagaaccat atataagtgc agtagtctct gtgaacattc aagcttctgc cttctccctc   3720
ctgtgagttt ggatgcacct actagatatc ttggtaagtc actgactgtc tatgcctggg   3780
aaagggtggg caggaggtgg ggcagtgcag gaaaagtggc actgtgaacc ctgcagccct   3840
agacaattgt actaaccttc ttctctttcc tctcctgaca ggttggtaac caagccacca   3900
tgaaggccaa cctgctggtg ctgctgtgtg ctctggctgc tgctgatgct gacaccatct   3960
gcattggcta ccatgccaac aacagcacag acacagtgga cactgtgctg gaaaagaatg   4020
```

-continued

```
tgacagtgac ccactctgtc aacctgcttg aggacagcca caatggcaag ctgtgcagac   4080
tgaagggcat tgcccctctg caactgggca agtgcaacat tgctggatgg ctgctgggca   4140
accctgagtg tgatcctctg ctgcctgtca gatcctggtc ctacattgtg gaaaccccta   4200
gctctgagaa tggcatctgc taccctgggg acttcattga ctatgaggaa ctgaaagaac   4260
agctgtcctc tgtcagcagc tttgagagat ttgaaatctt ccccaaagag agcagctggc   4320
ccaaccacaa caccaacaaa ggggtcacag ctgcctgtag ccatgagggc aagagcagct   4380
tctacagaaa cctgctgtgg ctgactgaga aagagggcag ctaccccaag ctgaagaact   4440
cctatgtgaa caagaagggc aaagaggtcc tggttctctg ggcatccac catcctagca    4500
acagcaaaga gcagcagaac ctgtaccaga atgagaatgc ctatgtgtct gttgtgacca   4560
gcaactacaa cagaaggttc acccctgaga ttgctgagag gcccaaagtg aaggaccagg   4620
ctggcagaat gaactactac tggaccctgc tgaagcctgg ggacaccatc atctttgagg   4680
ccaatggcaa cctgattgcc cctatgtatg cctttgctct gagcagaggc tttggctctg   4740
gcatcatcac cagcaatgcc agcatgcatg agtgcaatac caagtgtcag acccctctgg   4800
gagctatcaa cagcagcctg cctttccaga acatccatcc tgtgaccatt ggagagtgcc   4860
ccaaatatgt taggagtgcc aagctgagga tggtcactgg cctgagaaac atccccagca   4920
tccagtccag aggcctgttt ggagccattg ctggcttcat tgagggaggc tggacaggca   4980
tgattgatgg atggtatggc taccaccatc agaatgagca aggcagtggc tatgctgctg   5040
accagaaaag cacccagaat gctgtgaatg gcattacaaa caaagtgaac acagtgattg   5100
agaagatgaa catccagttc actgctgtgg ggaaagagtt caacaagctt gagaagagga   5160
tggaaaacct gaacaaaaaa gtggatgatg gcttcctgga catctggacc tacaatgctg   5220
agctgctggt cctcctggaa aatgagagaa ccctggactt ccatgacagc aatgtgaaga   5280
acctctatga gaaagtgaag tcccagctca agaacaatgc caaagaaatt ggcaatggct   5340
gctttgagtt ctaccacaag tgtgacaatg agtgcatgga atctgtcaga aatggcacct   5400
atgactaccc taagtactct gaggaaagca agctgaacag ggaaaaagtt gatggggtca   5460
agctggaatc catgggcatc taccagatca ttgtgggcat tgtggcaggc ctggctgtgc   5520
tggcagtggt ggttattgga gctgtggtgg cagcagtgat gtgcagaaga aagtcctctg   5580
gaggcaaagg tggcagctac tctcaggctg cctgttctga ttctgcccag ggctctgatg   5640
tgtccctgac agcttaaaga tctacttctg gctaataaaa gatcagagct ctagtgatct   5700
gtgtgttggt tttttgtgtc tgcattctag ctctagtgat cagcagttca acctgttgat   5760
agtatgtact aagctctcat gtttaatgta ctaagctctc atgtttaatg aactaaaccc   5820
tcatggctaa tgtactaagc tctcatggct aatgtactaa gctctcatgt ttcatgtact   5880
aagctctcat gtttgaacaa taaaattaat ataaatcagc aacttaaata gcctctaagg   5940
ttttaagttt tataagaaaa aaaagaatat ataaggcttt taaaggtttt aaggtttcct   6000
aggttatcct catatgagct cttagaaaaa ctcatccagc atcaaatgaa actgcaattt   6060
attcatatca ggattatcaa taccatattt ttgaaaaagt cttttctgta atgaaggaga   6120
aaactcaccc aggcagttcc ataggatggc aagatcctgg tatctgtctg caattccaac   6180
tcttccaaca tcaatacaac ctattaattt cccctcatca aaaataaggt tatcaagtga   6240
gaaatcacca tgagtgacca ctgaatctgg tgagaatggc aaaagattat gcatttcttt   6300
ccagacttgt tcaacaggcc agccatttct ctcatcatca aaatcactgg catcaaccaa   6360
accattattc attcttgatt gggcctgagc cagtctaaat actctatcag agttaaaagg   6420
```

acaattacaa acaggaatgg aatgcaatct tctcaggaac actgccaggg catcaacaat 6480
attttcacct gaatcaggat attcttccaa tacctggaat gctgttttcc ctgggatggc 6540
agtggtgagt aaccatgcat catcaggagt tctgataaaa tgcttgatgg ttggaagagg 6600
cataaattca gtcagccagt ttagtctgac catctcatct gtaacatcat tggcaacaga 6660
acctttgcca tgtttcagaa acaactctgg ggcatctggc ttcccataca atctatagat 6720
tgtggcacct gattgcccaa cattatctct agcccattta tacccatata aatcagcatc 6780
catgttggaa tttaatcttg gcctggagca agaggtttct ctttgaatat ggctcataca 6840
tgtgcacctc ctatagtgag ttgtattata ctatgcagat atactatgcc aatgtttaat 6900
tgtcag 6906

<210> SEQ ID NO 40
<211> LENGTH: 6918
<212> TYPE: DNA
<213> ORGANISM: Artificial sequence
<220> FEATURE:
<223> OTHER INFORMATION: Synthetic

<400> SEQUENCE: 40
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg ggactgggac tccagtgggt gttctttgtg gccctgctga 900
aaggggtgca ctgtgaagtc agactgctgg aaagtggtgg tggcctgcag gttcagctgg 960
tgcagtctgg ggctgaagtg aagaaacctg gcagctctgt gaaggtgtcc tgcacctcct 1020
ctgaagtgac cttcagcagc tttgccatca gctgggtcag acaggctcct ggacagggcc 1080
ttgaatggct tggaggcatc agccccatgt ttggcacccc taactatgcc cagaaattcc 1140
agggcagagt gaccatcaca gctgaccaga gcaccagaac agcctacatg gacctgagaa 1200
gtcttaggag tgaagataca gctgtgtact actgtgctag aagccccagc tacatctgct 1260
ctggtggcac ctgtgtgttt gaccactggg gccagggaac cctggtcaca gtttcttctg 1320
ccagcacaaa gggcccatct gtgttccctc tggcacccag cagcaagtct accagtggtg 1380
gaacagctgc cctgggctgt ctggtcaagg actactttcc tgagccagtg acagtgtcct 1440
ggaactctgg ggctctgaca tctggggtgc acacattccc tgctgtgctc cagtcctctg 1500

-continued

```
gcctgtacag cctcagctct gtggtcacag tgcctagctc tagcctgggc acccagacct   1560
acatctgcaa tgtgaaccac aagcctagca acaccaaggt ggacaagaag gctgagccca   1620
agagctgtga caagacccac acctgtcctc catgtcctgc tccagagctg cttggaggac   1680
cttctgtgtt tctgttccct ccaaagccaa aggacaccct gatgatcagc agaacccctg   1740
aagtgacatg tgtggtggtt gatgtgtccc atgaggaccc agaagtgaag ttcaattggt   1800
atgtggatgg tgttgaggtg cacaatgcca agaccaagcc tagagaggaa cagtacaaca   1860
gcacctacag agtggtgtct gtgctgacag tgctgcatca ggactggctg aatggcaaag   1920
agtacaagtg caaggtgtcc aacaaggccc tgcctgctcc tattgaaaag accatctcca   1980
aggccaaggg ccagcctagg gaaccccagg tttacacact gccacctagc agggatgagc   2040
tgaccaagaa ccaggtgtcc ctgacctgcc tggttaaggg cttctacccc tctgacattg   2100
ctgtggaatg ggagagcaat ggccagccag agaacaacta caagacaacc cctcctgtgc   2160
tggactctga tggctcattc ttcctgtact ccaagctcac agtggacaag tccagatggc   2220
agcaaggcaa tgtgttcagc tgctctgtga tgcatgaggc cctgcacaac cactacacac   2280
agaagtccct gagcctgtct cctggcaaga gaaagagaag gagtggaagt ggagctacta   2340
acttcagcct gctgaagcag gctggagatg tggaggagaa ccctggacct atggacttcc   2400
aggtgcagat catcagcttt ctgctgatct ctgcctctgt gatcatgagc agaggccagc   2460
ctggactgac acagcctcca tctgtgtcca agggcctgag acagacagcc acactgacct   2520
gcacaggcaa cagcaacaat gtgggcaatc aaggggctgc ctggctccag cagcatcagg   2580
gacatcctcc aaagctgctg agctacagaa acaatgacag accctctggc atctctgaga   2640
gattctctgc ctctaggagt ggcaacacag ccagcctgac catcactgga ctccagccag   2700
aggatgaggc tgactactac tgctccacct gggacagcag cctgtctgct gtggtttttg   2760
gtggtggcac caagctgaca gtgctgagaa cagtggctgc cccttctgtg ttcatcttcc   2820
caccatctga tgagcagctg aagtctggca cagcctctgt tgtgtgcctg ctgaacaact   2880
tctaccctag agaagccaag gtgcagtgga aggtggacaa tgccctccag tctggcaact   2940
cccaagagtc tgtgacagag caggacagca aggactccac ctacagcctg agcagcaccc   3000
tgacactgag caaggctgac tatgagaagc acaaagtcta tgcctgtgaa gtgacccacc   3060
agggcctgtc tagccctgtg accaagagct tcaacagggg agagagctga agatctactt   3120
ctggctaata aaagatcaga gctctagtga tctgtgtgtt ggtttttttgt gtctgcattc   3180
tagcatgtta cataacttat ggtaaatggc ctgcctggct gactgcccaa tgacccctgc   3240
ccaatgatgt caataatgat gtatgttccc atgtaatgcc aatagggact ttccattgat   3300
gtcaatgggt ggagtattta tggtaactgc ccacttggca gtacatcaag tgtatcatat   3360
gccaagtatg cccccctattg atgtcaatga tggtaaatgg cctgcctggc attatgccca   3420
gtacatgacc ttatgggact ttcctacttg gcagtacatc tatgtattag tcattgctat   3480
taccatggat tagtggagaa gagcatgctt gagggctgag tgcccctcag tgggcagaga   3540
gcacatggcc cacagtccct gagaagttgg ggggaggggt gggcaattga actggtgcct   3600
agagaaggtg gggcttgggt aaactgggaa agtgatgtgg tgtactggct ccaccttttt   3660
ccccagggtg ggggagaacc atatataagt gcagtagtct ctgtgaacat tcaagcttct   3720
gccttctccc tcctgtgagt ttggatgcac ctactagata tcttggtaag tcactgactg   3780
tctatgcctg ggaaagggtg ggcaggaggt ggggcagtgc aggaaaagtg gcactgtgaa   3840
ccctgcagcc ctagacaatt gtactaacct tcttctcttt cctctcctga caggttggta   3900
```

```
accaagccac catgaaggcc aacctgctgg tgctgctgtg tgctctggct gctgctgatg   3960
ctgacaccat ctgcattggc taccatgcca acaacagcac agacacagtg gacactgtgc   4020
tggaaaagaa tgtgacagtg acccactctg tcaacctgct tgaggacagc cacaatggca   4080
agctgtgcag actgaagggc attgcccctc tgcaactggg caagtgcaac attgctggat   4140
ggctgctggg caaccctgag tgtgatcctc tgctgcctgt cagatcctgg tcctacattg   4200
tggaaacccc tagctctgag aatggcatct gctaccctgg ggacttcatt gactatgagg   4260
aactgaaaga acagctgtcc tctgtcagca gctttgagag atttgaaatc ttccccaaag   4320
agagcagctg gcccaaccac aacaccaaca aaggggtcac agctgcctgt agccatgagg   4380
gcaagagcag cttctacaga aacctgctgt ggctgactga gaaagagggc agctacccca   4440
agctgaagaa ctcctatgtg aacaagaagg gcaaagaggt cctggttctc tggggcatcc   4500
accatcctag caacagcaaa gagcagcaga acctgtacca gaatgagaat gcctatgtgt   4560
ctgttgtgac cagcaactac aacagaaggt tcacccctga gattgctgag aggcccaaag   4620
tgaaggacca ggctggcaga atgaactact actggaccct gctgaagcct ggggacacca   4680
tcatctttga ggccaatggc aacctgattg cccctatgta tgcctttgct ctgagcagag   4740
gctttggctc tggcatcatc accagcaatg ccagcatgca tgagtgcaat accaagtgtc   4800
agacccctct gggagctatc aacagcagcc tgcctttcca gaacatccat cctgtgacca   4860
ttggagagtg ccccaaatat gttaggagtg ccaagctgag gatggtcact ggcctgagaa   4920
acatccccag catccagtcc agaggcctgt ttggagccat tgctggcttc attgagggag   4980
gctggacagg catgattgat ggatggtatg gctaccacca tcagaatgag caaggcagtg   5040
gctatgctgc tgaccagaaa agcacccaga atgctgtgaa tggcattaca aacaaagtga   5100
acacagtgat tgagaagatg aacatccagt tcactgctgt ggggaaagag ttcaacaagc   5160
ttgagaagag gatggaaaac ctgaacaaaa aagtggatga tggcttcctg gacatctgga   5220
cctacaatgc tgagctgctg gtcctcctgg aaaatgagag aaccctggac ttccatgaca   5280
gcaatgtgaa gaacctctat gagaaagtga agtcccagct caagaacaat gccaaagaaa   5340
ttggcaatgg ctgctttgag ttctaccaca agtgtgacaa tgagtgcatg gaatctgtca   5400
gaaatggcac ctatgactac cctaagtact ctgaggaaag caagctgaac agggaaaaag   5460
ttgatggggt caagctggaa tccatgggca tctaccagat cattgtgggc attgtggcag   5520
gcctggctgt gctggcagtg gtggttattg gagctgtggt ggcagcagtg atgtgcagaa   5580
gaaagtcctc tggaggcaaa ggtggcagct actctcaggc tgcctgttct gattctgccc   5640
agggctctga tgtgtccctg acagcttaaa gatctacttc tggctaataa aagatcagag   5700
ctctagtgat ctgtgtgttg gtttttttgtg tctgcattct agctctagtg atcagcagtt   5760
caacctgttg atagtatgta ctaagctctc atgtttaatg tactaagctc tcatgtttaa   5820
tgaactaaac cctcatggct aatgtactaa gctctcatgg ctaatgtact aagctctcat   5880
gtttcatgta ctaagctctc atgtttgaac aataaaatta atataaatca gcaacttaaa   5940
tagcctctaa ggttttaagt tttataagaa aaaaaagaat atataaggct tttaaaggtt   6000
ttaaggtttc ctaggttatc ctcatatgag ctcttagaaa aactcatcca gcatcaaatg   6060
aaactgcaat ttattcatat caggattatc aataccatat ttttgaaaaa gtcttttctg   6120
taatgaagga gaaaactcac ccaggcagtt ccataggatg gcaagatcct ggtatctgtc   6180
tgcaattcca actcttccaa catcaataca acctattaat ttcccctcat caaaaataag   6240
```

-continued

```
gttatcaagt gagaaatcac catgagtgac cactgaatct ggtgagaatg gcaaaagatt   6300

atgcatttct ttccagactt gttcaacagg ccagccattt ctctcatcat caaaatcact   6360

ggcatcaacc aaaccattat tcattcttga ttgggcctga gccagtctaa atactctatc   6420

agagttaaaa ggacaattac aaacaggaat ggaatgcaat cttctcagga acactgccag   6480

ggcatcaaca atattttcac ctgaatcagg atattcttcc aatacctgga atgctgtttt   6540

ccctgggatg gcagtggtga gtaaccatgc atcatcagga gttctgataa aatgcttgat   6600

ggttggaaga ggcataaatt cagtcagcca gtttagtctg accatctcat ctgtaacatc   6660

attggcaaca gaacctttgc catgtttcag aaacaactct ggggcatctg gcttcccata   6720

caatctatag attgtggcac ctgattgccc aacattatct ctagcccatt tatacccata   6780

taaatcagca tccatgttgg aatttaatct tggcctggag caagaggttt ctctttgaat   6840

atggctcata catgtgcacc tcctatagtg agttgtatta tactatgcag atatactatg   6900

ccaatgttta attgtcag                                                 6918
```

<210> SEQ ID NO 41
<211> LENGTH: 6904
<212> TYPE: DNA
<213> ORGANISM: Artificial sequence
<220> FEATURE:
<223> OTHER INFORMATION: Synthetic

<400> SEQUENCE: 41

```
cactatgtgg acatgaattc aattggctag caggagtcaa tgggaaaaac ccattggagc     60

caagtacact gactcaatag ggactttcca ttgggttttg cccagtacat aaggtcaata    120

gggggtgagt caacaggaaa gtcccattgg agccaagtac attgagtcaa tagggacttt    180

ccaatgggtt ttgcccagta cataaggtca atgggaggta agccaatggg tttttcccat    240

tactgacatg tatactgagt cattagggac tttccaatgg gttttgccca gtacataagg    300

tcaatagggg tgaatcaaca ggaaagtccc attggagcca agtacactga gtcaataggg    360

actttccatt gggttttgcc cagtacaaaa ggtcaatagg gggtgagtca atgggttttt    420

cccattattg gcacatacat aaggtcaata ggggtgacta gtggagaaga gcatgcttga    480

gggctgagtg cccctcagtg ggcagagagc acatggccca cagtccctga gaagttgggg    540

ggaggggtgg gcaattgaac tggtgcctag agaaggtggg gcttgggtaa actgggaaag    600

tgatgtggtg tactggctcc accttttttcc ccagggtggg ggagaaccat atataagtgc    660

agtagtctct gtgaacattc aagcttctgc cttctccctc ctgtgagttt ggtaagtcac    720

tgactgtcta tgcctgggaa agggtgggca ggagatgggg cagtgcagga aaagtggcac    780

tatgaaccct gcagccctag acaattgtac taaccttctt ctctttcctc tcctgacagg    840

ttggtaacca agccaccatg ggactgggac tccagtgggt gttctttgtg gccctgctga    900

aaggggtgca ctgtgaagtc agactgctgg aaagtggtgg tggcctgcag gttcagctgg    960

tgcagtctgg ggctgaagtg aagaaacctg gcagctctgt gaaggtgtcc tgcaaggcta   1020

gtggtggccc cttcagcatg acagccttca cctggctgag acaggctcct ggacagggcc   1080

ttgaatggat gggaggcatc agccccatct tcagaacccc taagtatgcc cagaaattcc   1140

agggcagagt gaccatcaca gctgatgaga gcaccaacac agccaacatg gaactgacca   1200

gcctgaagtc tgaggacact gctgtgtact actgtgccag aacactgagc agctaccagc   1260

ctaacaatga tgcctttgcc atctggggcc agggcaccat ggttacagtc agctctgcca   1320

gcacaaaggg cccatctgtg ttccctctgg cacccagcag caagtctacc agtggtggaa   1380
```

cagctgccct gggctgtctg gtcaaggact actttcctga gccagtgaca gtgtcctgga 1440
actctggggc tctgacatct ggggtgcaca cattccctgc tgtgctccag tcctctggcc 1500
tgtacagcct cagctctgtg gtcacagtgc ctagctctag cctgggcacc cagacctaca 1560
tctgcaatgt gaaccacaag cctagcaaca ccaaggtgga caagaaggct gagcccaaga 1620
gctgtgacaa gacccacacc tgtcctccat gtcctgctcc agagctgctt ggaggacctt 1680
ctgtgtttct gttccctcca aagccaaagg acaccctgat gatcagcaga acccctgaag 1740
tgacatgtgt ggtggttgat gtgtcccatg aggacccaga agtgaagttc aattggtatg 1800
tggatggtgt tgaggtgcac aatgccaaga ccaagcctag agaggaacag tacaacagca 1860
cctacagagt ggtgtctgtg ctgacagtgc tgcatcagga ctggctgaat ggcaaagagt 1920
acaagtgcaa ggtgtccaac aaggccctgc ctgctcctat tgaaaagacc atctccaagg 1980
ccaagggcca gcctagggaa ccccaggttt acacactgcc acctagcagg gatgagctga 2040
ccaagaacca ggtgtccctg acctgcctgg ttaagggctt ctacccctct gacattgctg 2100
tggaatggga gagcaatggc cagccagaga acaactacaa gacaacccct cctgtgctgg 2160
actctgatgg ctcattcttc ctgtactcca agctcacagt ggacaagtcc agatggcagc 2220
aaggcaatgt gttcagctgc tctgtgatgc atgaggccct gcacaaccac tacacacaga 2280
agtccctgag cctgtctcct ggcaagagaa agagaaggag tggaagtgga gctactaact 2340
tcagcctgct gaagcaggct ggagatgtgg aggagaaccc tggacctatg gacttccagg 2400
tgcagatcat cagctttctg ctgatctctg cctctgtgat catgagcaga ggccgagatt 2460
gtgctgacac agagccctgc cacactgtct cttagccctg gggagagagc cacactgagc 2520
tgtagagcca gccagtctgt gtcctcttac ctggcctggt atcagcagaa gcctggacag 2580
gctcccagac tgctgatcta tgatgccagc aacagagcca caggcatccc tgccagattc 2640
agtggctctg gcagtggcac agacttcacc ctgaccatca gcagactgga accagaggac 2700
tttgctgtgt acttctgcca gcagtatggc agcagccctc agtttggcca gggcacaaga 2760
ctggaaatca agagaacagt ggctgcccct tctgtgttca tcttcccacc atctgatgag 2820
cagctgaagt ctggcacagc ctctgttgtg tgcctgctga acaacttcta ccctagagaa 2880
gccaaggtgc agtggaaggt ggacaatgcc ctccagtctg gcaactccca agagtctgtg 2940
acagagcagg acagcaagga ctccacctac agcctgagca gcaccctgac actgagcaag 3000
gctgactatg agaagcacaa agtctatgcc tgtgaagtga cccaccaggg cctgtctagc 3060
cctgtgacca agagcttcaa caggggagag agctgaagat ctacttctgg ctaataaaag 3120
atcagagctc tagtgatctg tgtgttggtt ttttgtgtct gcattctagc atgttacata 3180
acttatggta aatggcctgc ctggctgact gcccaatgac ccctgcccaa tgatgtcaat 3240
aatgatgtat gttcccatgt aatgccaata gggactttcc attgatgtca atgggtggag 3300
tatttatggt aactgcccac ttggcagtac atcaagtgta tcatatgcca agtatgcccc 3360
ctattgatgt caatgatggt aaatggcctg cctggcatta tgcccagtac atgaccttat 3420
gggactttcc tacttggcag tacatctatg tattagtcat tgctattacc atggattagt 3480
ggagaagagc atgcttgagg gctgagtgcc cctcagtggg cagagagcac atggcccaca 3540
gtccctgaga agttgggggg aggggtgggc aattgaactg gtgcctagag aaggtggggc 3600
ttgggtaaac tgggaaagtg atgtggtgta ctggctccac ctttttcccc agggtggggg 3660
agaaccatat ataagtgcag tagtctctgt gaacattcaa gcttctgcct tctccctcct 3720

-continued

```
gtgagtttgg atgcacctac tagatatctt ggtaagtcac tgactgtcta tgcctgggaa   3780
agggtgggca ggaggtgggg cagtgcagga aaagtggcac tgtgaaccct gcagccctag   3840
acaattgtac taaccttctt ctctttcctc tcctgacagg ttggtaacca agccaccatg   3900
aaggccaacc tgctggtgct gctgtgtgct ctggctgctg ctgatgctga caccatctgc   3960
attggctacc atgccaacaa cagcacagac acagtggaca ctgtgctgga aaagaatgtg   4020
acagtgaccc actctgtcaa cctgcttgag gacagccaca atggcaagct gtgcagactg   4080
aagggcattg cccctctgca actgggcaag tgcaacattg ctggatggct gctgggcaac   4140
cctgagtgtg atcctctgct gcctgtcaga tcctggtcct acattgtgga aacccctagc   4200
tctgagaatg gcatctgcta ccctggggac ttcattgact atgaggaact gaaagaacag   4260
ctgtcctctg tcagcagctt tgagagattt gaaatcttcc ccaaagagag cagctggccc   4320
aaccacaaca ccaacaaagg ggtcacagct gcctgtagcc atgagggcaa gagcagcttc   4380
tacagaaacc tgctgtggct gactgagaaa gagggcagct accccaagct gaagaactcc   4440
tatgtgaaca agaagggcaa agaggtcctg gttctctggg gcatccacca tcctagcaac   4500
agcaaagagc agcagaacct gtaccagaat gagaatgcct atgtgtctgt tgtgaccagc   4560
aactacaaca gaaggttcac ccctgagatt gctgagaggc ccaaagtgaa ggaccaggct   4620
ggcagaatga actactactg gaccctgctg aagcctgggg acaccatcat ctttgaggcc   4680
aatggcaacc tgattgcccc tatgtatgcc tttgctctga gcagaggctt tggctctggc   4740
atcatcacca gcaatgccag catgcatgag tgcaatacca agtgtcagac ccctctggga   4800
gctatcaaca gcagcctgcc tttccagaac atccatcctg tgaccattgg agagtgcccc   4860
aaatatgtta ggagtgccaa gctgaggatg gtcactggcc tgagaaacat ccccagcatc   4920
cagtccagag gcctgtttgg agccattgct ggcttcattg agggaggctg gacaggcatg   4980
attgatggat ggtatggcta ccaccatcag aatgagcaag gcagtggcta tgctgctgac   5040
cagaaaagca cccagaatgc tgtgaatggc attacaaaca aagtgaacac agtgattgag   5100
aagatgaaca tccagttcac tgctgtgggg aaagagttca acaagcttga gaagaggatg   5160
gaaaacctga acaaaaaagt ggatgatggc ttcctggaca tctggaccta caatgctgag   5220
ctgctggtcc tcctggaaaa tgagagaacc ctggacttcc atgacagcaa tgtgaagaac   5280
ctctatgaga aagtgaagtc ccagctcaag aacaatgcca aagaaattgg caatggctgc   5340
tttgagttct accacaagtg tgacaatgag tgcatggaat ctgtcagaaa tggcacctat   5400
gactacccta agtactctga ggaaagcaag ctgaacaggg aaaaagttga tggggtcaag   5460
ctggaatcca tgggcatcta ccagatcatt gtgggcattg tggcaggcct ggctgtgctg   5520
gcagtggtgg ttattggagc tgtggtggca gcagtgatgt gcagaagaaa gtcctctgga   5580
ggcaaaggtg gcagctactc tcaggctgcc tgttctgatt ctgcccaggg ctctgatgtg   5640
tccctgacag cttaaagatc tacttctggc taataaaaga tcagagctct agtgatctgt   5700
gtgttggttt tttgtgtctg cattctagct ctagtgatca gcagttcaac ctgttgatag   5760
tatgtactaa gctctcatgt ttaatgtact aagctctcat gtttaatgaa ctaaaccctc   5820
atggctaatg tactaagctc tcatggctaa tgtactaagc tctcatgttt catgtactaa   5880
gctctcatgt ttgaacaata aaattaatat aaatcagcaa cttaaatagc ctctaaggtt   5940
ttaagtttta taagaaaaaa aagaatatat aaggctttta aaggttttaa ggtttcctag   6000
gttatcctca tatgagctct tagaaaaact catccagcat caaatgaaac tgcaatttat   6060
tcatatcagg attatcaata ccatattttt gaaaaagtct tttctgtaat gaaggagaaa   6120
```

-continued actcacccag gcagttccat aggatggcaa gatcctggta tctgtctgca attccaactc 6180
ttccaacatc aatacaacct attaatttcc cctcatcaaa aataaggtta tcaagtgaga 6240
aatcaccatg agtgaccact gaatctggtg agaatggcaa aagattatgc atttctttcc 6300
agacttgttc aacaggccag ccatttctct catcatcaaa atcactggca tcaaccaaac 6360
cattattcat tcttgattgg gcctgagcca gtctaaatac tctatcagag ttaaaaggac 6420
aattacaaac aggaatggaa tgcaatcttc tcaggaacac tgccagggca tcaacaatat 6480
tttcacctga atcaggatat tcttccaata cctggaatgc tgttttccct gggatggcag 6540
tggtgagtaa ccatgcatca tcaggagttc tgataaaatg cttgatggtt ggaagaggca 6600
taaattcagt cagccagttt agtctgacca tctcatctgt aacatcattg gcaacagaac 6660
ctttgccatg tttcagaaac aactctgggg catctggctt cccatacaat ctatagattg 6720
tggcacctga ttgcccaaca ttatctctag cccatttata cccatataaa tcagcatcca 6780
tgttggaatt taatcttggc ctggagcaag aggtttctct ttgaatatgg ctcatacatg 6840
tgcacctcct atagtgagtt gtattatact atgcagatat actatgccaa tgtttaattg 6900
tcag 6904

<210> SEQ ID NO 42
<211> LENGTH: 6105
<212> TYPE: DNA
<213> ORGANISM: Artificial sequence
<220> FEATURE:
<223> OTHER INFORMATION: Synthetic

<400> SEQUENCE: 42
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg ggactgggac tccagtgggt gttctttgtg gccctgctga 900
aaggggtgca ctgtgaagtc agactgctgg aaagtggtgg tggcctgcag gttcagctgg 960
tgcagtctgg ggctgaagtg aagaaacctg gcagctctgt gaaggtgtcc tgcaaggcta 1020
gtggtggcac cttctctgcc tatgccttca cctgggtcag acaggctcct ggacagggcc 1080
ttgaatggat gggaggcatc acaggcatgt ttggcacagc caactatgcc cagaaattcc 1140
agggcagagt gaccatcaca gctgatgagc tgaccagcac agcctacatg gaactgagca 1200

-continued

```
gcctgacctc tgaggacaca gccctgtact actgtgccag aggcctgtac tattatgagt   1260
ctagcctgga ctactggggc cagggcacac tggttacagt gtctagtgcc agcacaaagg   1320
gcccatctgt gttccctctg gcacccagca gcaagtctac cagtggtgga acagctgccc   1380
tgggctgtct ggtcaaggac tactttcctg agccagtgac agtgtcctgg aactctgggg   1440
ctctgacatc tggggtgcac acattccctg ctgtgctcca gtcctctggc ctgtacagcc   1500
tcagctctgt ggtcacagtg cctagctcta gcctgggcac ccagacctac atctgcaatg   1560
tgaaccacaa gcctagcaac accaaggtgg acaagaaggc tgagcccaag agctgtgaca   1620
agacccacac ctgtcctcca tgtcctgctc cagagctgct tggaggacct tctgtgtttc   1680
tgttccctcc aaagccaaag gacaccctga tgatcagcag aacccctgaa gtgacatgtg   1740
tggtggttga tgtgtcccat gaggacccag aagtgaagtt caattggtat gtggatggtg   1800
ttgaggtgca caatgccaag accaagccta gagaggaaca gtacaacagc acctacagag   1860
tggtgtctgt gctgacagtg ctgcatcagg actggctgaa tggcaaagag tacaagtgca   1920
aggtgtccaa caaggccctg cctgctccta ttgaaaagac catctccaag gccaagggcc   1980
agcctaggga accccaggtt tacacactgc cacctagcag ggatgagctg accaagaacc   2040
aggtgtccct gacctgcctg gttaagggct tctacccctc tgacattgct gtggaatggg   2100
agagcaatgg ccagccagag aacaactaca agacaacccc tcctgtgctg gactctgatg   2160
gctcattctt cctgtactcc aagctcacag tggacaagtc cagatggcag caaggcaatg   2220
tgttcagctg ctctgtgatg catgaggccc tgcacaacca ctacacacag aagtccctga   2280
gcctgtctcc tggcaagaga aagagaagga gtggaagtgg agctactaac ttcagcctgc   2340
tgaagcaggc tggagatgtg gaggagaacc ctggacctat ggacttccag gtgcagatca   2400
tcagctttct gctgatctct gcctctgtga tcatgagcag aggccagtct gtgctgaccc   2460
agcctccatc tgcatctgga agccctggcc agtctgtgac catcagctgt acaggcacca   2520
gctctgatgt tggaggctac aactctgtgt cctggtatca gcagcaccct ggcaaggccc   2580
ctaagctgat gatctatgaa gtgaccaaga ggccctctgg ggtgccagac agattctctg   2640
ccagcaagtc tggcaacaca gccagcctga cagtgtctgg cctgcaagct gaggatgagg   2700
ctgactactt ctgctgctcc tatgctggcc actctgccta tgtgtttggc actggcacca   2760
aagtgacagt gctgagaaca gtggctgccc cttctgtgtt catcttccca ccatctgatg   2820
agcagctgaa gtctggcaca gcctctgttg tgtgcctgct gaacaacttc taccctagag   2880
aagccaaggt gcagtggaag gtggacaatg ccctccagtc tggcaactcc caagagtctg   2940
tgacagagca ggacagcaag gactccacct acagcctgag cagcaccctg acactgagca   3000
aggctgacta tgagaagcac aaagtctatg cctgtgaagt gacccaccag ggcctgtcta   3060
gccctgtgac caagagcttc aacaggggag agagctgaag atctacttct ggctaataaa   3120
agatcagagc tctagtgatc tgtgtgttgg tttttgtgt ctgcattcta gcatgttaca   3180
taacttatgg taaatggcct gcctggctga ctgcccaatg acccctgccc aatgatgtca   3240
ataatgatgt atgttcccat gtaatgccaa tagggacttt ccattgatgt caatgggtgg   3300
agtatttatg gtaactgccc acttggcagt acatcaagtg tatcatatgc caagtatgcc   3360
ccctattgat gtcaatgatg gtaaatggcc tgcctggcat tatgcccagt acatgacctt   3420
atgggacttt cctacttggc agtacatcta tgtattagtc attgctatta ccatggatta   3480
gtggagaaga gcatgcttga gggctgagtg cccctcagtg ggcagagagc acatggccca   3540
cagtccctga gaagttgggg ggaggggtgg gcaattgaac tggtgcctag agaaggtggg   3600
```

gcttgggtaa actgggaaag tgatgtggtg tactggctcc accttttttcc ccagggtggg 3660
ggagaaccat atataagtgc agtagtctct gtgaacattc aagcttctgc cttctccctc 3720
ctgtgagttt ggatgcacct actagatatc ttggtaagtc actgactgtc tatgcctggg 3780
aaagggtggg caggaggtgg ggcagtgcag gaaaagtggc actgtgaacc ctgcagccct 3840
agacaattgt actaaccttc ttctctttcc tctcctgaca ggttggtaac caagccacca 3900
tgagagtgac agcccctaga acagtcctgc tgctcctgtc tgctgccctg gctctgacag 3960
aaacatgggc tggctccaga ctgaagggca ttgctcctct gcaactgggc aagtgcaaca 4020
ttgctggctg gctgctgggc aaccctgagt gtgatcctct gctgcctgtc agatcctggt 4080
cctacattgt ggaaacccct agctctgaga atggcatctg ctaccctggg gacttcattg 4140
actatgagga actgaaagaa cagctgtcct ctgtgtccag ctttgagaga tttgaaatct 4200
tccccaaaga gagcagctgg cccaaccaca acaccaacaa aggggtcaca gctgcctgta 4260
gccatgaggg caagagcagc ttctacagaa acctgctgtg gctgacagag aaagagggca 4320
gctaccccaa gctgaagaac tcctatgtga acaagaaggg caaagaggtc ctggttctct 4380
ggggcatcca ccatcctagc aacagcaaag agcagcagaa cctgtaccag aatgagaatg 4440
cctatgtgtc tgtggtcaca agcaactaca acagaaggtt cacccctgag attgctgaga 4500
ggcccaaagt gaaggaccag gctggcagaa tgaactacta ctggaccctg ctgaagcctg 4560
gggacaccat catctttgag gccaatggca acctgattgc ccctatgtat gcctttgctc 4620
tgagcagagg ctttggctct ggcatcatca cctctgtgga tggggtcaag ctggaatcca 4680
tgggcatcat tgtgggcatt gtggcaggcc tggctgtgct ggcagtggtg gttattggag 4740
ctgtggtggc tgctgtgatg tgcagaagaa agtcctctgg aggcaaaggt ggcagctact 4800
ctcaggctgc ctgttctgat tctgcccagg gctctgatgt gtccctgaca gcttaaagat 4860
ctacttctgg ctaataaaag atcagagctc tagtgatctg tgtgttggtt ttttgtgtct 4920
gcattctagc tctagtgatc agcagttcaa cctgttgata gtatgtacta agctctcatg 4980
tttaatgtac taagctctca tgtttaatga actaaaccct catggctaat gtactaagct 5040
ctcatggcta atgtactaag ctctcatgtt tcatgtacta agctctcatg tttgaacaat 5100
aaaattaata taaatcagca acttaaatag cctctaaggt tttaagtttt ataagaaaaa 5160
aaagaatata taaggctttt aaaggtttta aggtttccta ggttatcctc atatgagctc 5220
ttagaaaaac tcatccagca tcaaatgaaa ctgcaattta ttcatatcag gattatcaat 5280
accatatttt tgaaaaagtc ttttctgtaa tgaaggagaa aactcaccca ggcagttcca 5340
taggatggca agatcctggt atctgtctgc aattccaact cttccaacat caatacaacc 5400
tattaatttc ccctcatcaa aaataaggtt atcaagtgag aaatcaccat gagtgaccac 5460
tgaatctggt gagaatggca aaagattatg catttctttc cagacttgtt caacaggcca 5520
gccatttctc tcatcatcaa aatcactggc atcaaccaaa ccattattca ttcttgattg 5580
ggcctgagcc agtctaaata ctctatcaga gttaaaagga caattacaaa caggaatgga 5640
atgcaatctt ctcaggaaca ctgccagggc atcaacaata ttttcacctg aatcaggata 5700
ttcttccaat acctggaatg ctgttttccc tgggatggca gtggtgagta accatgcatc 5760
atcaggagtt ctgataaaat gcttgatggt tggaagaggc ataaattcag tcagccagtt 5820
tagtctgacc atctcatctg taacatcatt ggcaacagaa cctttgccat gtttcagaaa 5880
caactctggg gcatctggct tcccatacaa tctatagatt gtggcacctg attgcccaac 5940
attatctcta gcccatttat acccatataa atcagcatcc atgttggaat ttaatcttgg 6000
cctggagcaa gaggtttctc tttgaatatg gctcatacat gtgcacctcc tatagtgagt 6060
tgtattatac tatgcagata tactatgcca atgtttaatt gtcag 6105

<210> SEQ ID NO 43
<211> LENGTH: 6117
<212> TYPE: DNA
<213> ORGANISM: Artificial sequence
<220> FEATURE:
<223> OTHER INFORMATION: Synthetic

<400> SEQUENCE: 43
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg ggactgggac tccagtgggt gttctttgtg gccctgctga 900
aaggggtgca ctgtgaagtc agactgctgg aaagtggtgg tggcctgcag gttcagctgg 960
tgcagtctgg ggctgaagtg aagaaacctg gcagctctgt gaaggtgtcc tgcacctcct 1020
ctgaagtgac cttcagcagc tttgccatca gctgggtcag acaggctcct ggacagggcc 1080
ttgaatggct tggaggcatc agccccatgt ttggcacccc taactatgcc cagaaattcc 1140
agggcagagt gaccatcaca gctgaccaga gcaccagaac agcctacatg gacctgagaa 1200
gtcttaggag tgaagataca gctgtgtact actgtgctag aagccccagc tacatctgct 1260
ctggtggcac ctgtgtgttt gaccactggg gccagggaac cctggtcaca gtttcttctg 1320
ccagcacaaa gggcccatct gtgttccctc tggcacccag cagcaagtct accagtggtg 1380
gaacagctgc cctgggctgt ctggtcaagg actactttcc tgagccagtg acagtgtcct 1440
ggaactctgg ggctctgaca tctggggtgc acacattccc tgctgtgctc cagtcctctg 1500
gcctgtacag cctcagctct gtggtcacag tgcctagctc tagcctgggc acccagacct 1560
acatctgcaa tgtgaaccac aagcctagca acaccaaggt ggacaagaag gctgagccca 1620
agagctgtga caagacccac acctgtcctc catgtcctgc tccagagctg cttggaggac 1680
cttctgtgtt tctgttccct ccaaagccaa aggacaccct gatgatcagc agaacccctg 1740
aagtgacatg tgtggtggtt gatgtgtccc atgaggaccc agaagtgaag ttcaattggt 1800
atgtggatgg tgttgaggtg cacaatgcca agaccaagcc tagagaggaa cagtacaaca 1860
gcacctacag agtggtgtct gtgctgacag tgctgcatca ggactggctg aatggcaaag 1920
agtacaagtg caaggtgtcc aacaaggccc tgcctgctcc tattgaaaag accatctcca 1980
aggccaaggg ccagcctagg gaaccccagg tttacacact gccacctagc agggatgagc 2040
tgaccaagaa ccaggtgtcc ctgacctgcc tggttaaggg cttctacccc tctgacattg 2100
ctgtggaatg ggagagcaat ggccagccag agaacaacta caagacaacc cctcctgtgc 2160
tggactctga tggctcattc ttcctgtact ccaagctcac agtggacaag tccagatggc 2220
agcaaggcaa tgtgttcagc tgctctgtga tgcatgaggc cctgcacaac cactacacac 2280
agaagtccct gagcctgtct cctggcaaga gaaagagaag gagtggaagt ggagctacta 2340
acttcagcct gctgaagcag gctggagatg tggaggagaa ccctggacct atggacttcc 2400
aggtgcagat catcagcttt ctgctgatct ctgcctctgt gatcatgagc agaggccagc 2460
ctggactgac acagcctcca tctgtgtcca agggcctgag acagacagcc acactgacct 2520
gcacaggcaa cagcaacaat gtgggcaatc aaggggctgc ctggctccag cagcatcagg 2580
gacatcctcc aaagctgctg agctacagaa acaatgacag accctctggc atctctgaga 2640
gattctctgc ctctaggagt ggcaacacag ccagcctgac catcactgga ctccagccag 2700
aggatgaggc tgactactac tgctccacct gggacagcag cctgtctgct gtggtttttg 2760
gtggtggcac caagctgaca gtgctgagaa cagtggctgc cccttctgtg ttcatcttcc 2820
caccatctga tgagcagctg aagtctggca cagcctctgt tgtgtgcctg ctgaacaact 2880
tctaccctag agaagccaag gtgcagtgga aggtggacaa tgccctccag tctggcaact 2940
cccaagagtc tgtgacagag caggacagca aggactccac ctacagcctg agcagcaccc 3000
tgacactgag caaggctgac tatgagaagc acaaagtcta tgcctgtgaa gtgacccacc 3060
agggcctgtc tagccctgtg accaagagct tcaacagggg agagagctga agatctactt 3120
ctggctaata aaagatcaga gctctagtga tctgtgtgtt ggttttttgt gtctgcattc 3180
tagcatgtta cataacttat ggtaaatggc ctgcctggct gactgcccaa tgacccctgc 3240
ccaatgatgt caataatgat gtatgttccc atgtaatgcc aatagggact ttccattgat 3300
gtcaatgggt ggagtattta tggtaactgc ccacttggca gtacatcaag tgtatcatat 3360
gccaagtatg ccccctattg atgtcaatga tggtaaatgg cctgcctggc attatgccca 3420
gtacatgacc ttatgggact ttcctacttg gcagtacatc tatgtattag tcattgctat 3480
taccatggat tagtggagaa gagcatgctt gagggctgag tgcccctcag tgggcagaga 3540
gcacatggcc cacagtccct gagaagttgg ggggaggggt gggcaattga actggtgcct 3600
agagaaggtg gggcttgggt aaactgggaa agtgatgtgg tgtactggct ccaccttttt 3660
ccccagggtg ggggagaacc atatataagt gcagtagtct ctgtgaacat tcaagcttct 3720
gccttctccc tcctgtgagt ttggatgcac ctactagata tcttggtaag tcactgactg 3780
tctatgcctg ggaaagggtg ggcaggaggt ggggcagtgc aggaaaagtg gcactgtgaa 3840
ccctgcagcc ctagacaatt gtactaacct tcttctcttt cctctcctga caggttggta 3900
accaagccac catgagagtg acagccccta gaacagtcct gctgctcctg tctgctgccc 3960
tggctctgac agaaacatgg gctggctcca gactgaaggg cattgctcct ctgcaactgg 4020
gcaagtgcaa cattgctggc tggctgctgg gcaaccctga gtgtgatcct ctgctgcctg 4080
tcagatcctg gtcctacatt gtggaaaccc ctagctctga gaatggcatc tgctaccctg 4140
gggacttcat tgactatgag gaactgaaag aacagctgtc ctctgtgtcc agctttgaga 4200
gatttgaaat cttccccaaa gagagcagct ggcccaacca caacaccaac aaaggggtca 4260
cagctgcctg tagccatgag ggcaagagca gcttctacag aaacctgctg tggctgacag 4320
agaaagaggg cagctacccc aagctgaaga actcctatgt gaacaagaag ggcaaagagg 4380
tcctggttct ctggggcatc caccatccta gcaacagcaa agagcagcag aacctgtacc 4440
agaatgagaa tgcctatgtg tctgtggtca caagcaacta caacagaagg ttcacccctg 4500
agattgctga gaggcccaaa gtgaaggacc aggctggcag aatgaactac tactggaccc 4560
tgctgaagcc tggggacacc atcatctttg aggccaatgg caacctgatt gcccctatgt 4620
atgcctttgc tctgagcaga ggctttggct ctggcatcat cacctctgtg gatggggtca 4680
agctggaatc catgggcatc attgtgggca ttgtggcagg cctggctgtg ctggcagtgg 4740
tggttattgg agctgtggtg gctgctgtga tgtgcagaag aaagtcctct ggaggcaaag 4800
gtggcagcta ctctcaggct gcctgttctg attctgccca gggctctgat gtgtccctga 4860
cagcttaaag atctacttct ggctaataaa agatcagagc tctagtgatc tgtgtgttgg 4920
ttttttgtgt ctgcattcta gctctagtga tcagcagttc aacctgttga tagtatgtac 4980
taagctctca tgtttaatgt actaagctct catgtttaat gaactaaacc ctcatggcta 5040
atgtactaag ctctcatggc taatgtacta agctctcatg tttcatgtac taagctctca 5100
tgtttgaaca ataaaattaa tataaatcag caacttaaat agcctctaag gttttaagtt 5160
ttataagaaa aaaaagaata tataaggctt ttaaaggttt taaggtttcc taggttatcc 5220
tcatatgagc tcttagaaaa actcatccag catcaaatga aactgcaatt tattcatatc 5280
aggattatca ataccatatt tttgaaaaag tcttttctgt aatgaaggag aaaactcacc 5340
caggcagttc cataggatgg caagatcctg gtatctgtct gcaattccaa ctcttccaac 5400
atcaatacaa cctattaatt tcccctcatc aaaaataagg ttatcaagtg agaaatcacc 5460
atgagtgacc actgaatctg gtgagaatgg caaaagatta tgcatttctt tccagacttg 5520
ttcaacaggc cagccatttc tctcatcatc aaaatcactg gcatcaacca aaccattatt 5580
cattcttgat tgggcctgag ccagtctaaa tactctatca gagttaaaag gacaattaca 5640
aacaggaatg gaatgcaatc ttctcaggaa cactgccagg gcatcaacaa tattttcacc 5700
tgaatcagga tattcttcca atacctggaa tgctgttttc cctgggatgg cagtggtgag 5760
taaccatgca tcatcaggag ttctgataaa atgcttgatg gttggaagag gcataaattc 5820
agtcagccag tttagtctga ccatctcatc tgtaacatca ttggcaacag aacctttgcc 5880
atgtttcaga aacaactctg ggcatctggg cttcccatac aatctataga ttgtggcacc 5940
tgattgccca acattatctc tagcccattt atacccatat aaatcagcat ccatgttgga 6000
atttaatctt ggcctggagc aagaggtttc tctttgaata tggctcatac atgtgcacct 6060
cctatagtga gttgtattat actatgcaga tatactatgc caatgtttaa ttgtcag 6117

<210> SEQ ID NO 44
<211> LENGTH: 6103
<212> TYPE: DNA
<213> ORGANISM: Artificial sequence
<220> FEATURE:
<223> OTHER INFORMATION: Synthetic

<400> SEQUENCE: 44
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240

-continued

```
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc acctttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg ggactgggac tccagtgggt gttctttgtg gccctgctga    900
aaggggtgca ctgtgaagtc agactgctgg aaagtggtgg tggcctgcag gttcagctgg    960
tgcagtctgg ggctgaagtg aagaaacctg gcagctctgt gaaggtgtcc tgcaaggcta   1020
gtggtggccc cttcagcatg acagccttca cctggctgag acaggctcct ggacagggcc   1080
ttgaatggat gggaggcatc agccccatct tcagaacccc taagtatgcc cagaaattcc   1140
agggcagagt gaccatcaca gctgatgaga gcaccaacac agccaacatg gaactgacca   1200
gcctgaagtc tgaggacact gctgtgtact actgtgccag aacactgagc agctaccagc   1260
ctaacaatga tgcctttgcc atctggggcc agggcaccat ggttacagtc agctctgcca   1320
gcacaaaggg cccatctgtg ttccctctgg cacccagcag caagtctacc agtggtggaa   1380
cagctgccct gggctgtctg gtcaaggact actttcctga gccagtgaca gtgtcctgga   1440
actctggggc tctgacatct ggggtgcaca cattccctgc tgtgctccag tcctctggcc   1500
tgtacagcct cagctctgtg gtcacagtgc ctagctctag cctgggcacc cagacctaca   1560
tctgcaatgt gaaccacaag cctagcaaca ccaaggtgga caagaaggct gagcccaaga   1620
gctgtgacaa gacccacacc tgtcctccat gtcctgctcc agagctgctt ggaggacctt   1680
ctgtgtttct gttccctcca aagccaaagg acaccctgat gatcagcaga acccctgaag   1740
tgacatgtgt ggtggttgat gtgtcccatg aggacccaga agtgaagttc aattggtatg   1800
tggatggtgt tgaggtgcac aatgccaaga ccaagcctag agaggaacag tacaacagca   1860
cctacagagt ggtgtctgtg ctgacagtgc tgcatcagga ctggctgaat ggcaaagagt   1920
acaagtgcaa ggtgtccaac aaggccctgc ctgctcctat tgaaaagacc atctccaagg   1980
ccaagggcca gcctagggaa ccccaggttt acacactgcc acctagcagg gatgagctga   2040
ccaagaacca ggtgtccctg acctgcctgg ttaagggctt ctacccctct gacattgctg   2100
tggaatggga gagcaatggc cagccagaga acaactacaa gacaacccct cctgtgctgg   2160
actctgatgg ctcattcttc ctgtactcca agctcacagt ggacaagtcc agatggcagc   2220
aaggcaatgt gttcagctgc tctgtgatgc atgaggccct gcacaaccac tacacacaga   2280
agtccctgag cctgtctcct ggcaagagaa agagaaggag tggaagtgga gctactaact   2340
tcagcctgct gaagcaggct ggagatgtgg aggagaaccc tggacctatg gacttccagg   2400
tgcagatcat cagctttctg ctgatctctg cctctgtgat catgagcaga ggccgagatt   2460
gtgctgacac agagccctgc cacactgtct cttagccctg ggagagagc cacactgagc   2520
tgtagagcca gccagtctgt gtcctcttac ctggcctggt atcagcagaa gcctggacag   2580
```

-continued

```
gctcccagac tgctgatcta tgatgccagc aacagagcca caggcatccc tgccagattc   2640
agtggctctg gcagtggcac agacttcacc ctgaccatca gcagactgga accagaggac   2700
tttgctgtgt acttctgcca gcagtatggc agcagccctc agtttggcca gggcacaaga   2760
ctggaaatca agagaacagt ggctgcccct tctgtgttca tcttcccacc atctgatgag   2820
cagctgaagt ctggcacagc ctctgttgtg tgcctgctga acaacttcta ccctagagaa   2880
gccaaggtgc agtggaaggt ggacaatgcc ctccagtctg gcaactccca agagtctgtg   2940
acagagcagg acagcaagga ctccacctac agcctgagca gcaccctgac actgagcaag   3000
gctgactatg agaagcacaa agtctatgcc tgtgaagtga cccaccaggg cctgtctagc   3060
cctgtgacca agagcttcaa caggggagag agctgaagat ctacttctgg ctaataaaag   3120
atcagagctc tagtgatctg tgtgttggtt ttttgtgtct gcattctagc atgttacata   3180
acttatggta aatggcctgc ctggctgact gcccaatgac ccctgcccaa tgatgtcaat   3240
aatgatgtat gttcccatgt aatgccaata gggactttcc attgatgtca atgggtggag   3300
tatttatggt aactgcccac ttggcagtac atcaagtgta tcatatgcca agtatgcccc   3360
ctattgatgt caatgatggt aaatggcctg cctggcatta tgcccagtac atgaccttat   3420
gggactttcc tacttggcag tacatctatg tattagtcat tgctattacc atggattagt   3480
ggagaagagc atgcttgagg gctgagtgcc cctcagtggg cagagagcac atggcccaca   3540
gtccctgaga agttgggggg aggggtgggc aattgaactg gtgcctagag aaggtggggc   3600
ttgggtaaac tgggaaagtg atgtggtgta ctggctccac ctttttcccc agggtggggg   3660
agaaccatat ataagtgcag tagtctctgt gaacattcaa gcttctgcct tctccctcct   3720
gtgagtttgg atgcacctac tagatatctt ggtaagtcac tgactgtcta tgcctgggaa   3780
agggtgggca ggaggtgggg cagtgcagga aaagtggcac tgtgaaccct gcagccctag   3840
acaattgtac taaccttctt ctctttcctc tcctgacagg ttggtaacca agccaccatg   3900
agagtgacag cccctagaac agtcctgctg ctcctgtctg ctgccctggc tctgacagaa   3960
acatgggctg gctccagact gaagggcatt gctcctctgc aactgggcaa gtgcaacatt   4020
gctggctggc tgctgggcaa ccctgagtgt gatcctctgc tgcctgtcag atcctggtcc   4080
tacattgtgg aaacccctag ctctgagaat ggcatctgct accctgggga cttcattgac   4140
tatgaggaac tgaaagaaca gctgtcctct gtgtccagct ttgagagatt tgaaatcttc   4200
cccaaagaga gcagctggcc caaccacaac accaacaaag gggtcacagc tgcctgtagc   4260
catgagggca agagcagctt ctacagaaac ctgctgtggc tgacagagaa agagggcagc   4320
taccccaagc tgaagaactc ctatgtgaac aagaagggca aagaggtcct ggttctctgg   4380
ggcatccacc atcctagcaa cagcaaagag cagcagaacc tgtaccagaa tgagaatgcc   4440
tatgtgtctg tggtcacaag caactacaac agaaggttca cccctgagat tgctgagagg   4500
cccaaagtga aggaccaggc tggcagaatg aactactact ggaccctgct gaagcctggg   4560
gacaccatca tctttgaggc caatggcaac ctgattgccc ctatgtatgc ctttgctctg   4620
agcagaggct ttggctctgg catcatcacc tctgtggatg gggtcaagct ggaatccatg   4680
ggcatcattg tgggcattgt ggcaggcctg gctgtgctgg cagtggtggt tattggagct   4740
gtggtggctg ctgtgatgtg cagaagaaag tcctctggag gcaaaggtgg cagctactct   4800
caggctgcct gttctgattc tgcccagggc tctgatgtgt ccctgacagc ttaaagatct   4860
acttctggct aataaaagat cagagctcta gtgatctgtg tgttggtttt ttgtgtctgc   4920
attctagctc tagtgatcag cagttcaacc tgttgatagt atgtactaag ctctcatgtt   4980
```

```
taatgtacta agctctcatg tttaatgaac taaaccctca tggctaatgt actaagctct   5040

catggctaat gtactaagct ctcatgtttc atgtactaag ctctcatgtt tgaacaataa   5100

aattaatata aatcagcaac ttaaatagcc tctaaggttt taagttttat aagaaaaaaa   5160

agaatatata aggcttttaa aggttttaag gtttcctagg ttatcctcat atgagctctt   5220

agaaaaactc atccagcatc aaatgaaact gcaatttatt catatcagga ttatcaatac   5280

catatttttg aaaaagtctt ttctgtaatg aaggagaaaa ctcacccagg cagttccata   5340

ggatggcaag atcctggtat ctgtctgcaa ttccaactct tccaacatca atacaaccta   5400

ttaatttccc ctcatcaaaa ataaggttat caagtgagaa atcaccatga gtgaccactg   5460

aatctggtga gaatggcaaa agattatgca tttctttcca gacttgttca acaggccagc   5520

catttctctc atcatcaaaa tcactggcat caaccaaacc attattcatt cttgattggg   5580

cctgagccag tctaaatact ctatcagagt taaaaggaca attacaaaca ggaatggaat   5640

gcaatcttct caggaacact gccagggcat caacaatatt ttcacctgaa tcaggatatt   5700

cttccaatac ctggaatgct gttttccctg ggatggcagt ggtgagtaac catgcatcat   5760

caggagttct gataaaatgc ttgatggttg gaagaggcat aaattcagtc agccagttta   5820

gtctgaccat ctcatctgta acatcattgg caacagaacc tttgccatgt ttcagaaaca   5880

actctggggc atctggcttc ccatacaatc tatagattgt ggcacctgat tgcccaacat   5940

tatctctagc ccatttatac ccatataaat cagcatccat gttggaattt aatcttggcc   6000

tggagcaaga ggtttctctt tgaatatggc tcatacatgt gcacctccta tagtgagttg   6060

tattatacta tgcagatata ctatgccaat gtttaattgt cag                      6103
```

<210> SEQ ID NO 45
<211> LENGTH: 3977
<212> TYPE: DNA
<213> ORGANISM: Artificial sequence
<220> FEATURE:
<223> OTHER INFORMATION: Synthetic

<400> SEQUENCE: 45

```
cactatgtgt taattaaaat tatctctaag gcatgtgaac tggctgtctt ggttttcatc     60

tgtacttcat ctgctacctc tgtgacctga aacatattta taattccatt aagctgtgca    120

tatgatagat ttatcatatg tattttcctt aaaggatttt tgtaagaact aattgaattg    180

atacctgtaa agtctttatc acactaccca ataaataata aatctctttg ttcagctctc    240

tgtttctata aatatgtacc agttttattg tttttagtgg tagtgatttt attctctttc    300

tatatatata cacacacatg tgtgcattca taaatatata caatttttat gaataaaaaa    360

ttattagcaa tcaatattga aaaccactga tttttgttta tgtgagcaaa cagcagatta    420

aaaggaattt caattgcctg caggacatga attcaattgg ctagcaggag tcaatgggaa    480

aaacccattg gagccaagta cactgactca atagggactt tccattgggt tttgcccagt    540

acataaggtc aatagggggt gagtcaacag gaaagtccca ttggagccaa gtacattgag    600

tcaataggga ctttccaatg ggttttgccc agtacataag gtcaatggga ggtaagccaa    660

tgggtttttc ccattactga catgtatact gagtcattag ggactttcca atgggttttg    720

cccagtacat aaggtcaata ggggtgaatc aacaggaaag tcccattgga gccaagtaca    780

ctgagtcaat agggactttc cattgggttt tgcccagtac aaaaggtcaa tagggggtga    840

gtcaatgggt ttttcccatt attggcacat acataaggtc aataggggtg actagtggag    900
```

-continued aagagcatgc ttgagggctg agtgcccctc agtgggcaga gagcacatgg cccacagtcc 960
ctgagaagtt ggggggaggg gtgggcaatt gaactggtgc ctagagaagg tggggcttgg 1020
gtaaactggg aaagtgatgt ggtgtactgg ctccaccttt ttccccaggg tgggggagaa 1080
ccatatataa gtgcagtagt ctctgtgaac attcaagctt ctgccttctc cctcctgtga 1140
gtttggtaag tcactgactg tctatgcctg ggaaagggtg ggcaggagat ggggcagtgc 1200
aggaaaagtg gcactatgaa ccctgcagcc ctagacaatt gtactaacct tcttctcttt 1260
cctctcctga caggttggta accaagcttt ccatggctgg acctgccacc cagagcccca 1320
tgaagctgat ggccctgcag ctgctgctgt ggcacagtgc actctggaca gtgcaggaag 1380
ccacccccct gggccctgcc agctccctgc cccagagctt cctgctcaag tgcttagagc 1440
aagtgaggaa gatccagggg gatggggcag ctctccagga gaagctgtgt gccacctaca 1500
agctgtgcca ccctgaggag ctggtgctgc tgggacactc tctgggcatc ccctgggctc 1560
ccctgagcag ctgccccagc caggccctgc agctggcagg ctgcttgagc caactccata 1620
gtggcctttt cctctaccag gggctcctgc aggccctgga agggatctcc cctgagttgg 1680
gtcccacctt ggacacactg cagctggatg ttgctgactt tgccaccacc atctggcagc 1740
agatggaaga actgggaatg gcccctgccc tgcagcccac ccagggtgcc atgcctgcct 1800
ttgcctctgc tttccagaga agggcaggag gggtcctggt tgcctcccat ctgcagagct 1860
tcctggaggt gtcctacaga gttctaagac accttgccca gccctgatag atctacttct 1920
ggctaataaa agatcagagc tctagtgatc tgtgtgttgg tttttttgtgt ctgcattcta 1980
gcctgcagga attcagtcaa tatgttcacc ccaaaaaagc tgtttgttaa cttgtcaacc 2040
tcattctaaa atgtatatag aagcccaaaa gacaataaca aaaatattct tgtagaacaa 2100
aatgggaaag aatgttccac taaatatcaa gatttagagc aaagcatgag atgtgtgggg 2160
atagacagtg aggctgataa aatagagtag agctcagaaa cagacccatt gatatatgta 2220
agtgacctat gaaaaaaata tggcatttta caatgggaaa atgatggtct ttttcttttt 2280
tagaaaaaca gggaaatata tttatatgta aaaaataaaa gggaacccat atgtcatacc 2340
atacacacaa aaaaattcca gtgaattata agtctaaatg gagaaggcaa aactttaaat 2400
cttttagaaa ataatataga agcatgccat caagacttca gtgtagagaa aaatttctta 2460
tgactcaaag tcctaaccac aaagaaaaga ttgttaatta gattgcatga atattaagac 2520
ttatttttaa aattaaaaaa ccattaagaa aagtcaggcc atagaatgac agaaaatatt 2580
tgcaacaccc cagtaaagag aattgtaata tgcagattat aaaaagaagt cttacaaatc 2640
agtaaaaaat aaaactagac aaaaatttga acagatgaaa gagaaactct aaataatcat 2700
tacacatgag aaactcaatc tcagaaatca gagaactatc attgcatata cactaaatta 2760
gagaaatatt aaaaggctaa gtaacatctg tggcttaatt aatctagtga tcagcagttc 2820
aacctgttga tagtatgtac taagctctca tgtttaatgt actaagctct catgtttaat 2880
gaactaaacc ctcatggcta atgtactaag ctctcatggc taatgtacta agctctcatg 2940
tttcatgtac taagctctca tgtttgaaca ataaaattaa tataaatcag caacttaaat 3000
agcctctaag gttttaagtt ttataagaaa aaaaagaata tataaggctt ttaaaggttt 3060
taaggtttcc taggttatcc tcatatgagc tcttagaaaa actcatccag catcaaatga 3120
aactgcaatt tattcatatc aggattatca ataccatatt tttgaaaaag tcttttctgt 3180
aatgaaggag aaaactcacc caggcagttc cataggatgg caagatcctg gtatctgtct 3240
gcaattccaa ctcttccaac atcaatacaa cctattaatt tcccctcatc aaaaataagg 3300
ttatcaagtg agaaatcacc atgagtgacc actgaatctg gtgagaatgg caaaagatta 3360
tgcatttctt tccagacttg ttcaacaggc cagccatttc tctcatcatc aaaatcactg 3420
gcatcaacca aaccattatt cattcttgat tgggcctgag ccagtctaaa tactctatca 3480
gagttaaaag gacaattaca aacaggaatg gaatgcaatc ttctcaggaa cactgccagg 3540
gcatcaacaa tattttcacc tgaatcagga tattcttcca atacctggaa tgctgttttc 3600
cctgggatgg cagtggtgag taaccatgca tcatcaggag ttctgataaa atgcttgatg 3660
gttggaagag gcataaattc agtcagccag tttagtctga ccatctcatc tgtaacatca 3720
ttggcaacag aacctttgcc atgtttcaga aacaactctg gggcatctgg cttcccatac 3780
aatctataga ttgtggcacc tgattgccca acattatctc tagcccattt atacccatat 3840
aaatcagcat ccatgttgga atttaatctt ggcctggagc aagaggtttc tctttgaata 3900
tggctcatac atgtgcacct cctatagtga gttgtattat actatgcaga tatactatgc 3960
caatgtttaa ttgtcag 3977

<210> SEQ ID NO 46
<211> LENGTH: 4015
<212> TYPE: DNA
<213> ORGANISM: Artificial sequence
<220> FEATURE:
<223> OTHER INFORMATION: Synthetic

<400> SEQUENCE: 46
cactatgtgt taattaaaat tatctctaag gcatgtgaac tggctgtctt ggttttcatc 60
tgtacttcat ctgctacctc tgtgacctga aacatattta taattccatt aagctgtgca 120
tatgatagat ttatcatatg tattttcctt aaaggatttt tgtaagaact aattgaattg 180
atacctgtaa agtctttatc acactaccca ataaataata aatctctttg ttcagctctc 240
tgtttctata aatatgtacc agttttattg tttttagtgg tagtgatttt attctctttc 300
tatatatata cacacacatg tgtgcattca taaatatata caatttttat gaataaaaaa 360
ttattagcaa tcaatattga aaaccactga tttttgttta tgtgagcaaa cagcagatta 420
aaaggaattt caattgcctg caggacatga attctcatag ctagcatgtt acataactta 480
tggtaaatgg cctgcctggc tgactgccca atgacccctg cccaatgatg tcaataatga 540
tgtatgttcc catgtaatgc caatagggac tttccattga tgtcaatggg tggagtattt 600
atggtaactg cccacttggc agtacatcaa gtgtatcata tgccaagtat gccccctatt 660
gatgtcaatg atggtaaatg gcctgcctgg cattatgccc agtacatgac cttatgggac 720
tttcctactt ggcagtacat ctatgtatta gtcattgcta ttaccatggt gatgggtttt 780
ggcagtacat caatgggtgt ggatagtggt ttgacccatg gggatttcca agtctccacc 840
ccattgatgc caatgggagt ttgttttggc accaaaatca atgggacttt ccaaaatgtt 900
gtaacaactc tgccccattg atggaaatgg gtggtaggtg tgtgtggtgg gaggtctata 960
taagcagagc ttgtttagtg aactggatgc acctactaga tatccatatg gctatcatct 1020
ctccttcaat atccatcatc cctacctgag gcatccatcc aatcatgttg agtatatttc 1080
tgcatcctcc atcctgtggt gcctcctgaa ctgattcatc attctaggta agtttaaagc 1140
tcaggtatag acatggcctt tgtcatgatc tcccttggag cctacctaga ctcatcatgc 1200
tctccaatct ttgcctgacc ctgcttgctc aactctaatt ctttgtttat ttttctgttc 1260
tgatcattta cagatccaag ctgtgacatg atccctacca tatgttggag tgtaggtaac 1320
caagctttcc atggctggac ctgccaccca gagccccatg aagctgatgg ccctgcagct 1380
gctgctgtgg cacagtgcac tctggacagt gcaggaagcc accccccctgg gccctgccag 1440 ctccctgccc cagagcttcc tgctcaagtg cttagagcaa gtgaggaaga tccaggggga 1500
tggggcagct ctccaggaga agctgtgtgc cacctacaag ctgtgccacc ctgaggagct 1560
ggtgctgctg ggacactctc tgggcatccc ctgggctccc ctgagcagct gccccagcca 1620
ggccctgcag ctggcaggct gcttgagcca actccatagt ggccttttcc tctaccaggg 1680
gctcctgcag gccctggaag ggatctcccc tgagttgggt cccaccttgg acacactgca 1740
gctggatgtt gctgactttg ccaccaccat ctggcagcag atggaagaac tgggaatggc 1800
ccctgccctg cagcccaccc agggtgccat gcctgccttt gcctctgctt tccagagaag 1860
ggcaggaggg gtcctggttg cctcccatct gcagagcttc ctggaggtgt cctacagagt 1920
tctaagacac cttgcccagc cctgatagat ctacttctgg ctaataaaag atcagagctc 1980
tagtgatctg tgtgttggtt ttttgtgtct gcattctagc ctgcaggaat tcagtcaata 2040
tgttcacccc aaaaaagctg tttgttaact tgtcaacctc attctaaaat gtatatagaa 2100
gcccaaaaga caataacaaa aatattcttg tagaacaaaa tgggaaagaa tgttccacta 2160
aatatcaaga tttagagcaa agcatgagat gtgtggggat agacagtgag gctgataaaa 2220
tagagtagag ctcagaaaca gacccattga tatatgtaag tgacctatga aaaaaatatg 2280
gcattttaca atgggaaaat gatggtcttt ttcttttta gaaaaacagg gaaatatatt 2340
tatatgtaaa aaataaaagg gaacccatat gtcataccat acacacaaaa aaattccagt 2400
gaattataag tctaaatgga gaaggcaaaa ctttaaatct tttagaaaat aatatagaag 2460
catgccatca agacttcagt gtagagaaaa atttcttatg actcaaagtc ctaaccacaa 2520
agaaaagatt gttaattaga ttgcatgaat attaagactt atttttaaaa ttaaaaaacc 2580
attaagaaaa gtcaggccat agaatgacag aaaatatttg caacacccca gtaaagagaa 2640
ttgtaatatg cagattataa aaagaagtct tacaaatcag taaaaaataa aactagacaa 2700
aaatttgaac agatgaaaga gaaactctaa ataatcatta cacatgagaa actcaatctc 2760
agaaatcaga gaactatcat tgcatataca ctaaattaga gaaatattaa aaggctaagt 2820
aacatctgtg gcttaattaa tctagtgatc agcagttcaa cctgttgata gtatgtacta 2880
agctctcatg tttaatgtac taagctctca tgtttaatga actaaaccct catggctaat 2940
gtactaagct ctcatggcta atgtactaag ctctcatgtt tcatgtacta agctctcatg 3000
tttgaacaat aaaattaata taaatcagca acttaaatag cctctaaggt tttaagtttt 3060
ataagaaaaa aaagaatata taaggctttt aaaggtttta aggtttccta ggttatcctc 3120
atatgagctc ttagaaaaac tcatccagca tcaaatgaaa ctgcaattta ttcatatcag 3180
gattatcaat accatatttt tgaaaaagtc ttttctgtaa tgaaggagaa aactcaccca 3240
ggcagttcca taggatggca agatcctggt atctgtctgc aattccaact cttccaacat 3300
caatacaacc tattaatttc ccctcatcaa aaataaggtt atcaagtgag aaatcaccat 3360
gagtgaccac tgaatctggt gagaatggca aaagattatg catttctttc cagacttgtt 3420
caacaggcca gccatttctc tcatcatcaa aatcactggc atcaaccaaa ccattattca 3480
ttcttgattg ggcctgagcc agtctaaata ctctatcaga gttaaaagga caattacaaa 3540
caggaatgga atgcaatctt ctcaggaaca ctgccagggc atcaacaata ttttcacctg 3600
aatcaggata ttcttccaat acctggaatg ctgttttccc tgggatggca gtggtgagta 3660
accatgcatc atcaggagtt ctgataaaat gcttgatggt tggaagaggc ataaattcag 3720
tcagccagtt tagtctgacc atctcatctg taacatcatt ggcaacagaa cctttgccat 3780
gtttcagaaa caactctggg gcatctggct tcccatacaa tctatagatt gtggcacctg 3840
attgcccaac attatctcta gcccatttat acccatataa atcagcatcc atgttggaat 3900
ttaatcttgg cctggagcaa gaggtttctc tttgaatatg gctcatacat gtgcacctcc 3960
tatagtgagt tgtattatac tatgcagata tactatgcca atgtttaatt gtcag 4015

<210> SEQ ID NO 47
<211> LENGTH: 5014
<212> TYPE: DNA
<213> ORGANISM: Artificial sequence
<220> FEATURE:
<223> OTHER INFORMATION: Synthetic

<400> SEQUENCE: 47
cactatgtgt taattaaaat tatctctaag gcatgtgaac tggctgtctt ggttttcatc 60
tgtacttcat ctgctacctc tgtgacctga aacatattta taattccatt aagctgtgca 120
tatgatagat ttatcatatg tattttcctt aaaggatttt tgtaagaact aattgaattg 180
atacctgtaa agtctttatc acactaccca ataaataata aatctctttg ttcagctctc 240
tgtttctata aatatgtacc agttttattg tttttagtgg tagtgatttt attctctttc 300
tatatatata cacacacatg tgtgcattca taaatatata caatttttat gaataaaaaa 360
ttattagcaa tcaatattga aaaccactga tttttgttta tgtgagcaaa cagcagatta 420
aaaggaattt caattgcctg caggacatga attcaattgg ctagcaggag tcaatgggaa 480
aaacccattg gagccaagta cactgactca atagggactt tccattgggt tttgcccagt 540
acataaggtc aataggggt gagtcaacag gaaagtccca ttggagccaa gtacattgag 600
tcaataggga ctttccaatg ggttttgccc agtacataag gtcaatggga ggtaagccaa 660
tgggtttttc ccattactga catgtatact gagtcattag ggactttcca atgggttttg 720
cccagtacat aaggtcaata ggggtgaatc aacaggaaag tcccattgga gccaagtaca 780
ctgagtcaat agggactttc cattgggttt tgcccagtac aaaaggtcaa taggggtga 840 gtcaatgggt ttttcccatt attggcacat acataaggtc aataggggtg actagtggag 900
aagagcatgc ttgagggctg agtgcccctc agtgggcaga gagcacatgg cccacagtcc 960
ctgagaagtt ggggggaggg gtgggcaatt gaactggtgc ctagagaagg tggggcttgg 1020
gtaaactggg aaagtgatgt ggtgtactgg ctccaccttt ttccccaggg tgggggagaa 1080
ccatatataa gtgcagtagt ctctgtgaac attcaagctt ctgccttctc cctcctgtga 1140
gtttggtaag tcactgactg tctatgcctg ggaaagggtg ggcaggagat ggggcagtgc 1200
aggaaaagtg gcactatgaa ccctgcagcc ctagacaatt gtactaacct tcttctcttt 1260
cctctcctga caggttggta accaagcttt ccatggagga tgctaagaac atcaagaagg 1320
ggcctgcccc cttctacccc ctggaggatg gcacagctgg ggagcagctg cacaaggcta 1380
tgaagagata tgccctggtg cctggcacta ttgccttcac agatgctcac attgaagtgg 1440
acatcaccta tgctgagtac tttgagatgt cagtgaggct ggctgaggct atgaaaagat 1500
atgggctgaa cactaatcac aggattgtgg tgtgttcaga gaactcactg cagttcttca 1560
tgcctgtgct gggagccctg ttcattggag tggctgtggc ccctgctaat gacatctaca 1620
atgagaggga gctgctgaac tctatgggca tcagtcagcc tacagtggtg tttgtgtcta 1680
agaagggcct gcagaaaatc ctgaatgtgc agaagaagct gcctatcatt cagaaaatca 1740

-continued

```
tcatcatgga ctctaagaca gactatcagg gctttcagtc tatgtacacc tttgtgacta   1800
gtcacctgcc ccctggcttc aatgagtatg actttgtgcc tgagtcattt gacagggaca   1860
agactattgc cctgatcatg aactcatcag gctctacagg cctgcctaag ggagtggccc   1920
tgcctcacag gacagcctgt gtgagattca gtcatgctag ggaccctatc tttggcaatc   1980
agatcatccc tgacacagct atcctgtcag tggtgccctt tcatcatggc tttggcatgt   2040
tcactaccct gggctacctg atctgtggct tcagagtggt gctgatgtac agatttgagg   2100
aggagctgtt cctgagatca ctgcaggact acaaaattca gtcagccctg ctggtgccta   2160
ccctgttcag cttctttgct aagtctaccc tgattgacaa gtatgacctg tctaacctgc   2220
atgagattgc ctcaggggga gccccccctgt ctaaggaagt gggggaagct gtggctaaga   2280
gatttcacct gcctggcatc aggcagggct atggcctgac agagactacc tcagctattc   2340
tgatcacccc tgagggggat gacaagcctg ggctgtgggg caaagtggtg cctttctttg   2400
aggctaaagt ggtggacctg gacacaggca agaccctggg agtgaatcag agggggggagc   2460
tgtgtgtgag aggccctatg atcatgtcag gctatgtgaa caaccctgag gctactaatg   2520
ccctgattga taaggatggc tggctgcact caggggacat tgcctactgg gatgaggatg   2580
agcacttctt cattgtggac aggctgaagt cactcatcaa gtacaagggc tatcaagtgg   2640
ccccagctga gttagagtca atcttacttc agcaccctaa catctttgat gctggagtgg   2700
caggcttacc tgatgatgat gctggggagt tacctgctgc tgtggtggtg ttagagcatg   2760
gcaagactat gacagagaaa gagattgtgg attatgtggc tagtcaagtc actacagcta   2820
agaagctcag ggggggagtg gtctttgtgg atgaagtgcc taagggcctc acaggcaagt   2880
tagatgctag gaagatcagg gagatcctca tcaaggctaa gaagggggggc aagattgctg   2940
tttaaagatc tacttctggc taataaaaga tcagagctct agtgatctgt gtgttggttt   3000
tttgtgtctg cattctagcc tgcaggaatt cagtcaatat gttcacccca aaaaagctgt   3060
ttgttaactt gtcaacctca ttctaaaatg tatatagaag cccaaaagac aataacaaaa   3120
atattcttgt agaacaaaat gggaaagaat gttccactaa atatcaagat ttagagcaaa   3180
gcatgagatg tgtggggata gacagtgagg ctgataaaat agagtagagc tcagaaacag   3240
acccattgat atatgtaagt gacctatgaa aaaaatatgg cattttacaa tgggaaaatg   3300
atggtctttt tctttttttag aaaaacaggg aaatatattt atatgtaaaa aataaaaggg   3360
aacccatatg tcataccata cacacaaaaa aattccagtg aattataagt ctaaatggag   3420
aaggcaaaac tttaaatctt ttagaaaata atatagaagc atgccatcaa gacttcagtg   3480
tagagaaaaa tttcttatga ctcaaagtcc taaccacaaa gaaaagattg ttaattagat   3540
tgcatgaata ttaagactta tttttaaaat taaaaaacca ttaagaaaag tcaggccata   3600
gaatgacaga aaatatttgc aacaccccag taaagagaat tgtaatatgc agattataaa   3660
aagaagtctt acaaatcagt aaaaaataaa actagacaaa aatttgaaca gatgaaagag   3720
aaactctaaa taatcattac acatgagaaa ctcaatctca gaaatcagag aactatcatt   3780
gcatatacac taaattagag aaatattaaa aggctaagta acatctgtgg cttaattaat   3840
ctagtgatca gcagttcaac ctgttgatag tatgtactaa gctctcatgt ttaatgtact   3900
aagctctcat gtttaatgaa ctaaaccctc atggctaatg tactaagctc tcatggctaa   3960
tgtactaagc tctcatgttt catgtactaa gctctcatgt ttgaacaata aaattaatat   4020
aaatcagcaa cttaaatagc ctctaaggtt ttaagtttta taagaaaaaa aagaatatat   4080
aaggctttta aaggttttaa ggtttcctag gttatcctca tatgagctct tagaaaaact   4140
```

catccagcat caaatgaaac tgcaatttat tcatatcagg attatcaata ccatattttt 4200
gaaaaagtct tttctgtaat gaaggagaaa actcacccag gcagttccat aggatggcaa 4260
gatcctggta tctgtctgca attccaactc ttccaacatc aatacaacct attaatttcc 4320
cctcatcaaa aataaggtta tcaagtgaga aatcaccatg agtgaccact gaatctggtg 4380
agaatggcaa aagattatgc atttctttcc agacttgttc aacaggccag ccatttctct 4440
catcatcaaa atcactggca tcaaccaaac cattattcat tcttgattgg gcctgagcca 4500
gtctaaatac tctatcagag ttaaaaggac aattacaaac aggaatggaa tgcaatcttc 4560
tcaggaacac tgccagggca tcaacaatat tttcacctga atcaggatat tcttccaata 4620
cctggaatgc tgttttccct gggatggcag tggtgagtaa ccatgcatca tcaggagttc 4680
tgataaaatg cttgatggtt ggaagaggca taaattcagt cagccagttt agtctgacca 4740
tctcatctgt aacatcattg gcaacagaac ctttgccatg tttcagaaac aactctgggg 4800
catctggctt cccatacaat ctatagattg tggcacctga ttgcccaaca ttatctctag 4860
cccatttata cccatataaa tcagcatcca tgttggaatt taatcttggc ctggagcaag 4920
aggtttctct ttgaatatgg ctcatacatg tgcacctcct atagtgagtt gtattatact 4980
atgcagatat actatgccaa tgtttaattg tcag 5014

<210> SEQ ID NO 48
<211> LENGTH: 4392
<212> TYPE: DNA
<213> ORGANISM: Artificial sequence
<220> FEATURE:
<223> OTHER INFORMATION: Synthetic

<400> SEQUENCE: 48
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc acctttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg ggactgggac tccagtgggt gttctttgtg gccctgctga 900
aaggggtgca ctgtgaagtc agactgctgg aaagtggtgg tggcctggtc aagccagagg 960
gctctctgaa gctgagctgt gtggcttctg gcttcacctt ctctgactac ttcatgagct 1020
gggtcagaca ggcccctggc aaaggccttg aatgggttgc ccacatctac accaagagct 1080
acaactatgc cacctactac tctggctctg tgaagggcag attcaccatc agcagagatg 1140

-continued

```
acagcagatc catggtgtac ctccagatga acaacctgag aacagaggac acagccacct   1200
attactgcac cagagatggc tctggctacc ccagcctgga tttttggggc cagggcaccc   1260
aagtgacagt cagctctgcc acaaccacag ctccctctgt gtacccactg gctccagcct   1320
gtgacagcac cacaaagtct gccagcacaa agggcccatc tgtgttccct ctggcaccca   1380
gcagcaagtc taccagtggt ggaacagctg ccctgggctg tctggtcaag gactactttc   1440
ctgagccagt gacagtgtcc tggaactctg ggctctgac atctggggtg cacacattcc   1500
ctgctgtgct ccagtcctct ggcctgtaca gcctcagctc tgtggtcaca gtgcctagct   1560
ctagcctggg cacccagacc tacatctgca atgtgaacca caagcctagc aacaccaagg   1620
tggacaagaa ggctgagccc aagagctgtg acaagaccca cacctgtcct ccatgtcctg   1680
ctccagagct gcttggagga ccttctgtgt ttctgttccc tccaaagcca aaggacaccc   1740
tgatgatcag cagaacccct gaagtgacat gtgtggtggt tgatgtgtcc catgaggacc   1800
cagaagtgaa gttcaattgg tatgtggatg gtgttgaggt gcacaatgcc aagaccaagc   1860
ctagagagga acagtacaac agcacctaca gagtggtgtc tgtgctgaca gtgctgcatc   1920
aggactggct gaatggcaaa gagtacaagt gcaaggtgtc caacaaggcc ctgcctgctc   1980
ctattgaaaa gaccatctcc aaggccaagg gccagcctag ggaaccccag gtttacacac   2040
tgccacctag cagggatgag ctgaccaaga accaggtgtc cctgacctgc ctggttaagg   2100
gcttctaccc ctctgacatt gctgtggaat gggagagcaa tggccagcca gagaacaact   2160
acaagacaac ccctcctgtg ctggactctg atggctcatt cttcctgtac tccaagctca   2220
cagtggacaa gtccagatgg cagcaaggca atgtgttcag ctgctctgtg atgcatgagg   2280
ccctgcacaa ccactacaca cagaagtccc tgagcctgtc tcctggcaag agaaagagaa   2340
ggagtggaag tggagctact aacttcagcc tgctgaagca ggctggagat gtggaggaga   2400
accctggacc tatggacttc caggtgcaga tcatcagctt tctgctgatc tctgcctctg   2460
tgatcatgag cagaggctat gagctgaccc agcctccttc tgcttctgtg aatgtgggag   2520
aagctgtgaa gatcacctgt tctggggacc agctgcctaa gtactttgct gactggttcc   2580
accagaggag tgaccagacc atcctgcaag tgatctatga tgacaacaag aggccctctg   2640
gcatccctga gagaatctct ggcagcagct ctggcaccac agccacactg accatcagag   2700
atgtcagagc tgaggatgaa ggggactact actgcttctc tggctatgtg gactctgaca   2760
gcaagctgta tgtgtttggc agtggcaccc agctgacagt gcttggagga cccaagagca   2820
gaacagtggc tgccccttct gtgttcatct tcccaccatc tgatgagcag ctgaagtctg   2880
gcacagcctc tgttgtgtgc ctgctgaaca acttctaccc tagagaagcc aaggtgcagt   2940
ggaaggtgga caatgccctc cagtctggca actcccaaga gtctgtgaca gagcaggaca   3000
gcaaggactc cacctacagc ctgagcagca ccctgacact gagcaaggct gactatgaga   3060
agcacaaagt ctatgcctgt gaagtgaccc accagggcct gtctagccct gtgaccaaga   3120
gcttcaacag gggagagagc tgaagatcta cttctggcta ataaaagatc agagctctag   3180
tgatctgtgt gttggttttt tgtgtctgca ttctagctct agtgatcagc agttcaacct   3240
gttgatagta tgtactaagc tctcatgttt aatgtactaa gctctcatgt ttaatgaact   3300
aaaccctcat ggctaatgta ctaagctctc atggctaatg tactaagctc tcatgtttca   3360
tgtactaagc tctcatgttt gaacaataaa attaatataa atcagcaact taaatagcct   3420
ctaaggtttt aagttttata agaaaaaaaa gaatatataa ggcttttaaa ggttttaagg   3480
tttcctaggt tatcctcata tgagctctta gaaaaactca tccagcatca aatgaaactg   3540
```

caatttattc atatcaggat tatcaatacc atatttttga aaaagtcttt tctgtaatga 3600
aggagaaaac tcacccaggc agttccatag gatggcaaga tcctggtatc tgtctgcaat 3660
tccaactctt ccaacatcaa tacaacctat taatttcccc tcatcaaaaa taaggttatc 3720
aagtgagaaa tcaccatgag tgaccactga atctggtgag aatggcaaaa gattatgcat 3780
ttctttccag acttgttcaa caggccagcc atttctctca tcatcaaaat cactggcatc 3840
aaccaaacca ttattcattc ttgattgggc ctgagccagt ctaaatactc tatcagagtt 3900
aaaaggacaa ttacaaacag gaatggaatg caatcttctc aggaacactg ccagggcatc 3960
aacaatattt tcacctgaat caggatattc ttccaatacc tggaatgctg ttttccctgg 4020
gatggcagtg gtgagtaacc atgcatcatc aggagttctg ataaaatgct tgatggttgg 4080
aagaggcata aattcagtca gccagtttag tctgaccatc tcatctgtaa catcattggc 4140
aacagaacct ttgccatgtt tcagaaacaa ctctggggca tctggcttcc catacaatct 4200
atagattgtg gcacctgatt gcccaacatt atctctagcc catttatacc catataaatc 4260
agcatccatg ttggaattta atcttggcct ggagcaagag gtttctcttt gaatatggct 4320
catacatgtg cacctcctat agtgagttgt attatactat gcagatatac tatgccaatg 4380
tttaattgtc ag 4392

<210> SEQ ID NO 49
<211> LENGTH: 2376
<212> TYPE: DNA
<213> ORGANISM: Artificial sequence
<220> FEATURE:
<223> OTHER INFORMATION: Synthetic

<400> SEQUENCE: 49
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg agagtgacag cccctagaac agtcctgctg ctcctgtctg 900
ctgccctggc tctgacagaa acatgggctg gcagcagcat catcaacttt gagaagctga 960
ttgtgggcat tgtggctggc ctggctgtgc tggcagtggt ggttattgga gctgtggtgg 1020
ctgctgtgat gtgcagaaga aagtcctctg gaggcaaagg tggcagctac tcccaggctg 1080
cctgttctga ttctgcccag ggctctgatg tgtccctgac agcttaaaga tctacttctg 1140
gctaataaaa gatcagagct ctagtgatct gtgtgttggt tttttgtgtc tgcattctag 1200
ctctagtgat cagcagttca acctgttgat agtatgtact aagctctcat gtttaatgta 1260
ctaagctctc atgtttaatg aactaaaccc tcatggctaa tgtactaagc tctcatggct 1320
aatgtactaa gctctcatgt ttcatgtact aagctctcat gtttgaacaa taaaattaat 1380
ataaatcagc aacttaaata gcctctaagg ttttaagttt tataagaaaa aaaagaatat 1440
ataaggcttt taaaggtttt aaggtttcct aggttatcct catatgagct cttagaaaaa 1500
ctcatccagc atcaaatgaa actgcaattt attcatatca ggattatcaa taccatattt 1560
ttgaaaaagt cttttctgta atgaaggaga aaactcaccc aggcagttcc ataggatggc 1620
aagatcctgg tatctgtctg caattccaac tcttccaaca tcaatacaac ctattaattt 1680
cccctcatca aaaataaggt tatcaagtga gaaatcacca tgagtgacca ctgaatctgg 1740
tgagaatggc aaaagattat gcatttcttt ccagacttgt tcaacaggcc agccatttct 1800
ctcatcatca aaatcactgg catcaaccaa accattattc attcttgatt gggcctgagc 1860
cagtctaaat actctatcag agttaaaagg acaattacaa acaggaatgg aatgcaatct 1920
tctcaggaac actgccaggg catcaacaat attttcacct gaatcaggat attcttccaa 1980
tacctggaat gctgttttcc ctgggatggc agtggtgagt aaccatgcat catcaggagt 2040
tctgataaaa tgcttgatgg ttggaagagg cataaattca gtcagccagt ttagtctgac 2100
catctcatct gtaacatcat tggcaacaga acctttgcca tgtttcagaa acaactctgg 2160
ggcatctggc ttcccataca atctatagat tgtggcacct gattgcccaa cattatctct 2220
agcccattta tacccatata aatcagcatc catgttggaa tttaatcttg gcctggagca 2280
agaggtttct ctttgaatat ggctcataca tgtgcacctc ctatagtgag ttgtattata 2340
ctatgcagat atactatgcc aatgtttaat tgtcag 2376

<210> SEQ ID NO 50
<211> LENGTH: 2379
<212> TYPE: DNA
<213> ORGANISM: Artificial sequence
<220> FEATURE:
<223> OTHER INFORMATION: Synthetic

<400> SEQUENCE: 50
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg agagtgacag cccctagaac agtcctgctg ctcctgtctg 900
ctgccctggc tctgacagaa acatgggctg gcagcagccc cagctatgcc taccaccagt 960
tcattgtggg cattgtggct ggcctggctg tgctggcagt ggtggttatt ggagctgtgg 1020
tggctgctgt gatgtgcaga agaaagtcct ctggaggcaa aggtggcagc tactcccagg 1080
ctgcctgttc tgattctgcc cagggctctg atgtgtccct gacagcttaa agatctactt 1140
ctggctaata aaagatcaga gctctagtga tctgtgtgtt ggttttttgt gtctgcattc 1200
tagctctagt gatcagcagt tcaacctgtt gatagtatgt actaagctct catgtttaat 1260
gtactaagct ctcatgttta atgaactaaa ccctcatggc taatgtacta agctctcatg 1320
gctaatgtac taagctctca tgtttcatgt actaagctct catgtttgaa caataaaatt 1380
aatataaatc agcaacttaa atagcctcta aggttttaag ttttataaga aaaaaaagaa 1440
tatataaggc ttttaaaggt tttaaggttt cctaggttat cctcatatga gctcttagaa 1500
aaactcatcc agcatcaaat gaaactgcaa tttattcata tcaggattat caataccata 1560
tttttgaaaa agtcttttct gtaatgaagg agaaaactca cccaggcagt tccataggat 1620
ggcaagatcc tggtatctgt ctgcaattcc aactcttcca acatcaatac aacctattaa 1680
tttcccctca tcaaaaataa ggttatcaag tgagaaatca ccatgagtga ccactgaatc 1740
tggtgagaat ggcaaaagat tatgcatttc tttccagact tgttcaacag gccagccatt 1800
tctctcatca tcaaaatcac tggcatcaac caaaccatta ttcattcttg attgggcctg 1860
agccagtcta aatactctat cagagttaaa aggacaatta caaacaggaa tggaatgcaa 1920
tcttctcagg aacactgcca gggcatcaac aatattttca cctgaatcag gatattcttc 1980
caatacctgg aatgctgttt tccctgggat ggcagtggtg agtaaccatg catcatcagg 2040
agttctgata aaatgcttga tggttggaag aggcataaat tcagtcagcc agtttagtct 2100
gaccatctca tctgtaacat cattggcaac agaacctttg ccatgtttca gaaacaactc 2160
tggggcatct ggcttcccat acaatctata gattgtggca cctgattgcc caacattatc 2220
tctagcccat ttatacccat ataaatcagc atccatgttg gaatttaatc ttggcctgga 2280
gcaagaggtt tctctttgaa tatggctcat acatgtgcac ctcctatagt gagttgtatt 2340
atactatgca gatatactat gccaatgttt aattgtcag 2379

<210> SEQ ID NO 51
<211> LENGTH: 5466
<212> TYPE: DNA
<213> ORGANISM: Artificial sequence
<220> FEATURE:
<223> OTHER INFORMATION: Synthetic

<400> SEQUENCE: 51
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480

-continued

```
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc accttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg ggactgggac tccagtgggt gttctttgtg gccctgctga    900
aaggggtgca ctgtgaagtc agactgctgg aaagtggtgg tggcctggtc aagccagagg    960
gctctctgaa gctgagctgt gtggcttctg gcttcacctt ctctgactac ttcatgagct   1020
gggtcagaca ggcccctggc aaaggccttg aatgggttgc ccacatctac accaagagct   1080
acaactatgc cacctactac tctggctctg tgaagggcag attcaccatc agcagagatg   1140
acagcagatc catggtgtac ctccagatga acaacctgag aacagaggac acagccacct   1200
attactgcac cagagatggc tctggctacc ccagcctgga tttttggggc cagggcaccc   1260
aagtgacagt cagctctgcc acaaccacag ctccctctgt gtacccactg gctccagcct   1320
gtgacagcac cacaaagtct gccagcacaa agggcccatc tgtgttccct ctggcaccca   1380
gcagcaagtc taccagtggt ggaacagctg ccctgggctg tctggtcaag gactactttc   1440
ctgagccagt gacagtgtcc tggaactctg gggctctgac atctggggtg cacacattcc   1500
ctgctgtgct ccagtcctct ggcctgtaca gcctcagctc tgtggtcaca gtgcctagct   1560
ctagcctggg cacccagacc tacatctgca atgtgaacca caagcctagc aacaccaagg   1620
tggacaagaa ggctgagccc aagagctgtg acaagaccca cacctgtcct ccatgtcctg   1680
ctccagagct gcttggagga ccttctgtgt ttctgttccc tccaaagcca aaggacaccc   1740
tgatgatcag cagaacccct gaagtgacat gtgtggtggt tgatgtgtcc catgaggacc   1800
cagaagtgaa gttcaattgg tatgtggatg gtgttgaggt gcacaatgcc aagaccaagc   1860
ctagagagga acagtacaac agcacctaca gagtggtgtc tgtgctgaca gtgctgcatc   1920
aggactggct gaatggcaaa gagtacaagt gcaaggtgtc caacaaggcc ctgcctgctc   1980
ctattgaaaa gaccatctcc aaggccaagg gccagcctag ggaaccccag gtttacacac   2040
tgccacctag cagggatgag ctgaccaaga accaggtgtc cctgacctgc ctggttaagg   2100
gcttctaccc ctctgacatt gctgtggaat gggagagcaa tggccagcca gagaacaact   2160
acaagacaac ccctcctgtg ctggactctg atggctcatt cttcctgtac tccaagctca   2220
cagtggacaa gtccagatgg cagcaaggca atgtgttcag ctgctctgtg atgcatgagg   2280
ccctgcacaa ccactacaca cagaagtccc tgagcctgtc tcctggcaag agaaagagaa   2340
ggagtggaag tggagctact aacttcagcc tgctgaagca ggctggagat gtggaggaga   2400
accctggacc tatggacttc caggtgcaga tcatcagctt tctgctgatc tctgcctctg   2460
tgatcatgag cagaggctat gagctgaccc agcctccttc tgcttctgtg aatgtgggag   2520
aagctgtgaa gatcacctgt tctggggacc agctgcctaa gtactttgct gactggttcc   2580
accagaggag tgaccagacc atcctgcaag tgatctatga tgacaacaag aggccctctg   2640
gcatccctga gagaatctct ggcagcagct ctggcaccac agccacactg accatcagag   2700
atgtcagagc tgaggatgaa ggggactact actgcttctc tggctatgtg gactctgaca   2760
gcaagctgta tgtgtttggc agtggcaccc agctgacagt gcttggagga cccaagagca   2820
gaacagtggc tgccccttct gtgttcatct tcccaccatc tgatgagcag ctgaagtctg   2880
```

```
gcacagcctc tgttgtgtgc ctgctgaaca acttctaccc tagagaagcc aaggtgcagt   2940
ggaaggtgga caatgccctc cagtctggca actcccaaga gtctgtgaca gagcaggaca   3000
gcaaggactc cacctacagc ctgagcagca ccctgacact gagcaaggct gactatgaga   3060
agcacaaagt ctatgcctgt gaagtgaccc accagggcct gtctagccct gtgaccaaga   3120
gcttcaacag gggagagagc tgaagatcta cttctggcta ataaaagatc agagctctag   3180
tgatctgtgt gttggttttt tgtgtctgca ttctagcatg ttacataact tatggtaaat   3240
ggcctgcctg gctgactgcc caatgacccc tgcccaatga tgtcaataat gatgtatgtt   3300
cccatgtaat gccaataggg actttccatt gatgtcaatg ggtggagtat ttatggtaac   3360
tgcccacttg gcagtacatc aagtgtatca tatgccaagt atgcccccta ttgatgtcaa   3420
tgatggtaaa tggcctgcct ggcattatgc ccagtacatg accttatggg actttcctac   3480
ttggcagtac atctatgtat tagtcattgc tattaccatg gattagtgga gaagagcatg   3540
cttgagggct gagtgcccct cagtgggcag agagcacatg gcccacagtc cctgagaagt   3600
tgggggggagg ggtgggcaat tgaactggtg cctagagaag gtggggcttg ggtaaactgg   3660
gaaagtgatg tggtgtactg gctccacctt tttccccagg gtgggggaga accatatata   3720
agtgcagtag tctctgtgaa cattcaagct tctgccttct ccctcctgtg agtttggatg   3780
cacctactag atatcttggt aagtcactga ctgtctatgc ctgggaaagg gtgggcagga   3840
ggtggggcag tgcaggaaaa gtggcactgt gaaccctgca gccctagaca attgtactaa   3900
ccttcttctc tttcctctcc tgacaggttg gtaaccaagc caccatgaga gtgacagccc   3960
ctagaacagt cctgctgctc ctgtctgctg ccctggctct gacagaaaca tgggctggca   4020
gcagccccag ctatgcctac caccagttca ttgtgggcat tgtggctggc ctggctgtgc   4080
tggcagtggt ggttattgga gctgtggtgg ctgctgtgat gtgcagaaga aagtcctctg   4140
gaggcaaagg tggcagctac tcccaggctg cctgttctga ttctgcccag ggctctgatg   4200
tgtccctgac agcttaaaga tctacttctg gctaataaaa gatcagagct ctagtgatct   4260
gtgtgttggt tttttgtgtc tgcattctag ctctagtgat cagcagttca acctgttgat   4320
agtatgtact aagctctcat gtttaatgta ctaagctctc atgtttaatg aactaaaccc   4380
tcatggctaa tgtactaagc tctcatggct aatgtactaa gctctcatgt ttcatgtact   4440
aagctctcat gtttgaacaa taaaattaat ataaatcagc aacttaaata gcctctaagg   4500
ttttaagttt tataagaaaa aaaagaatat ataaggcttt taaaggtttt aaggtttcct   4560
aggttatcct catatgagct cttagaaaaa ctcatccagc atcaaatgaa actgcaattt   4620
attcatatca ggattatcaa taccatattt ttgaaaaagt cttttctgta atgaaggaga   4680
aaactcaccc aggcagttcc ataggatggc aagatcctgg tatctgtctg caattccaac   4740
tcttccaaca tcaatacaac ctattaattt cccctcatca aaaataaggt tatcaagtga   4800
gaaatcacca tgagtgacca ctgaatctgg tgagaatggc aaaagattat gcatttcttt   4860
ccagacttgt tcaacaggcc agccatttct ctcatcatca aaatcactgg catcaaccaa   4920
accattattc attcttgatt gggcctgagc cagtctaaat actctatcag agttaaaagg   4980
acaattacaa acaggaatgg aatgcaatct tctcaggaac actgccaggg catcaacaat   5040
attttcacct gaatcaggat attcttccaa tacctggaat gctgttttcc ctgggatggc   5100
agtggtgagt aaccatgcat catcaggagt tctgataaaa tgcttgatgg ttggaagagg   5160
cataaattca gtcagccagt ttagtctgac catctcatct gtaacatcat tggcaacaga   5220
```

acctttgcca tgtttcagaa acaactctgg ggcatctggc ttcccataca atctatagat 5280
tgtggcacct gattgcccaa cattatctct agcccattta tacccatata aatcagcatc 5340
catgttggaa tttaatcttg gcctggagca agaggtttct ctttgaatat ggctcataca 5400
tgtgcacctc ctatagtgag ttgtattata ctatgcagat atactatgcc aatgtttaat 5460
tgtcag 5466

<210> SEQ ID NO 52
<211> LENGTH: 5463
<212> TYPE: DNA
<213> ORGANISM: Artificial sequence
<220> FEATURE:
<223> OTHER INFORMATION: Synthetic

<400> SEQUENCE: 52
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg ggactgggac tccagtgggt gttctttgtg gccctgctga 900
aaggggtgca ctgtgaagtc agactgctgg aaagtggtgg tggcctggtc aagccagagg 960
gctctctgaa gctgagctgt gtggcttctg gcttcacctt ctctgactac ttcatgagct 1020
gggtcagaca ggcccctggc aaaggccttg aatgggttgc ccacatctac accaagagct 1080
acaactatgc cacctactac tctggctctg tgaagggcag attcaccatc agcagagatg 1140
acagcagatc catggtgtac ctccagatga acaacctgag aacagaggac acagccacct 1200
attactgcac cagagatggc tctggctacc ccagcctgga tttttggggc cagggcaccc 1260
aagtgacagt cagctctgcc acaaccacag ctccctctgt gtacccactg gctccagcct 1320
gtgacagcac cacaaagtct gccagcacaa agggcccatc tgtgttccct ctggcaccca 1380
gcagcaagtc taccagtggt ggaacagctg ccctgggctg tctggtcaag gactactttc 1440
ctgagccagt gacagtgtcc tggaactctg ggctctgac atctggggtg cacacattcc 1500
ctgctgtgct ccagtcctct ggcctgtaca gcctcagctc tgtggtcaca gtgcctagct 1560
ctagcctggg cacccagacc tacatctgca atgtgaacca caagcctagc aacaccaagg 1620
tggacaagaa ggctgagccc aagagctgtg acaagaccca cacctgtcct ccatgtcctg 1680
ctccagagct gcttggagga ccttctgtgt ttctgttccc tccaaagcca aaggacaccc 1740
tgatgatcag cagaacccct gaagtgacat gtgtggtggt tgatgtgtcc catgaggacc 1800

-continued

```
cagaagtgaa gttcaattgg tatgtggatg gtgttgaggt gcacaatgcc aagaccaagc   1860
ctagagagga acagtacaac agcacctaca gagtggtgtc tgtgctgaca gtgctgcatc   1920
aggactggct gaatggcaaa gagtacaagt gcaaggtgtc caacaaggcc ctgcctgctc   1980
ctattgaaaa gaccatctcc aaggccaagg gccagcctag ggaaccccag gtttacacac   2040
tgccacctag cagggatgag ctgaccaaga accaggtgtc cctgacctgc ctggttaagg   2100
gcttctaccc ctctgacatt gctgtggaat gggagagcaa tggccagcca gagaacaact   2160
acaagacaac ccctcctgtg ctggactctg atggctcatt cttcctgtac tccaagctca   2220
cagtggacaa gtccagatgg cagcaaggca atgtgttcag ctgctctgtg atgcatgagg   2280
ccctgcacaa ccactacaca cagaagtccc tgagcctgtc tcctggcaag agaaagagaa   2340
ggagtggaag tggagctact aacttcagcc tgctgaagca ggctggagat gtggaggaga   2400
accctggacc tatggacttc caggtgcaga tcatcagctt tctgctgatc tctgcctctg   2460
tgatcatgag cagaggctat gagctgaccc agcctccttc tgcttctgtg aatgtgggag   2520
aagctgtgaa gatcacctgt tctggggacc agctgcctaa gtactttgct gactggttcc   2580
accagaggag tgaccagacc atcctgcaag tgatctatga tgacaacaag aggccctctg   2640
gcatccctga gagaatctct ggcagcagct ctggcaccac agccacactg accatcagag   2700
atgtcagagc tgaggatgaa ggggactact actgcttctc tggctatgtg gactctgaca   2760
gcaagctgta tgtgtttggc agtggcaccc agctgacagt gcttggagga cccaagagca   2820
gaacagtggc tgccccttct gtgttcatct tcccaccatc tgatgagcag ctgaagtctg   2880
gcacagcctc tgttgtgtgc ctgctgaaca acttctaccc tagagaagcc aaggtgcagt   2940
ggaaggtgga caatgccctc cagtctggca actcccaaga gtctgtgaca gagcaggaca   3000
gcaaggactc cacctacagc ctgagcagca ccctgacact gagcaaggct gactatgaga   3060
agcacaaagt ctatgcctgt gaagtgaccc accagggcct gtctagccct gtgaccaaga   3120
gcttcaacag gggagagagc tgaagatcta cttctggcta ataaaagatc agagctctag   3180
tgatctgtgt gttggttttt tgtgtctgca ttctagcatg ttacataact tatggtaaat   3240
ggcctgcctg gctgactgcc caatgacccc tgcccaatga tgtcaataat gatgtatgtt   3300
cccatgtaat gccaataggg actttccatt gatgtcaatg ggtggagtat ttatggtaac   3360
tgcccacttg gcagtacatc aagtgtatca tatgccaagt atgcccccta ttgatgtcaa   3420
tgatggtaaa tggcctgcct ggcattatgc ccagtacatg accttatggg actttcctac   3480
ttggcagtac atctatgtat tagtcattgc tattaccatg gattagtgga gaagagcatg   3540
cttgagggct gagtgcccct cagtgggcag agagcacatg gcccacagtc cctgagaagt   3600
tggggggagg ggtgggcaat tgaactggtg cctagagaag gtggggcttg ggtaaactgg   3660
gaaagtgatg tggtgtactg gctccacctt tttccccagg gtgggggaga accatatata   3720
agtgcagtag tctctgtgaa cattcaagct tctgccttct ccctcctgtg agtttggatg   3780
cacctactag atatcttggt aagtcactga ctgtctatgc ctgggaaagg gtgggcagga   3840
ggtggggcag tgcaggaaaa gtggcactgt gaaccctgca gccctagaca attgtactaa   3900
ccttcttctc tttcctctcc tgacaggttg gtaaccaagc caccatgaga gtgacagccc   3960
ctagaacagt cctgctgctc ctgtctgctg ccctggctct gacagaaaca tgggctggca   4020
gcagcatcat caactttgag aagctgattg tgggcattgt ggctggcctg gctgtgctgg   4080
cagtggtggt tattggagct gtggtggctg ctgtgatgtg cagaagaaag tcctctggag   4140
```

gcaaaggtgg cagctactcc caggctgcct gttctgattc tgcccagggc tctgatgtgt 4200
ccctgacagc ttaaagatct acttctggct aataaaagat cagagctcta gtgatctgtg 4260
tgttggtttt ttgtgtctgc attctagctc tagtgatcag cagttcaacc tgttgatagt 4320
atgtactaag ctctcatgtt taatgtacta agctctcatg tttaatgaac taaaccctca 4380
tggctaatgt actaagctct catggctaat gtactaagct ctcatgtttc atgtactaag 4440
ctctcatgtt tgaacaataa aattaatata aatcagcaac ttaaatagcc tctaaggttt 4500
taagttttat aagaaaaaaa agaatatata aggcttttaa aggttttaag gtttcctagg 4560
ttatcctcat atgagctctt agaaaaactc atccagcatc aaatgaaact gcaatttatt 4620
catatcagga ttatcaatac catatttttg aaaaagtctt ttctgtaatg aaggagaaaa 4680
ctcacccagg cagttccata ggatggcaag atcctggtat ctgtctgcaa ttccaactct 4740
tccaacatca atacaaccta ttaatttccc ctcatcaaaa ataaggttat caagtgagaa 4800
atcaccatga gtgaccactg aatctggtga gaatggcaaa agattatgca tttctttcca 4860
gacttgttca acaggccagc catttctctc atcatcaaaa tcactggcat caaccaaacc 4920
attattcatt cttgattggg cctgagccag tctaaatact ctatcagagt taaaaggaca 4980
attacaaaca ggaatggaat gcaatcttct caggaacact gccagggcat caacaatatt 5040
ttcacctgaa tcaggatatt cttccaatac ctggaatgct gttttccctg ggatggcagt 5100
ggtgagtaac catgcatcat caggagttct gataaaatgc ttgatggttg gaagaggcat 5160
aaattcagtc agccagttta gtctgaccat ctcatctgta acatcattgg caacagaacc 5220
tttgccatgt ttcagaaaca actctggggc atctggcttc ccatacaatc tatagattgt 5280
ggcacctgat tgcccaacat tatctctagc ccatttatac ccatataaat cagcatccat 5340
gttggaattt aatcttggcc tggagcaaga ggtttctctt tgaatatggc tcatacatgt 5400
gcacctccta tagtgagttg tattatacta tgcagatata ctatgccaat gtttaattgt 5460
cag 5463

<210> SEQ ID NO 53
<211> LENGTH: 9477
<212> TYPE: DNA
<213> ORGANISM: Artificial sequence
<220> FEATURE:
<223> OTHER INFORMATION: Synthetic

<400> SEQUENCE: 53
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc acctttttcc ccagggtggg ggagaaccat atataagtgc 660
agtagtctct gtgaacattc aagcttctgc cttctccctc ctgtgagttt ggtaagtcac 720

-continued

```
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg ggctggtccc tgatcctgct gttcctggtg gctgtggcca    900
ccagagtgct gagccaggtg cagctgcagc agcctggggc tgagcttgtg aaacctgggg    960
cctctgtgaa gatgagctgc aaggcctctg gctacacctt caccagctac aacatgcact   1020
gggtcaagca gacccctggc agaggcctgg aatggattgg agccatctac cctggcaatg   1080
gggacacctc ctacaaccag aagttcaagg gcaaggccac cctgacagct gacaagagca   1140
gcagcacagc ctacatgcag ctgtccagcc tgacctctga ggactctgct gtgtactact   1200
gtgccaggtc cacctactat gggggagact ggtacttcaa tgtgtgggga gctggcacca   1260
cagtgacagt gtctgctgcc agcaccaagg gcccctctgt gtttcctctg gcccccagca   1320
gcaagagcac ctctggggga acagctgccc tgggctgcct tgtgaaggac tacttccctg   1380
agcctgtgac tgtgtcctgg aactctgggg ccctgacatc tggggtgcac accttccctg   1440
cagtgctgca gtccagtggc ctgtactccc tgtcctctgt tgtgacagtg cccagctcca   1500
gcctgggcac ccagacctac atctgcaatg tgaaccacaa gcccagcaac accaaggtgg   1560
acaagaaggc tgagcccaag agctgtgaca agacccacac ctgtcccccc tgtcctgccc   1620
ctgaactgct gggaggacct tctgtgttcc tgttcccacc caagcccaag gataccctga   1680
tgatcagcag aacccctgaa gtgacctgtg tggtggtgga tgtgtcccat gaggacccag   1740
aagtgaagtt caattggtat gtggatgggg tggaagtgca caatgccaag accaagccca   1800
gagaggaaca gtacaacagc acctacagag tggtgtctgt gctgactgtg ctgcaccagg   1860
actggctgaa tggcaaagag tacaagtgca aggtgtccaa caaggccctg ccagccccca   1920
ttgagaaaac catcagcaag gccaagggcc agcctagaga accccaggtg tacacactgc   1980
cccctagcag ggatgagctg accaagaacc aggtgtccct gacatgcctt gtgaaaggct   2040
tctacccctc tgacattgct gtggaatggg agagcaatgg acagcctgag aacaactaca   2100
agaccacccc ccctgtgctg gactctgatg gctcattctt cctgtacagc aagctgacag   2160
tggacaagtc cagatggcag cagggcaatg tgttcagctg ctctgtgatg catgaggccc   2220
tgcacaacca ctacacccag aaaagcctgt ccctgtcccc tggcaagaga gcaaagaggg   2280
gaagtggagc tactaacttc agcctgctga agcaggctgg agatgtggag gagaaccctg   2340
gacctatgga cttccaggtg cagatcatca gctttctgct gatctctgcc tctgtgatca   2400
tgagcagagg ccagattgtg ctgagccaga gccctgccat cctgtctgca agccctgggg   2460
agaaagtgac catgacctgc agagccagca gctctgtgtc ctacatccac tggttccagc   2520
agaagcctgg cagcagcccc aagccttgga tctatgccac cagcaacctg gcatctgggg   2580
tgccagtcag attctctggc tctggatctg gcaccagcta cagcctgacc atcagcagag   2640
tggaagctga ggatgctgcc acctactact gccagcagtg gaccagcaat ccccccacct   2700
ttggaggggg caccaagctg gaaatcaaga gaacagtggc tgccccctct gtgttcatct   2760
tcccaccctc tgatgagcag ctgaagtctg gaacagcctc tgttgtgtgc ctgctgaaca   2820
acttctaccc cagagaagcc aaggtgcagt ggaaggtgga caatgccctg cagtctggca   2880
actcccagga atctgtgaca gagcaggaca gcaaggactc cacctactcc ctgagcagca   2940
ccctgaccct gagcaaggct gactatgaga agcacaaagt gtatgcctgt gaagtgaccc   3000
accagggcct gtccagccct gtgaccaaga gcttcaacag aggggagagc tgaagatcta   3060
```

```
cttctggcta ataaaagatc agagctctag tgatctgtgt gttggttttt tgtgtctgca   3120
ttctagcatg ttacataact tatggtaaat ggcctgcctg gctgactgcc caatgacccc   3180
tgcccaatga tgtcaataat gatgtatgtt cccatgtaat gccaataggg actttccatt   3240
gatgtcaatg ggtggagtat ttatggtaac tgcccacttg gcagtacatc aagtgtatca   3300
tatgccaagt atgcccccta ttgatgtcaa tgatggtaaa tggcctgcct ggcattatgc   3360
ccagtacatg accttatggg actttcctac ttggcagtac atctatgtat tagtcattgc   3420
tattatctag cttctgccag agtgtgtgag ggcctccagt ggctgcccct cccccacagc   3480
aggggtgggg tcctgtgccc actggaagga gtgggcttgg ggtgggtggt gctgattggc   3540
tggggtgggc ctgatgctga tgtggctata agagaccaca agtgacctgc agggccagat   3600
gttctttgct gaagatgcac ctactagata tccatatggc tatcatctct ccttcaatat   3660
ccatcatccc tacctgaggc atccatccaa tcatgttgag tatatttctg catcctccat   3720
cctgtggtgc ctcctgaact gattcatcat tctaggtaag tttaaagctc aggtatagac   3780
atggcctttg tcatgatctc ccttggagcc tacctagact cagcatgctc tccaatcttt   3840
gcctgaccct gcttgctcaa ctctaattct ttgtttattt ttctgttctg atcatttaca   3900
gatccaagct gtgacatgat cctaccatag gttggagtgt aggtaaccaa gccaccatgg   3960
actacaagga ccatgatggg gattataagg atcatgacat tgattacaag gatgatgatg   4020
acaagatggc ccctaagaag aagaggaaag ttggcatcca tggggtgcca gctgctgaca   4080
agaagtacag cattggcctg gacattggca ccaactctgt tggctgggct gtgatcactg   4140
atgagtacaa ggtgcccagc aagaagttca aggtcctggg caacacagac aggcacagca   4200
tcaagaagaa cctgattgga gccctgctgt ttgactctgg ggagacagct gaggccacca   4260
gactgaagag aacagccaga agaagataca caagaagaaa gaacaggatc tgctacctgc   4320
aagaaatctt cagcaatgag atggccaaag tggatgacag cttcttccac agactggaag   4380
agtccttcct ggtggaagag gacaagaaac atgagagaca ccccatcttt ggcaacattg   4440
tggatgaggt ggcctaccat gagaagtacc ccaccatcta ccacctgaga aagaaactgg   4500
tggacagcac agacaaggct gacctgagac tgatctacct ggctctggcc cacatgatca   4560
agttcagagg ccacttcctg attgaagggg atctgaaccc tgacaactct gatgtggaca   4620
agctgtttat ccagctggtg cagacctaca accagctgtt tgaggaaaac cccatcaatg   4680
ccagtggtgt tgatgccaag gccatcctgt ctgccagact gagcaagagc agaaggctgg   4740
aaaatctgat tgcccagctg cctggggaga agaagaatgg cctgtttggc aacctcattg   4800
ccctgagcct gggcctgaca cctaacttca agagcaactt tgacctggct gaggatgcca   4860
agctccagct gtccaaggac acctatgatg atgatctgga caacctgctg gcccagattg   4920
gggaccagta tgctgacctg ttcctggctg ccaagaacct gtctgatgcc atcctgctgt   4980
ctgacatcct gagagtgaac acagagatca caaaggcccc tctgtctgcc tctatgatca   5040
agagatatga tgagcaccac caggacctga cactgctgaa ggctcttgtt agacagcagc   5100
tgccagagaa gtacaaagag attttctttg accagagcaa gaatggctat gctggctaca   5160
ttgatggtgg tgcctctcaa gaagagttct acaagttcat caagcccatc ctggaaaaga   5220
tggatggcac agaggaactg ctggtcaagc tgaacagaga ggacctgctg agaaagcaga   5280
ggacctttga caatggcagc atccctcacc agatccacct gggagagctg catgctatcc   5340
tgagaaggca agaggatttc tacccattcc tgaaggacaa cagagagaag attgagaaga   5400
tcctgacctt cagaatcccc tactatgtgg gccctctggc tagaggcaac agcagatttg   5460
```

-continued cctggatgac cagaaagtct gaggaaacca tcacaccctg gaactttgag gaagtggtgg 5520
acaaaggggc ctctgctcag agcttcattg agagaatgac aaactttgac aagaatctgc 5580
ccaatgagaa ggtgctgccc aagcacagcc tgctgtatga gtacttcaca gtgtacaatg 5640
agctgacaaa agtgaaatat gtgacagagg gaatgagaaa gcctgccttc ctgtctgggg 5700
agcagaaaaa ggccattgtg gacctgcttt tcaagaccaa cagaaaagtg acagtgaagc 5760
agctgaaaga ggactacttc aagaaaattg agtgctttga ttctgtggaa atctctggtg 5820
ttgaggacag gttcaatgcc tctctgggca cataccatga cctgctcaag attatcaagg 5880
acaaggactt cctggacaat gaggaaaatg aggacatcct tgaggacatt gtgctgacac 5940
tgaccctgtt tgaagatagg gaaatgattg aggaaaggct caagacatat gcccacctgt 6000
ttgatgacaa agtgatgaag caactcaaga gaagaagata tacaggctgg ggcagactgt 6060
ccagaaagct gatcaatgga atcagggaca agcagagtgg caagacaatc ctggatttcc 6120
tgaagtctga tggctttgcc aataggaact tcatgcagct gatccatgat gacagcctca 6180
ccttcaaaga ggacattcag aaggcccaag tctctggcca aggggacagc ctgcatgagc 6240
acattgctaa cctggctggc agccctgcta tcaagaaggg catcctccag actgtgaagg 6300
tggtggatga gcttgtgaaa gtgatgggca gacacaagcc tgagaacatt gtgattgaga 6360
tggctagaga gaaccagacc acacagaagg gacagaagaa cagcagagaa aggatgaaga 6420
ggattgaaga gggcatcaaa gagctgggca gccagatcct gaaagagcac cctgttgaga 6480
acacccagct ccagaatgag aagctgtacc tgtactactt gcagaatggc agggatatgt 6540
atgtggacca agagctggac atcaacagac tgtctgacta tgatgtggat catattgtgc 6600
cccagagctt tctgaaggat gactccattg acaacaaggt gctgactagg agtgacaaga 6660
acaggggcaa gtctgacaat gtgccctctg aagaggtggt caagaagatg aagaactatt 6720
ggaggcagct cctgaatgcc aaactgatca cccagaggaa gtttgacaac ctgaccaagg 6780
ctgagagagg tggactctct gaactggata aggctggctt catcaagagg cagcttgtgg 6840
aaaccagaca gatcaccaaa catgtggctc agatcctgga cagcagaatg aacactaagt 6900
atgatgagaa tgataagctc atcagggaag tgaaagtcat caccctgaag tccaagctgg 6960
tgtctgactt taggaaagac ttccagtttt acaaagtcag agagatcaac aactaccacc 7020
atgctcatga tgcctacctg aatgctgttg tgggcacagc cctgatcaaa aagtacccta 7080
agctggaatc tgagtttgtg tatggggact acaaagtgta tgatgtcaga aagatgattg 7140
ccaagtctga acaagagatt ggcaaggcta cagccaagta cttcttctac agcaacatca 7200
tgaatttctt caagactgag atcaccctgg ctaatgggga gatcagaaag aggccactga 7260
ttgagacaaa tggagagact ggggagattg tgtgggacaa gggcagagac tttgccacag 7320
tcagaaaggt gctgtctatg ccccaagtga acattgtcaa gaaaacagag gtgcagactg 7380
gtggcttctc caaagagagc atcctgccta agaggaacag tgacaagctg attgccagaa 7440
agaaggactg ggaccccaag aagtatggag gctttgacag ccccacagtg gcctactctg 7500
tgctggtggt ggccaaggtg gaaaagggca agagcaaaaa gctcaagagt gtgaaagagc 7560
tgctgggcat caccatcatg gaaaggtcca gctttgagaa gaaccctatt gacttccttg 7620
aggccaaggg ctacaaagaa gtgaaaaagg acctgatcat caagctcccc aagtactctc 7680
tgtttgaact ggaaaatggg agaaagagga tgctggcttc tgctggggaa ctccagaaag 7740
gcaatgaact ggccctgcct agcaaatatg tcaacttcct gtacctggcc agccactatg 7800
agaaactgaa gggcagccca gaggataatg agcaaaagca gctttttgtg gaacagcaca 7860
agcactacct ggatgagatc attgagcaaa tctctgagtt cagcaagagg gtcatcctgg 7920
cagatgccaa cctggacaaa gtgctgagtg cctacaacaa gcacagggac aaacccatca 7980
gagagcaggc agagaacatc atccacctgt tcaccctgac caacctggga gcccctgctg 8040
ccttcaagta ctttgacacc accattgata ggaagaggta caccagcacc aaagaggtcc 8100
tggatgctac cctgatccac cagagcatca ctggcctgta tgagacaaga attgacctgt 8160
ctcagcttgg aggggacaag aggcctgctg ccacaaagaa agcaggccag gccaaaaaga 8220
agaagtgaag atctacttct ggctaataaa agatcagagc tctagtgatc tgtgtgttgg 8280 tttttgtgt ctgcattcta gctctagtga tcagcagttc aacctgttga tagtatgtac 8340
taagctctca tgtttaatgt actaagctct catgtttaat gaactaaacc ctcatggcta 8400
atgtactaag ctctcatggc taatgtacta agctctcatg tttcatgtac taagctctca 8460
tgtttgaaca ataaaattaa tataaatcag caacttaaat agcctctaag gttttaagtt 8520
ttataagaaa aaaaagaata tataaggctt ttaaaggttt taaggtttcc taggttatcc 8580
tcatatgagc tcttagaaaa actcatccag catcaaatga aactgcaatt tattcatatc 8640
aggattatca ataccatatt tttgaaaaag tcttttctgt aatgaaggag aaaactcacc 8700
caggcagttc cataggatgg caagatcctg gtatctgtct gcaattccaa ctcttccaac 8760
atcaatacaa cctattaatt tcccctcatc aaaaataagg ttatcaagtg agaaatcacc 8820
atgagtgacc actgaatctg gtgagaatgg caaaagatta tgcatttctt tccagacttg 8880
ttcaacaggc cagccatttc tctcatcatc aaaatcactg gcatcaacca aaccattatt 8940
cattcttgat tgggcctgag ccagtctaaa tactctatca gagttaaaag gacaattaca 9000
aacaggaatg gaatgcaatc ttctcaggaa cactgccagg gcatcaacaa tattttcacc 9060
tgaatcagga tattcttcca atacctggaa tgctgttttc cctgggatgg cagtggtgag 9120
taaccatgca tcatcaggag ttctgataaa atgcttgatg gttggaagag gcataaattc 9180
agtcagccag tttagtctga ccatctcatc tgtaacatca ttggcaacag aacctttgcc 9240
atgtttcaga aacaactctg gggcatctgg cttcccatac aatctataga ttgtggcacc 9300
tgattgccca acattatctc tagcccattt atacccatat aaatcagcat ccatgttgga 9360
atttaatctt ggcctggagc aagaggtttc tctttgaata tggctcatac atgtgcacct 9420
cctatagtga gttgtattat actatgcaga tatactatgc caatgtttaa ttgtcag 9477

<210> SEQ ID NO 54
<211> LENGTH: 5822
<212> TYPE: DNA
<213> ORGANISM: Artificial sequence
<220> FEATURE:
<223> OTHER INFORMATION: Synthetic

<400> SEQUENCE: 54
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg ggctggtccc tgatcctgct gttcctggtg gctgtggcca 900
ccagagtgct gagccaggtg cagctgcagc agcctggggc tgagcttgtg aaacctgggg 960
cctctgtgaa gatgagctgc aaggcctctg gctacacctt caccagctac aacatgcact 1020
gggtcaagca gacccctggc agaggcctgg aatggattgg agccatctac cctggcaatg 1080
gggacacctc ctacaaccag aagttcaagg gcaaggccac cctgacagct gacaagagca 1140
gcagcacagc ctacatgcag ctgtccagcc tgacctctga ggactctgct gtgtactact 1200
gtgccaggtc cacctactat gggggagact ggtacttcaa tgtgtgggga gctggcacca 1260
cagtgacagt gtctgctgcc agcaccaagg gccccctctgt gtttcctctg gcccccagca 1320
gcaagagcac ctctgggggga acagctgccc tgggctgcct tgtgaaggac tacttccctg 1380
agcctgtgac tgtgtcctgg aactctgggg ccctgacatc tggggtgcac accttccctg 1440
cagtgctgca gtccagtggc ctgtactccc tgtcctctgt tgtgacagtg cccagctcca 1500
gcctgggcac ccagacctac atctgcaatg tgaaccacaa gcccagcaac accaaggtgg 1560
acaagaaggc tgagcccaag agctgtgaca agacccacac ctgtcccccc tgtcctgccc 1620
ctgaactgct gggaggacct tctgtgttcc tgttcccacc caagcccaag gataccctga 1680
tgatcagcag aacccctgaa gtgacctgtg tggtggtgga tgtgtcccat gaggacccag 1740
aagtgaagtt caattggtat gtggatgggg tggaagtgca caatgccaag accaagccca 1800
gagaggaaca gtacaacagc acctacagag tggtgtctgt gctgactgtg ctgcaccagg 1860
actggctgaa tggcaaagag tacaagtgca aggtgtccaa caaggccctg ccagccccca 1920
ttgagaaaac catcagcaag gccaagggcc agcctagaga accccaggtg tacacactgc 1980
cccctagcag ggatgagctg accaagaacc aggtgtccct gacatgcctt gtgaaaggct 2040
tctacccctc tgacattgct gtggaatggg agagcaatgg acagcctgag aacaactaca 2100
agaccacccc ccctgtgctg gactctgatg gctcattctt cctgtacagc aagctgacag 2160
tggacaagtc cagatggcag cagggcaatg tgttcagctg ctctgtgatg catgaggccc 2220
tgcacaacca ctacacccag aaaagcctgt ccctgtcccc tggcaagaga gcaaagaggg 2280
gaagtggagc tactaacttc agcctgctga agcaggctgg agatgtggag gagaaccctg 2340
gacctatgga cttccaggtg cagatcatca gctttctgct gatctctgcc tctgtgatca 2400
tgagcagagg ccagattgtg ctgagccaga gccctgccat cctgtctgca agccctgggg 2460
agaaagtgac catgacctgc agagccagca gctctgtgtc ctacatccac tggttccagc 2520
agaagcctgg cagcagcccc aagccttgga tctatgccac cagcaacctg gcatctgggg 2580
tgccagtcag attctctggc tctggatctg gcaccagcta cagcctgacc atcagcagag 2640
tggaagctga ggatgctgcc acctactact gccagcagtg gaccagcaat ccccccacct 2700
ttggaggggg caccaagctg gaaatcaaga gaacagtggc tgccccctct gtgttcatct 2760

-continued

```
tcccaccctc tgatgagcag ctgaagtctg gaacagcctc tgttgtgtgc ctgctgaaca   2820
acttctaccc cagagaagcc aaggtgcagt ggaaggtgga caatgccctg cagtctggca   2880
actcccagga atctgtgaca gagcaggaca gcaaggactc cacctactcc ctgagcagca   2940
ccctgaccct gagcaaggct gactatgaga agcacaaagt gtatgcctgt gaagtgaccc   3000
accagggcct gtccagccct gtgaccaaga gcttcaacag aggggagagc tgaagatcta   3060
cttctggcta ataaaagatc agagctctag tgatctgtgt gttggttttt tgtgtctgca   3120
ttctagcatg ttacataact tatggtaaat ggcctgcctg gctgactgcc caatgacccc   3180
tgcccaatga tgtcaataat gatgtatgtt cccatgtaat gccaataggg actttccatt   3240
gatgtcaatg ggtggagtat ttatggtaac tgcccacttg gcagtacatc aagtgtatca   3300
tatgccaagt atgcccccta ttgatgtcaa tgatggtaaa tggcctgcct ggcattatgc   3360
ccagtacatg accttatggg actttcctac ttggcagtac atctatgtat tagtcattgc   3420
tattatctag cttctgccag agtgtgtgag ggcctccagt ggctgcccct cccccacagc   3480
aggggtgggg tcctgtgccc actggaagga gtgggcttgg ggtgggtggt gctgattggc   3540
tggggtgggc ctgatgctga tgtggctata agagaccaca agtgacctgc agggccagat   3600
gttctttgct gaagatgcac ctactagata tccatatggc tatcatctct ccttcaatat   3660
ccatcatccc tacctgaggc atccatccaa tcatgttgag tatatttctg catcctccat   3720
cctgtggtgc ctcctgaact gattcatcat tctaggtaag tttaaagctc aggtatagac   3780
atggcctttg tcatgatctc ccttggagcc tacctagact cagcatgctc tccaatcttt   3840
gcctgaccct gcttgctcaa ctctaattct ttgtttattt ttctgttctg atcatttaca   3900
gatccaagct gtgacatgat cctaccatag gttggagtgt aggtaaccaa gctttccatg   3960
gctggacctg ccacccagag ccccatgaag ctgatggccc tgcagctgct gctgtggcac   4020
agtgcactct ggacagtgca ggaagccacc cccctgggcc ctgccagctc cctgccccag   4080
agcttcctgc tcaagtgctt agagcaagtg aggaagatcc agggggatgg ggcagctctc   4140
caggagaagc tgtgtgccac ctacaagctg tgccaccctg aggagctggt gctgctggga   4200
cactctctgg gcatcccctg ggctcccctg agcagctgcc ccagccaggc cctgcagctg   4260
gcaggctgct tgagccaact ccatagtggc cttttcctct accaggggct cctgcaggcc   4320
ctggaaggga tctcccctga gttgggtccc accttggaca cactgcagct ggatgttgct   4380
gactttgcca ccaccatctg gcagcagatg gaagaactgg gaatggcccc tgccctgcag   4440
cccacccagg gtgccatgcc tgcctttgcc tctgctttcc agagaagggc aggaggggtc   4500
ctggttgcct cccatctgca gagcttcctg gaggtgtcct acagagttct aagacacctt   4560
gcccagccct gatagatcta cttctggcta ataaaagatc agagctctag tgatctgtgt   4620
gttggttttt tgtgtctgca ttctagctct agtgatcagc agttcaacct gttgatagta   4680
tgtactaagc tctcatgttt aatgtactaa gctctcatgt ttaatgaact aaaccctcat   4740
ggctaatgta ctaagctctc atggctaatg tactaagctc tcatgtttca tgtactaagc   4800
tctcatgttt gaacaataaa attaatataa atcagcaact taaatagcct ctaaggtttt   4860
aagttttata agaaaaaaaa gaatatataa ggcttttaaa ggttttaagg tttcctaggt   4920
tatcctcata tgagctctta gaaaaactca tccagcatca aatgaaactg caatttattc   4980
atatcaggat tatcaatacc atatttttga aaaagtcttt tctgtaatga aggagaaaac   5040
tcacccaggc agttccatag gatggcaaga tcctggtatc tgtctgcaat tccaactctt   5100
ccaacatcaa tacaacctat taatttcccc tcatcaaaaa taaggttatc aagtgagaaa   5160
```

tcaccatgag tgaccactga atctggtgag aatggcaaaa gattatgcat ttctttccag 5220
acttgttcaa caggccagcc atttctctca tcatcaaaat cactggcatc aaccaaacca 5280
ttattcattc ttgattgggc ctgagccagt ctaaatactc tatcagagtt aaaaggacaa 5340
ttacaaacag gaatggaatg caatcttctc aggaacactg ccagggcatc aacaatattt 5400
tcacctgaat caggatattc ttccaatacc tggaatgctg ttttccctgg gatggcagtg 5460
gtgagtaacc atgcatcatc aggagttctg ataaaatgct tgatggttgg aagaggcata 5520
aattcagtca gccagtttag tctgaccatc tcatctgtaa catcattggc aacagaacct 5580
ttgccatgtt tcagaaacaa ctctggggca tctggcttcc catacaatct atagattgtg 5640
gcacctgatt gcccaacatt atctctagcc catttatacc catataaatc agcatccatg 5700
ttggaattta atcttggcct ggagcaagag gtttctcttt gaatatggct catacatgtg 5760
cacctcctat agtgagttgt attatactat gcagatatac tatgccaatg tttaattgtc 5820
ag 5822

<210> SEQ ID NO 55
<211> LENGTH: 3255
<212> TYPE: DNA
<213> ORGANISM: Artificial sequence
<220> FEATURE:
<223> OTHER INFORMATION: Synthetic

<400> SEQUENCE: 55
gaattctcat agctagcatg ttacataact tatggtaaat ggcctgcctg gctgactgcc 60
caatgacccc tgcccaatga tgtcaataat gatgtatgtt cccatgtaat gccaataggg 120
actttccatt gatgtcaatg ggtggagtat ttatggtaac tgcccacttg gcagtacatc 180
aagtgtatca tatgccaagt atgcccccta ttgatgtcaa tgatggtaaa tggcctgcct 240
ggcattatgc ccagtacatg accttatggg actttcctac ttggcagtac atctatgtat 300
tagtcattgc tattaccatg gtgatgggtt ttggcagtac atcaatgggt gtggatagtg 360
gtttgaccca tggggatttc caagtctcca ccccattgat gccaatggga gtttgttttg 420
gcaccaaaat caatgggact ttccaaaatg ttgtaacaac tctgccccat tgatggaaat 480
gggtggtagg tgtgtgtggt gggaggtcta tataagcaga gcttgtttag tgaactggat 540
gcacctacta gatatcagac attgaggtgt atttcactca agaggtgaaa tacacctcaa 600
tgtctttttt tctagatact aagcttggcg taatcatggt catagctgtt tcctgtgtga 660
aattgttatc cgctcacaat tccacacaac atacgagccg gaagcataaa gtgtaaagcc 720
tggggtgcct aatgagtgag ctaactcaca ttaattgcgt tgcgctcact gcccgctttc 780
cagtcgggaa acctgtcgtg ccagctgcat taatgaatcg gccaacgcgc ggggagaggc 840
ggtttgcgta ttgggcgctc ttccgcttcc tcgctcactg actcgctgcg ctcggtcgtt 900
cggctgcggc gagcggtatc agctcactca aaggcggtaa tacggttatc cacagaatca 960
ggggataacg caggaaagaa catgtgagca aaaggccagc aaaaggccag gaaccgtaaa 1020
aaggccgcgt tgctggcgtt tttccatagg ctccgccccc ctgacgagca tcacaaaaat 1080
cgacgctcaa gtcagaggtg gcgaaacccg acaggactat aaagatacca ggcgtttccc 1140
cctggaagct ccctcgtgcg ctctcctgtt ccgaccctgc cgcttaccgg atacctgtcc 1200
gcctttctcc cttcgggaag cgtggcgctt tctcatagct cacgctgtag gtatctcagt 1260
tcggtgtagg tcgttcgctc caagctgggc tgtgtgcacg aaccccccgt tcagcccgac 1320
cgctgcgcct tatccggtaa ctatcgtctt gagtccaacc cggtaagaca cgacttatcg 1380
ccactggcag cagccactgg taacaggatt agcagagcga ggtatgtagg cggtgctaca 1440
gagttcttga agtggtggcc taactacggc tacactagaa gaacagtatt tggtatctgc 1500
gctctgctga agccagttac cttcggaaaa agagttggta gctcttgatc cggcaaacaa 1560
accaccgctg gtagcggtgg tttttttgtt tgcaagcagc agattacgcg cagaaaaaaa 1620
ggatctcaag aagatccttt gatcttttct acggggtctg acgctcagtg gaacgaaaac 1680
tcacgttaag ggattttggt catgagatta tcaaaaagga tcttcaccta gatcctttta 1740
aattaaaaat gaagttttaa atcaatctaa agtatatatg agtaaacttg gtctgacagt 1800
taccaatgct taatcagtga ggcacctatc tcagcgatct gtctatttcg ttcatccata 1860
gttgcctgac tccccgtcgt gtagataact acgatacggg agggcttacc atctggcccc 1920
agtgctgcaa tgataccgcg agacccacgc tcaccggctc cagatttatc agcaataaac 1980
cagccagccg gaagggccga gcgcagaagt ggtcctgcaa ctttatccgc ctccatccag 2040
tctattaatt gttgccggga agctagagta agtagttcgc cagttaatag tttgcgcaac 2100
gttgttgcca ttgctacagg catcgtggtg tcacgctcgt cgtttggtat ggcttcattc 2160
agctccggtt cccaacgatc aaggcgagtt acatgatccc ccatgttgtg caaaaaagcg 2220
gttagctcct tcggtcctcc gatcgttgtc agaagtaagt tggccgcagt gttatcactc 2280
atggttatgg cagcactgca taattctctt actgtcatgc catccgtaag atgcttttct 2340
gtgactggtg agtactcaac caagtcattc tgagaatagt gtatgcggcg accgagttgc 2400
tcttgcccgg cgtcaatacg ggataatacc gcgccacata gcagaacttt aaaagtgctc 2460
atcattggaa aacgttcttc ggggcgaaaa ctctcaagga tcttaccgct gttgagatcc 2520
agttcgatgt aacccactcg tgcacccaac tgatcttcag catcttttac tttcaccagc 2580
gtttctgggt gagcaaaaac aggaaggcaa aatgccgcaa aaaagggaat aagggcgaca 2640
cggaaatgtt gaatactcat actcttcctt tttcaatatt attgaagcat ttatcagggt 2700
tattgtctca tgagcggata catatttgaa tgtatttaga aaaataaaca aataggggtt 2760
ccgcgcacat ttccccgaaa agtgccacct gacgtctaag aaaccattat tatcatgaca 2820
ttaacctata aaaataggcg tatcacgagg ccctttcgtc tcgcgcgttt cggtgatgac 2880
ggtgaaaacc tctgacacat gcagctcccg gagacggtca cagcttgtct gtaagcggat 2940
gccgggagca gacaagcccg tcagggcgcg tcagcgggtg ttggcgggtg tcggggctgg 3000
cttaactatg cggcatcaga gcagattgta ctgagagtgc accatatgcg gtgtgaaata 3060
ccgcacagat gcgtaaggag aaaataccgc atcaggcgcc attcgccatt caggctgcgc 3120
aactgttggg aagggcgatc ggtgcgggcc tcttcgctat tacgccagct ggcgaaaggg 3180
ggatgtgctg caaggcgatt aagttgggta acgccagggt tttcccagtc acgacgttgt 3240
aaaacgacgg ccagt 3255

<210> SEQ ID NO 56
<211> LENGTH: 3260
<212> TYPE: DNA
<213> ORGANISM: Artificial sequence
<220> FEATURE:
<223> OTHER INFORMATION: Synthetic

<400> SEQUENCE: 56
gaattctcat agctagcatg ttacataact tatggtaaat ggcctgcctg gctgactgcc 60
caatgacccc tgcccaatga tgtcaataat gatgtatgtt cccatgtaat gccaataggg 120

```
actttccatt gatgtcaatg ggtggagtat ttatggtaac tgcccacttg gcagtacatc    180
aagtgtatca tatgccaagt atgcccccta ttgatgtcaa tgatggtaaa tggcctgcct    240
ggcattatgc ccagtacatg accttatggg actttcctac ttggcagtac atctatgtat    300
tagtcattgc tattaccatg gtgatgggtt ttggcagtac atcaatgggt gtggatagtg    360
gtttgaccca tggggatttc caagtctcca ccccattgat gccaatggga gtttgttttg    420
gcaccaaaat caatgggact ttccaaaatg ttgtaacaac tctgccccat tgatggaaat    480
gggtggtagg tgtgtgtggt gggaggtcta tataagcaga gcttgtttag tgaactggat    540
gcacctacta gatatccctt aatagttgca gccaaatcct tcctgtcaga tttggctgca    600
actattaagg ttttttctag atactaagct tggcgtaatc atggtcatag ctgtttcctg    660
tgtgaaattg ttatccgctc acaattccac acaacatacg agccggaagc ataaagtgta    720
aagcctgggg tgcctaatga gtgagctaac tcacattaat tgcgttgcgc tcactgcccg    780
ctttccagtc gggaaacctg tcgtgccagc tgcattaatg aatcggccaa cgcgcgggga    840
gaggcggttt gcgtattggg cgctcttccg cttcctcgct cactgactcg ctgcgctcgg    900
tcgttcggct gcggcgagcg gtatcagctc actcaaaggc ggtaatacgg ttatccacag    960
aatcagggga taacgcagga aagaacatgt gagcaaaagg ccagcaaaag gccaggaacc   1020
gtaaaaaggc cgcgttgctg gcgtttttcc ataggctccg cccccctgac gagcatcaca   1080
aaaatcgacg ctcaagtcag aggtggcgaa acccgacagg actataaaga taccaggcgt   1140
ttccccctgg aagctccctc gtgcgctctc ctgttccgac cctgccgctt accggatacc   1200
tgtccgcctt tctcccttcg ggaagcgtgg cgctttctca tagctcacgc tgtaggtatc   1260
tcagttcggt gtaggtcgtt cgctccaagc tgggctgtgt gcacgaaccc cccgttcagc   1320
ccgaccgctg cgccttatcc ggtaactatc gtcttgagtc caacccggta agacacgact   1380
tatcgccact ggcagcagcc actggtaaca ggattagcag agcgaggtat gtaggcggtg   1440
ctacagagtt cttgaagtgg tggcctaact acggctacac tagaagaaca gtatttggta   1500
tctgcgctct gctgaagcca gttaccttcg gaaaaagagt tggtagctct tgatccggca   1560
aacaaaccac cgctggtagc ggtggttttt ttgtttgcaa gcagcagatt acgcgcagaa   1620
aaaaaggatc tcaagaagat cctttgatct tttctacggg gtctgacgct cagtggaacg   1680
aaaactcacg ttaagggatt ttggtcatga gattatcaaa aaggatcttc acctagatcc   1740
ttttaaatta aaaatgaagt tttaaatcaa tctaaagtat atatgagtaa acttggtctg   1800
acagttacca atgcttaatc agtgaggcac ctatctcagc gatctgtcta tttcgttcat   1860
ccatagttgc ctgactcccc gtcgtgtaga taactacgat acgggagggc ttaccatctg   1920
gccccagtgc tgcaatgata ccgcgagacc cacgctcacc ggctccagat ttatcagcaa   1980
taaaccagcc agccggaagg gccgagcgca gaagtggtcc tgcaacttta tccgcctcca   2040
tccagtctat taattgttgc cgggaagcta gagtaagtag ttcgccagtt aatagtttgc   2100
gcaacgttgt tgccattgct acaggcatcg tggtgtcacg ctcgtcgttt ggtatggctt   2160
cattcagctc cggttcccaa cgatcaaggc gagttacatg atcccccatg ttgtgcaaaa   2220
aagcggttag ctccttcggt cctccgatcg ttgtcagaag taagttggcc gcagtgttat   2280
cactcatggt tatggcagca ctgcataatt ctcttactgt catgccatcc gtaagatgct   2340
tttctgtgac tggtgagtac tcaaccaagt cattctgaga atagtgtatg cggcgaccga   2400
gttgctcttg cccggcgtca atacgggata ataccgcgcc acatagcaga actttaaaag   2460
```

tgctcatcat tggaaaacgt tcttcggggc gaaaactctc aaggatctta ccgctgttga 2520
gatccagttc gatgtaaccc actcgtgcac ccaactgatc ttcagcatct tttactttca 2580
ccagcgtttc tgggtgagca aaaacaggaa ggcaaaatgc cgcaaaaaag ggaataaggg 2640
cgacacggaa atgttgaata ctcatactct tcctttttca atattattga agcatttatc 2700
agggttattg tctcatgagc ggatacatat ttgaatgtat ttagaaaaat aaacaaatag 2760
gggttccgcg cacatttccc cgaaaagtgc cacctgacgt ctaagaaacc attattatca 2820
tgacattaac ctataaaaat aggcgtatca cgaggccctt tcgtctcgcg cgtttcggtg 2880
atgacggtga aaacctctga cacatgcagc tcccggagac ggtcacagct tgtctgtaag 2940
cggatgccgg gagcagacaa gcccgtcagg gcgcgtcagc gggtgttggc gggtgtcggg 3000
gctggcttaa ctatgcggca tcagagcaga ttgtactgag agtgcaccat atgcggtgtg 3060
aaataccgca cagatgcgta aggagaaaat accgcatcag gcgccattcg ccattcaggc 3120
tgcgcaactg ttgggaaggg cgatcggtgc gggcctcttc gctattacgc cagctggcga 3180
aagggggatg tgctgcaagg cgattaagtt gggtaacgcc agggttttcc cagtcacgac 3240
gttgtaaaac gacggccagt 3260

<210> SEQ ID NO 57
<211> LENGTH: 6800
<212> TYPE: DNA
<213> ORGANISM: Artificial sequence
<220> FEATURE:
<223> OTHER INFORMATION: Synthetic

<400> SEQUENCE: 57
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc acctttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg gactacaagg accatgatgg ggattataag gatcatgaca 900
ttgattacaa ggatgatgat gacaagatgg cccctaagaa gaagaggaaa gttggcatcc 960
atggggtgcc agctgctgac aagaagtaca gcattggcct ggacattggc accaactctg 1020
ttggctgggc tgtgatcact gatgagtaca aggtgcccag caagaagttc aaggtcctgg 1080
gcaacacaga caggcacagc atcaagaaga acctgattgg agccctgctg tttgactctg 1140
gggagacagc tgaggccacc agactgaaga gaacagccag aagaagatac acaagaagaa 1200
agaacaggat ctgctacctg caagaaatct tcagcaatga gatggccaaa gtggatgaca 1260
gcttcttcca cagactggaa gagtccttcc tggtggaaga ggacaagaaa catgagagac 1320
accccatctt tggcaacatt gtggatgagg tggcctacca tgagaagtac cccaccatct 1380
accacctgag aaagaaactg gtggacagca cagacaaggc tgacctgaga ctgatctacc 1440
tggctctggc ccacatgatc aagttcagag gccacttcct gattgaaggg gatctgaacc 1500
ctgacaactc tgatgtggac aagctgttta tccagctggt gcagacctac aaccagctgt 1560
ttgaggaaaa ccccatcaat gccagtggtg ttgatgccaa ggccatcctg tctgccagac 1620
tgagcaagag cagaaggctg gaaaatctga ttgcccagct gcctggggag aagaagaatg 1680
gcctgtttgg caacctcatt gccctgagcc tgggcctgac acctaacttc aagagcaact 1740
ttgacctggc tgaggatgcc aagctccagc tgtccaagga cacctatgat gatgatctgg 1800
acaacctgct ggcccagatt ggggaccagt atgctgacct gttcctggct gccaagaacc 1860
tgtctgatgc catcctgctg tctgacatcc tgagagtgaa cacagagatc acaaaggccc 1920
ctctgtctgc ctctatgatc aagagatatg atgagcacca ccaggacctg acactgctga 1980
aggctcttgt tagacagcag ctgccagaga agtacaaaga gattttcttt gaccagagca 2040
agaatggcta tgctggctac attgatggtg gtgcctctca agaagagttc tacaagttca 2100
tcaagcccat cctggaaaag atggatggca cagaggaact gctggtcaag ctgaacagag 2160
aggacctgct gagaaagcag aggacctttg acaatggcag catccctcac cagatccacc 2220
tgggagagct gcatgctatc ctgagaaggc aagaggattt ctacccattc ctgaaggaca 2280
acagagagaa gattgagaag atcctgacct tcagaatccc ctactatgtg ggccctctgg 2340
ctagaggcaa cagcagattt gcctggatga ccagaaagtc tgaggaaacc atcacaccct 2400
ggaactttga ggaagtggtg gacaaagggg cctctgctca gagcttcatt gagagaatga 2460
caaactttga caagaatctg cccaatgaga aggtgctgcc caagcacagc ctgctgtatg 2520
agtacttcac agtgtacaat gagctgacaa aagtgaaata tgtgacagag ggaatgagaa 2580
agcctgcctt cctgtctggg gagcagaaaa aggccattgt ggacctgctt ttcaagacca 2640
acagaaaagt gacagtgaag cagctgaaag aggactactt caagaaaatt gagtgctttg 2700
attctgtgga aatctctggt gttgaggaca ggttcaatgc ctctctgggc acataccatg 2760
acctgctcaa gattatcaag gacaaggact tcctggacaa tgaggaaaat gaggacatcc 2820
ttgaggacat tgtgctgaca ctgaccctgt ttgaagatag ggaaatgatt gaggaaaggc 2880
tcaagacata tgcccacctg tttgatgaca aagtgatgaa gcaactcaag agaagaagat 2940
atacaggctg ggcagactg tccagaaagc tgatcaatgg aatcagggac aagcagagtg 3000
gcaagacaat cctggatttc ctgaagtctg atggctttgc caataggaac ttcatgcagc 3060
tgatccatga tgacagcctc accttcaaag aggacattca gaaggcccaa gtctctggcc 3120
aaggggacag cctgcatgag cacattgcta acctggctgg cagccctgct atcaagaagg 3180
gcatcctcca gactgtgaag gtggtggatg agcttgtgaa agtgatgggc agacacaagc 3240
ctgagaacat tgtgattgag atggctagag agaaccagac cacacagaag ggacagaaga 3300
acagcagaga aaggatgaag aggattgaag agggcatcaa agagctgggc agccagatcc 3360
tgaaagagca ccctgttgag aacacccagc tccagaatga gaagctgtac ctgtactact 3420
tgcagaatgg cagggatatg tatgtggacc aagagctgga catcaacaga ctgtctgact 3480
atgatgtgga tcatattgtg ccccagagct ttctgaagga tgactccatt gacaacaagg 3540
tgctgactag gagtgacaag aacaggggca agtctgacaa tgtgccctct gaagaggtgg 3600

-continued

```
tcaagaagat gaagaactat tggaggcagc tcctgaatgc caaactgatc acccagagga   3660
agtttgacaa cctgaccaag gctgagagag gtggactctc tgaactggat aaggctggct   3720
tcatcaagag gcagcttgtg gaaaccagac agatcaccaa acatgtggct cagatcctgg   3780
acagcagaat gaacactaag tatgatgaga atgataagct catcagggaa gtgaaagtca   3840
tcaccctgaa gtccaagctg gtgtctgact ttaggaaaga cttccagttt tacaaagtca   3900
gagagatcaa caactaccac catgctcatg atgcctacct gaatgctgtt gtgggcacag   3960
ccctgatcaa aaagtaccct aagctggaat ctgagtttgt gtatggggac tacaaagtgt   4020
atgatgtcag aaagatgatt gccaagtctg aacaagagat tggcaaggct acagccaagt   4080
acttcttcta cagcaacatc atgaatttct tcaagactga gatcaccctg gctaatgggg   4140
agatcagaaa gaggccactg attgagacaa atggagagac tggggagatt gtgtgggaca   4200
agggcagaga ctttgccaca gtcagaaagg tgctgtctat gccccaagtg aacattgtca   4260
agaaaacaga ggtgcagact ggtggcttct ccaaagagag catcctgcct aagaggaaca   4320
gtgacaagct gattgccaga aagaaggact gggaccccaa gaagtatgga ggctttgaca   4380
gccccacagt ggcctactct gtgctggtgg tggccaaggt ggaaaagggc aagagcaaaa   4440
agctcaagag tgtgaaagag ctgctgggca tcaccatcat ggaaaggtcc agctttgaga   4500
agaaccctat tgacttcctt gaggccaagg gctacaaaga agtgaaaaag gacctgatca   4560
tcaagctccc caagtactct ctgtttgaac tggaaaatgg gagaaagagg atgctggctt   4620
ctgctgggga actccagaaa ggcaatgaac tggccctgcc tagcaaatat gtcaacttcc   4680
tgtacctggc cagccactat gagaaactga agggcagccc agaggataat gagcaaaagc   4740
agctttttgt ggaacagcac aagcactacc tggatgagat cattgagcaa atctctgagt   4800
tcagcaagag ggtcatcctg gcagatgcca acctggacaa agtgctgagt gcctacaaca   4860
agcacaggga caaacccatc agagagcagg cagagaacat catccacctg ttcaccctga   4920
ccaacctggg agcccctgct gccttcaagt actttgacac caccattgat aggaagaggt   4980
acaccagcac caaagaggtc ctggatgcta ccctgatcca ccagagcatc actggcctgt   5040
atgagacaag aattgacctg tctcagcttg gaggggacaa gaggcctgct gccacaaaga   5100
aagcaggcca ggccaaaaag aagaagtgaa gatctacttc tggctaataa aagatcagag   5160
ctctagtgat ctgtgtgttg gttttttgtg tctgcattct agcatgaggg cctatttccc   5220
atgattcctt catatttgca tatacgatac aaggctgtta gagagataat tggaattaat   5280
ttgactgtaa acacaaagat attagtacaa aatacgtgac gtagaaagta ataatttctt   5340
gggtagtttg cagttttaaa attatgtttt aaaatggact atcatatgct taccgtaact   5400
tgaaagtatt tcgatttctt ggctttatat atcttgtgga aaggacgaaa caccggcgat   5460
tccgctataa atgcggtttt agagctagaa atagcaagtt aaaataaggc tagtccgtta   5520
tcaacttgaa aaagtggcac cgagtcggtg ctttttttgtt ttagagctag aaatagcaag   5580
ttaaaataag gctagtccgt ttttagcgcg tgcgccaatt ctagctctag tgatcagcag   5640
ttcaacctgt tgatagtatg tactaagctc tcatgtttaa tgtactaagc tctcatgttt   5700
aatgaactaa accctcatgg ctaatgtact aagctctcat ggctaatgta ctaagctctc   5760
atgtttcatg tactaagctc tcatgtttga acaataaaat taatataaat cagcaactta   5820
aatagcctct aaggttttaa gttttataag aaaaaaaaga atatataagg cttttaaagg   5880
ttttaaggtt tcctaggtta tcctcatatg agctcttaga aaaactcatc cagcatcaaa   5940
tgaaactgca atttattcat atcaggatta tcaataccat atttttgaaa aagtcttttc   6000
```

tgtaatgaag gagaaaactc acccaggcag ttccatagga tggcaagatc ctggtatctg 6060
tctgcaattc caactcttcc aacatcaata caacctatta atttcccctc atcaaaaata 6120
aggttatcaa gtgagaaatc accatgagtg accactgaat ctggtgagaa tggcaaaaga 6180
ttatgcattt ctttccagac ttgttcaaca ggccagccat ttctctcatc atcaaaatca 6240
ctggcatcaa ccaaaccatt attcattctt gattgggcct gagccagtct aaatactcta 6300
tcagagttaa aaggacaatt acaaacagga atggaatgca atcttctcag gaacactgcc 6360
agggcatcaa caatattttc acctgaatca ggatattctt ccaatacctg gaatgctgtt 6420
ttccctggga tggcagtggt gagtaaccat gcatcatcag gagttctgat aaaatgcttg 6480
atggttggaa gaggcataaa ttcagtcagc cagtttagtc tgaccatctc atctgtaaca 6540
tcattggcaa cagaaccttt gccatgtttc agaaacaact ctggggcatc tggcttccca 6600
tacaatctat agattgtggc acctgattgc ccaacattat ctctagccca tttataccca 6660
tataaatcag catccatgtt ggaatttaat cttggcctgg agcaagaggt ttctctttga 6720
atatggctca tacatgtgca cctcctatag tgagttgtat tatactatgc agatatacta 6780
tgccaatgtt taattgtcag 6800

<210> SEQ ID NO 58
<211> LENGTH: 6800
<212> TYPE: DNA
<213> ORGANISM: Artificial sequence
<220> FEATURE:
<223> OTHER INFORMATION: Synthetic

<400> SEQUENCE: 58
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc acctttttcc ccagggtggg ggagaaccat atataagtgc 660
agtagtctct gtgaacattc aagcttctgc cttctccctc ctgtgagttt ggtaagtcac 720
tgactgtcta tgcctgggaa agggtgggca ggagatgggg cagtgcagga aaagtggcac 780
tatgaaccct gcagccctag acaattgtac taaccttctt ctctttcctc tcctgacagg 840
ttggtaacca agccaccatg gactacaagg accatgatgg ggattataag gatcatgaca 900
ttgattacaa ggatgatgat gacaagatgg cccctaagaa gaagaggaaa gttggcatcc 960
atggggtgcc agctgctgac aagaagtaca gcattggcct ggacattggc accaactctg 1020
ttggctgggc tgtgatcact gatgagtaca aggtgcccag caagaagttc aaggtcctgg 1080
gcaacacaga caggcacagc atcaagaaga acctgattgg agccctgctg tttgactctg 1140
gggagacagc tgaggccacc agactgaaga gaacagccag aagaagatac acaagaagaa 1200
agaacaggat ctgctacctg caagaaatct tcagcaatga gatggccaaa gtggatgaca 1260
gcttcttcca cagactggaa gagtccttcc tggtggaaga ggacaagaaa catgagagac 1320
accccatctt tggcaacatt gtggatgagg tggcctacca tgagaagtac cccaccatct 1380
accacctgag aaagaaactg gtggacagca cagacaaggc tgacctgaga ctgatctacc 1440
tggctctggc ccacatgatc aagttcagag gccacttcct gattgaaggg gatctgaacc 1500
ctgacaactc tgatgtggac aagctgttta tccagctggt gcagacctac aaccagctgt 1560
ttgaggaaaa ccccatcaat gccagtggtg ttgatgccaa ggccatcctg tctgccagac 1620
tgagcaagag cagaaggctg gaaaatctga ttgcccagct gcctggggag aagaagaatg 1680
gcctgtttgg caacctcatt gccctgagcc tgggcctgac acctaacttc aagagcaact 1740
ttgacctggc tgaggatgcc aagctccagc tgtccaagga cacctatgat gatgatctgg 1800
acaacctgct ggcccagatt ggggaccagt atgctgacct gttcctggct gccaagaacc 1860
tgtctgatgc catcctgctg tctgacatcc tgagagtgaa cacagagatc acaaaggccc 1920
ctctgtctgc ctctatgatc aagagatatg atgagcacca ccaggacctg acactgctga 1980
aggctcttgt tagacagcag ctgccagaga agtacaaaga gattttcttt gaccagagca 2040
agaatggcta tgctggctac attgatggtg gtgcctctca agaagagttc tacaagttca 2100
tcaagcccat cctggaaaag atggatggca cagaggaact gctggtcaag ctgaacagag 2160
aggacctgct gagaaagcag aggacctttg acaatggcag catccctcac cagatccacc 2220
tgggagagct gcatgctatc ctgagaaggc aagaggattt ctacccattc ctgaaggaca 2280
acagagagaa gattgagaag atcctgacct tcagaatccc ctactatgtg ggccctctgg 2340
ctagaggcaa cagcagattt gcctggatga ccagaaagtc tgaggaaacc atcacaccct 2400
ggaactttga ggaagtggtg gacaaagggg cctctgctca gagcttcatt gagagaatga 2460
caaactttga caagaatctg cccaatgaga aggtgctgcc caagcacagc ctgctgtatg 2520
agtacttcac agtgtacaat gagctgacaa aagtgaaata tgtgacagag ggaatgagaa 2580
agcctgcctt cctgtctggg gagcagaaaa aggccattgt ggacctgctt ttcaagacca 2640
acagaaaagt gacagtgaag cagctgaaag aggactactt caagaaaatt gagtgctttg 2700
attctgtgga aatctctggt gttgaggaca ggttcaatgc ctctctgggc acataccatg 2760
acctgctcaa gattatcaag gacaaggact tcctggacaa tgaggaaaat gaggacatcc 2820
ttgaggacat tgtgctgaca ctgaccctgt ttgaagatag ggaaatgatt gaggaaaggc 2880
tcaagacata tgcccacctg tttgatgaca aagtgatgaa gcaactcaag agaagaagat 2940
atacaggctg gggcagactg tccagaaagc tgatcaatgg aatcagggac aagcagagtg 3000
gcaagacaat cctggatttc ctgaagtctg atggctttgc caataggaac ttcatgcagc 3060
tgatccatga tgacagcctc accttcaaag aggacattca gaaggcccaa gtctctggcc 3120
aaggggacag cctgcatgag cacattgcta acctggctgg cagccctgct atcaagaagg 3180
gcatcctcca gactgtgaag gtggtggatg agcttgtgaa agtgatgggc agacacaagc 3240
ctgagaacat tgtgattgag atggctagag agaaccagac cacacagaag ggacagaaga 3300
acagcagaga aaggatgaag aggattgaag agggcatcaa agagctgggc agccagatcc 3360
tgaaagagca ccctgttgag aacacccagc tccagaatga gaagctgtac ctgtactact 3420
tgcagaatgg cagggatatg tatgtggacc aagagctgga catcaacaga ctgtctgact 3480
atgatgtgga tcatattgtg ccccagagct ttctgaagga tgactccatt gacaacaagg 3540
tgctgactag gagtgacaag aacaggggca agtctgacaa tgtgccctct gaagaggtgg 3600

-continued

```
tcaagaagat gaagaactat tggaggcagc tcctgaatgc caaactgatc acccagagga   3660
agtttgacaa cctgaccaag gctgagagag gtggactctc tgaactggat aaggctggct   3720
tcatcaagag gcagcttgtg gaaaccagac agatcaccaa acatgtggct cagatcctgg   3780
acagcagaat gaacactaag tatgatgaga atgataagct catcagggaa gtgaaagtca   3840
tcaccctgaa gtccaagctg gtgtctgact ttaggaaaga cttccagttt tacaaagtca   3900
gagagatcaa caactaccac catgctcatg atgcctacct gaatgctgtt gtgggcacag   3960
ccctgatcaa aaagtaccct aagctggaat ctgagtttgt gtatggggac tacaaagtgt   4020
atgatgtcag aaagatgatt gccaagtctg aacaagagat tggcaaggct acagccaagt   4080
acttcttcta cagcaacatc atgaatttct tcaagactga gatcaccctg gctaatgggg   4140
agatcagaaa gaggccactg attgagacaa atggagagac tggggagatt gtgtgggaca   4200
agggcagaga ctttgccaca gtcagaaagg tgctgtctat gccccaagtg aacattgtca   4260
agaaaacaga ggtgcagact ggtggcttct ccaaagagag catcctgcct aagaggaaca   4320
gtgacaagct gattgccaga aagaaggact gggaccccaa gaagtatgga ggctttgaca   4380
gccccacagt ggcctactct gtgctggtgg tggccaaggt ggaaaagggc aagagcaaaa   4440
agctcaagag tgtgaaagag ctgctgggca tcaccatcat ggaaaggtcc agctttgaga   4500
agaaccctat tgacttcctt gaggccaagg gctacaaaga agtgaaaaag gacctgatca   4560
tcaagctccc caagtactct ctgtttgaac tggaaaatgg gagaaagagg atgctggctt   4620
ctgctgggga actccagaaa ggcaatgaac tggccctgcc tagcaaatat gtcaacttcc   4680
tgtacctggc cagccactat gagaaactga agggcagccc agaggataat gagcaaaagc   4740
agctttttgt ggaacagcac aagcactacc tggatgagat cattgagcaa atctctgagt   4800
tcagcaagag ggtcatcctg gcagatgcca acctggacaa agtgctgagt gcctacaaca   4860
agcacaggga caaacccatc agagagcagg cagagaacat catccacctg ttcaccctga   4920
ccaacctggg agcccctgct gccttcaagt actttgacac caccattgat aggaagaggt   4980
acaccagcac caaagaggtc ctggatgcta ccctgatcca ccagagcatc actggcctgt   5040
atgagacaag aattgacctg tctcagcttg gaggggacaa gaggcctgct gccacaaaga   5100
aagcaggcca ggccaaaaag aagaagtgaa gatctacttc tggctaataa aagatcagag   5160
ctctagtgat ctgtgtgttg gttttttgtg tctgcattct agcatgaggg cctatttccc   5220
atgattcctt catatttgca tatacgatac aaggctgtta gagagataat tggaattaat   5280
ttgactgtaa acacaaagat attagtacaa aatacgtgac gtagaaagta ataatttctt   5340
gggtagtttg cagttttaaa attatgtttt aaaatggact atcatatgct taccgtaact   5400
tgaaagtatt tcgatttctt ggctttatat atcttgtgga aaggacgaaa caccgctgcc   5460
gggatggcta ctatggtttt agagctagaa atagcaagtt aaaataaggc tagtccgtta   5520
tcaacttgaa aaagtggcac cgagtcggtg ctttttttgtt ttagagctag aaatagcaag   5580
ttaaaataag gctagtccgt ttttagcgcg tgcgccaatt ctagctctag tgatcagcag   5640
ttcaacctgt tgatagtatg tactaagctc tcatgtttaa tgtactaagc tctcatgttt   5700
aatgaactaa accctcatgg ctaatgtact aagctctcat ggctaatgta ctaagctctc   5760
atgtttcatg tactaagctc tcatgtttga acaataaaat taatataaat cagcaactta   5820
aatagcctct aaggttttaa gttttataag aaaaaaaaga atatataagg cttttaaagg   5880
ttttaaggtt tcctaggtta tcctcatatg agctcttaga aaaactcatc cagcatcaaa   5940
```

tgaaactgca atttattcat atcaggatta tcaataccat atttttgaaa aagtcttttc 6000
tgtaatgaag gagaaaactc acccaggcag ttccatagga tggcaagatc ctggtatctg 6060
tctgcaattc caactcttcc aacatcaata caacctatta atttcccctc atcaaaaata 6120
aggttatcaa gtgagaaatc accatgagtg accactgaat ctggtgagaa tggcaaaaga 6180
ttatgcattt ctttccagac ttgttcaaca ggccagccat ttctctcatc atcaaaatca 6240
ctggcatcaa ccaaaccatt attcattctt gattgggcct gagccagtct aaatactcta 6300
tcagagttaa aaggacaatt acaaacagga atggaatgca atcttctcag gaacactgcc 6360
agggcatcaa caatattttc acctgaatca ggatattctt ccaatacctg gaatgctgtt 6420
ttccctggga tggcagtggt gagtaaccat gcatcatcag gagttctgat aaaatgcttg 6480
atggttggaa gaggcataaa ttcagtcagc cagtttagtc tgaccatctc atctgtaaca 6540
tcattggcaa cagaaccttt gccatgtttc agaaacaact ctggggcatc tggcttccca 6600
tacaatctat agattgtggc acctgattgc ccaacattat ctctagccca tttataccca 6660
tataaatcag catccatgtt ggaatttaat cttggcctgg agcaagaggt ttctctttga 6720
atatggctca tacatgtgca cctcctatag tgagttgtat tatactatgc agatatacta 6780
tgccaatgtt taattgtcag 6800

<210> SEQ ID NO 59
<211> LENGTH: 7373
<212> TYPE: DNA
<213> ORGANISM: Artificial sequence
<220> FEATURE:
<223> OTHER INFORMATION: Synthetic

<400> SEQUENCE: 59
cactatgtgg acatgaattc aattggctag cagactagtc ccaccgaaag gttgctcctt 60
aacacaggct aaggaccagc ttctttggga gagaacagac gcaggggcgg gagggaaaaa 120
gggagaggca gacgtcactt ccccttggcg gctctggcag cagattggtc ggttgagtgg 180
cagaaaggca gacggggact gggcaaggca ctgtcggtga catcacggac agggcgactt 240
ctatgtagat gaggcagcgc agaggctgct gcttcgccac ttgctgcttc gccacgaagg 300
agttcccgtg ccctgggagc gggttcagga ccgcggatcg gaagtgagaa tcccagctgt 360
gtgtcagggc tggaaagggc tcgggagtgc gcggggcaag tgaccgtgtg tgtaaagagt 420
gaggcgtatg aggctgtgtc ggggcagagc ccgaagatcc agtttggcga ttccgctata 480
aatgcggttt tagagctaga aatagcaagt taaaataagg ctagtccgtt atcaacttga 540
aaaagtggca ccgagtcggt gcagatctgg aggagtttca aaaacagacc tggcagcatc 600
tagcaggagt caatgggaaa aacccattgg agccaagtac actgactcaa tagggacttt 660
ccattgggtt ttgcccagta cataaggtca ataggggtg agtcaacagg aaagtcccat 720
tggagccaag tacattgagt caatagggac tttccaatgg gttttgccca gtacataagg 780
tcaatgggag gtaagccaat gggtttttcc cattactgac atgtatactg agtcattagg 840
gactttccaa tgggttttgc ccagtacata aggtcaatag gggtgaatca acaggaaagt 900
cccattggag ccaagtacac tgagtcaata gggactttcc attgggtttt gcccagtaca 960
aaaggtcaat agggggtgag tcaatgggtt tttcccatta ttggcacata cataaggtca 1020
ataggggtga ctagtggaga agagcatgct tgagggctga gtgcccctca gtgggcagag 1080
agcacatggc ccacagtccc tgagaagttg gggggagggg tgggcaattg aactggtgcc 1140
tagagaaggt ggggcttggg taaactggga aagtgatgtg gtgtactggc tccacctttt 1200
tccccagggt gggggagaac catatataag tgcagtagtc tctgtgaaca ttcaagcttc 1260
tgccttctcc ctcctgtgag tttggtaagt cactgactgt ctatgcctgg gaaagggtgg 1320
gcaggagatg gggcagtgca ggaaaagtgg cactatgaac cctgcagccc tagacaattg 1380
tactaacctt cttctctttc ctctcctgac aggttggtaa ccaagccacc atggactaca 1440
aggaccatga tggggattat aaggatcatg acattgatta caaggatgat gatgacaaga 1500
tggcccctaa gaagaagagg aaagttggca tccatggggt gccagctgct gacaagaagt 1560
acagcattgg cctggacatt ggcaccaact ctgttggctg ggctgtgatc actgatgagt 1620
acaaggtgcc cagcaagaag ttcaaggtcc tgggcaacac agacaggcac agcatcaaga 1680
agaacctgat tggagccctg ctgtttgact ctggggagac agctgaggcc accagactga 1740
agagaacagc cagaagaaga tacacaagaa gaaagaacag gatctgctac ctgcaagaaa 1800
tcttcagcaa tgagatggcc aaagtggatg acagcttctt ccacagactg gaagagtcct 1860
tcctggtgga agaggacaag aaacatgaga gacaccccat ctttggcaac attgtggatg 1920
aggtggccta ccatgagaag taccccacca tctaccacct gagaaagaaa ctggtggaca 1980
gcacagacaa ggctgacctg agactgatct acctggctct ggcccacatg atcaagttca 2040
gaggccactt cctgattgaa ggggatctga accctgacaa ctctgatgtg gacaagctgt 2100
ttatccagct ggtgcagacc tacaaccagc tgtttgagga aaaccccatc aatgccagtg 2160
gtgttgatgc caaggccatc ctgtctgcca gactgagcaa gagcagaagg ctggaaaatc 2220
tgattgccca gctgcctggg gagaagaaga atggcctgtt tggcaacctc attgccctga 2280
gcctgggcct gacacctaac ttcaagagca actttgacct ggctgaggat gccaagctcc 2340
agctgtccaa ggacacctat gatgatgatc tggacaacct gctggcccag attggggacc 2400
agtatgctga cctgttcctg gctgccaaga acctgtctga tgccatcctg ctgtctgaca 2460
tcctgagagt gaacacagag atcacaaagg cccctctgtc tgcctctatg atcaagagat 2520
atgatgagca ccaccaggac ctgacactgc tgaaggctct tgttagacag cagctgccag 2580
agaagtacaa agagattttc tttgaccaga gcaagaatgg ctatgctggc tacattgatg 2640
gtggtgcctc tcaagaagag ttctacaagt tcatcaagcc catcctggaa aagatggatg 2700
gcacagagga actgctggtc aagctgaaca gagaggacct gctgagaaag cagaggacct 2760
ttgacaatgg cagcatccct caccagatcc acctgggaga gctgcatgct atcctgagaa 2820
ggcaagagga tttctaccca ttcctgaagg acaacagaga gaagattgag aagatcctga 2880
ccttcagaat cccctactat gtgggccctc tggctagagg caacagcaga tttgcctgga 2940
tgaccagaaa gtctgaggaa accatcacac cctggaactt tgaggaagtg gtggacaaag 3000
gggcctctgc tcagagcttc attgagagaa tgacaaactt tgacaagaat ctgcccaatg 3060
agaaggtgct gcccaagcac agcctgctgt atgagtactt cacagtgtac aatgagctga 3120
caaaagtgaa atatgtgaca gagggaatga gaaagcctgc cttcctgtct ggggagcaga 3180
aaaaggccat tgtggacctg cttttcaaga ccaacagaaa agtgacagtg aagcagctga 3240
aagaggacta cttcaagaaa attgagtgct ttgattctgt ggaaatctct ggtgttgagg 3300
acaggttcaa tgcctctctg ggcacatacc atgacctgct caagattatc aaggacaagg 3360
acttcctgga caatgaggaa aatgaggaca tccttgagga cattgtgctg acactgaccc 3420
tgtttgaaga tagggaaatg attgaggaaa ggctcaagac atatgcccac ctgtttgatg 3480
acaaagtgat gaagcaactc aagagaagaa gatatacagg ctggggcaga ctgtccagaa 3540

```
agctgatcaa tggaatcagg gacaagcaga gtggcaagac aatcctggat ttcctgaagt   3600
ctgatggctt tgccaatagg aacttcatgc agctgatcca tgatgacagc ctcaccttca   3660
aagaggacat tcagaaggcc caagtctctg gccaagggga cagcctgcat gagcacattg   3720
ctaacctggc tggcagccct gctatcaaga agggcatcct ccagactgtg aaggtggtgg   3780
atgagcttgt gaaagtgatg ggcagacaca agcctgagaa cattgtgatt gagatggcta   3840
gagagaacca gaccacacag aagggacaga agaacagcag agaaaggatg aagaggattg   3900
aagagggcat caaagagctg ggcagccaga tcctgaaaga gcaccctgtt gagaacaccc   3960
agctccagaa tgagaagctg tacctgtact acttgcagaa tggcagggat atgtatgtgg   4020
accaagagct ggacatcaac agactgtctg actatgatgt ggatcatatt gtgccccaga   4080
gctttctgaa ggatgactcc attgacaaca aggtgctgac taggagtgac aagaacaggg   4140
gcaagtctga caatgtgccc tctgaagagg tggtcaagaa gatgaagaac tattggaggc   4200
agctcctgaa tgccaaactg atcacccaga ggaagtttga caacctgacc aaggctgaga   4260
gaggtggact ctctgaactg gataaggctg gcttcatcaa gaggcagctt gtggaaacca   4320
gacagatcac caaacatgtg gctcagatcc tggacagcag aatgaacact aagtatgatg   4380
agaatgataa gctcatcagg gaagtgaaag tcatcaccct gaagtccaag ctggtgtctg   4440
actttaggaa agacttccag ttttacaaag tcagagagat caacaactac caccatgctc   4500
atgatgccta cctgaatgct gttgtgggca cagccctgat caaaaagtac cctaagctgg   4560
aatctgagtt tgtgtatggg gactacaaag tgtatgatgt cagaaagatg attgccaagt   4620
ctgaacaaga gattggcaag gctacagcca agtacttctt ctacagcaac atcatgaatt   4680
tcttcaagac tgagatcacc ctggctaatg gggagatcag aaagaggcca ctgattgaga   4740
caaatggaga gactggggag attgtgtggg acaagggcag agactttgcc acagtcagaa   4800
aggtgctgtc tatgccccaa gtgaacattg tcaagaaaac agaggtgcag actggtggct   4860
tctccaaaga gagcatcctg cctaagagga acagtgacaa gctgattgcc agaaagaagg   4920
actgggaccc caagaagtat ggaggctttg acagccccac agtggcctac tctgtgctgg   4980
tggtggccaa ggtggaaaag ggcaagagca aaaagctcaa gagtgtgaaa gagctgctgg   5040
gcatcaccat catggaaagg tccagctttg agaagaaccc tattgacttc cttgaggcca   5100
agggctacaa agaagtgaaa aaggacctga tcatcaagct ccccaagtac tctctgtttg   5160
aactggaaaa tgggagaaag aggatgctgg cttctgctgg ggaactccag aaaggcaatg   5220
aactggccct gcctagcaaa tatgtcaact tcctgtacct ggccagccac tatgagaaac   5280
tgaagggcag cccagaggat aatgagcaaa agcagctttt tgtggaacag cacaagcact   5340
acctggatga gatcattgag caaatctctg agttcagcaa gagggtcatc ctggcagatg   5400
ccaacctgga caaagtgctg agtgcctaca acaagcacag ggacaaaccc atcagagagc   5460
aggcagagaa catcatccac ctgttcaccc tgaccaacct gggagcccct gctgccttca   5520
agtactttga caccaccatt gataggaaga ggtacaccag caccaaagag gtcctggatg   5580
ctaccctgat ccaccagagc atcactggcc tgtatgagac aagaattgac ctgtctcagc   5640
ttggaggggga caagaggcct gctgccacaa agaaagcagg ccaggccaaa aagaagaagt   5700
gaagatctac ttctggctaa taaaagatca gagctctagt gatctgtgtg ttggtttttt   5760
gtgtctgcat tctagcatga gggcctattt cccatgattc cttcatattt gcatatacga   5820
tacaaggctg ttagagagat aattggaatt aatttgactg taaacacaaa gatattagta   5880
caaaatacgt gacgtagaaa gtaataattt cttgggtagt ttgcagtttt aaaattatgt   5940
```

```
tttaaaatgg actatcatat gcttaccgta acttgaaagt atttcgattt cttggcttta   6000
tatatcttgt ggaaaggacg aaacaccggc gattccgcta taaatgcggt tttagagcta   6060
gaaatagcaa gttaaaataa ggctagtccg ttatcaactt gaaaaagtgg caccgagtcg   6120
gtgctttttt gttttagagc tagaaatagc aagttaaaat aaggctagtc cgtttttagc   6180
gcgtgcgcca attctagctc tagtgatcag cagttcaacc tgttgatagt atgtactaag   6240
ctctcatgtt taatgtacta agctctcatg tttaatgaac taaaccctca tggctaatgt   6300
actaagctct catggctaat gtactaagct ctcatgtttc atgtactaag ctctcatgtt   6360
tgaacaataa aattaatata aatcagcaac ttaaatagcc tctaaggttt taagttttat   6420
aagaaaaaaa agaatatata aggcttttaa aggttttaag gtttcctagg ttatcctcat   6480
atgagctctt agaaaaactc atccagcatc aaatgaaact gcaatttatt catatcagga   6540
ttatcaatac catatttttg aaaaagtctt ttctgtaatg aaggagaaaa ctcacccagg   6600
cagttccata ggatggcaag atcctggtat ctgtctgcaa ttccaactct tccaacatca   6660
atacaaccta ttaatttccc ctcatcaaaa ataaggttat caagtgagaa atcaccatga   6720
gtgaccactg aatctggtga gaatggcaaa agattatgca tttctttcca gacttgttca   6780
acaggccagc catttctctc atcatcaaaa tcactggcat caaccaaacc attattcatt   6840
cttgattggg cctgagccag tctaaatact ctatcagagt taaaaggaca attacaaaca   6900
ggaatggaat gcaatcttct caggaacact gccagggcat caacaatatt ttcacctgaa   6960
tcaggatatt cttccaatac ctggaatgct gttttccctg ggatggcagt ggtgagtaac   7020
catgcatcat caggagttct gataaaatgc ttgatggttg gaagaggcat aaattcagtc   7080
agccagttta gtctgaccat ctcatctgta acatcattgg caacagaacc tttgccatgt   7140
ttcagaaaca actctggggc atctggcttc ccatacaatc tatagattgt ggcacctgat   7200
tgcccaacat tatctctagc ccatttatac ccatataaat cagcatccat gttggaattt   7260
aatcttggcc tggagcaaga ggtttctctt tgaatatggc tcatacatgt gcacctccta   7320
tagtgagttg tattatacta tgcagatata ctatgccaat gtttaattgt cag          7373
```

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82
<211> LENGTH: 5089
<212> TYPE: DNA
<213> ORGANISM: Artificial sequence
<220> FEATURE:
<223> OTHER INFORMATION: Synthetic

<400> SEQUENCE: 82
cactatgtgg acatgaattc aattggctag caggagtcaa tgggaaaaac ccattggagc 60
caagtacact gactcaatag ggactttcca ttgggttttg cccagtacat aaggtcaata 120
gggggtgagt caacaggaaa gtcccattgg agccaagtac attgagtcaa tagggacttt 180
ccaatgggtt ttgcccagta cataaggtca atgggaggta agccaatggg tttttcccat 240
tactgacatg tatactgagt cattagggac tttccaatgg gttttgccca gtacataagg 300
tcaatagggg tgaatcaaca ggaaagtccc attggagcca agtacactga gtcaataggg 360
actttccatt gggttttgcc cagtacaaaa ggtcaatagg gggtgagtca atgggttttt 420
cccattattg gcacatacat aaggtcaata ggggtgacta gtggagaaga gcatgcttga 480
gggctgagtg cccctcagtg ggcagagagc acatggccca cagtccctga gaagttgggg 540
ggaggggtgg gcaattgaac tggtgcctag agaaggtggg gcttgggtaa actgggaaag 600
tgatgtggtg tactggctcc accttttttcc ccagggtggg ggagaaccat atataagtgc 660
agtagtctct gtgaacattc aagcttctgc cttctccctc ctgtgagttt ggtaagtcac 720

```
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaaccg cggccgcggc tcgagggtac caacttaaaa aaaaaaatca aaatgggctg    900
gtccctgatc ctgctgttcc tggtggctgt ggccaccaga gtgctgagcc aggtgcagct    960
gcagcagcct ggggctgagc ttgtgaaacc tggggcctct gtgaagatga gctgcaaggc   1020
ctctggctac accttcacca gctacaacat gcactgggtc aagcagaccc ctggcagagg   1080
cctggaatgg attggagcca tctaccctgg caatggggac acctcctaca accagaagtt   1140
caagggcaag gccaccctga cagctgacaa gagcagcagc acagcctaca tgcagctgtc   1200
cagcctgacc tctgaggact ctgctgtgta ctactgtgcc aggtccacct actatggggg   1260
agactggtac ttcaatgtgt ggggagctgg caccacagtg acagtgtctg ctgccagcac   1320
caagggcccc tctgtgtttc ctctggcccc cagcagcaag agcacctctg gggggaacagc   1380
tgccctgggc tgccttgtga aggactactt ccctgagcct gtgactgtgt cctggaactc   1440
tggggccctg acatctgggg tgcacacctt ccctgcagtg ctgcagtcca gtggcctgta   1500
ctccctgtcc tctgttgtga cagtgcccag ctccagcctg ggcacccaga cctacatctg   1560
caatgtgaac cacaagccca gcaacaccaa ggtggacaag aaggctgagc ccaagagctg   1620
tgacaagacc cacacctgtc ccccctgtcc tgcccctgaa ctgctgggag gaccttctgt   1680
gttcctgttc ccacccaagc ccaaggatac cctgatgatc agcagaaccc ctgaagtgac   1740
ctgtgtggtg gtggatgtgt cccatgagga cccagaagtg aagttcaatt ggtatgtgga   1800
tggggtggaa gtgcacaatg ccaagaccaa gcccagagag gaacagtaca acagcaccta   1860
cagagtggtg tctgtgctga ctgtgctgca ccaggactgg ctgaatggca aagagtacaa   1920
gtgcaaggtg tccaacaagg ccctgccagc ccccattgag aaaaccatca gcaaggccaa   1980
gggccagcct agagaacccc aggtgtacac actgcccccct agcagggatg agctgaccaa   2040
gaaccaggtg tccctgacat gccttgtgaa aggcttctac ccctctgaca ttgctgtgga   2100
atgggagagc aatggacagc ctgagaacaa ctacaagacc acccccccctg tgctggactc   2160
tgatggctca ttcttcctgt acagcaagct gacagtggac aagtccagat ggcagcaggg   2220
caatgtgttc agctgctctg tgatgcatga ggccctgcac aaccactaca cccagaaaag   2280
cctgtccctg tcccctggca agagaaagag aaggagtgga agtggagcta ctaacttcag   2340
cctgctgaag caggctggag atgtggagga gaaccctgga cctatggact tccaggtgca   2400
gatcatcagc tttctgctga tctctgcctc tgtgatcatg agcagaggcc agattgtgct   2460
gagccagagc cctgccatcc tgtctgcaag ccctggggag aaagtgacca tgacctgcag   2520
agccagcagc tctgtgtcct acatccactg gttccagcag aagcctggca gcagccccaa   2580
gccttggatc tatgccacca gcaacctggc atctggggtg ccagtcagat tctctggctc   2640
tggatctggc accagctaca gcctgaccat cagcagagtg gaagctgagg atgctgccac   2700
ctactactgc cagcagtgga ccagcaatcc ccccaccttt ggagggggca ccaagctgga   2760
aatcaagaga acagtggctg ccccctctgt gttcatcttc ccaccctctg atgagcagct   2820
gaagtctgga acagcctctg ttgtgtgcct gctgaacaac ttctacccca gagaagccaa   2880
ggtgcagtgg aaggtggaca atgccctgca gtctggcaac tcccaggaat ctgtgacaga   2940
gcaggacagc aaggactcca cctactccct gagcagcacc ctgaccctga gcaaggctga   3000
ctatgagaag cacaaagtgt atgcctgtga agtgacccac cagggcctgt ccagccctgt   3060
gaccaagagc ttcaacagag ggagagagctg aagatctaaa taacaaatca attgttttat   3120
```

aatattctta ctattctttg attatgtaat aaaatgtgat cattaggaag attactaaaa 3180
atataaaaaa tatgagttct gtgtgtataa caaatgctgt aaactccaca attgtgtttg 3240
ttgcaaataa acccatgatt atttgattaa aattgttgtt ttctttgttc atagacaata 3300
gtgtgttttg cctaaacttg tactgcataa actccatgct agtgtatagc aagctagtgg 3360
ctaactcttg ccccaccaaa gtagattctt caaaatcctc aatttcatca ccctcctcca 3420
agtttaacat ttggccttct gaattaactt ctaaagatgc cacataatct aataaatgaa 3480
atagagattc aaacttggct tcatcttcct tttctaccat ttcctaaaag aactctggca 3540
taaactctat gatttctctg gacttggtgt tgtctaaact ctcaaagtac tcagtcagga 3600
acttgctcta catgtcttct ggaaactctc tctgaaacat gttgttgtaa cctaactggt 3660
cccatagctc caaaaccaaa tctgccagct tcaatagaat gagcactatg cctacaatgg 3720
agctggcttg gatagctatt ctagttaact gcctgccttt taaactaatt cttgaagact 3780
aaagggcctc ttgatactcc tatttttata ggttaatgtc atgataataa tggtttctta 3840
tctagtactt ctggctaata aaagatcaga gctctagtga tctgtgtgtt ggttttttgt 3900
gtctgcattc tagctctagt gatcagcagt tcaacctgtt gatagtatgt actaagctct 3960
catgtttaat gtactaagct ctcatgttta atgaactaaa ccctcatggc taatgtacta 4020
agctctcatg gctaatgtac taagctctca tgtttcatgt actaagctct catgtttgaa 4080
caataaaatt aatataaatc agcaacttaa atagcctcta aggttttaag ttttataaga 4140
aaaaaaagaa tatataaggc ttttaaaggt tttaaggttt cctaggttat cctcatatga 4200
gctcttagaa aaactcatcc agcatcaaat gaaactgcaa tttattcata tcaggattat 4260
caataccata tttttgaaaa agtcttttct gtaatgaagg agaaaactca cccaggcagt 4320
tccataggat ggcaagatcc tggtatctgt ctgcaattcc aactcttcca acatcaatac 4380
aacctattaa tttcccctca tcaaaaataa ggttatcaag tgagaaatca ccatgagtga 4440
ccactgaatc tggtgagaat ggcaaaagat tatgcatttc tttccagact tgttcaacag 4500
gccagccatt tctctcatca tcaaaatcac tggcatcaac caaaccatta ttcattcttg 4560
attgggcctg agccagtcta aatactctat cagagttaaa aggacaatta caaacaggaa 4620
tggaatgcaa tcttctcagg aacactgcca gggcatcaac aatattttca cctgaatcag 4680
gatattcttc caatacctgg aatgctgttt tccctgggat ggcagtggtg agtaaccatg 4740
catcatcagg agttctgata aaatgcttga tggttggaag aggcataaat tcagtcagcc 4800
agtttagtct gaccatctca tctgtaacat cattggcaac agaacctttg ccatgtttca 4860
gaaacaactc tggggcatct ggcttcccat acaatctata gattgtggca cctgattgcc 4920
caacattatc tctagcccat ttatacccat ataaatcagc atccatgttg gaatttaatc 4980
ttggcctgga gcaagaggtt tctctttgaa tatggctcat acatgtgcac ctcctatagt 5040
gagttgtatt atactatgca gatatactat gccaatgttt aattgtcag 5089

<210> SEQ ID NO 83
<211> LENGTH: 7312
<212> TYPE: DNA
<213> ORGANISM: Artificial sequence
<220> FEATURE:
<223> OTHER INFORMATION: Synthetic

<400> SEQUENCE: 83
cactatgtgt taattaaaat tatctctaag gcatgtgaac tggctgtctt ggttttcatc 60

-continued

```
tgtacttcat ctgctacctc tgtgacctga aacatattta taattccatt aagctgtgca    120
tatgatagat ttatcatatg tattttcctt aaaggatttt tgtaagaact aattgaattg    180
atacctgtaa agtctttatc acactaccca ataaataata aatctctttg ttcagctctc    240
tgtttctata aatatgtacc agttttattg tttttagtgg tagtgatttt attctctttc    300
tatatatata cacacacatg tgtgcattca taaatatata caatttttat gaataaaaaa    360
ttattagcaa tcaatattga aaaccactga tttttgttta tgtgagcaaa cagcagatta    420
aaaggaattt gaattctcat agctagcagg agtcaatggg aaaaacccat tggagccaag    480
tacactgact caatagggac tttccattgg gttttgccca gtacataagg tcaatagggg    540
gtgagtcaac aggaaagtcc cattggagcc aagtacattg agtcaatagg gactttccaa    600
tgggttttgc ccagtacata aggtcaatgg gaggtaagcc aatgggtttt tcccattact    660
gacatgtata ctgagtcatt agggactttc caatgggttt tgcccagtac ataaggtcaa    720
taggggtgaa tcaacaggaa agtcccattg gagccaagta cactgagtca atagggactt    780
tccattgggt tttgcccagt acaaaaggtc aatagggggt gagtcaatgg gtttttccca    840
ttattggcac atacataagg tcaatagggg tgactagtgg agaagagcat gcttgagggc    900
tgagtgcccc tcagtgggca gagagcacat ggcccacagt ccctgagaag ttgggggggag    960
gggtgggcaa ttgaactggt gcctagagaa ggtggggctt gggtaaactg ggaaagtgat   1020
gtggtgtact ggctccacct tttccccag ggtgggggag aaccatatat aagtgcagta   1080
gtctctgtga acattcaagc ttctgccttc tccctcctgt gagtttggta agtcactgac   1140
tgtctatgcc tgggaaaggg tgggcaggag atggggcagt gcaggaaaag tggcactatg   1200
aaccctgcag ccctagacaa ttgtactaac cttcttctct ttcctctcct gacaggttgg   1260
taaccaagcc accatggtcc tccagacaca ggtgttcatc agcctgctgc tgtggatcag   1320
tggtgcctat ggacaggtcc agctgcaaga gtctggccct ggacttgtca gacccagcca   1380
gacactgagc ctgacctgta cagtctctgg cttcagcctg accagctact ctgtgcactg   1440
ggtcagacag cctccaggca gaggactgga atggctggga gtgatctggg ccagtggtgg   1500
cacagactac aactctgccc tgatgagcag actgagcatc ctgaaggaca acagcaagaa   1560
ccaggtgtcc ctgagactgt cctctgtgac agctgctgat acagctgtgt acttctgtgc   1620
cagagatcct cctagctctc tgctgagact ggactactgg ggccagggca caacagtgac   1680
agtgtccagt gccagcacaa agggcccctc tgtgtttcct ctggctccca gcagcaagag   1740
caccagtggt ggaactgctg ccctgggctg tctggtcaag gactactttc ctgagcctgt   1800
gactgtgtcc tggaactctg gggctctgac atctggggtg cacacattcc ctgctgtgct   1860
gcaatcctct ggcctgtaca gcctcagctc tgtggtcaca gtgcctagct ctagcctggg   1920
cacccagacc tacatctgca atgtgaacca caagcctagc aacaccaagg tggacaagaa   1980
ggctgagccc aagagctgtg acaagaccca cacctgtcct ccatgtcctg ctccagagct   2040
gcttggagga cccagtgtgt tcctgtttcc tccaaagcca aaggacaccc tgatgatcag   2100
cagaacccct gaagtgacct gtgtggtggt ggatgtgtcc catgaggacc ctgaagtcaa   2160
gttcaattgg tatgtggatg gtgttgaggt gcacaatgcc aagaccaagc ctagagagga   2220
acagtacaac agcacctaca gagtggtgtc agtgctgaca gtgctgcacc aggactggct   2280
gaatggcaaa gagtacaagt gcaaggtgtc caacaaggcc ctgcctgctc ctattgaaaa   2340
gaccatcagc aaggccaagg gccagcctag ggaaccccag gtttacacac tgccacctag   2400
cagagatgag ctgaccaaaa atcaggtttc cctgacctgc ctggttaagg gcttctaccc   2460
```

ctctgacatt gctgtggaat gggagagcaa tggccagcct gagaacaact acaagacaac 2520
ccctcctgtg ctggactctg atggctcatt cttcctgtac tccaagctga ctgtggacaa 2580
aagcagatgg cagcaaggca atgtgttcag ctgctctgtg atgcatgagg ccctgcacaa 2640
ccactacacc cagaagtccc tgtctctgag ccctggcaag tgaagatcta cttctggcta 2700
ataaaagatc agagctctag tgatctgtgt gttggttttt tgtgtctgca ttctagcaga 2760
gccccactgt gttcatctta cagatggaaa tactgacatt cagaggagtt agttaacttg 2820
cctaggtgat tcagctaata agtgcaagaa agatttcaat ccaaggtgat ttgattctga 2880
agcctgtgct aatcacatta caccaagcta caacttcatt tataaataat aagtcagctt 2940
tcaagggcct ttcaggtgtc ctgcacttct acaagctgtg ccatttagtg aacacaaaat 3000
gagccttctg atgaagtagt cttttcatta tttcagatat tagaacacta aaattcttag 3060
ctgccagctg attgaaggct gggacaaaat tcaaacatgc atctacaaca atatatatct 3120
caatgttagt ctccaaattc tattgacttc aactcaagag aatataaaga gctagtcttt 3180
atacactctt taaggtatga tatcatctgg aaagtaacaa aattgatgca aatttgaatg 3240
aactttatca tggtgtattt acacaatgtg tttcttctcc ctgcaatgta tttctttctc 3300
taattccttc catttgatct ttcatacaca atctggttct gatgtatgtt ttttggatgc 3360
acttttcaac tccaaaagac agagctagtt actttcttcc tggtgctcca agcactgtat 3420
ttgtatctgt attcaagccc tttgcaatat tgtactggat cattatttca cctctaggat 3480
ggcttcccca ggcaacttgt gttcacccag agactacatt ttgtatcttg ttgacctttg 3540
aacttccacc agtgtctaaa aataatatgt atgcaaaatt acttgctatg agaatgtata 3600
attaaacaat ataaaaagga gaagcaagga gagaaacaca ggtgtgtatt tgtgtttgtg 3660
tgcttaaaag gcagtgtgga aaaggaagaa atgccattta tagtgaggag acaaagttat 3720
attacctctt atctggcttt taaggagatt ttgctgagct aaaaatccta tattcataga 3780
aaagccttac ctgagttgcc aatacctcaa ttcagtctag catgttacat aacttatggt 3840
aaatggcctg cctggctgac tgcccaatga cccctgccca atgatgtcaa taatgatgta 3900
tgttcccatg taatgccaat agggactttc cattgatgtc aatgggtgga gtatttatgg 3960
taactgccca cttggcagta catcaagtgt atcatatgcc aagtatgccc cctattgatg 4020
tcaatgatgg taaatggcct gcctggcatt atgcccagta catgacctta tgggactttc 4080
ctacttggca gtacatctat gtattagtca ttgctattat ctagcactag tggagaagag 4140
catgcttgag ggctgagtgc ccctcagtgg gcagagagca catggcccac agtccctgag 4200
aagttggggg gaggggtggg caattgaact ggtgcctaga gaaggtgggg cttgggtaaa 4260
ctgggaaagt gatgtggtgt actggctcca cctttttccc cagggtgggg gagaaccata 4320
tataagtgca gtagtctctg tgaacattca agcttctgcc ttctccctcc tgtgagtttg 4380
gtaagtcact gactgtctat gcctgggaaa gggtgggcag gagatggggc agtgcaggaa 4440
aagtggcact atgaaccctg cagccctaga caattgtact aaccttcttc tctttcctct 4500
cctgacaggt tggtaaccaa gccaccatgg tgctgcaaac ccaggttttc atttctctgc 4560
tcctctggat tagtggtgct tatggggaca ttgtgatgac acagagccct agcagcctgt 4620
ctgcctctgt gggagacaga gtgaccatca catgcaagtc cagccagagt ctgctgaact 4680
ctggcaacca gaagaactac ctggcctggt atcagcaaaa gcctggcaag gcccctaagc 4740
tgctcatcta tggggccagc accagagagt ctggggtccc agatagattc tctggctctg 4800

-continued

```
gatctggcac tgacttcacc ttcaccatca gctccctgca accagaggac attgccacct   4860
actactgcca gaatgtgcac agcttcccat tcacctttgg acagggcact aaggtggaaa   4920
tcaagaggac tgtggctgct ccttctgtgt tcatcttccc accatcagat gaacagctga   4980
agagtggcac agcctctgtt gtgtgcctgc tcaacaactt ctaccctaga gaagccaagg   5040
tgcagtggaa agtggacaat gccctccagt ctggcaacag ccaagaatct gtgactgagc   5100
aggactccaa ggacagcaca tacagcctga gcagcacact gaccctgagc aaggctgact   5160
atgagaagca caaagtctat gcctgtgaag tgacacacca gggcctgtct agcccagtga   5220
ccaagtcctt caacagggga gagagctgaa gatctacttc tggctaataa aagatcagag   5280
ctctagtgat ctgtgtgttg gtttttgtg tctgcattct agcagtcaat atgttcaccc   5340
caaaaaagct gtttgttaac ttgtcaacct cattctaaaa tgtatataga agcccaaaag   5400
acaataacaa aaatattctt gtagaacaaa atgggaaaga atgttccact aaatatcaag   5460
atttagagca aagcatgaga tgtgtgggga tagacagtga ggctgataaa atagagtaga   5520
gctcagaaac agacccattg atatatgtaa gtgacctatg aaaaaaatat ggcattttac   5580
aatgggaaaa tgatggtctt tttcttttt agaaaaacag ggaaatatat ttatatgtaa   5640
aaaataaaag ggaacccata tgtcatacca tacacacaaa aaaattccag tgaattataa   5700
gtctaaatgg agaaggcaaa actttaaatc ttttagaaaa taatatagaa gcatgccatc   5760
aagacttcag tgtagagaaa aatttcttat gactcaaagt cctaaccaca aagaaaagat   5820
tgttaattag attgcatgaa tattaagact tatttttaaa attaaaaaac cattaagaaa   5880
agtcaggcca tagaatgaca gaaaatattt gcaacacccc agtaaagaga attgtaatat   5940
gcagattata aaaagaagtc ttacaaatca gtaaaaaata aaactagaca aaaatttgaa   6000
cagatgaaag agaaactcta aataatcatt acacatgaga aactcaatct cagaaatcag   6060
agaactatca ttgcatatac actaaattag agaaatatta aaaggctaag taacatctgt   6120
ggcttaatta atctagctct agtgatcagc agttcaacct gttgatagta tgtactaagc   6180
tctcatgttt aatgtactaa gctctcatgt ttaatgaact aaaccctcat ggctaatgta   6240
ctaagctctc atggctaatg tactaagctc tcatgtttca tgtactaagc tctcatgttt   6300
gaacaataaa attaatataa atcagcaact taaatagcct ctaaggtttt aagttttata   6360
agaaaaaaaa gaatatataa ggcttttaaa ggttttaagg tttcctaggt tatcctcata   6420
tgagctctta gaaaaactca tccagcatca aatgaaactg caatttattc atatcaggat   6480
tatcaatacc atatttttga aaaagtcttt tctgtaatga aggagaaaac tcacccaggc   6540
agttccatag gatggcaaga tcctggtatc tgtctgcaat tccaactctt ccaacatcaa   6600
tacaacctat taatttcccc tcatcaaaaa taaggttatc aagtgagaaa tcaccatgag   6660
tgaccactga atctggtgag aatggcaaaa gattatgcat ttctttccag acttgttcaa   6720
caggccagcc atttctctca tcatcaaaat cactggcatc aaccaaacca ttattcattc   6780
ttgattgggc ctgagccagt ctaaatactc tatcagagtt aaaaggacaa ttacaaacag   6840
gaatggaatg caatcttctc aggaacactg ccagggcatc aacaatattt tcacctgaat   6900
caggatattc ttccaatacc tggaatgctg ttttccctgg gatggcagtg gtgagtaacc   6960
atgcatcatc aggagttctg ataaaatgct tgatggttgg aagaggcata aattcagtca   7020
gccagtttag tctgaccatc tcatctgtaa catcattggc aacagaacct ttgccatgtt   7080
tcagaaacaa ctctggggca tctggcttcc catacaatct atagattgtg gcacctgatt   7140
gcccaacatt atctctagcc catttatacc catataaatc agcatccatg ttggaattta   7200
```

atcttggcct ggagcaagag gtttctcttt gaatatggct catacatgtg cacctcctat 7260
agtgagttgt attatactat gcagatatac tatgccaatg tttaattgtc ag 7312

<210> SEQ ID NO 84
<211> LENGTH: 7300
<212> TYPE: DNA
<213> ORGANISM: Artificial sequence
<220> FEATURE:
<223> OTHER INFORMATION: Synthetic

<400> SEQUENCE: 84
cactatgtgt taattaaaat tatctctaag gcatgtgaac tggctgtctt ggttttcatc 60
tgtacttcat ctgctacctc tgtgacctga aacatattta taattccatt aagctgtgca 120
tatgatagat ttatcatatg tattttcctt aaaggatttt tgtaagaact aattgaattg 180
atacctgtaa agtctttatc acactaccca ataaataata aatctctttg ttcagctctc 240
tgtttctata aatatgtacc agttttattg tttttagtgg tagtgatttt attctctttc 300
tatatatata cacacacatg tgtgcattca taaatatata caatttttat gaataaaaaa 360
ttattagcaa tcaatattga aaaccactga tttttgttta tgtgagcaaa cagcagatta 420
aaaggaattt gaattctcat agctagcagg agtcaatggg aaaaacccat tggagccaag 480
tacactgact caatagggac tttccattgg gttttgccca gtacataagg tcaatagggg 540
gtgagtcaac aggaaagtcc cattggagcc aagtacattg agtcaatagg gactttccaa 600
tgggttttgc ccagtacata aggtcaatgg gaggtaagcc aatgggtttt tcccattact 660
gacatgtata ctgagtcatt agggactttc caatgggttt tgcccagtac ataaggtcaa 720
taggggtgaa tcaacaggaa agtcccattg gagccaagta cactgagtca atagggactt 780
tccattgggt tttgcccagt acaaaaggtc aatagggggt gagtcaatgg gtttttccca 840
ttattggcac atacataagg tcaatagggg tgactagtgg agaagagcat gcttgagggc 900
tgagtgcccc tcagtgggca gagagcacat ggcccacagt ccctgagaag ttggggggag 960
gggtgggcaa ttgaactggt gcctagagaa ggtggggctt gggtaaactg ggaaagtgat 1020
gtggtgtact ggctccacct ttttccccag ggtgggggag aaccatatat aagtgcagta 1080
gtctctgtga acattcaagc ttctgccttc tccctcctgt gagtttggta agtcactgac 1140
tgtctatgcc tgggaaaggg tgggcaggag atggggcagt gcaggaaaag tggcactatg 1200
aaccctgcag ccctagacaa ttgtactaac cttcttctct ttcctctcct gacaggttgg 1260
taaccaagcc accatgggat ggtccctgat cctgctgttt ctggtggctg tggccaccag 1320
agtgctgtct gaagtgcagc tggtggaatc tggccctggc ctggttaagc cctctgacat 1380
cctgagcctg acctgtgctg tgtctggcta cagcatcagc agcaactact actggggctg 1440
gatcagacag cctcctggca aaggcctgga atggattggc agcatctacc actctggctc 1500
cacctactac aagcccagcc tggaaagcag actgggcatc tctgtggaca ccagcaagaa 1560
ccagttcagc ctgaagctga gctttgtgtc tgctgctgac actgctgtgt actactgtgc 1620
cagacatgtt aggagtggct accctgacac agcctactac tttgataagt ggggccaggg 1680
caccctggtc acagtgtctg cttctacaaa gggcccctct gtgttcccac tggctcctag 1740
cagcaagagc accagtggtg gaacagctgc cctgggctgt ctggtcaagg actactttcc 1800
tgagccagtg acagtgtcct ggaactctgg ggctctgact tctggggtgc acacattccc 1860
tgctgtgctc cagtcctctg gcctgtacag cctgtcctct gtggtcactg tgccaagctc 1920

-continued

```
tagcctgggc acccagacct acatctgcaa tgtgaaccac aagcctagca acaccaaggt   1980
ggacaagaag gctgagccca agagctgtga caagacccac acctgtcctc catgtcctgc   2040
tccagagctg cttggaggac cttctgtgtt tctgttccct ccaaagccaa aggacaccct   2100
gatgatcagc agaacccctg aagtgacctg tgtggtggtg gatgtgtccc atgaggaccc   2160
agaagtgaag ttcaattggt atgtggatgg tgttgaggtg cacaatgcca agaccaagcc   2220
tagagaggaa cagtacaaca gcacctacag ggttgtgtca gtgctgactg tgctgcacca   2280
ggactggctg aatggcaaag agtacaagtg caaggtgtcc aacaaggccc tgcctgctcc   2340
tattgaaaag accatcagca aggccaaggg acagcctagg gaaccccagg tgtacacact   2400
gccacctagc agagatgagc tgaccaagaa tcaggtgtcc ctgacatgcc ttgtgaaggg   2460
cttctaccct tctgacattg cagtggaatg ggagagcaat ggccagcctg agaacaacta   2520
caagacaacc cctcctgtgc tggactctga tggctcattc ttcctgtact ccaagctgac   2580
agtggacaag tccagatggc agcaaggcaa tgtgttcagc tgctctgtga tgcatgaggc   2640
cctgcacaac cactacacac agaagtccct gtctctgagc cctggcaagt gaagatctac   2700
ttctggctaa taaaagatca gagctctagt gatctgtgtg ttggtttttt gtgtctgcat   2760
tctagcagag ccccactgtg ttcatcttac agatggaaat actgacattc agaggagtta   2820
gttaacttgc ctaggtgatt cagctaataa gtgcaagaaa gatttcaatc caaggtgatt   2880
tgattctgaa gcctgtgcta atcacattac accaagctac aacttcattt ataaataata   2940
agtcagcttt caagggcctt tcaggtgtcc tgcacttcta caagctgtgc catttagtga   3000
acacaaaatg agccttctga tgaagtagtc ttttcattat ttcagatatt agaacactaa   3060
aattcttagc tgccagctga ttgaaggctg ggacaaaatt caaacatgca tctacaacaa   3120
tatatatctc aatgttagtc tccaaattct attgacttca actcaagaga atataaagag   3180
ctagtcttta tacactcttt aaggtatgat atcatctgga aagtaacaaa attgatgcaa   3240
atttgaatga actttatcat ggtgtattta cacaatgtgt ttcttctccc tgcaatgtat   3300
ttctttctct aattccttcc atttgatctt tcatacacaa tctggttctg atgtatgttt   3360
tttggatgca cttttcaact ccaaaagaca gagctagtta ctttcttcct ggtgctccaa   3420
gcactgtatt tgtatctgta ttcaagccct ttgcaatatt gtactggatc attatttcac   3480
ctctaggatg gcttccccag gcaacttgtg ttcacccaga gactacattt tgtatcttgt   3540
tgacctttga acttccacca gtgtctaaaa ataatatgta tgcaaaatta cttgctatga   3600
gaatgtataa ttaaacaata taaaaaggag aagcaaggag agaaacacag gtgtgtattt   3660
gtgtttgtgt gcttaaaagg cagtgtggaa aaggaagaaa tgccatttat agtgaggaga   3720
caaagttata ttacctctta tctggctttt aaggagattt tgctgagcta aaaatcctat   3780
attcatagaa aagccttacc tgagttgcca atacctcaat tcagtctagc atgttacata   3840
acttatggta aatggcctgc ctggctgact gcccaatgac ccctgcccaa tgatgtcaat   3900
aatgatgtat gttcccatgt aatgccaata gggactttcc attgatgtca atgggtggag   3960
tatttatggt aactgcccac ttggcagtac atcaagtgta tcatatgcca agtatgcccc   4020
ctattgatgt caatgatggt aaatggcctg cctggcatta tgcccagtac atgaccttat   4080
gggactttcc tacttggcag tacatctatg tattagtcat tgctattatc tagcactagt   4140
ggagaagagc atgcttgagg gctgagtgcc cctcagtggg cagagagcac atggcccaca   4200
gtccctgaga agttgggggg aggggtgggc aattgaactg gtgcctagag aaggtggggc   4260
ttgggtaaac tgggaaagtg atgtggtgta ctggctccac ctttttcccc agggtggggg   4320
```

```
agaaccatat ataagtgcag tagtctctgt gaacattcaa gcttctgcct tctccctcct   4380
gtgagtttgg taagtcactg actgtctatg cctgggaaag ggtgggcagg agatggggca   4440
gtgcaggaaa agtggcacta tgaaccctgc agccctagac aattgtacta accttcttct   4500
ctttcctctc ctgacaggtt ggtaaccaag ccaccatggc ctgggctctg ctgcttctgg   4560
gactgctgtc tcactgcaca ggcagtgtga ccagctatgt gctgacccag cctccatctg   4620
tgtctgtggc tccaggggag acagccagaa tcagctgtgg tggcaacaac attggcacaa   4680
aggtgctgca ctggtatcag cagactccag gacaggcacc agtgctggtg gtgtatgatg   4740
actctgacag accctctggc atcccagaga ggttctctgg cagcaactct ggcaacacag   4800
ccacactgac catctccaga gtggaagttg gagatgaggc tgattactac tgccaagtgt   4860
gggacatcag cacagaccag gctgtgtttg gtggtggcac caagctcact gtgctgggcc   4920
aacctaaagc tgccccttct gtgacactgt tcccacctag ctctgaggaa ctccaggcta   4980
acaaggccac acttgtgtgc ctgatcagtg acttctaccc aggggctgtg actgtggcct   5040
ggaaggctga tagcagccct gtgaaggctg gggttgagac aaccacacct agcaagcaga   5100
gcaacaacaa atatgctgcc agcagctacc tgagtctgac ccctgagcag tggaagtccc   5160
acagatccta cagctgtcaa gtgacccatg agggctccac agtggaaaag acagtggccc   5220
ctacagagtg ctcctgaaga tctacttctg gctaataaaa gatcagagct ctagtgatct   5280
gtgtgttggt tttttgtgtc tgcattctag cagtcaatat gttcacccca aaaaagctgt   5340
ttgttaactt gtcaacctca ttctaaaatg tatatagaag cccaaaagac aataacaaaa   5400
atattcttgt agaacaaaat gggaaagaat gttccactaa atatcaagat ttagagcaaa   5460
gcatgagatg tgtggggata gacagtgagg ctgataaaat agagtagagc tcagaaacag   5520
acccattgat atatgtaagt gacctatgaa aaaaatatgg cattttacaa tgggaaaatg   5580
atggtctttt tctttttag aaaaacaggg aaatatattt atatgtaaaa aataaaaggg   5640
aacccatatg tcataccata cacacaaaaa aattccagtg aattataagt ctaaatggag   5700
aaggcaaaac tttaaatctt ttagaaaata atatagaagc atgccatcaa gacttcagtg   5760
tagagaaaaa tttcttatga ctcaaagtcc taaccacaaa gaaaagattg ttaattagat   5820
tgcatgaata ttaagactta tttttaaaat taaaaaacca ttaagaaaag tcaggccata   5880
gaatgacaga aaatatttgc aacaccccag taaagagaat tgtaatatgc agattataaa   5940
aagaagtctt acaaatcagt aaaaaataaa actagacaaa aatttgaaca gatgaaagag   6000
aaactctaaa taatcattac acatgagaaa ctcaatctca gaaatcagag aactatcatt   6060
gcatatacac taaattagag aaatattaaa aggctaagta acatctgtgg cttaattaat   6120
ctagctctag tgatcagcag ttcaacctgt tgatagtatg tactaagctc tcatgtttaa   6180
tgtactaagc tctcatgttt aatgaactaa accctcatgg ctaatgtact aagctctcat   6240
ggctaatgta ctaagctctc atgtttcatg tactaagctc tcatgtttga acaataaaat   6300
taatataaat cagcaactta aatagcctct aaggttttaa gttttataag aaaaaaaaga   6360
atatataagg cttttaaagg ttttaaggtt tcctaggtta tcctcatatg agctcttaga   6420
aaaactcatc cagcatcaaa tgaaactgca atttattcat atcaggatta tcaataccat   6480
atttttgaaa aagtcttttc tgtaatgaag gagaaaactc acccaggcag ttccatagga   6540
tggcaagatc ctggtatctg tctgcaattc caactcttcc aacatcaata caacctatta   6600
atttcccctc atcaaaaata aggttatcaa gtgagaaatc accatgagtg accactgaat   6660
```

```
ctggtgagaa tggcaaaaga ttatgcattt ctttccagac ttgttcaaca ggccagccat   6720

ttctctcatc atcaaaatca ctggcatcaa ccaaaccatt attcattctt gattgggcct   6780

gagccagtct aaatactcta tcagagttaa aaggacaatt acaaacagga atggaatgca   6840

atcttctcag gaacactgcc agggcatcaa caatattttc acctgaatca ggatattctt   6900

ccaatacctg gaatgctgtt ttccctggga tggcagtggt gagtaaccat gcatcatcag   6960

gagttctgat aaaatgcttg atggttggaa gaggcataaa ttcagtcagc cagtttagtc   7020

tgaccatctc atctgtaaca tcattggcaa cagaaccttt gccatgtttc agaaacaact   7080

ctggggcatc tggcttccca tacaatctat agattgtggc acctgattgc ccaacattat   7140

ctctagccca tttataccca tataaatcag catccatgtt ggaatttaat cttggcctgg   7200

agcaagaggt ttctctttga atatggctca tacatgtgca cctcctatag tgagttgtat   7260

tatactatgc agatatacta tgccaatgtt taattgtcag                          7300
```

```
<210> SEQ ID NO 85
<211> LENGTH: 8128
<212> TYPE: DNA
<213> ORGANISM: Artificial sequence
<220> FEATURE:
<223> OTHER INFORMATION: Synthetic

<400> SEQUENCE: 85

cactatgtgt taattaaaat tatctctaag gcatgtgaac tggctgtctt ggttttcatc     60

tgtacttcat ctgctacctc tgtgacctga aacatattta taattccatt aagctgtgca    120

tatgatagat ttatcatatg tattttcctt aaaggatttt tgtaagaact aattgaattg    180

atacctgtaa agtctttatc acactaccca ataaataata aatctctttg ttcagctctc    240

tgtttctata aatatgtacc agttttattg tttttagtgg tagtgatttt attctctttc    300

tatatatata cacacacatg tgtgcattca taaatatata caatttttat gaataaaaaa    360

ttattagcaa tcaatattga aaaccactga tttttgttta tgtgagcaaa cagcagatta    420

aaaggaattt gaattctcat agctagcagg agtcaatggg aaaaacccat tggagccaag    480

tacactgact caatagggac tttccattgg gttttgccca gtacataagg tcaatagggg    540

gtgagtcaac aggaaagtcc cattggagcc aagtacattg agtcaatagg gactttccaa    600

tgggttttgc ccagtacata aggtcaatgg gaggtaagcc aatgggtttt tcccattact    660

gacatgtata ctgagtcatt agggactttc caatgggttt tgcccagtac ataaggtcaa    720

taggggtgaa tcaacaggaa agtcccattg gagccaagta cactgagtca atagggactt    780

tccattgggt tttgcccagt acaaaaggtc aatagggggt gagtcaatgg gtttttccca    840

ttattggcac atacataagg tcaatagggg tgactagtgg agaagagcat gcttgagggc    900

tgagtgcccc tcagtgggca gagagcacat ggcccacagt ccctgagaag ttgggggggag    960

gggtgggcaa ttgaactggt gcctagagaa ggtggggctt gggtaaactg ggaaagtgat   1020

gtggtgtact ggctccacct ttttccccag ggtgggggag aaccatatat aagtgcagta   1080

gtctctgtga acattcaagc ttctgccttc tccctcctgt gagtttggta agtcactgac   1140

tgtctatgcc tgggaaaggg tgggcaggag atggggcagt gcaggaaaag tggcactatg   1200

aaccctgcag ccctagacaa ttgtactaac cttcttctct ttcctctcct gacaggttgg   1260

taaccaagcc accatggtcc tccagacaca ggtgttcatc agcctgctgc tgtggatcag   1320

tggtgcctat ggacaggtcc agctgcaaga gtctggccct ggacttgtca gacccagcca   1380

gacactgagc ctgacctgta cagtctctgg cttcagcctg accagctact ctgtgcactg   1440
```

-continued

```
ggtcagacag cctccaggca gaggactgga atggctggga gtgatctggg ccagtggtgg   1500
cacagactac aactctgccc tgatgagcag actgagcatc ctgaaggaca acagcaagaa   1560
ccaggtgtcc ctgagactgt cctctgtgac agctgctgat acagctgtgt acttctgtgc   1620
cagagatcct cctagctctc tgctgagact ggactactgg ggccagggca caacagtgac   1680
agtgtccagt gccagcacaa agggcccctc tgtgtttcct ctggctccca gcagcaagag   1740
caccagtggt ggaactgctg ccctgggctg tctggtcaag gactactttc ctgagcctgt   1800
gactgtgtcc tggaactctg gggctctgac atctggggtg cacacattcc ctgctgtgct   1860
gcaatcctct ggcctgtaca gcctcagctc tgtggtcaca gtgcctagct ctagcctggg   1920
cacccagacc tacatctgca atgtgaacca caagcctagc aacaccaagg tggacaagaa   1980
ggctgagccc aagagctgtg acaagaccca cacctgtcct ccatgtcctg ctccagagct   2040
gcttggagga cccagtgtgt tcctgtttcc tccaaagcca aaggacaccc tgatgatcag   2100
cagaacccct gaagtgacct gtgtggtggt ggatgtgtcc catgaggacc ctgaagtcaa   2160
gttcaattgg tatgtggatg gtgttgaggt gcacaatgcc aagaccaagc ctagagagga   2220
acagtacaac agcacctaca gagtggtgtc agtgctgaca gtgctgcacc aggactggct   2280
gaatggcaaa gagtacaagt gcaaggtgtc caacaaggcc ctgcctgctc ctattgaaaa   2340
gaccatcagc aaggccaagg gccagcctag ggaaccccag gtttacacac tgccacctag   2400
cagagatgag ctgaccaaaa atcaggtttc cctgacctgc ctggttaagg gcttctaccc   2460
ctctgacatt gctgtggaat gggagagcaa tggccagcct gagaacaact acaagacaac   2520
ccctcctgtg ctggactctg atggctcatt cttcctgtac tccaagctga ctgtggacaa   2580
aagcagatgg cagcaaggca atgtgttcag ctgctctgtg atgcatgagg ccctgcacaa   2640
ccactacacc cagaagtccc tgtctctgag ccctggcaag agaaagagaa ggagtggctc   2700
tggggccacc aactttagcc tgctgaaaca ggctggggat gttgaagaga accctggacc   2760
tatggtgctg caaacccagg ttttcatttc tctgctcctc tggattagtg gtgcttatgg   2820
ggacattgtg atgacacaga gccctagcag cctgtctgcc tctgtgggag acagagtgac   2880
catcacatgc aagtccagcc agagtctgct gaactctggc aaccagaaga actacctggc   2940
ctggtatcag caaaagcctg gcaaggcccc taagctgctc atctatgggg ccagcaccag   3000
agagtctggg gtcccagata gattctctgg ctctggatct ggcactgact tcaccttcac   3060
catcagctcc ctgcaaccag aggacattgc cacctactac tgccagaatg tgcacagctt   3120
cccattcacc tttggacagg gcactaaggt ggaaatcaag aggactgtgg ctgctccttc   3180
tgtgttcatc ttcccaccat cagatgaaca gctgaagagt ggcacagcct ctgttgtgtg   3240
cctgctcaac aacttctacc ctagagaagc caaggtgcag tggaaagtgg acaatgccct   3300
ccagtctggc aacagccaag aatctgtgac tgagcaggac tccaaggaca gcacatacag   3360
cctgagcagc acactgaccc tgagcaaggc tgactatgag aagcacaaag tctatgcctg   3420
tgaagtgaca caccagggcc tgtctagccc agtgaccaag tccttcaaca ggggagagag   3480
ctgaagatct acttctggct aataaaagat cagagctcta gtgatctgtg tgttggtttt   3540
ttgtgtctgc attctagcag agccccactg tgttcatctt acagatggaa atactgacat   3600
tcagaggagt tagttaactt gcctaggtga ttcagctaat aagtgcaaga aagatttcaa   3660
tccaaggtga tttgattctg aagcctgtgc taatcacatt acaccaagct acaacttcat   3720
ttataaataa taagtcagct ttcaagggcc tttcaggtgt cctgcacttc tacaagctgt   3780
```

-continued

```
gccatttagt gaacacaaaa tgagccttct gatgaagtag tcttttcatt atttcagata   3840
ttagaacact aaaattctta gctgccagct gattgaaggc tgggacaaaa ttcaaacatg   3900
catctacaac aatatatatc tcaatgttag tctccaaatt ctattgactt caactcaaga   3960
gaatataaag agctagtctt tatacactct ttaaggtatg atatcatctg gaaagtaaca   4020
aaattgatgc aaatttgaat gaactttatc atggtgtatt tacacaatgt gtttcttctc   4080
cctgcaatgt atttctttct ctaattcctt ccatttgatc tttcatacac aatctggttc   4140
tgatgtatgt tttttggatg cacttttcaa ctccaaaaga cagagctagt tactttcttc   4200
ctggtgctcc aagcactgta tttgtatctg tattcaagcc ctttgcaata ttgtactgga   4260
tcattatttc acctctagga tggcttcccc aggcaacttg tgttcaccca gagactacat   4320
tttgtatctt gttgaccttt gaacttccac cagtgtctaa aaataatatg tatgcaaaat   4380
tacttgctat gagaatgtat aattaaacaa tataaaaagg agaagcaagg agagaaacac   4440
aggtgtgtat ttgtgtttgt gtgcttaaaa ggcagtgtgg aaaaggaaga aatgccattt   4500
atagtgagga gacaaagtta tattacctct tatctggctt ttaaggagat tttgctgagc   4560
taaaaatcct atattcatag aaaagcctta cctgagttgc caatacctca attcagtcta   4620
gcaggagtca atgggaaaaa cccattggag ccaagtacac tgactcaata gggactttcc   4680
attgggtttt gcccagtaca taaggtcaat agggggtgag tcaacaggaa agtcccattg   4740
gagccaagta cattgagtca atagggactt tccaatgggt tttgcccagt acataaggtc   4800
aatgggaggt aagccaatgg gtttttccca ttactgacat gtatactgag tcattaggga   4860
ctttccaatg ggttttgccc agtacataag gtcaataggg gtgaatcaac aggaaagtcc   4920
cattggagcc aagtacactg agtcaatagg gactttccat tgggttttgc ccagtacaaa   4980
aggtcaatag ggggtgagtc aatgggtttt tcccattatt ggcacataca taaggtcaat   5040
aggggtgact agtggagaag agcatgcttg agggctgagt gcccctcagt gggcagagag   5100
cacatggccc acagtccctg agaagttggg gggaggggtg ggcaattgaa ctggtgccta   5160
gagaaggtgg ggcttgggta aactgggaaa gtgatgtggt gtactggctc caccttttc    5220
cccagggtgg gggagaacca tatataagtg cagtagtctc tgtgaacatt caagcttctg   5280
ccttctccct cctgtgagtt tggtaagtca ctgactgtct atgcctggga aagggtgggc   5340
aggagatggg gcagtgcagg aaaagtggca ctatgaaccc tgcagcccta gacaattgta   5400
ctaaccttct tctctttcct ctcctgacag gttggtaacc aagctttcca tggctggacc   5460
tgccacccag agccccatga agctgatggc cctgcagctg ctgctgtggc acagtgcact   5520
ctggacagtg caggaagcca ccccccctggg ccctgccagc tccctgcccc agagcttcct   5580
gctcaagtgc ttagagcaag tgaggaagat ccagggggat ggggcagctc tccaggagaa   5640
gctgtgtgcc acctacaagc tgtgccaccc tgaggagctg gtgctgctgg gacactctct   5700
gggcatcccc tgggctcccc tgagcagctg ccccagccag gccctgcagc tggcaggctg   5760
cttgagccaa ctccatagtg gcctttttcct ctaccagggg ctcctgcagg ccctggaagg   5820
gatctcccct gagttgggtc ccaccttgga cacactgcag ctggatgttg ctgactttgc   5880
caccaccatc tggcagcaga tggaagaact gggaatggcc cctgccctgc agcccaccca   5940
gggtgccatg cctgcctttg cctctgcttt ccagagaagg gcaggagggg tcctggttgc   6000
ctcccatctg cagagcttcc tggaggtgtc ctacagagtt ctaagacacc ttgcccagcc   6060
ctgatagatc tacttctggc taataaaaga tcagagctct agtgatctgt gtgttggttt   6120
tttgtgtctg cattctagca gtcaatatgt tcaccccaaa aaagctgttt gttaacttgt   6180
```

caacctcatt ctaaaatgta tatagaagcc caaaagacaa taacaaaaat attcttgtag 6240
aacaaaatgg gaaagaatgt tccactaaat atcaagattt agagcaaagc atgagatgtg 6300
tggggataga cagtgaggct gataaaatag agtagagctc agaaacagac ccattgatat 6360
atgtaagtga cctatgaaaa aaatatggca ttttacaatg ggaaaatgat ggtctttttc 6420
ttttttagaa aaacagggaa atatatttat atgtaaaaaa taaaagggaa cccatatgtc 6480
ataccataca cacaaaaaaa ttccagtgaa ttataagtct aaatggagaa ggcaaaactt 6540
taaatctttt agaaaataat atagaagcat gccatcaaga cttcagtgta gagaaaaatt 6600
tcttatgact caaagtccta accacaaaga aaagattgtt aattagattg catgaatatt 6660
aagacttatt tttaaaatta aaaaaccatt aagaaaagtc aggccataga atgacagaaa 6720
atatttgcaa caccccagta aagagaattg taatatgcag attataaaaa gaagtcttac 6780
aaatcagtaa aaaataaaac tagacaaaaa tttgaacaga tgaaagagaa actctaaata 6840
atcattacac atgagaaact caatctcaga aatcagagaa ctatcattgc atatacacta 6900
aattagagaa atattaaaag gctaagtaac atctgtggct taattaatct agctctagtg 6960
atcagcagtt caacctgttg atagtatgta ctaagctctc atgtttaatg tactaagctc 7020
tcatgtttaa tgaactaaac cctcatggct aatgtactaa gctctcatgg ctaatgtact 7080
aagctctcat gtttcatgta ctaagctctc atgtttgaac aataaaatta atataaatca 7140
gcaacttaaa tagcctctaa ggttttaagt tttataagaa aaaaaagaat atataaggct 7200
tttaaaggtt ttaaggtttc ctaggttatc ctcatatgag ctcttagaaa aactcatcca 7260
gcatcaaatg aaactgcaat ttattcatat caggattatc aataccatat ttttgaaaaa 7320
gtcttttctg taatgaagga gaaaactcac ccaggcagtt ccataggatg gcaagatcct 7380
ggtatctgtc tgcaattcca actcttccaa catcaataca acctattaat ttcccctcat 7440
caaaaataag gttatcaagt gagaaatcac catgagtgac cactgaatct ggtgagaatg 7500
gcaaaagatt atgcatttct ttccagactt gttcaacagg ccagccattt ctctcatcat 7560
caaaatcact ggcatcaacc aaaccattat tcattcttga ttgggcctga gccagtctaa 7620
atactctatc agagttaaaa ggacaattac aaacaggaat ggaatgcaat cttctcagga 7680
acactgccag ggcatcaaca atattttcac ctgaatcagg atattcttcc aatacctgga 7740
atgctgtttt ccctgggatg gcagtggtga gtaaccatgc atcatcagga gttctgataa 7800
aatgcttgat ggttggaaga ggcataaatt cagtcagcca gtttagtctg accatctcat 7860
ctgtaacatc attggcaaca gaacctttgc catgtttcag aaacaactct ggggcatctg 7920
gcttcccata caatctatag attgtggcac ctgattgccc aacattatct ctagcccatt 7980
tatacccata taaatcagca tccatgttgg aatttaatct tggcctggag caagaggttt 8040
ctctttgaat atggctcata catgtgcacc tcctatagtg agttgtatta tactatgcag 8100
atatactatg ccaatgttta attgtcag 8128

<210> SEQ ID NO 86
<211> LENGTH: 3288
<212> TYPE: DNA
<213> ORGANISM: Artificial sequence
<220> FEATURE:
<223> OTHER INFORMATION: Synthetic

<400> SEQUENCE: 86
cactatgtgg acatgaattc aattggctag caggagtcaa tgggaaaaac ccattggagc 60

-continued

```
caagtacact gactcaatag ggactttcca ttgggttttg cccagtacat aaggtcaata    120
gggggtgagt caacaggaaa gtcccattgg agccaagtac attgagtcaa tagggacttt    180
ccaatgggtt ttgcccagta cataaggtca atgggaggta agccaatggg tttttcccat    240
tactgacatg tatactgagt cattagggac tttccaatgg gttttgccca gtacataagg    300
tcaatagggg tgaatcaaca ggaaagtccc attggagcca agtacactga gtcaataggg    360
actttccatt gggttttgcc cagtacaaaa ggtcaatagg gggtgagtca atgggttttt    420
cccattattg gcacatacat aaggtcaata ggggtgacta gtggagaaga gcatgcttga    480
gggctgagtg cccctcagtg ggcagagagc acatggccca cagtccctga gaagttgggg    540
ggaggggtgg gcaattgaac tggtgcctag agaaggtggg gcttgggtaa actgggaaag    600
tgatgtggtg tactggctcc acctttttcc ccagggtggg ggagaaccat atataagtgc    660
agtagtctct gtgaacattc aagcttctgc cttctccctc ctgtgagttt ggtaagtcac    720
tgactgtcta tgcctgggaa agggtgggca ggagatgggg cagtgcagga aaagtggcac    780
tatgaaccct gcagccctag acaattgtac taaccttctt ctctttcctc tcctgacagg    840
ttggtaacca agccaccatg gaagaacccc agtctgaccc ctctgtggaa cctcctctga    900
gccaagagac attctctgac ctgtggaagc tgctgcctga gaacaatgtg ctgagccctc    960
tgcctagcca ggccatggat gatctgatgc tgtcccctga tgacattgag cagtggttca   1020
cagaggaccc tggacctgat gaggccccta gaatgcctga agctgcccct agagttgccc   1080
ctgctcctgc tgctcctaca ccagctgctc cagctccagc accttcttgg cctctgtcta   1140
gctctgtgcc cagccagaaa acctaccagg gcagctatgg cttcaggctg ggctttctgc   1200
actctggcac agccaagtct gtgacctgca catacagccc tgctctgaac aagatgttct   1260
gtcagctggc caagacctgt cctgtgcagc tgtgggttga cagcacacct cctccaggca   1320
caagagtcag agccatggcc atctacaagc agagccagca catgacagag gttgtcagaa   1380
gatgccctca ccatgagagg tgctctgatt ctgatggact ggcccctcct cagcacctga   1440
tcagagtgga aggcaacctg agagtggaat acctggatga cagaaacacc ttcaggcact   1500
ctgtggtggt gccctatgag cctcctgaag tgggctctga ttgcaccacc atccactaca   1560
actacatgtg caacagcagc tgcatgggag gcatgaacag aaggcccatc ctgaccatca   1620
tcaccctgga agatagctct ggcaacctgc tgggcagaaa cagctttgaa gtcagagtgt   1680
gtgcctgtcc aggcagagac agaagaactg aggaagagaa cctgagaaag aaaggggagc   1740
cacaccatga gctgccacct ggctctacca aaagagccct gcctaacaac accagcagca   1800
gccctcagcc taagaaaaag cccctggatg gggagtactt cacactccag atcagaggca   1860
gggaaagatt tgagatgttc agggaactga atgaggccct ggaactgaag gatgcccagg   1920
ctggaaaaga gcctggaggc agcagagccc atagcagcca cctgaagtct aagaagggcc   1980
agagcaccag cagacacaag aaactgatgt tcaagacaga gggccctgac tctgactgaa   2040
gatctacttc tggctaataa aagatcagag ctctagtgat ctgtgtgttg gttttttgtg   2100
tctgcattct agctctagtg atcagcagtt caacctgttg atagtatgta ctaagctctc   2160
atgtttaatg tactaagctc tcatgtttaa tgaactaaac cctcatggct aatgtactaa   2220
gctctcatgg ctaatgtact aagctctcat gtttcatgta ctaagctctc atgtttgaac   2280
aataaaatta atataaatca gcaacttaaa tagcctctaa ggttttaagt tttataagaa   2340
aaaaaagaat atataaggct tttaaaggtt ttaaggtttc ctaggttatc ctcatatgag   2400
ctcttagaaa aactcatcca gcatcaaatg aaactgcaat ttattcatat caggattatc   2460
```

-continued

```
aataccatat ttttgaaaaa gtcttttctg taatgaagga gaaaactcac ccaggcagtt   2520

ccataggatg gcaagatcct ggtatctgtc tgcaattcca actcttccaa catcaataca   2580

acctattaat ttcccctcat caaaaataag gttatcaagt gagaaatcac catgagtgac   2640

cactgaatct ggtgagaatg gcaaaagatt atgcatttct ttccagactt gttcaacagg   2700

ccagccattt ctctcatcat caaaatcact ggcatcaacc aaaccattat tcattcttga   2760

ttgggcctga gccagtctaa atactctatc agagttaaaa ggacaattac aaacaggaat   2820

ggaatgcaat cttctcagga acactgccag ggcatcaaca atattttcac ctgaatcagg   2880

atattcttcc aatacctgga atgctgtttt ccctgggatg gcagtggtga gtaaccatgc   2940

atcatcagga gttctgataa aatgcttgat ggttggaaga ggcataaatt cagtcagcca   3000

gtttagtctg accatctcat ctgtaacatc attggcaaca gaacctttgc catgtttcag   3060

aaacaactct ggggcatctg gcttcccata caatctatag attgtggcac ctgattgccc   3120

aacattatct ctagcccatt tatacccata taaatcagca tccatgttgg aatttaatct   3180

tggcctggag caagaggttt ctctttgaat atggctcata catgtgcacc tcctatagtg   3240

agttgtatta tactatgcag atatactatg ccaatgttta attgtcag               3288
```

SYSTEMS AND METHODS FOR NUCLEIC ACID EXPRESSION IN VIVO

The present application claims priority to U.S. Provisionals application 62/475,477 filed Mar. 23, 2017, which is herein incorporated by reference in its entirety.

SEQUENCE LISTING

This application incorporates by reference in its entirety the Computer Readable Form (CRF) of a Sequence Listing in ASCII text format submitted via EFS-Web. The Sequence Listing text file submitted via EFS-Web is entitled "14755-004-999_Sub_SL.txt", was created on Oct. 21, 2022 and is 411,062 bytes in size.

FIELD OF THE INVENTION

The present invention provides compositions, systems, kits, and methods for expression of one or more biomolecules in a subject, human or non-human mammal, (e.g., at therapeutic levels for the extended periods of time required to produce therapeutic effects). In certain embodiments, compositions, systems, kits, and methods are provided that comprise a first composition comprising polycationic structures (e.g., empty cationic liposomes, cationic micelles, cationic emulsions, or cationic polymers) and a second composition comprising expression vectors (e.g., non-viral expression vectors not associated with liposomes or other carriers) encoding one or more biomolecules of interest.

BACKGROUND

The simplest non-viral gene delivery system uses naked expression vector DNA. Direct injection of free DNA into certain tissues, particularly muscle, has been shown to produce high levels of gene expression, and the simplicity of this approach has led to its adoption in a number of clinical protocols. In particular, this approach has been applied to the gene therapy of cancer where the DNA can be injected either directly into the tumor or can be injected into muscle cells in order to express tumor antigens that might function as a cancer vaccine.

Although direct injection of plasmid DNA has been shown to lead to gene expression, the overall level of expression is much lower than with either viral or liposomal vectors. Naked DNA is also generally thought to be unsuitable for systemic administration due to the presence of serum nucleases. As a result, direct injection of plasmid DNA appears to be limited to only a few applications involving tissues that are easily accessible to direct injection such as skin and muscle cells.

SUMMARY OF THE INVENTION

The present invention provides compositions, systems, kits, and methods for expression of one or more biomolecules in a subject, human or non-human mammal, (e.g., at therapeutic levels for the extended periods of time required to produce therapeutic effects). In certain embodiments, compositions, systems, kits, and methods are provided that comprise a first composition comprising polycationic structures (e.g., empty cationic liposomes, cationic micelles, cationic emulsions, or cationic polymers) and a second composition comprising expression vectors (e.g., non-viral expression vectors not associated with liposomes or other carriers) encoding one or more biomolecules of interest. In some embodiments, the compositions, systems, kits, and methods may employ one or more components of the compositions, systems, kits, and methods described in U.S. patent application Ser. No. 15/268,000, filed Sep. 16, 2016, the disclosure of which is herein incorporated by reference in its entirety.

In some embodiments, provided herein are compositions, kits, and/or systems comprising: a) a first composition comprising a first amount of polycationic structures liposomes, wherein the first composition is free, or essentially free, of nucleic acid molecules; and b) a second composition comprising an expression vector (e.g., one or more expression vectors that express a biomolecule of interest) (e.g., a therapeutically effective amount of one or more expression vectors). In some embodiments, the compositions, kits, and/or systems have one or more or all of the following properties: i) the ratio of the first amount of said polycationic structures to the expression vectors is 5:1 to 25:1; ii) 2.0% to 6.0%, or 2.0% to 20% (e.g., 2% . . . 5% . . . 10% . . . 15% . . . or 20%) of the first composition comprises dexamethasone palmitate and/or dexamethasone; iii) the first composition further comprises neutral lipid; and iv) the polycationic structures comprise empty liposomes, wherein the empty liposomes present in the first composition have a z-average diameter of about 20-85 nm.

In some embodiments, provided herein are aqueous compositions comprising or consisting essentially of: a) polycationic structures present in said composition at a concentration of between 500 nM and 500 mM; b) dexamethasone and/or dexamethasone palmitate present in said composition at a concentration between 1-10% of said composition; and c) a physiologically tolerable buffer, and wherein said composition is free, or essentially free, of nucleic acid molecules. In some embodiments, said polycationic structure are cationic lipids that are present as small unilamellar vesicles. In some embodiments, said physiologically tolerable buffer is selected from the group consisting of: saline buffer, 5% dextrose in water, lactated ringers buffer, and any combination thereof. In some embodiments, said polycationic structures comprise DOTAP. In some embodiments, said polycationic structures are present in said composition at a concentration of between 800 nM and 1500 nM, or between 10 mM and 100 mM.

In some embodiments, provided herein are aqueous compositions comprising or consisting essentially of: a) neutral lipids present in said composition at a concentration of between 500 nM and 500 mM; b) dexamethasone and/or dexamethasone palmitate present in said composition at a concentration between 1-10% of said composition; and c) a physiologically tolerable buffer, and wherein said composition is free, or essentially free, of nucleic acid molecules. In some embodiments, said neutral lipids are present as multilamellar vesicles. In some embodiments, said physiologically tolerable buffer is selected from the group consisting of: saline buffer, 5% dextrose in water, lactated ringers buffer, and any combination thereof. In some embodiments, said neutral lipids comprise DMPC. In some embodiments, said neutral lipids are present in said composition at a concentration of between 800 nM and 1500 nM, or between 10 mM and 100 mM.

In some embodiments, provided herein are aqueous compositions comprising or consisting essentially of: a) polycationic structures present in said composition at a concentration of between 500 nM and 500 mM; b) neutral lipids present in said composition at a concentration of between 500 nM and 500 mM; and c) a physiologically tolerable buffer, and wherein said composition is free, or essentially free, of nucleic acid molecules. In some embodiments, said neutral lipids are present as multi-lamellar vesicles. In some embodiments, compositions comprise neutral liposomes with (e.g., extruded to) mean diameters of 75-250 nm (e.g., 100 nm, 150 nm, 200 nm, etc.). In some embodiments, said polycationic structure are cationic lipids that are present as small unilamellar vesicles. In some embodiments, said polycationic structure are cationic lipids that are present as multilamellar vesicles. In some embodiments, compositions further comprise: d) dexamethasone, wherein said dexamethasone is present in a concentration such that it is 1-10% of said composition. In some embodiments, compositions further comprise: d) dexamethasone palmitate, wherein said dexamethasone palmitate is present in a concentration such that it is 1-10% of said composition. In some embodiments, said neutral lipids comprise DMPC. In some embodiments, said neutral lipids are present in said composition at a concentration of between 800 nM and 1300 nM, or between 10 mM and 100 mM. In some embodiments, said polycationic structures comprise DOTAP. In some embodiments, said polycationic structures are present in said composition at a concentration of between 800 nM and 1500 nM, or between 10 mM and 100 mM.

In some embodiments, provided herein are compositions, kits, and/or systems comprising: a) a first composition comprising a first amount of polycationic structures liposomes, wherein the first composition is free, or essentially free, of nucleic acid molecules; and b) a second composition comprising a therapeutically effective amount of expression vectors, wherein the expression vectors comprise circularized synthetically amplified nucleic acid, or minicircle DNA, encoding one or more biomolecules (e.g., therapeutic biomolecules). In some embodiments, the synthetically amplified nucleic acid is produced by a polymerase chain reaction. In some embodiments, no cells are used in the production of the vector (e.g., the vector is not recombinantly expressed in culture for its production). In some embodiments, the vector consists of the nucleic acid encoding one or more biomolecules and one or more promoters and enhancers operatively linked thereto.

In some embodiments, the one or more biomolecules is a therapeutic biomolecule. In some embodiments, the therapeutic biomolecule is an antibody. In some embodiments, the antibody is a broadly neutralizing antibody. In some embodiments, the broadly neutralizing antibody specifically binds to a pathogen or pathogen component. In some embodiments, the pathogen is a virus. In some embodiments, the antibody specifically binds to a tumor antigen. In some embodiments, the mAb or antigen-binding portion thereof specifically binds to a cytokine.

In some embodiments, one or more antibodies comprise a first antibody that specifically binds to a first target molecule, a second antibody that specifically binds to a second, different, target molecule, and in some embodiments, a third antibody that specifically binds to a third, different, target molecule.

In some embodiments, the one or more biomolecules comprise a CRISPR/Cas9 component (e.g., for use in gene therapy, research, or diagnostic applications).

In some embodiments, the one or more biomolecules comprise a nucleic acid (e.g., a therapeutic or diagnostic nucleic acid). In some embodiments, the nucleic acid is an antisense oligonucleotide (see e.g., U.S. Pat. Nos. 7,592,440, 7,919,472, and 9,045,754, herein incorporated by reference in their entireties). In some embodiments, the nucleic acid is a ribozyme. In some embodiments, the nucleic acid is an shRNA, miRNA, siRNA, piRNA, snoRNA, tsRNA, or srRNA.

In some embodiments, the expression vectors comprise a super enhancer regulating expression of at least one of the one or more biomolecules. In some embodiments, the expression vectors encode a first therapeutic biomolecule and a second therapeutic biomolecule, wherein said first and second therapeutic biomolecules express for different lengths of time than one another (e.g., expressed using different promoters and/or enhancers or expressed in different expression cassettes within the vectors). In certain embodiments, the expression vectors encode a first therapeutic biomolecule and a second therapeutic biomolecule, wherein said first and second therapeutic biomolecules are the same (e.g., a single vector has two expression cassettes that both express the same or different therapeutic biomolecule). In further embodiments, the expression vectors encode a first therapeutic biomolecule, a second therapeutic biomolecule, and a third therapeutic biomolecule wherein said first, second, third therapeutic biomolecules are all the same (e.g., a single vector has three expression cassettes that all express the same or different therapeutic biomolecule).

In some embodiments, the expression vectors comprise an R6K origin of replication. In some embodiments, the expression vectors are CpG-free or CpG-reduced. In some embodiments, the expression vectors are not CpG-free or CpG-reduced.

Further provided herein are methods of using the compositions, kits, and/or system described herein. For example, in some embodiments, provided herein are methods of expressing one or more therapeutic biomolecules in a subject, comprising: a) administering a first composition of the system into a subject; and b) administering a second composition of the system into said subject.

In some embodiments, provided herein are methods of expressing two or more therapeutic biomolecules in a subject for different durations, comprising: a) administering a first composition of a system into a subject; and b) administering (e.g., subsequently, within 300 minutes) a second composition of the system into the subject, wherein the vectors express first and second biomolecules each in a separate cassette or under the control of different promoters and/or enhances such that the first and second biomolecules express for different lengths of time than one another in the subject. For example, the first molecule expressed from the first cassette is present for at least seven, or 21 or 100 days following injection, whereas the biomolecule expressed from the second cassette remains present for less than seven days or fourteen 14 days.

In some embodiments, step b) of the method occurs from 1 to 400 minutes after step a) (e.g., 1, 2, 3, 4, 5, 6, 7, 8, 9, 10, 12, 15, 20, 30, 40, 50, 100, 200, 300, 400 minutes or any increments therein between). In some embodiments, the biomolecule or biomolecules are expressed at a desired (e.g., therapeutic) level in the subject for at least 7 consecutive days (e.g., at least 30 days, at least 1 year or any increments therein between). In certain embodiments, the first therapeutic biomolecule expresses for at least 7 days (e.g., 7 . . . 14 . . . 21 . . . 190 . . . 365 days) at therapeutic levels, and the second therapeutic biomolecule expresses at a level that is at least 50% reduced (e.g., at least 50% . . . 65% . . . 75% . . . 90% . . . or 99% reduced) at day 7 compared to the initial expression of said second therapeutic biomolecules on day 1. In particular embodiments, the first therapeutic biomolecule expresses for at least 14 days at therapeutic levels, and the second therapeutic biomolecule expresses at a level that is at least 75% reduced at day 14 compared to the initial expression of said second therapeutic biomolecules on day 1. In additional embodiments, the first therapeutic biomolecules comprises a CRISP or a monoclonal antibody sequence (or fragment thereof, such as F(ab)2), and the second therapeutic biomolecule comprises a Cas9 protein.

In some embodiments (e.g., to increase expression levels of the desired biomolecule), the methods further comprise step c): repeating steps a) and b) one or more times.

In some embodiments, the biomolecules are therapeutic biomolecules. Any suitable or desired therapeutic biomolecule may be selected. In some embodiments, the one or more therapeutic biomolecules comprises an anti-PCSK9 monoclonal antibody that expresses at sufficient levels to reduce LDL (e.g., in a human subject). In some embodiments, the one or more therapeutic biomolecules expresses an anti-influenza A stem antigen monoclonal antibody (e.g., that broadly immunizes against a wide spectrum of influenza A strains). In some embodiments, the one or more therapeutic biomolecules expresses a combination of anti-CD20 and anti-CD47 monoclonal antibodies. In some embodiments, the one or more therapeutic biomolecules expresses an anti-PD-1 monoclonal antibody, one or more self-tumor neoantigens, and optionally one or more immunomodulatory cytokines.

In some embodiments, the present invention provides compositions, systems, kits, and methods for expression of a protein or proteins and/or biologically active nucleic acid molecule(s) in a subject (e.g., at therapeutic levels for the extended periods of time required to produce therapeutic effects in the host). In certain embodiments, systems and kits are provided that comprise a first composition comprising a first amount of polycationic structures (e.g., empty cationic liposomes, empty cationic micelles, or empty cationic emulsions), and a second composition comprising a therapeutically effective amount of expression vector(s) (e.g., non-viral expression vectors not associated with liposomes) (e.g., that are CpG-free or CpG-reduced), where the expression vectors comprise a first nucleic acid sequence encoding: i) a first therapeutic protein (or non-therapeutic protein, such as a marker protein), and/or ii) a first biologically active nucleic acid molecule. In certain embodiments, the expression vector comprises a second, third, or fourth nucleic acid sequence encoding a second, third, and/or fourth therapeutic or non-therapeutic protein, and/or a second, third, or fourth biologically active nucleic acid molecule. In some embodiments, the first nucleic acid sequences further encode a second, third, fourth, fifth, and/or sixth therapeutic protein, and/or a second, third, fourth, fifth, and/or sixth biologically active nucleic acid molecule. In other embodiments, such first and second compositions are sequentially administered (e.g., systemically) to a subject such that the therapeutic protein(s) and/or the biologically active nucleic acid molecule(s) is/are expressed in the subject (e.g., at a therapeutic level (e.g., for at least 5 or at least 50 days, or at least 100 . . . 200 . . . or at least 400 days), such that disease(s) or condition(s) is/are treated or physiological trait(s) is/are altered; at a prophylactic level (e.g., for at least 5 or at least 50 days, or at least 100 . . . 200 . . . or at least 400 days), such that disease(s), condition(s), and/or infection(s) is/are prevented).

In some embodiments, provided herein are methods of expressing a first therapeutic protein and/or a biologically active nucleic acid molecule in a subject (e.g., human or non-human mammal) comprising: a) administering (e.g., systemically) a first composition to a subject, wherein the first composition comprises first amount of polycationic structures (e.g., empty cationic liposomes, empty cationic micelles, or empty cationic emulsions) and wherein the first composition is free, or essentially free, of nucleic acid molecules (e.g., nucleic acid is un-detectable or barely detectable in the composition); and b) administering (e.g., systemically, intravascularly, etc.) a second composition to the subject (e.g., initiating within about 2 . . . 10 . . . 50 . . . 100 . . . 200 . . . 300 . . . 400 minutes of administering the first composition), wherein the second composition comprises an amount of expression vectors (e.g., non-viral expression vectors not associated with liposomes or any other carrier), wherein the expression vectors are CpG-free or CpG-reduced, wherein each of the expression vectors comprise nucleic acid sequence(s) encoding: i) first, second, third, fourth, fifth, and/or sixth therapeutic protein(s) or non-therapeutic, and/or ii) first, second, third, fourth, fifth, and/or sixth biologically active nucleic acid molecule(s). In certain embodiments, as a result of the administering the first composition and the administering the second composition, the first therapeutic or non-therapeutic protein and/or the biologically active nucleic acid molecule is/are expressed in the subject (e.g., at a therapeutic level, for at least 5 . . . 50 . . . 100 . . . 300 days . . . 400 days or longer, with respect to a disease or condition, or at an effective level sufficient to alter a physiological or disease trait). In certain embodiments, the polycationic structures (e.g., empty liposomes) present in the first composition have a z-average diameter of about 20-85 nm (e.g., 20 . . . 25 . . . 30 . . . 40 . . . 45 . . . 50 . . . 55 . . . 60 . . . 65 . . . 70 . . . 75 . . . 80 . . . 85 nm). In certain embodiments, the polycationic structures are empty liposomes with a z-average diameter of about 72-76 nm, and are small uni-lammellar vesicles.

In some embodiments, provided herein are methods of expressing a first therapeutic or non-therapeutic protein and/or a biologically active nucleic acid molecule in a subject comprising: a) administering a first composition to a subject, wherein the subject has at least one symptom of a disease or condition, or has at least physiological trait to be altered, wherein the first composition comprises a first amount of polycationic structures (e.g., empty cationic liposomes, empty cationic micelles, or empty cationic emulsions), and wherein the first composition is free, or essentially free, of nucleic acid molecules; and b) administering (or initiating administration of) a second composition to the subject within about 100 minutes or about 200 . . . or 400 minutes of administering said first composition, wherein the second composition comprises a therapeutically effective amount of expression vectors (e.g., wherein the expression vectors are CpG-free or CpG-reduced), wherein the expression vectors each comprise a first nucleic acid sequence encoding: i) a first therapeutic or non-therapeutic protein, and/or ii) a first biologically active nucleic acid molecule, c) administering dexamethasone palmitate and/or neutral lipids to the subject, either in said first and/or second composition, or present in a third composition (e.g., within 100 or 200 . . . or 400 minutes of administration of the first or second compositions). In some embodiments, as a result of the administering the first composition, the administering the second composition, and the administering of the dexamethasone palmitate and/or neutral lipids, the first therapeutic protein and/or the biologically active nucleic acid molecule is/are expressed in the subject at a therapeutic level with respect to the disease or condition, or at an effective level sufficient to alter the physiological or disease trait.

In certain embodiments, dexamethasone palmitate is in the first composition, and wherein 2.0% to 20.0% (e.g., 2.0% . . . 2.5% . . . 3.0% . . . 10% . . . 15% . . . or 20%) of the first composition comprises the dexamethasone palmitate. In certain embodiments, the dexamethasone palmitate is administered in the third composition, which is administered before the first and/or second composition is administered, or is administered after the first and/or second composition, but within 100 . . . 400 minutes thereof. In certain embodiments, the methods further comprise d) administering dexamethasone to the subject, either in the first and/or second and/or third composition, or present in a fourth composition (e.g., initiating within 100 or 300 minutes of administration of the first or second or third compositions, such as before any of the administrations or after the other administrations). In certain embodiments, the polycationic structures (e.g., empty liposomes) present in the first composition have a z-average diameter of about 20-85 nm (e.g., 20 . . . 25 . . . 30 . . . 40 . . . 45 . . . 50 . . . 55 . . . 60 . . . 65 . . . 70 . . . 75 . . . 80 . . . 85 nm). In certain embodiments, the polycationic structures are empty liposomes with a z-average diameter of about 72-76 nm, and are small uni-lammellar vesicles.

In some embodiments, A) the ratio is 10:1 to 18:1; B) 2.0% to 20.0% of the first composition comprises dexamethasone or dexamethasone palmitate; and/or C) each of the expression vectors each comprise only a single expression cassette (i.e., no other expression cassettes are present in each vector), wherein the expression cassette comprises the first nucleic acid sequence encoding the first therapeutic protein and a second nucleic acid sequence encoding a second therapeutic protein, and wherein the expression cassette encodes a self-cleaving peptide sequence (or other cleavage sequence) between the first and second nucleic acid sequences. In certain embodiments, the self-cleaving peptide comprises F2A, P2A, T2A or E2A. In some embodiments, a furin recognition site and/or (S)GSG linker are included upstream of self-cleaving peptides to enhance the cleavage efficiency. In particular embodiments, the first therapeutic protein comprises a monoclonal antibody light chain and the second therapeutic protein comprises a heavy chain of said monoclonal antibody (e.g., the light and heavy chains combine to form a monoclonal antibody fragment (e.g., Fab) or monoclonal antibody when expresses in a subject). In certain embodiments, the polycationic structures comprise empty liposomes. In particular embodiments, the empty liposomes present in said first composition have an average diameter of about 50-85 nm. In certain embodiments, the methods further comprise administering an agent or additional regulating expression vectors, either in said first and/or second composition, or present in a third composition, wherein the agent increases or decreases the expression at the therapeutic or effective level, and/or the length of time of the expression at said therapeutic or effective level, compared to when the drug agent is not administered to said subject (e.g., for therapeutics that need to be expressed for only a certain, limited amount of time). In particular embodiments, the agent is selected from colchicine, dexamethasone, dexamethasone palmitate, neutral lipids, valproic acid, theophylline, sildenafil, amlexanox, chloroquine, SAHA, and L-arginine+sildenafil.

In some embodiments, the expression vectors each further comprise a regulating nucleic acid sequence, wherein the regulating nucleic acid sequence reduces the duration of expression of the first nucleic acid sequence that would occur in the absence of said regulating nucleic acid sequence. In other embodiments, the regulating nucleic acid sequence is selected from the group consisting of: a promoter, an enhancer, a second nucleic acid sequence encoding a second protein, and/or a second biologically active nucleic acid molecule. In additional embodiments, the first amount of polycationic structures in the first composition comprises a mixture of at least a first and second different types of cationic liposomes that reduces the expression of the first therapeutic protein and/or first biologically active nucleic acid molecule compared to such expression when only said first or only said second type of cationic liposomes are employed in said method. In particular embodiments, the therapeutic protein is expressed at a level that is above 1 ug/ml (e.g., 1.1-1.5 ug/ml), and wherein said therapeutic protein is expressed at the level in said subject for at least 7 consecutive days (e.g., at least 7 . . . 21 . . . 50 . . . 100 . . . or 400 days).

In certain embodiments, provided herein are methods of expressing a first therapeutic protein and/or a biologically active nucleic acid molecule in a subject comprising: a) administering (e.g., systemically) a first composition to a subject, wherein the subject has at least one symptom of a disease or condition, is at risk of infection from one or more infectious diseases, or has at least physiological trait to be altered (e.g., level of hematopoietic stem cells), wherein the first composition comprises a first amount of polycationic structures (e.g., empty cationic liposomes, empty cationic micelles, or empty cationic emulsions), and wherein the first composition is free, or essentially free, of nucleic acid molecules; and b) administering (e.g., systemically) a second composition to the subject be initiated (or completed) within about 2 . . . 10 . . . 25 . . . 100 . . . 200 or 400 minutes of administering the first composition, wherein the second composition comprises a therapeutically effective amount of expression vectors (e.g., plasmid), wherein the expression vectors are CpG-free or CpG-reduced (e.g., the nucleic acid sequence of the expression vector has been altered to contain fewer CpG di-nucleotides than normally present in the wild-type version of the sequences in the vector) or are CpG-containing vectors (e.g, the wild-type C-CSF is employed, which contains a plurality of CpG dinucleotides), wherein the expression vectors each comprise nucleic acid sequence(s) encoding: i) a first therapeutic protein (or first and second therapeutic proteins, or first, second, and third therapeutic proteins, etc.), and/or ii) a first biologically active nucleic acid molecule (or first and second or more biologically active nucleic acid molecules), and wherein, as a result of the administering the first composition and the administering the second composition, and wherein, as a result of administering the first and second compositions, the therapeutic protein(s) and/or the biologically active nucleic acid molecule(s) is/are expressed in the subject at a therapeutic level with respect to the disease or condition, or at an effective level sufficient to alter the physiological or disease trait.

In certain embodiments, the expression vectors are not associated with polycationic structures (e.g., empty cationic liposomes, empty cationic micelles, or empty cationic emulsions)), or other molecules, in the second composition (and there are no detectable polycationic structures present in the second composition). In other embodiments, the expression vectors are naked, non-viral, expression vectors (e.g., plasmids). In certain embodiments, the expression vectors are viral expression vectors (e.g., adeno-associated viral vector or adenovirus vector or synthetic mRNA, miRNA, ribozyme or shRNA nucleic acid vectors). In particular embodiments, the first and/or second composition is administered systemically, regionally, transcutaneously, intradermally, orally, intramuscularly, intravenously, into the gastrointestinal tract, bladder or by pulmonary inhalation, or by an intrathecal or intraventricular route.

In certain embodiments, the therapeutic protein or proteins and/or biologically active nucleic acid molecule or molecules is/are expressed at the therapeutic or effective level in the subject on consecutive days for at least 5 . . . 20 . . . 63 . . . 100 . . . 200 . . . 300 days . . . 1 year or more. In some embodiments, the methods further comprise: c) testing the subject (e.g., body imaging or scanning), or a sample (e.g., blood, serum, plasma, tissue, urine, etc.) from the subject, after at least 5 . . . 20 . . . 63 . . . 100 . . . 200 . . . 300 days . . . or 1 year from the administering the first and second compositions, and determining that the therapeutic protein(s) and/or biologically active nucleic acid molecule(s) is/are being expressed in the subject at the therapeutic or effective level (e.g., therapeutic levels have been sustained in the subject for a time period required to produce therapeutic and/or prophylactic effects in the subject due the single treatment of the first and second compositions). In additional embodiments, the methods further comprise: d) generating a written and/or electronic report that indicates the therapeutic protein and/or biologically active nucleic acid molecule is/are being expressed in the subject at the therapeutic or effective level (e.g., for a certain amount of time). In other embodiments, the report is sent to the treating clinician or practitioner and/or patient from a lab that conducted the test.

In some embodiments, the therapeutic protein and/or biologically active nucleic acid molecule is/are expressed at a level of at least 50 pg/ml . . . 100 . . . 500 . . . 1000 . . . 1500 . . . 4000 . . . 8000 . . . 9500 . . . 1,000,000 pg/ml (1 ug/ml) . . . 1.5 ug/ml or higher, and wherein a blood, serum, or plasma sample (or other biological sample) from the subject is assayed to determine that the therapeutic or effective level is achieved for at least 5 . . . 7 . . . 10 . . . 25 . . . 45 . . . 63 . . . 150 . . . 300 days, or longer, after the administration of the first and second compositions. In other embodiments, the therapeutic protein(s) is/are expressed at a level that is at least 50 pg/ml or at least 100 pg/ml or at least 500, 1,000,000 pg/ml (1 ug/ml) . . . 1.5 ug/ml or higher, and wherein the therapeutic protein is expressed at the level in the subject for at least 5 . . . 7 . . . 10 . . . 25 . . . 45 . . . 63 . . . 150 . . . 300 . . . 350 consecutive days. In certain embodiments, the therapeutic protein and/or biologically active nucleic acid molecule is expressed (e.g., at therapeutic levels) in the subject without clinically significant elevated toxicity (e.g., as measured by ALT (alanine aminotransferase) and/or AST (aspartate aminotransferase)) after at least 48 hours following the administration of the first and second compositions.

In certain embodiments, the therapeutic protein is human G-CSF (e.g., as encoded by SEQ ID NO:1, or sequence with at least 98% identity with SEQ ID NO:1) and is expressed in the subject at a therapeutic level of at least 100 pg/ml as measured in a blood, serum, or plasma sample, wherein the therapeutic protein is expressed in the subject for at least seven days, and wherein the disease, condition, or physiological trait is selected from the group consisting of: neutropenia caused by chemotherapy, non-elevated levels of hematopoietic stem cells in blood of a stem cell donor or recipient, heart degeneration, cerebral ischemia, amyotrophic lateral sclerosis, neutrophil deficiency diseases, and radiation exposure. In particular embodiments, the G-CSF is expressed for at least 5, or 6, or 7 days, but no more than about 10 days (e.g., using drugs, promoter/enhancer combinations, additional expression cassette within the nucleic acid vector or additional expressed proteins to limit production to about 10 days to avoid any toxic neutrophilia-related side effects by expression beyond about 10 days). In other embodiments, the therapeutic protein is Rituximab or similar anti-CD20 antibody or antibody fragment. In some embodiments, the therapeutic protein is human Factor IX or similar protein.

In particular embodiments, the therapeutic protein or proteins and/or biologically active nucleic acid molecule or molecules is/are expressed in the subject for a sufficient amount of time at the therapeutic level to reduce or eliminate the at least one symptom (or all symptoms) without the subject having to receive any other treatment that provides the therapeutic protein(s) and/or biologically active nucleic acid molecule(s) to the subject. In further embodiments, during the sufficient time, the subject does not receive any other specific treatment (e.g., no other specific therapeutic treatment that provides the therapeutic protein or biologically active nucleic acid molecule(s) to the subject). In certain embodiments, the subject has multiple symptoms of a disease or diseases, and wherein the sufficient amount of time is such that all or substantially all of the multiple symptoms of the disease(s) and/or the condition(s) are reduced or eliminated in the subject (e.g., permanently, or for at least 20 days . . . 50 days . . . 200 days . . . 1 year or longer). In other embodiments, during the sufficient time, the subject does not receive the any other disease-specific treatment.

In some embodiments, the first amount of the polycationic structures (e.g., empty cationic liposomes, empty cationic micelles, or empty cationic emulsions) is about 0.01-70, 30-50, or 20-60, μmoles per 1 kilogram of the subject (e.g., 0.01 . . . 1 . . . 10 . . . 20 . . . 40 . . . or 60 μmoles per kilogram). In other embodiments, the ratio of the first amount of the polycationic structures (e.g., empty cationic lipids) to the therapeutically effective amount of the expression vectors is 0.5:1 to 25:1, nmoles of polycationic structures (e.g., empty cationic lipids) to 1 μg of expression vectors (e.g., 0.5:1 . . . 1:1 . . . 4:1 . . . 8:1 . . . 12:1 . . . 17:1 . . . 21:1 . . . or 25:1). In certain embodiments, the ratio of the first amount of the polycationic structures (e.g., empty cationic lipids) to the therapeutically effective amount of the expression vectors is 7:1 to 13:1, nmoles of polycationic structures (e.g., empty cationic lipids) to 1 μg of expression vectors. In particular embodiments, the therapeutically effective amount of the expression vectors is 0.001-8.0 milligrams of the expression vectors per 1 kilogram of the subject (e.g., 0.001 . . . 0.1 . . . 3.0 . . . 4.5 . . . 5.7 . . . 7.1 . . . 8.0 milligrams per kilogram). In some embodiments, the therapeutically effective amount of expression vectors is 0.001 to 1 μg per 1 kilogram of the subject (e.g., 0.001 . . . 0.01 . . . 0.1 . . . 1 μg per kilogram of subject). In certain embodiments, the therapeutically effective amount of the expression vectors is about 0.01-4.0 milligrams of the expression vectors per 1 kilogram of the subject.

In some embodiments, the first nucleic acid sequence encodes the first or first and second, or first, second, and third, therapeutic protein(s). In additional embodiments, the first nucleic acid sequence encodes the biologically active nucleic acid molecule(s). In other embodiments, the subject is a human. In additional embodiments, the expression vectors are CpG-free. In other embodiments, the expression vectors are CpG-reduced. In other embodiments, the therapeutic protein(s) is/are human protein(s) or animal protein(s).

In some embodiments, the polycationic structures do not contain cholesterol (e.g., cholesterol free empty cationic micelles or liposomes). In certain embodiments, the cationic liposomes each comprise at least 60% DOTAP and/or DPTAP (e.g., 60% . . . 75% . . . 85% . . . 95% . . .

98% . . . 100% DOTAP and/or DPTAP). In other embodiments, all or substantially all of the cationic liposomes are multi-lamellar vesicles. In further embodiments, all or substantially all of the cationic liposomes are uni-lamellar vesicles. In further embodiments, the cationic liposomes each comprise at least 99% DOTAP or 99% DPTAP. In further embodiments, the empty cationic liposomes each comprise DOTAP and cholesterol. In additional embodiments, the cationic liposomes each comprise about one-third cholesterol and about two-thirds DOTAP and/or DPTAP. In further embodiments, the first nucleic acid sequence encodes human G-CSF (e.g., as shown in SEQ ID NO:1).

In certain embodiments, the biologically active nucleic acid molecule(s) comprises sequence(s) selected from: shRNA sequence(s), miRNA sequence(s), antisense sequence(s), ribozyme(s), and/or CRISPR single guide RNA sequence(s) (sgRNA). In other embodiments, the CRISPR sgRNA comprises: i) a Cas9 nuclease-recruiting sequence (tracRNA), and ii) a target-specific sequence (crRNA) that hybridizes to a sgRNA target site. In particular embodiments, the biologically active nucleic acid molecule targets human p65 (aka, NF-kappa-B p65 or RELA). Any desired combination of one or more RNA sequences may be encoded in a vector or in combination with non-RNA encoded molecules of interest. For example, in some embodiments, multiple expression cassettes (e.g., 2, 3, 4, etc.) are included in the vector, each expressing a different molecule of interest. In some embodiments, the molecules of interest comprise multiple single CRISPR/Cas9 guide cassettes contained in the vector.

In further embodiments, each of the expression vectors further comprises a second nucleic acid sequence encoding: i) a second therapeutic protein, and/or ii) a second biologically active nucleic acid molecule. In some embodiments, each of the expression vectors further comprises a third nucleic acid sequence encoding: i) a third, and/or fourth therapeutic protein, and/or ii) a third, and/or fourth biologically active nucleic acid molecule. In further embodiments, each of the expression vectors further comprise a first promoter associated with the first nucleic acid sequence, and a second promoter associated with the second nucleic acid sequence, and wherein the first and second promoters are the same or different. In other embodiments, the therapeutic or effective expression level of the first nucleic acid sequence and/or the length of time of the therapeutic or effective expression level, is reduced compared to the expression level or the length of time, when the second nucleic acid is not present and/or expressed from the expression vectors. In other embodiments, the first nucleic acid sequence is expressed at the therapeutic level for at least 5 days, but less than 21 days (e.g., 5 . . . 7 . . . 13 . . . 16 . . . 20 . . . and 21 days). In certain embodiments, the first nucleic acid sequence encodes the therapeutic protein, and wherein the therapeutic protein comprises human G-CSF.

In other embodiments, the expression vector provides the expression at the therapeutic or effective level for a first length of time and/or at a first level of expression when each of the expression vectors comprises a first promoter and first enhancer associated with the first nucleic acid sequence, and wherein the first length of time and/or expression level is altered when a second promoter, different from the first promoter, replaces the first promoter, and/or a second enhancer, different from the second enhancer, replaces the second promoter, on the expression vectors. In other embodiments, the expression at the therapeutic or effective level for a first length of time is for at least 10 . . . 15 . . . 45 . . . 100 . . . 200 . . . 300 days, and wherein replacement with the second promoter and/or second enhancer reduces expression at the therapeutic or effective level to a second length of time that is less than 10 . . . 15 . . . 45 . . . 100 . . . 200 days. In other embodiments, each of the expression vectors comprises a first promoter and a first enhancer, and wherein the first promoter and the first enhancer cause expression at the therapeutic level for at least 5 days, but less than 21 . . . 15 . . . or 10 days. In particular embodiments, the first nucleic acid sequence encodes the therapeutic protein, and wherein the therapeutic protein comprises human G-CSF.

In some embodiments, the methods further comprise administering a drug agent or agents, either in the first and/or second composition, or present in a third composition, wherein the drug agent or agents increase or decrease the expression of the first nucleic acid (e.g., at the therapeutic or effective level, and/or the length of time of the expression at the therapeutic or effective level), compared to when the drug agent or agents are not administered to the subject. In particular embodiments, the drug agent increases the expression level of the first nucleic acid in the subject, and wherein the drug is selected from colchicine, an immunosuppressant, dexamethasone, dexamethasone palmitate, sildenafil, or L-arginine+sildenafil. In certain embodiments, the drug (e.g., dexamethasone or dexamethasone palmitate) is present at between 2.0% and 20.0% of a polycationic structure (e.g., empty cationic lipid composition), such as at 2.0% . . . 2.5% . . . 3.5% . . . 4.5% . . . 6.0% . . . 15% . . . or 20%). In other embodiments, the drug (e.g., dexamethasone or dexamethasone palmitate), is administered to the subject before or after the polycationic structure and vector compositions are administered. In certain embodiments, the polycationic structures (e.g., empty liposomes) present in the first composition have a z-average diameter of about 20-85 nm (e.g., 20 . . . 25 . . . 30 . . . 40 . . . 45 . . . 50 . . . 55 . . . 60 . . . 65 . . . 70 . . . 75 . . . 80 . . . 85 nm). In certain embodiments, the polycationic structures are empty liposomes with a z-average diameter of about 72-76 nm, and are small uni-lammellar vesicles. In some embodiments, drug agents (e.g., dexamethasone) are provided to a subject prior to dosing of the first and/or second composition, in addition to incorporating such agents into the first composition.

In other embodiments, the therapeutic protein is expressed at a level of at least two times higher (or at least 3 or 4 or 5 times higher) when the drug agent is administered to the subject compared to when the drug agent is not administered to the subject. In particular embodiments, the drug agent decreases the expression level of the first nucleic acid sequence, and wherein the drug agent is L-arginine. In further embodiments, the therapeutic protein is expressed at a level of at least two times (or at least three times or four times) lower when the drug agent is administered to the subject compared to when the drug agent is not administered to the subject. In some embodiments, the drug agent comprises an anti-inflammatory agent. In additional embodiments, the drug agent is selected from the group consisting of: amlexanox, chloroquine, valproic acid, theophylline, DHA, prostaglandin, and SAHA.

In further embodiments, the expression vectors are free of operable matrix attachment region (MAR) sequences. In certain embodiments, the expression vectors are free of operable EBNA-1 and/or EBV viral sequences. In certain embodiments the subject's blood pressure, immediately prior to said administering said first and second compositions, is not altered (e.g., no physical transfection aids are applied to the subject to attempt to increase expression of the first nucleic acid sequence). In certain embodiments, the expression vectors comprise at least one of the following: an R6K origin of replication (e.g., located in the 3' or 5' UTR of a gene in the vector), an hr3 enhancer, a BV3 signal sequence, a Syn21 sequence, a delta-p10 sequence, or an MITD (MHC class I trafficking signal) sequence.

In particular embodiments, the therapeutic level and/or effective level is at least 150 . . . 100 . . . 500 . . . 1000 . . . 1500 . . . 5000 . . . 1,000,000 pg/ml (1 ug/ml) . . . 1.5 ug/ml or higher, and wherein a blood, serum, or plasma sample (or other biological sample) from the subject is determined to be at the therapeutic level and/or effective level at least 7 . . . 10 . . . 25 . . . 45 . . . 63 . . . 150 . . . 300 . . . 400 days or more after the administration of the first and second compositions. In particular embodiments, the sample from the subject is tested with an ELISA assay or by mass spectrometry to determine the expression level.

In some embodiments, the methods further comprise administering a therapeutically effective amount of neutral liposomes to the subject, wherein the neutral liposomes are present in the first and/or second composition, and/are administered in a third composition, and wherein the therapeutically effective amount of neutral liposomes are administered to the subject prior to the administering the second composition. In certain embodiments, the neutral liposomes comprise at least material selected from: phospholipon 90H, hydrogenated soy PC, stearic and palmitic. In other embodiments, the therapeutically effective amount of neutral liposomes are present in the first composition or present in a third composition administered to the subject. In further embodiments, the neutral liposomes are multilamellar vesicles or extruded to 0.2 or 0.1 um. In particular embodiments, administering the therapeutically effective amount of the neutral liposomes causes expression of the first therapeutic protein and/or the biologically active nucleic acid molecule in the subject that is at least 3 . . . 4 . . . 25 . . . 100 . . . 350 . . . or 600 times higher than occurs when the neutral liposomes are not administered to the subject. In certain embodiments, the ratio of empty cationic liposomes to the neutral liposomes administered to the subject is between about 2:1 and 1:5 (e.g., 2:1 . . . 1:1 . . . 2:5 . . . 1:5).

In some embodiments, provided herein are methods of expressing a first therapeutic protein and/or a biologically active nucleic acid molecule in a subject comprising: a) administering a first composition to a subject, wherein the first composition comprises an anti-inflammatory agent; and b) administering or initiating administration of, a second composition to the subject within about 2 minutes . . . 20 minutes . . . 1 hour . . . 24 hours . . . 5 days . . . 7 days . . . 9 days or more of administering the first composition, wherein the second composition comprises a therapeutically effective amount of polyplexes, wherein each polyplex comprises an expression vector and polyethylenimine, wherein the expression vector is CpG-free or CpG-reduced, wherein each expression vector comprises a first nucleic acid sequence encoding: i) a first therapeutic protein (and/or first and second proteins), and/or ii) a first (and/or first and second) biologically active nucleic acid molecule, and wherein, as a result of administering the first composition and administering the second composition, the first therapeutic protein and/or the biologically active nucleic acid molecule is/are expressed in the subject. In further embodiments, the subject has at least one symptom of a disease or condition, or has at least one physiological trait desired to be altered, and wherein the first therapeutic protein and/or the biologically active nucleic acid molecule is expressed at a therapeutic level with respect to the disease, condition, or physiological trait to be altered. In some embodiments, the anti-inflammatory agent is selected from the group consisting of amlexanox, chloroquine, and suberanilohydroxamic acid (SAHA).

In some embodiments, the expression vector comprises a plasmid or other non-viral vector. In further certain embodiments, the administration in step b) is accomplished by systemically administering the second composition.

In some embodiments, provided herein are systems or kits comprising: a) a first composition comprising a first amount of polycationic structures (e.g., empty cationic liposomes, empty cationic micelles, or empty cationic emulsions), wherein the first composition is free, or essentially free, of nucleic acid molecules; and b) a second composition comprises a therapeutically effective amount of expression vectors (e.g., non-viral and not associated with liposomes or other carrier molecules), wherein the expression vectors are CpG-free or CpG-reduced, wherein each of the expression vectors comprises a first nucleic acid sequence encoding: i) a first therapeutic protein or non-therapeutic protein, and/or ii) a first biologically active nucleic acid molecule. In other embodiments, the expression vectors are a naked, non-viral expression vectors (e.g., plasmid). In certain embodiments, at least one of the following applies: i) wherein the ratio of the first amount of the polycationic structure (e.g., empty cationic liposome) to the therapeutically effective amount of expression vectors is 2:1 to 25:1 or 5:1 to 25:1; ii) wherein 2.0% to 20.0% of the first composition comprises dexamethasone palmitate; iii) wherein the first composition further comprises neutral lipid, and iv) wherein the polycationic structures comprise empty liposomes, and wherein the empty liposomes present in the first composition have a z-average diameter of about 20-85 nm (e.g., 20 . . . 25 . . . 30 . . . 40 . . . 45 . . . 50 . . . 55 . . . 60 . . . 65 . . . 70 . . . 75 . . . 80 . . . 85 nm). In certain embodiments, the vectors are viral vectors (e.g., AAV or adeno viral vectors). In particular embodiments, the therapeutic protein is human G-CSF (e.g., as shown in SEQ ID NO:1), or the wild-type human G-CSF which contains a plurality of CpG dinucleotides.

In particular embodiments, the first amount of the polycationic structure (e.g., empty cationic liposomes) is between 0.1 to 7.0 millimoles (e.g., 0.1 . . . 5.0 . . . 7.0 millimoles) or 1.5 and 5.0 millimoles (e.g., suitable amount for administration to a human subject). In other embodiments, the ratio of the first amount of the polycationic structure (e.g., empty cationic liposome) to the therapeutically effective amount of the expression vectors is 0.5:1 to 25:1, nmoles of empty cationic lipid to 1 μg of expression vectors (e.g., 0.5:1 . . . 1:1 . . . 5:1 . . . 10:1 . . . 15:1 . . . 25:1). In some embodiments, the ratio of the first amount of the polycationic structure (e.g., empty cationic lipid) to the therapeutically effective amount of the expression vectors is 7:1 to 13:1, nmoles of polycationic structure to 1 μg of expression vectors (e.g., 7:1 . . . 10:1 . . . or 13:1). In other embodiments, the therapeutically effective amount of the expression vectors is between 0.1 and 800 milligrams (e.g., suitable amount for administration to a human subject, such as when the vector is a plasmid). In certain embodiments, the amount is 1 . . . 25 . . . 400 . . . or 800 milligrams of expression vectors for human administration.

In other embodiments, the first nucleic acid sequence encodes the first therapeutic protein. In additional embodiments, the first nucleic acid sequence encodes the biologically active nucleic acid molecule. In particular embodiments, the expression vectors are CpG-free. In other embodiments, the expression vectors are CpG-reduced. In further embodiments, the first therapeutic protein is a human protein. In other embodiments, the first nucleic acid sequence encodes the therapeutic protein, and wherein the therapeutic protein comprises human G-CSF, Rituximab, a monoclonal antibody or monoclonal antibody fragment (e.g., Fab), or human Factor IX.

In certain embodiments, the empty cationic liposomes, micelles, or emulsions, each comprise at least 60% DOTAP and/or DPTAP (e.g., 60% . . . 75% . . . 85% . . . 95% . . . 98% . . . 100% DOTAP and/or DPTAP), and may be cholesterol-free (e.g., no detectable cholesterol in the composition). In other embodiments, all or substantially all of the empty cationic liposomes, micelles, or emulsions are multilamellar vesicles. In further embodiments, all or substantially all of the empty cationic liposomes, micelles, or emulsions are either unilamellar, multilamellar, or oligolamellar vesicles. In further embodiments, the empty cationic liposomes, micelle, or emulsions each comprise at least 99% DOTAP or at least 99% DPTAP, and may be cholesterol free. In further embodiments, the empty cationic liposomes each comprise DOTAP and/or DPTAP and cholesterol. In additional embodiments, the empty cationic liposomes, micelles, or emulsions each comprise about one-third cholesterol and about two-thirds DOTAP and/or DPTAP.

In certain embodiments, the first biologically active nucleic acid molecule comprises a sequence selected from: an siRNA or shRNA sequence, a miRNA sequence, an antisense sequence, a CRISPR multimerized single guide, and a CRISPR single guide RNA sequence (sgRNA). In other embodiments, the CRISPR sgRNA comprises: i) a Cas9 nuclease-recruiting sequence (tracRNA), and ii) a target-specific sequence (crRNA) that hybridizes to a sgRNA target site.

In further embodiments, each of the expression vectors further comprises a second nucleic acid sequence encoding: i) a second therapeutic protein, and/or ii) a second biologically active nucleic acid molecule. In further embodiments, each of the expression vectors further comprise a first promoter associated with the first nucleic acid sequence, and a second promoter associated with the second nucleic acid sequence, and wherein the first and second promoters are the same or different.

In some embodiments, the kits and systems further comprise a first container and a second container, and wherein the first composition is present in the first container and the second composition is present in the second container. In other embodiments, kits and systems further comprise a packaging component (e.g., cardboard box, plastic pouch, etc.), wherein the first container and the second container are inside the packaging component.

In certain embodiments, the kits and systems further comprise a drug agent or drug agents, wherein the drug agent(s) are present in the first and/or second compositions, or is present in a third composition. In additional embodiments, the drug agent is selected from colchicine, an immunosuppressant, dexamethasone, sildenafil, L-arginine, or L-arginine+sildenafil. In further embodiments, the drug agent comprises an anti-inflammatory agent. In further embodiments, the drug agent is selected from the group consisting of: amlexanox, valproic acid, theophylline, chloroquine, and SAHA.

In particular embodiments, the expression vectors are free of operable matrix attachment region (MAR) sequences. In additional embodiments, the expression vectors are free of operable EBNA-1 and/or EBV viral sequences.

In certain embodiments, the kits and systems further comprise a therapeutically effective amount of neutral liposomes, wherein the neutral liposomes are present in the first and/or second compositions, or is present in a third composition. In additional embodiments, the therapeutically effective amount of neutral liposomes are present in the first composition. In other embodiments, the neutral liposomes are multilamellar or oligo- or uni-lamellar vesicles. In further embodiments, the ratio of empty cationic liposomes or micelles to the neutral liposomes is between about 2:1 and 1:5 (e.g., 2:1 . . . 1:1 . . . 3:5 . . . 1:5).

In some embodiments, provided herein are a first composition and a second, separate, composition for combined use in the treatment of a disease amenable to treatment with in vivo expression of a first therapeutic protein and/or biologically active nucleic acid molecule, wherein the first composition comprises a first amount of polycationic structures (e.g., empty cationic liposomes, empty cationic micelles, or empty cationic emulsions), wherein the first composition is free, or essentially free, of nucleic acid molecules; and b) a second composition that comprises a therapeutically effective amount of expression vectors, wherein the expression vectors are CpG-free or CpG-reduced, wherein each of the expression vectors comprises a first nucleic acid sequence encoding: i) a first therapeutic protein, and/or ii) a first biologically active nucleic acid molecule.

In certain embodiments, provided herein are methods of expressing a first therapeutic protein and/or a biologically active nucleic acid molecule in a subject comprising: a) administering a first composition to a subject, wherein the first composition comprises a first amount of polycationic structures (e.g., empty cationic liposomes, empty cationic micelles, or empty cationic emulsions), and wherein the first composition is free, or essentially free, of nucleic acid molecules; and b) administering a second composition to the subject within about 100 minutes or 200 minutes of administering the first composition, wherein the second composition comprises a therapeutically effective amount of non-viral expression vectors, wherein the expression vectors are CpG-free or CpG-reduced, wherein the expression vectors each comprise a first nucleic acid sequence encoding: i) a first therapeutic protein, and/or ii) a first biologically active nucleic acid molecule, and wherein, as a result of administering the first composition and administering about the second composition, the first therapeutic protein and/or the biologically active nucleic acid molecule is/are expressed in the subject at a level above (e.g., at least 150 . . . 300 . . . 575 . . . 1000 . . . 1500 . . . 2000 . . . 5000 . . . or 1,000,000 pg/ml) (e.g., as measured in a serum sample from the subject (e.g., after 7 . . . 25 . . . 50 days from the first and second administrations).

In certain embodiments, provided herein are methods comprising: administering a composition to a subject comprising a therapeutically effective amount of non-viral expression vectors that are CpG-free or CpG-reduced, or CpG containing vectors, and comprise a first nucleic acid sequence encoding: i) a first therapeutic protein, and/or ii) a first biologically active nucleic acid molecule, and wherein, as a result of administering the first and second compositions, the first therapeutic protein and/or the biologically active nucleic acid molecule is/are expressed in the subject at a level above 100 pg/ml (e.g., at least 150 . . . 400 . . . 1200 . . . 2000 . . . 5000 . . . or more than 1,000,000 pg/ml) (e.g., as measured in a serum sample from the subject (e.g., after 7 . . . 25 . . . 50 days from the first and second administrations).

In certain embodiments, the polycationic structures comprise empty cationic liposomes, micelles, or emulsions. In other embodiments, the polycationic structures comprise one or more of the following, either alone or combined with polycationic structures: linear or branched polyethyleneimine, dendrimers (e.g., 4th generation pamaam dendrimer based on ethylene diamine, polylysine, polyarginine, and protamine sulfate), poly-lysine, and protamine sulfate. In certain embodiments, the polycationic structures are provided as a cationic emulsion. In particular embodiments, the surfactants in the emulsions are selected from: cetylpyridinium chloride, cetyltrimethylammonium bromide or the like. In other embodiments, the emulsions further comprise a neutral component, such as tweens, spans and triglycerides. In particular embodiments, the emulsions comprise a cationic lipid, such as, for example, DOTAP, DPTAP, DOTMA, or DDAB. In some embodiments, the emulsions are self-emulsifying emulsions or microemulsions (SEDDS, SMEDDS).

In some embodiments, provided herein are methods of expressing a first and second proteins and/or first and second biologically active nucleic acid molecules in a subject comprising: a) administering a first composition to a subject, wherein the subject has at least one symptom of a disease or condition, or has at least physiological trait to be altered, wherein said first composition comprises a first amount of polycationic structures, and wherein said first composition is free, or essentially free, of nucleic acid molecules; and b) administering a second composition to said subject within about 100 minutes of administering the first composition, wherein the second composition comprises a therapeutically effective amount of expression vectors, wherein the expression vectors are non-viral and are CpG-free or CpG-reduced, wherein the expression vectors each comprise: i) a first expression cassette encoding: A) a first protein, and/or B) a first biologically active nucleic acid molecule, and ii) a second expression cassette encoding: A) a second protein and/or B) a second biologically active nucleic acid molecule. In certain embodiments, as a result of the administering the first composition and the administering the second composition, the first and second proteins and/or said first and second biologically active nucleic acid molecule is/are expressed in the subject at a therapeutic level with respect to the disease or condition, or at an effective level sufficient to alter said physiological or disease trait.

In particular embodiments, the first protein comprises a monoclonal antibody light chain, and the second protein comprises a heavy chain of said monoclonal antibody. In other embodiments, the first and second expression cassettes both comprise regulatory elements. In additional embodiments, the regulatory elements are the same or different in said first and second expression cassettes.

In some embodiments, provided herein are methods of expressing a monoclonal antibody (mAb), Fab, F(ab)2, and/or scFv in a subject comprising: a) administering a first composition to a subject, wherein the subject has at least one symptom of a disease or condition, or has at least physiological trait to be altered, wherein the first composition comprises a first amount of polycationic structures, and wherein the first composition is free, or essentially free, of nucleic acid molecules; and b) administering a second composition to the subject within about 300 minutes of administering the first composition, wherein the second composition comprises a therapeutically effective amount of expression vectors encoding the mAb, the Fab, the F(ab)2, and/or scFv, and wherein, as a result of the administering the first composition and the administering the second composition, the first therapeutic protein is expressed in the subject at a therapeutic level with respect to the disease or condition, or at an effective level sufficient to alter the physiological or disease trait.

In certain embodiments, the ratio of the first amount of the polycationic structures to the therapeutically effective amount of expression vectors is 5:1 to 25:1. In further embodiments, the expression vectors are CpG-free or CpG-reduced. In other embodiments, the expression vectors contain a plurality of CpG motifs, and/or are not CpG-free or CpG-reduced. In additional embodiments, the mAb, the Fab, the F(ab)2, and/or the scFv is/are expressed at a therapeutic level in the subject for at least 7 consecutive days without any further administering. In other embodiments, the at least 7 consecutive days is at least 190 consecutive days without any further administering.

In some embodiments, the F(ab)2 is selected from the group consisting of: F(ab')2 Afelimomab, Alacizumab pegol, Dorlimomab aritox, Erlizumab, and Igovomab. In additional embodiments, the Fab is selected from the group consisting of: Abciximab, Anatumomab mafenatox, Citatuzumab bogatox, Nacolomab tafenatox, Naptumomab estafenatox, Nofetumomab merpentan, Ranibizumab, Tadocizumab, Telimomab aritox, Arcitumomab, Bectumomab, Biciromab, Certolizumab pegol, and Sulesomab. In certain embodiments, the scFv is selected from the group consisting of: Efungumab, Oportuzumab monatox, and Pexelizumab.

In particular embodiments, the mAb is selected from the group consisting of: 3F8, 8H9, Abagovomab, Abituzumab, Abrilumab, Actoxumab, Adalimumab, Adecatumumab, Aducanumab, Afasevikumab, Afutuzumab, Alemtuzumab, Alirocumab, Altumomab pentetate, Amatuximab, Anetumab ravtansine, Anifrolumab, Anrukinzumab, Apolizumab, Ascrinvacumab, Aselizumab, Atezolizumab, Atinumab, Atlizumab, Atorolimumab, Avelumab, Bapineuzumab, Basiliximab, Bavituximab, Begelomab, Belimumab, Benralizumab, Bertilimumab, Besilesomab, Bevacizumab, Bezlotoxumab, Bimagrumab, Bimekizumab, Bivatuzumab mertansine, Bleselumab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, cBR96-doxorubicin immunoconjugate, Cedelizumab, Cergutuzumab amunaleukin, Cetuximab, Ch.14.18, Cixutumumab, Clazakizumab, Clenoliximab, Clivatuzumab tetraxetan, Codrituzumab, Coltuximab ravtansine, Conatumumab, Concizumab, CR6261, Crenezumab, Crotedumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dinutuximab, Diridavumab, Domagrozumab, Drozitumab, Duligotumab, Dupilumab, Durvalumab, Dusigitumab, Ecromeximab, Eculizumab, Edobacomab, Edrecolomab, Efalizumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, and Epratuzumab.

In some embodiments, the mAb is selected from the group consisting of: Erenumab, Etaracizumab, Etrolizumab, Evinacumab, Evolocumab, Exbivirumab, Fanolesomab, Faralimomab, Farletuzumab, Fasinumab, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fulranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, IMAB362, Imalumab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Ipilimumab, Iratumumab, Isatuximab, Itolizumab, Ixekizumab, Keliximab, Labetuzumab, Lampalizumab, Lanadelumab, Landogrozumab, Laprituximab emtansine, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, MABp1, Mapatumumab, Margetuximab, Matuzumab, Mavrilimumab, Mepolizumab, Metelimumab, Milatuzumab, Minretumomab, Mirvetuximab soravtansine, Mitumomab, Mogamulizumab, Monalizumab, Morolimumab, Motavizumab, Moxetumomab pasudotox, Muromonab-CD3, Namilumab, Naratuximab emtansine, Narnatumab, Natalizumab, Navicixizumab, Navivumab, Nebacumab, Necitumumab, Nemolizumab, Nerelimomab, Nesvacumab, Nimotuzumab, Nivolumab, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oregovomab, Orticumab, Otelixizumab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, and Pasotuxizumab.

In certain embodiments, the mAb is selected from the group consisting of: Pateclizumab, Patritumab, Pembrolizumab, Perakizumab, Pertuzumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, Quilizumab, Racotumomab, Radretumab, Rafivirumab, Ralpancizumab, Ramucirumab, Raxibacumab, Refanezumab, Regavirumab, Reslizumab, Rilotumumab, Rinucumab, Risankizumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, SGN-CD19A, SGN-CD33A, Sibrotuzumab, Sifalimumab, Siltuximab, Simtuzumab, Siplizumab, Sirukumab, Sofituzumab vedotin, Solanezumab, Sontuzumab, Stamulumab, Suvizumab, Tabalumab, Tacatuzumab tetraxetan, Talizumab, Tamtuvetmab, Tanezumab, Taplitumomab paptox, Tarextumab, Tefibazumab, Tenatumomab, Teneliximab, Teplizumab, Teprotumumab, Tesidolumab, Tetulomab, Tezepelumab, Ticilimumab, Tigatuzumab, Tildrakizumab, Timolumab, Tisotumab vedotin, Tocilizumab, Toralizumab, Tosatoxumab, Tovetumab, Tralokinumab, Trastuzumab, Trastuzumab emtansine, Tregalizumab, Tremelimumab, Trevogrumab, Tucotuzumab celmoleukin, Ublituximab, Ulocuplumab, Urelumab, Urtoxazumab, Ustekinumab, Utomilumab, Vadastuximab talirine, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Vobarilizumab, Volociximab, Vorsetuzumab mafodotin, Votumumab, Xentuzumab, Zalutumumab, Zanolimumab, Zatuximab, Ziralimumab, and Zolimomab aritox.

In particular embodiments, the disease or condition comprises a viral or bacterial infection. In other embodiments, the disease or condition comprises cardiovascular disease or atherosclerosis. In further embodiments, the disease or condition comprises an autoimmune disease. In certain embodiments, the disease or condition comprises cancer (e.g., lung cancer, ovarian cancer, skin cancer, lymphoma, brain cancer, prostate cancer, pancreatic cancer, breast cancer, thyroid cancer, colon cancer, etc.). In further embodiments, the method further comprises at least one of the following: i) wherein 2.0% to 20% % of the first composition comprises dexamethasone palmitate; ii) wherein the first composition further comprises neutral lipid; and iii) wherein the polycationic structures comprise empty liposomes, and wherein the empty liposomes present in the first composition have a z-average diameter of about 20-85 nm.

In some embodiments, provided herein are systems and kits comprising: a first composition comprising a first amount of polycationic structures liposomes, wherein the first composition is free, or essentially free, of nucleic acid molecules; and b) a second composition comprising a therapeutically effective amount of expression vectors, wherein the expression vectors comprise nucleic acid sequences encoding a monoclonal antibody (mAb), Fab, F(ab)2, and/or scFv. In further embodiments, the monoclonal antibody (mAb), Fab, F(ab)2, and/or scFv is selected from those recited above and in Table 3 below.

In certain embodiments, at least one of the following applies: i) wherein the ratio of the first amount of the polycationic structures to the therapeutically effective amount of expression vectors is 5:1 to 25:1; ii) wherein 2.0% to 20% of the first composition comprises dexamethasone palmitate; iii) wherein the first composition further comprises neutral lipid; and iv) wherein the polycationic structures comprise empty liposomes, and wherein the empty liposomes present in the first composition have a z-average diameter of about 20-85 nm.

In some embodiments, the neutral lipids comprises 1,2-Dimyristoyl-SN-glycero-3-phosphocholine (DMPC; Dimyristoylphosphatidylcholine). In other embodiments, the neutral lipids are selected from: distearoyl phosphatidyl choline (DSPC), dipalmitoyl phosphatidylcholine (DPPC), palmitoyl oleoyl phosphatidylcholine (POPC), palmitoyl stearoyl phosphatidylcholine (PSPC), egg phosphatidylcholine (EPC), hydrogenated or non-hydrogenated soya phosphatidylcholine (HSPC), or sunflower phosphatidylcholine.

DESCRIPTION OF THE FIGURES

FIG. 1 the CpG-free modified nucleic sequence of h-GCSF (SEQ ID NO:1) and the amino acid sequence of h-GCSF (SEQ ID NO:2). The positions where CpG dinucleotides have been eliminated are shown in underline in SEQ ID NO:1. These sequences are examples of modified h-GCSF that could be used with the methods, compositions, systems, and kits herein.

Figure 3:
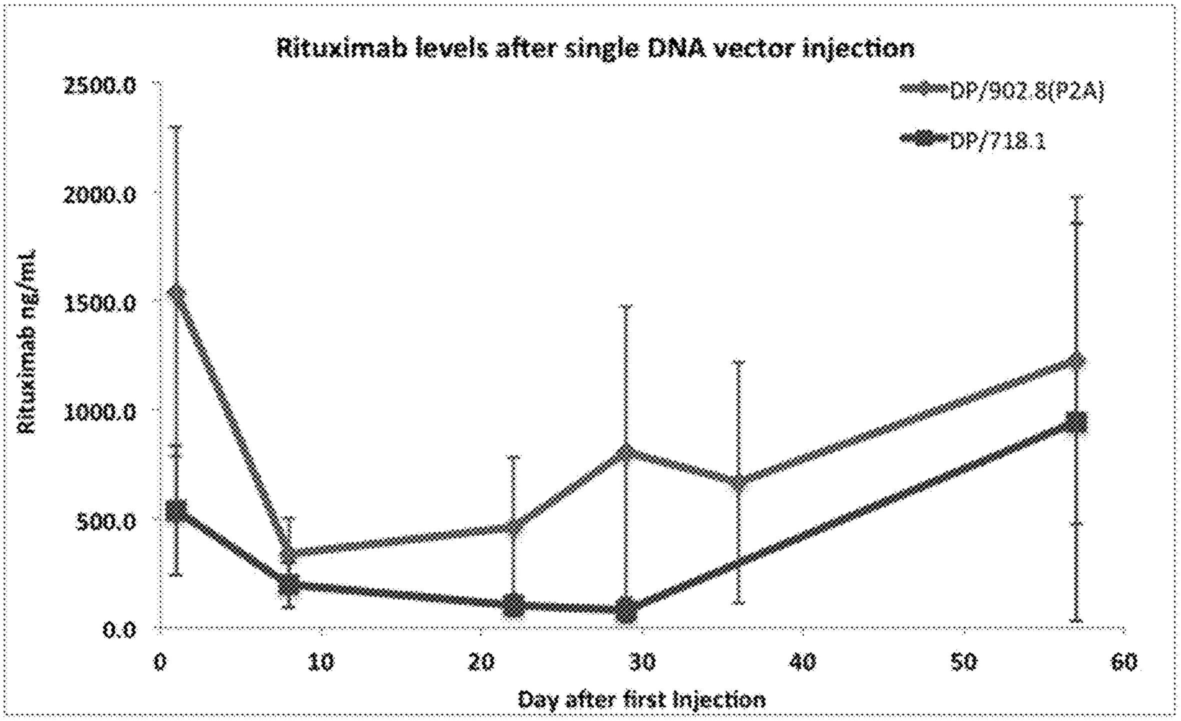

FIG. 3 shows serum anti-CD20 levels produced in mice by sequential, IV cationic liposome injection followed by IV injection of either a dual cassette or a single cassette 2A containing DNA vector in mice.

Figure 4:
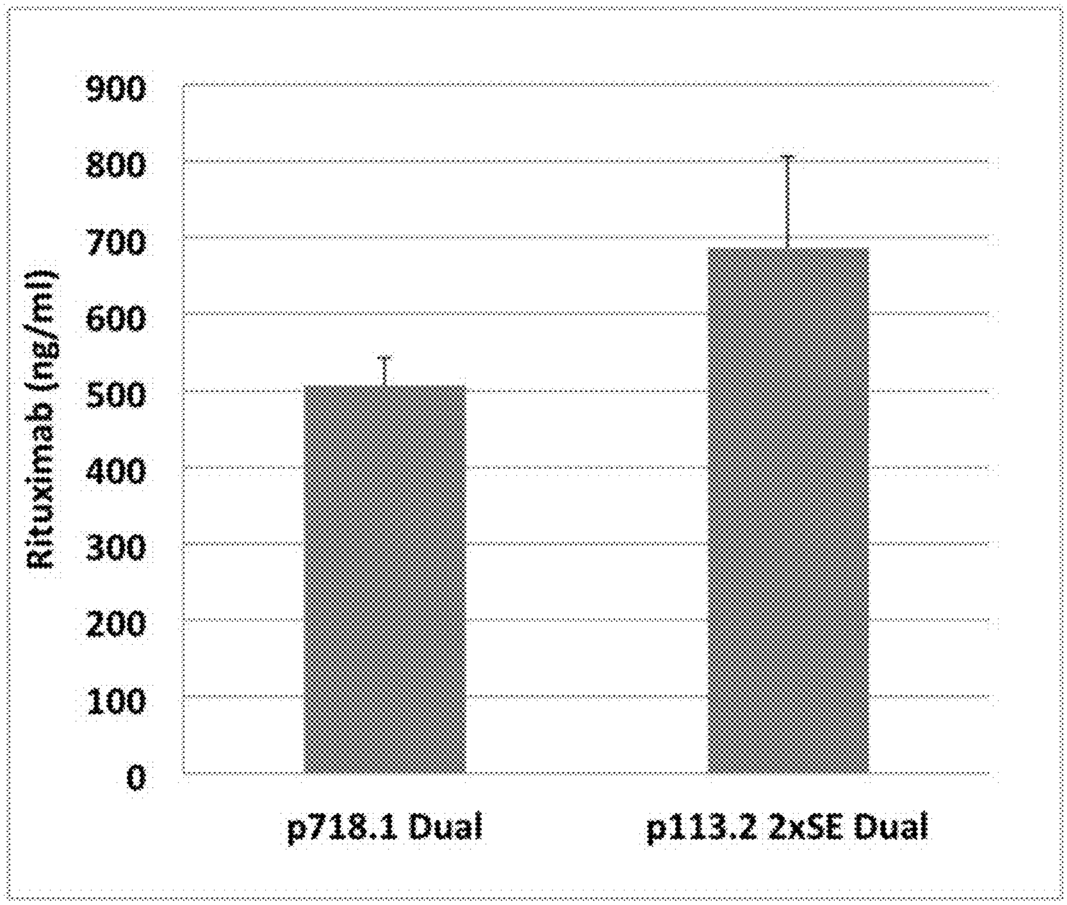

FIG. 4 shows that incorporation of super enhancer elements into DNA expression vectors increases serum anti-CD20 mAb levels in mice, 24 hrs after a single IV injection of a dual cassette anti-CD20 DNA vector.

FIG. 5 shows plasmid 715.1 2a (P2A) (SEQ ID NO:3) which encodes the anti-CD20 mAb heavy and light chain cDNAs separated by a 2A self-cleaving peptide.

FIG. 6 shows plasmid 718.1 (SEQ ID NO:4), which is dual expression cassette plasmid vector that encode the anti-CD20 mAb heavy and light chain cDNAs respectively.

FIG. 7 shows plasmid 902.8 (P2A) (SEQ ID NO:5), which encodes the anti-CD20 mAb heavy and light chain cDNAs separated by a 2A self-cleaving peptide.

FIG. 8 shows plasmid p113.2 (SEQ ID NO:6), which is identical to p718.1, but includes a single super enhancer upstream of the second coding cassette.

Figure 9:
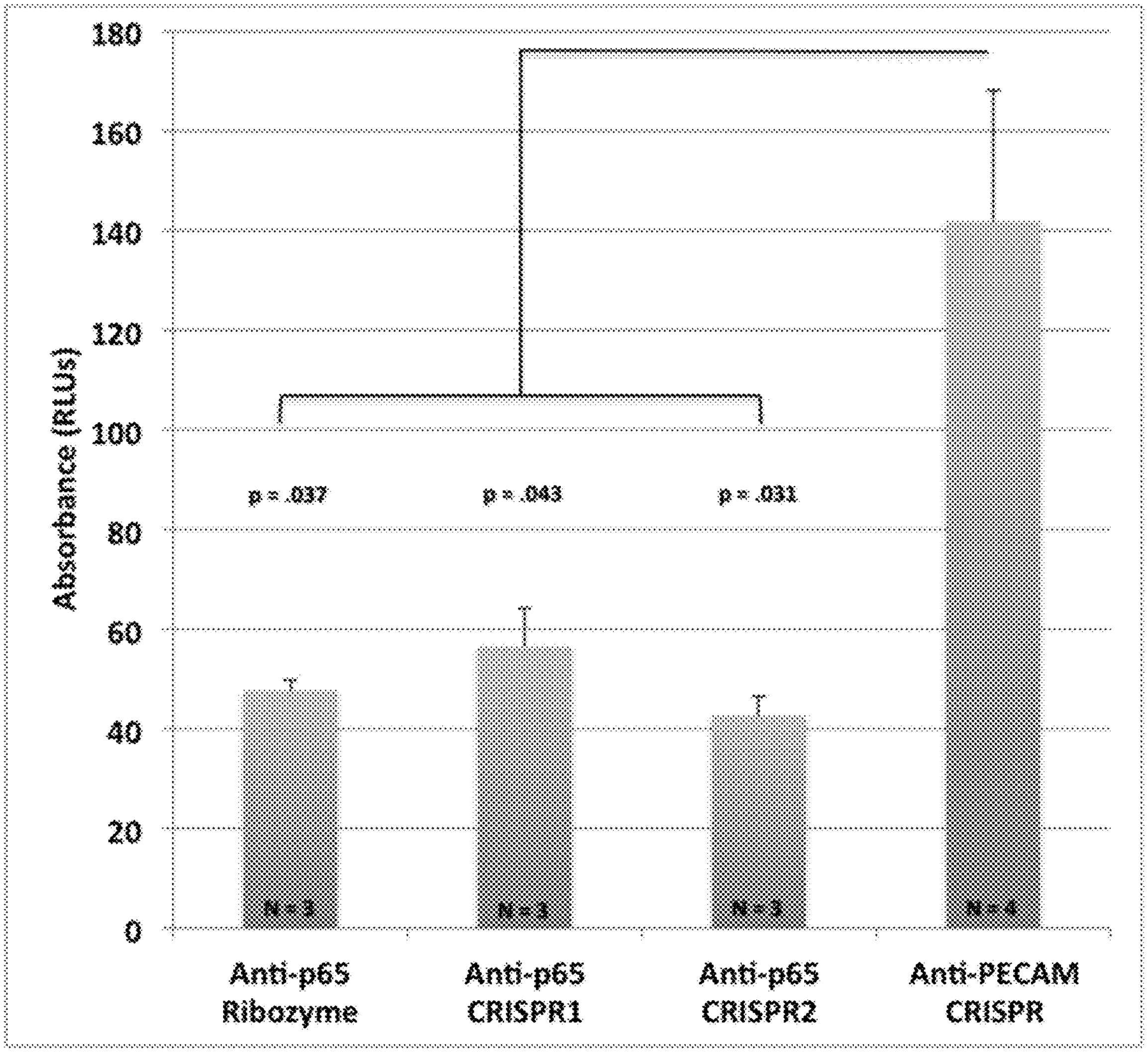

FIG. 9 shows anti-p65 CRISPR/Cas9- and anti-p65 ribozyme-mediated knockdown of mouse NFkB-p65 protein 8 days and 1 day, respectively, after IV injection in mice.

Figure 10:
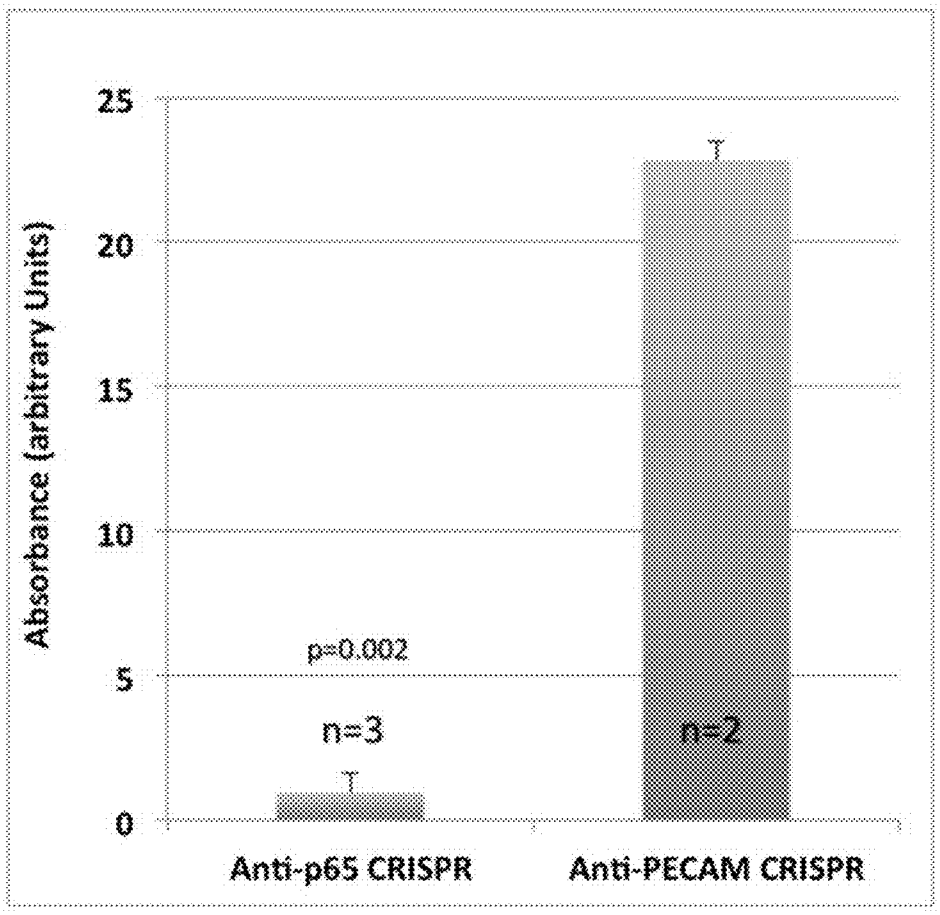

FIG. 10 shows anti-p65 CRISPR-mediated knockdown of mouse NFkB-p65 protein 13 days after IV injection.

Figure 11:
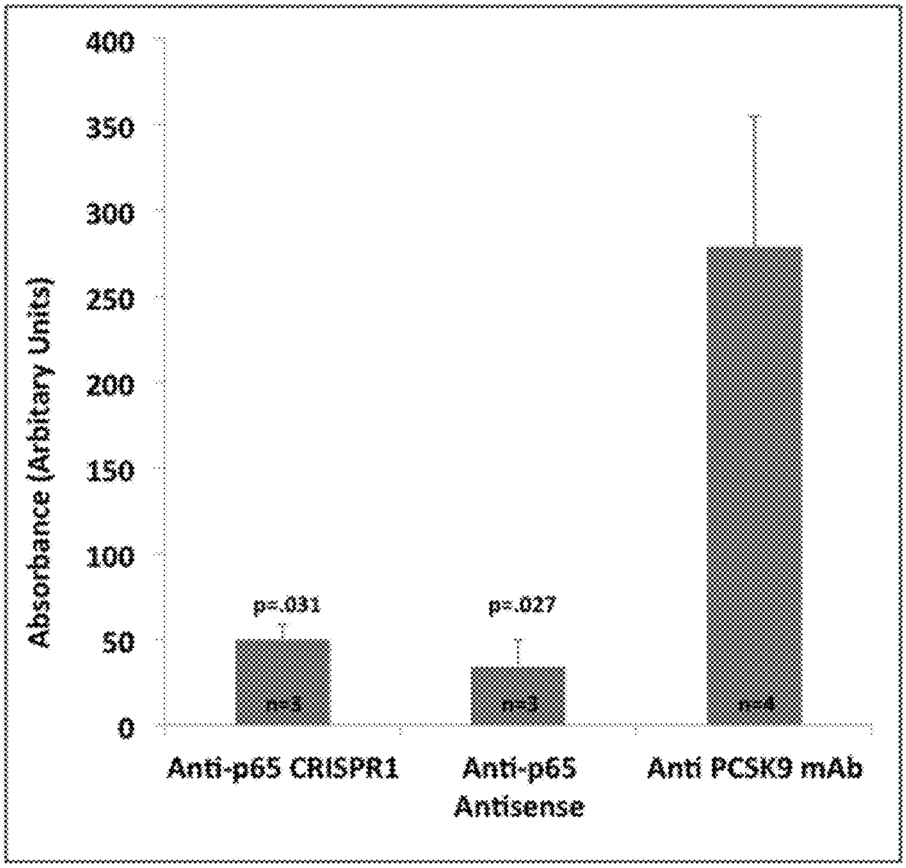

FIG. 11 shows anti-p65 CRISPR and anti-p65 antisense-mediated knockdown of mouse NFkB-p65 protein 13 days and 1 day, respectively, after IV injection in mice.

Figure 12:
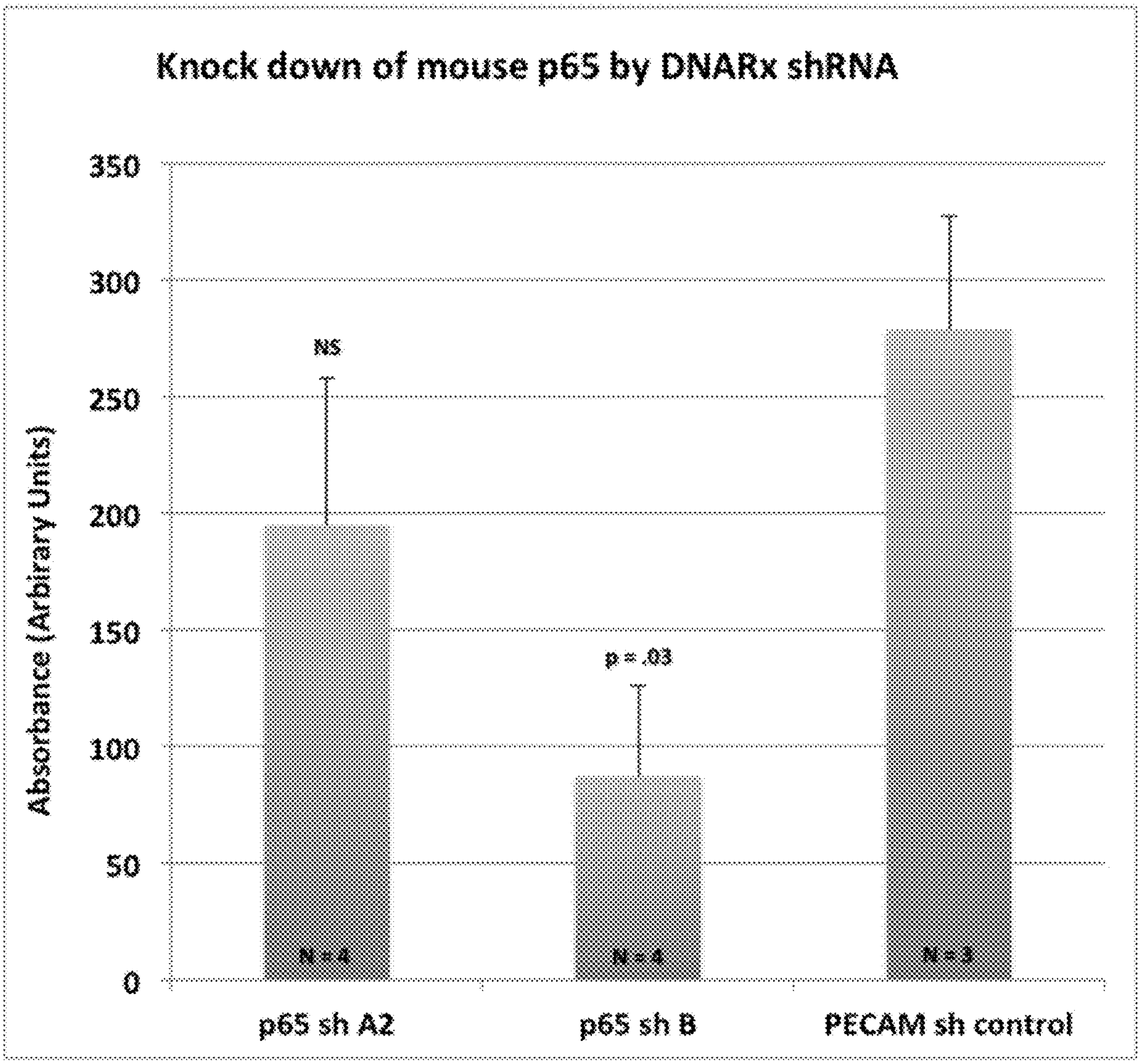

FIG. 12 shows anti-p65 shRNA-mediated knockdown of mouse NFkB-p65 protein 1 day after IV injection in mice.

FIG. 13 shows a ribozyme anti-p65 plasmid (SEQ ID NO:7).

FIG. 14 shows a CRISPR1 anti-p65 plasmid (SEQ ID NO:8).

FIG. 15 shows a CRISPR2 anti-p65 plasmid (SEQ ID NO:9).

FIG. 16 shows a CRISPR anti-p65 plasmid (SEQ ID NO:10).

Figure 17A:
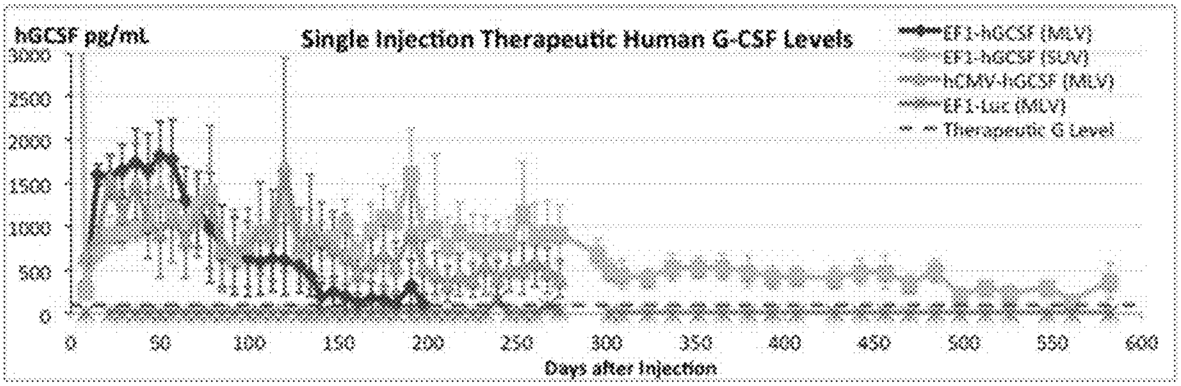
Figure 17B:
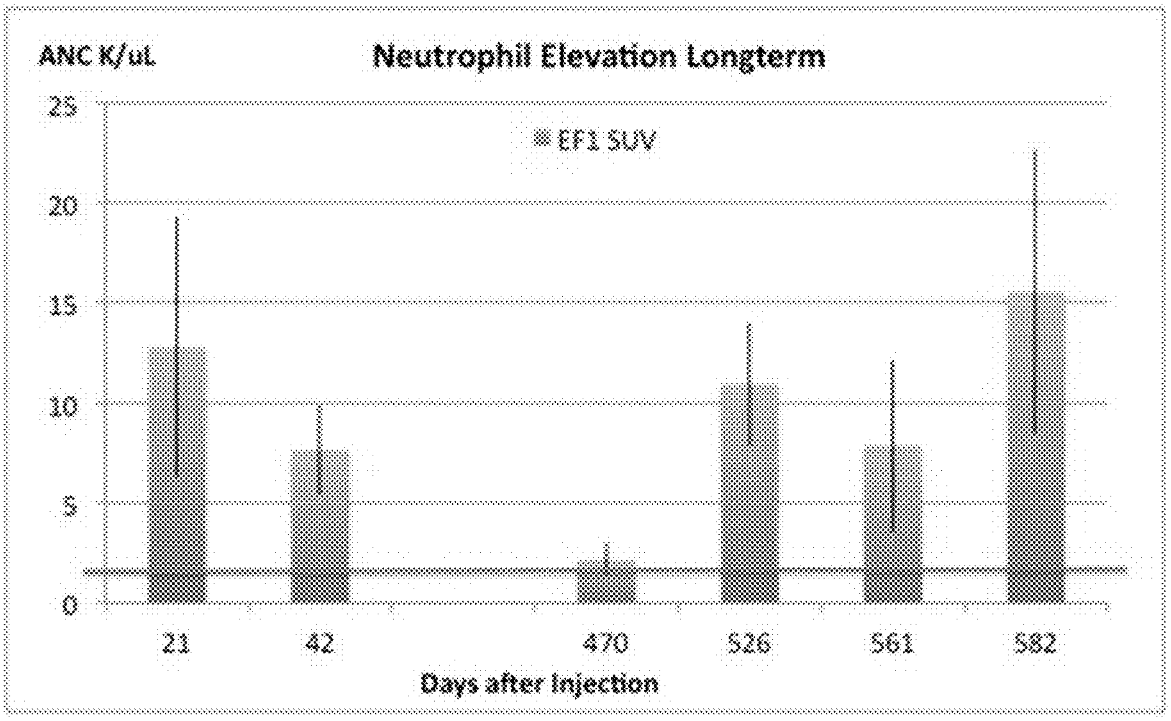

FIGS. 17A-B show results of Example 3 which describes experiments conducted that demonstrate a single IV, sequential injection of cationic liposomes followed up by a plasmid DNA vector encoding the human G-CSF gene produces supra-therapeutic human G-CSF serum protein levels (FIG. 17A) and elevated absolute neutrophil counts (ANC) above normal ANC levels (blue line) (FIG. 17B) for at least the next 582 days in mice.

Figure 18:
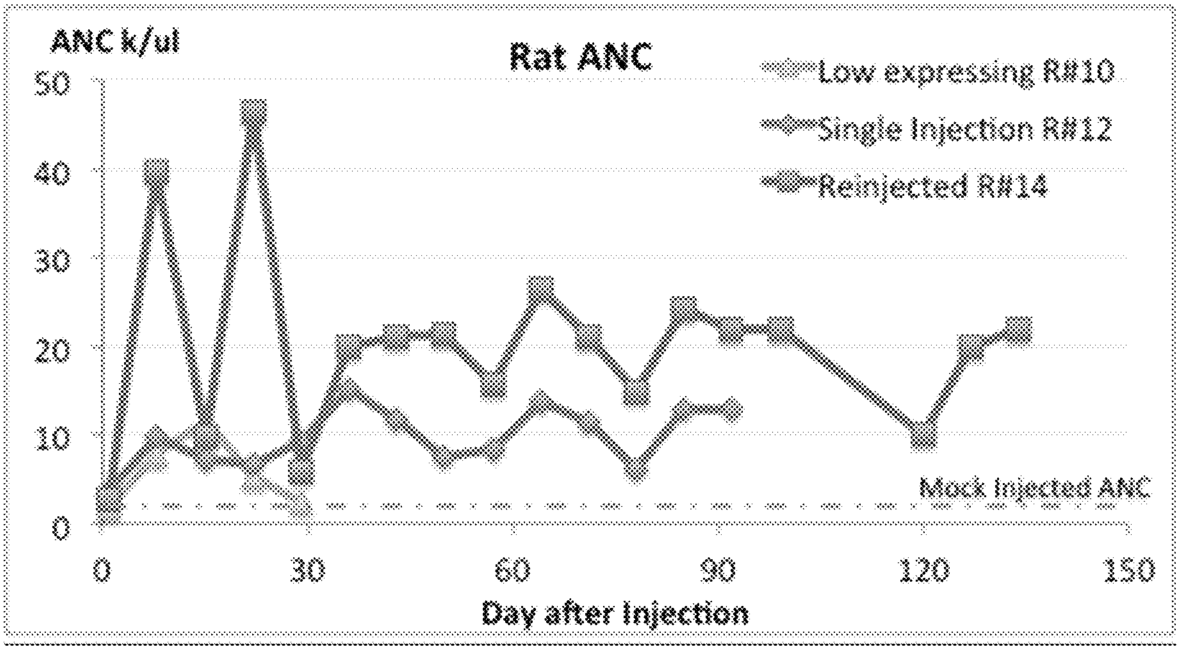

FIG. 18 shows neutrophil elevation in rat serum following sequential IV injections of DOTAP cationic liposomes followed by plasmid DNA encoding HG-CSF.

FIG. 19 shows the plasmid sequence for Anti-p65 antisense plasmid (SEQ ID NO:11).

FIG. 20 shows the plasmid sequence for an anti-mouse NFkB-p65 shRNA vector p65 shB (FIG. 20, SEQ ID NO:12).

Figure 21:
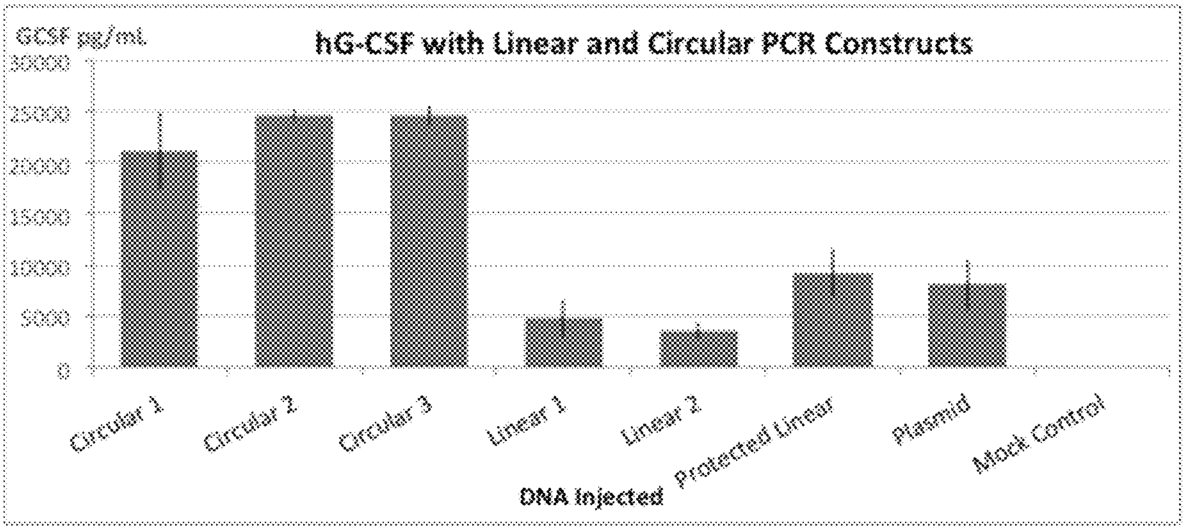

FIG. 21 shows levels of human G-CSF in mouse serum, 24 hours after sequential IV injection of 1050 nmoles of DOTAP cationic liposomes, followed by 70 ug of either HG-CSF plasmid- or different forms of PCR generated, HG-CSF expression cassette DNA.

Figure 22:
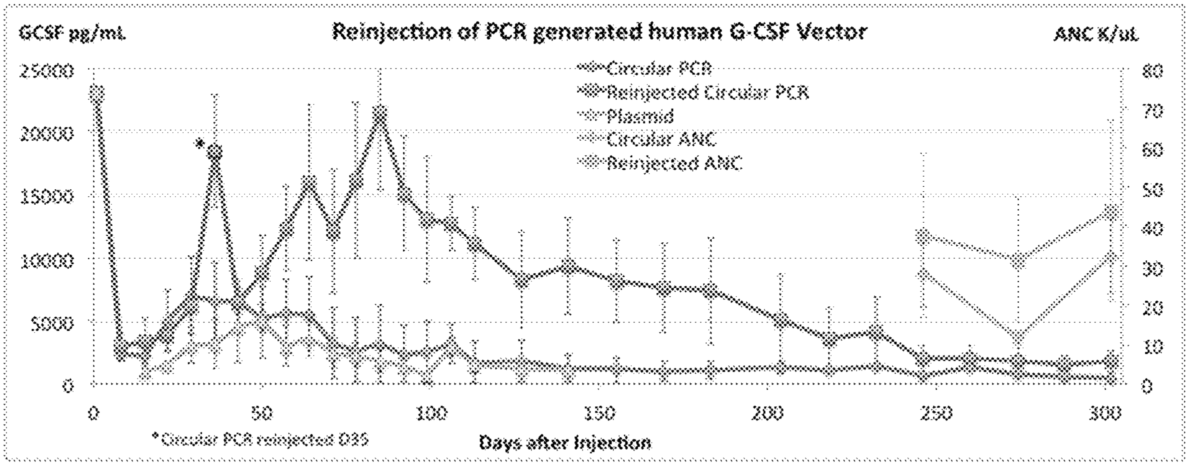

FIG. 22 shows levels of human G-CSF in mouse serum or plasma (left axis) and thousands per microliter absolute neutrophil counts (ANC) in whole blood (right axis) in mice for at least the next 302 days after initial injection.

Figure 23:
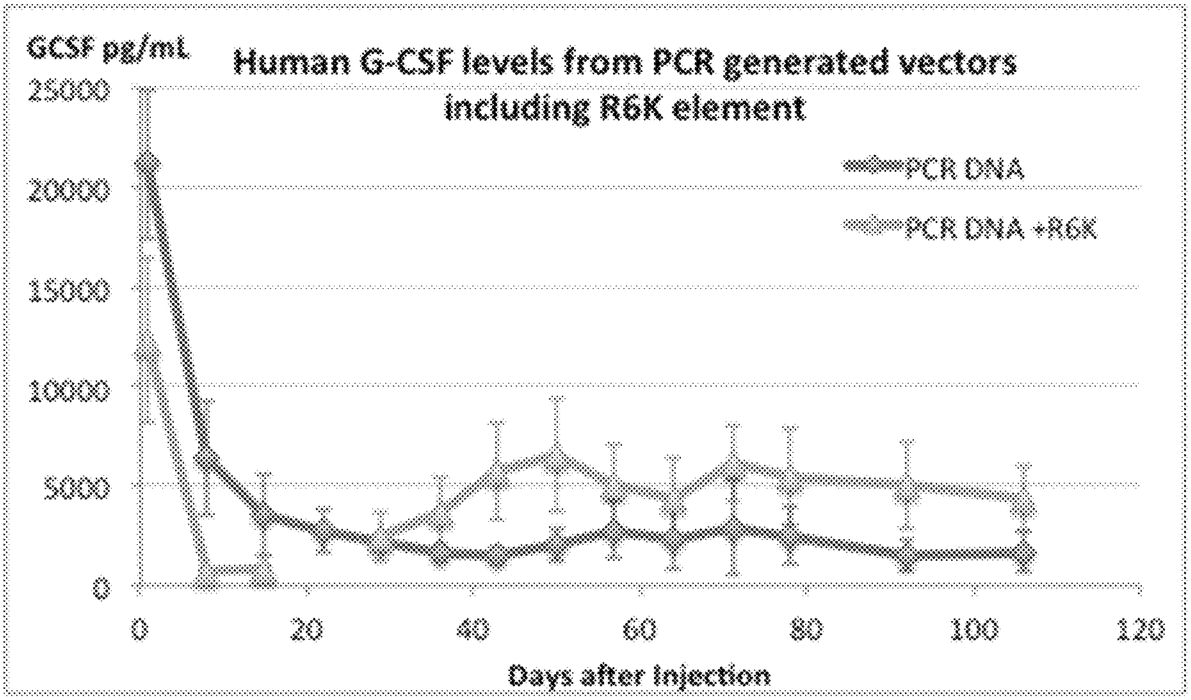

FIG. 23 shows human G-CSF levels in mouse serum for 106 days following one sequential injection of cationic liposomes followed by PCR generated DNA with or without an R6K origin of replication.

Figure 24:
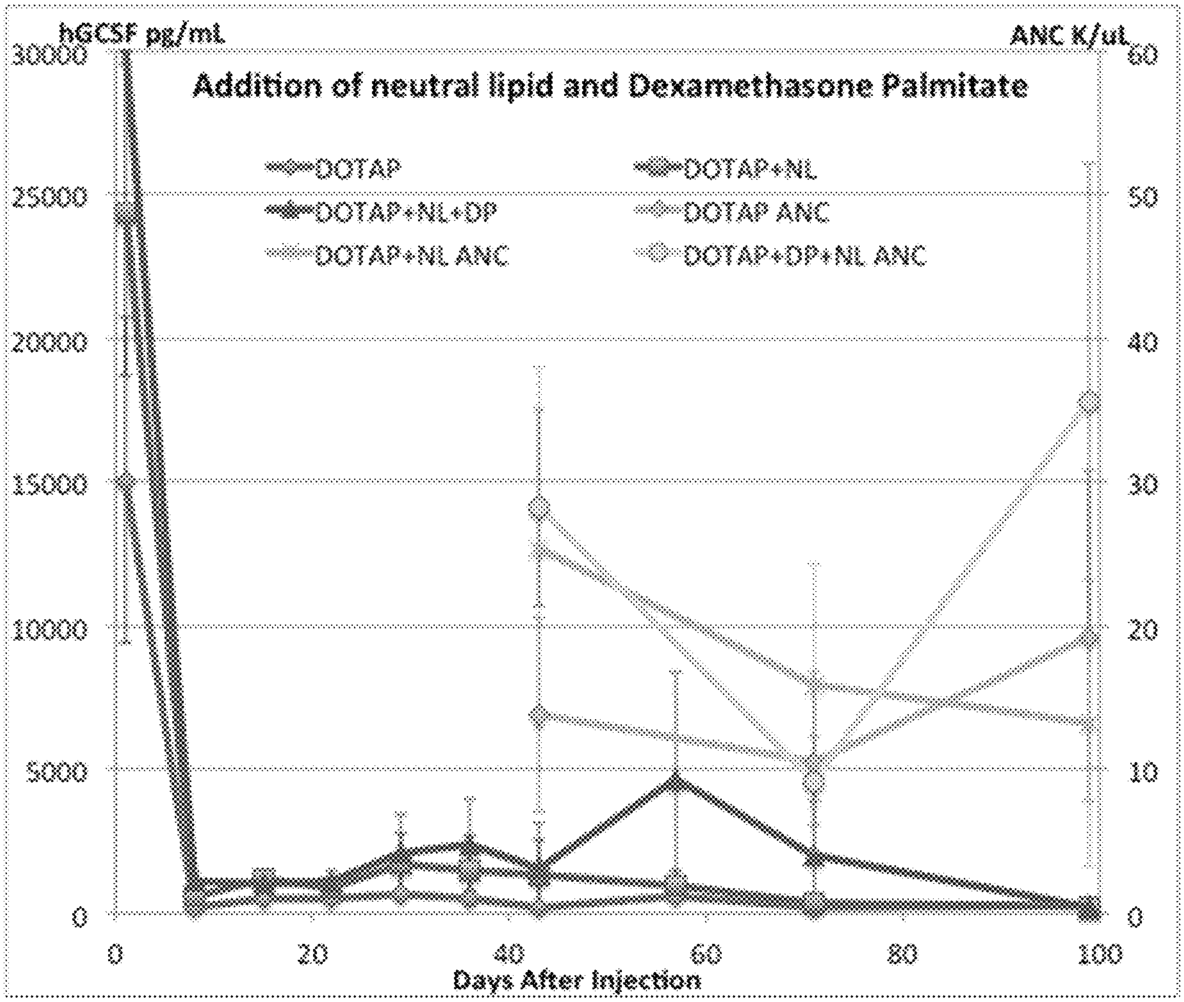

FIG. 24 shows human G-CSF and corresponding absolute neutrophil counts (ANC, right axis) levels in mice injected sequentially with cationic liposomes with or without neutral lipids or dexamethasone palmitate, followed by plasmid DNA.

Figure 25:
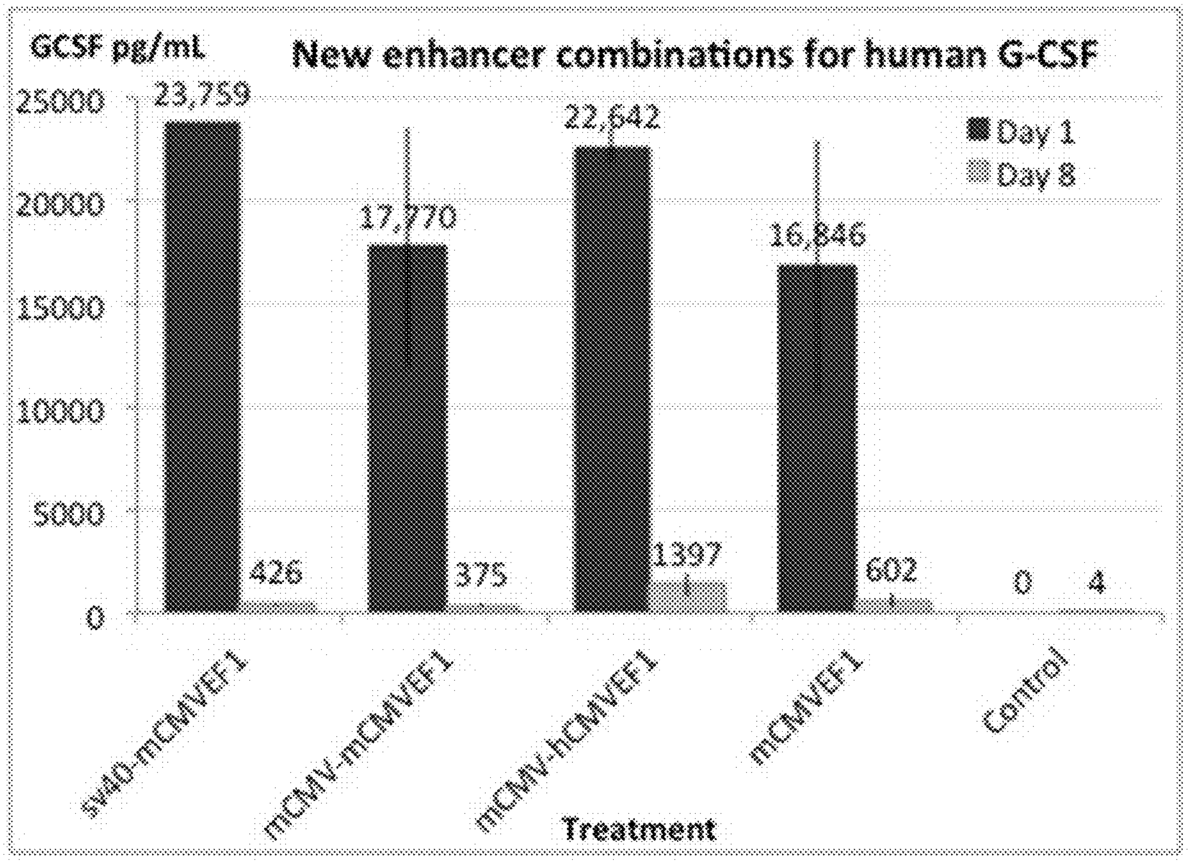

FIG. 25 shows the results of Example 6, which shows that use of an second enhancer increases increase human G-CSF expression in mice 1 and 8 days after sequential IV injection.

FIG. 26 shows the nucleic acid sequence of plasmid sv40-mCMVEF1 (SEQ ID NO:13).

FIG. 27 shows the nucleic acid sequence of plasmid mCMV-mCMVEF1 (SEQ ID NO:14).

FIG. 28 shows the nucleic acid sequence of plasmid mCMV-hCMVEF1 (SEQ ID NO:15).

FIG. 29 shows the nucleic acid sequence of plasmid mCMVEF1 (SEQ ID NO:16).

Figure 30:
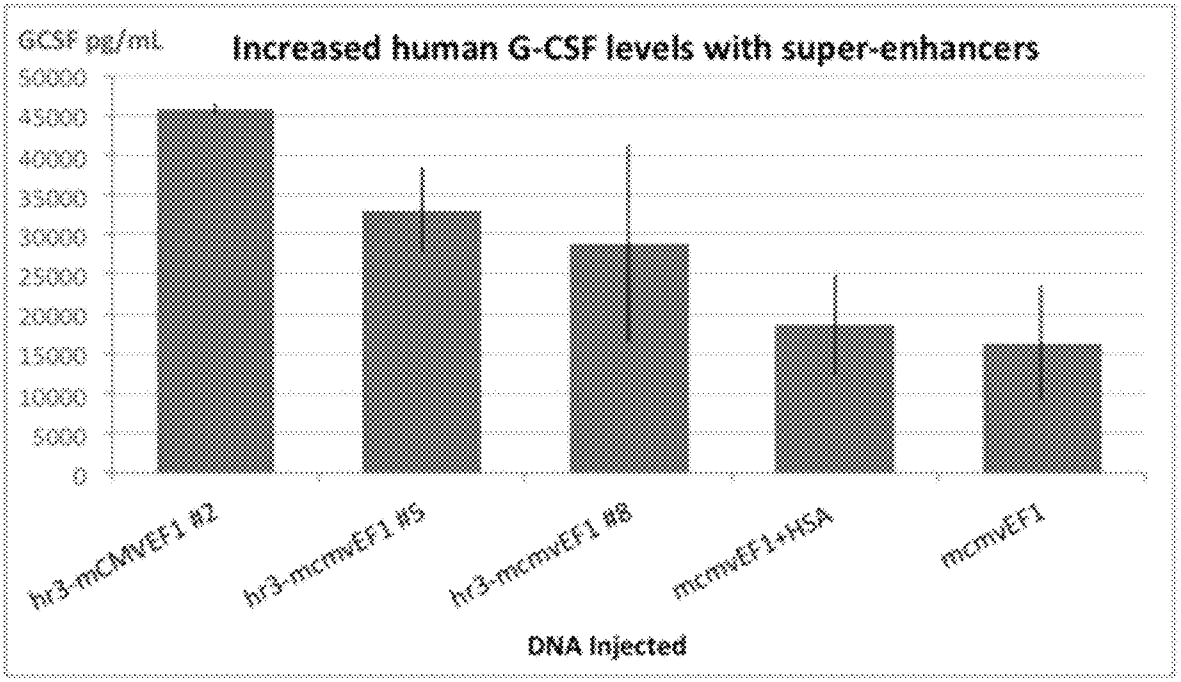

FIG. 30 shows mouse serum levels of human G-CSF, 24 hours after sequential IV injection of liposomes followed by plasmid DNA (first three groups in figure contain super-enhancer elements).

FIG. 31 shows the nucleic acid sequence of plasmid hr3-mCMVEF1 #2 (SEQ ID NO:17).

FIG. 32 shows the nucleic acid sequence of plasmid hr3-mcmvEF1 #5 (SEQ ID NO:18).

FIG. 33 shows the nucleic acid sequence of plasmid hr3-mcmvEF1 #18 (SEQ ID NO:19).

Figure 34:
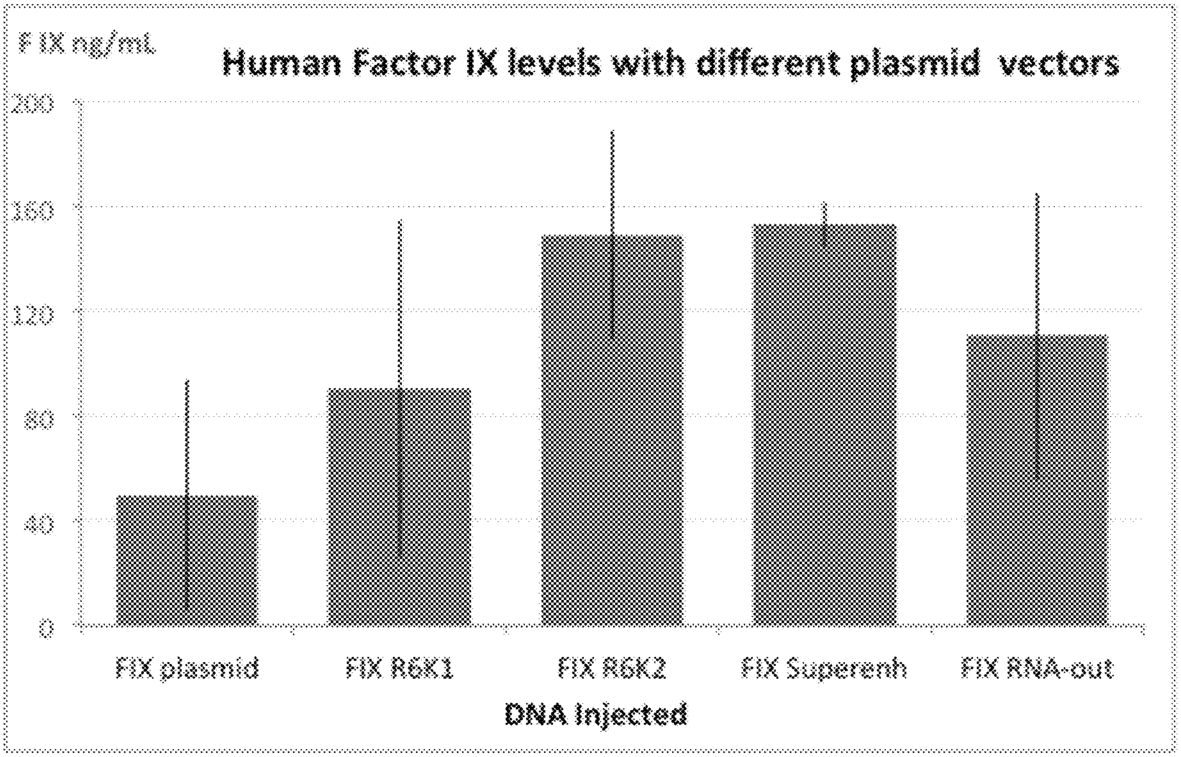

FIG. 34 shows plasma concentration of human Factor IX at 24 hrs after sequential IV injection of liposomes and various different FIX DNA expression plasmids.

FIG. 35 shows the nucleic acid sequence of FIX plasmid (SEQ ID NO:20).

FIG. 36 shows the nucleic acid sequence of FIX R6K1 (SEQ ID NO:21).

FIG. 37 shows the nucleic acid sequence of FIX R6K2 (SEQ ID NO:22).

FIG. 38 shows the nucleic acid sequence of FIX Superenh (SEQ ID NO:23).

FIG. 39 shows the nucleic acid sequence of FIX RNA-out (SEQ ID NO:24).

Figure 40:
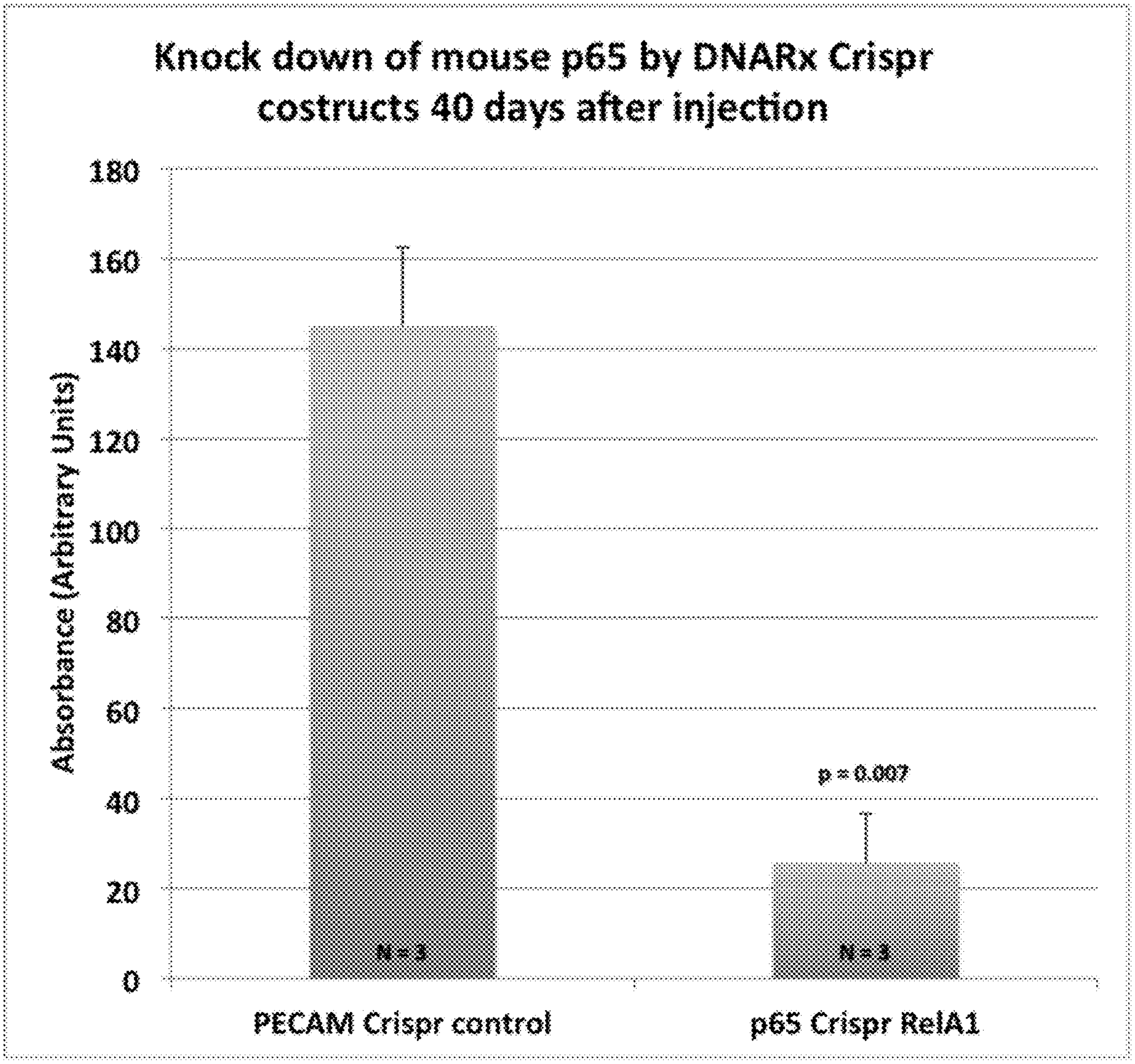

FIG. 40 shows anti-p65 CRISPR/Cas9-mediated knockdown of mouse NFkB-p65 protein 40 days after sequential IV injection in mice.

Figure 41A:
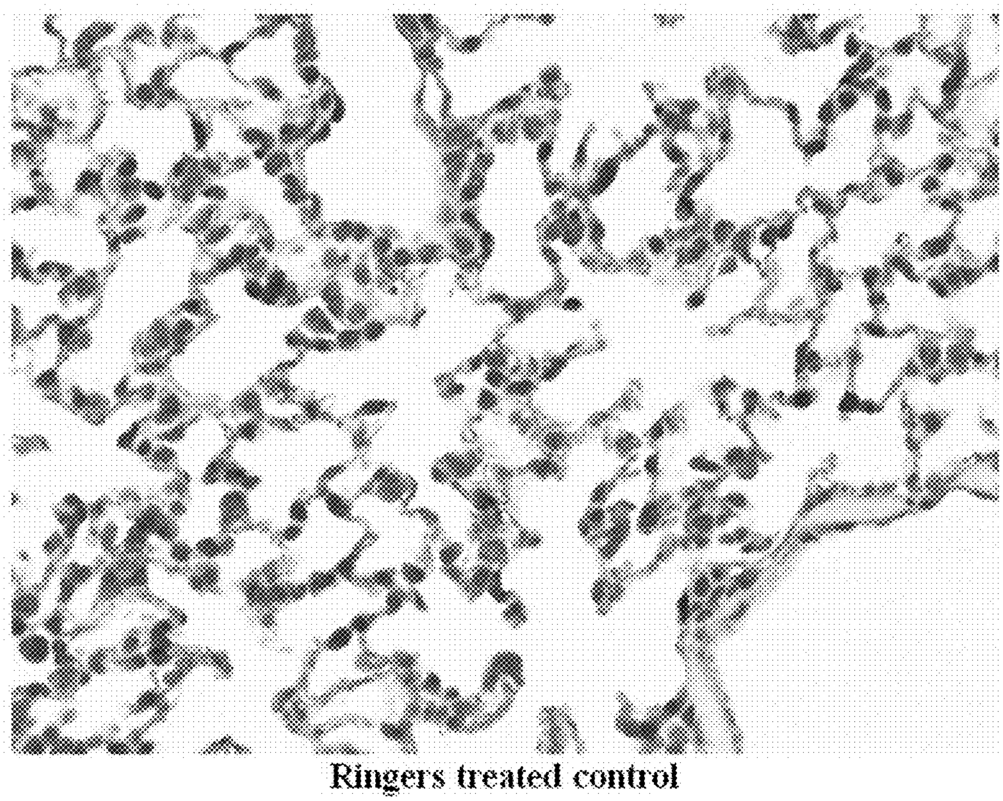
Figure 41B:
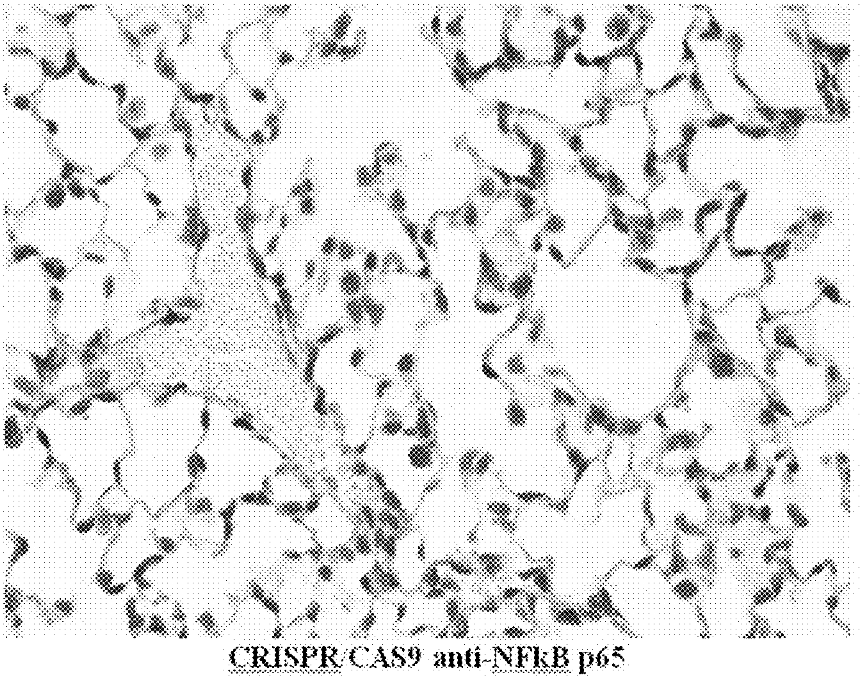

FIGS. 41A-B show immunohistochemistry stained slides from experiments on mice with one sequential IV injection of a CRISPR/Cas9 anti-NFkB p65 plasmid DNA vector. FIG. 41A shows ringers treated control, and FIG. 41B shows the CRISPR/Cas9 anti-NFkB p65 treated mouse tissue.

Figure 42A:
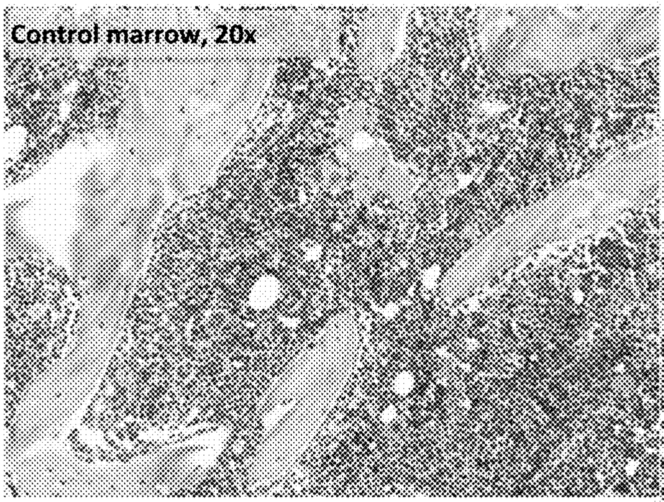
Figure 42B:
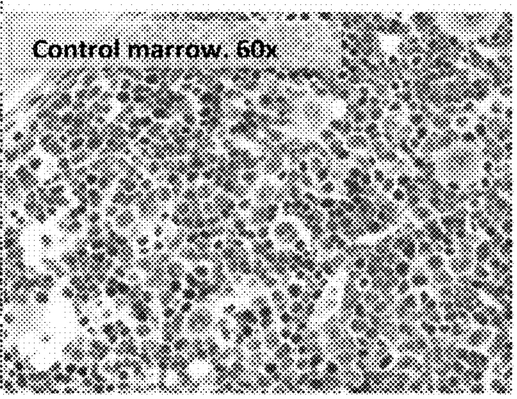
Figure 42C:
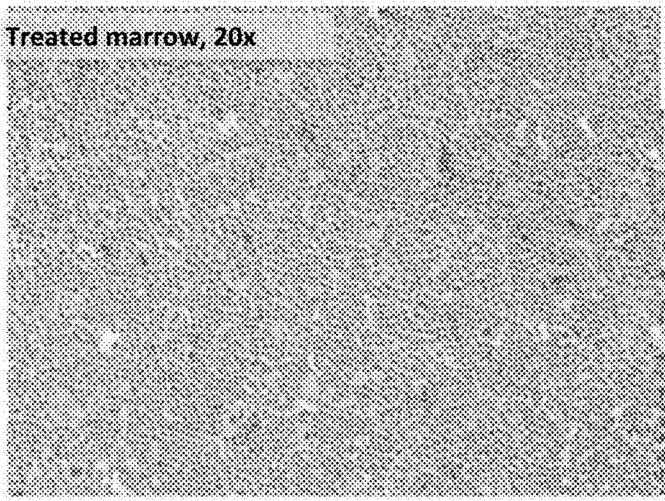
Figure 42D:
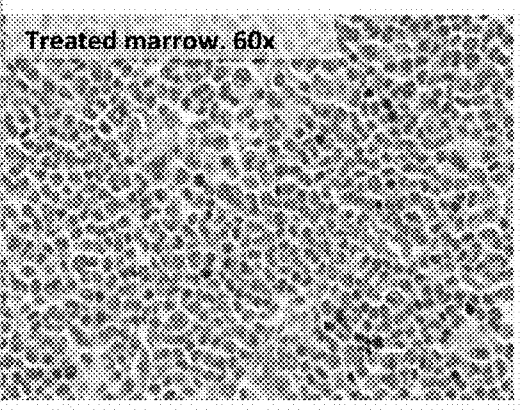

FIGS. 42A-D show IHC results in bone marrow of control and treated mouse 582 days after a single sequential IV injection of cationic liposomes, then an HG-CSF DNA expression vector. FIGS. 42A (20×) and 42B (60×), control bone marrow, show a diverse mix of cell types surround bony trabeculae of normal femoral medullary cavity, with dark-staining erythoid cells particularly obvious. FIGS. 42C (20×) and 42D (60×), treated bone marrow, show a monotonous nearly solid sheet of pale-staining cells replace bony trabecular elements in femoral marrow pale staining myeloid lineage cells (polymorphonuclear leukocytes) with oval, indented oval, band and segmented forms replace most other cell types within femoral marrow.

Figure 43A:
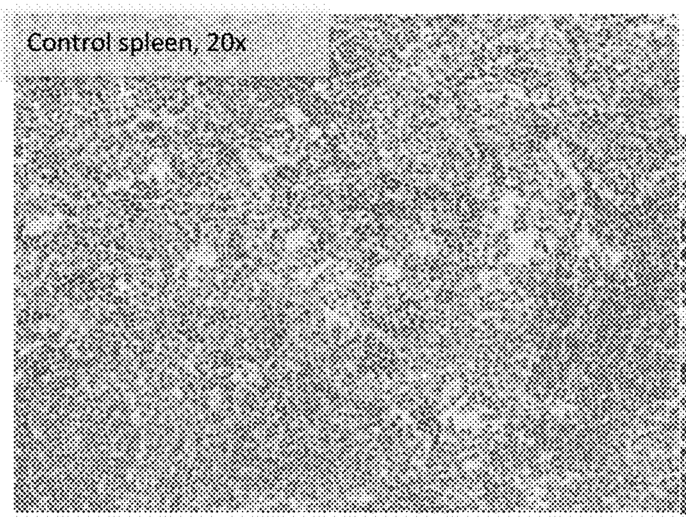
Figure 43B:
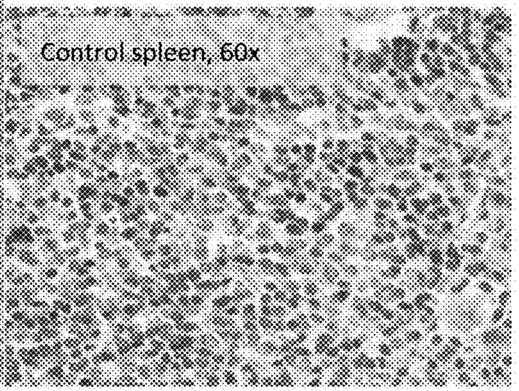
Figure 43C:
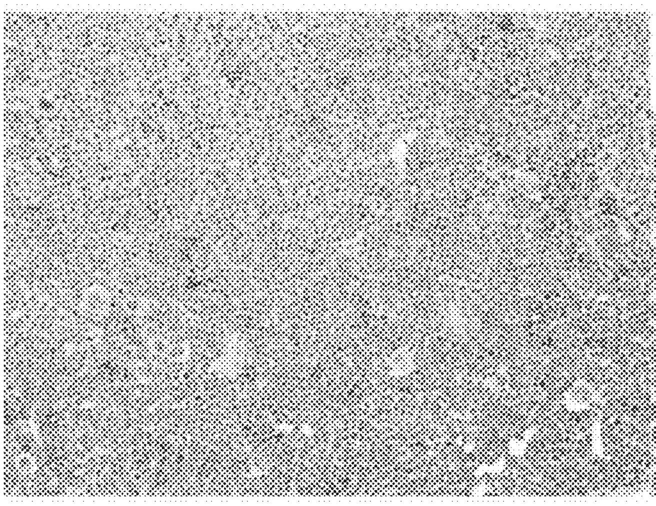
Figure 43D:
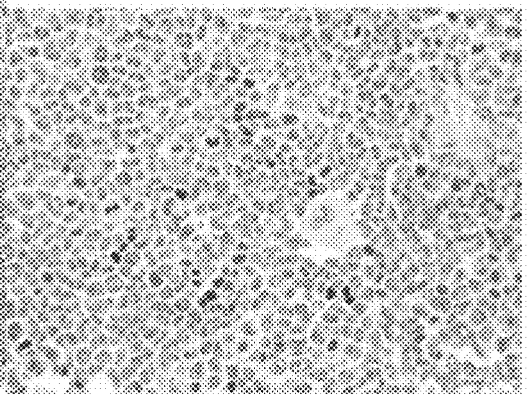

FIGS. 43A-D show IHC results in spleen tissue of control and treated mouse 582 days after a single sequential IV injection of cationic liposomes, then an HG-CSF DNA expression vector. FIGS. 43A (20×) and 43B (60×), control spleens, show red/dark portions of white (lymphoid) pulp of normal spleen showing diverse cell population. FIGS. 43C (20×) and 43D (60×), treated spleen, show pale-staining myeloid lineage cells (polymorphonuclear leukocytes) with oval, indented oval, band and segmented forms replace most other cell types.

Figure 44A:
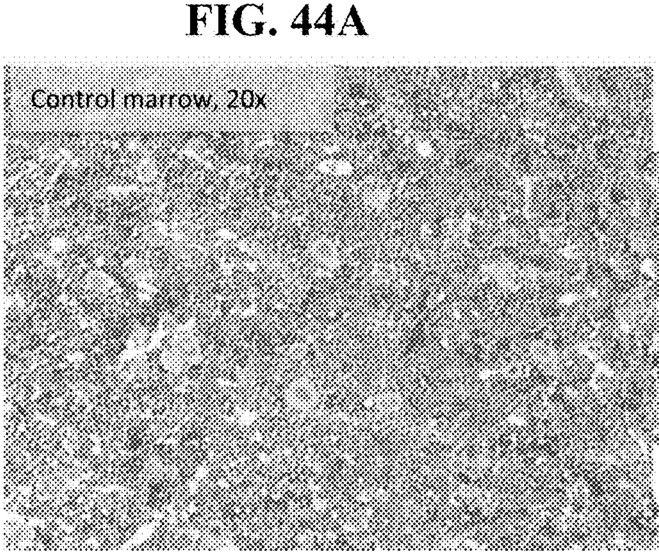
Figure 44B:
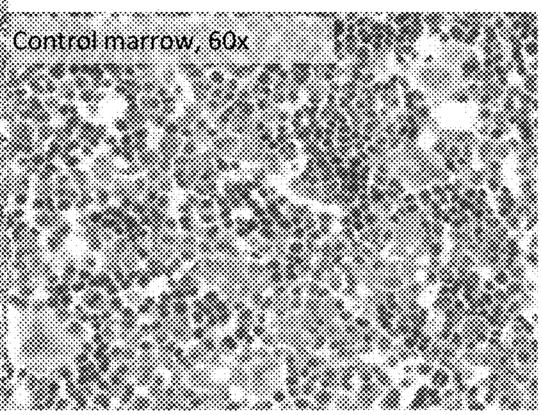
Figure 44C:
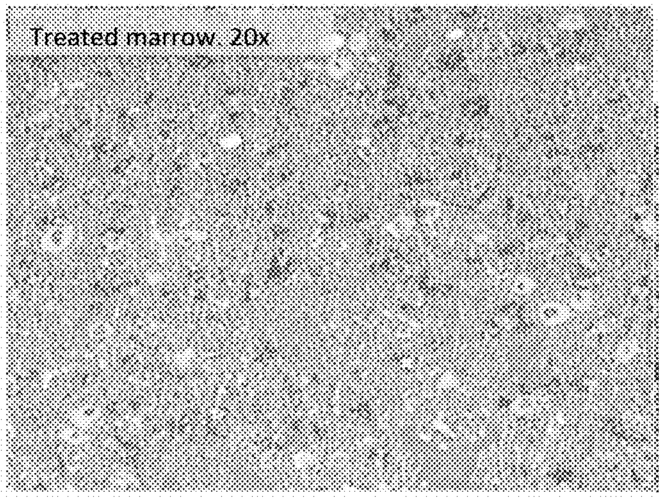
Figure 44D:
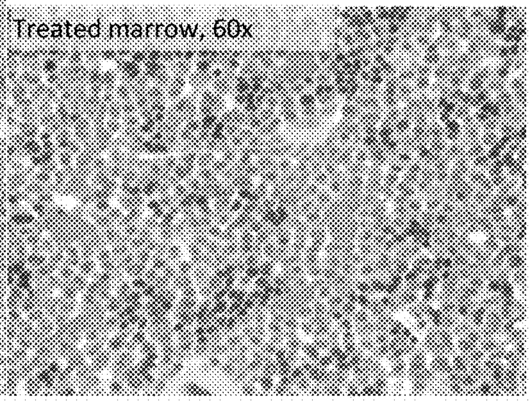

FIGS. 44A-D show IHC results in bone marrow tissue of control and treated rat 168 days after last sequential IV injection of cationic liposomes, then an HG-CSF DNA. FIGS. 44A (20×) and 42B (60×), control bone marrow, show a diversity of cell types with round, dark staining erythroid lineage particularly obvious in femoral marrow. FIGS. 44C (20×) and 44D (60×), treated bone marrow, show pale staining myeloid lineage cells (polymorphonuclear leukocytes) with oval, indented oval, band and segmented forms predominate in femoral marrow. A few clusters of dark-staining erythroid lineage cells remain.

Figure 45A:
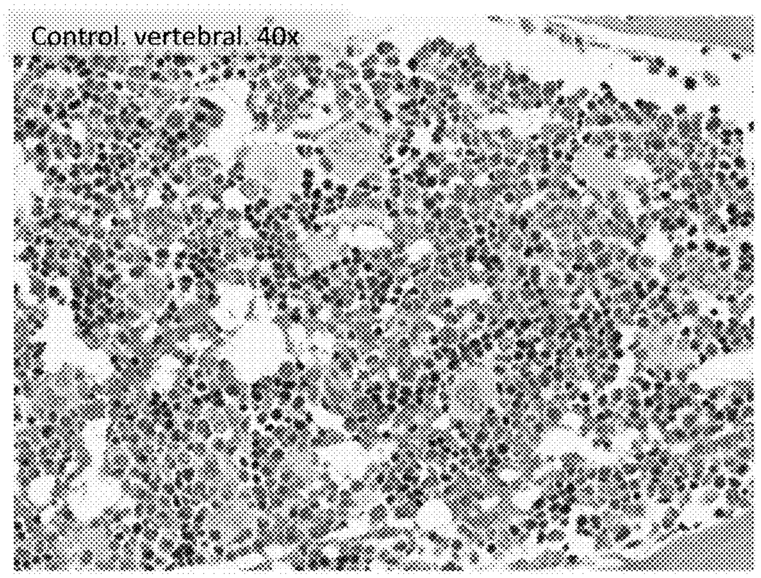
Figure 45B:
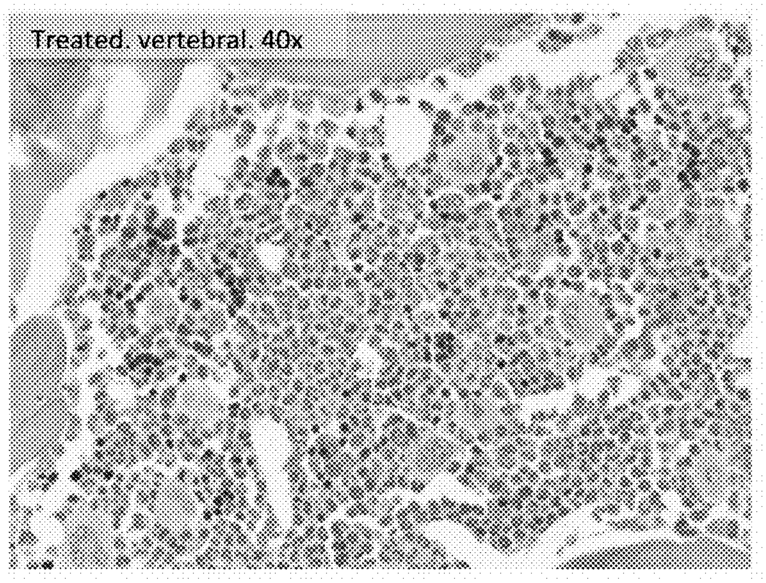

FIGS. 45A-B. FIG. 45A, from the same experiment as FIG. 44, shows control rat, vertebral body at 40×, while FIG. 45B shows the HGCSF rat vertebral body at 40×.

FIG. 46 shows the nucleic acid sequence of plasmid DNARx-31H4-2A (SEQ ID NO:25) which encodes anti-PCSK9 mAb heavy and light chain cDNAs separated by a 2A self-cleaving peptide.

FIG. 47 shows the nucleic acid sequence of plasmid DNARx-31H4 (SEQ ID NO:26) which is a dual expression cassette plasmid vector that encodes a different versions of anti-PCSK9 mAb heavy and light chain cDNA.

FIG. 48 shows the nucleic acid sequence of plasmid DNARx-21B12 (P2A) (SEQ ID NO:27) which encodes anti-PCSK9 mAb heavy and light chain cDNAs separated by a 2A self-cleaving peptide.

FIG. 49 shows the nucleic acid sequence of plasmid DNARx-21B12 (SEQ ID NO:28) which is a dual expression cassette plasmid vector that encodes different versions of anti-PCSK9 mAb heavy and light chain cDNAs.

FIG. 50 shows the nucleic acid sequence of plasmid DNARx-CD47-2A (P2A) (SEQ ID NO:29) which encodes anti-CD47 mAb heavy and light chain cDNAs separated by a 2A self-cleaving peptide.

FIG. 51 shows the nucleic acid sequence of plasmid DNARx-CD47 (SEQ ID NO:30) which is a dual expression cassette plasmid vector that encodes the anti-CD47 mAb heavy and light chain cDNAs respectively.

FIG. 52 shows the nucleic acid sequence of plasmid DNARx-D8-2A (SEQ ID NO:31).

FIG. 53 shows the nucleic acid sequence of plasmid DNARx-F10-2A (SEQ ID NO:32).

FIG. 54 shows the nucleic acid sequence of plasmid DNARx-A66-2A (P2A) (SEQ ID NO:33).

FIG. 55 shows the nucleic acid sequence of plasmid DNARx-D8 (SEQ ID NO:34).

FIG. 56 shows the nucleic acid sequence of plasmid DNARx-F10 (SEQ ID NO:35).

FIG. 57 shows the nucleic acid sequence of plasmid DNARx-A66 (SEQ ID NO:36).

FIG. 58 shows the nucleic acid sequence of plasmid DNARx-HA-MITD (SEQ ID NO:37).

FIG. 59 shows the nucleic acid sequence of plasmid DNARx-SEC-partial HA-MITD (SEQ ID NO:38).

FIG. 60 shows the nucleic acid sequence of plasmid DNARx-D8-2A-HA-MITD (SEQ ID NO:39).

FIG. 61 shows the nucleic acid sequence of plasmid DNARx-F10-2A-HA-MITD (SEQ ID NO:40).

FIG. 62 shows the nucleic acid sequence of plasmid DNARx-A66-2A-HA-MITD (SEQ ID NO:41).

FIG. 63 shows the nucleic acid sequence of plasmid DNARx-D8-2A-SEC-partial-HA-MITD (SEQ ID NO:42).

FIG. 64 shows the nucleic acid sequence of plasmid DNARx-F10-2A-SEC-partial-HA-MITD (SEQ ID NO:43).

FIG. 65 shows the nucleic acid sequence of plasmid DNARx-A66-2A SEC-partial-MITD (SEQ ID NO:44).

FIG. 66 shows the nucleic acid sequence of plasmid 011215 #7 (SEQ ID NO:45).

FIG. 67 shows the nucleic acid sequence of plasmid 011315 #2 (SEQ ID NO:46).

FIG. 68 shows the nucleic acid sequence of plasmid 122014 #235 (SEQ ID NO:47).

FIG. 69 shows the nucleic acid sequence of plasmid DNARx-PD1-2A (P2A) (SEQ ID NO:48).

FIG. 70 shows the nucleic acid sequence of plasmid DNARx-SEC-OVA-MITD (SEQ ID NO:49).

FIG. 71 shows the nucleic acid sequence of plasmid DNARx-SEC-gp70-MITD (SEQ ID NO:50).

FIG. 72 shows the nucleic acid sequence of plasmid DNARx-PD1-2A OVA (SEQ ID NO:51).

FIG. 73 shows the nucleic acid sequence of plasmid DNARx-PD1-2A gp70 (SEQ ID NO:52).

FIG. 74 shows the nucleic acid sequence of plasmid DNARx CD20-2A Cas9 (SEQ ID NO:53).

FIG. 75 shows the nucleic acid sequence of plasmid DNARx CD20-2A HG-CSF (SEQ ID NO:54).

FIG. 76 shows the nucleic acid sequence of plasmid p65 shA2 (SEQ ID NO:55).

FIG. 77 shows the nucleic acid sequence of plasmid PECAM sh control is SEQ ID NO:56, FIG. 77.

Figure 78:
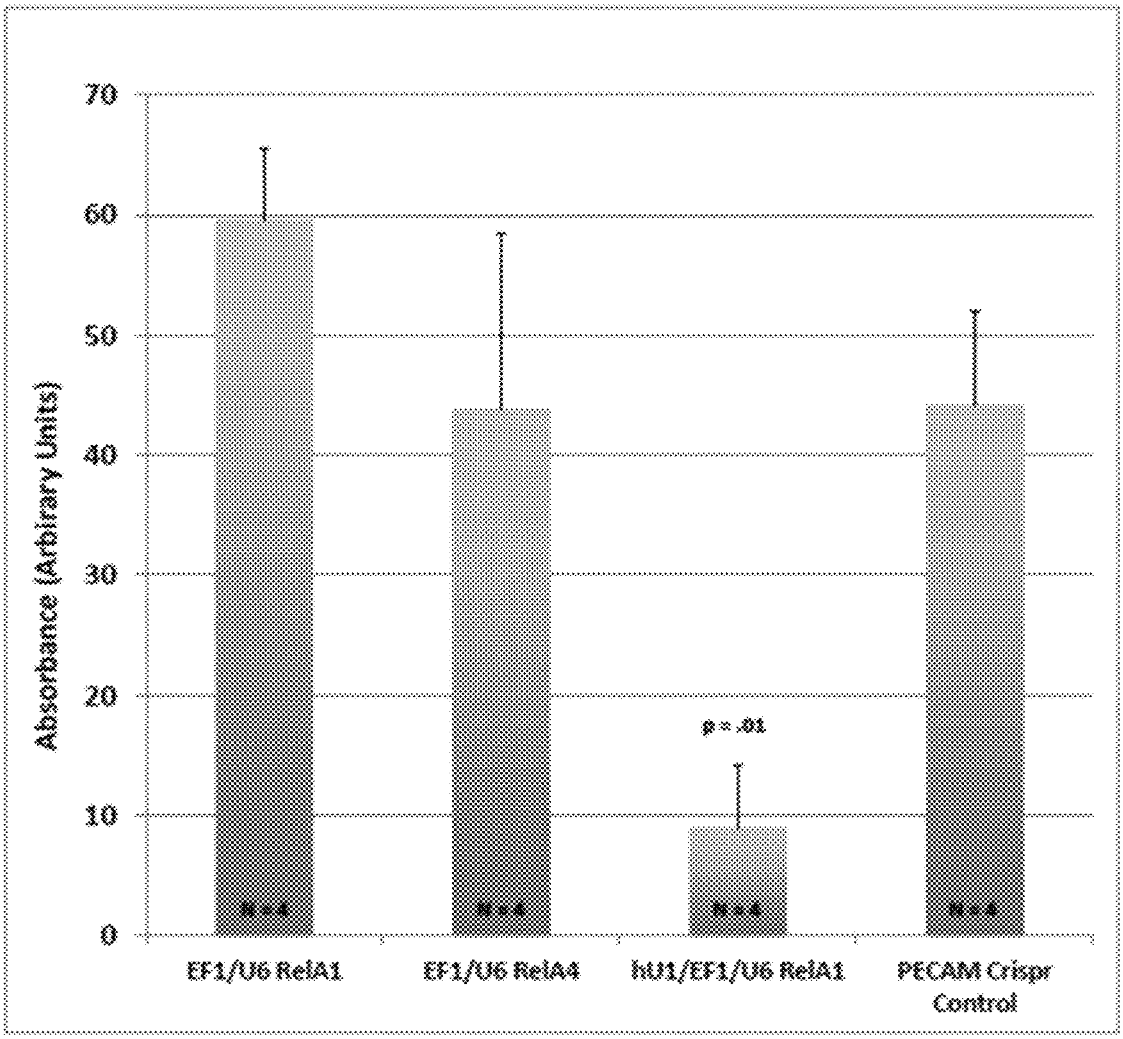

FIG. 78 shows anti-p65 CRISPR-mediated knockdown of mouse NFkB-p65 protein 10 days after IV injection.

FIG. 79 shows the nucleic acid sequence of plasmid EF1/U6 RelA1 (020117 #5) (SEQ ID NO:57).

FIG. 80 shows the nucleic acid sequence of plasmid EF1/U6 RelA4 (020117 #8) (SEQ ID NO:58).

FIG. 81 shows the nucleic acid sequence of plasmid hu1/EF1/U6 RelA1 (021417 #3) (SEQ ID NO:59).

Figure 82:
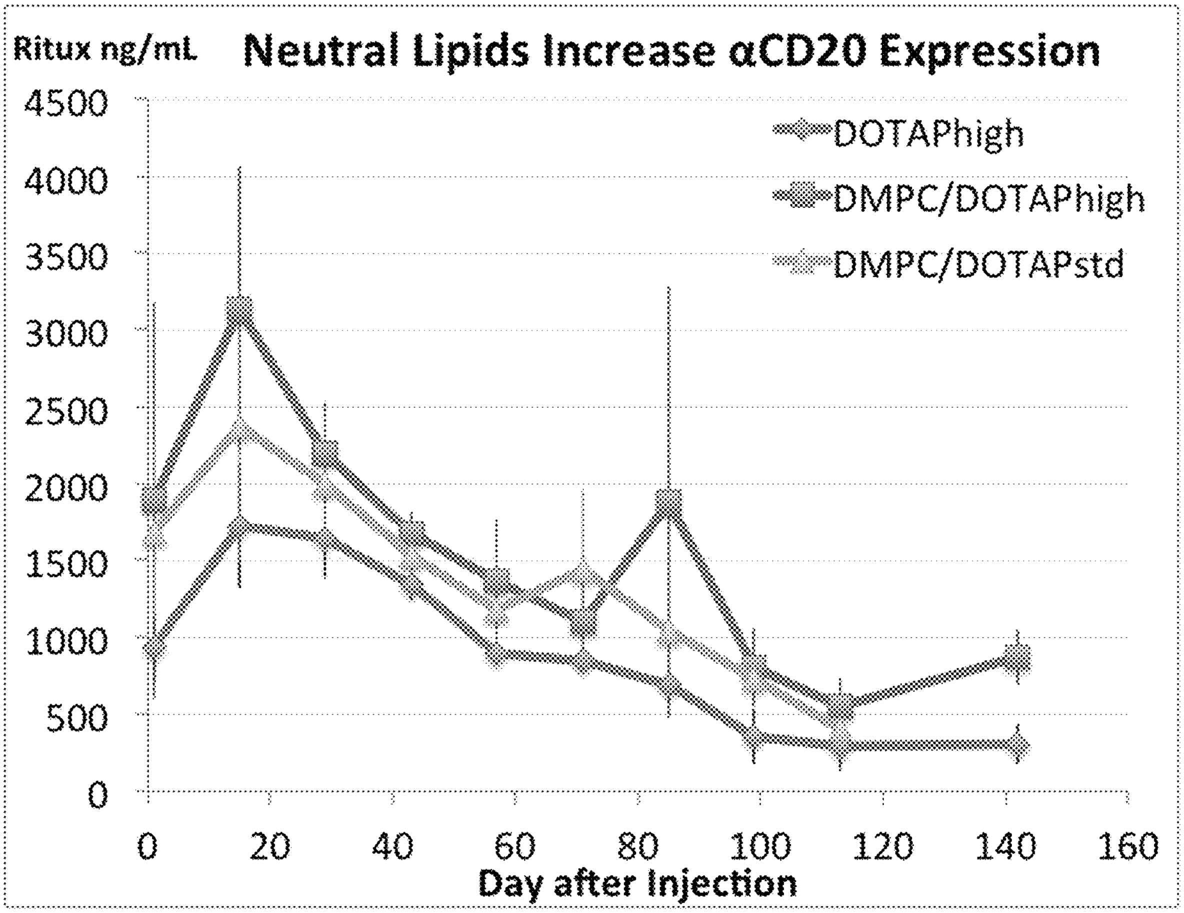

FIG. 82 shows results of Example 18, which describes how the inclusion of neutral lipids (DMPC) with cationic liposomes increases serum anti-CD20 monoclonal antibody levels in mice.

Figure 83:
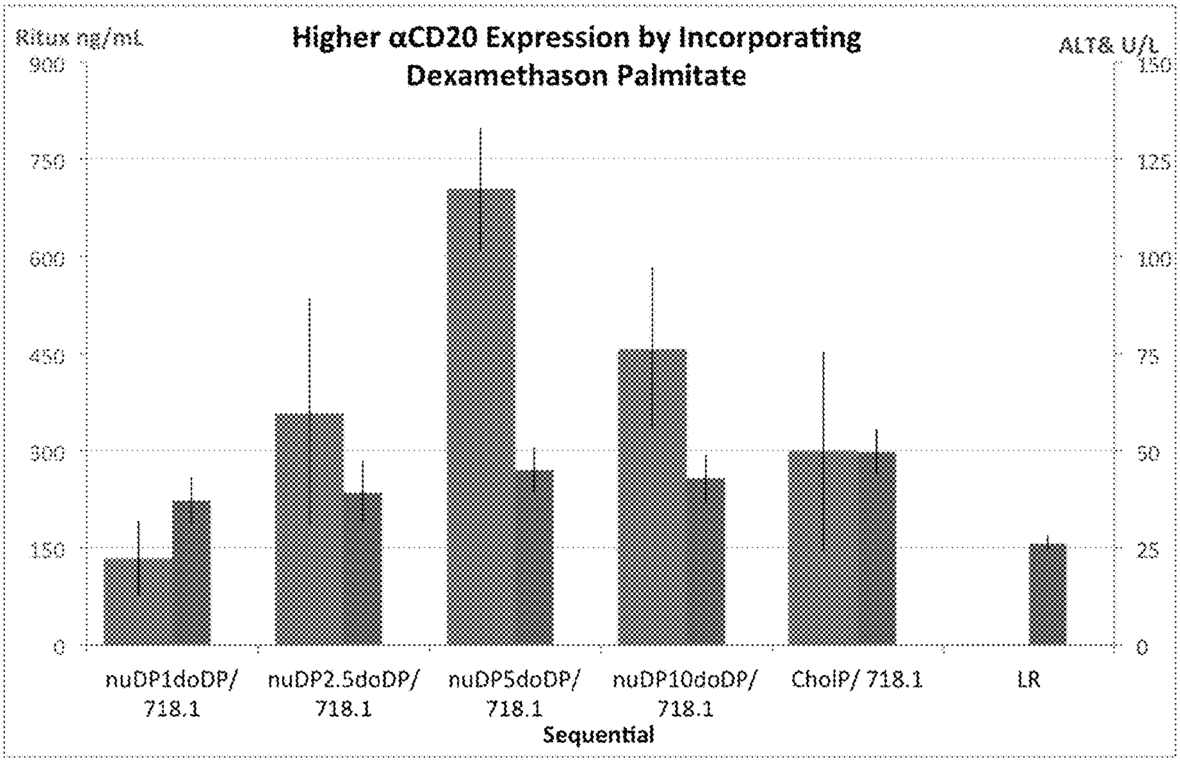

FIG. 83 shows results from Example 19, which describes that employing dexamethasone palmitate with neutral liposomes further increases gene expression in vivo.

Figure 84:
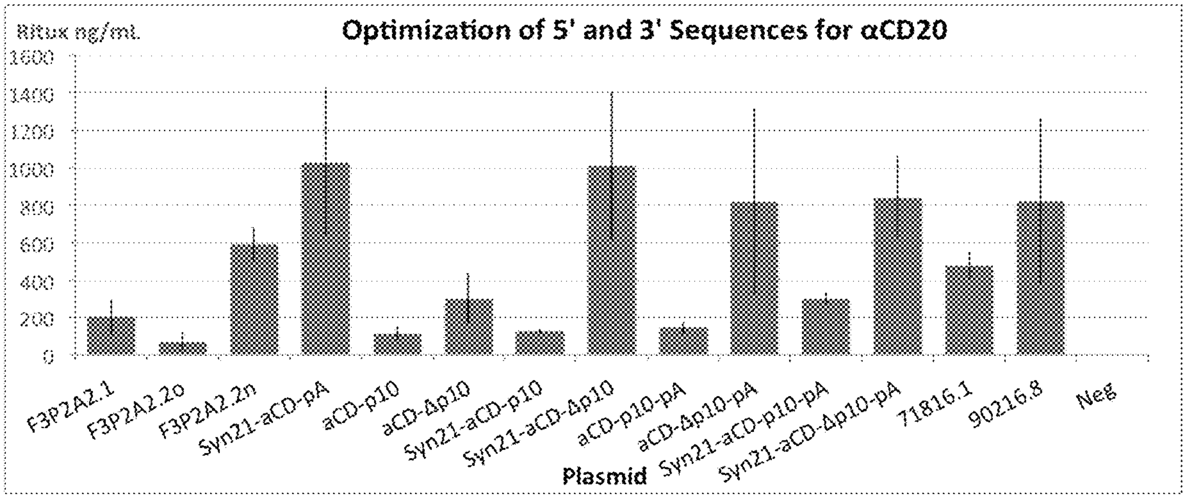

FIG. 84 shows results from Example 20, which describes how including Syn 21 and/or delta-p10 sequences into the vectors increases gene expression.

FIG. 85 shows the nucleic acid sequence of a vector construct that expresses anti-CD20 antibody, and includes Syn21 and delta-p10 sequence (SEQ ID NO:82).

Figure 86A:
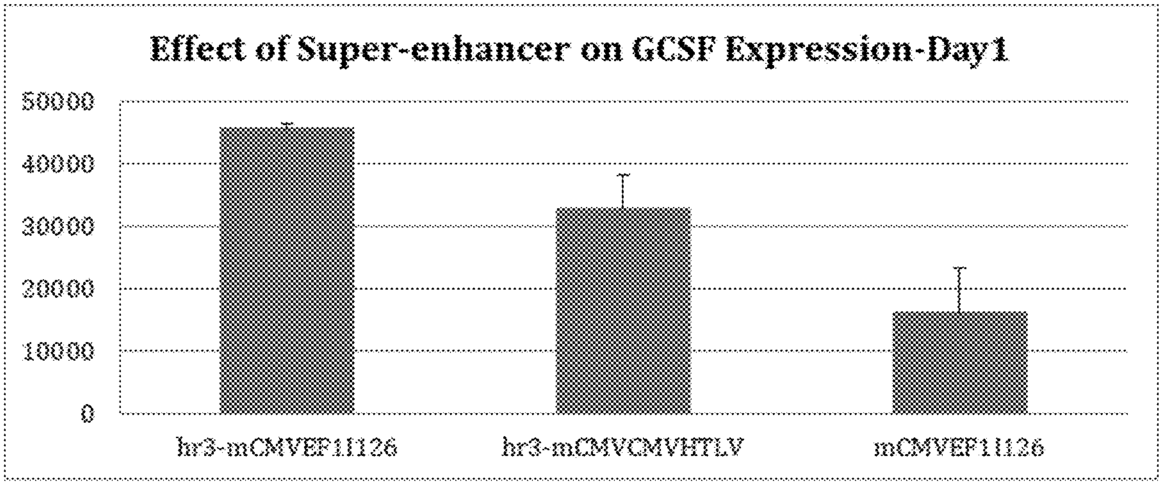
Figure 86B:
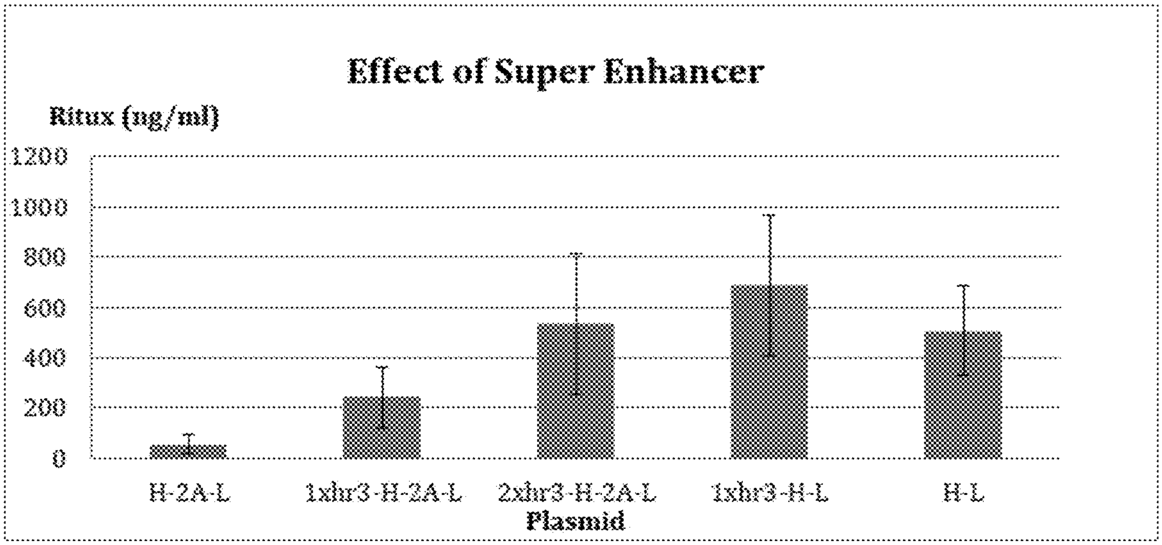

FIGS. 86A-B show the results of Example 21, which shows increased G CSF expression (FIG. 86A) and increased Rituximab anti-CD20 expression (FIG. 86*b*) when the hr3 super enhancer is included in the plasmid.

Figure 87A:
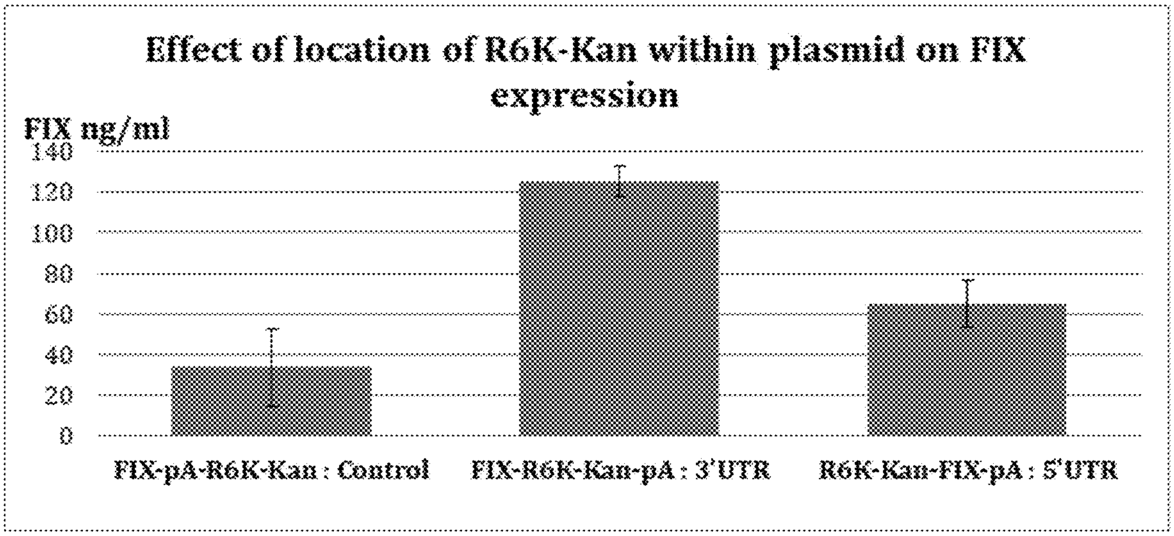
Figure 87B:
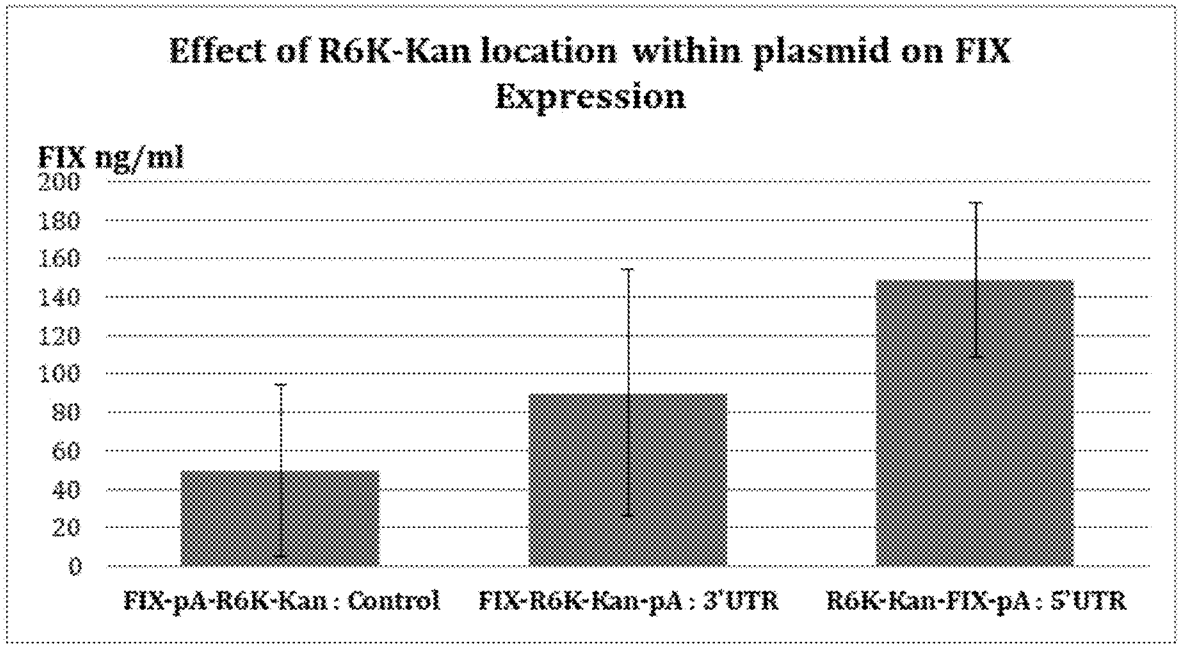

FIGS. 87A-B show the results from Example 22, which describes that locating the R6K origin of replication in the 3' or 5' UTR of the Factor IX gene increased expression levels at both the 75 ug level (FIG. 87A) and the 60 ug level (FIG. 87B).

Figure 88A:
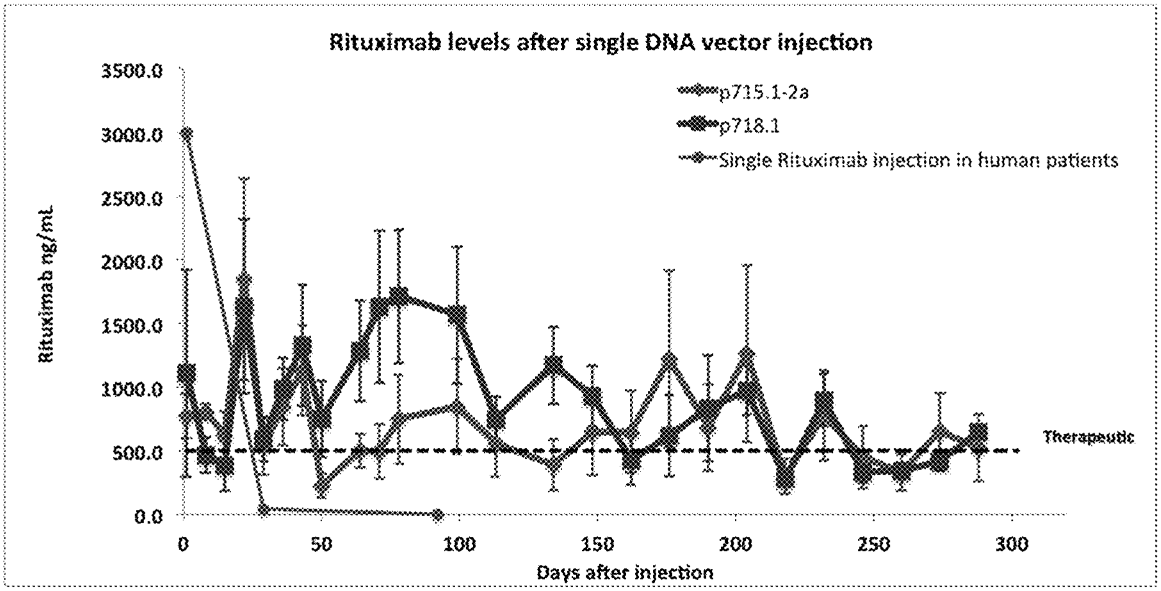

FIG. 88A shows results from Example 23, which shows long-term Rituximab expression levels at different time points over 284 days, showing long-term expression.

Figure 88B:
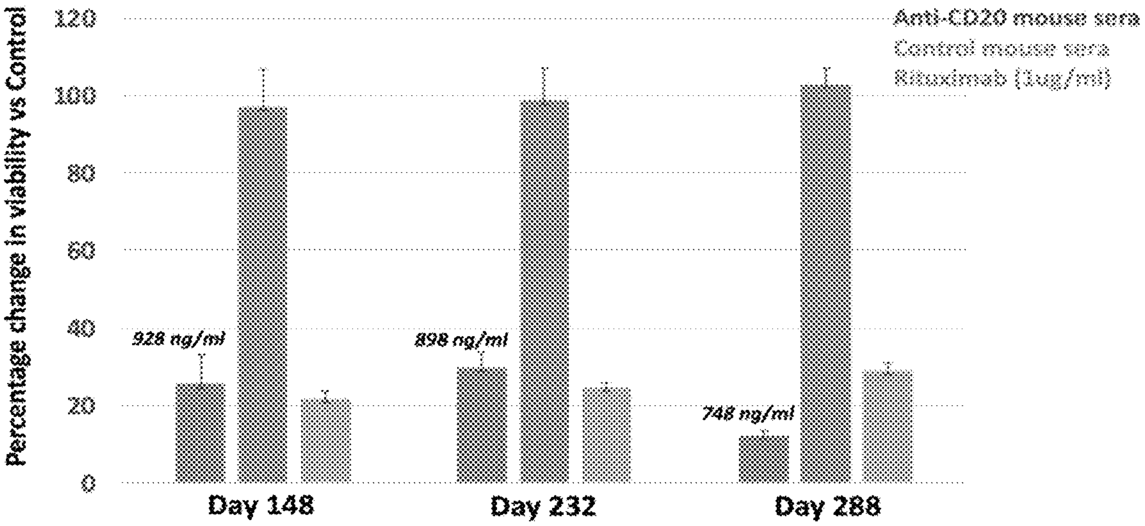

FIG. 88B shows results from Example 23, which shows that the anti-CD20 mouse sera was able to induce human tumor cell lysis at levels comparable to Rituximab protein.

Figure 89:
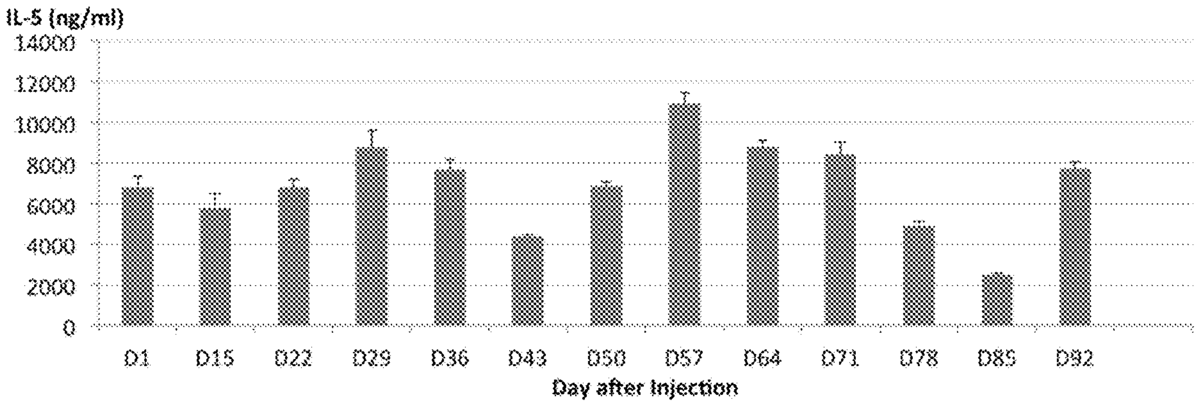

FIG. 89 shows the results from Example 24, which shows therapeutic anti-IL-5 mAb (2B6) serum levels expressed for at least 92 days in mice.

FIG. 90 shows the nucleic acid sequence of the dual cassette, single plasmid DNA vector used in Example 24, which encodes the anti-human interleukin-5 mAb (Mepoluzimab; 2B6) heavy chain and light chain cDNAs.

Figure 91A:
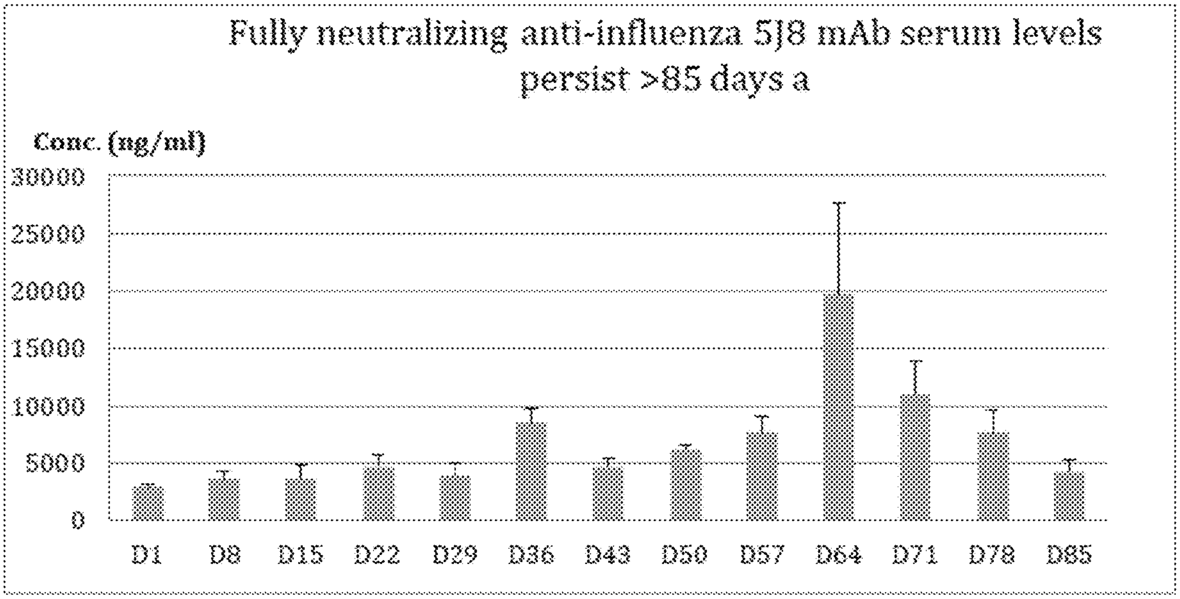

FIG. 91A shows the results from Example 25, which shows that fully neutralizing anti-influenze antibody (5J8) is expressed for at least 85 days in mice.

Figure 91B:
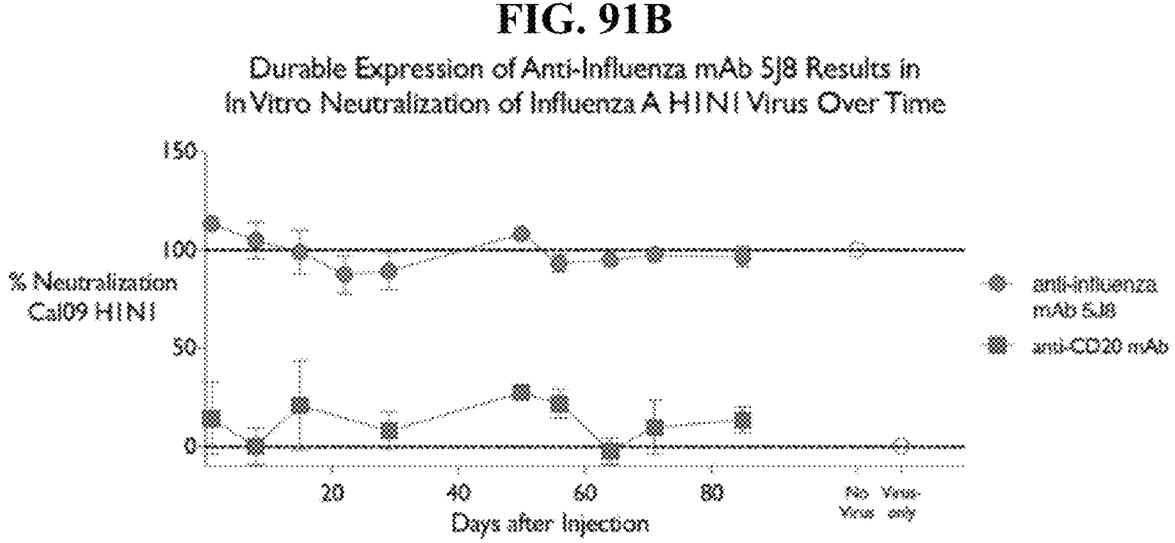

FIG. 91B shows the results from Example 25, which shows anti-influenza antibody expressed effectively neutralizes the Cal09 epidemic influenza strain for >92 days.

FIG. 92 shows the nucleic acid sequence (SEQ ID NO:84) of the dual cassette, single plasmid DNA vector used in Example 25, which encodes the anti-influenza antibody (5J8) heavy chain and light chain cDNAs.

Figure 93:
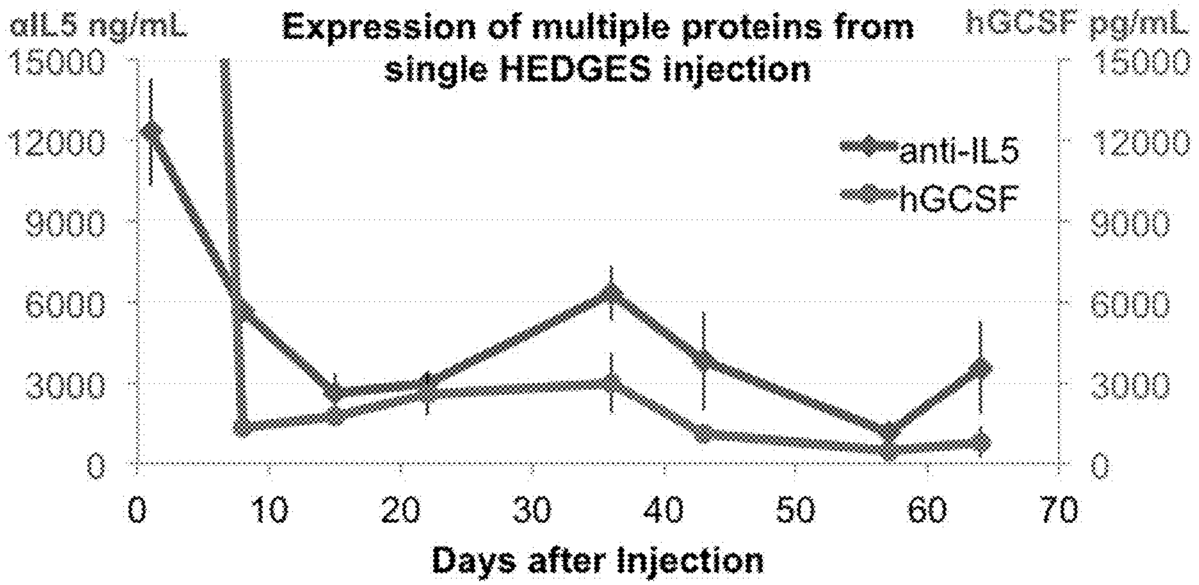

FIG. 93 shows the results of Example 26, which shows the expression levels in mice of anti-IL-5mAb as well as hG-CSF were at therapeutic levels for at least 66 days.

FIG. 94 shows the nucleic acids sequence (SEQ ID NO:85) of the triple cassette, single plasmid DNA vector used in Example 26, which encodes the anti-human interleukin-5 mAb (Mepoluzimab; 2B6) heavy chain and light chain cDNAs and the human G-CSF cDNA.

Figure 95:
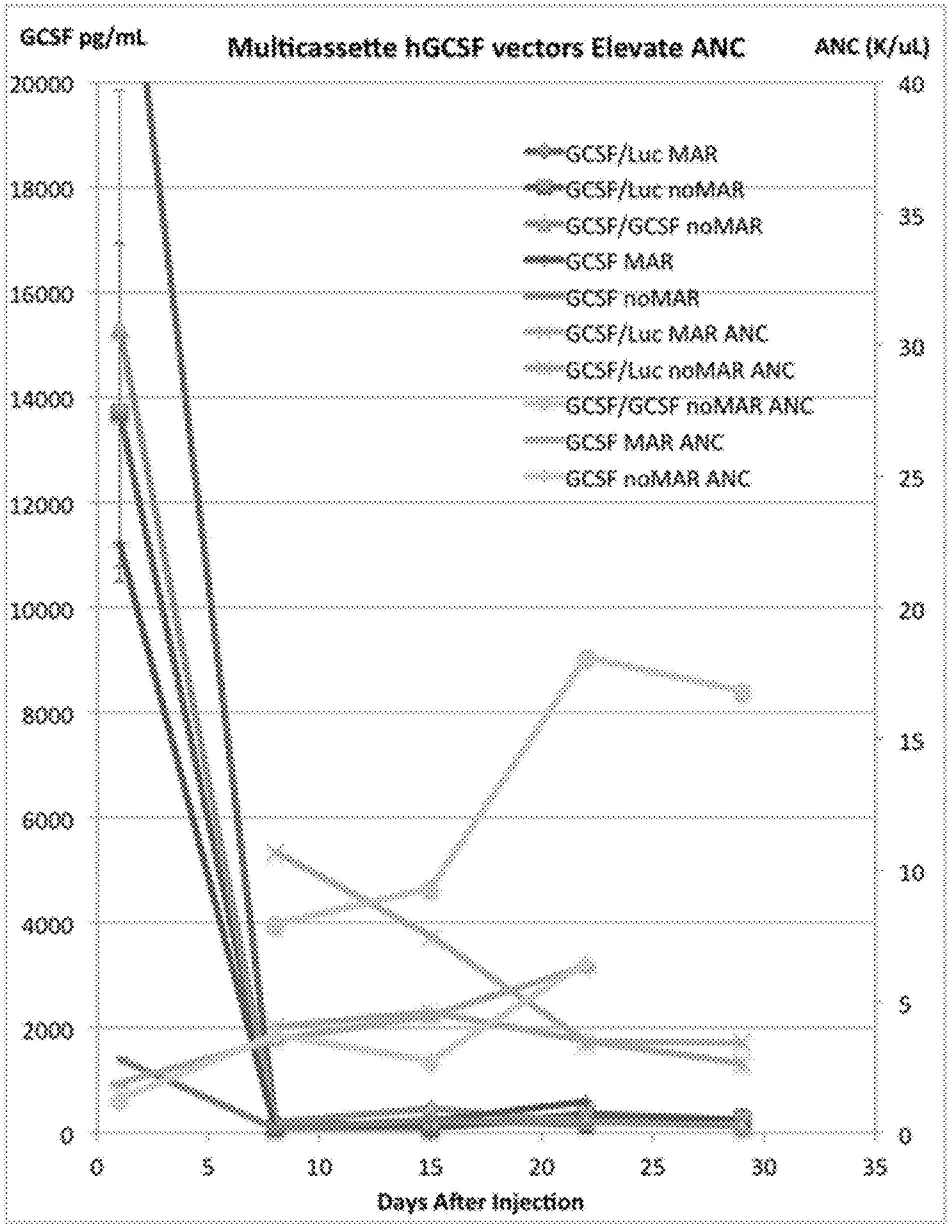

FIG. 95 shows results from Example 27, which shows dual-cassette cDNA for hG-CSF expression provides higher serum levels in mice than single cassette hG-CSF expression.

Figure 96:
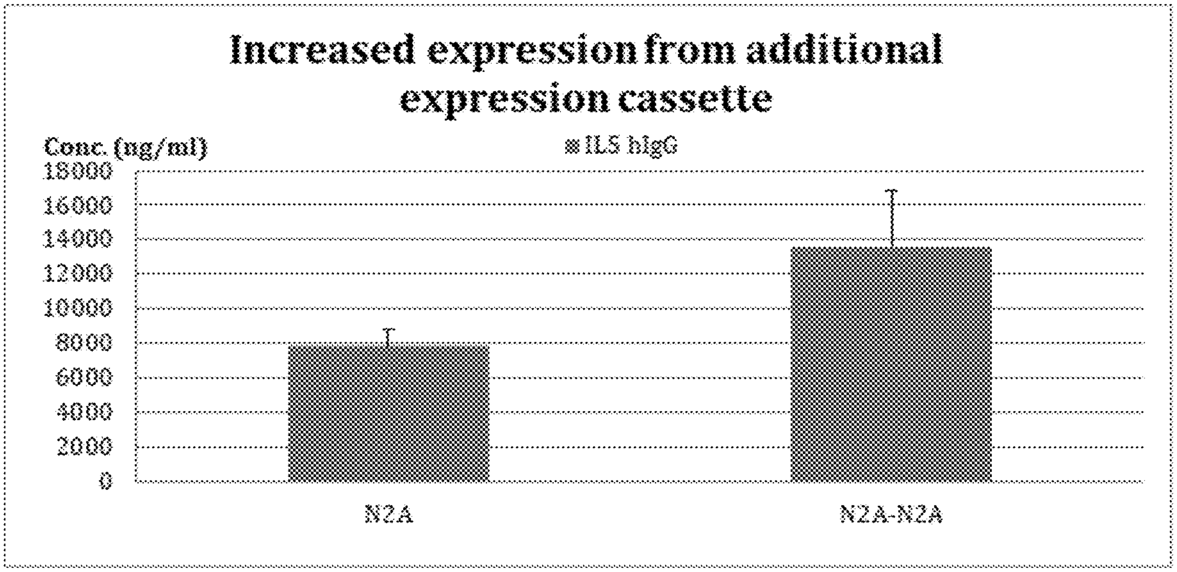

FIG. 96 shows results from Example 28, which shows that the dual cassette vector expressing anti-human IL-5 heavy and light chains produces higher anti-human IL-5 serum mAb levels than the single cassette anti-human IL-5 encoding DNA vector.

Figure 97:
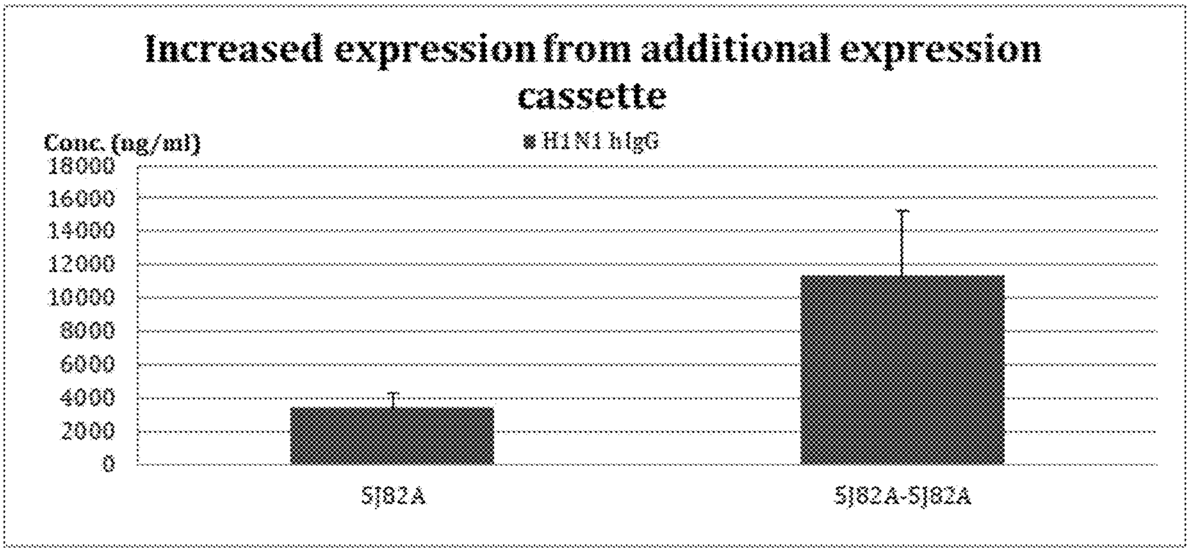

FIG. 97 show the results from Example 29, which shows that the dual cassette vector expressing anti-5J8 mAb produces higher anti-5J8 serum mAb levels in vivo than the single cassette anti-5J8 encoding DNA vector.

Figure 98:

FIG. 98 shows the results from Example 30, which shows how a dual cassette single plasmid expresses different mAbs in vivo, and how two single cassette plasmids that are co-injected express different mAbs in vivo.

Figure 99A:
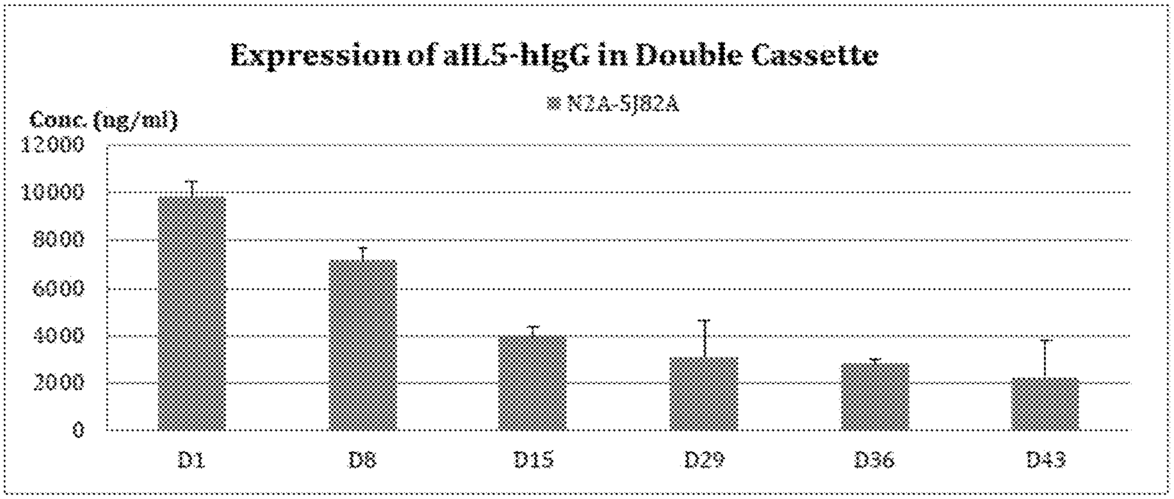
Figure 99B:
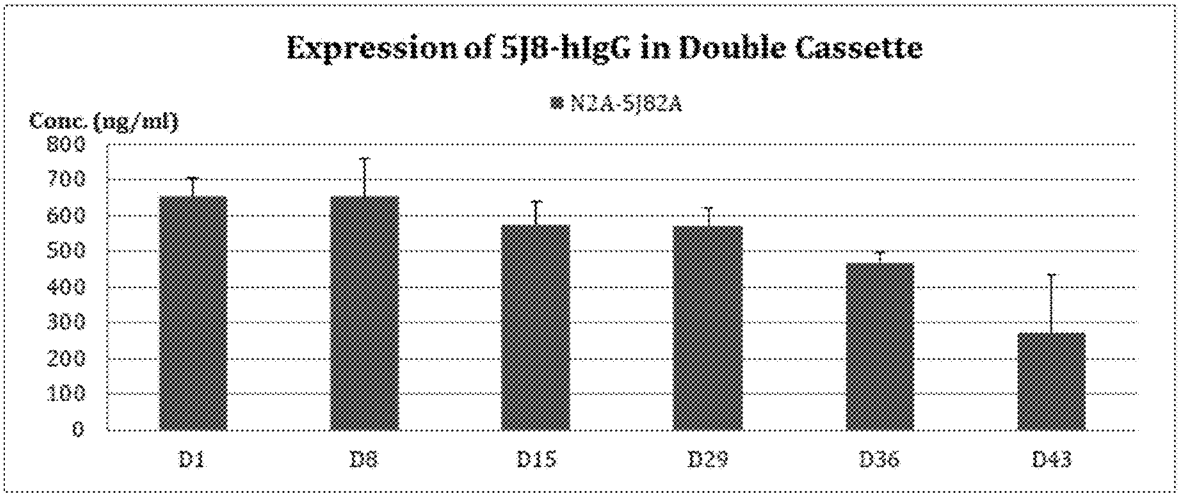

FIGS. 99A-B. FIG. 99A shows results from Example 31, which shows serum expression levels of the anti-human IL-5 mAb over 43 days, and FIG. 99B shows serum expression levels of the anti-influenza A mAb over 43 days.

Figure 100:
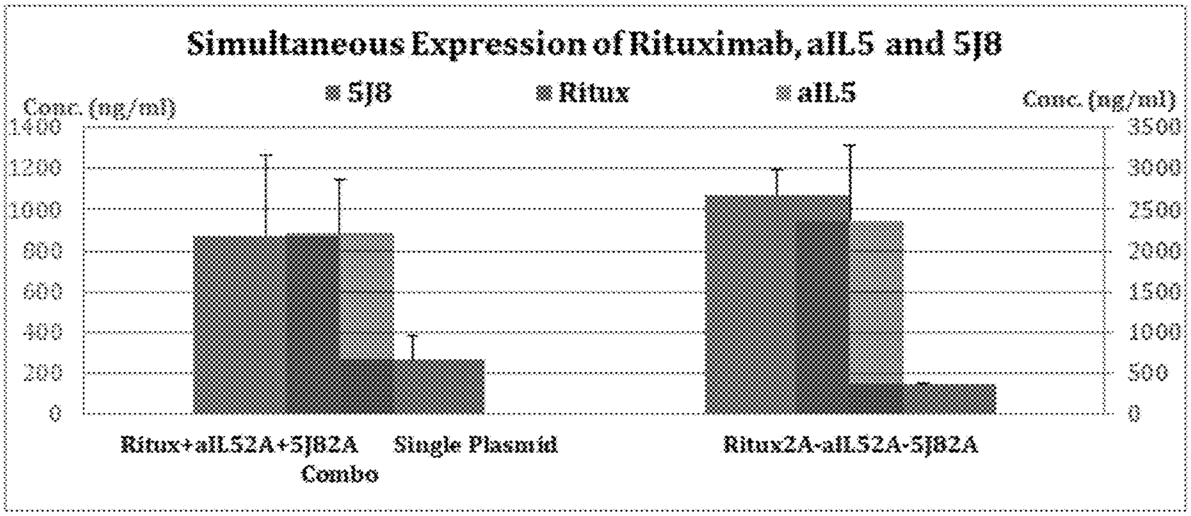

FIG. 100 shows the results from Example 32, which shows simultaneous expression of Rituximab (anti-CD20), anti-IL5 mAb, and anti-influenza mAb, both from a single vector (left side), as well as by co-injection of three separate vectors (right side).

Figure 101:
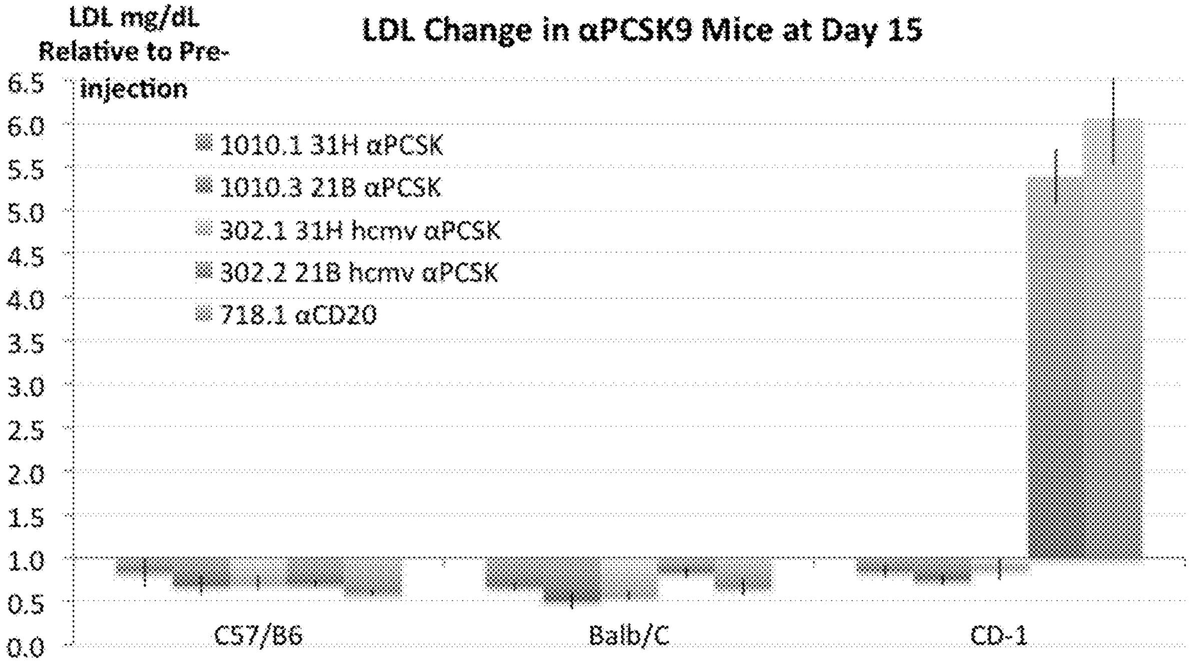

FIG. 101 shows the results of Example 33, which shows that a single plasmid vector expressing anti-PCSK9 mAbs reduces LDL levels in mice.

Figure 102:
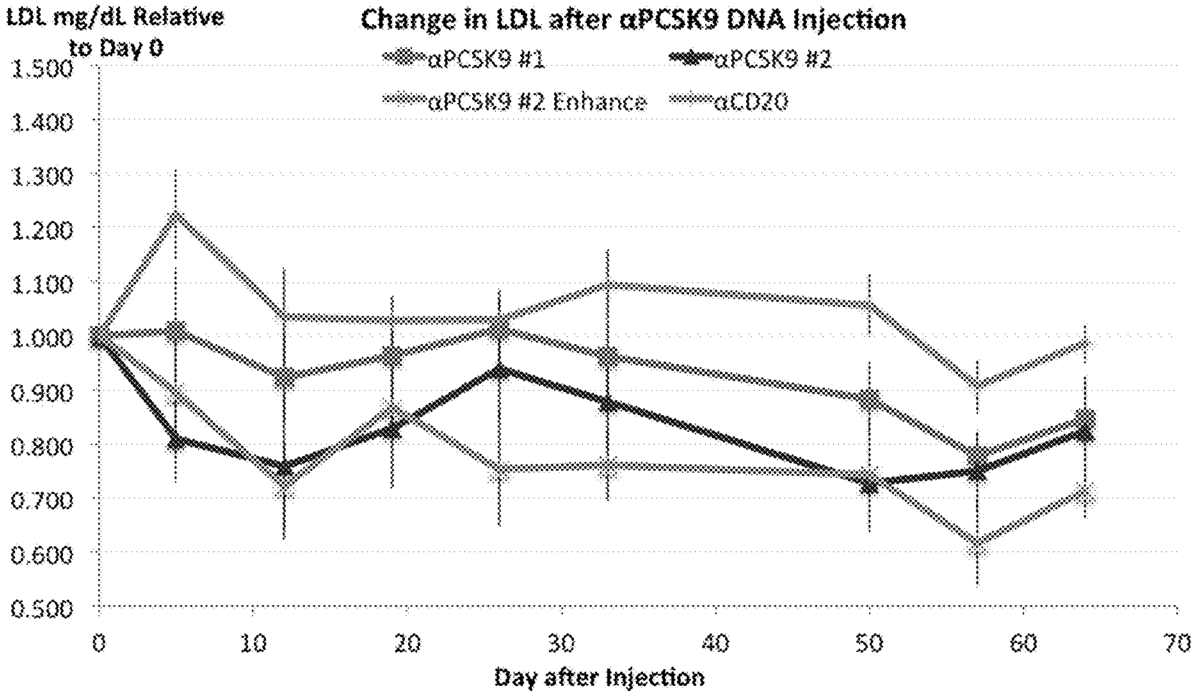

FIG. 102 shows the results of Example 34, which shows long-term reduction in LDL levels in mice expressing anti-PCSK9 mAbs.

Figure 103:
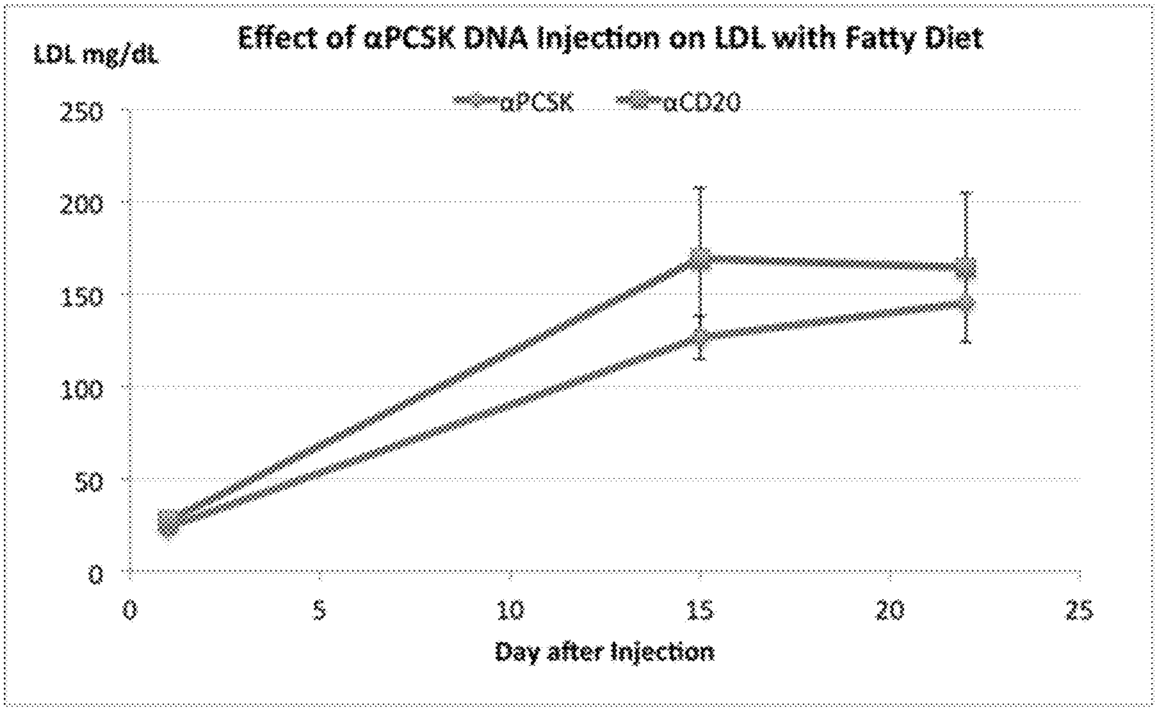

FIG. 103 shows the results of Example 35, which shows that mice expressing the anti-PCSK9 mAbs had lower LDL levels over time compared to the control mice expressing the control anti-CD20 antibodies.

Figure 104:
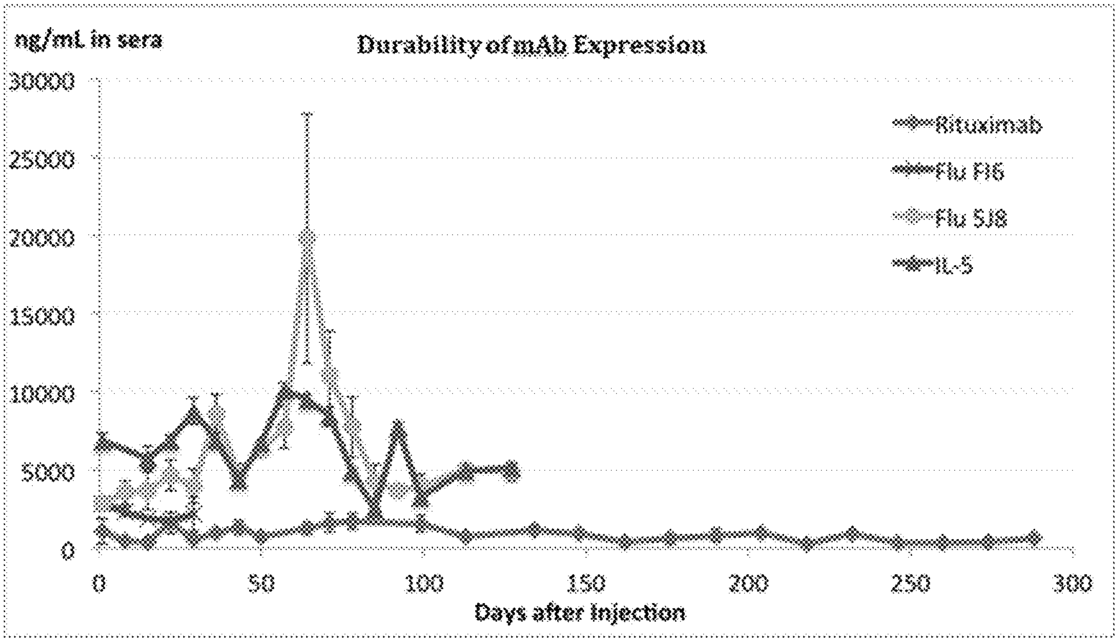

FIG. 104 show the results of Example 36, which shows expression of anti-flu FI6 mAb for about 25 days, expression of anti-flu 5J8 mAb and anti-IL4 mAB for over 100 days, and expression of Rituximab for over 275 days.

Figure 105:
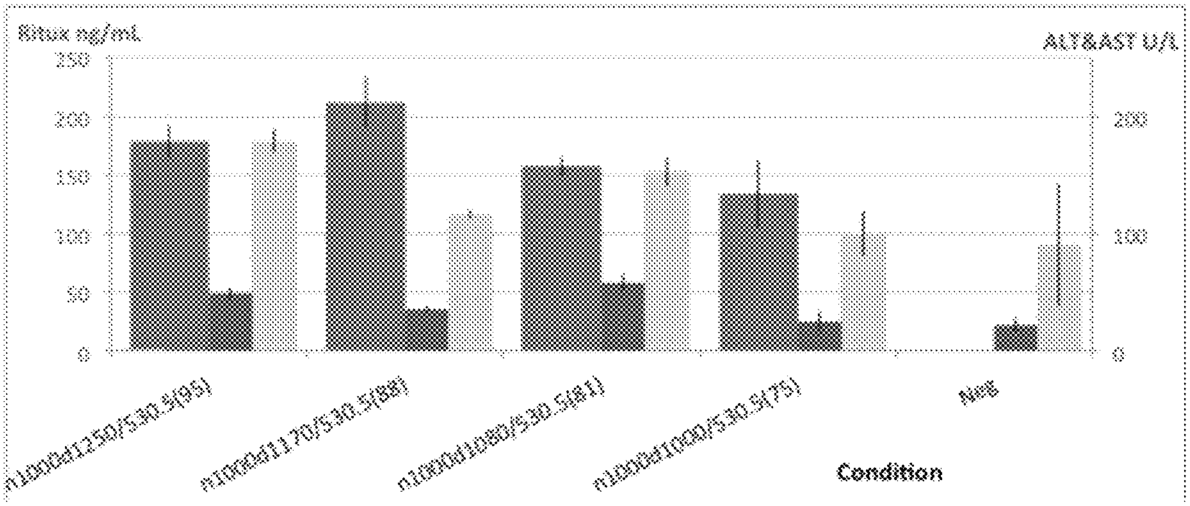

FIG. 105 shows results from Example 37, which shows good expression levels from all four plasmid doses tested.

Figure 106:
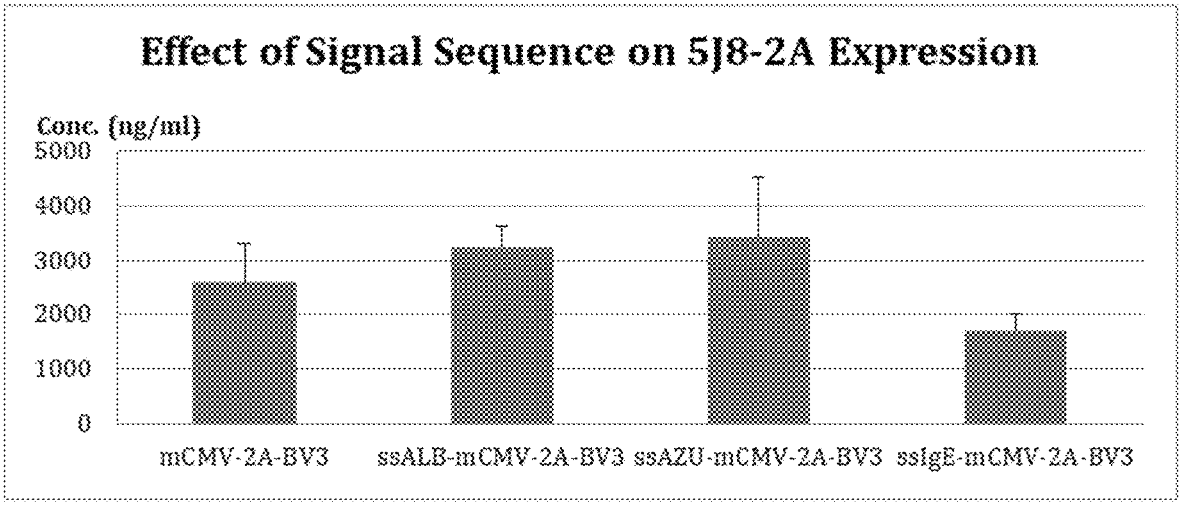

FIG. 106 shows the results of Example 38, which shows enhanced expression of the 5J8 mAb by using the BV3 signal sequence.

Figure 107A:
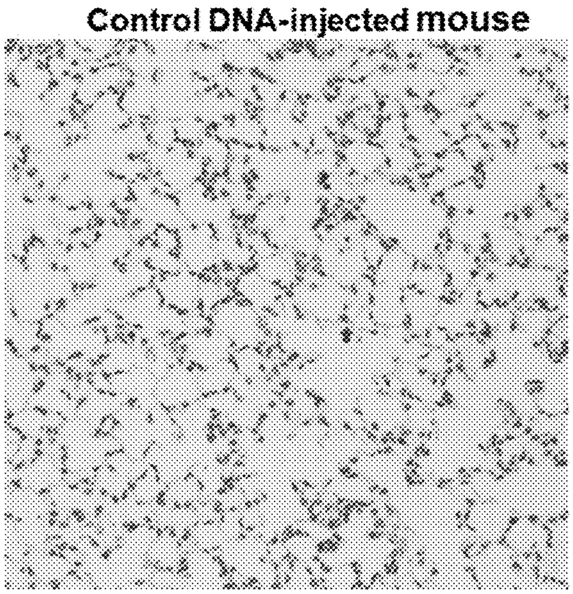
Figure 107B:
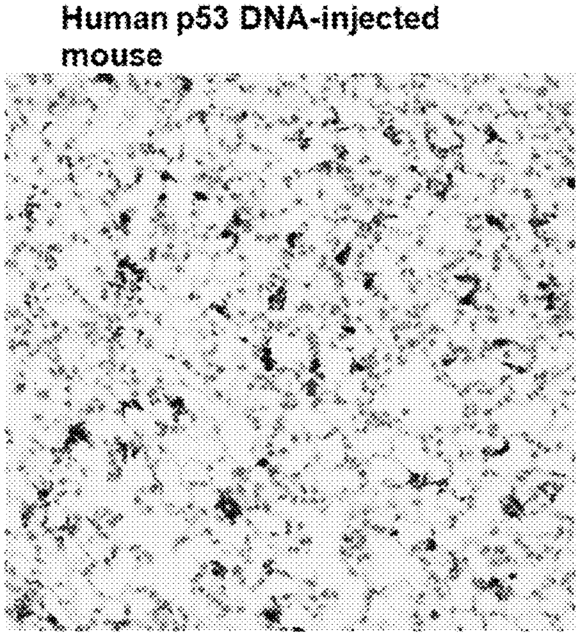
Figure 107C:
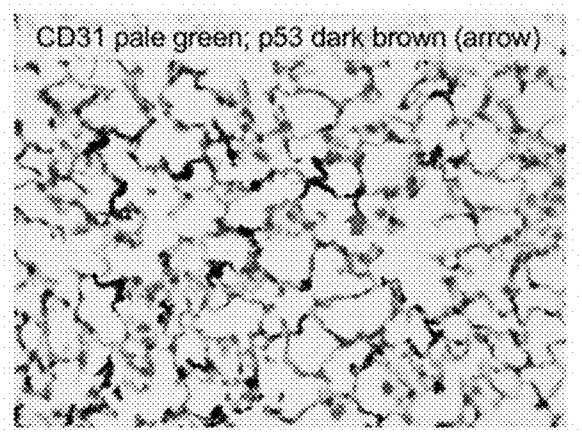
Figure 107D:
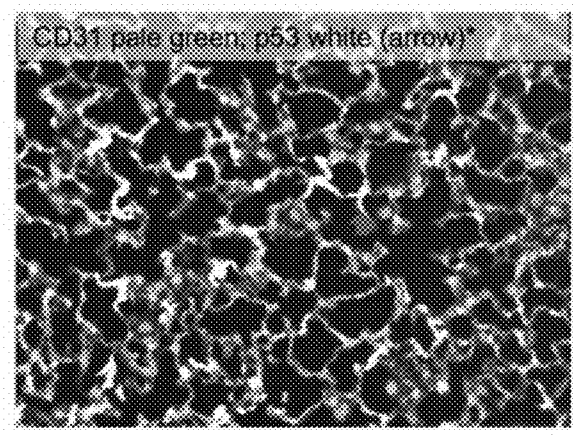

FIGS. 107A-D show results from Example 39. FIG. 107A shows control mouse lung tissue, and FIG. 107B shows human p53 injected mouse lung tissue stained for p53, showing that the p53 gene is widely expressed in mouse lungs. FIGS. 107C and 107D, shows stained mouse tissue showing predominate vascular endothelial cell human p53 expression in p53-injected mice.

FIG. 108 shows the nucleic acid sequence (SEQ ID NO:86) plasmid DNA vector used in Example 39, which encodes human p53.

Figure 109:
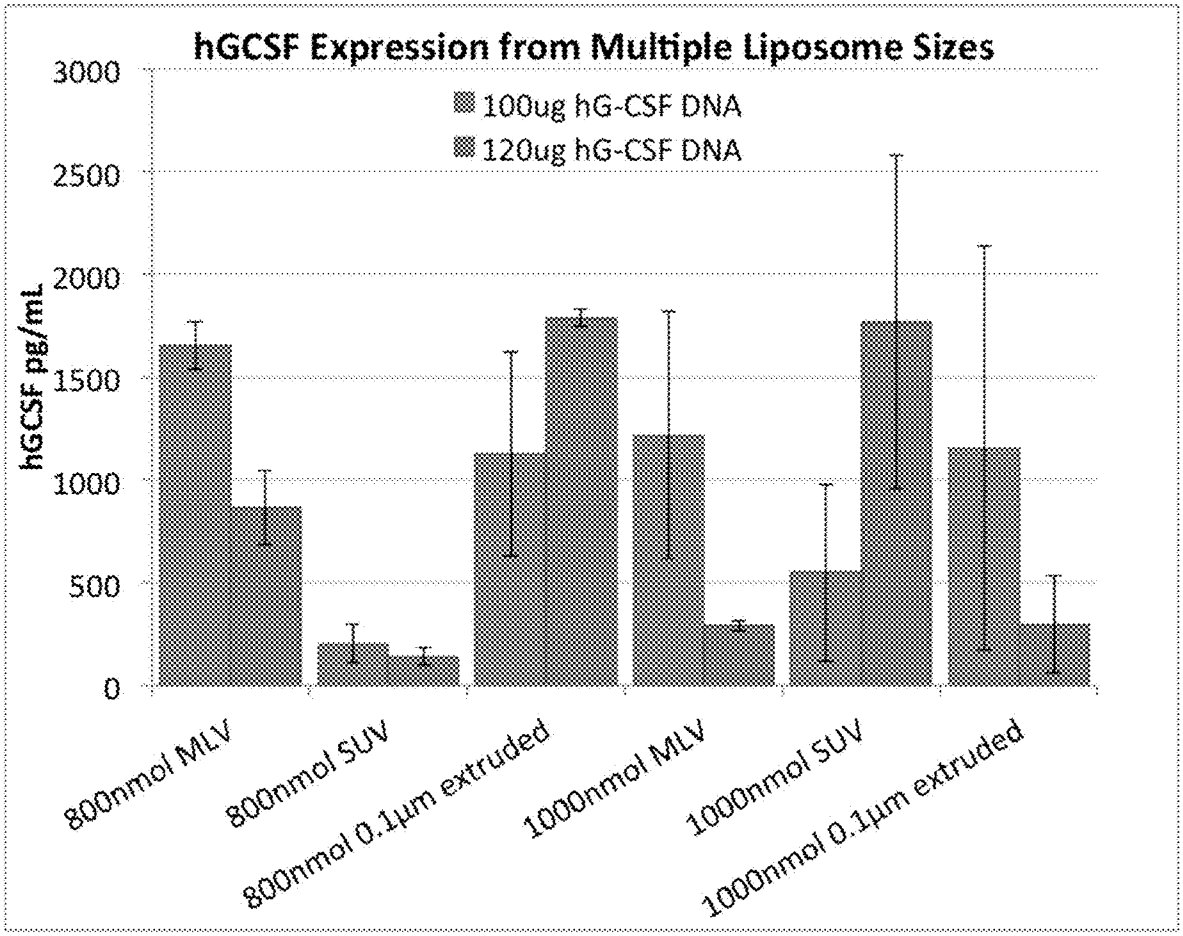

FIG. 109 shows injection of DOTAP liposomes as SUV, 0.1 μm extruded or MLV each efficiently expresses hG-CSF in mice. Three mice per group were given sequential IV injections. The first injection contained either 800 nmol or 1000 nmol of cationic liposomes. The cationic liposomes were one of three sizes: MLV, SUV, or 0.1 micron extruded. The first injection was followed two minutes later by a second injection of plasmid vector encoding hG-CSF, injected at either 100 ug or 120 ug.

Figure 110:
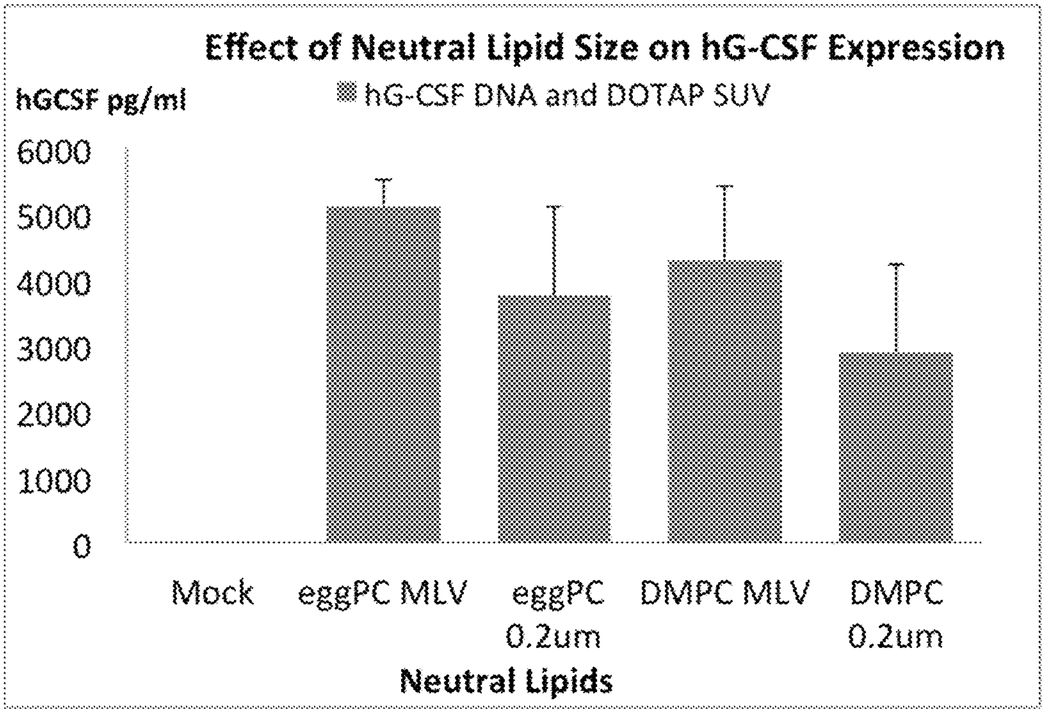

FIG. 110 shows co-injection of either DMPC or egg PC neutral liposomes as either 0.2 μm extruded or MLV each efficiently expresses hG-CSF in mice. Three mice per group were given sequential IV injections. The first injection contained 800 nmol of DOTAP SUV cationic liposomes, along with 500 nmol neutral liposomes. Neutral liposomes were either egg PC or DMPC, and were either MLV or 0.2 micron extruded. The first injection was followed two minutes later by 90 ug of plasmid vector encoding hG-CSF DNA.

DEFINITIONS

As used herein, the phrase "CpG-reduced" refers to a nucleic acid sequence or expression vector that has less CpG di-nucleotides than present in the wild-type versions of the sequence or vector. "CpG-free" means the subject nucleic acid sequence or vector does not have any CpG di-nucleotides. An initial sequence, that contains CpG dinucleotides (e.g., wild-type version of human G-CSF), may be modified to remove CpG dinucleotides by altering the nucleic acid sequence. Such CpG di-nucleotides can be suitably reduced or eliminated not just in a coding sequence, but also in the non-coding sequences, including, e.g., 5' and 3' untranslated regions (UTRs), promoter, enhancer, polyA, ITRs, introns, and any other sequences present in the nucleic acid molecule or vector.

As used herein, "empty liposomes" refers to liposomes that do not contain nucleic acid molecules but that may contain other bioactive molecules (e.g., liposomes that are only composed of the lipid molecules themselves, or only lipid molecules and a small molecule drug).

As used herein, "empty cationic micelles" refers to cationic micelles that do not contain nucleic acid molecules but that may contain other bioactive molecules (e.g., micelles that are only composed of lipid and surfactant molecules themselves, or only lipid and surfactant molecules and a small molecule drug).

As used herein, "empty cationic emulsions" refers to cationic emulsions or microemulsions that do not contain nucleic acid molecules but that may contain other bioactive molecules.

DETAILED DESCRIPTION

The present invention provides compositions, systems, kits, and methods for expression of one or more biomolecules in a subject, human or non-human mammal, (e.g., at therapeutic levels for the extended periods of time required to produce therapeutic effects). In certain embodiments, compositions, systems, kits, and methods are provided that comprise a first composition comprising polycationic structures (e.g., empty cationic liposomes, cationic micelles, cationic emulsions, or cationic polymers) and a second composition comprising expression vectors (e.g., non-viral expression vectors not associated with liposomes or other carriers) encoding one or more biomolecules of interest.

The present disclosure provides methods, systems, and compositions, that allow a single injection (e.g., intravenous injection) of cationic liposomes, followed shortly thereafter by injection (e.g., intravenous injection) of vectors encoding a therapeutic protein produces circulating protein levels many times (e.g., 2-20 times higher) than the therapeutic serum level for the protein for a prolonged period, such at 190 days or over 500 days. Thus, the approach provided herein allows for successful therapeutic application of systemic non-viral gene delivery.

In addition, the systems, methods, and compositions provided herein provide a versatile (e.g., non-viral) gene delivery and expression platform that can much more precisely control the duration of expression of delivered genes at therapeutic levels. This ability to control the duration of expression of delivered genes addresses a need within the gene therapy field, the ability to control the duration at which proteins are expressed at therapeutic levels. Specifically, there is now a wide and expanding spectrum of FDA-approved, recombinant, secreted human protein therapies. Different approved protein therapies must be present at therapeutic levels for very different durations in order to both effectively and safely treat patients. Recommended treatment durations of different protein therapies vary from less than two weeks (HG-CSF) to the lifetime of the patient (factor IX). For example, recombinant human G-CSF protein, Neupogen, is given daily for only the first 10 days of each three-week chemotherapy cycle. Serum HG-CSF levels return to baseline approximately 14 hours after each daily Neupogen dose. This 10 day treatment schedule is used because its neutrophil increasing effect is indicated only during this approximately 10 day period of chemotherapy-induced neutropenia. G-CSF elevation from days 11 to 21 is generally not beneficial, as the patient's own neutrophil producing capacity returns. Giving Neupogen beyond day 10 can cause toxic, neutrophilia-related side effects. In contrast, anti-TNF antibodies are routinely administered for months or years, and factor IX replacement for the lifetime of the patient. Thus, different proteins must be produced at therapeutic levels for different durations, from less than two weeks to the lifetime of the patient. Therefore, a gene therapy approach that can control the duration of gene expression at therapeutic levels it produces in patients achieves therapeutic endpoints while avoiding toxic side effects for a wide spectrum of now FDA-approved, human therapeutic proteins. Provided herein are various technologies that can be employed to provide this control.

In certain embodiments, the present disclosure employs polycationic structures (e.g., empty cationic liposomes, empty cationic micelles, or empty cationic emulsions) not containing vector DNA, which are administered to a subject prior to vector administration. In certain embodiments, the polycationic structures are cationic lipids and/or are provided as an emulsion. The present disclosure is not limited to the cationic lipids employed, which can be composed, in some embodiments, of one or more of the following: DDAB, dimethyldioctadecyl ammonium bromide; DPTAP (1,2-dipalmitoyl 3-trimethylammonium propane); DHA; prostaglandin, N-[1-(2,3-Dioloyloxy)propyl]-N,N,N-trimethylammonium methylsulfate; 1,2-diacyl-3-trimethylammonium-propanes, (including but not limited to, dioleoyl (DOTAP), dimyristoyl, dipalmitoyl, disearoyl); 1,2-diacyl-3-dimethylammonium-propanes, (including but not limited to, dioleoyl, dimyristoyl, dipalmitoyl, disearoyl) DOTMA, N-[1-[2,3-bis(oleoyloxy)]propyl]-N,N,N-trimethylammonium-m chloride; DOGS, dioctadecylamidoglycylspermine; DC-cholesterol, 3.beta.-[N—(N',N'-dimethylaminoethane) carbamoyl]cholesterol; DOSPA, 2,3-dioleoyloxy-N-(2(sperminecarboxamido)-ethyl)-N,N-dimethyl-1-propanami-nium trifluoroacetate; 1,2-diacyl-sn-glycero-3-ethylphosphocholines (including but not limited to dioleoyl (DOEPC), dilauroyl, dimyristoyl, dipalmitoyl, distearoyl, palmitoyl-oleoyl); beta-alanyl cholesterol; CTAB, cetyl trimethyl ammonium bromide; diC14-amidine, N-t-butyl-N'-tetradecyl-3-tetradecylaminopropionamidine; 14Dea2, O,O'-ditetradecanolyl-N-(trimethylammonioacetyl) diethanolamine chloride; DOSPER, 1,3-dioleoyloxy-2-(6-carboxy-spermyl)-propylamide; N,N,N,N-tetramethyl-N,N-bis(2-hydroxylethyl)-2,3-dioleoyloxy-1,4-butan-ediammonium iodide; 1-[2-acyloxy)ethyl]2-alkyl (alkenyl)-3-(2-hydroxyethyl-) imidazolinium chloride derivatives such as 1-[2-(9(Z)-octadecenoyloxy)eth-yl]-2-(8(Z)-heptadecenyl-3-(2-hydroxyethyl)imidazolinium chloride (DOTIM), 1-[2-(hexadecanoyloxy)ethyl]-2-pentadecyl-3-(2-hydroxyethyl) imidazolinium chloride (DPTIM); 1-[2-tetradecanoyloxy) ethyl]-2-tridecyl-3-(2-hydroxyeth-yl)imidazolium chloride (DMTIM) (e.g., as described in Solodin et al. (1995) Biochem. 43:13537-13544, herein incorporated by reference); 2,3-dialkyloxypropyl quaternary ammonium compound derivates, containing a hydroxyalkyl moiety on the quaternary amine, such as 1,2-dioleoyl-3-dimethyl-hydroxyethyl ammonium bromide (DORI); 1,2-dioleyloxypropyl-3-dimethyl-hydroxyethyl ammonium bromide (DORIE); 1,2-dioleyloxypropyl-3-dimethyl-hydroxypropyl ammonium bromide (DORIE-HP), 1,2-dioleyloxypropyl-3-dimethyl-hydroxybutyl ammonium bromide (DORIE-HB); 1,2-dioleyloxypropyl-3-dimethyl-hydroxypentyl ammonium bromide (DORIE-HPe); 1,2-dimyristyloxypropyl-3-dimethyl-hydroxylethyl ammonium bromide (DMRIE); 1,2-dipalmityloxypropyl-3-dimethyl-hydroxyethyl ammonium bromide (DPRIE); 1,2-disteryloxypropyl-3-dimethyl-hydroxyethyl ammonium bromide (DSRIE) (e.g., as described in Felgner et al. (1994) J. Biol. Chem. 269:2550-2561, herein incorporated by reference in its entirety). Many of the above-mentioned lipids are available commercially from, e.g., Avanti Polar Lipids, Inc.; Sigma Chemical Co.; Molecular Probes, Inc.; Northern Lipids, Inc.; Roche Molecular Biochemicals; and Promega Corp.

In certain embodiments, the neutral lipids employed with the methods, compositions, systems, and kits includes diacylglycerophosphorylcholine wherein the acyl chains are generally at least 12 carbons in length (e.g., 12 . . . 14 . . . 20 . . . 24 . . . or more carbons in length), and may contain one or more cis or trans double bonds. Examples of said compounds include, but are not limited to, distearoyl phosphatidyl choline (DSPC), dimyristoyl phosphatidylcholine (DMPC), dipalmitoyl phosphatidylcholine (DPPC), palmitoyl oleoyl phosphatidylcholine (POPC), palmitoyl stearoyl phosphatidylcholine (PSPC), egg phosphatidylcholine (EPC), hydrogenated or non-hydrogenated soya phosphatidylcholine (HSPC), or sunflower phosphatidylcholine.

In certain embodiments, the neutral lipids include, for example, up to 70 mol diacylglycerophosphorylethanolamine/100 mol phospholipid (e.g., 10/100 mol . . . 25/100 mol . . . 50/100 . . . 70/100 mol). In some embodiments, the diacylglycerophosphorylethanolamine has acyl chains that are generally at least 12 carbons in length (e.g., 12 . . . 14 . . . 20 . . . 24 . . . or more carbons in length), and may contain one or more cis or trans double bonds. Examples of such compounds include, but are not limited to distearoylphosphatidylethanolamine (DSPE), dimyristoylphosphatidylethanolamine (DMPE), dipalmitoylphosphatidylethanolamine (DPPE), palmitoyloleoylphosphatidylethanolamine (POPE), egg phosphatidylethanolamine (EPE), and transphosphatidylated phosphatidylethanolamine (t-EPE), which can be generated from various natural or semisynthetic phosphatidylcholines using phospholipase D.

In certain embodiments, the present disclosure employs CpG-reduced or CpG-free expression vectors. An initial sequence that contains CpG dinucleotides (e.g., wild-type version of human G-CSF), may be modified to remove CpG dinucleotides by altering the nucleic acid sequence. FIG. 1 shows a CpG-free version of human G-CSF, with sequences that have been changed to removed CpGs underlined. Such CpG di-nucleotides can be suitably reduced or eliminated not just in a coding sequence, but also in the non-coding sequences, including, e.g., 5' and 3' untranslated regions (UTRs), promoter, enhancer, polyA, ITRs, introns, and any other sequences present in the nucleic acid molecule or vector. CpG di-nucleotides may be located within a codon triplet for a selected amino acid. There are five amino acids (serine, proline, threonine, alanine, and arginine) that have one or more codon triplets that contain a CpG di-nucleotide. All five of these amino acids have alternative codons not containing a CpG di-nucleotide that can be changed to, to avoid the CpG but still code for the same amino acid as shown in Table 1 below. Therefore, the CpG di-nucleotides allocated within a codon triplet for a selected amino acid may be changed to a codon triplet for the same amino acid lacking a CpG di-nucleotide.

TABLE 1

| Amino Acid | DNA Codons Containing CpG | DNA Codons Lacking CpG |
|---|---|---|
| Serine (Ser or S) | TCG | TCT, TCC, TCA, AGT, AGC |
| Proline (Pro or P) | CCG | CCT, CCC, CCA, |
| Threonine (Thr or T) | ACG | ACA, ACT, ACC |
| Alanine (Ala or A) | GCG | GCT, GCC, GCA |
| Arginine (Arg or R) | CGT, CGC, CGA, CGG | AGA, AGG |

In addition, within the coding region, the interface between triplets should be taken into consideration. For example, if an amino acid triplet ends in a C-nucleotide which is then followed by an amino acid triplet which can start only with a G-nucleotide (e.g., Valine, Glycine, Glutamic Acid, Alanine, Aspartic Acid), then the triplet for the first amino acid triplet is changed to one which does not end in a C-nucleotide. Methods for making CpG free sequences are shown, for example, in U.S. Pat. No. 7,244,609, which is herein incorporated by reference. A commercial service provided by INVIVOGEN is also available to produce CpG free (or reduced) nucleic acid sequences/vectors (plasmids). A commercial service provided by ThermoScientific produces CpG free nucleotide.

Provided below in Table 2 are exemplary promoters and enhancers that may be used in the vectors described herein. Such promoters, and other promoters known in the art, may be used alone or with any of the enhancers, or enhancers, known in the art. Additionally, when multiple proteins or biologically active nucleic acid molecules (e.g., two, three, four, or more) are expressed from the same vector, the same or different promoters may be used in conjunction with the subject nucleic acid sequence.

TABLE 2

| Promoter | Enhancer |
|---|---|
| CMV | human CMV |
| EF1α | mouse CMV |
| Ferritin (Heavy/Light) Chain | SV40 |
| GRP94 | Ubc |
| U1 | AP1 |
| UbC | hr3 |
| Beta Actin | IE2 |
| PGK1 | IE6 |
| GRP78 | E2-RS |
| CAG | MEF2 |
| SV40 | C/EBP |
| TRE | HNF-1 |

The present disclosure is not limited by the type of therapeutic proteins that is expressed. In certain embodiments, the therapeutic protein comprises an antibody or antibody fragments (e.g., F(ab) or F(ab')2). In other embodiments, the therapeutic protein is selected from the group consisting of an anti-inflammatory protein, coagulation protein, anti-cancer protein, anti-sepsis protein, etc. Example of therapeutic proteins that can be expressed with the methods, systems, and compositions described herein include the therapeutic monoclonal antibodies (mAbs), Fabs, F(ab)2s, and scFv's that are shown in Table 3 below.

TABLE 3

| Antibody Name | Trade name | Type | Source | Target | Use |
|---|---|---|---|---|---|
| 3F8 | | mab | mouse | GD2 ganglioside | neuroblastoma |
| 8H9 | | mab | mouse | B7-H3 | neuroblastoma, sarcoma, metastatic brain cancers |
| Abagovomab | | mab | mouse | CA-125 (imitation) | ovarian cancer |
| Abciximab | ReoPro | Fab | chimeric | CD41 (integrin alpha-IIb) | platelet aggregation inhibitor |
| Abituzumab | | mab | humanized | CD51 | cancer |
| Abrilumab | | mab | human | integrin α4β7 | inflammatory bowel disease, ulcerative colitis, Crohn's disease |
| Actoxumab | | mab | human | *Clostridium difficile* | *Clostridium difficile* colitis |

TABLE 3-continued

| Antibody Name | Trade name | Type | Source | Target | Use |
|---|---|---|---|---|---|
| Adalimumab | Humira | mab | human | TNF-α | Rheumatoid arthritis, Crohn's Disease, Plaque Psoriasis, Psoriatic Arthritis, Ankylosing Spondylitis, Juvenile Idiopathic Arthritis, Hemolytic disease of the newborn |
| Adecatumumab | | mab | human | EpCAM | prostate and breast cancer |
| Aducanumab | | mab | human | beta-amyloid | Alzheimer's disease |
| Afasevikumab | | mab | human | IL17A and IL17F | — |
| Afelimomab | | $F(ab')_2$ | mouse | TNF-α | sepsis |
| Afutuzumab | | mab | humanized | CD20 | lymphoma |
| Alacizumab pegol | | $F(ab')_2$ | humanized | VEGFR2 | cancer |
| ALD518 | | — | humanized | IL-6 | rheumatoid arthritis |
| Alemtuzumab | Lemtrada, Campath | mab | humanized | CD52 | Multiple sclerosis |
| Alirocumab | | mab | human | PCSK9 | hypercholesterolemia |
| Altumomab pentetate | Hybri-ceaker | mab | mouse | CEA | colorectal cancer (diagnosis) |
| Amatuximab | | mab | chimeric | mesothelin | cancer |
| Anatumomab mafenatox | | Fab | mouse | TAG-72 | non-small cell lung carcinoma |
| Anetumab ravtansine | | mab | human | MSLN | cancer |
| Anifrolumab | | mab | human | interferon α/β receptor | systemic lupus erythematosus |
| Anrukinzumab (= IMA-638) | | mab | humanized | IL-13 | asthma |
| Apolizumab | | mab | humanized | HLA-DR— | hematological cancers |
| Arcitumomab | CEA-Scan | Fab' | mouse | CEA | gastrointestinal cancers (diagnosis) |
| Ascrinvacumab | | mab | human | activin receptor-like kinase 1 | cancer |
| Aselizumab | | mab | humanized | L-selectin (CD62L) | severely injured patients |
| Atezolizumab | | mab | humanized | CD274 | cancer |
| Atinumab | | mab | human | RTN4 | — |
| Atlizumab (= tocilizumab) | Actemra, RoActemra | mab | humanized | IL-6 receptor | rheumatoid arthritis |
| Atorolimumab | | mab | human | Rhesus factor | hemolytic disease of the newbom[citation needed] |
| Avelumab | | mab | human | CD274 | — |
| Bapineuzumab | | mab | humanized | beta amyloid | Alzheimer's disease |
| Basiliximab | Simulect | mab | chimeric | CD25 (α chain of IL-2 receptor) | prevention of organ transplant rejections |
| Bavituximab | | mab | chimeric | phosphatidylserine | cancer, viral infections |
| Bectumomab | LymphoScan | Fab' | mouse | CD22 | non-Hodgkin's lymphoma (detection) |
| Begelomab | | mab | mouse | DPP4 | — |
| Belimumab | Benlysta, LymphoStat-B | mab | human | BAFF | non-Hodgkin lymphoma etc. |
| Benralizumab | | mab | humanized | CD125 | asthma |
| Bertilimumab | | mab | human | CCL11 (eotaxin-1) | severe allergic disorders |
| Besilesomab | Scintimun | mab | mouse | CEA-related antigen | inflammatory lesions and metastases (detection) |
| Bevacizumab | Avastin | mab | humanized | VEGF-A | metastatic cancer, retinopathy of prematurity |
| Bezlotoxumab | | mab | human | *Clostridium difficile* | *Clostridium difficile colitis* |
| Biciromab | FibriScint | Fab' | mouse | fibrin II, beta chain | thromboembolism (diagnosis) |
| Bimagrumab | | mab | human | ACVR2B | myostatin inhibitor |
| Bimekizumab | | mab | humanized | IL 17A and IL 17F | — |
| Bivatuzumab mertansine | | mab | humanized | CD44 v6 | squamous cell carcinoma |
| Bleselumab | | mab | human | CD40 | — |
| Blinatumomab | | BiTE | mouse | CD19 | pre-B ALL (CD19+) |
| Blontuvetmab | Blontress | mab | veterinary | CD20 | — |
| Blosozumab | | mab | humanized | SOST | osteoporosis |
| Bococizumab | | mab | humanized | neural apoptosis-regulated proteinase 1 | dyslipidemia |

TABLE 3-continued

| Antibody Name | Trade name | Type | Source | Target | Use |
|---|---|---|---|---|---|
| Brazikumab | | mab | human | IL23 | Crohn's disease |
| Brentuximab vedotin | | mab | chimeric | CD30 (TNFRSF8) | hematologic cancers |
| Briakinumab | | mab | human | IL-12, IL-23 | psoriasis, rheumatoid arthritis, inflammatory bowel diseases, multiple sclerosis |
| Brodalumab | | mab | human | IL-17 | inflammatory diseases |
| Brolucizumab | | mab | humanized | VEGFA | wet age-related macular degeneration |
| Brontictuzumab | | mab | humanized | Notch 1 | cancer |
| Burosumab | | mab | human | FGF 23 | X-linked hypophosphatemia |
| Cabiralizumab | | mab | humanized | CSF1R | — |
| Canakinumab | Ilaris | mab | human | IL -1— | rheumatoid arthritis |
| Cantuzumab mertansine | | mab | humanized | mucin CanAg | colorectal cancer etc. |
| Cantuzumab ravtansine | | mab | humanized | MUC1 | cancers |
| Caplacizumab | | mab | humanized | VWF | thrombotic thrombocytopenic purpura, thrombosis |
| Capromab pendetide | Prostascint | mab | mouse | prostatic carcinoma cells | prostate cancer (detection) |
| Carlumab | | mab | human | MCP-1 | oncology/immune indications |
| Carotuximab | | mab | chimeric | endoglin | — |
| Catumaxomab | Removab | 3funct | rat/mouse hybrid | EpCAM, CD3 | ovarian cancer, malignant ascites, gastric cancer |
| cBR96-doxorubicin immunoconjugate | | mab | humanized | Lewis-Y antigen | cancer |
| Cedelizumab | | mab | humanized | CD4 | prevention of organ transplant rejections, treatment of autoimmune diseases |
| Cergutuzumab amunaleukin | | mab | humanized | IL2 | — |
| Certolizumab pegol | Cimzia | Fab' | humanized | TNF-α | Crohn's disease Rheumatoid arthritis axial spondyloarthritis psoriasis arthritis |
| Cetuximab | Erbitux | mab | chimeric | EGFR | metastatic colorectal cancer and head and neck cancer |
| Ch.14.18 | | mab | chimeric | GD2 ganglioside | neuroblastoma |
| Citatuzumab bogatox | | Fab | humanized | EpCAM | ovarian cancer and other solid tumors |
| Cixutumumab | | mab | human | IGF-1 receptor (CD221) | solid tumors |
| Clazakizumab | | mab | humanized | *Oryctolagus cuniculus* | rheumatoid arthritis |
| Clenoliximab | | mab | chimeric | CD4 | rheumatoid arthritis |
| Clivatuzumab tetraxetan | hPAM4-Cide | mab | humanized | MUC1 | pancreatic cancer |
| Codrituzumab | | mab | humanized | glypican 3 | cancer |
| Coltuximab ravtansine | | mab | chimeric | CD19 | cancer |
| Conatumumab | | mab | human | TRAIL-R2 | cancer |
| Concizumab | | mab | humanized | TFPI | bleeding |
| CR6261 | | mab | human | Influenza A hemagglutinin | infectious disease/influenza A |
| Crenezumab | | mab | humanized | 1-40-β-amyloid | Alzheimer's disease |
| Crotedumab | | mab | human | GCGR | diabetes |
| Dacetuzumab | | mab | humanized | CD40 | hematologic cancers |
| Daclizumab | Zenapax | mab | humanized | CD25 (α chain of IL-2 receptor) | prevention of organ transplant rejections |
| Dalotuzumab | | mab | humanized | IGF-1 receptor (CD221) | cancer etc. |
| Dapirolizumab pegol | | mab | humanized | CD154 (CD40L) | — |
| Daratumumab | | mab | human | CD38 (cyclic ADP ribose hydrolase) | cancer |
| Dectrekumab | | mab | human | IL-13 | — |
| Demcizumab | | mab | humanized | DLL4 | cancer |
| Denintuzumab mafodotin | | mab | humanized | CD19 | cancer |
| Denosumab | Prolia | mab | human | RANKL | osteoporosis, bone metastases etc. |
| Depatuxizumab mafodotin | | mab | chimeric/humanized | EGFR | cancer |

TABLE 3-continued

| Antibody Name | Trade name | Type | Source | Target | Use |
|---|---|---|---|---|---|
| Derlotuximab biotin | | mab | chimeric | histone complex | recurrent glioblastoma multiforme |
| Detumomab | | mab | mouse | B-lymphoma cell | lymphoma |
| Dinutuximab | | mab | chimeric | GD2 ganglioside | neuroblastoma |
| Diridavumab | | mab | human | hemagglutinin | influenza A |
| Domagrozumab | | mab | humanized | GDF-8 | Duchenne muscular dystrophy |
| Dorlimomab aritox | | $F(ab')_2$ | mouse | — | — |
| Drozitumab | | mab | human | DR5 | cancer etc. |
| Duligotumab | | mab | human | ERBB3 (HER3) | testicular cancer |
| Dupilumab | | mab | human | IL4 | atopic diseases |
| Durvalumab | | mab | human | CD274 | cancer |
| Dusigitumab | | mab | human | ILGF2 | cancer |
| Ecromeximab | | mab | chimeric | GD3 ganglioside | malignant melanoma |
| Eculizumab | Soliris | mab | humanized | C5 | paroxysmal nocturnal hemoglobinuria, atypical HUS |
| Edobacomab | | mab | mouse | endotoxin | sepsis caused by Gram-negative bacteria |
| Edrecolomab | Panorex | mab | mouse | EpCAM | colorectal carcinoma |
| Efalizumab | Raptiva | mab | humanized | LFA-1 (CD11a) | psoriasis (blocks T-cell migration) |
| Efungumab | Mycograb | scFv | human | Hsp90 | invasive Candida infection |
| Eldelumab | | mab | human | interferon gamma-induced protein | Crohn's disease, ulcerative colitis |
| Elgemtumab | | mab | human | ERBB3 (HER3) | cancer |
| Elotuzumab | | mab | humanized | SLAMF7 | multiple myeloma |
| Elsilimomab | | mab | mouse | IL-6 | — |
| Emactuzumab | | mab | humanized | CSF1R | cancer |
| Emibetuzumab | | mab | humanized | HHGFR | cancer |
| Emicizumab | | mab | humanized | activated F9, F10 | haemophilia A |
| Enavatuzumab | | mab | humanized | TWEAK receptor | cancer etc. |
| Enfortumab vedotin | | mab | human | AGS-22M6 | cancer expressing Nectin-4 |
| Enlimomab pegol | | mab | mouse | ICAM-1 (CD54) | — |
| Enoblituzumab | | mab | humanized | CD276 | cancer |
| Enokizumab | | mab | humanized | IL9 | asthma |
| Enoticumab | | mab | human | DLL4 | — |
| Ensituximab | | mab | chimeric | 5AC | cancer |
| Epitumomab cituxetan | | mab | mouse | episialin | — |
| Epratuzumab | | mab | humanized | CD22 | cancer, SLE |
| Erenumab | | mab | human | CGRP | migraine |
| Erlizumab | | $F(ab')_2$ | humanized | ITGB2 (CD18) | heart attack, stroke, traumatic shock |
| Ertumaxomab | Rexomun | 3funct | rat/mouse hybrid | HER2/neu, CD3 | breast cancer etc. |
| Etaracizumab | Abegrin | mab | humanized | integrin $\alpha v\beta 3$ | melanoma, prostate cancer, ovarian cancer etc. |
| Etrolizumab | | mab | humanized | integrin $\alpha 7$ $\beta 7$ | inflammatory bowel disease |
| Evinacumab | | mab | human | angiopoietin 3 | dyslipidemia |
| Evolocumab | | mab | human | PCSK9 | hypercholesterolemia |
| Exbivirumab | | mab | human | hepatitis B surface antigen | hepatitis B |
| Fanolesomab | NeutroSpec | mab | mouse | CD15 | appendicitis (diagnosis) |
| Faralimomab | | mab | mouse | interferon receptor | — |
| Farletuzumab | | mab | humanized | folate receptor 1 | ovarian cancer |
| Fasinumab | | mab | human | HNGF | acute sciatic pain |
| FBTA05 | Lymphomun | 3funct | rat/mouse hybrid | CD20 | chronic lymphocytic leukaemia |
| Felvizumab | | mab | humanized | respiratory syncytial virus | respiratory syncytial virus infection |
| Fezakinumab | | mab | human | IL-22 | rheumatoid arthritis, psoriasis |
| Fibatuzumab | | mab | humanized | ephrin receptor A3 | — |
| Ficlatuzumab | | mab | humanized | HGF | cancer etc. |
| Figitumumab | | mab | human | IGF-1 receptor (CD221) | adrenocortical carcinoma, non-small cell lung carcinoma etc. |
| Firivumab | | mab | human | influenza A virus hemagglutinin | — |
| Flanvotumab | | mab | human | TYRP1 (gly coprote in 75) | melanoma |
| Fletikumab | | mab | human | IL 20 | rheumatoid arthritis |
| Fontolizumab | HuZAF | mab | humanized | IFN-$\gamma$ | Crohn's disease etc. |
| Foralumab | | mab | human | CD3 epsilon | — |

TABLE 3-continued

| Antibody Name | Trade name | Type | Source | Target | Use |
|---|---|---|---|---|---|
| Foravirumab | | mab | human | rabies virus glycoprotein | rabies (prophylaxis) |
| Fresolimumab | | mab | human | TGF-β | idiopathic pulmonary fibrosis, focal segmental glomerulosclerosis, cancer |
| Fulranumab | | mab | human | NGF | pain |
| Futuximab | | mab | chimeric | EGFR | cancer |
| Galcanezumab | | mab | humanized | calcitonin | migraine |
| Galiximab | | mab | chimeric | CD80 | B-cell lymphoma |
| Ganitumab | | mab | human | IGF-1 receptor (CD221) | cancer |
| Gantenerumab | | mab | human | beta amyloid | Alzheimer's disease |
| Gavilimomab | | mab | mouse | CD147 (basigin) | graft versus host disease |
| Gemtuzumab ozogamicin | Mylotarg | mab | humanized | CD33 | acute myelogenous leukemia |
| Gevokizumab | | mab | humanized | IL-1β | diabetes etc. |
| Girentuximab | Rencarex | mab | chimeric | carbonic anhydrase 9 (CA-IX) | clear cell renal cell carcinoma[84] |
| Glembatumumab vedotin | | mab | human | GPNMB | melanoma, breast cancer |
| Golimumab | Simponi | mab | human | TNF-α | rheumatoid arthritis, psoriatic arthritis, ankylosing spondylitis |
| Gomiliximab | | mab | chimeric | CD23 (IgE | allergic asthma receptor) |
| Guselkumab | | mab | human | IL23 | psoriasis |
| Ibalizumab | | mab | humanized | CD4 | HIV infection |
| Ibritumomab tiuxetan | Zevalin | mab | mouse | CD20 | non-Hodgkin's lymphoma |
| Icrucumab | | mab | human | VEGFR-1 | cancer etc. |
| Idarucizumab | | mab | humanized | dabigatran | reversal of anticoagulant effects of dabigatran |
| Igovomab | Indimacis-125 | $F(ab')_2$ | mouse | CA-125 | ovarian cancer (diagnosis) |
| IMAB362 | | mab | human | CLDN18.2 | gastrointestinal adenocarcinomas and pancreatic tumor |
| Imalumab | | mab | human | MIF | cancer |
| Imciromab | Myoscint | mab | mouse | cardiac myosin | cardiac imaging |
| Imgatuzumab | | mab | humanized | EGFR | cancer |
| Inclacumab | | mab | human | selectin P | cardiovascular disease |
| Indatuximab ravtansine | | mab | chimeric | SDC1 | cancer |
| Indusatumab vedotin | | mab | human | GUCY2C | cancer |
| Inebilizumab | | mab | humanized | CD19 | cancer, systemic sclerosis, multiple sclerosis |
| Infliximab | Remicade | mab | chimeric | TNF-α | rheumatoid arthritis, ankylosing spondylitis, psoriatic arthritis, psoriasis, Crohn's disease, ulcerative colitis |
| Inolimomab | | mab | mouse | CD25 (α chain of IL-2 receptor) | graft versus host disease |
| Inotuzumab ozogamicin | | mab | humanized | CD22 | ALL |
| Intetumumab | | mab | human | CD51 | solid tumors (prostate cancer, melanoma) |
| Ipilimumab | Yervoy | mab | human | CD152 | melanoma |
| Iratumumab | | mab | human | CD30 (TNFRSF8) | Hodgkin's lymphoma |
| Isatuximab | | mab | chimeric | CD38 | cancer |
| Itolizumab | | mab | humanized | CD6 | — |
| Ixekizumab | | mab | humanized | IL 17A | autoimmune diseases |
| Keliximab | | mab | chimeric | CD4 | chronic asthma |
| Labetuzumab | CEA-Cide | mab | humanized | CEA | colorectal cancer |
| Lampalizumab | | mab | humanized | CFD | geographic atrophy secondary to age-related macular degeneration |
| Lanadelumab | | mab | human | kallikrein | angioedema |
| Landogrozumab disorders | | mab | humanized | GDF-8 | muscle wasting |
| Laprituximab emtansine | | mab | chimeric | EGFR | — |

TABLE 3-continued

| Antibody Name | Trade name | Type | Source | Target | Use |
|---|---|---|---|---|---|
| Lebrikizumab | | mab | humanized | IL-13 | asthma |
| Lemalesomab | | mab | mouse | NCA-90 (granulocyte antigen) | diagnostic agent |
| Lendalizumab | | mab | humanized | C5 | — |
| Lenzilumab | | mab | human | CSF2 | — |
| Lerdelimumab | | mab | human | TGF beta 2 | reduction of scarring after glaucoma surgeiy |
| Lexatumumab | | mab | human | TRAIL-R2 | cancer |
| Libivirumab | | mab | human | hepatitis B surface antigen | hepatitis B |
| Lifastuzumab vedotin | | mab | humanized | phosphate-sodium co-transporter | cancer |
| Ligelizumab | | mab | humanized | IGHE | severe asthma and chronic spontaneous urticaria |
| Lilotomab satetraxetan | | mab | mouse | CD37 | cancer |
| Lintuzumab | | mab | humanized | CD33 | cancer |
| Lirilumab | | mab | human | KIR2D | solid and hematological cancers |
| Lodelcizumab | | mab | humanized | PCSK9 | hypercholesterolemia |
| Lokivetmab | | mab | veterinary | *Canis lupus familiaris* IL31 | — |
| Lorvotuzumab mertansine | | mab | humanized | CD56 | cancer |
| Lucatumumab | | mab | human | CD40 | multiple myeloma, non-Hodgkin's lymphoma, Hodgkin's lymphoma |
| Lulizumab pegol | | mab | humanized | CD28 | autoimmune diseases |
| Lumiliximab | | mab | chimeric | CD23 (IgE receptor) | chronic lymphocytic leukemia |
| Lumretuzumab | | mab | humanized | ERBB3 (HER3) | cancer |
| MABp1 | Xilonix | mab | human | IL1A | colorectal cancer |
| Mapatumumab | | mab | human | TRAIL-R1 | cancer |
| Margetuximab | | mab | humanized | ch4D5 | cancer |
| Maslimomab | | — | mouse | T-cell receptor | — |
| Matuzumab | | mab | humanized | EGFR | colorectal, lung and stomach cancer |
| Mavrilimumab | | mab | human | GMCSF receptor α-chain | rheumatoid arthritis |
| Mepolizumab | Bosatria | mab | humanized | IL-5 | asthma and white blood cell diseases |
| Metelimumab | | mab | human | TGF beta 1 | systemic scleroderma |
| Milatuzumab | | mab | humanized | CD74 | multiple myeloma and other hematological malignancies |
| Minretumomab | | mab | mouse | TAG-72 | tumor detection (and therapy—) |
| Mirvetuximab soravtansine | | mab | chimeric | folate receptor alpha | cancer |
| Mitumomab | | mab | mouse | GD3 ganglioside | small cell lung carcinoma |
| Mogamulizumab | | mab | humanized | CCR4 | cancer |
| Monalizumab | | mab | humanized | KLRC1 | — |
| Morolimumab | | mab | human | Rhesus factor | — |
| Motavizumab | Numax | mab | humanized | respiratory syncytial virus | respiratory syncytial virus (prevention) |
| Moxetumomab pasudotox | | mab | mouse | CD22 | cancer |
| Muromonab-CD3 | Orthoclone OKT3 | mab | mouse | CD3 | prevention of organ transplant rejections |
| Nacolomab tafenatox | | Fab | mouse | C242 | antigen colorectal cancer |
| Namilumab | | mab | human | CSF2 | — |
| Naptumomab estafenatox | | Fab | mouse | 5T4 | non-small cell lung carcinoma, renal cell carcinoma |
| Naratuximab emtansine | | mab | chimeric | CD37 | — |
| Narnatumab | | mab | human | RON | cancer |
| Natalizumab | Tysabri | mab | humanized | integrin α4 | multiple sclerosis, Crohn's disease |
| Navicixizumab | | mab | chimeric/humanized | DLL4 | — |
| Navivumab | | mab | human | influenza A virus hemagglutinin HA | — |
| Nebacumab | | mab | human | endotoxin | sepsis |
| Necitumumab | | mab | human | EGFR | non-small cell lung carcinoma |

TABLE 3-continued

| Antibody Name | Trade name | Type | Source | Target | Use |
|---|---|---|---|---|---|
| Nemolizumab | | mab | humanized | IL31RA | eczema[106] |
| Nerelimomab | | mab | mouse | TNF-α | — |
| Nesvacumab | | mab | human | angiopoietin 2 | cancer |
| Nimotuzumab | Theracim, Theraloc | mab | humanized | EGFR | squamous cell carcinoma, head and neck cancer, nasopharyngeal cancer, glioma |
| Nivolumab | Opdivo | mab | human | PD-1 | cancer |
| Nofetumomab merpentan | Verluma | Fab | mouse | — | cancer (diagnosis) |
| Obiltoxaximab | | mab | chimeric | *Bacillus anthracis* anthrax | *Bacillus anthracis* spores |
| Obinutuzumab | Gazyva | mab | humanized | CD20 | Chronic lymphatic leukemia |
| Ocaratuzumab | | mab | humanized | CD20 | cancer |
| Ocrelizumab | | mab | humanized | CD20 | rheumatoid arthritis, lupus erythematosus etc. |
| Odulimomab | | mab | mouse | LFA-1 (CD11a) | prevention of organ transplant rejections, immunological diseases |
| Ofatumumab | Arzerra | mab | human | CD20 | chronic lymphocytic leukemia etc. |
| Olaratumab | | mab | human | PDGF-R α | cancer |
| Olokizumab | | mab | humanized | IL6 | — |
| Omalizumab | Xolair | mab | humanized | IgE Fc region | allergic asthma |
| Onartuzumab | | mab | humanized | human scatter factor receptor kinase | cancer |
| Ontuxizumab | | mab | chimeric/humanized | TEM1 | cancer |
| Opicinumab | | mab | human | LINGO-1 | multiple sclerosis |
| Oportuzumab monatox | | scFv | humanized | EpCAM | cancer |
| Oregovomab | OvaRex | mab | mouse | CA-125 | ovarian cancer |
| Orticumab | | mab | human | oxLDL | — |
| Otelixizumab | | mab | chimeric/humanized | CD3 | diabetes mellitus type 1 |
| Otlertuzumab | | mab | humanized | CD37 | cancer |
| Oxelumab | | mab | human | OX-40 | asthma |
| Ozanezumab | | mab | humanized | NOGO-A | ALS and multiple sclerosis |
| Ozoralizumab | | mab | humanized | TNF-α | inflammation |
| Pagibaximab | | mab | chimeric | lipoteichoic acid | sepsis (*Staphylococcus*) |
| Palivizumab | Synagis, Abbosynagis | mab | humanized | F protein of respiratory syncytial virus | respiratory syncytial virus (prevention) |
| Pamrevlumab | | mab | human | CTGF | — |
| Panitumumab | Vectibix | mab | human | EGFR | colorectal cancer |
| Pankomab | | mab | humanized | tumor specific glycosylation of MUC1 | ovarian cancer |
| Panobacumab | | mab | human | *Pseudomonas aeruginosa* | *Pseudomonas aeruginosa* infection |
| Parsatuzumab | | mab | human | EGFL7 | cancer |
| Pascolizumab | | mab | humanized | IL-4 | asthma |
| Pasotuxizumab | | mab | chimeric/humanized | folate hydrolase | cancer |
| Pateclizumab | | mab | humanized | LTA | TNF |
| Patritumab | | mab | human | ERBB3 (HER3) | cancer |
| Pembrolizumab | | mab | humanized | PDCD1 | melanoma and other cancers |
| Pemtumomab | Theragyn | — | mouse | MUC1 | cancer |
| Perakizumab | | mab | humanized | IL 17A | arthritis |
| Pertuzumab | Omnitarg | mab | humanized | HER2/neu | cancer |
| Pexelizumab | | scFv | humanized | C5 | reduction of side effects of cardiac surgery |
| Pidilizumab | | mab | humanized | PD-1 | cancer and infectious diseases |
| Pinatuzumab vedotin | | mab | humanized | CD22 | cancer |
| Pintumomab | | mab | mouse | adenocarcinoma antigen | adenocarcinoma (imaging) |
| Placulumab | | mab | human | human TNF | pain and inflammatory diseases |
| Plozalizumab | | mab | humanized | CCR2 | diabetic nephropathy and arteriovenous graft patency |
| Pogalizumab | | mab | humanized | TNFR superfamily member 4 | — |

TABLE 3-continued

| Antibody Name | Trade name | Type | Source | Target | Use |
|---|---|---|---|---|---|
| Polatuzumab vedotin | | mab | humanized | CD79B | cancer |
| Ponezumab | | mab | humanized | human beta-amyloid | Alzheimer's disease |
| Prezalizumab | | mab | humanized | ICOSL | — |
| Priliximab | | mab | chimeric | CD4 | Crohn's disease, multiple sclerosis |
| Pritoxaximab | | mab | chimeric | *E. coli* shiga toxin type-1 | — |
| Pritumumab | | mab | human | vimentin | brain cancer |
| PRO 140 | | — | humanized | CCR5 | HIV infection |
| Quilizumab | | mab | humanized | IGHE | asthma |
| Racotumomab | | mab | mouse | N-glycolylneuraminic acid | cancer |
| Radretumab | | mab | human | fibronectin extra domain-B | cancer |
| Rafivirumab | | mab | human | rabies virus glycoprotein | rabies (prophylaxis) |
| Ralpancizumab | | mab | humanized | neural apoptosis-regulated proteinase 1 | dyslipidemia |
| Ramucirumab | Cyramza | mab | human | VEGFR2 | solid tumors |
| Ranibizumab | Lucentis | Fab | humanized | VEGF-A | macular degeneration (wet form) |
| Raxibacumab | | mab | human | anthrax toxin, protective antigen | anthrax (prophylaxis and treatment) |
| Refanezumab | | mab | humanized | myelin-associated glycoprotein | recovery of motor function after stroke |
| Regavirumab | | mab | human | cytomegalovirus glycoprotein B | cytomegalovirus infection |
| Reslizumab | | mab | humanized | IL-5 | inflammations of the airways, skin and gastrointestinal tract |
| Rilotumumab | | mab | human | HGF | solid tumors |
| Rinucumab | | mab | human | platelet-derived growth factor receptor beta | neovascular age-related macular degeneration |
| Risankizumab | | mab | humanized | IL23A | — |
| Rituximab | MabThera, Rituxan | mab | chimeric | CD20 | lymphomas, leukemias, some autoimmune disorders |
| Rivabazumab pegol | | mab | humanized | *Pseudomonas aeruginosa* type III secretion system | — |
| Robatumumab | | mab | human | IGF-1 receptor (CD221) | cancer |
| Roledumab | | mab | human | MID | — |
| Romosozumab | | mab | humanized | sclerostin | osteoporosis |
| Rontalizumab | | mab | humanized | IFN-α | systemic lupus erythematosus |
| Rovalpituzumab tesirine | | mab | humanized | DLL3 | — |
| Rovelizumab | LeukArrest | mab | humanized | CD11, CD18 | haemonrhagic shock etc. |
| Ruplizumab | Antova | mab | humanized | CD154 (CD40L) | rheumatic diseases |
| Sacituzumab govitecan | | mab | humanized | tumor-associated calcium signal transducer 2 | cancer |
| Samalizumab | | mab | humanized | CD200 | cancer |
| Sapelizumab | | mab | humanized | IL6R | — |
| Sarilumab | | mab | human | IL6 | rheumatoid arthritis, ankylosing spondylitis |
| Satumomab pendetide | | mab | mouse | TAG-72 | cancer (diagnosis) |
| Secukinumab | | mab | human | IL17A | uveitis, rheumatoid arthritis psoriasis |
| Seribantumab | | mab | human | ERBB3 (HER3) | cancer |
| Setoxaximab | | mab | chimeric | *E. coli* shiga toxin type-2 | — |
| Sevirumab | | — | human | cytomegalovirus | cytomegalovirus infection |
| SGN-CD19A | | mab | humanized | CD19 | acute lymphoblastic leukemia and B-cell non-Hodgkin lymphoma |
| SGN-CD33A | | mab | humanized | CD33 | Acute myeloid leukemia |
| Sibrotuzumab | | mab | humanized | FAP | cancer |
| Sifalimumab | | mab | humanized | IFN-α | SLE, dermatomyositis, polymyositis |

TABLE 3-continued

| Antibody Name | Trade name | Type | Source | Target | Use |
|---|---|---|---|---|---|
| Siltuximab | | mab | chimeric | IL-6 | cancer |
| Simtuzumab | | mab | humanized | LOXL2 | fibrosis |
| Siplizumab | | mab | humanized | CD2 | psoriasis, graft-versus-host disease (prevention) |
| Sirukumab | | mab | human | IL-6 | rheumatoid arthritis |
| Sofituzumab vedotin | | mab | humanized | CA-125 | ovarian cancer |
| Solanezumab | | mab | humanized | beta amyloid | Alzheimer's disease |
| Solitomab | | BiTE | mouse | EpCAM | — |
| Sonepcizumab | | — | humanized | sphingosine-1-phosphate | choroidal and retinal neovascularization |
| Sontuzumab | | mab | humanized | episialin | — |
| Stamulumab | | mab | human | myostatin | muscular dystrophy |
| Sulesomab | LeukoScan | Fab' | mouse | NCA-90 (granulocyte antigen) | osteomyelitis (imaging) |
| Suvizumab | | mab | humanized | HIV-1 | viral infections |
| Tabalumab | | mab | human | BAFF | B-cell cancers |
| Tacatuzumab tetraxetan | AFP-Cide | mab | humanized | alpha-fetoprotein | cancer |
| Tadocizumab | | Fab | humanized | integrin αIIbβ3 | percutaneous coronary intervention |
| Talizumab | | mab | humanized | IgE | allergic reaction |
| Tamtuvetmab | Tactress | mab | veterinary | CD52 | — |
| Tanezumab | | mab | humanized | NGF | pain |
| Taplitumomab paptox | | mab | mouse | CD19 | cancer[citation needed] |
| Tarextumab | | mab | human | Notch receptor | cancer |
| Tefibazumab | Aurexis | mab | humanized | clumping factor A | *Staphylococcus aureus* infection |
| Telimomab aritox | | Fab | mouse | — | — |
| Tenatumomab | | mab | mouse | tenascin C | cancer |
| Teneliximab | | mab | chimeric | CD40 | autoimmune diseases and prevention of organ transplant rejection |
| Teplizumab | | mab | humanized | CD3 | diabetes mellitus type 1 |
| Teprotumumab | | mab | human | IGF-1 receptor (CD221) | hematologic tumors |
| Tesidolumab | | mab | human | C5 | — |
| Tetulomab | | mab | humanized | CD37 | cancer[141] |
| Tezepelumab | | mab | human | TSLP | asthma, atopic dermatitis |
| TGN1412 | | — | humanized | CD28 | chronic lymphocytic leukemia, rheumatoid arthritis |
| Ticilimumab (= tremelimumab) | | mab | human | CTLA-4 | cancer |
| Tigatuzumab | | mab | humanized | TRAIL-R2 | cancer |
| Tildrakizumab | | mab | humanized | IL23 | immunologically mediated inflammatory disorders |
| Timolumab | | mab | human | AOC3 | — |
| Tisotumab vedotin | | mab | human | coagulation factor III | — |
| TNX-650 | | — | humanized | IL-13 | Hodgkin's lymphoma |
| Tocilizumab (= atlizumab) | Actemra, RoActemra | mab | humanized | IL-6 receptor | rheumatoid arthritis |
| Toralizumab | | mab | humanized | CD154 (CD4OL) | rheumatoid arthritis, lupus nephritis etc. |
| Tosatoxumab | | mab | human | *Staphylococcus aureus* | — |
| Tositumomab | Bexxar | — | mouse | CD20 | follicular lymphoma |
| Tovetumab | | mab | human | CD140a | cancer |
| Tralokinumab | | mab | human | IL-13 | asthma etc. |
| Trastuzumab | Herceptin | mab | humanized | HER2/neu | breast cancer |
| Trastuzumab emtansine | Kadcyla | mab | humanized | HER2/neu | breast cancer |
| TRBS07 | Ektomab | 3funct | — | GD2 ganglioside | melanoma |
| Tregalizumab | | mab | humanized | CD4 | — |
| Tremelimumab | | mab | human | CTLA-4 | cancer |
| Trevogrumab | | mab | human | growth differentiation factor 8 | muscle atrophy due to orthopedic disuse and sarcopenia |
| Tucotuzumab celmoleukin | | mab | humanized | EpCAM | cancer |
| Tuvirumab | | — | human | hepatitis B virus | chronic hepatitis B |
| Ublituximab | | mab | chimeric | MS4A1 | cancer |
| Ulocuplumab | | mab | human | CXCR4 (CD184) | hematologic malignancies |

TABLE 3-continued

| Antibody Name | Trade name | Type | Source | Target | Use |
|---|---|---|---|---|---|
| Urelumab | | mab | human | 4-1BB (CD137) | cancer etc. |
| Urtoxazumab | | mab | humanized | *Escherichia coli* | diarrhoea caused by *E. coli* |
| Ustekinumab | Stelara | mab | human | IL-12, IL-23 | multiple sclerosis, psoriasis, psoriatic arthritis |
| Utomilumab | | mab | human | 4-1BB (CD137) | cancer |
| Vadastuximab talirine | | mab | chimeric | CD33 | — |
| Vandortuzumab vedotin | | mab | humanized | STEAP1 | cancer |
| Vantictumab | | mab | human | Frizzled receptor | cancer |
| Vanucizumab | | mab | humanized | angiopoietin 2 | cancer |
| Vapaliximab | | mab | chimeric | AOC3 (VAP-1) | — |
| Varlilumab | | mab | human | CD27 | solid tumors and hematologic malignancies |
| Vatelizumab | | mab | humanized | ITGA2 (CD49b) | — |
| Vedolizumab | Entyvio | mab | humanized | integrin $\alpha 4\beta 7$ | Crohn's disease, ulcerative colitis |
| Veltuzumab | | mab | humanized | CD20 | non-Hodgkin's lymphoma |
| Vepalimomab | | mab | mouse | AOC3 (VAP-1) | inflammation |
| Vesencumab | | mab | human | NRP1 | solid malignancies |
| Visilizumab | Nuvion | mab | humanized | CD3 | Crohn's disease, ulcerative colitis |
| Vobarilizumab | | mab | humanized | IL6R | inflammatory autoimmune diseases |
| Volociximab | | mab | chimeric | integrin $\alpha 5\beta 1$ | solid tumors |
| Vorsetuzumab mafodotin | | mab | humanized | CD70 | cancer |
| Votumumab | HumaSPECT | mab | human | tumor antigen CTAA16.88 | colorectal tumors |
| Xentuzumab | | mab | | IGF1, IGF2 | — |
| Zalutumumab | HuMax-EGFr | mab | human | EGFR | squamous cell carcinoma of the head and neck |
| Zanolimumab | HuMax-CD4 | mab | human | CD4 | rheumatoid arthritis, psoriasis, T-cell lymphoma |
| Zatuximab | | mab | chimeric | HER1 | cancer |
| Ziralimumab | | mab | human | CD147 (basigin) | — |
| Zolimomab aritox | | mab | mouse | CD5 | systemic lupus erythematosus, graft-versus-host disease |

Further examples of therapeutic proteins that can be expressed with the methods, systems, and compositions described herein include the therapeutic monoclonal antibodies (mAbs), Fabs, F(ab)2s, and scFv's, such as broadly neutralizing anti-HIV monoclonals, including antibody 10-1074 (Caskey et al., Nat Med. 2017 February; 23(2):185-191, Epub 2017 Jan. 16, herein incorporated by reference in its entirety); HIV-1 antibody 3BNC117 (Scheid, et al., Nature. 2016 Jul. 28; 535(7613):556-60, herein incorporated by reference in its entirety); and VRC01 (see, e.g., Bar et al., N Engl J Med. 2016 Nov. 24; 375(21):2037-2050, herein incorporated by reference in its entirety).

In some embodiments, compositions and systems herein are provided and/or administered in doses selected to elicit a therapeutic and/or prophylactic effect in an appropriate subject (e.g., mouse, human, etc.). In some embodiments, a therapeutic dose is provided. In some embodiments, a prophylactic dose is provided. Dosing and administration regimes are tailored by the clinician, or others skilled in the pharmacological arts, based upon well-known pharmacological and therapeutic/prophylactic considerations including, but not limited to, the desired level of pharmacologic effect, the practical level of pharmacologic effect obtainable, toxicity. Generally, it is advisable to follow well-known pharmacological principles for administrating pharmaceutical agents (e.g., it is generally advisable to not change dosages by more than 50% at time and no more than every 3-4 agent half-lives). For compositions that have relatively little or no dose-related toxicity considerations, and where maximum efficacy is desired, doses in excess of the average required dose are not uncommon. This approach to dosing is commonly referred to as the "maximal dose" strategy. In certain embodiments, a dose (e.g., therapeutic of prophylactic) is about 0.01 mg/kg to about 200 mg/kg (e.g., 0.01 mg/kg, 0.02 mg/kg, 0.05 mg/kg, 0.1 mg/kg, 0.2 mg/kg, 0.5 mg/kg, 1.0 mg/kg, 2.0 mg/kg, 5.0 mg/kg, 10 mg/kg, 20 mg/kg, 50 mg/kg, 100 mg/kg, 200 mg/kg, or any ranges therebetween (e.g., 5.0 mg/kg to 100 mg/kg)). In some embodiments, a subject is between 0.1 kg (e.g., mouse) and 150 kg (e.g., human), for example, 0.1 kg, 0.2 kg, 0.5 kg, 1.0 kg, 2.0 kg, 5.0 kg, 10 kg, 20 kg, 50 kg, 100 kg, 200 kg, or any ranges therebetween (e.g., 40-125 kg). In some embodiments, a dose comprises between 0.001 mg and 40,000 mg (e.g., 0.001 mg, 0.002 mg, 0.005 mg, 0.01 mg, 0.02 mg, 0.05 mg, 0.1 kg, 0.2 mg, 0.5 mg, 1.0 mg, 2.0 mg, 5.0 mg, 10 mg, 20 mg, 50 mg, 100 mg, 200 mg, 500 mg, 1,000 mg, 2,000 mg, 5,000 mg, 10,000 mg, 20,000 mg, 40,000 mg, or ragnes therebetween.

EXAMPLES

In all of the Examples below, all of the expression vectors are CpG free except for Genscript px458-relA1 (SEQ ID NO:8) and Genscript px458-relA4 (SEQ ID NO:9), both of which are CpG-laden sequences which are commercially available (see, www followed by "genscript.com/CRISPR-gRNA-constructs.html.").

Example 1

Long-Term Therapeutic Rituximab Expression

This Example describes experiments conducted that demonstrate long-term expression of monoclonal antibody Rituximab at therapeutic serum levels following a single injection of either a dual cassette or single cassette plasmid vector encoding Rituximab.

First Example

In a first example, three mice were injected per group. Each mouse received a single IV injection of 1050 nmoles of DOTAP cationic liposomes containing 2.5% dexamethasone palmitate (DP) incorporated into the liposome bilayer. This was followed two minutes later by a single IV injection of 75 ug of one of two different plasmid DNAs encoding anti-CD20 (Rituximab). Both groups were treated two hours prior to IV injection with an IP injection of 40 mg/kg dexamethasone. Plasmid 715.1 2a (P2A), shown in FIG. 5 (SEQ ID NO:3) encodes the anti-CD20 mAb heavy and light chain cDNAs separated by a 2A self-cleaving peptide. Plasmid 718.1, shown in FIG. 6 (SEQ ID NO:4), is dual expression cassette plasmid vector that encode the anti-CD20 mAb heavy and light chain cDNAs respectively. Serum levels of anti-CD20 were determined by ELISA 24 hours following injection and in 7-day intervals thereafter. The ELISA kit was purchased from Eagle Biosciences.

Figure 2A:
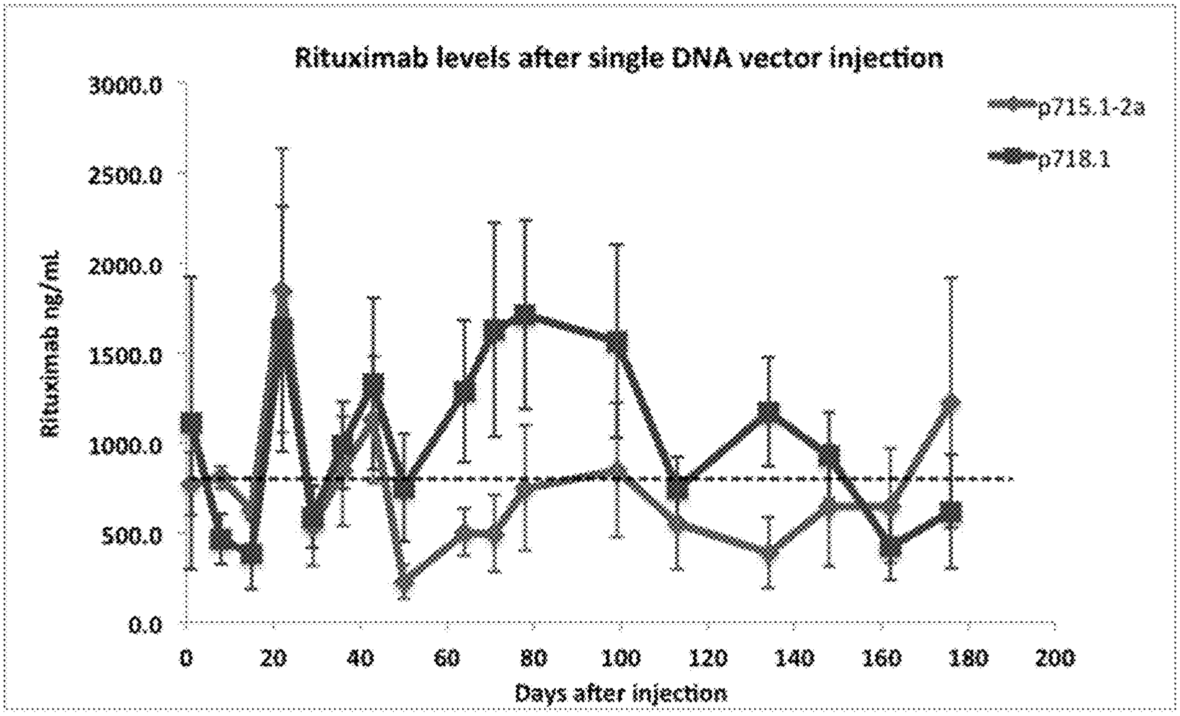
FIG. 2A shows that a single IV, sequential injection of cationic liposomes followed by either a dual cassette or a single expression cassette plasmid DNA vector encoding Rituximab produces long term therapeutic serum levels of Rituximab protein.

The results are shown in FIG. 2A. Injection of each plasmid produced serum anti-CD20 mAb protein levels approaching or above 1 at ug/ml levels, 24 hrs post injection. Serum anti-CD20 mAb protein levels are sustained within this range in both groups for at least the next 178 days. Serum anti-CD20 mAb protein levels were undetectable in mice receiving the same protocol except that the DNA vector encoded human G-CSF cDNA. These data demonstrate that dual cassette, as well as single cassette plasmid DNA vectors encoding anti-CD20 mAb can produce prolonged, sustained serum anti-CD20 mAb protein levels after a single IV injection.

Second Example

Figure 2B:
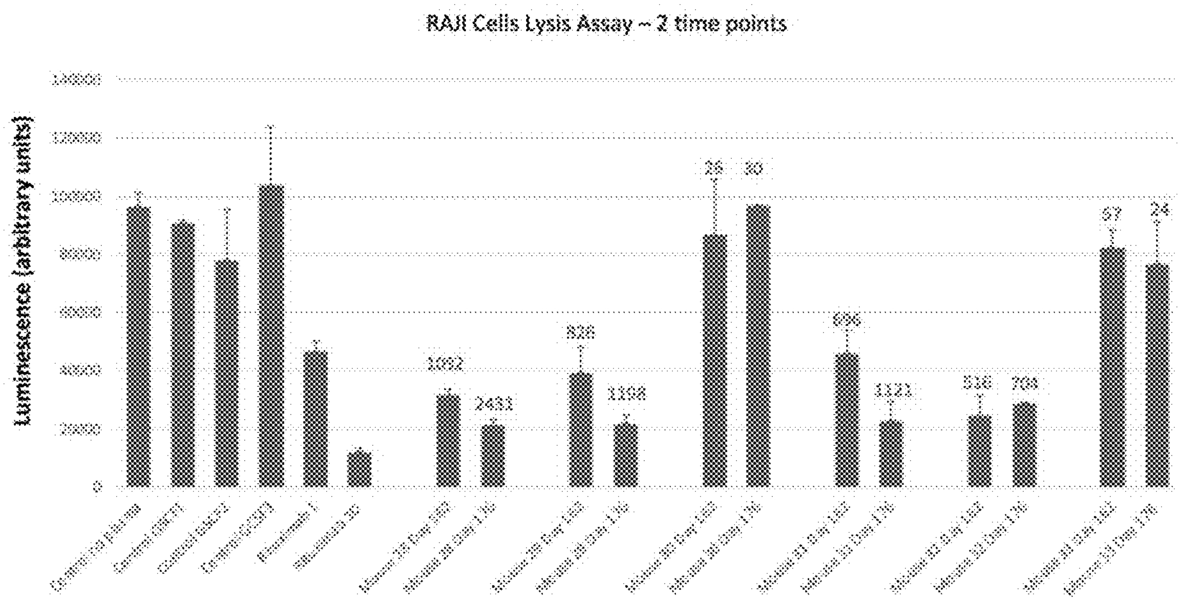
FIG. 2B shows, as described in Example 1, sera from mice sequentially injected with cationic liposomes followed by a dual cassette anti-CD20 DNA expression vector 162 and subsequently 176 days earlier (see FIG. 2A) lyses CD 20 positive Raji human B lymphoma cells as effectively as high concentrations of recombinant Rituximab monoclonal antibody protein.

In a second example, Raji cells (5×10 4 cells/well) were plated in 96 well plates using RPMI+10% FBS medium. Next day cells were incubated with Rituximab (0.5, 1, 10 ug/ml) or mouse serum samples (20 ul/well, duplicate samples) for 1 h at room temperature. Twenty microliters of pooled normal human plasma (Innovative Research) was then added to all wells (except the Rituximab control condition) and the plates incubated for another 12 h at 37 C. Cell viability was measured using the PROMEGA Cell titer Glo reagent according to the manufacturer's instructions. Results are shown in FIG. 2B, where values are shown as percentage change from the control conditions (no treatment). Rituximab concentrations for each mouse sample rested are shown in FIG. 2B. Ctrl 1-2 samples refer to mouse serum from mice injected with a control plasmid (encoding for G-CSF). Bars represent standard deviation for duplicate samples.

Serum from mice sequentially injected with cationic liposomes, then a plasmid DNA vector encoding either anti-CD20 mAb 148 days earlier or human G-CSF was analyzed first by ELISA for concentration determination of anti-CD20. The numbers in red font placed above the bars represent the concentration of Rituxumab for the corresponding serum samples (ng/ml). Using a cell lysis assay, sera isolated from anti-CD20 DNA vector-injected mice 148 days earlier lysed CD-20+ human Raji cells at a level comparable to Raji cells treated with a high concentration of recombinant Rituximab protein (Invivogen). These data (in FIG. 2B) show that anti-CD20 DNA vector-injected mice produce fully bioactive Rituximab mAb protein for at least 176 days after a single DNA vector injection.

Third Example

In a third example, three mice were injected per group. Each mouse received a single IV injection of 1000 nmoles of DOTAP cationic liposomes containing 2.5% dexamethasone palmitate (DP) incorporated into the liposome bilayer. This was followed two minutes later by a single IV injection of 75 ug of one of two different plasmid DNAs encoding anti-CD20 (Rituximab). Both groups were treated two hours prior to IV injection with an IP injection of 40 mg/kg dexamethasone. Plasmid 902.8 (P2A), shown in FIG. 7 (SEQ ID NO:5) encodes the anti-CD20 mAb heavy and light chain cDNAs separated by a 2A self-cleaving peptide. Plasmid 718.1, shown in FIG. 6 (SEQ ID NO:4), is a dual expression cassette plasmid vector that encode the anti-CD20 mAb heavy and light chain cDNAs respectively. Serum levels of anti-CD20 were determined by ELISA 24 hours following injection and in 7-day intervals thereafter. The ELISA kit was purchased from Eagle Biosciences. The results in FIG. 3 shows that injection of each plasmid produced serum anti-CD20 mAb protein levels approaching or above 1 at ug/ml levels, 24 hrs post injection. Serum anti-CD20 mAb protein levels were within this range for both groups at 57 days after injection.

Fourth Example

In a fourth example, three mice were injected per group. Each mouse received a single IV injection of 1000 nmoles of DOTAP cationic liposomes and 1000 nmoles of DMPC neutral liposomes, each containing 2.5% dexamethasone palmitate (DP) incorporated into the liposome bilayer. This was followed two minutes later by a single IV injection of 75 ug of plasmid DNA encoding anti-CD20 (Rituximab). Both groups were treated two hours prior to IV injection with an IP injection of 40 mg/kg dexamethasone. Plasmid p718.1 is a dual expression cassette plasmid vector that encodes the anti-CD20 mAb heavy and light chain cDNAs respectively. Plasmid p113.2, shown in FIG. 8 (SEQ ID NO:6), is identical, but includes a single super enhancer upstream of the second coding cassette. Serum levels of anti-CD20 were determined by ELISA 24 hours following injection. The ELISA kit was provided by Eagle Biosciences. The results are shown in FIG. 4. Both groups express anti-CD20 at 24 hrs post sequential injection. The addition of a single super enhancer element increases production of serum anti-CD20 mAb protein in mice at this time point.

Example 2

Expression of Biologically Active Nucleic Acid

This Example describes experiments conducted that demonstrate IV, sequential injection of cationic liposomes then plasmid DNA vectors encoding CPISPR/Cas9, shRNA, ribozyme or anti-sense sequences specifically targeting mouse NFkB-p65 each suppresses p65 expression in mice.

First Example

In a first example, three or four mice were injected per group. Each mouse received a single IV injection of 1000 nmoles of DOTAP cationic liposomes containing 2.5% dexamethasone palmitate (DP) incorporated into the liposome bilayer. This was followed two minutes later by a single IV injection of 75 ug of plasmid DNA encoding the indicated CRISPR- or ribozyme-based plasmids to suppress expression of endogenous mouse NFkB-p65. The plasmids used are as follows: ribozyme (FIG. 13, SEQ ID NO:7), CRISPR1 (FIG. 14, SEQ ID NO:8), CRISPR2 (FIG. 15, SEQ ID NO:9), and CRISPR (FIG. 16, SEQ ID NO:10). The control group received an CRISPR/Cas9 plasmid identical to the anti-NFkB-p65 CRISPR plasmids except the 20 bp targeting sequence targeted mouse PECAM instead. All groups were treated two hours prior to IV injection with an IP injection of 40 mg/kg dexamethasone.

Tissue preparation and anti-mouse-p65 ELISA methods were as follows. Lung lysates were generated 24 hours after injection (Anti-p65 Ribozyme) and 8 days after injection (Anti-p65 CRISPR1/2) by dissection into 500 uL of prepared 1× Triton lysis buffer on ice. Samples include both lungs per animal. Each sample was homogenized (Polytron PT 2100) for 30 seconds, pulse sonicated (Misonix XL2000 Microson Ultrasonic Cell Disruptor XL 2000), and centrifuged for 10 minutes at 4 C, and the lysate was aspirated from the tissue pellet. Protein concentration from each lysate was then determined using a BCA total protein assay purchased from Thermo Fisher. Protein normalized lysate was added to a 96 well plate ELISA from Cell Signaling Technologies (PathScan Total NF-κB p65 Sandwich ELISA Kit) in duplicate as per the manufacture's instructions. The plate was then analyzed in a (Molecular Devices Spectramax M5) plate reader. After recording absorbance from the plate, a standard curve generated using murine B16 melanoma cell supernatant was fit by 4PL analysis. Error bars represent the standard error of the mean.

The results of this example are shown in FIG. 9. These data demonstrate that anti-mouse NFkB-p65 CRISPR/Cas9—as well as ribozyme, plasmid-based targeting vectors reduce the expression of endogenous mouse p65 at 8 days and 1 day respectively following their systemic injection.

Second Example

The methods for this example are the same as above. The results are shown in FIG. 10. These data demonstrate that an anti-mouse NFkB-p65 CRISPR/Cas9, plasmid-based targeting vector reduces the expression of endogenous mouse p65, 13 days following its systemic injection in mice. Additionally, NFkB-p65 immunohistochemistry methods were performed on tissue sections from these mice.

Paraffin embedded sections of mouse lung were batch (sections from controls and treated animals) stained on a Leica Bond autostainer with a primary rabbit Mab to C-terminus of p65 (Anti-NF-kB p65 antibody [E379] (ab32536)-ABCAM). Peroxidase labeled secondary. The IHC stained slides were scanned in brightfield at 20× magnification using the Hamamatsu NanoZoomer Digital Pathology System. The digital images were then imported into Visiopharm software for quantitative analysis.

Using the Visiopharm Image Analysis module, five scattered, representative regions of lung parenchyma (ROIs) of each sample were randomly selected by the HIC image analysis technician and manually delineated for further quantitative analysis. The software converted the initial digital image into grayscale values using three features, RGB-B with a mean and polynomial smoothing filter, Contrast Red-Blue, and HDAB-DAB with minimum H&E-Eosin filter. Visiopharm software was then trained to label positive brown staining, hematoxylin counterstain, and blank space using a Bayesian classification scheme. All ROIs were processed in batch mode using this configuration to generate the desired outputs.

TABLE 2

| | Classification Scheme: Bayesian | | | |
|---|---|---|---|---|
| Measurement | Area NfKb ($\mu m^2$) | Area Tissue ($\mu m^2$) | Total Area ($\mu m^2$) | Ratio NfKb |
| Animal 143-39 | 123566.69 | 483901.69 | 607468.38 | 0.2034125 |
| Animal Ringers Cntrl | 287497.75 | 467149.91 | 754647.69 | 0.3809695 |

The ratio of NFkB was determined by dividing the Area NFkB by the Total Area of lung parenchyma. The difference between the control (Ringers) and the treated lung (143-39) ratios shows an approximately 53% reduction in NfKb staining. This finding is consistent with visual observations of stained sections. The results are shown in FIG. 41. FIG. 41A shows ringers treated control, and FIG. 41B shows the CRISPR/Cas9 anti-NFkB p65 treated mice tissue. These results demonstrate that one sequential IV injection of an CRISPR/Cas9 anti-NFkB p65 plasmid DNA vector reduced p65 protein levels by more than 50% throughout the lungs of mice injected 13 days before with the anti-NFkB p65 versus control DNA vector.

Third Example

The methods for this example are the same as above. The results are shown in FIG. 11. These data demonstrate that anti-mouse NFkB-p65 CRISPR/Cas9—as well as anti-sense, plasmid-based targeting vectors (FIG. 19, SEQ ID NO:11) reduce the expression of endogenous mouse p65 at 13 days and 1 day respectively following their systemic injection.

Fourth Example

The methods for this example are the same as above. The results are shown in FIG. 12. These data demonstrate that the anti-mouse NFkB-p65 shRNA vector p65 shB (FIG. 20, SEQ ID NO:12) and plasmid p65 shA2 (SEQ ID NO:55; FIG. 76), plasmid-based targeting vector reduces the expression of endogenous mouse p65 at 1 day following its systemic injection. Control plasmid PECAM sh control is SEQ ID NO:56, FIG. 77.

Example 3

Long-Term G-CSF Expression

This Example describes experiments conducted that demonstrate a single IV, sequential injection of cationic liposomes followed up by a plasmid DNA vector encoding the human G-CSF gene produces supra-therapeutic human G-CSF serum protein levels (FIG. 17A) and elevated absolute neutrophil counts (ANC) (FIG. 17B) for at least the next 582 days in mice. Thus, a single IV sequential liposome DNA injection can produce therapeutic serum levels of the DNA vector-encoded protein for more than one and a half years in fully immune-competent mice. The two HG-CSF plasmids employed were 011215 #7 (SEQ ID NO:45; FIG. 66), and 011315 #2 (SEQ ID NO:46; FIG. 67); and the negative control was plasmid 122014 #235 (SEQ ID NO:47; FIG. 68).

In another example, plasmid encoding HG-CSF was injected into rats. Rats No. 10 and No. 12 were given one sequential injection each, while rat 14 was re-injected twice, on days 7 and 21 after initial injection. Rat No. 10 was injected IV with 3000 nmol DOTAP SUV followed by 300 ug MARless plasmid DNA encoding HG-CSF. Rat No. 12 was injected with 3 mg Dexamethasone (IP) followed by IV injections of 3000 nmol DOTAP SUV and then 300 ug MARless plasmid DNA encoding HG-CSF. Rat No. 14 was injected at the start of the experiment with 3000 nmol DOTAP SUV and then 300 ug MAR-containing plasmid DNA encoding HG-CSF. Rat 14 was later injected on day 7 with 3 mg Dexamethasone (IP) followed by IV injections of 3300 nmol DOTAP SUV and then 330 ug MAR-containing plasmid DNA encoding HG-CSF. On day 21, rat no. 14 was injected with 3 mg Dexamethasone (IP) followed by IV injections of 4400 nmol DOTAP SUV and then 330 ug MAR-containing plasmid DNA encoding HG-CSF.

Results are shown in FIG. 18, which shows neutrophil elevation in rat serum following sequential IV injections of DOTAP cationic liposomes followed by plasmid DNA encoding HG-CSF. These results demonstrate that repeated sequential IV cationic liposome injection followed by an HG-CS plasmid DNA vector can produce sustained elevation of absolute neutrophil counts well at least the next 100 days. They also show that a dexamethasone pre-injection followed by a single sequential IV cationic liposome injection followed by an HG-CSF plasmid DNA vector can also produce sustained elevation of absolute neutrophil counts.

Example 4

Administration of PCR-Generated DNA Vectors Substantially Increases Both the Level and Duration Protein Product Production This Example describes experiments conducted that demonstrate that administration of PCR-generated DNA vectors substantially increases both the level and duration of DNA vector gene-encoded protein product production in mice when compared to plasmid DNA.

Circularized, PCR Generated DNA Vector Increases the Level of Serum Human G-CSF Production in Mice Methods: To generate DNA expression vectors by PCR, the HG-CSF expression cassette was amplified by PCR, using a primer pair containing the corresponding enzyme restriction site or a primer pair with a stem-loop configuration (for protected linear product) using Q5 High-Fidelity Polymerase (New England Biolab). The purified PCR product was digested with the corresponding enzyme (BamHI) at 10 U/ug then heat inactivated at 85 C for 20 min. Ligation of purified digested PCR was performed at 1 or 50 ng/ul with 80 T4DNA ligase Unit/ug of digested PCR at room temperature for 1 hr, then heat inactivated at 65 C for 20 min. For the 1 ng/ul ligation condition, the volume was reduced with Millipore filtration Ultra15 before purification. The ligated PCR product was then eluted with lactated ringers from the purification column before being subjected to the final 0.2 uM filtration. All purification steps were performed using a Purelink PCR purification kit (Thermofisher).

Results are shown in FIG. 21, which shows levels of human G-CSF in mouse serum, 24 hours after sequential IV injection of 1050 nmoles of DOTAP cationic liposomes, followed by 70 ug of either HG-CSF plasmid- or different forms of PCR generated, HG-CSF expression cassette DNA. Mice receiving circularized, PCR generated DNA show higher levels of serum HG-CSF than those receiving either linear, PCR generated DNA or plasmid DNA.

Circularized, PCR Generated DNA Vector Increases the Level and Duration of Serum Human G-CSF and ANCs. Furthermore, a Single Re-Injection of PCR Generating DNA Substantially Increases Long-Term, High-Level Human G-CSF Levels in Mice FIG. 22 shows levels of human G-CSF in mouse serum or plasma (left axis) and thousands per microliter absolute neutrophil counts (ANC) in whole blood (right axis) in mice for at least the next 302 days after initial injection. Mice were sequentially injected IV with cationic liposomes followed by PCR generated DNA. One group was given a repeat sequential injection of lipid and PCR DNA at Day 35, yielding significantly higher serum HG-CSF levels over the next 200 days. Heparinized whole blood was analyzed for ANC, and plasma was analyzed for HG-CSF by ELISA. Mice show significantly elevated levels of neutrophils 300 days after injection. Mean ANC in control (mock and un-injected) mice are 2K/uL. Thus, a single repeat injection of PCR generated vector DNA can substantially raise serum HG-CSF levels of the vector-expressed protein product as well as ANC for extended periods.

Inclusion of R6K DNA Sequence into Circularized, PCR Generated DNA Vector Increases the Level and Duration of Serum Human G-CSF Production in Mice Methods: 27 g mice were injected IV with DOTAP SUV cationic liposomes, followed by circularized PCR DNA encoding HG-CSF, with or without an origin of replication (R6K). Mice were subsequently bled every 7 or 14 days. FIG. 23 shows human G-CSF levels in mouse serum for 106 days following one sequential injection of cationic liposomes followed by PCR generated DNA with or without an R6K origin of replication. Thus, incorporation of selected DNA sequences, including R6K, can significantly increase serum levels of the DNA vector encoded protein for extended periods.

Example 5

Neutral Lipid and Dexamethasone Palmitate Increases Serum Levels

This Example describes experiments conducted that demonstrate that the addition of neutral lipid and dexamethasone palmitate to sequential IV administration of a human G-CSF expression vector significantly increases both human G-CSF serum levels and ANC for prolonged periods in mice.

Methods: Mice were injected with one of three different liposome preparations. 1050 nmol DOTAP SUV alone, 1050 nmol DOTAP SUV mixed with 1050 nmol DMPC neutral lipid, or 1050 nmol SUV containing 2.5% Dexamethasone Palmitate mixed with 1050 nmol DMPC. The lipid injection was followed 2 minutes later by injection of a MAR containing plasmid coding for expression of human G-CSF. Mice were subsequently bled every 7 or 14 days. Heparinized whole blood was analyzed for neutrophil counts, and plasma was analyzed for HG-CSF by ELISA. Untreated control mice are consistently <3K/uL.

FIG. 24 shows human G-CSF and corresponding absolute neutrophil counts (ANC, right axis) levels in mice injected sequentially with cationic liposomes with or without neutral lipids or Dexamethasone Palmitate, followed by plasmid DNA. Mice show significantly elevated levels of neutrophils 99 days after injection. Mice receiving neutral lipids plus Dex palmitate show the highest ANC counts over time.

Example 6

Use of a Second Enhancer to Increase Serum Levels of Expressed Protein

This Example describes experiments conducted that demonstrate that the addition of a second enhancer in a human G-CSF DNA expression plasmid can increase human G-CSF serum levels after sequential IV injection in mice.

Methods: Mice were injected first with 1000 nmol each of DOTAP containing 2.5% Dexamethasone Palmitate and DMPC containing 2.5% Dexamethasone Palmitate. This was followed two minutes later by plasmids encoding HG-CSF. The four plasmids that were employed sv40-mCMVEF1 (SEQ ID NO:13; FIG. 26); mCMV-mCMVEF1 (SEQ ID NO:14; FIG. 27); mCMV-hCMVEF1 (SEQ ID NO:15; FIG. 28); and mCMVEF1 (SEQ ID NO:16; FIG. 29). The first three expression constructs contained extra enhancer sequences. Mice were bled as previously described.

FIG. 25 shows the results of this example. As shown in this Figure, enhancer combinations increase human G-CSF expression in mice 1 and 8 days after sequential IV injection. Shown are the results of a single treatment of liposomes followed by plasmids encoding human G-CSF and containing a series of different enhancer elements in combinations of two.

Example 7

Use of Super Enhancers

This Example describes experiments conducted that demonstrate that the addition of super enhancer sequences in a human G-CSF DNA expression plasmid can increase human G-CSF serum levels after sequential IV injection in mice.

Methods: Mice were first injected with 1000 nmol each of DOTAP containing 2.5% Dexamethasone Palmitate and DMPC neutral lipid containing 2.5% Dexamethasone Palmitate. This was followed 2 minutes later by HG-CSF encoding plasmids with or without super-enhancer elements (hr3). The hr3-containing plasmids are as follows: hr3-mCMVEF1 #2 (SEQ ID NO:17; FIG. 31); hr3-mcmvEF1 #5 (SEQ ID NO:18; FIG. 32); and hr3-mcmvEF1 #18 (SEQ ID NO:19; FIG. 33). One of the groups receiving the plasmid without a super-enhancer element (4th bar) was supplemented with 2.5% human serum albumin (HSA).

In FIG. 30, shown are mouse serum levels of human G-CSF, 24 hours after sequential IV injection of liposomes followed by plasmid DNA. Plasmids of the first three groups contain super-enhancer elements. Also shown is plasmid injected together with human serum albumin (HSA). Each of the three different DNA vectors containing a super enhancer element produced higher serum human G-CSF levels then the corresponding DNA vector lacking a super enhancer.

Example 8

Use of Super Enhancers

This Example describes experiments conducted that demonstrate that the addition of super enhancer, R6K or RNA-out DNA sequence in a human factor nine DNA expression plasmid can increase human factor nine serum levels after sequential IV injection in mice.

Methods: 27 g mice were injected IV with DOTAP SUV cationic liposomes, followed by DNA encoding human Factor IX. Both plasmid and circularized PCR constructs were used, with or without an origin of replication (R6K).

FIG. 34 shows plasma concentration of human Factor IX at 24 hrs after sequential IV injection of liposomes and various different FIX DNA expression plasmids. The plasmids used were: FIX plasmid (SEQ ID NO:20; FIG. 35); FIX R6K1 (SEQ ID NO:21; FIG. 36); FIX R6K2 (SEQ ID NO:22; FIG. 37); FIX Superenh (SEQ ID NO:23; FIG. 38); and FIX RNA-out (SEQ ID NO:24; FIG. 39). In addition to the control FIX plasmid (1st bar), plasmids included two different PCR generated DNA with R6K Element, FIX plasmid containing a super-enhancer and a FIX plasmid generated using RNA-out. Each of the modified DNA vectors produced higher human FIX serum protein levels one day after injection.

Example 9

CRISPR/Cas9 Mediated Knockdown 10 Days and 40 Days after Injection

This Example describes experiments conducted that demonstrate anti-p65 CRISPR/Cas9-mediated knockdown of mouse NFkB-p65 protein 10 days and 40 days after sequential IV injection in mice.

Mouse Treatment Methods:

Three or four mice were injected per group. Each mouse received a single IV injection of 1000 nmoles of DOTAP cationic liposomes containing 2.5% dexamethasone palmitate (DP) incorporated into the liposome bilayer. This was followed two minutes later by a single IV injection of 75 ug of plasmid DNA encoding the indicated CRISPR- or ribozyme-based plasmids to suppress expression of endogenous mouse NFkB-p65. PECAM CRISPR control is shown in SEQ ID NO:10, and p65 CRISPR RelA1 is shown in SEQ ID NO:8. Plasmid EF1/U6 RelA1 (020117 #5) (SEQ ID NO:57) is shown in FIG. 79; plasmid EF1/U6 RelA4 (020117 #8) (SEQ ID NO:58) is shown in FIG. 80; and plasmid hu1/EF1/U6 RelA1 (021417 #3) (SEQ ID NO:59) is shown in FIG. 81. The control group received an CRISPR/Cas9 plasmid identical to the anti-NFkB-p65 CRISPR plasmids except the 20 bp targeting sequence targeted mouse PECAM instead. All groups were treated two hours prior to IV injection with an IP injection of 40 mg/kg dexamethasone.

Tissue Preparation and Anti-Mouse-p65 ELISA Methods.

Lung lysates were generated 24 hours after injection (Anti-p65 Ribozyme) and 8 days after injection (Anti-p65 CRISPR1/2) by dissection into 500 uL of prepared 1× Triton lysis buffer on ice. Samples include both lungs per animal. Each sample was homogenized (Polytron PT 2100) for 30 seconds, pulse sonicated (Misonix XL2000 Microson Ultrasonic Cell Disruptor XL 2000), and centrifuged for 10 minutes at 4 C, and the lysate was aspirated from the tissue pellet. Protein concentration from each lysate was then determined using a BCA total protein assay purchased from Thermo Fisher. Protein normalized lysate was added to a 96 well plate ELISA from Cell Signaling Technologies (PathScan Total NF-κB p65 Sandwich ELISA Kit) in duplicate as per the manufacture's instructions. The plate was then analyzed in a (Molecular Devices Spectramax M5) plate reader. After recording absorbance from the plate, a standard curve generated using murine B16 melanoma cell supernatant was fit by 4PL analysis. Error bars represent the standard error of the mean.

Description of Results:

These data, shown in FIG. 78 and FIG. 40, which demonstrate that anti-mouse NFkB-p65 CRISPR/Cas9—as well as ribozyme, plasmid-based targeting vectors reduce the expression of endogenous mouse p65, 10 and 40 days following its systemic injection in mice.

Example 10

Long-Term HG-CSF Expression in Mice

This Example describes experiments conducted that demonstrate that a mouse sacrificed 582 days after a single sequential IV injection of cationic liposomes, then an HG-CSF DNA expression vector shows very large numbers of neutrophils in spleen and bone marrow not present in control mouse. Methods were as follows. Control mouse was un-injected. Treated 27 g mouse was injected IV with 800 nmol DOTAP SUV cationic liposomes, followed by 90 ug plasmid DNA encoding hG-CSF and euthanized 582 days after injection. Mice were exsanguinated and organs preserved in 10% neutral buffered formalin. FIG. 42 shows IHC results in bone marrow. In particular, FIGS. 42*a* (20×) and 42*b* (60×), control bone marrow, show a diverse mix of cell types surround bony trabeculae of normal femoral medullary cavity, with dark-staining erythoid cells particularly obvious. FIGS. 42*c* (20×) and 42*d* (60×), treated bone marrow, show a monotonous nearly solid sheet of pale-staining cells replace bony trabecular elements in femoral marrow pale staining myeloid lineage cells (polymorphonuclear leukocytes) with oval, indented oval, band and segmented forms replace most other cell types within femoral marrow. FIG. 43 shows IHC results in spleen tissue. FIGS. 43*a* (20×) and 43*b* (60×), control spleens, show red/dark portions of white (lymphoid) pulp of normal spleen showing diverse cell population. FIGS. 43*c* (20×) and 43*d* (60×), treated spleen, show pale-staining myeloid lineage cells (pmn's) with oval, indented oval, band and segmented forms replace most other cell types.

Example 11

Long-Term HG-CSF Expression in Rat

This Example describes experiments conducted that demonstrate that a rat sacrificed 168 days after last sequential IV injection of cationic liposomes, then an HG-CSF DNA expression vector shows very large numbers of neutrophils in bone marrow not present in control rat. The methods were as follows. Control rat was un-injected. Treated rat: a 150 g female rat was injected at the start of the experiment with 3000 nmol DOTAP SUV and then 300 ug of a DNA expression vector encoding HG-CSF. The treated rat was later injected on day 7 with 3 mg dexamethasone (IP) followed by IV injections of 3300 nmol DOTAP SUV and then 330 ug of the DNA expression vector encoding HG-CSF. On day 21, the treated rat was re-injected with 3 mg dexamethasone (IP) followed by IV injections of 4400 nmol DOTAP SUV and then 330 ug of the DNA expression vector encoding HG-CSF. Rats were euthanized, exsanguinated, and organs preserved in 10% neutral buffered formalin. FIG. 44 shows IHC results in bone marrow. In particular, FIGS. 44*a* (20×) and 42*b* (60×), control bone marrow, show a diversity of cell types with round, dark staining erythroid lineage particularly obvious in femoral marrow. FIGS. 44*c* (20×) and 44*d* (60×), treated bone marrow, show pale staining myeloid lineage cells (polymorphonuclear leukocytes) with oval, indented oval, band and segmented forms predominate in femoral marrow. A few clusters of dark-staining erythroid lineage cells remain. FIG. 45*a* shows control rat, vertebral body at 40×, while FIG. 45*b* shows the HGCSF rat vertebral body at 40×.

Example 12

Expression of Anti-Human PCSK9 Monoclonal Antibody

This Example describes sequential IV injection of cationic liposomes followed by a DNA expression vector encoding anti-human PCSK9 monoclonal antibody to reduce LDL in mice. Five CD-1 mice are injected per group. For the 2 months prior to injection, mice are placed on a high cholesterol and cholic acid diet to increase LDL cholesterol (Envigo Atherogenic Teklad Diet TD.02028). Each mouse then receives a single IV injection of 1050 nmoles of DOTAP cationic liposomes containing 2.5% dexamethasone palmitate (DP) incorporated into the liposome bilayer, followed two minutes later by a single IV injection of 75 ug of one of three different plasmid DNAs encoding an anti-human PCSK9 monoclonal antibody (mAb) or a plasmid DNA encoding an anti-human CD20 monoclonal antibody as a control group. All groups are treated two hours prior to IV injection with an IP injection of 40 mg/kg dexamethasone. DNARx-31H4-2A (SEQ ID NO:25; FIG. 46) and DNARx-21B12 (P2A) (SEQ ID NO:27; FIG. 48) encodes anti-PCSK9 mAb heavy and light chain cDNAs separated by a 2A self-cleaving peptide. Plasmids DNARx-31H4 (SEQ ID NO:26; FIG. 47) and DNARx-21B12 (SEQ ID NO:28; FIG. 49) are dual expression cassette plasmid vectors that encode different versions of anti-PCSK9 mAb heavy and light chain cDNAs respectively. Serum levels of mouse LDL cholesterol are measured 1 week prior to injection, then 24 hours following injection and in 7-day intervals thereafter. The serum LDL assay is photometric, involving the enzymatic breakdown of LDL substrate in the presence of another compound to form a dye. The color intensity of the dye is then measured by absorbance assay and is performed by the UC Davis Veterinary diagnostic laboratory. It is anticipated that the LDL levels in the treated mice will be reduced, but not in the control mice.

Example 13

Expression of Anti-Human CD47 Monoclonal Antibody

This Example describes sequential IV injection of cationic liposomes followed by a DNA expression vector encoding anti-human CD47 monoclonal antibody to suppress Raji, human B cell lymphoma tumor progression in tumor-bearing nude mice. Five athymic nude mice are injected per group. Mice receive $0.1\times10^5$-$2\times10^6$ Raji cells subcutaneously in the shoulder or flank. Ten to fourteen days later, or when tumors reach a volume of 70-100 mm3, each mouse receives a single IV injection of 1050 nmoles of DOTAP cationic liposomes containing 2.5% dexamethasone palmitate (DP) incorporated into the liposome bilayer, followed two minutes later by a single IV injection of 75 ug of a DNA expression plasmid encoding an anti-human CD47 monoclonal antibody or a plasmid DNA encoding an anti-human PCSK9 monoclonal antibody as a control group. All groups are treated two hours prior to IV injection with an IP injection of 40 mg/kg dexamethasone. DNARx-CD47-2A (P2A) (SEQ ID NO:29; FIG. 50) encodes anti-CD47 mAb heavy and light chain cDNAs separated by a 2A self-cleaving peptide. DNARx-CD47 (SEQ ID NO:30; FIG. 51) is a dual expression cassette plasmid vector that encodes the anti-CD47 mAb heavy and light chain cDNAs respectively. Tumor volume is measured by caliper on a weekly or twice weekly basis following DNA expression vector injection. It is anticipated that tumor volume in the treated mice will be reduced, but not in the control mice.

Example 14

Expression of Anti-Human CD47 and Anti-Human CD20 Monoclonal Antibodies

This Example describes sequential IV injection of cationic liposomes followed by a DNA expression vector encoding anti-human CD47 monoclonal antibody, anti-human CD20 monoclonal antibody or both anti-human CD47 and anti-CD20 monoclonal antibodies to suppress Raji, human B cell lymphoma tumor progression in tumor-bearing nude mice. Five athymic nude mice are injected per group. Mice receive $0.1\times10^5$-$2\times10^6$ Raji cells subcutaneously in the shoulder or flank. Ten to fourteen days later, or when tumors reach a volume of 70-100 $mm^3$, each mouse receives a single IV injection of 1050 nmoles of DOTAP cationic liposomes containing 2.5% dexamethasone palmitate (DP) incorporated into the liposome bilayer, followed two minutes later by a single IV injection of 75 ug of a DNA expression plasmid encoding an anti-human CD47 monoclonal antibody, an anti-human CD20 monoclonal antibody, anti-human CD47 plus anti-CD20 monoclonal antibodies, or a plasmid DNA encoding an anti-human PCSK9 monoclonal antibody as a control group. All groups were treated two hours prior to IV injection with an IP injection of 40 mg/kg dexamethasone.

DNARx-CD47-2A (P2A) (SEQ ID NO:29; FIG. 50) encodes anti-CD47 mAb heavy and light chain cDNAs separated by a 2A self-cleaving peptide and Plasmid 715.1 2a (P2A) (SEQ ID NO:3) encodes anti-CD20 mAb heavy and light chain cDNAs separated by a 2A self-cleaving peptide. DNARx-CD47 (SEQ ID NO:30; FIG. 51) is a dual expression cassette plasmid vector that encodes the anti-CD47 mAb heavy and light chain cDNAs. Tumor volume is measured by caliper on a weekly or twice weekly basis following DNA expression vector injection. It is anticipated that tumor volume in the treated mice will be reduced, but not in the control mice.

Example 15

Expression of Anti-Influenza Stem Antigen Monoclonal Antibodies

This Example describes sequential IV injection of cationic liposomes followed by a DNA expression vector encoding anti-influenza A stem antigen to prevent and/or treat influenza A in mice. Five C57B16 mice are injected per group. Prior to injection, mice are inoculated with 2×MLD50 of PR/8/34 (H1N1), HKx31 (H3N1) or B/Lee/40 viral strains of influenza. The respective MLD50 of a challenge virus are determined by infection of unvaccinated mice with increasing amounts of virus. The mice are monitored for weight loss and mortality for 14-20 days following infection. Each mouse then receives a single IV injection of 1050 nmoles of DOTAP cationic liposomes containing 2.5% dexamethasone palmitate (DP) incorporated into the liposome bilayer, followed two minutes later by a single IV injection of 75 ug of one of three different plasmid DNAs encoding an anti-influenza A stem antigen monoclonal antibody or a plasmid DNA encoding an anti-human CD20 monoclonal antibody as a control group. All groups are treated two hours prior to IV injection with an IP injection of 40 mg/kg dexamethasone.

Plasmids DNARx-D8-2A (SEQ ID NO:31; FIG. 52), DNARx-F10-2A (SEQ ID NO:32; FIG. 53) and DNARx-A66-2A (P2A) (SEQ ID NO:33; FIG. 54) encode anti-influenza A stem antigen mAb heavy and light chain cDNAs separated by a 2A self-cleaving peptide. Plasmids DNARx-D8 (SEQ ID NO:34; FIG. 55), DNARx-F10 (SEQ ID NO:35; FIG. 56) and DNARx-A66 (SEQ ID NO:36; FIG. 57) are dual expression cassette plasmid vectors that encode different versions of anti-influenza A stem antigen heavy and light chain cDNAs respectively. Plasmid DNARx-HA-MITD (SEQ ID NO:37; FIG. 58) encodes that HA from PR/8/34 (H1N1) with MHC class I transmembrane and cytosolic domains (MITD) and plasmid DNARx-SEC-partial HA-MITD (SEQ ID NO:38; FIG. 59) encodes that partial HA from PR/8/34 (H1N1) with MHC class I signal peptide fragment (SEC) and transmembrane and cytosolic domains (MITD). Plasmids DNARx-D8-2A-HA-MITD (SEQ ID NO:39; FIG. 60), DNARx-F10-2A-HA-MITD (SEQ ID NO:40; FIG. 61), DNARx-A66-2A-HA-MITD (SEQ ID NO:41; FIG. 62), DNARx-D8-2A-SEC-partial-HA-MITD (SEQ ID NO:42; FIG. 63), DNARx-F10-2A-SEC-partial-HA-MITD (SEQ ID NO:43; FIG. 64) and DNARx-A66-2A SEC-partial-MITD (SEQ ID NO:44; FIG. 65) are dual expression cassette plasmid in which the first expression cassette encodes anti-influenza A stem antigen mAb heavy and light chain cDNAs separated by a 2A self-cleaving peptide and the second expression cassette encodes HA from PR/8/34 (H1N1) with MHC class I transmembrane and cytosolic domains (MITD) or partial HA from PR/8/34 (H1N1) with MHC class I signal peptide fragment (SEC) and transmembrane and cytosolic domains (MITD). The presence of influenza nucleoprotein in mouse serum is detected by ELISA using influenza A- or B-specific anti-nucleoprotein antibodies (Millipore, Billerica, Mass.). It is anticipated that treated mice will have their influenza prevented or treated, while the controls will not.

Example 16

Expression of Anti-Mouse PD-1 Monoclonal Antibodies, Ovalbumin, and gp-70

This Example describes sequential IV injection of cationic liposomes then a DNA expression vector encoding anti-mouse PD-1 monoclonal antibody, ovalbumin, gp-70, anti-mouse PD-1 monoclonal antibody plus ovalbumin or anti-mouse PD-1 monoclonal antibody plus gp-70 to suppress B16 melanoma or CT26 colon tumor progression in tumor-bearing mice. Five C57B16 mice are injected subcutaneously in the flank with $2\times10^5$ B16 cells per animal, or five BALBC mice are injected subcutaneously in the flank with $2\times10^5$ CT26 cells per animal. At day four following inoculation, each mouse receives a single IV injection of 1050 nmoles of DOTAP cationic liposomes containing 2.5% dexamethasone palmitate (DP) incorporated into the liposome bilayer, followed two minutes later by a single IV injection of 75 ug of a DNA expression plasmid encoding an anti-mouse PL-1 monoclonal antibody, ovalbumin, gp-70, or a plasmid DNA encoding an anti-human PCSK9 monoclonal antibody as a control group. All groups are treated two hours prior to IV injection with an IP injection of 40 mg/kg dexamethasone. Plasmid DNARx-PD1-2A (P2A) (SEQ ID NO:48; FIG. 69) encodes anti-PD-1 mAb heavy and light chain cDNAs separated by a 2A self-cleaving peptide, plasmid DNARx-SEC-OVA-MITD (SEQ ID NO:49; FIG. 70) encodes the ovalbumin restricted epitope H2Kb and MHC class I signal peptide fragment (SEC) and the transmembrane and cytosolic domains (MITD), plasmid DNARx-SEC-gp70-MITD (SEQ ID NO:50; FIG. 71) encodes the H-2Ld-restricted peptide antigen AH1 and MHC class I signal peptide fragment (SEC) and the transmembrane and cytosolic domains (MITD). Plasmid DNARx-PD1-2A OVA (SEQ ID NO:51; FIG. 72) or DNARx-PD1-2A gp70 (SEQ ID NO:52; FIG. 73) is a dual expression cassette plasmid vector that encodes the anti-PD-1 mAb heavy and light chain cDNAs separated by a 2A self-cleaving peptide in the first expression cassette and either the ovalbumin restricted epitope H2Kb or H-2Ld-restricted peptide antigen AH1 and MHC class I signal peptide fragment (SEC) and the transmembrane and cytosolic domains (MITD) in the second expression cassette. Tumor volume is measured by caliper every three to four days and animals with tumors exceeding 15 mm in volumetric diameter and/or show signs of impaired health are euthanized. It is anticipated that tumor volume in the treated mice will be reduced, but not in the control mice.

Example 17

Expression of Anti-Human Anti-CD20 Monoclonal Antibodies, Human G-CSF, and Streptococcal Cas9

This Example describes sequential IV injection of cationic liposomes followed by DNA expression vectors encoding anti-human anti-CD20 monoclonal antibody, human G-CSF, streptococcal Cas9, anti-CD20 monoclonal antibody plus HG-CSF or anti-CD20 monoclonal antibody plus Cas9 in mice. Five CD-1 mice are injected per group. Each mouse receives a single IV injection of 1050 nmoles of DOTAP cationic liposomes containing 2.5% dexamethasone palmitate (DP) incorporated into the liposome bilayer, followed two minutes later by a single IV injection of 75 ug plasmid DNAs encoding an anti-human CD20 monoclonal antibody (mAb), HG-CSF, Cas9, anti-human CD20 monoclonal antibody plus HG-CSF, anti-human CD20 monoclonal antibody plus HG-CSF or a plasmid DNA encoding an anti-human CD20 monoclonal antibody plus luciferase as a control group. All groups are treated two hours prior to IV injection with an IP injection of 40 mg/kg dexamethasone. Plasmid DNARx CD20-2A Cas9 (SEQ ID NO:53; FIG. 74) or DNARx CD20-2A HG-CSF (SEQ ID NO:54; FIG. 75) is a dual expression cassette plasmid vector that the first expression cassette encodes the anti-CD20 mAb heavy and light chain cDNAs separated by a 2A self-cleaving peptide and driven by mCMV-EF1 while the second expression cassette encodes Cas9 or HG-CSF and driven by hCMV-ferritin heavy chain promoter. Serum levels of anti-CD20 and HG-CSF will be measured by specific ELISAs every seven days after injection as previously described in the methods, while Cas9 protein levels will be measured by Cas9 ELISA and/or Western blot form mouse lung lysates of previously injected mice every 7 days after injection. Both assays will be use the following validated capture antibody: MAC133 Anti-Cas9 Antibody, clone 7A9 (Millipore).

Example 18

In Vivo Expression of Anti-Human Anti-CD20 Monoclonal Antibodies is Increased with Neutral Liposomes This Example describes how co-injecting of neutral liposomes with cationic liposomes increases mouse serum anti-CD20 monoclonal antibody levels over time versus injecting the same cationic liposomes without neutral liposomes. Three mice per group were given IP injections of Dexamethasone at a level of 40 mg/kg. Two hours later they were sequentially injected, first with 1000 nmol or 1250 nmol DOTAP SUV, with or without 1000 nmol DMPC (1,2-Dimyristoyl-SN-glycero-3-phosphocholine) neutral lipid, and then 75 ug of plasmid vector containing Rituximab (anti-CD20 monoclonal antibody) cDNA. Serum levels of Rituximab protein were measured by ELISA after 24 hours and every 2-3 weeks thereafter. Results are shown in FIG. 82, which shows that the inclusion of neutral lipids with cationic liposomes increases serum anti-CD20 monoclonal antibody levels.

Example 19

In Vivo Expression of Anti-Human Anti-CD20 Monoclonal Antibodies is Increased with Neutral Liposomes and Dexamethasone Palmitate This Example describes how incorporating dexamethasone palmitate into neutral liposomes further increases gene expression. Three mice per group were given IP injections of Dexamethasone at a level of 40 mg/kg. Two hours later they were sequentially injected, first with 1000 nmol DOTAP SUV containing 2.5% Dexamethasone Palmitate, and 1000 nmol DMPC neutral lipid containing 1, 2.5, 5, or 10% Dexamethasone Palmitate, and then 75 ug of plasmid vector containing Rituximab cDNA. Serum levels of Rituximab protein were measured by ELISA after 24 hours. The results are shown in FIG. 83, which shows that employing dexamethasone palmitate with neutral liposomes further increases gene expression in vivo.

Example 20

Inclusion of Syn 21 and/or Delta-p10 in Vector Increases In Vivo Gene Expression This Example describes how including Syn 21 and/or delta-p10 sequences 5' or 3' of the anti-CD20 mAb heavy and light chain cDNA's increases serum anti-CD20 mAb levels in mice. Three mice per group were given IP injections of Dexamethasone at a level of 40 mg/kg. Two hours later they were sequentially injected, first with 1000 nmol DOTAP SUV and 1000 nmol DMPC neutral lipid, both containing 2.5% Dexamethasone Palmitate, and then 75 ug of plasmid vector containing Rituximab cDNA. A representative vector construct, containing both the Syn21 and delta-p10 sequences, is shown in SEQ ID NO:82 (FIG. 85). Serum levels of Rituximab protein were measured by ELISA after 24 hours. Results are shown in FIG. 84, which shows that including Syn 21 and/or delta-p10 sequences into the vectors increases gene expression.

Example 21

Inclusion of hr3 Super Enhancer in Vector Increases In Vivo Gene Expression

This Example describes how the addition of a five prime hr3 super enhancer sequence increases the expression of human G CSF as well as anti-CD 20 monoclonal antibody in mice. Three mice per group were given IP injections of Dexamethasone at a level of 40 mg/kg. Two hours later they were sequentially injected, first with 1000 nmol DOTAP SUV and 1000 nmol DMPC neutral lipid, both containing 2.5% Dexamethasone Palmitate, and then 75 ug of plasmid vector containing human G-CSF or Rituximab cDNA. Serum levels of hG-CSF or Rituximab protein were measured by ELISA after 24 hours. The results are shown in FIG. 86, which shows increased G CSF expression (FIG. 86A) and increased Rituximab anti-CD20 expression (FIG. 86*b*) when the hr3 super enhancer is included in the plasmid.

Example 22

Inclusion of R6K in 3' or 5' UTR Region Increases In Vivo Gene Expression

This Example describes how the insertion of an R6K origin of replication sequence either in the 5' UTR or 3'UTR of the human factor nine cDNA, increases the level of human factor nine serum levels produced in mice. Three mice per group were given IP injections of Dexamethasone at a level of 40 mg/kg. Two hours later they were sequentially injected, first with 1000 nmol DOTAP SUV and 1000 nmol DMPC neutral lipid, both containing 2.5% Dexamethasone Palmitate, and then 75 ug (FIG. 87A) or 60 ug (FIG. 87B) of plasmid vector containing Factor IX cDNA. Plasma levels of Factor IX protein were measured by ELISA after 24 hours. Results are shown in FIG. 87, which shows that locating the R6K origin of replication in the 3' or 5' UTR of the Factor IX gene increased expression levels at both the 75 ug level (FIG. 87A) and the 60 ug level (FIG. 87B).

Example 23

Long-Term Anti-CD20 Antibody Expression after Single Vector Injection

This Example describes how mouse serum Rituximab levels produced 148, 232 and 284 days after a single Rituximab DNA injection remain therapeutically effective (FIG. 88A), inducing levels of CD20+ human tumor cell lysis comparable to recombinant Rituximab protein. Three mice per group were given IP injections of Dexamethasone at a level of 40 mg/kg. Two hours later they were sequentially injected, first with 1050 nmol DOTAP SUV containing 2.5% Dexamethasone Palmitate, and then 75 ug of plasmid vector containing Rituximab cDNA. Serum levels of Rituximab protein were measured by ELISA after 24 hours and every 1-2 weeks thereafter. The results are shown in FIG. 88. FIG. 88A shows long-term Rituximab levels at different time points over 284 days, showing long-term expression. FIG. 88B shows that the anti-CD20 mouse sera was able to induce human tumor cell lysis at levels comparable to Rituximab protein.

Example 24

Long-Term Anti-IL5 Antibody Expression after Single Vector Injection

This Example describes how one sequential IV injection of a dual cassette, single plasmid DNA vector (SEQ ID NO:83; FIG. 90) encoding the anti-human interleukin-5 mAb (Mepoluzimab; 2B6) heavy chain and light chain cDNAs produces therapeutic anti-IL-5 mAb serum levels in mice for >92 days, as assayed by ELISA. Three mice per group were given IP injections of Dexamethasone at a level of 40 mg/kg. Two hours later they were sequentially injected, first with 1120 nmol DOTAP SUV containing 2.5% Dexamethasone Palmitate along with 1000 nmol DMPC MLB containing 5% Dexamethasone Palmitate, and then 85 ug of plasmid vector containing anti-IL-5 cDNA (2B6). Serum levels of anti-IL-5 mAb were measured by ELISA after 24 hours and every 1-2 weeks thereafter. The results are shown in FIG. 89, which shows therapeutic anti-IL-5 mAb (2B6) serum levels expressed for at least 92 days.

Example 25

Long-Term Anti-Flu Antibody Expression after Single Vector Injection

This Example describes how one sequential IV injection of a dual cassette, single plasmid DNA vector (SEQ ID NO:84, FIG. 92) encoding the anti-influenza 5J8 mAb heavy chain and light chain cDNAs produces therapeutic anti-influenza A mAb serum levels by ELISA (FIG. 91A) effectively neutralizes the Cal09 epidemic influenza strain (FIG. 91B) for >85 days. Three mice per group were given IP injections of Dexamethasone at a level of 40 mg/kg. Two hours later they were sequentially injected, first with 1120 nmol DOTAP SUV containing 2.5% Dexamethasone Palmitate along with 1000 nmol DMPC MLV containing 5% Dexamethasone Palmitate, and then 85 ug of plasmid vector containing cDNA for the anti-flu antibody. Serum levels of anti-flu protein were measured by ELISA after 24 hours and every 1-2 weeks thereafter. The neutralization methods were as follows. Serum from mice injected with anti-flu cDNA at various time points was heat-killed, diluted 1:40 in DMEM/BSA, then mixed with 100×TCID50 of X-179 Cal09 H1N1 virus. One hour later 30,000 MDCK2 cells were added to the serum/virus mixture along with TPCK-treated trypsin. Following a 16-18 hour incubation, MDCK2 cells were scored for infection using an influenza A-specific immunoassay against viral nucleoprotein.

Example 26

Long Term Expression

This Example describes how sequential IV injection of a single plasmid DNA vector (SEQ ID NO:85, FIG. 94) encoding the anti-human interleukin-5 mAb (Mepoluzimab; 2B6) heavy chain and light chain cDNAs and the human G-CSF cDNA produces therapeutic anti-IL-5mAb as well as hG-CSF serum levels by ELISA for >66 days. Three mice per group were given IP injections of Dexamethasone at a level of 40 mg/kg. Two hours later they were sequentially injected, first with 1120 nmol DOTAP SUV containing 2.5% Dexamethasone Palmitate along with 1000 nmol DMPC MLV containing 5% Dexamethasone Palmitate, and then 88 ug of plasmid vector containing cDNA for anti-IL-5 mAb and hG-CSF. Serum levels of each protein were measured by ELISA after 24 hours and every 1-3 weeks thereafter. Results are shown in FIG. 93, which shows the expression levels in mice of anti-IL-5mAb as well as hG-CSF were at therapeutic levels for at least 66 days.

Example 27

Dual Cassette Provides Increased Expression

This Example describes how a dual expression cassette, single plasmid vector containing two hG-CSF cassettes produces higher absolute neutrophil counts over time than a single cassette hG-CSF vector. Three mice per group were given IP injections of Dexamethasone at a level of 40 mg/kg. Two hours later they were sequentially injected, first with 1000 nmol DOTAP SUV and 1000 nmol DMPC MLV, both containing 2.5% Dexamethasone Palmitate, and then 75 ug of plasmid vector containing a dual-cassette cDNA for hG-CSF. Plasma levels of hG-CSF protein were measured by ELISA after 24 hours and every 1-2 weeks thereafter. Absolute Neutrophil Count (ANC) was assessed from whole blood. FIG. 95 show the results of this Example, which shows that the dual cassette expression of the same encoded protein provides higher serum levels in mice than single-cassette expression of the encoded protein.

Example 28

Dual Cassette Provides Increased Expression

This Example describes how a dual expression cassette, single plasmid vector, each cassette containing an identical anti-human IL-5 heavy and light chain mAb cDNAs separated by a porcine teschovirus-1 2A (P2A) self cleaving peptide sequence produces higher anti-human IL-5 serum mAb levels in mice than a single cassette anti-human IL-5 mAb encoding DNA vector. Three mice per group were given IP injections of Dexamethasone at a level of 40 mg/kg. Two hours later they were sequentially injected, first with 1120 nmol DOTAP SUV containing 2.5% Dexamethasone Palmitate along with 1000 nmol DMPC MLV containing 5% Dexamethasone Palmitate, and then 88 ug of plasmid vector containing cDNA for and IL-5. Serum levels of IL-5 protein were measured by ELISA after 24 hours. Results are shown in FIG. 96, which shows that the dual cassette vector expressing anti-human IL-5 heavy and light chains produces higher anti-human IL-5 serum mAb levels than the single cassette anti-human IL-5 encoding DNA vector.

Example 29

Dual Cassette Provides Increased Expression

This Example describes how a dual expression cassette, single plasmid vector, each cassette containing an identical anti-influenza A heavy and light chain monoclonal antibody 5J8 cDNAs separated by a porcine teschovirus-1 2A (P2A) self cleaving peptide sequence produces higher anti-5J8 mAb serum levels in mice than a single cassette anti-human IL-5 mAb encoding DNA vector. Three mice per group were given IP injections of Dexamethasone at a level of 40 mg/kg. Two hours later they were sequentially injected, first with 1120 nmol DOTAP SUV containing 2.5% Dexamethasone Palmitate along with 1000 nmol DMPC MLV containing 5% Dexamethasone Palmitate, and then 88 ug of plasmid vector containing cDNA for IL-5. Serum levels of IL-5 protein were measured by ELISA after 24 hours. The results are shown in FIG. 97, which shows that the dual cassette vector expressing anti-5J8 mAb produces higher anti-5J8 serum mAb levels than the single cassette anti-5J8 encoding DNA vector.

Example 30

Dual Cassette Single Plasmid Expression of Different mAbs, and Co-Injection of Two Single Cassette Plasmids Expressing Different mAbs This Example describes how one IV injection of a dual expression cassette, single plasmid vector, one cassette containing an anti-influenza A heavy and light chain monoclonal antibody 5J8 cDNAs separated by a porcine teschovirus-1 2A (P2A) self cleaving peptide sequence, and the second cassette containing an anti-human IL-5 heavy and light chain monoclonal antibody cDNAs (2B6) separated by a porcine teschovirus-1 2A (P2A) self cleaving peptide produces significant serum levels of both monoclonal antibodies in mice. Furthermore, one IV co-injection of two different single expression cassette DNA vectors encoding the intact heavy and light chain monoclonal antibodies anti-influenza 5J8 and anti-human IL-5 (2B6) respectively also produce significant serum levels of both monoclonal antibodies in mice. Three mice per group were given IP injections of Dexamethasone at a level of 40 mg/kg. Two hours later they were sequentially injected, first with 1120 nmol DOTAP SUV containing 2.5% Dexamethasone Palmitate along with 1000 nmol DMPC MLV containing 5% Dexamethasone Palmitate, and then 88 ug of plasmid vector. Serum levels of protein were measured by ELISA after 24 hours. The results are shown in FIG. 98, which shows how a dual cassette single plasmid expresses different mAbs in vivo, and how two single cassette plasmids that are co-injected express different mAbs in vivo.

Example 31

Dual Cassette Single Plasmid Expression of Different mAbs

This Example describes how one IV injection of a dual expression cassette, single plasmid vector, one cassette containing an anti-influenza A heavy and light chain monoclonal antibody 5J8 cDNAs separated by a porcine teschovirus-1 2A (P2A) self cleaving peptide sequence and the second cassette containing an anti-human IL-5 heavy (2B6) and light chain monoclonal antibody cDNAs separated by a porcine teschovirus-1 2A (P2A) self cleaving peptide produces significant serum levels of both monoclonal antibodies in mice. Three mice per group were given IP injections of Dexamethasone at a level of 40 mg/kg. Two hours later they were sequentially injected, first with 1120 nmol DOTAP SUV containing 2.5% Dexamethasone Palmitate along with 1000 nmol DMPC MLV containing 5% Dexamethasone Palmitate, and then 88 ug of plasmid vector. Serum levels of protein were measured by ELISA after 24 hours. The results are shown in FIG. 99. FIG. 99A shows serum expression levels of the anti-human IL-5 mAb over 43 days, and FIG. 99B shows serum expression levels of the anti-influenza A mAb over 43 days.

Example 32

Triple Cassette Single Plasmid Expression of Different mAbs

This Example describes how one IV injection of a triple expression cassette, single plasmid vector, one cassette containing an anti-influenza A heavy and light chain monoclonal antibody 5J8 cDNAs separated by a porcine teschovirus-1 2A (P2A) self cleaving peptide sequence, the second cassette containing an anti-human IL-5 heavy and light chain monoclonal antibody cDNA's separated by a porcine teschovirus-1 2A (P2A) self cleaving peptide, and the third cassette containing an anti-human CD20 heavy and light chain monoclonal antibody cDNAs separated by a porcine teschovirus-1 2A (P2A) self cleaving peptide produces significant serum levels of all three different monoclonal antibodies in mice. Furthermore, one IV co-injection of three different single expression cassette DNA vectors encoding the intact heavy and light chain monoclonal antibodies: anti-influenza 5J8, anti-human IL-5, and anti-human CD20 mAbs respectively also produce significant serum levels of all three different monoclonal antibodies in mice. Three mice per group were given IP injections of Dexamethasone at a level of 40 mg/kg. Two hours later they were sequentially injected, first with 1120 nmol DOTAP SUV containing 2.5% Dexamethasone Palmitate along with 1000 nmol DMPC MLV containing 5% Dexamethasone Palmitate, and then 88 ug of plasmid vector. Serum levels of protein were measured by ELISA after 24 hours. The results are shown in FIG. 100, which shows simultaneous expression of Rituximab (anti-CD20), anti-IL5 mAb, and anti-influenza mAb, both from a single vector (left side), as well as by co-injection of three separate vectors (right side).

Example 33

Expression of Anti-PCSK9 mAbs to Reduce LDL Levels

This Example describes how one IV injection of a single plasmid vector expressing anti-PCSK9 mAbs reduces LDL levels in mice. Three mice per group were given IP injections of Dexamethasone at a level of 40 mg/kg. Two hours later they were sequentially injected, first with 1000 nmol each of DOTAP SUV and DMPC MLV, both containing 2.5% Dexamethasone Palmitate, and then 75 ug of plasmid vector. Plasma levels of LDL cholesterol were measured 15 days after injection and plotted according to proportion relative to LDL cholesterol measurements on the same mice prior to injection. FIG. 101 shows the results, which shows that a single plasmid vector expressing anti-PCSK9 mAbs reduces LDL levels in mice.

Example 34

Expression of Anti-PCSK9 mAbs Provides Long-Lasting Reduction of LDL Levels

This Example describes how expression of anti-PCSK9 mAbs in vivo provides long-lasting reduction of LDL levels. Mice were assessed for serum LDL levels prior to injection. On the day of injection, three mice per group were given IP injections of Dexamethasone at a level of 40 mg/kg. Two hours later they were sequentially injected, first with 1000 nmol DOTAP SUV and 1000 nmol DMPC MLV, both containing 2.5% Dexamethasone Palmitate, and then 75 ug of plasmid vector encoding the light and have chain of an anti-PCSK9 mAb. Serum levels of LDL cholesterol were measured every 7-21 days thereafter. The results are shown in FIG. 102, which show long-term reduction in LDL levels in mice expressing anti-PCSK9 mAbs.

Example 35

Expression of Anti-PCSK9 mAbs Reduces LDL Levels in Mice on Fatty Diet

This Example describes how expression of anti-PCSK9 mAbs in vivo provides reduction of LDL levels in mice on a fatty diet compared to control (anti-CD20 mAb expression). Mice were assessed for serum LDL levels prior to injection. On the day of injection, three mice per group were given IP injections of Dexamethasone at a level of 40 mg/kg. Two hours later they were sequentially injected, first with 1000 nmol DOTAP SUV and 1000 nmol DMPC MLV, both containing 2.5% Dexamethasone Palmitate, and then 75 ug of plasmid vector. The day after injection, mice were switched to a fatty, cholesterol-elevating diet. Serum levels of LDL cholesterol were measured every 7-14 days thereafter. FIG. 103 shows the results, which shows that mice expressing the anti-PCSK9 mAbs had lower LDL levels over time compared to the control mice expressing the control anti-CD20 antibodies.

Example 36

Durability of mAb Expression

This Example describes how the long-term expression of mAbs, including Rituximab (anti-CD20 mAb), anti-flu mAb (FI6), anti-flu mAb (5J8), and anti-IL5 mAb. Three mice per group were given IP injections of Dexamethasone at a level of 40 mg/kg. Two hours later they were sequentially injected. Sequential injections for Rituximab comprised injections of Dexamethasone at a level of 40 mg/kg. Two hours later they were sequentially injected, first with 1050 nmol DOTAP SUV containing 2.5% Dexamethasone Palmitate, and then 75 ug of plasmid vector containing Rituximab cDNA. Sequential injections for anti-flu and anti-IL-5 antibodies comprised 1120 nmol DOTAP SUV containing 2.5% Dexamethasone Palmitate along with 1000 nmol DMPC MLV containing 5% Dexamethasone Palmitate, and then 88 ug of plasmid vector. Serum levels of protein were measured by ELISA after 24 hours, and then every 7-21 days thereafter. The results are shown in FIG. 104, which shows expression of anti-flu FI6 mAb for about 25 days, expression of anti-flu 5J8 mAb and anti-IL4 mAB for over 100 days, and expression of Rituximab for over 275 days.

Example 37

Various Plasmid Vector Doses

This Example describes a comparison of expression levels from four different doses of plasmid vector expressing Rituximab. Three mice per group were given IP injections of Dexamethasone at a level of 40 mg/kg. Two hours later they were sequentially injected as follows. Liposomes were injected first, composed of 1000 nmol DMPC MLV containing 5% Dexamethasone Palmitate as well as 1000, 1080, 1170, or 1250 nmol DOTAP SUV containing 2.5% Dexamethasone Palmitate; plasmid vector was injected second in doses of 75, 81, 88, or 95 ug. Serum levels of protein were measured by ELISA after 24 hours. Results are shown in FIG. 105, which shows good expression levels from all four plasmid doses.

Example 38

Enhanced mAb Expression

This Example describes how the ALB and AZU signal sequences enhance the expression of the 5J8 mAb. Three mice per group were given IP injections of Dexamethasone at a level of 40 mg/kg. Two hours later they were sequentially injected, first with 1120 nmol DOTAP SUV containing 2.5% Dexamethasone Palmitate along with 1000 nmol DMPC MLV containing 5% Dexamethasone Palmitate, and then 88 ug of plasmid vector. Serum levels of protein were measured by ELISA after 24 hours. The results are shown in FIG. 106, which shows enhanced expression of the 5J8 mAb by using the ALB and AZU signal sequence.

Example 39

P53 Expression In Vivo

This Example describes how the human p53 gene is widely expressed in mouse lungs 24 hours after IV injection, and further how the human p53 gene is expressed predominately in vascular endothelial cells. Three mice per group were given IP injections of Dexamethasone at a level of 40 mg/kg. Two hours later they were sequentially injected, first with DOTAP SUV liposomes and DMPC neutral lipids, both at 1000 nmol with 2.5% Dex Palmitate by weight, then two minutes later, 75 ug per mouse of plasmid vector encoding human p53 (FIG. 108, SEQ ID NO:86). Lungs were harvested and processed for immunohistochemistry 24 hrs post injection. Lung sections were stained for human p53 (brown color). FIG. 107A shows control mouse lung tissue, and FIG. 107B shows human p53 injected mouse lung tissue stained for p53, showing that the p53 gene is widely expressed in mouse lungs. Lung tissue from the treated mice was dual-stained for human p53 and mouse CD31 (PE-CAM), a vascular endothelial cell-specific marker. Co-localization of p53 and CD31, in FIGS. 107C and 107D, shows predominate vascular endothelial cell human p53 expression in p53-injected mice. FIGS. 107C and 107D shows the same tissue section, with different stains. CD31 staining in both figures is extensive since alveolar walls are lined by continuous endothelium.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of expressing a monoclonal antibody (mAb) or antigen binding portion thereof in a subject comprising:

a) administering dexamethasone to a subject infected with a virus, b) administering a first composition to said subject, wherein said first composition comprises:

i) a first amount of cationic liposomes, wherein said cationic liposomes comprise cationic lipids and dexamethasone palmitate, and wherein said cationic liposomes are small uni-lamellar vesicles (SUVs), and ii) neutral liposomes, wherein said neutral liposomes comprises neutral lipids and dexamethasone palmitate, and wherein said neutral liposomes are multi-lamellar vesicles (MLV), and wherein said first composition is free, or essentially free, of nucleic acid molecules; and c) administering a second composition to said subject within about 300 minutes of administering said first composition, wherein said second composition comprises a therapeutically effective amount of non-viral expression vectors encoding said mAb or antigen binding portion thereof, wherein said mAb or antigen binding portion thereof specifically binds to said virus, and wherein, as a result of said administering said dexamethasone, said administering said first composition and said administering said second composition, said mAb or antigen binding portion thereof is expressed in said subject.

2. The method of claim 1, wherein said antigen binding portion thereof is a Fab, F(ab)2, and/or scFv.

3. The method of claim 1, wherein said virus is influenza A.

4. The method of claim 1, wherein said administering of said second composition is within about 100 minutes of administering said first composition.

5. The method of claim 1, wherein said administering of said second composition is within about 10 minutes of administering said first composition.

6. The method of claim 1, wherein said administering of said second composition is within about 5 minutes of administering said first composition.

7. The method of claim 1, wherein said non-viral expression vectors are CpG-reduced.

8. The method of claim 1, wherein said non-viral expression vectors are CpG-free.

9. The method of claim 1, wherein said mAb or antigen binding portion thereof comprises said mAb.

10. The method of claim 9, wherein each of said non-viral expression vectors comprises a plasmid that encodes both an antibody heavy chain and an antibody light chain.

* * * * *